United States Patent
Fu et al.

(12)

(10) Patent No.: US 6,583,112 B1
(45) Date of Patent: Jun. 24, 2003

(54) GENE PRODUCTS RELATED TO WERNER'S SYNDROME

(76) Inventors: Ying-Hui Fu, 7417 28th Ave, NW., Seattle, WA (US) 98117; Chang-En Yu, 5709 60th Ave. NE., Seattle, WA (US) 98105; Junko Oshima, 5200 Ravenna Ave. NE., Seattle, WA (US) 98105; John T. Mulligan, 5823 17th Ave. NE., Seattle, WA (US) 98105; Gerard D. Schellenberg, 7031 19th Ave. NW., Seattle, WA (US) 98117

( * ) Notice: Subject to any disclaimer, the term of this patent is extended or adjusted under 35 U.S.C. 154(b) by 0 days.

(21) Appl. No.: 09/618,166

(22) Filed: Jul. 17, 2000

Related U.S. Application Data

(63) Continuation of application No. 08/781,891, filed on Dec. 27, 1996, now Pat. No. 6,090,620, which is a continuation-in-part of application No. 08/632,175, filed on Apr. 12, 1996, now abandoned, which is a continuation-in-part of application No. 08/594,242, filed on Jan. 30, 1996, now abandoned, which is a continuation-in-part of application No. 08/580,539, filed on Dec. 29, 1995, now abandoned.

(60) Provisional application No. 60/009,409, filed on Dec. 29, 1995, and provisional application No. 60/010,835, filed on Jan. 30, 1996.

(51) Int. Cl.[7] ............................................. C07K 14/00
(52) U.S. Cl. ......................................... 514/2; 530/350
(58) Field of Search .......................... 435/325, 6, 69.1, 435/455, 320.1; 536/23.5, 24.31; 530/350, 300; 514/2

(56) References Cited

U.S. PATENT DOCUMENTS 6,090,620 A * 7/2000 Fu et al. .................... 435/325

FOREIGN PATENT DOCUMENTS

WO        WO 97/24435    * 7/1997

OTHER PUBLICATIONS

Goto et al., "Genetic linkage of Werner's syndrome to five markers on chromosome 8," *Nature* 355: 735–738, 1992.

Imamura et al., "Cloning of a mouse homoloque of the human Werner Syndrome gene and assignment to 8A4 by fluorescence in Situ hybridization," *Genomics* 41: 298–300, 1997.

Kurimasa et al., "Construction of 110 cosmid markers and a 4.5–Mb YAC contig on human chromosome 8p12–q11," *Genomics* 28: 147–153, 1995.

Lombard and Guarente, "Cloning the gene for Werner syndrome: a disease with many symptoms of premature aging," *Trends in Genetics* 12(8): 283–286, 1996.

Nakura et al., "Genetic association between chromosome 8 microsatellites and Werner syndrome (WRN)," *American Journal of Human Genetics* 57(4 Suppl.): A266, Abstract No. 1544, 1995.

Oshima et al., "Homozygous and compound heterozygous mutations at the Werner syndrome locus," *Human Molecular Genetics* 5(12): 1909–1913, 1996.

Puranam and Blackshear, "Cloning and characterization of RECQL, a potential human homoloque of the *Escherichia coli* DNA helicase RecQ," *Journal of Biological Chemistry* 269(47): 29838–29845, 1994.

Seki et al., "Molecular cloning of cDNA encoding human DNA helicase Q1 which has homology to *Escherichia coli* Rec Q helicase and localization of the gene at chromosome 12p12," *Nucleic Acids Research* 22(22): 4566–4573, 1994.

Thweatt et al "A novel cDNA overexpressed in Werner Syndrome (WS) fibroblasts inhibit colony formation in normal human fibroblasts and in HeLa Cells," *FASEB Journal* 9(6): A1270, Abstract No. 84, 1995.

Ye et al., "Genetic association between chromosome 8 microsatellite (MS8–134) and Werner Syndrome (WRN): Chromosome Microdissection and homozygosity mapping," *Genomics* 28: 566–569, 1995.

Yu et al., "Linkage disequilibrium and haplotype studies of chromosome 8p 11.1–21.1 markers and Werner Syndrome," *Am. J. Hum. Genet.* 55: 356–364, 1994.

Yu et al., "Positional cloning of the Werner's Syndrome gene," *Science* 272: 258–262, 1996.

Yu et al., "Mutations in the consensus helicase domains of the Werner Syndrome gene," *Am. J. Hum. Genet.* 60: 330–341, 1997.

GenBank Accenssion No. T39125, "EST27m19 WATM1 *Homo sapiens* cDNA clone 27, mRNA sequence," located at http://www.ncbi.nlm.nih.gov.

Genbank Accession No. R58879, "NIB2278R Normalized infant brain, Bento Soures *Homo Sapiens* cDNA 5' end, mRNA sequence," located at http://wwwncbi.nlm.nih.gov.

Wall, *Theriogenology*, vol. 45, pp. 57–68, 1996.

Kappel et al., *Current Opinion in Biotechnology*, vol. 3, pp. 548–553, 1992.

Srojek & Wagner, Genetic Engineering: Principles and Methods, vol. 10, pp. 221–246, 1998.

Houdebine, Journal of Biotechnology, vol. 34, pp. 269–287, 1994.

Bradley et al., Biotechnology, vol. 10, pp. 534–539, May 1992.

Seki et al., Nucleic Acids Research, vol. 22, pp. 4566–4573, Abstract only, Nov. 11, 1994.

Umezu et al., Proceedings of the National Academy of Sciences, USA, vol. 87, pp. 5363–5367, Abstract only Jul. 1990.

* cited by examiner

*Primary Examiner*—Karen Cochrane Carlson
(74) *Attorney, Agent, or Firm*—SEED Intellectual Property Law Group PLLC

(57) ABSTRACT

The present invention discloses nucleic acid molecules encoding WRN gene products, expression vectors and host cells suitable for expressing such products.

4 Claims, 77 Drawing Sheets

```
TGTGCGCCGGGGAGGCGCCGGCTTGTACTCGGCAGCGCGGGAATAAAGTTTGCTGATTTG    60
GTGTCTAGCCTGGATGCCTGGGTTGCAGCCCTGCTTGTGGTGGCGCTCCACAGTCATCCG   120
GCTGAAGAAGACCTGTTGGACTGGATCTTCTCGGGTTTTCTTTCAGATATTGTTTTGTAT   180
TTACCCATGAAGACATTGTTTTTTGGACTCTGCAAATAGGACATTTCAAAGATGAGTGAA   240
AAAAAATTGGAAACAACTGCACAGCAGCGGAAATGTCCTGAATGGATGAATGTGCAGAAT   300
AAAAGATGTGCTGTAGAAGAAAGAAAGGCATGTGTTCGGAAGAGTGTTTTTGAAGATGAC   360
CTCCCCTTCTTAGAATTCACTGGATCCATTGTGTATAGTTACGATGCTAGTGATTGCTCT   420
TTCCTGTCAGAAGATATTAGCATGAGTCTATCAGATGGGGATGTGGTGGGATTTGACATG   480
GAGTGGCCACCATTATACAATAGAGGGAAACTTGGCAAAGTTGCACTAATTCAGTTGTGT   540
GTTTCTGAGAGCAAATGTTACTTGTTCCACGTTTCTTCCATGTCAGTTTTTCCCCAGGGA   600
TTAAAAATGTTGCTTGAAAATAAAGCAGTTAAAAAGGCAGGTGTAGGAATTGAAGGAGAT   660
CAGTGGAAACTTCTACGTGACTTTGATATCAAATTGAAGAATTTTGTGGAGTTGACAGAT   720
GTTGCCAATAAAAAGCTGAAATGTACAGAGACCTGGAGCCTTAACAGTCTGGTTAAACAC   780
CTCTTAGGTAAACAGCTCCTGAAAGACAAGTCTATCCGCTGTAGCAATTGGAGTAAATTT   840
CCTCTCACTGAGGACCAGAAACTGTATGCAGCCACTGATGCTTATGCTGGTTTTATTATT   900
TACCGAAATTTAGAGATTTTGGATGATACTGTGCAAAGGTTTGCTATAAATAAAGAGGAA   960
GAAATCCTACTTAGCGACATGAACAAACAGTTGACTTCAATCTCTGAGGAAGTGATGGAT  1020
CTGGCTAAGCATCTTCCTCATGCTTTCAGTAAATTGGAAAACCCACGGAGGGTTTCTATC  1080
TTACTAAAGGATATTTCAGAAAATCTATATTCACTGAGGAGGATGATAATTGGGTCTACT  1140
AACATTGAGACTGAACTGAGGCCCAGCAATAATTTAAACTTATTATCCTTTGAAGATTCA  1200
ACTACTGGGGGAGTACAACAGAAACAAATTAGAGAACATGAAGTTTTAATTCACGTTGAA  1260
GATGAAACATGGGACCCAACACTTGATCATTTAGCTAAACATGATGGAGAAGATGTACTT  1320
GGAAATAAAGTGGAACGAAAAGAAGATGGATTTGAAGATGGAGTAGAAGACAACAAATTG  1380
AAAGAGAATATGGAAAGAGCTTGTTTGATGTCGTTAGATATTACAGAACATGAACTCCAA  1440
ATTTTGGAACAGCAGTCTCAGGAAGAATATCTTAGTGATATTGCTTATAAATCTACTGAG  1500
CATTTATCTCCCAATGATAATGAAAACGATACGTCCTATGTAATTGAGAGTGATGAAGAT  1560
TTAGAAATGGAGATGCTTAAGCATTTATCTCCCAATGATAATGAAAACGATACGTCCTAT  1620
GTAATTGAGAGTGATGAAGATTTAGAAATGGAGATGCTTAAGTCTTTAGAAAACCTCAAT  1680
AGTGGCACGGTAGAACCAACTCATTCTAAATGCTTAAAAATGGAAAGAAATCTGGGTCTT  1740
CCTACTAAAGAAGAAGAAGAAGATGATGAAAATGAAGCTAATGAAGGGGAAGAAGATGAT  1800
GATAAGGACTTTTTGTGGCCAGCACCCAATGAAGAGCAAGTTACTTGCCTCAAGATGTAC  1860
TTTGGCCATTCCAGTTTTAAACCAGTTCAGTGGAAAGTGATTCATTCAGTATTAGAAGAA  1920
AGAAGAGATAATGTTGCTGTCATGGCAACTGGATATGGAAAGAGTTTGTGCTTCCAGTAT  1980
CCACCTGTTTATGTAGGCAAGATTGGCCTTGTTATCTCTCCCCTTATTTCTCTGATGGAA  2040
GACCAAGTGCTACAGCTTAAAATGTCCAACATCCCAGCTTGCTTCCTTGGATCAGCACAG  2100
TCAGAAAATGTTCTAACAGATATTAAATTAGGTAAATACCGGATTGTATACGTAACTCCA  2160
GAATACTGTTCAGGTAACATGGGCCTGCTCCAGCAACTTGAGGCTGATATTGGTATCACG  2220
CTCATTGCTGTGGATGAGGCTCACTGTATTTCTGAGTGGGGCATGATTTTAGGGATTCA   2280
TTCAGGAAGTTGGGCTCCCTAAAGACAGCACTGCCAATGGTTCCAATCGTTGCACTTACT  2340
GCTACTGCAAGTTCTTCAATCCGGGAAGACATTGTACGTTGCTTAAATCTGAGAAATCCT  2400
CAGATCACCTGTACTGGTTTTGATCGACCAAACCTGTATTTAGAAGTTAGGCGAAAAACA  2460
GGGAATATCCTTCAGGATCTGCAGCCATTTCTTGTCAAAACAAGTTCCCACTGGGAATTT  2520
GAAGGTCCAACAATCATCTACTGTCCTTCTAGAAAAATGACACAACAAGTTACAGGTGAA  2580
CTTAGGAAACTTAATCTATCCTGTGGAACATACCATGCGGGCATGAGTTTTAGCACAAGG  2640
AAAGACATTCATCATAGGTTTGTAAGAGATGAAATTCAGTGTGTCATAGCTACCATAGCT  2700
```

*Fig. 2A-1*

```
TTTGGAATGGGCATTAATAAAGCTGACATTCGCCAAGTCATTCATTACGGTGCTCCTAAG    2760
GACATGGAATCATATTATCAGGAGATTGGTAGAGCTGGTCGTGATGGACTTCAAAGTTCT    2820
TGTCACGTCCTCTGGGCTCCTGCAGACATTAACTTAAATAGGCACCTTCTTACTGAGATA    2880
CGTAATGAGAAGTTTCGATTATACAAATTAAAGATGATGGCAAAGATGGAAAAATATCTT    2940
CATTCTAGCAGATGTAGGAGACAAATCATCTTGTCTCATTTTGAGGACAAACAAGTACAA    3000
AAAGCCTCCTTGGGAATTATGGGAACTGAAAAATGCTGTGATAATTGCAGGTCCAGATTG    3060
GATCATTGCTATTCCATGGATGACTCAGAGGATACATCCTGGGACTTTGGTCCACAAGCA    3120
TTTAAGCTTTTGTCTGCTGTGGACATCTTAGGCGAAAAATTTGGAATTGGGCTTCCAATT    3180
TTATTTCTCCGAGGATCTAATTCTCAGCGTCTTGCCGATCAATATCGCAGGCACAGTTTA    3240
TTTGGCACTGGCAAGGATCAAACAGAGAGTTGGTGGAAGGCTTTTTCCCGTCAGCTGATC    3300
ACTGAGGGATTCTTGGTAGAAGTTTCTCGGTATAACAAATTTATGAAGATTTGCGCCCTT    3360
ACGAAAAAGGGTAGAAATTGGCTTCATAAAGCTAATACAGAATCTCAGAGCCTCATCCTT    3420
CAAGCTAATGAAGAATTGTGTCCAAAGAAGTTTCTTCTGCCTAGTTCGAAAACTGTATCT    3480
TCGGGCACCAAAGAGCATTGTTATAATCAAGTACCAGTTGAATTAAGTACAGAGAAGAAG    3540
TCTAACTTGGAGAAGTTATATTCTTATAAACCATGTGATAAGATTTCTTCTGGGAGTAAC    3600
ATTTCTAAAAAAAGTATCATGGTACAGTCACCAGAAAAAGCTTACAGTTCCTCACAGCCT    3660
GTTATTTCGGCACAAGAGCAGGAGACTCAGATTGTGTTATATGGCAAATTGGTAGAAGCT    3720
AGGCAGAAACATGCCAATAAAATGGATGTTCCCCCAGCTATTCTGGCAACAAACAAGATA    3780
CTGGTGGATATGGCCAAAATGAGACCAACTACGGTTGAAAACGTAAAAAGGATTGATGGT    3840
GTTTCTGAAGGCAAAGCTGCCATGTTGGCCCCTCTGTTGGAAGTCATCAAACATTTCTGC    3900
CAAACAAATAGTGTTCAGACAGACCTCTTTTCAAGTACAAAACCTCAAGAAGAACAGAAG    3960
ACGAGTCTGGTAGCAAAAAATAAAATATGCACACTTTCACAGTCTATGGCCATCACATAC    4020
TCTTTATTCCAAGAAAAGAAGATGCCTTTGAAGAGCATAGCTGAGAGCAGGATTCTGCCT    4080
CTCATGACAATTGGCATGCACTTATCCCAAGCGGTGAAAGCTGGCTGCCCCCTTGATTTG    4140
GAGCGAGCAGGCCTGACTCCAGAGGTTCAGAAGATTATTGCTGATGTTATCCGAAACCCT    4200
CCCGTCAACTCAGATATGAGTAAAATTAGCCTAATCAGAATGTTAGTTCCTGAAAACATT    4260
GACACGTACCTTATCCACATGGCAATTGAGATCCTTAAACATGGTCCTGACAGCGGACTT    4320
CAACCTTCATGTGATGTCAACAAAAGGAGATGTTTTCCCGGTTCTGAAGAGATCTGTTCA    4380
AGTTCTAAGAGAAGCAAGGAAGAAGTAGGCATCAATACTGAGACTTCATCTGCAGAGAGA    4440
AAGAGACGATTACCTGTGTGGTTTGCCAAAGGAAGTGATACCAGCAAGAAATTAATGGAC    4500
AAAACGAAAGGGGAGGTCTTTTTAGTTAAGCTGGCAATTACCAGAACAATTATGTTTCT    4560
TGCTGTATTATAAGAGGATAGCTATATTTTATTTCTGAAGAGTAAGGAGTAGTATTTTGG    4620
CTTAAAAATCATTCTAATTACAAAGTTCACTGTTTATTGAAGAACTGGCATCTTAAATCA    4680
GCCTTCCGCAATTCATGTAGTTTCTGGGTCTTCTGGGAGCCTACGTGAGTACATCACCTA    4740
ACAGAATATTAAATTAGACTTCCTGTAAGATTGCTTTAAGAAACTGTTACTGTCCTGTTT    4800
TCTAATCTCTTTATTAAAACAGTGTATTTGGAAAATGTTATGTGCTCTGATTTGATATAG    4860
ATAACAGATTAGTAGTTACATGGTAATTATGTGATATAAAATATTCATATATTATCAAAA    4920
TTCTGTTTTGTAAATGTAAGAAAGCATAGTTATTTACAAATTGTTTTTACTGTCTTTTG    4980
AAGAAGTTCTTAAATACGTTGTTAAATGGTATTAGTTGACCAGGGCAGTGAAAATGAAAC    5040
CGCATTTTGGGTGCCATTAAATAGGGAAAAAACATGTAAAAAATGTAAAATGGAGACCAA    5100
TTGCACTAGGCAAGTGTATATTTTGTATTTTATATACAATTTCTATTATTTTTCAAGTAA    5160
TAAAACAATGTTTTTCATACTGAATATTAAAAAAAAAAAAAAAAAAAAA              5208
```

*Fig. 2A-2*

```
MSEKKLETTAQQRKCPEWMNVQNKRCAVEERKACVRKSVFEDDLPFLEFTGSIVYSYDAS      60
DCSFLSEDISMSLSDGDVVGFDMEWPPLYNRGKLGKVALIQLCVSESKCYLFHVSSMSVF     120
PQGLKMLLENKAVKKAGVGIEGDQWKLLRDFDIKLKNFVELTDVANKKLKCTETWSLNSL     180
VKHLLGKQLLKDKSIRCSNWSKFPLTEDQKLYAATDAYAGFIIYRNLEILDDTVQRFAIN     240
KEEEILLSDMNKQLTSISEEVMDLAKHLPHAFSKLENPRRVSILLKDISENLYSLRRMII     300
GSTNIETELRPSNNLNLLSFEDSTTGGVQQKQIREHEVLIHVEDETWDPTLDHLAKHDGE     360
DVLGNKVERKEDGFEDGVEDNKLKENMERACLMSLDITEHELQILEQQSQEEYLSDIAYK     420
STEHLSPNDNENDTSYVIESDEDLEMEMLKHLSPNDNENDTSYVIESDEDLEMEMLKSLE     480
NLNSGTVEPTHSKCLKMERNLGLPTKEEEEDDENEANEGEEDDDKDFLWPAPNEEQVTCL     540
KMYFGHSSFKPVQWKVIHSVLEERRDNVAVMATGYGKSLCFQYPPVYVGKIGLVISPLIS     600
LMEDQVLQLKMSNIPACFLGSAQSENVLTDIKLGKYRIVYVTPEYCSGNMGLLQQLEADI     660
GITLIAVDEAHCISEWGHDFRDSFRKLGSLKTALPMVPIVALTATASSSIREDIVRCLNL     720
RNPQITCTGFDRPNLYLEVRRKTGNILQDLQPFLVKTSSHWEFEGPTIIYCPSRKMTQQV     780
TGELRKLNLSCGTYHAGMSFSTRKDIHHRFVRDEIQCVIATIAFGMGINKADIRQVIHYG     840
APKDMESYYQEIGRAGRDGLQSSCHVLWAPADINLNRHLLTEIRNEKFRLYKLKMMAKME     900
KYLHSSRCRRQIILSHFEDKQVQKASLGIMGTEKCCDNCRSRLDHCYSMDDSEDTSWDFG     960
PQAFKLLSAVDILGEKFGIGLPILFLRGSNSQRLADQYRRHSLFGTGKDQTESWWKAFSR    1020
QLITEGFLVEVSRYNKFMKICALTKKGRNWLHKANTESQSLILQANEELCPKKFLLPSSK    1080
TVSSGTKEHCYNQVPVELSTEKKSNLEKLYSYKPCDKISSGSNISKKSIMVQSPEKAYSS    1140
SQPVISAQEQETQIVLYGKLVEARQKHANKMDVPPAILATNKILVDMAKMRPTTVENVKR    1200
IDGVSEGKAAMLAPLLEVIKHFCQTNSVQTDLFSSTKPQEEQKTSLVAKNKICTLSQSMA    1260
ITYSLFQEKKMPLKSIAESRILPLMTIGMHLSQAVKAGCPLDLERAGLTPEVQKIIADVI    1320
RNPPVNSDMSKISLIRMLVPENIDTYLIHMAIEILKHGPDSGLQPSCDVNKRRCFPGSEE    1380
ICSSSKRSKEEVGINTETSSAERKRRLPVWFAKGSDTSKKLMDKTKRGGLFS           1432
```

*Fig. 2B*

```
                          v         v         v         v                v
                                                          TTTGGAATTGGG      12
     v        v        v         v         v         v          v
CTTCCAATTTTATTTCTCCGAGGATCTGGTCTCACTCTGTTGCTCAGTCTGTAGTGCAGT              72
  v        v        v         v         v         v         v
GGTGTCATCATAGCTCACTGCAGTCTTGATCTCCTGAGCTCAAACGATTCTCCTGCCTCA             132
  v        v         v         v         v         v         v
GCTCCTGCTTCAGCCTCCTGAGTAGCGGAACAACAGAATTCTCAGCGTCTTGCCGATCAA             192
  v        v         v         v         v         v         v
TATCGCAGGCACAGTTTATTTGGCACTGGCAAGGATCAAACAGAGAGTTGGTGGAAGGCT             252
  v        v         v         v         v         v         v
TTTTCCCGTCAGCTGATCACTGAGGGATTCTTGGTAGAAGTTTCTCGGTATAACAAATTT             312
  v        v         v         v         v         v         v
ATGAAGATTTGCGCCCTTACGAAAAAGGGTAGAAATTGGCTTCATAAAGCTAATACAGAA             372
MetLysIleCysAlaLeuThrLysLysGlyArgAsnTrpLeuHisLysAlaAsnThrGlu              20
  v        v         v         v         v         v         v
TCTCAGAGCCTCATCCTTCAAGCTAATGAAGAATTGTGTCCAAAGAAGTTTCTTCTGCCT             432
SerGlnSerLeuIleLeuGlnAlaAsnGluGluLeuCysProLysLysPheLeuLeuPro              40
  v        v         v         v         v         v         v
AGTTCGAAAACTGTATCTTCGGGCACCAAAGAGCATTGTTATAATCAAGTACCAGTTGAA             492
SerSerLysThrValSerSerGlyThrLysGluHisCysTyrAsnGlnValProValGlu              60
  v        v         v         v         v         v         v
TTAAGTACAGAGAAGAAGTCTAACTTGGAGAAGTTATATTCTTATAAACCATGTGATAAG             552
LeuSerThrGluLysLysSerAsnLeuGluLysLeuTyrSerTyrLysProCysAspLys              80
  v        v         v         v         v         v         v
ATTTCTTCTGGGAGTAACATTTCTAAAAAAAGTATCATGGTACAGTCACCAGAAAAAGCT             612
IleSerSerGlySerAsnIleSerLysLysSerIleMetValGlnSerProGluLysAla             100
  v        v         v         v         v         v         v
TACAGTTCCTCACAGCCTGTTATTTCGGCACAAGAGCAGGAGACTCAGATTGTGTTATAT             672
TyrSerSerSerGlnProValIleSerAlaGlnGluGlnGluThrGlnIleValLeuTyr             120
  v        v         v         v         v         v         v
GGCAAATTGGTAGAAGCTAGGCAGAAACATGCCAATAAAATGGATGTTCCCCCAGCTATT             732
GlyLysLeuValGluAlaArgGlnLysHisAlaAsnLysMetAspValProProAlaIle             140
  v        v         v         v         v         v         v
CTGGCAACAAACAAGATACTGGTGGATATGGCCAAAATGAGACCAACTACGGTTGAAAAC             792
LeuAlaThrAsnLysIleLeuValAspMetAlaLysMetArgProThrThrValGluAsn             160
  v        v         v         v         v         v         v
GTAAAAAGGATTGATGGTGTTTCTGAAGGCAAAGCTGCCATGTTGGCCCCTCTGTTGGAA             852
ValLysArgIleAspGlyValSerGluGlyLysAlaAlaMetLeuAlaProLeuLeuGlu             180
  v        v         v         v         v         v         v
GTCATCAAACATTTCTGCCAAACAAATAGTGTTCAGACAGACCTCTTTTCAAGTACAAAA             912
ValIleLysHisPheCysGlnThrAsnSerValGlnThrAspLeuPheSerSerThrLys             200
```

*Fig. 3A*

| | |
|---|---|
| CCTCAAGAAGAACAGAAGACGAGTCTGGTAGCAAAAAATAAAATATGCACACTTTCACAG | 972 |
| ProGlnGluGluGlnLysThrSerLeuValAlaLysAsnLysIleCysThrLeuSerGln | 220 |
| TCTATGGCCATCACATACTCTTTATTCCAAGAAAAGAAGATGCCTTTGAAGAGCATAGCT | 1032 |
| SerMetAlaIleThrTyrSerLeuPheGlnGluLysLysMetProLeuLysSerIleAla | 240 |
| GAGAGCAGGATTCTGCCTCTCATGACAATTGGCATGCACTTATCCCAAGCGGTGAAAGCT | 1092 |
| GluSerArgIleLeuProLeuMetThrIleGlyMetHisLeuSerGlnAlaValLysAla | 260 |
| GGCTGCCCCCTTGATTTGGAGCGAGCAGGCCTGACTCCAGAGGTTCAGAAGATTATTGCT | 1152 |
| GlyCysProLeuAspLeuGluArgAlaGlyLeuThrProGluValGlnLysIleIleAla | 280 |
| GATGTTATCCGAAACCCTCCCGTCAACTCAGATATGAGTAAAATTAGCCTAATCAGAATG | 1212 |
| AspValIleArgAsnProProValAsnSerAspMetSerLysIleSerLeuIleArgMet | 300 |
| TTAGTTCCTGAAAACATTGACACGTACCTTATCCACATGGCAATTGAGATCCTTAAACAT | 1272 |
| LeuValProGluAsnIleAspThrTyrLeuIleHisMetAlaIleGluIleLeuLysHis | 320 |
| GGTCCTGACAGCGGACTTCAACCTTCATGTGATGTCAACAAAAGGAGATGTTTTCCCGGT | 1332 |
| GlyProAspSerGlyLeuGlnProSerCysAspValAsnLysArgArgCysPheProGly | 340 |
| TCTGAAGAGATCTGTTCAAGTTCTAAGAGAAGCAAGGAAGAAGTAGGCATCAATACTGAG | 1392 |
| SerGluGluIleCysSerSerSerLysArgSerLysGluGluValGlyIleAsnThrGlu | 360 |
| ACTTCATCTGCAGAGAGAAAGAGACGATTACCTGTGTGGTTTGCCAAAGGAAGTGATACC | 1452 |
| ThrSerSerAlaGluArgLysArgArgLeuProValTrpPheAlaLysGlySerAspThr | 380 |
| AGCAAGAAATTAATGGACAAAACGAAAAGGGGAGGTCTTTTTAGTTAAGCTGGCAATTAC | 1512 |
| SerLysLysLeuMetAspLysThrLysArgGlyGlyLeuPheSer>>> | 395 |
| CAGAACAATTATGTTTCTTGCTGTATTATAAGAGGATAGCTATATTTTATTTCTGAAGAG | 1572 |
| TAAGGAGTAGTATTTTGGCTTAAAAATCATTCTAATTACAAAGTTCACTGTTTATTGAAG | 1632 |
| AACTGGCATCTTAAATCAGCCTTCCGCAATTCATGTAGTTTCTGGGTCTTCTGGGAGCCT | 1692 |
| ACGTGAGTACATCACCTAACAGAATATTAAATTAGACTTCCTGTAAGATTGCTTTAAGAA | 1752 |
| ACTGTTACTGTCCTGTTTTCTAATCTCTTTATTAAAACAGTGTATTTGGAAAATGTTATG | 1812 |
| TGCTCTGATTTGATATAGATAACAGATTAGTAGTTACATGGTAATTATGTGATATAAAAT | 1872 |
| ATTCATATATTATCAAAATTCTGTTTTGTAAATGTAAGAAAGCATAGTTATTTTACAAAT | 1932 |

*Fig. 3B*

```
TGTTTTTACTGTCTTTTGAAGAAGTTCTTAAATACGTTGTTAAATGGTATTAGTTGACCA  1992
GGGCAGTGAAAATGAAACCGCATTTTGGGTGCCATTAAATAGGGAAAAACATGTAAAAA  2052
ATGTAAAATGGAGACCAATTGCACTAGGCAAGTGTATATTTTGTATTTTATATACAATTT  2112
CTATTATTTTTCAAGTAATAAAACAATGTTTTTCATACTGAATATTAAAAAAAAAAAAAA  2172
AAAAAA                                                         2178
```

*Fig. 3C*

```
agein.12.27_helicases.msf{Agein.12.27.f2.pro}     1  .......... .......... .......... .......... ..........   50
agein.12.27_helicases.msf{recq_ecoli.pro}            .......... .......... .......... .......... ..........
agein.12.27_helicases.msf{YABC_SCHPO.pro}            .......... .......... .......... .......... ..........
agein.12.27_helicases.msf{recq_human.pro}            .......... .......... .......... .......... ..........
agein.12.27_helicases.msf{BLM.pro}                   MAAVPQNNLQ EQLERHSART LNNKLSLSKP KFSGFTFKKK TSSDNNVSVT agein.12.27_helicases.msf{Agein.12.27.f2.pro}    51  .......... .......... .......... .......... ..........  100
agein.12.27_helicases.msf{recq_ecoli.pro}            .......... .......... .......... .......... ..........
agein.12.27_helicases.msf{YABC_SCHPO.pro}            .......... .......... .......... .......... ...MTVTKTNL
agein.12.27_helicases.msf{recq_human.pro}            .......... .......... .......... .......... ..........
agein.12.27_helicases.msf{BLM.pro}                   NVSVAKTPVL RNKDVNVTED FSFSEPLPNT TNQQRVKDFF KNAPAGQETQ agein.12.27_helicases.msf{Agein.12.27.f2.pro}   101  .......... .......... .......... .......... ..........  150
agein.12.27_helicases.msf{recq_ecoli.pro}            .......... .......... .......... .......... ..........
agein.12.27_helicases.msf{YABC_SCHPO.pro}            NRHLDWFFRE SPQKIENVTS PIKTLDFVKV KVSSSDIVVK DSIPHKSKNV
agein.12.27_helicases.msf{recq_human.pro}            .......... .......... .......... .......... ..........
agein.12.27_helicases.msf{BLM.pro}                   RGGSKSLLPD FLQTPKEVVC TTQNTPTVKK SRDTALKKLE FSSSPDSLST agein.12.27_helicases.msf{Agein.12.27.f2.pro}   151  .......... .......... .......... .......... ..........  200
agein.12.27_helicases.msf{recq_ecoli.pro}            .......... .......... .......... .......... ..........
agein.12.27_helicases.msf{YABC_SCHPO.pro}            FDDFDDGYAI DLTEEHQS.. .......... .......... SSLNNLK
agein.12.27_helicases.msf{recq_human.pro}            .......... .......... .......... .......... WKDVEGPNIL
agein.12.27_helicases.msf{BLM.pro}                   INDWDDMDDF DTSETSKSFV TPPQSHFVRV STAQKSKKGK RNFFKAQLYT agein.12.27_helicases.msf{Agein.12.27.f2.pro}   201  .......... .......... .......... .......... ..........  250
agein.12.27_helicases.msf{recq_ecoli.pro}            .......... .......... .......... .......... ..........
agein.12.27_helicases.msf{YABC_SCHPO.pro}            KPIKKIAVPA SESEEDFDDV PSSESEQIDL TEEQKDDSEW EVFQSCQPLA VNTADTTVSH
agein.12.27_helicases.msf{recq_human.pro}            .......... .......... .......... .......... ..........
agein.12.27_helicases.msf{BLM.pro}                   TNTVKTDLPP PSSESEQIDL TEEQKDDSEW LSSDVICIDD GPIAEVHINE
```

Fig. 4A

```
agein.12.27_helicases.msf(Agein.12.27.f2.pro)    251                                                              300
agein.12.27_helicases.msf(recq_ecoli.pro)            ..........  ..........  ..........  ..........  ..........
agein.12.27_helicases.msf(YABC_SCHPO.pro)            ..........  ..........  ..........  ..........  ..........
agein.12.27_helicases.msf(recq_human.pro)            ..........  ..........  ..........  ..........  ..........
        agein.12.27_helicases.msf(BLM.pro)           STSSSNVPRS  LNKIHDPSRF  IKDNDVENRI  HVSSASKVAS  ISNTSKPNPI agein.12.27_helicases.msf(Agein.12.27.f2.pro)    301                                                              350
agein.12.27_helicases.msf(recq_ecoli.pro)            DAQESDSLKT  HLEDERDNSE  KKKNLEEAEL  HSTEKVPCIE  FDDDDYDTDF
agein.12.27_helicases.msf(YABC_SCHPO.pro)            ..........  ..........  ..........  ..........  ..........
agein.12.27_helicases.msf(recq_human.pro)            ..........  ..........  ..........  ..........  ..........
        agein.12.27_helicases.msf(BLM.pro)           VSENPISATS  VSIEIPIKPK  ELSNNLPFPR  LNNNNTNNNN  DNNAIEKRDS agein.12.27_helicases.msf(Agein.12.27.f2.pro)    351                                                              400
agein.12.27_helicases.msf(recq_ecoli.pro)            VPPSPEEIIS  ASSSSSKCLS  TLKDLDTSDR  KEDVLSTSKD  LLSKPEKMSM
agein.12.27_helicases.msf(YABC_SCHPO.pro)            ..........  ..........  ..........  ..........  ..........
agein.12.27_helicases.msf(recq_human.pro)            ..........  ..........  ..........  ..........  ..........
        agein.12.27_helicases.msf(BLM.pro)           ASPTPSSVSS  QISIDFSTWP  H.....QNLL  QYLDILRDEK  SEISDRIIEV agein.12.27_helicases.msf(Agein.12.27.f2.pro)    401                                                              450
agein.12.27_helicases.msf(recq_ecoli.pro)            QELNPETSTD  CDARQISLQQ  QLIHVMEHIC  KLIDTIPDDK  LKLLDCGNEL
agein.12.27_helicases.msf(YABC_SCHPO.pro)            ..........  ..........  ..........  ..........  ..........
agein.12.27_helicases.msf(recq_human.pro)            ..........  ..........  ..........  ..........  ..........
        agein.12.27_helicases.msf(BLM.pro)           MERYPFSSRF  KEWIPKRDIL  SQKISSVLEV  LSNNNNSNNN  NGNNGT....

agein.12.27_helicases.msf(Agein.12.27.f2.pro)    451                                                              500
agein.12.27_helicases.msf(recq_ecoli.pro)            LQQRNIRRKL  LTEVDFNKSD  ASLLGSLWRY  RPDSLDGPME  GDSCPTGNSM
agein.12.27_helicases.msf(YABC_SCHPO.pro)            ..........  ..........  ..........  ..........  ...EDGFEDG
agein.12.27_helicases.msf(recq_human.pro)            ..........  ..VPNAKTFF  TPPSSITQQV  PFPSTIIPES  TVKENSTRPY
        agein.12.27_helicases.msf(BLM.pro)           KELNFSHLPS  NSVSPGDCLL  TTTLGKTGFS  ATRKNLFERP  LFNTHLQKSF
```

Fig. 4B

```
                                                    501                                                       550
agein.12.27_helicases.msf{Agein.12.27.f2.pro)       VEDNKLKENM ERACLMSLDI TEHELQILEQ QSQEEYLSDI AYKSTEHLSP
agein.12.27_helicases.msf{recq_ecoli.pro)           .......... .......... .......... .......... ..........
agein.12.27_helicases.msf{YABC_SCHPO.pro)           VNSHLVANDK ITATPFHS.. .......... .......... EAVV SPLQSNIRNS
agein.12.27_helicases.msf{recq_human.pro)           .......... .......... .......... .......... MASV SALTEEL.DS
agein.12.27_helicases.msf{BLM.pro)                  VSSNWAETPR LGKKNESSYF PGNVLTSTAV KDQNKHTASI NDLERETQPS 551                                                       600
agein.12.27_helicases.msf{Agein.12.27.f2.pro)       NDNENDTSYV IESDEDLEME MLKHLSPNDN ENDTSYVIES DEDLEMEMLK
agein.12.27_helicases.msf{recq_ecoli.pro)           .......... DDADFTFNIT DPINDESGAS SDVVVIDDEE DDIENRPLNQ
agein.12.27_helicases.msf{YABC_SCHPO.pro)           DIAEFDEFDI QIQELTERQQ ELI....... .......QK KKVLTKKIKQ
agein.12.27_helicases.msf{recq_human.pro)           ITSELHAVEI DDFDDDDDWE DIMHNLAASK SSTAAYQPIK EGRPIKSVSE
agein.12.27_helicases.msf{BLM.pro)                  Y..DIDNFDI 601                                                       650
agein.12.27_helicases.msf{Agein.12.27.f2.pro)       SLENLNSGTV EPTHSKCCLKM ERNLGLPTKE EEEDDENEAN EGEEDDDKDF
agein.12.27_helicases.msf{recq_ecoli.pro)           ALKASKAAV. ...SNASLLQ SSSLDRPLLG EMKDKNHKVL .......AQAEV
agein.12.27_helicases.msf{YABC_SCHPO.pro)           CLEDSDAGA. ...SNE..YD SSPAAW.... .......... MPSLDDPM..
agein.12.27_helicases.msf{recq_human.pro)           RLSSAKTDCL PVSSTAQNIN FSESIQNYTD KSAQNLASRN ........NK..
agein.12.27_helicases.msf{BLM.pro)                                                              LKHERFQS..

651                                                       700
agein.12.27_helicases.msf{Agein.12.27.f2.pro)       LWPAPNEEQV TCLKMYFGHS SFKPVQWKVI HSVLEERRDN VAVMATGYGK
agein.12.27_helicases.msf{recq_ecoli.pro)           LNLESGAKQV ..LQETFGYQ QFRPGQEEII DTVLSG.RDC LVVMPTGGGK
agein.12.27_helicases.msf{YABC_SCHPO.pro)           LSYPWSKEVL GCLKHKFHLK GFRKNQLEAI NGTLSG.KDV FILMPTGGGK
agein.12.27_helicases.msf{recq_human.pro)           EDFPWSGKVK DILQNVFKLE KFRPLQLETI NVTMAG.KEV FLVMPTGGGK
agein.12.27_helicases.msf{BLM.pro)                  LSFPHTKEMM KIFHKKFGLH NFRTNQLEAI NAALLG.EDC FILMPTGGGK 701                                                       750
agein.12.27_helicases.msf{Agein.12.27.f2.pro)       SLCFQYPPVY VG....KIGL VISPLISLME DQVLQLKMSN IPACFLGSAQ
agein.12.27_helicases.msf{recq_ecoli.pro)           SLCYQIPALL LN....GLTV VVSPLISLMK DQVDQLQANG VAAACLNSTQ
agein.12.27_helicases.msf{YABC_SCHPO.pro)           SLCYQLPAVI EGGASRGVTL VISPLLSLMQ DQLDHLRKLN IPSLPLSGEQ
agein.12.27_helicases.msf{recq_human.pro)           SLCYQLPAL. ...CSDGFTL VICPLISLME DQLMVLKQLG ISATMLNASS
agein.12.27_helicases.msf{BLM.pro)                  SLCYQLPA.. ...CVSPGVTV VISPLRSLIV DQVQKLTSLD IPATYLTGDK
```

Fig. 4C

```
                                                                                                      800
751
agein.12.27_helicases.msf(Agein.12.27.f2.pro)   SE....NVLT DI..KLGKYR IVYVTPE...  YCSGNMGLLQ QLEADIGITL
agein.12.27_helicases.msf(recq_ecoli.pro)       TREQQLEVMT GC..RTGQIR LLYIAPE...  ..RLMLDNFL EHLAHWNPVL
agein.12.27_helicases.msf(YABC_SCHPO.pro)       PADERRQVIS FLMAKNVLVK LLYVTPEGLA  SNGAITRVLK SLYERKLLAR
agein.12.27_helicases.msf(recq_human.pro)       SKEHVKWVHD EMVNKNSELK LIYVTPEKIA  KSKMFMSRLE KAYEARRFTR
agein.12.27_helicases.msf(BLM.pro)              TDSEATNIYL QLSKKDPIIK LLYVTPEKIC  ASNRLISTLE NLYERKLLAR
                                                                                                      850
801
agein.12.27_helicases.msf(Agein.12.27.f2.pro)   IAVDEAHCIS EWGHDFRDSF RKLGSLKTAL  PMVPIVALTA TASSSIREDI
agein.12.27_helicases.msf(recq_ecoli.pro)       LAVDEAHCIS QWGHDFRPEY AALGQLRQRF  PTLPFMALTA TADDTTRQDI
agein.12.27_helicases.msf(YABC_SCHPO.pro)       IVIDEAHCVS HWGHDFRPDY KQLGLLRDRY  QGIPFMALTA TANEIVKKDI
agein.12.27_helicases.msf(recq_human.pro)       IAVDEVHCCS QWGHDFRPDY KALGILKRQF  PNASLIGLTA TATNHVLTDA
agein.12.27_helicases.msf(BLM.pro)              FVIDEAHCVS QWGHDFRQDY KRMNMLRQKF  PSVPVMALTA TANPRVQKDI
                                                                                                      900
851
agein.12.27_helicases.msf(Agein.12.27.f2.pro)   VRCLNLRNPQ ITCTGFDRPN LYLEVRRKTG  NILQDLQPFL VKTSSHWEFE
agein.12.27_helicases.msf(recq_ecoli.pro)       VRLLGLNDPL IQISSFDRPN IRYMLMEK..  ..FKPLDQLM RYVQEQRGKS
agein.12.27_helicases.msf(YABC_SCHPO.pro)       INTLRMENCL ELKSSFNRPN LFYEIKPK..  ..KDLYTELY RFISNGHLHE
agein.12.27_helicases.msf(recq_human.pro)       QKILCIEKCF TFTASFNRPN LYYEVRQKPS  NTEDFIEDIV KLINGRYKGQ
agein.12.27_helicases.msf(BLM.pro)              LTQLKILRPQ VFSMSFNRHN LKYYVLPKKP  KKVAF..DCL EWIRKHHPYD
                                                                                                      950
901
agein.12.27_helicases.msf(Agein.12.27.f2.pro)   GPTIIYCPSR KMTQQVTGEL RK.LNLSCGT  YHAGMSFSTR KDIHHRFVR.
agein.12.27_helicases.msf(recq_ecoli.pro)       G..IIYCNSR AKVEDTAAAL QS.KGISAAA  YHAGLENNVR ADVQEKFQR.
agein.12.27_helicases.msf(YABC_SCHPO.pro)       S.GIIYCLSR TSCEQVAAKL RNDYGLKAWH  YHAGLEKVER QRIQNEW.QS
agein.12.27_helicases.msf(recq_human.pro)       S.GIIYCFSQ KDSEQVTVSL QN.LGIHAGA  YHANLEPEDK TTVHRKW.SA
agein.12.27_helicases.msf(BLM.pro)              S.GIIYCLSR RECDTMADTL QRD.GLAALA  YHAGLSDSAR DEVQQKWINQ
                                                                                                      1000
951
agein.12.27_helicases.msf(Agein.12.27.f2.pro)   DEIQCVIATI AFGMGINKAD IRQVIHYGAP  KDMESYYQEI GRAGRDGLQS
agein.12.27_helicases.msf(recq_ecoli.pro)       DDLQIVVATV AFGMGINKPN VRFVVHFDIP  RNIESYYQET GRAGRDGLPA
agein.12.27_helicases.msf(YABC_SCHPO.pro)       GSYKIIVATI AFGMGVDKGD VRFVIHHSFP  KSLEGYYQET GRAGRDGKPA
agein.12.27_helicases.msf(recq_human.pro)       NEIQVVVATV AFGMGIDKPD VRFVIHSMS   KSMENYYQES GRAGRDDMKA
agein.12.27_helicases.msf(BLM.pro)              DGCQVICATI AFGMGIDKPD VRFVIHASLP  KSVEGYYQES GRAGRDGEIS
```

*Fig. 4D*

```
                                              1001
agein.12.27_helicases.msf(Agein.12.27.f2.pro) SCHVLWAPAD INLNRHLL.. TEIRNEKFRL YKLKMMAKME KYLHS.SRCR 1050
agein.12.27_helicases.msf(recq_ecoli.pro)     EAMLFYDPAD MAWLRRCL.. EEKPQGQLQD IERHKLNAMG AFAEA.QTCR
agein.12.27_helicases.msf(YABC_SCHPO.pro)     HCIMFYSYKD HVTFQKLIMS G.DGDAETKE RQRQMLRQVI QFCENKTDCR
agein.12.27_helicases.msf(recq_human.pro)     DCILYYGFGD IFRISSMVVM E.NVG..... ..QQKLYEMV SYCQNISKSR
agein.12.27_helicases.msf(BLM.pro)            HCLLFYTYHD VTRLKRLIMM EKDGNHHTRE THFNNLYSMV HYCENITECR
                                              1051                                              1100
agein.12.27_helicases.msf(Agein.12.27.f2.pro) RQIILSHFED KQVQKASLGI MGTEKCCDNC RSRLDHCYSM DDSEDTSWDF
agein.12.27_helicases.msf(recq_ecoli.pro)     RLVLLNYFGE .......... .GRQEPCGNC DICLDPPKQY DGSTD.....
agein.12.27_helicases.msf(YABC_SCHPO.pro)     RKQVLAYFGE N.FDKV.HCR K...GCDIC ..CEEATYIK QDMTEFSLQA
agein.12.27_helicases.msf(recq_human.pro)     RVLMAQHFDE V.WNSE.ACN K...MCDNC ..CKDSAFER TNITEYCRDL
agein.12.27_helicases.msf(BLM.pro)            RIQLLAYFGE NGFNPD.FCK KHPDVSCDNC ..CKTKDYKT RDVTDDVKSI
                                              1101                                              1150
agein.12.27_helicases.msf(Agein.12.27.f2.pro) GPQAFKLLSA VDI....... LGEKFGIGLP ILFLRGSNSQ RLAD.QYRRH
agein.12.27_helicases.msf(recq_ecoli.pro)     ...AQIALST IGR....... VNQRFGMGYV VEVIRGANNQ RIRDYGHDKL
agein.12.27_helicases.msf(YABC_SCHPO.pro)     IKLLK...S. .......... ISGKATLLQL MDIFRGSKSA KIVENGWDRL
agein.12.27_helicases.msf(recq_human.pro)     IKILKQAEE. .......... LNEKLTPLKL IDSWMGKGAA KLRVAG....
agein.12.27_helicases.msf(BLM.pro)            VRFVQEHSSS QGMRNIKHVG PSGRFTMNML VDIFLGSKSA KIQSGIFGK.
                                              1151                                              1200
agein.12.27_helicases.msf(Agein.12.27.f2.pro) SLFGTGKDQT ESWWKAFSRQ LITEGFLVEV SRYNKFMKIC ALTKKGRNWL
agein.12.27_helicases.msf(recq_ecoli.pro)     KVYGMGRDKS HEHWVSVIRQ LIHLGLVTQ. .......... ..........
agein.12.27_helicases.msf(YABC_SCHPO.pro)     EGAGVGKLLN RGDSERLFHH LVSEGVFVEK VEANRRG.FV SAYVVP.GRQ
agein.12.27_helicases.msf(recq_human.pro)     ...VVAPTLP REDLEKIIAH FLIQQYLKED YSFTAYA.AI SYLKIG.PKA
agein.12.27_helicases.msf(BLM.pro)            ......GSAYS RHNAERLFKK LILDKILDED LYINANDQAI AYVMLG.NKA
                                              1201                                              1250
agein.12.27_helicases.msf(Agein.12.27.f2.pro) HKANTESQSL ILQANEELCP KKFLLPSSKT VSSGTKEHCY NQVPVELSTE
agein.12.27_helicases.msf(recq_ecoli.pro)     NIAQHSALQL TEAARPVLAE SSLQLAVPRI V......... .........AL
agein.12.27_helicases.msf(YABC_SCHPO.pro)     TIINSVLAGK RRIILDVKES SSKPDTSSRS LSRSKTLPAL REYQLKSTTA
agein.12.27_helicases.msf(recq_human.pro)     NLLNNEAHAI TMQVTKSTQN SFRAESSQTC HS........ ..........
agein.12.27_helicases.msf(BLM.pro)            ..QTVLNGN LKVDFMETEN SS........ .........S VKKQKALVA.
```

*Fig. 4E*

```
                                    1300                                              1350
agein.12.27_helicases.msf<Agein.12.27.f2.pro>  KKSNLEKLYS YKPCDKISSG SNISKKSIMV QSPEKAYSSS QPVISAQEQE
agein.12.27_helicases.msf<recq_ecoli.pro>      KPKAMQK... ......... SFG GNYDRK.... .........
agein.12.27_helicases.msf<YABC_SCHPO.pro>      SVDCSIGTRE VDEIYDSQMP PVKPSLIHSR NKIDLEELSG QKFMSEYEID
agein.12.27_helicases.msf<recq_human.pro>      QGDKKNGGKK IQATSRRRLQ TCFSNLV... .LRIQELRK EKSM......
        agein.12.27_helicases.msf<BLM.pro>     .......... .......... .......... .KVSQREEMV KKCLG..ELT 1301                                              1400
agein.12.27_helicases.msf<Agein.12.27.f2.pro>  TQIVLYGKLV EAR.QKHANK MDVPPAILAT NKILVDMAKM RPTTVENVKR
agein.12.27_helicases.msf<recq_ecoli.pro>      ...LFAKLR KLR.KSIADE SNVPPYVVFN DATLIEMAEQ MPITASEMLS
agein.12.27_helicases.msf<YABC_SCHPO.pro>      VMTRCLKDLK LLR.SNLMAI DDSRVSSYFT DSVLLSMAKK LPRNVKELKE
agein.12.27_helicases.msf<recq_human.pro>      .....MPDMN VTKFSN.... .......... .......... ..........
        agein.12.27_helicases.msf<BLM.pro>     EVCKSLGKVF GVHYFNI... .......... .FN TVTLKKLAES LSSDPEVLLQ 1351                                              1400
agein.12.27_helicases.msf<Agein.12.27.f2.pro>  IDGVSEGKAA MLA.PLLEVI KHFCQTNSVQ TDLFSSTKPQ EEQKTSLVAK
agein.12.27_helicases.msf<recq_ecoli.pro>      VNGVGMRKLE RFGKPFMALI RAHVDGDDEE .......... ..........
agein.12.27_helicases.msf<YABC_SCHPO.pro>      IHGVSNEKAV NLGPKFLQVI QKFIDEKEQN LEGTELDPSL QSLDTDYPID
agein.12.27_helicases.msf<recq_human.pro>      IDGVIEDKLE KYGAEVISVL QKYSE..... .......... ..........
        agein.12.27_helicases.msf<BLM.pro>     .......... .......... .......... .......WT SPAEDSSPGI 1401                                              1450
agein.12.27_helicases.msf<Agein.12.27.f2.pro>  NKICTLSQSM AITYSLFQEK KMPLKSIAES RILPLMTIGM HLSQAVKAGC
agein.12.27_helicases.msf<recq_ecoli.pro>      TNALSLDHEQ GFSDDSDSVY EPSSPIEEGD EEVDGQQRKDI LNFMNSQSLT
agein.12.27_helicases.msf<YABC_SCHPO.pro>      .......... .......... .......... .......... ..........
agein.12.27_helicases.msf<recq_human.pro>      SLSSSSRGPGR SAAEELDEEI PVSSHYFASK TRNERKRKKM PASQRSKRRK
        agein.12.27_helicases.msf<BLM.pro>     .......... .......... .......... .......... ..........

1451                                              1500
agein.12.27_helicases.msf<Agein.12.27.f2.pro>  PLDLERAGLT PEVQKIIADV IRNPPVNSDM SKISLIRMLV PENIDTYLIH
agein.12.27_helicases.msf<recq_ecoli.pro>      QTGSVPKRKS TSYTRPSKSY RHKRGS...T SYSRKRKYST SQKDSRKTSK
agein.12.27_helicases.msf<YABC_SCHPO.pro>      .......... .......... .......... .......... ..........
agein.12.27_helicases.msf<recq_human.pro>      TASSGSKAKG GSATCRKISS KTKSSSIIGS SSASHTSQAT SGANSKLGIM
        agein.12.27_helicases.msf<BLM.pro>     .......... .......... .......... .......... ..........
```

*Fig. 4F*

```
                                 1501
agein.12.27_helicases.msf(Agein.12.27.f2.pro)   MAIEILKHGP DSGLQPSCDV NKRRCFPGSE EICSSSKRSK EEVGINTETS
agein.12.27_helicases.msf(recq_ecoli.pro)       .......... .......... .......... .......... ..........
agein.12.27_helicases.msf(YABC_SCHPO.pro)       SANTSFIHPM VKQNYR.... .......... .......... ..........
agein.12.27_helicases.msf(recq_human.pro)       APPKPINRPF LKPSYAFS.. .......... .......... ..........
           agein.12.27_helicases.msf(BLM.pro)   .......... .......... .......... .......... ..........
                                 1551                                                            1600
agein.12.27_helicases.msf(Agein.12.27.f2.pro)   SAERKRRLPV WFAKGSDTSK KLMDKTKRGG LFS*AGNYQN NYVSCCIIRG
agein.12.27_helicases.msf(recq_ecoli.pro)       .......... .......... .......... .......... ..........
agein.12.27_helicases.msf(YABC_SCHPO.pro)       .......... .......... .......... .......... ..........
agein.12.27_helicases.msf(recq_human.pro)       .......... .......... .......... .......... ..........
           agein.12.27_helicases.msf(BLM.pro)   .......... .......... .......... .......... ..........
```

*Fig. 4G*

```
TATATTATGG CTATTTTTCT TTCTTATCTA TTTGTATTTT TATTGTTATT ACCTAAAAAA     60
AAATTTTCTA TGTCTTATCA CTAATTCTTC CCTAAAATTT CCCACAATTG TGTAAACTTA    120
CCTCAGTATA TTCATAGATA TGAGACATTC TATCAATTTT ACCCTCTTAA AGATGCAGAA    180
ATAATGCATT ATGTTTCATC CCACCATCTT TAATGAGAAG CTTCCATCTT AGATTAATAT    240
TAGAGAATGT TAAAATACTC TGCAATCAGG TAAGGACGCT TGAAACTTCA TCATAATGCA    300
AAAGTTTTCT TTAACACAAT AAATATTTTG AACCCCTTTC GTGTCTTGTA TTCATAGGAG    360
TTCAGATAGA CCACTTTATT TACTATTTTT TATAGAGAGT GAACAGAAAT CCCATTTCTA    420
GTCACCAGTC CTTAATCTGT AAATCAGGCA GATAATCTGT AAATGATTGG TTGAAATCAC    480
ATTGAATTCC ACTTTGTGCC AGGGACTTAA GTTAACGAAC AAATTATTCT TACAAAAAGG    540
TATAAATGTA AGGTTTTCAT TCCGCTAAAT ATGTTTGTCA AACTGTGTTG TGATTGTTC     600
TCAGTGTGTC ATAGCTACCA TAGCTTTTGG AATGGGCATT AATAAAGCTG ACATTCGCCA    660
AGTCATTCAT TACGGTGCTC CTAAGGACAT GGAATCATAT TATCAGGAGA TTGGTAGAGC    720
TGGTCGTGAT GGACTTCAAA GTTCTTGTCA CGTCCTCTGG GCTCCTGCAG ACATTAACTT    780
AAATAGGTAA AAAAAATTTA TTGTTTTTAC TCTTGCAGAT TTCTTTCTTG CTTTCCATAT    840
AAACCTCAAA AGTGTTTGAG GCTATTTCCA GTATCCCAAG TAATTTGTGA GTGCATTTAA    900
AGTAAAAAAA AAAAAAAAAG AAAAATAAAA CCTCCCCAAA TCCAGAGGAC ATGTAAGAAG    960
AACATTTGTG GTAAGAGTTG CCACTGGAG ATGAGCTAAT TTCAGCATGC CTTAGTTAGT    1020
GTGAGGAATT AACTAAATCA GGACAATACT TGGGCCTGTC ACAGAGATCC TATGGAATAC   1080
TTTCCTACCA TTGTGCATTA ATGAACAGGT TCTTTTCCTC TCCTCAGATC CTGTCAAGTT   1140
GCGATGTCTT CAGCCATAGT TACTTCAACT ACCACTGATT TTGTTACTGA TTCTTTCTTC   1200
CCATGCTACA GTGGTGATTA TTCCAGAGGA TTTCTCTCAG TCCCTATTTG ACTCTTGTTA   1260
CTATTTGTTT TCTTGGTTAG TTCCATGAGA CCATGCCAGT TCTCCTTGAC TGTGTATGAA   1320
TCATTGTGTT GCACTGTACT GACAGACTGC CGTAAGTCAA TATTAAGTGT TCAGTATCTA   1380
AGTGCAGGAG AACCTTTCTA CTTAAGTACT CAACAAGTAG TTTGTTGGCA CTTAAGTTCT   1440
ATGAGATTTT TTGTTGTAAA GGAAAACATT ATCTTGCAAA GATTTTGGGG CAGCATTTAC   1500
CAATACTTTG TTCCTTCATC CGTAGGAAAA AGAATCTCAG GAGAAAAACC TATACATGGT   1560
AACCAATGGG GCTGCCAAGC TGATGAAGTA TTTTCAGAGT ACACCTTTGT GTAGCTGAAT   1620
AAATTGAGAT CTTGAATGGA CATATTAGCT CATTTTAGTA AAATGATAAG AGAGTGCCTC   1680
CCACTACAGT TTTTGTTTTT ATGCATCATT AAACAATGTG TTTTTGATTG TCCACTGTGT   1740
TCCATGAACT ATGCTATGTG TGGGAGATAT AGTAGTAAAG AAAAGCAAAG TACCTGCTTC   1800
CATAGAATTC AGTATAATGG GAATGGTAAT TCTTTAGAGA ATCACATAAC TATGGATACA   1860
TAGGCTTCAT TTTACTGTTC TCCTTTTGTG TTTGAAAATG TCAACAATCA AAATTTTGTA   1920
AAAAAGGAAT CATGCAACAT ATTTAAAATT ATAACTGTGT TAAGTGTAAT GAAGGGAAAT   1980
TGCACTGAGT AGTAAGAATA TATAATGGTG TGTGGTATTT CCCAAGTTAA AAAGGTCAGA   2040
TAAGGCTTCC TTGTGGAAGT GATAGTTCAA ATCTGAAAGA AGAATAGGAA TTAATTAGGT   2100
AAAAATGTTT GATGCAAATT TTAAGATTTT CCTTCTGAGT AGTCAGTAGC TTTTCCTTCT   2160
TAACATAGAA GATGACAAAA CCATCCTTTT TTTGTACATA ACAATTCTTG TTTTCCTTTA   2220
GACAGTTGTA TCTGTCAAGC TTCTTATGAT CTAATTTAAA TAATTGGGAT AGAACACAGC   2280
TGTACATGTT ACTATTAAAT ATGGAATATA TCAAACATAA GTTGATTCCT ACCAGTTCTG   2340
ATTTTATTTG TGTATTTTGT TAAAGGTACT GAGGACATTA ATATCCAGTT TTATATTGTG   2400
CATTTGAAGG TTCATCAATA AATACAATTC TTGTTTCTCT GGGTCTTAAA AGATATTTTA   2460
AATGGTTATC TCATTAAGAT TTAACAGGAA ATAACAGTGA TTCAAATCAA ATAGTGGTGC   2520
CAGAAACCCA TACTTGAATT TTGGGTATAG ACAGGTTACC CTTTGCATCA ATCCTGAGGA   2580
AACTAAAACT ATAGGATTAA TCAGGATAAA AAAGAATTGA GCAAGGATTC AGGAGGGATC   2640
TGTATCATCC TGGTGACAAC CCTCTTCTAG AAAAAACTAG AAAGTCTAAG AATAAATGAA   2700
GTTGCTGGTT CTCACCTGGA AAGGTCAGTT ACTCACAAAA TTTTTAGAGT CTATCTTATG   2760
CCATAATTCT ACTACTGAGA GAAGAAACTT GTCCAGTCAT CATGTAACTC TCATGTAAAT   2820
TTATGTTTTT AATTGCAGAA TTCATACCAC AGGCAAAGTC CCAATGTCTG CATTTGCTGT   2880
TACCTTAAAT AGTCAAACCC CAAAGTTATT GTAATCTTTT TTTAACAGAG AATAATTTGC   2940
AGAGTAATCT CGGTCCGGTA GATCTTTCAG TGGATCCCAA ATGATTGCCA TGAATGGTTT   3000
AGAATTTTTT TAATTTTCAA GTTGTTTTTA TTCTGTGGAA TACTGGCTTA TTTTTGTAGT   3060
CCCAAAAGAA AAATAAATAT TTATTTATTT GCCGTTAAGA GTTGTAGTTT TGTTTTCTCA   3120
AATTTGTCCT GACACTGACG AGATTAGTTA AATGTAGGTC ATCTGAACCA AATACAAGGA   3180
AGGAAGGACC CAGTTCTGAA GAGTGTGGGC ATTTCTTTTC TTGTTTTTTT TTTTTTTTTT   3240
TTTTTTTTTT CTATAGGAGG GGAACGAGGT GAACTAAACA AACAAAATAA AGCAAAAAAG   3300
AACTGATTTT TATCCCTTGA GGTAGAAAGA ATGAGATTAC AGTGGACCCC CTTGTCTGCA   3360
TTTTCACTTT CTATGTTTTA GTTACTCACA ACCACGTCCA AAATGTTAAA TAGAAAATTC   3420
CAGAAATAAA CAATTTATAA ATTTTAAATC AGTGGTGGCT TTGAGTACTG TAATGAAATT   3480
TTGTGCCATC CCACTCAGTC GGCCTCGACT TCCCTTAGAA TCATCCCTTT GTCCGGTGCA   3540
TTCACGTTGT ATTTACTCCC TGTCTGTTAG TCACTTGTTG CAGTATCACA GTGCTTGTGT   3600
TCAAGTAACG CTTATTTTAC TTAAGAATGA CCCCAAAGCA CAAGAGTACT GTGCCTAATT   3660
TATAAATTAA ACTTTTTCAT AGGTATATAC ATATAGGAAA AAACATAATA CATACAGGAT   3720
TTGGTTGGTA CTATTCTGCG GCTTCAGGCA TCCACTGGAC GTCTTGGAAT GTATCCCTTG   3780
TGGATAAGGA GGAACTGTAT ATGGTTAACC TAGGAGCTAG AGTCAACAGT TGGAAGAGAC   3840
TTTGGGGATA ATTACATGGA AGGGCATGGT GGGTGGTCGT TTCAGATGAC AAGAATGTTT   3900
TTGAATAACG GATCATTTGT GTCTTCAGAC TTTCCAGAAC TCCTTGAAA TTATGCAGAG    3960
GTATTTAATC AGTCAGAAGG TTGAATAGTC AAATTATTAG TGAGTGAAGT CTATTTTGAT   4020
GAGGATTTTA CTAATGCTGT CCCTTAGATG TTATAAGTAA ATCGTTGTTT TCTTTTGAAA   4080
TATCTGAAAC CTAGTTAACA TGGACTTTCA TTTGTTCTTG TAAAGATATG CAAAGCTATT   4140
TGGGAGATTG TCATCATCTG ATATTTGATA TTCATGGGCT TTCTTCACAG AAGACTAGAA   4200
```

*Fig. 5A*

```
ATTAACAGAG TCATGATGAA TTATGGCTGC ATTGACTTTA AAAAACAAAC ACCTCCTTAA 4260
TGTTATTTAA CAATTTTGAA TAAATTTGAT ATGGCAAACA AATCAGTTAT AATCGATTGA 4320
GAAAGGAACT TAATTCTAAT ACTTGACTGG TGTCCCATAA TAACCCATAA TACTAAGAGA 4380
CAGTTTTGGA GGGCGAGAAG TCCTGAAGAG CTGATAGAGA TAAAGGTTCA AATTTGAGCT 4440
TCTTTCAGTG TTCCTTACGT CAATGCTTTT AGTTTCTCAT ACAAAATAAA ATAAAGAATA 4500
ACCTTTTTAC TGGGAAAAGG TAAAAATTAA TAAATTGTAG AAGCATTGTT TGAAGCCAAA 4560
AAGTGTGTGA CATGTAAATT GAAATGAAAA ACCTTAGAGT TTTTGATACT TTTTCAAAGC 4620
AGCTAAAGAA TTGATACTTG GACACAGGAA GAATTTTTTT TCAAAAGCAA TTTTTATAAA 4680
ATCAGAAAAA TGTTTACCTC TTGTTGGGGG CATTGACTGG AAAGGAATAC AACAGAACTT 4740
TCTGAGATGC TAGAAATGTT TTTTTATCTT GATGGGGTGT GGGTTTTGTA GATAATGAAA 4800
AATAAACAGT AAAAAATAAG TAAAAAAAAA AGTAAGAAAG TTGCCAATAC AGTTTTACAT 4860
ATTCCTGTGA TGTTTTTAAT CGACAGGCAC CTTCTTACTG AGATACGTAA TGAGAAGTTT 4920
CGATTATACA AATTAAAGAT GATGGCAAAG ATGGAAAAAT ATCTTCATTC TAGCAGATGT 4980
AGGAGACAGT ATGTATTATT TATTTTATGC CAATAGTATG GATTTATGGA TGATGCTCTT 5040
TTAAGACAAC AATTTGGCTA AATAATTATC AGTATTTTGA AAAAATATTT TGTTGCTGTT 5100
ACATGTGTGC TGAATTTTTA AGGCTAACTT CTTTGTGTCT GAGTAAACTG AAGTCAAATA 5160
ATGAAGTCCC AAGTGAATCA ATTAATGGTG ATTTTACCTC ATTATTTTCA GGAATGAACT 5220
TAACATATAC GTTTCTGTTC TTTTATTTAA TTTAAAATTT TGTCTTGGGT AGAATCATCT 5280
TGTCTCATTT TGAGGACAAA CAAGTACAAA AAGCCTCCTT GGGAATTATG GGAACTGAAA 5340
AATGCTGTGA TAATTGCAGG TCCAGGTAAA GATTTCTTAT TATAGATGGA CATTCTAAAA 5400
GTCTTTCTTT CTCTTCCTTT TCATGTTTAA CTGAATTTTT GTTGAATGAT AAGTATTTCA 5460
GTTTTTTAAA CAAAACAATG AATGTGTTTA GATATGAGAA AGCAAACAAT ATTAAAGTAT 5520
TTTGCTTAAA AAATAGATAA AGCAATAAAA TGGTAGCCCT AAATCTAAAC ATATCAATAG 5580
TTATGTTAAA TGTAAATGAT CTAAAATATT ATTTAAAGGC GTAAATTGTA AGAATTGGTT 5640
TAAAAACATG ACCCTGTTCT GTACGTTGTC CACAAGAAAT CCACTGTAAT TATATAGATA 5700
GGTTTAAAAA AGAATGAAAC ATTACATTCC ATGAAAACAT TAATCAAAAG GAAGTTGGAG 5760
TTACTTTAAT ATCAGACAAT GGACACTTTG GAGCAAAGAA TATTATCAGG ATAAAGAAGG 5820
ATATTATATG ATGTAAAAGA ATCATTTCAC CAATGTATCA GTCAGGGTTC ACCAGAGAAA 5880
TAGGACGATT GATATTATGG AGATATATAT ATATATATAT ATATATATAT ATATATATAT 5940
ATATATATAT ATATATATAT ATGGGGAGGG AAAGGAAGAA CAAATATGGG GAGAGAGGGA 6000
TGAGGCGACT GATTTTGAAG AATTAGCTCA CGAAATTGTG GGGGTTGGCA AGTCTGAAAT 6060
TTGTAGAGCA GGTCAATAGG CTGGAAACTC AGGCAAGAGG TGATGTTGCA GTCTTGAGGC 6120
AGAATTTCTT CTCTAGCAAA CCTAGTTTTT GCCCTTTAGT CCTGCCACTG AGTGGATGAG 6180
GCCCACCCAC ATTATTGACA ATAATCTCCT TTACTTAAAG TCAACTGATT ATAAATGTTA 6240
ATCACGTCTA CAAAATATTT TACAGCAACA TCTAGATTAG TGTTTGACCA AACAACTGAG 6300
CATCATAGGC TAGCCAAGTT GATGCATAAT ATTAATCATC ACAACCAAGA AGACATCATC 6360
CTAAATATAT ATATATATCT ACTTAACAAA AAGACTGACA GAACTGAAAG GAGAAATAGA 6420
GAAATCTACA GTTACATTTG GTGACTTCCA GCATCTCTCA ATAATCAATA AAACTGACAG 6480
ACCAAAAAAT CAGTAAGAAG ACAGAAGAAA TGAACAGGAT TATCAGCATG CTGGATCTCA 6540
TTGACCTTTT TAGAACATTC TACCCAACAA CAGTAGAGTA CACATTCAAG TGCAGATGCA 6600
GTATTCATGA ACATGGATTA TATTCAGAGT CATAAAACAA ACCTTAACAA ATTTAAGAAT 6660
CTTGTATTTG TATATTTTTT GACTAGAATG GAATTAAACT AGAAAACAAT AACAGAAAGA 6720
TAACAGAAAA GTCTCTAAAC CTTAGAAATT AAATAACACA CTTATAAATA AATCCATGAG 6780
TCAAAGAGGA AGTCTCAAGG CAAATCAGAA AATGTTTTGA ACTGAATGAA ATGAAAATAC 6840
AAAATGTGTG AGATGCAGCT AATGCAATAC TGAGAAGGAA ATTTATAGCA TTAAATACCT 6900
ATGTAATAAA AGAAGAAAGG TCTCAAATCA GTACCTAAGC TTACATCTTA AGCAACAAGC 6960
AAATAAGAGC AAAATAAATC AAAATGAAGT AAACATAAGG AAATAACAAA GAACATAAGT 7020
CAATGAATAG AAAAGCTATG GTCATACCAC TGCTGTCCAG CCTGGGTGAC AGAGTGAGAC 7080
CCTATGTCAA AAAAAATTAA AAACAAAGCA GCATGCAGCA TTCATTGTCA GTGAATAGAA 7140
AATGGGAAAA CAATAGAGAA AATCAACTCA AAAGCTCATT CTGTATAAAG ATCAACAAAA 7200
TTGATATAAA CTTCTAACAA GACTGACGGN AAAGANGAAA AGACACAGAA GACCAATACC 7260
AGGAATGAAA GAGGGAATTT CACTACAGAC CTCCCAGGTA TTACTAGGGA TGATAAGGGA 7320
ACACTATGAA CAACTCAGAA CATAACTTTA ATAATTTAGA TGAAATGGAT CAATTTCTTG 7380
ATAATCTCAA GCTAATTAAA CTTACAGTGA ATTAGATAAC CTGCATAGTG TTACAACCAT 7440
TAGAGGGATT GAATTCTATG TTAAAAATCT CTGAAAATAA AATCCCCTAG CCCAAAGAAT 7500
TTCAATGACA AATTCTACCA AACATTTAGA AGACAAAATA ATACCAATTC TATAGCATGA 7560
TTCCATTTAT ATAATAGTCT TTGAAACATA AAACTATACT AGAGGGATGA AGAAAAGATC 7620
AGTGGTTATT AGAGATTGGG GGAGGGAGAA GGTATGATTC CAAAGGATAG TACAAGGCAG 7680
TATTTTGGAG TGATAGATTT ATCGTGCCCT GATTGTGATG GGAGTTAGAT GAATCTATGG 7740
ATATCTTAAA ATGTGTAGAA CTTTACACAT ACATACAACC AATTTGCCTA TGTTAATTGA 7800
AAAAATAAAA TAAAAACAAA TTATTTACCT GGTGGGTTAG CTACGTACCT AAGTTCAATA 7860
GCTGCGTTAC TGTAAGACAA AAGAAGCATT ATTAGGGATG GAGTTGTTNC TCTGTGTAAT 7920
GACAAATACT TCCTTCACTA AGAAGACAGA ATTGTTTTAT GCACCTTTAA AAAAAAACAA 7980
AAACAAAAAA AATACAACCA ACAAACAGTA ACTTGCTGGT GCGGTGGCTC ACACTTGTAG 8040
TATTAGCACT TTGGGAGGCT GAGGTGGGAG GATCAGTTGA GACCAGGATT TTTAAGACCA 8100
GTCTGGGCAA AAAACCGAGA CTGTGTCTCT ACAAAAATAA AAAATAAATA AAAAAAATTA 8160
GCTAGGCATA GCATTATGTG CCTCTAGTCC CAGCTACTCT GGAGGCTAAG GTGGAAAGAT 8220
CGCTTGAGCC TGGAAGGTTG AGACTGCAGT TGCAGTGAGC CATGATGGCA CCACTACACT 8280
CCAGGCTGGG CATCAGAGTA AGACTCTGTC TCACATAAAA AAAATAATAA TAATGATAAA 8340
AACTAGTCTG GGCATGGTGG CTCACACCTG TAGTCCCAGT CCTTTGGAAG GCCGAGGCAA 8400
```

*Fig. 5B*

```
GAGAATTGCT TGAACCCAAG ACTTTGAGAA CAGCCTGGGC AACATAGCAA GACCCCATCT  8460
CTATTTAAAA AAAAAAACAA ACTTAAAAAT CCAGCAAATA CATAAAGCAC AAAGCCGACA  8520
GAAGAGGTGG AGAAATCAAC AAATCCACCA TCAAAGTGGG AGAATTTGAT ATAATTTTAA  8580
GTTATTGGTA GGGTAAACAA TCCAAAAATT AGTACACTGT AGAAAATTTG GTCAACATAG  8640
TAATAAGTTT GCTTATTACT ATTTATCAGT ATACATAGTA TACTGATTTA TCAGATACAT  8700
AGTATATGGA GCCCTAGAGC AAGCAACTAT AGCAGTGTAT CTCAAGTATT TTTACTTCAT  8760
GACCCACATA GCAAATGATA TGTGTATATA ACACACTGGG CTAATTGTCA GAGTTCAGTT  8820
TCTGTCCAAA ACCCTAAGAT CTGGAGTGAT TAACCTTTCA GCACTCTTAG AACTCACTTG  8880
TTTGTAGCAC ACTGATTGAG AAGCACTGAA AGACTTCACT CCTCAAACAT ACATGGAATA  8940
TTTCTAAAAA CTATGTATTG GGCCGGGTGC AGTGGCTCAT GCCTGTAATC CCAGCACTTT  9000
GGGAGGCCGA GGCGGGTGGA TCCCGAGGTC AGGAGATCGA GACCATCCTG GCTAACATGA  9060
TGAAACGCCG TCTCTACTAA AAATACAAAA AATTAGCCGG ATGTGGTGGC GAGTGCCTGT  9120
AGTCCCAGCT ACTCGGGAGG CTGAGGCAGG AGAATGGTGT GAACCCAGGA GGCGGAGTTG  9180
CAGTGAGCCG AGATCGTGCC ACTGCACTCC AGCCTGGGCA ACAGAGCGAG ACTCTGTCTC  9240
AAAAAAAACC AACCAACTGA ACAAACAAAA AAACTAAAAA ACAAAAACAA AAAAACTATG  9300
TATTAGAGCA TGGGTTGGCA AACTATGGCC TGTAGGCAAA TCTGCATGCT GTTTTATTTT  9360
TTTTATTTTT TTGACATAGG GTCACTACAG GCTGTCACAC AGGCTGGAGA GCAGTGGTAT  9420
GATCATAGCT CACTGTAACC TCAAATTCCT GGGCTCAAGC AATTCTCTTG CCTCACCTCA  9480
GCTTCCCAAG TAGCTACAGG CATGCACTAC CAGACCCAGT TAATTAAAAC AAATTTTTTT  9540
TTGGTAGAGA CAGTCTCAGT ATGTTGCCCA GGCTGGTTTT CAAACTCCTT GCCTCAATCA  9600
GTCCTCCTAC TTCAGCCTCC TAAAGTGCTG GGATTATAGG CCTGAGCCAT CACGCTTGAC  9660
TAATGTTTTT GTAAATAAAG TTTTCTCAGA ACACAGCCAT GCCTTTTGTT TATGTGTTAT  9720
GTAGGGCTGC CTGAGTTAAG TAGTTGGCTA CAAAGCCTAT CATGGCCTAT AAAGCCTGAA  9780
ATACTTACTA TCTGGTCCTT TATAGAAAGT GTTTTCTGAC CCTGTACTAG ACTAGCTTGT  9840
CTCAAAATTC TTCAATGAAT TTGGAAGTTT TCTCACCACA TTTTCTGACC ATAATGCACT  9900
TGAGTTAGAA GTAAATAAGC AGATAAACAA CAAAATCCTC ATGCATTTGG AAATTAAAAA  9960
TAACACTTAA ATAATTCATA TTCAAAGAAA AAATCAAACT GGAAATTAAA AAAAATTTTA 10020
AACCTACAGA TAACTACATT AATATGCATT AACATTTTTA GAACTTAGGG ATAGTTACAA 10080
TGATATACAT TAAAACTGGT AAGAGGCTGG GTGCGTTGGC TCACGCCTGT AATCCCAGCA 10140
CTTTGGGAGG CCGAGGCTGG GGGATCACGA GGTCAAGAGA TTGAAACCAT CCTGGCCAAC 10200
ATGGTGAAAT CCCGTCTCTA CTAAAAATAC AAAAATCAGC TGGGCGTGGT GGCACGCGCC 10260
TGTAGTCCCA GCTACTTGGG AGGCTGAGGC AGGAGAATCG CTTGAACCTG GGAGGCGGAG 10320
GTTGCCGTGA GCCGAGATTG GCCACTGCA CTCCAGCCTG GCGACAGAGC GACACTCTTG 10380
TCTCAAAAAA AAAACAAAAA AAAAAACAAA AAAAAAAACT AGTAAGAGGT CCCAGTGGCT 10440
CACACCTGTC ATTCTAGCTC TTTGGGAGAC TGAGGAGAGA GGATCAGTTG AGGCCAGGAT 10500
TCAAGACCAG TCTGGGCAAC ATAACGAGAC CGCATCTCTA CAAAATTTTA ATAACAACAA 10560
CAAAAAAACT GGTAAGAGGC AACATTGAAT AGTACTTTGT GGGAGTTTAT TAGCTTGAAA 10620
TACTCATAAT AGAAAAGAAA ATTAATCAGC TAAGCATCTC ACTAAAGAGA TTAGGAGAAT 10680
AAACCTAAGC ATAGTTTTTT TCCCCCAAAC ATTATTATAT CTGGAATATT GAATGCATTC 10740
TTATTGCTAT TTCAAAGATA CTTACTCTAA GGAAAGCAAT TGAATTAGGT AGTTGAACTC 10800
TATAGTAGAT TTTCTTTAAT GAGTCCTTTT GTTCTCAACC TACTTAAATA ATTCTCATTT 10860
GAATTTATGA TAGTTTCAGA TCTACCCAAA GGGTGACTTA GGAATTTAAC TTCTAAATCT 10920
ATTTAAATGA AAGGTTTATA ATCTTTGTGT CATATTTTAC AGTCGTTAGC GTTTAACAAT 10980
TTATAGCATA GGATTTGGGT TTTTTTTTTT TTCATTTTAA AGAAGAAGTT TATTTAAGCA 11040
AGACACTTGA CTAAGGGAAG ACTATCTTGG AGTTATTATT ACTAGAGTAA TTTATTTCTA 11100
CTTAAAGACA GATTGCCCCA CAAGTAACAG CTACATAAAA AACAGTTGTA AAATTGTCCT 11160
TGGTTTTACA ATGATAAATG AAAAAACATTA AAATTCTCTA ATTGAACAAG GTATGCAAGG 11220
ATTTTTATAT TGTTTTTTGC TAAAACTATG ACAGCAAAAT AACATCCTGG AGTATAAAGA 11280
TAAGAGCTGA ATGAGCAGGC CACTAGGGGA CAAAGGGAGT CTTTTCACAG AACCAATGCT 11340
TCTTTTGCCC ACCCCATCTC CATCGAAGTC AATCTAAACA TATTATTGGC CATTTAGTTA 11400
AAAAAAGAAA GAAAAGNAAA AGCAATATGC TTGTGGACAT ACACCAGTTA CTTTATGTGC 11460
AATAAAAGAG TAGGAAGGGG AAGGTGAAAG AATAGAGAAA ACTATGTAGT CAGGATGTGG 11520
TGGAACCAAA TTGCAACTTT CTTTTTTTTTT TTTTTTTTTT TTTTTGAGAC AGAGTTTTGC 11580
TCTTGTCACC CAGGCTGGAG TGTAGTGGTG GCCCAATCTT GGCTCACTGC AACCTCCGCC 11640
TCTCAGATTC AAGCCATTCT CCTGCCTCAG CCTTCTGAGT AGCTGGGATT ACAGGTGCAT 11700
GCCACCATGC CTGGCTAATT TTTGTATTTT TAGTAGAGAT GGGTTTTCAC CATGTTGGCC 11760
AGGCTGGTCT TGAATGCCTG ACTTCAAGTG ATCCACCCGC CTCAGCCTCC CAAAGTGCTG 11820
GGATTACAGG CGTGAGCACT GCGCCTGGCC AAATTGTAGC TTTCTAATTG AGACTGTCTT 11880
CTTGGTCTGG AAGAGCAGAG TTCTGCAGTA AAATAACAGG TCCCCCTTTT AGTAGACATC 11940
TCCATGTCTG CTGCTGGAAC ACATCAGTTT TGTCTTAAGC CTCACTTCCA AATGTGCAGA 12000
TGTGTCTGGT TCATTGATTG GCTGCCTGTC AAATTGAAAC CTGATCTGCC TCATTGGCAA 12060
ACCGTGCCCC TTACAATAGG CTTTCATTGG TTTACTAAGC GGTGTGGTGC GTGGCTGTTC 12120
ATCTTAAACT GCACCACAGT TTAAGATGAA CCTTCAAATG AACATTATCC TTGTTCTCAG 12180
TCTTGACTTT CCTTGGGCTT TTTGTGGACC CTGGTGAGTG TGGCAGTCTC CTCAGCTGCT 12240
GCTTCACAAA AGAGGTACCA GGTCTGCCCC GAATAGGTGA GCCCTAAAC AGGACCAGGA 12300
GTGGCAGAAG AAAGAGGCAG CAACTGAGAT GTGTTTTTTC TAAGCTGAAA GGCTTTTTTT 12360
TTTTTTTTTT GCAACACACC TTTAACACTA AAGTCCAATA TTTATATAAT TNGGTCAAGT 12420
AAGTGGAGCT GTTCTAGCTA TAAATATGGC AACTCTGCTT GCTCGTCCTA TTATTGACAT 12480
TATTCCTTTC TGTGGTCTGA GGTGCCTCCC ATGAAACTTG CTTCTAGGAC ACTAGGATTG 12540
AGAACCATNC AGCGTAACAT ATCTGTTACG CTACAATAGT TTATTTTCAT ATTTTAGCTA 12600
```

*Fig. 5C*

```
CTTTACATAC TCGGGTATAA TGAACTTTAT TCATAGCTTC TGAAGCAGTT GGCACATTTG 12660
AGATATTTTT TACTTGGCTA ATTGTTATGC TAAATCTTTT GATTTCTAAA GATACATGCC 12720
TTTGCTAAGC TTTCTTCAAA TGTTATTATT TTTATTTAGA TTGGATCATT GCTATTCCAT 12780
GGATGACTCA GAGGATACAT CCTGGGACTT TGGTCCACAA GCATTTAAGC TTTTGTCTGC 12840
TGTGGACATC TTAGGCGAAA AATTTGGAAT TGGGCTTCCA ATTTTATTTC TCCGAGGATC 12900
TGTAAGTATA TATCTGTGAA TTCCCTTCAT AGATCTTCTT TTACTTCTAT TACACTTTTC 12960
TTCAGAGGTT TGCAGTATTA TGATTGTAAC TTTGACTTCA GATGGGTGAC TAGGAACTCA 13020
TAGAGTCTTA CTAAGTTCCA GTTAAACACT ACATTCATTA CTTTGGATAA AACCCGTGTG 13080
TATGGCATCT TCTGCTGTTT TCATGTTCAA GCCGATGTTC AGCTCTGCAG CTCAGTCTGG 13140
AAGCATTGTG TTAATTTATC ACATTGCATT TGGGTGAATC CCTAGACTAG TCTTGCTTAG 13200
GATAATTAGG AAAAGTTAAC TTTCATTGTA TCAAGGGACA GGTAGAACAA AATTGTCCTT 13260
TTGTCCAGGA AACTATTAAA TTCTTCAAGG AAAACTTTAG TTATAGGGAT TATTTTTTAA 13320
ATGTCTAATT TCAGTAACAA TATTTGGGAC ATATTTATTT TTCCTTCTGT TTCCTATCAG 13380
AAGTATTTAA AGTTATAAGA AAATTGTGGT TTTTGCCTTT ACTAATGAAT AAATAATCAA 13440
TTAAATTCAG TTACTTTTTT TTGGAGTGAT TGATGTTCCA GTATTCTTCT AAACAACCAC 13500
GGGTACAAAT GTGAATAAGA TAGGACCGTT GCAGTCCAAG AGCTTGTTCT GTAGTCCTTT 13560
CCTTTATATG ATTTTTTCCC CTGATTTAGA AGTCTATAAA GCAAAGCTAA GTATTACACA 13620
CTGATAATGG CTGAATAAAT CAAGAGCAAG AGATAGGATA CTTTGCAAAT ATGCATATTT 13680
ATTAAAAATG TACTTTAAAA TAGAGATTAA AATTCTCGTA TTGAATGTAG AATAGGTAAG 13740
CATTTATTTG TGAAATACTC GAATGCTTCA TGTAAATACT TTCTGAGTTT GTATTTTTAG 13800
AAAGGAACAT TTTGGAGGCT GAGGCAGGAG AATGGCGTGA ACGTGGGAGG CGGAGCTTGC 13860
AGTGAGCTGA GATTGTGCCA CTGCACTCCA GCCTGCGCGA CAGAGCAAGA TTCTGTCTCA 13920
ATAAAAAAAA AAAAAGAAAC ATATTTATTA AATTAGTTGT GAAATATTTT TAATGAAATA 13980
TATTGAAAAC TTCTGTTGAT TTTTCATGTA CTGATGTTTT TAGATTCTAA ATGGAGTTTA 14040
AAATTTTGTT TGTAAATCAC AAGTTGGATT AGAAATTTAA TAGTAGAAGT GTTGCCTAAG 14100
GACTATTTTA GGTGCTGTGA GTGAAACTGT ATTTTTTATA ACAAGAATTT TAGTTGTAAG 14160
GGACAGCTTA AATATAATTG AGATCTGTGA AAATGTATTC TGTCTCTATC ACCTTCAGAA 14220
CCTGTGTATC TCAGTTGAAT GTATAATTTA TAAAAATTAT TCTTGTTTTA ATTTGGTGTA 14280
ATCCAGCCAT ATCCAGTATC AACAAATAAG TCTAAGTAGG CTCCTTGACA AACTTGAACT 14340
GGCCACAAGA GAGATCAGAT TTCACCTATT AAAAAACCAA ATCAGACCAC TTACACTGAC 14400
AGTCTCTTCT GGGAGTCCTC AAATTAAGAA GTCTATCCTT TGTGAAATAT TACACTACCC 14460
TTGCTAGATA AAACTTTTCT AAAAGTACCA CTTAATGAAA ATCTGTAGAC ACTAAATGCA 14520
ATGAAAATAA GGCATTGTTT TTTTTTCTCC CCATTTCAGT GATCTTGGTA TCCTGGGATA 14580
TTGTTTTTAA AATTATCGTT ATAATTCCTT TGAGAATTTA GTGAAACGTT CCCTTTAACC 14640
AACTTAGGAA AAATTAATAT CTTTGTACAT GATTTTGAGC TGTAAAATAA ACATTTTAAA 14700
CTGGGAATAA TTGGAGTTTA GTTAAAGAGA TAATGTATAT AAATATATAA CATAGTAGCA 14760
GCATATAATT CTGTCTTACA CAAGATTTTT CTGAATAGTA TAAACAGTTA TGTAGCCTAT 14820
CTAGGAGTTT GTGAATAGAG TTTAAAATTT TGTTTTGAAG CTGCAAATTT GATTAGAAAT 14880
TAAACAGTAA AGTTATTACT TAAGGAACTT CGTTTTAGCT GTCTGAACAA CTTACTGTAT 14940
AAAAATCTTT AAACATTCTG TATAAATATG TGATAAGATA TGCAATGACC TTAATTTTAT 15000
AGATTAGAAA ATAAAAACAC ACTCATTAAT TTACATAACT GACAGATTAA GTGAAACTTC 15060
TCTTCTGATC ACGTTAGCAG AATGCCAAAT CTTGTCGTGG CACTAGAATT AGACGGTAGT 15120
TTTGATAATA CATGATTTGA CTATAGACAT TTGTTGAAAC TATTGGTAGT TTAATCACT 15180
CTTGTAATTT TCAAACTATC TAACGGGAGA GGATTATCCA TCCTGTTTTC TAGACAAACT 15240
GTTTCATCTG AATGAAATAT ATTCCTAGAG ATAATTATCA CTACTTCATC TTTTGGTTTT 15300
ATTTTGCACA TAGAATTATA GTTCACAATG ACTTTCTGAA GCTCTAAAGT TGCAGCTGTG 15360
AGCTTCTTTG GCCTGTAGGG ACTGGGAAAA AGCACCCCCG TCCTCCCCCA AGCCCCCCCA 15420
CCAAAAAAAG TTAAAGTGTT TTTAACAATA GCTGTGGGCT TTTTGTAGTT TCAGAACTTA 15480
GGAGTTGCCC AGGCTGGAAT GCAGTGGTGT GATCATAGCT TGATGCAGCC TTGAACTCCT 15540
GGGTTCAAGC AATCCTCCCA CCTCAGCCTC CAGAGTAGCT GGGACCACAG GTGCCACCCC 15600
ACCCAGCTAT TTTTTTTATT TTTTAATTTT TTGTAGGTA TGGGGTCTCC CCATGTTGCC 15660
CTGCCTGTCT CAAACTCCAG GGCTCTCAGG TGATACCCAC CACCCTTGGC CTCCCAAAGC 15720
ACCGAGAGTC ACTGTGCCAG GCTGAGTTTA AAATTTCTTG AGTTGGAGTT TATGGCTATT 15780
TTTTCCACTA GTTATTAAAC ATGTATTTTT GTATAAGGCA CTGTATTACA TTTTGTGGGG 15840
GGATTCAAAG CTAAATTAGA TGAGACGCAT CATCTATTAT GGAAGATGTT ACTTAAGAAG 15900
AAATGAGTGT AATGTAGCAG AGAATTGATT AAGGGACGTA TGAATACATA TAAATGCTGT 15960
TGAAGTTCTG AAGAGAGAGA GTGTTTAGAG AAATTAGGAG AGTCTTTGTG AAGTTATCAC 16020
TAGAACTTCC TATTTTTGTG GAATATATAG TAGATTTTGG TGTGATACTG TGGATTTGGA 16080
CATTCACTCA GAGAAGGAAT GAGGGAAGAA TGGTGGAGAA GAATGGCATT CACAGTACAA 16140
AAAGCAACTG TGACTTTTAA AGAAGTTAAT ATGGAGAAGT GGCAAGTCTT TCTTCTCTC 16200
TTCTCTTCTC TTCTCTTCTC TCTTCTTTTT CTTTTTTCTT TTTTCTCTG TCAGATACTG 16260
TTGTAAAGAC TTTGCTTTTA CCGGAAACTG ATACGTTGGG TCATGTACCC TGGCCAGTCA 16320
GTTCTCTTTA TTCTAACACT TAGCCGATCA ATTAGATTTC CACATTCCAT GATATGTCAG 16380
TTTTGGTGAC CCTTATTTTT CCACCTGGTT TATAAAGGGA AAGAATGTGA TATGTCACCC 16440
AGGCTCTGGA GTACAGTGGC ATGATCATAG GTCACAGCAG CCTCAAAGTT TCCAGTTCAA 16500
GCGATCCTAC CTCCTTGGCT TCCTGAGTAT GTGGCACTAC AGGTGCATGC CACCATGCCC 16560
AGCTAACTTT TTTGTAGAGA CAGGGTCTCC CTATGTTTCC CAGGCTGGTC TTGAACCCCT 16620
GACCTCAAGT GATCCGCCCA CCTTGGCTTC CCAAGATATT GGCATTACAG GCATGAGCCA 16680
CTGTGCCGGC CTGAAAATTT CTCTTTTGAG ATGGCATCCC ACAGAAGTAT ACCTGCTTAG 16740
AGCTAACACT GGTAAAAAGA CTATTTAACC CTATTGCCTT ATTTTACTGT AGTTGAGATT 16800
```

*Fig. 5D*

```
GAGTTAAACT GAAAGCTGAA TGACCTGTCC TAGGTCATAC TGTTACTTTG TGCCAGAGTC  16860
AGGATGAGCA AATGGATTTC CTGCCTGCTA GTCTAGTGTC TTTTCTATTT ATTGTGCTGT  16920
AACATACAGT TTTAAATTTG TATTTTTATG CCCAATGGAC ATGGTAGCTC ACACCTGTAA  16980
TTTCAGCACT TTTGGGAAGC CGAGGTGGGG GGATTGCTCG AGACCAGGAG TTCAAGATGA  17040
GCCTGGGCAA CATAGCGAGA CTCCGTCTCT ATAAAAAAAA ATTTAAAAAT TAGCTGAGTG  17100
GTGATGTGTG TGCGTGTAGT CCTCCTTGTG GGAGGTTGAG GTGGGAGGAT CGATTGAATC  17160
TAGGAATTCA GGACTGCAGT GAGCCATGAT TACACCACTG CACTCCAGCC TGGGTGACAG  17220
AGCAATACCC TGTCTCGAAT GAATGAATGA ATGAATGAAT GAATGAATGA ATGCCCAAAT  17280
CCGTAAGCTA TGTTCTGTAT AGCAGCTTTT TCATCATAGG CAGTTTTTAC TCTTATCAGT  17340
GGACAACCTA CAAAATTAAC TAAACACTTA AGCAATTAAC AGAGGAGGCC TTGTTCAGAG  17400
TGAGAAATCA TTAAGCATTT GTTGTTGAAA TTTCTTACTG TACTCTGTTT TAATTCTGTT  17460
TTTTTTTTTT TTTAATGTTA CTTGTTTTAG TTTGGATTCC TAGTTGAAAA GGGAATATGA  17520
TTCCTTTAAA ACAAAGATAC TCTGCTTTAA AGCAAAGGTA TATCATCCTC TTCATGGTGA  17580
TTGCCATGGA AACAAGACAA TGTAAATTTA TTCAAATAGT ACACAGTTTT TATAGTTATT  17640
GATCATGAGG GGAAGGGACA GTTAATCCCT ACTGATCAGA TAAAACCTCA TTGTTTCATA  17700
CTAATAAATG GTTTTTTTAT GCTTATGAAA GGAAAAGCCA GAAGGGTAAT TTTAGTGTT   17760
TAGAGAGCTA GTGATTCTAG TTAGGGAACT TAATACCTTT GAAGTTATTA GTTTGCAAGC  17820
AATAGAATCT ACTACTACCA AGGTGACCCC TAGCAGATGT AGAGTACCAT TAACAAGTGT  17880
TCCAGGGAAG GAAAGCCAAC TAGATACCAA GTCATGCTTT TTACTCTTAG ATTAAGAAAT  17940
TCAGGTTGAG TTAAAGGATC AGCTGTTAAC TAATAAAAAG CAGATTAATA TTACAGAGCC  18000
AGGCTCTGTC CTGGTTATGG ACTTAATCTT CACAGCATCC TCAAGAGATA AAAATGAATA  18060
TACCTGCATA TTAGATGAGG AAATAGAAGA TAAGTAACTT GCCAGAGCTA TGACGTGAAC  18120
TCAGGTAATG TAGCTTAAGA GCCCCCACAT GTATGTATAT TGGGTGTGTG TGTGGAGGGG  18180
GTGCGTGTGA GTGCTTGTGC ATGCGTGTGG TATAATAAGA AAAAATTAGC ATTTATGCCT  18240
GTAATCCCAG CACTTTGGGA GACCGAGGCA CGAGGATCTC TCAACCCCAG GAGTTCAAGA  18300
CCAGTCTAGG CAACATAGCG AGACCCTACC TCTACAAAAA AAGTTTTAAA AATATTAGCG  18360
GGCATGGTGG AATACACCTG TAGTCTCAGC TGCTTGGGAC GCTGAGGTGG GAGGATCCTT  18420
GAGTCCAGGA GATTGAGGCT ACAGTGAGCT ATGATGACAC CTCTGCACTC CAGCTTGGGT  18480
GACAAAGAGA GACCCTGTCT CCAAAAAAAA AAATTAGAAC TAGTTATCTG GAGGCCTGTG  18540
TTCTAGTCCT AGCTTTAGTA CGGCTACACA GTGACACATT AGGCTACCAT TTAACATCTT  18600
TGAACCTCTG ATAATTTGTT AACAATATGG GTAAAAATGA CTAAGATAAA TCAAAGAGCT  18660
CCAGCATTCC CTCCAGCTCT GAAATTCTAT GATGTTTTAT CTTATTTTAC TTACAAAAAT  18720
AAATTATATT ATGTATATTT AAAGTATACA ATTTGATGTT ATGGGTTACC TATAGTAAAA  18780
TGATTACTAT AATGAAACTA ATTAACATAT CCATCATCTT ATATTGTTAA CCATTTTTTT  18840
GTTTTTGTGG CAAAAGCAGC TGAAATCCAC TCATTTAGCA GGAATCCCAA ATACAGTTCA  18900
GTTGTATTAA TTGTAATTCT CATGTTGTAC ATTCGATCTC TAGACTTGTT TATGCTACAT  18960
ATGTTTGACT TTTAAACATT CTACTCAAAT CAACCCTAAG TCAGGGTTAG CACAGACAGG  19020
ACTTGTTAAC AAGGTAGAAG GTGCCACATT GTACCTGGGT GTTTATATTT CTCTAAATCT  19080
TGTTCTGATC ATATTTTAAT AAATATAATC ATCAGGACAC CAAAATTCAT TCCTTAGCTA  19140
TTAAAAAATT CTATTCTATT TTATTGTTAA GATTTAGGAG AGCATGGTAC AGATTCTCTT  19200
AACTATACCT ATCAGAAGCC TATGTTTTAA GTCCAATGTA TAGGCACTGC TCTGTTTGTC  19260
TCTGGTGGGA ACTTACCCTG CTTTACCTAA TTTCATCCTA GCTTCCTTTT TGTGAAAGAT  19320
CACCCTTGCT TAGCCTATTT TTTGGCAAAT CTACACCTTG GAAATAGTAG TAAATGACAT  19380
AAGCATATTA ATATTTATGA TGTGATTTAT TTTTGTTTTC AAGTCATATA CTGGGGAAGA  19440
TTCTCAAATA TTAAAACAAT GTATCTTTAC ATTTATGTAT GTCGTTCTTG TTCTGTTTTA  19500
GAAGGCTTGT ATTTGCATTT TTAACATTCC AAAAGGTAAA CCTGTAATCA TAATGTTTTC  19560
ATCAATTCAA TAAAACCATT ACGTTTGTAA TAGAGAGCCC TATAGTTGCC TTAGTTAAGT  19620
TTGCTGCAAC TCATTTTATA TATTCTTTTA ATTTTGATCC CTGGATTTTT AATTGATTAT  19680
TAAACCTTCA TTAGGATATA TATGAAATGT AAAAATATTG AGTTATAATC TACCGTTTTC  19740
TAAAATTTTA TACTGCATTT TTATATAGAA ATTCAAATTG CTCATAATCA TTCTAGTGAA  19800
TTTAAGTAGA AAGGTATTTA TTACTAGGTA TTAAATGGCT TATAATATTG TTGACAAGGT  19860
TCCACTGCAA AATAGTTCAC CAAGGGAGCT GTGGCCTCTT CTGTGATCAA GAAGCCATCT  19920
GTCAACTTGG GAAGCTTCCA CTATAGCACC TAACCCCAGA CTACATTGAG TAGGAAGCTG  19980
TAATAATCAG GAAGCTTCTA CCTTTGCATG CTCTGCAAAC CAACGTGAAC CTGCTGTAAT  20040
TTGTAACCAC AAAATGGATG CCTGTTGATA CTTACGAAGC TCATCATTGT ATGCTGGGTT  20100
CTTTGCTAAT ACTTTCTTAT AAAAATTAAA TACCTCCACA ATCATGCATG CTAGCAGAAA  20160
CAGCAGAGGA GTAGCCTTAG CCTCACTTCC TGCTTATACC TGTCATGCAG ATATACAGAA  20220
CCCAGAACCC TAGCTGAAAG GGAGTTTGAG AACTAGTATT TGTATTGTCC CAGATTCTGC  20280
AGTGGAAGAA TTCATAGTGG ATGGAAGTTA GAATGACCCT TGAATTACAA TCGGCCACAT  20340
TCATCACAAA TACATTAAAT AAGAGTAATT TGCCATAAAG CTCTATGTTT GTATACTTCT  20400
TTGTTTTTTT TTTTTTTTTT TTTTTTTTTT GAGACAGGGT CTCACTCTGT TGCTCAGTCT  20460
GTAGTGCAGT GGTGTCATCA TAGCTCACTG CAGTCTTGAT CTCCTGAGCT CAAACGATTC  20520
TCCTGCCTCA GCTCCTGTT CAGCCTCCTG AGTAGCGGAA CAACAGGTAC ACACCACCAC  20580
ACTTTGCTAA TTTTTTATTT TTATTTTTTA GTAGAGATGT GGGTCTCACT GTGTTGCCCA  20640
GGATGGTCTC GAACTCCTGG GCTTAAGTGA TCCTCCCAAA GTGTTGGGAT TACAGGCATG  20700
AACCACTGTG CCTGGCCCAT ATACTACATA TATTTAAAAG TAGTATTTAA ATGTGTAGGA  20760
TGAATGAAAG AGGCAGTAAG AGAACAAAGT GAATGAAAAA GTATTCTAT ATGAAGTGAA  20820
AGCAGGAGAG TCCTCTCTGT TAGAGAACAA CAGAATTGCA TATGACAGAC TAGCTTCTT   20880
AATATTTCTA GAACTTGATG GCTGTGAAGA GCGTCCCGTA GGAATTCTCC CTTCACTTAG  20940
GAAAACATAC CTCAAAACCA TCAGCTGTTT AGCATGCACC TGCTTTTCCT GGTATATCTC  21000
```

*Fig. 5E*

```
AGTGAAGCAG CTAAATTGTA AATGATTAAG TAAACTTTGC AGTGTATCAT GTGCAAAAGC 21060
ACAGTAAAAA CAAAAATGCA TTGGAAGCTG TGAGTTGTTG CACTGCACTC ATGGATGAAT 21120
AGCTGTTGGT TCGCATTGCG TTTTTTTGTT TTGTTTTGTT TTGTTTTTTT GAGATGGAGT 21180
CTTGCTCTGT TGCCCAGGCT GGAGTGCAGT GGCGTGATCT CGGCTCACTG CAAGCTCTGC 21240
CTCCCAGATT CACGCCATCC TCCTGCCTCA GCCTCCCGAG CAGCTGGGAC CACAGGTGCC 21300
CGCCACAACA CCTGGCTAAT TTTTTGTATT TTTAGTAGAG ACGGGGTTTC ACCATGTTAG 21360
CCATGATGGT CTCAATCTCC TGACCTCGTG ATCTGCCTGC CTTGGCCTCC CAAAGTGCTA 21420
GGATTACAGG CATGCCGCAT TGCGTTTTAT ATAATTCTCA TGGTTCTAGT CTCGAGCTGT 21480
AGGATTTTGA TCACTGTTTC AAACAATAAT GTGAGTTTGC TAAGAGGTCT AAATAACAAA 21540
AGCTAAGTGT CCAAACACAT ATCCAAACCT ATACACTGGG CAATGCATCT GAATTATATG 21600
TGAAATTTCC TGCCATTATT TAAGACACAA AAGGAACATT ATTTTGATAA TGTATTTATT 21660
TGTGAGTGGA GTGTTCAGAA TGAGCACGAT GGGTATAACA TTTTTGTAGG TTTTTAAAGT 21720
TGAAATTTAG TGTAAATCCA AAGAATCAAT AGACAAGTCT GTGTTTTACT TAACCTATAT 21780
GTTTAAATTA GCATTTTTAG ATACTGATTT TATTCCTAAT TTCAGAATTC TCAGCGTCTT 21840
GCCGATCAAT ATCGCAGGCA CAGTTTATTT GGCACTGGCA AGGATCAAAC AGAGAGTTGG 21900
TGGAAGGCTT TTTCCCGTCA GCTGATCACT GAGGGATTCT TGGTAGAAGT TTCTCGGTAT 21960
AACAAATTTA TGAAGATTTG CGCCCTTACG AAAAAGGTAA ACAGTGTAGG AGTCTGCCTG 22020
TTTGACTTAA TTTTGTTTCC CACTCCACAT TAAAAGATCC TTTTTGCTTT TAATAGGGTA 22080
GAAATTGGCT TCATAAAGCT AATACAGAAT CTCAGAGCCT CATCCTTCAA GCTAATGAAG 22140
AATTGTGTCC AAAGAAGTTT CTTCTGCCTA GGTTCATTTT TCAGTTTTTT TCTTGTAACT 22200
TCTGCATTTT TTGTTGCTAT TTATGTGATT CAAATTATAC CAGTTTATAG GCCTCTCACA 22260
AGTAAAATGA ATTGCCTGTT TGTTTTTGTA TGCCTATTTT AGTCAGTTTG GGGGAAGGGA 22320
TCTGTGAGGA AAGGATAAGT CATAGAGCAC TTTTCTTTTT TAAGAGACAG AGTCTCTCTG 22380
TGTTGCTCAA GCTGGAGTGC AGTGGTGCGA TCATAGCTTA CTGCAGCCTC GATCTCGTGG 22440
GCCCAAGTAA TCCTCAGCCA CCTGAGTAGA TGGGACTACA GACATGCACT ACTATGCCCA 22500
GCTAATATAT TTTAATTTTT TGTATAGAGA CAGGGTCTTC TAGTGCTTCC TAGGCTGGTC 22560
TTGAACTCCT GAGCTCAAGT GATCCTCCTG CCTCAGCCTC CCAAACTACT GGGATTACAG 22620
GCATGATCCA CCGCTCCCAG CCAGAACATT TTCTTGGTTG ATGGGAAGTA GCTGACCATG 22680
GTATTTAGAA AACTTCTTTC TCATCGATTA AAGAAGCAGT ACTGAAATCA ATGCGGAGGA 22740
ATCCATATAT CATATTTACT TCTGGTGTGT AGAAGTGGAA AGGGAATACA TTTGTTGCTT 22800
ACTTTTTTGT ACCTTTACAT GTGATTGATC ACTTGTGAGT TTTTTCTTTC AAACATCTTA 22860
AAGCTTCCAG AGCTTTTTCT AGAAAAAAAA ACCAGTTTTA AGAATCACCA GTTCTAAAAG 22920
GGTAATATCT TATTCATCTT TCTGAGAATG GAGTATCATG ATTCATGAAT TAGATACTTG 22980
CATCTTAACA TTTGAAATAA TTTAATTTTA TTATTTTTTA GTTCGAAAAC TGTATCTTCG 23040
GGCACCAAAG AGCATTGTTA TAATCAAGTA CCAGTTGAAT TAAGTACAGA GAAGAAGGTT 23100
TGTTTTAAAG AAATTGTTCT GACTTATTTC ATTCTTTATT GATTCAAATT CTGTTTAAAA 23160
TTTTATATTT TAATTCCTTT CCAATTAAAG AGAAAATGGC ATATATAACA AAGCATAAAA 23220
TTCGGCCAGG GAAGTGATGT GAACAGACTA AAATTTATTG TATATAATTT CTGGGGCTAA 23280
TAAAGAATTG GAGGTATTTG AGAAAGGAAT TAATTTGGGT TCTTTTAAAC CTATCTGCTA 23340
ACTCATTTGG CTTAGAGTAG TCACATGTTA TAATACTTAT AGTGATCAA AAAATTGATT 23400
CCTAAGTGTT CTTATTAAAG ACACACACAC ACACACACAC ACACACACAC ATTCTTTCTC 23460
TCTCTCTCTC TCACACACAC ACACATGCAC ACACACTTAT GTACTTTCTT GCTTTTTTTG 23520
ACCTAAGATC TTAGATAACT ATTACAGATT AAATACTAAT CCACTGGCAG ACTTCAGCTA 23580
ATTAGAACAC TGGAATAATA GGCAAGCATA GTGAATTACA TTTTCTGGTG AACTTTTTCT 23640
GCTTTATTGA AGTATGCAGA ATGTAAATGA ATTGTTTTTA TAACTTTGGC ACTTGCTGTA 23700
TCTTAGAACA TTCTTTTGAT GATTATTTT CTGTAGTTTT GGGAGAGATA AGACATTGGA 23760
ATGCGTTTCT AACTACCTTT AGAACTTTAG AAACTGATAA TTTAGGAGGT TATTTTCAGG 23820
TGATTAATTT GACAGCTTGA TTAGGCAAAG AAAAAATTGT GATTTTGAGA TTTTTGTTTC 23880
TTATTTTCTT CACATTTAAA AGTTTTTTGA AACTTTTTTT AATGGACCTT TATATGTTTA 23940
AATGCAGTCT AACTTGGAGA AGTTATATTC TTATAAACCA TGTGATAAGA TTTCTTCTGG 24000
GAGTAACATT TCTAAAAAAA GGTACAGAGT TCCATATTTC TATGTTCTAT ACTTGCTTTA 24060
TGAGTACTTT TTTTTCTAAA GAGAAAGAAC TGTCAGATGT TGGGCTATTT CATTGGCAAA 24120
AGGAAGTTAA ATTTAAAACA TAAGCTTTTC AGTATTAGAA TGATCAAAGT GAGCTATAAA 24180
AGAATAATGT TAATTTAATA GCTAACACTT CTTGGATATT ACTGTTTGTC AGGCATTATG 24240
TTAAATGCTA AGAACTTTAT ATGTGATATC TCATTTAATT CTTACAAGAG TCTAACAGCT 24300
GTTACTATTT ATCGCCATTT TATAGTTGAA GATACCAAGG GTTAAGAAGT TGACAAACTT 24360
GTTCAAGAGC ATACAGCTAA TGGCCGAGCT GGCTTTCAAG TCTATATTTG TCTACCTCTA 24420
GCATCAAGAC ACTATTTATT TTTCTTTGTA TGAAATATAT ACAGGCATAC TTTGTTTTAT 24480
TGTGCCTGGC TTTATTGTGA CTTGCAGATA TTGCATTTCT TATAAATTGA AGGTTTGTGG 24540
CAACCCTGCG TCAAACAGGT CATATTAGCC CCATTTTCCA ATAGCATGTT CTGTTGTCAT 24600
GTCTTTGTGT TATATTTTGG TAGTTCTTGA CTGCCATTC ACCATTTCTC TCCCTCTCCT 24660
CGGGTCTCCC TGTTCCCTGA GATACAACAA AATTGAAATT AGGCCAATTA ATAACTCTAT 24720
AATAGTCTCT AAGTGTGTTT TTTTTTTTTT TCGAGACTGA GTCTCACTCT GTTGTTCAGG 24780
CTGGAGTGCA GTAGCACAAT CTCGGCTCAC TGCAATCTTC GCCTCCGGG TTCAAGCGAT 24840
TCTCCTGTCT TAGCCTCCTG AGTAGCTGGG ACTACAGGCG CCCCCGATC ATGTCTGCCT 24900
AATTTTTTGTA TTTTTAGTAG AGATGGGTTT TTGCCGTGTT GGTCAGGTGG ATCTTGAACT 24960
CCTGAACTCA GGTGATCCGC CTGCCTTGGC CTCCCAAAGT GCTGGGATTA CAGGTGTGAG 25020
CCGCTGTGCC TGGCCCATCT CTAAGTGTTT AAGAGAAAGG AAGATTCACA TGTCTCTCAA 25080
TTTAAATCAA AAGCTAAAAG TGATTAGGCT TAGTGAGGAA GCCATGTCGA AAGCTGAGAT 25140
AGGCCAAAAG CTAGGCCCCT TGCACCAAAC AGTTAGTTTG CAAAGGCAAA AGTTCCTGAA 25200
```

*Fig. 5F*

```
GGAAATTAAA AATGCTACCC CAGTGAATAA AACAATGATA AGAAAGCAAA GCAGGCTTTT  25260
TGCTGATATG GAGAAAGTTT TAGTGGTCTT TATAGGAGAT TAAACCAGCC ACAACATTCC  25320
CTTGAGCCAA AGCCTAATCC AGAGCAAAGC CCTAACTCTC TTCAATTCTC TGAAAGCTGA  25380
GAGAGGTGAG GAAGCTGCAG AATAAAAGTT TGAGGCCAGC AGAGGTTGGT TCATGAGGTT  25440
TAAGGAAAGA AGCCATCTCC ATAACATAAA AGTGCAAAGT GAAACAGCAA GTGCTGGTAT  25500
AGAAGCTGTA GCAAGTTATC CAGAAGATCT AGCTAAGATC ATCGATGAAG GTGCCTGCAC  25560
TAACAGACTT TGAATGTAGA CCAAATGCTT TCTACCAGAA GAAGAAGCTG TCTAGTACTT  25620
TCATAGCTAG AGAGAAGTCA ATGCCTGGCT TCAAAGCTTC AAAGGACAAG CTGACTCTCT  25680
TGTTAGAAGC TGATGCAGCT GGTGACTTTA AGTTGAAGCC AGTGCTCAAT TAGCATTCTG  25740
AAAATCCTAG GGCCCTTAAG AATTATGCTA TATCTACTCT GCCTTTGCTA CATACATGTA  25800
ACAACAAAGT CTTGATGATA CCTGTTTACA GCATGGTTTC CTGAATACTT TAAGCCCATT  25860
GTTGAAACCT GCTTAGACAA AAGATTCCTT TCAAAATGTT ATTGCTCATT GACAACACTT  25920
AGTCACCAAG AGCCGTAATG GAGACATACA AGGAGACTAA CGTTGTTTTC ATGCCTGCTC  25980
GCTTAACATC CATTCTGTAG CTCATGGATC AAGAAGTAAA TTAACCTTTT AAGTATTATT  26040
ATTTAAGAAA TACAGTTTGT AATGCTTTAG CTTCTGTAGA TAGTGATTAT CAGAGATGGG  26100
TTTTTAAGAG GTTTTCCAGA AAACCTTCTG GAAAATATTC ACTATTCTAG AAGTCATGAA  26160
GAATATTTGT GATTCAGGAG AGTAGGTCAG AATATCAATA TTAATAGGAA TTTGGAAGAA  26220
GTCGATTCTT ATTAAAATCA AGAGTTTAGT GATAGACATA CTGAGTTTGG GATACCTGTG  26280
GAGTAGTCCA GAAGTTAATT TAAATATATG GGCTTAGTGT ACAGAAGTGA GCAGGGTGCT  26340
TATATATGAA TAAATATTAT TTTAAGATAT ATTTAAATTT TCCTTAAAAT AATACCTATA  26400
CTTGATATAA AAAGTTAATT GGAAATTAGT GGCTTATGAC AAGCATACCA GCCCACACTC  26460
TTCCCAAACC CACTTTGCTC TTATTCATAG AAGCTGTCAT CTTCAAATCT TCCAGCTGAT  26520
TTCCCTGGCG TGTGCCTTCT TATTTCTGAA TGACACGCTT AGAGTACTAT TTTTTTGACT  26580
TAGCAATTTT AGAAATTTTC TACTCATCTC CTATTATGGT AGATTTCCCC TCCTTCATTC  26640
CTCCTCCAAT ATAATTATAT TTCGTCATAT TAATAATTTG TTTATATATA TTTTTAATAT  26700
AATATGATAA TATTGTATTT ATATTATTAA AACTACACAA ATATTATATA CACACTACTA  26760
ACCCAACCGT GTTATTATGG CCACCACTAC CTTTATTTTT TTCCTTGTGT TAGTGATTGT  26820
CTTTGTTTTA TTTTCTTGGT TTTGAGTATT CCTTTTACTA ATTTTCTTTT TTCCTATTTC  26880
AATCTCTCAT TATTTGTTTA CTCATTTGGA GTGTTCCTTG ACTTTTATCC CCTCTTACCT  26940
AGTGACATTT TAATTTTAGT TATCAAATTT TTAATTTCTA AGAATGCTTC TTGTTCTCTT  27000
CTTGTTTCTT CTTCCCCACC AGCCAAAAAT CTATGATGTT ATAGCAAGGA TCATACATTG  27060
TTTCCCAGTA GGTTAAGAAA CCTTGGTTAA AACCTGTTGT ATCCCAGTAA GTTAAAAGAC  27120
GTTAACGTGT CATCTTCAGT ATGGATGAAA GAATATTTTC TTTCAAAAGC AGTTGGTTGA  27180
GGAAGAGAAT GGGACAAATG CTCTTTTTAA AACACCAATT TTGTGATGAA CTCAAATTGC  27240
AATTTTAACT TTACCATTAT AATGAATGTA TTTGATCCAA AATGTTTAAA ATCTAGGCTG  27300
TTGTCATTTA AATAACAAAT TACCTTACTG GTATCATGAA GAATAAATGT TTGTACTGAT  27360
TTGGAAAGAC ATTCTCATTT AGGGGATGAA ATAGAAAGTC AATGAGGAGA AAGAAAAGCT  27420
TTTATTATTT ATTTTCTTTT AAATATTTTA GTATCATGGT ACAGTCACCA GAAAAAGCTT  27480
ACAGTTCCTC ACAGCCTGTT ATTTCGGCAC AAGAGCAGGA GACTCAGGTA AGGCTTTTGT  27540
AAAAAGGTAA TTAGTTTATG ATAGGATAGT TATGATTCTA TGTATGCTTA AAATTCTGTA  27600
TTTTGCCAGC ATTTTAAAAA TTGTTCTTAA GCTAAGAGTC TGAGTTTATA TTTCAGTTTA  27660
TATTCATTCT AAGGAAAAAT GTGGTATCTG AAGCTCTAAA AATAAAGGAC TAGATCTTTT  27720
AAGTACACTT TAAAAAGTGT TGTTTCTTTG TTTTTTGTTC AGATTGTGTT ATATGGCAAA  27780
TTGGTAGAAG CTAGGCAGAA ACATGCCAAT AAAATGGATG TTCCCCCAGC TATTCTGGCA  27840
ACAAACAAGA TACTGGTGGA TATGGCCAAA ATGAGGTAAA CTATCTTTTG CATGTGTTCT  27900
CATTTATTTC CTTCTAACAA AATAGATTTG GAAAATATAT CTAAGTTGAT AATATGACCA  27960
TAGCTTCCAC TGTCACATCT GGGAGGTGAC TCAGATTCCC CCTGCTGCGA TGCTTATCTC  28020
TTTGCCAAGC TTTAGTACCG TGTTTCTGTA TGAATAAAAA CCAGTTACGT TTTCAGCAAT  28080
CATATTCAAT ATTTATAAAA TCTAACTCAT TATTTACCCA CCCTGCATTT TATCCAAATG  28140
CCGAAACTCC TCTTTTTGGA TTCTTTATTT TTGATTATCT TACCATCACA TTTGTAGTCA  28200
GAGGTTCCTA ATGCTTAAAA CCTCTGATCT GAATTTTCTC TCCTCCAATA TAAAACCCCT  28260
TCGTCTTCCT CTTCTTCTTC TTCATTTTTT TTTTTTTTTT TGTCTGAAGA CTTGTCTCAC  28320
TGTGTTGCCC AGGCTGGAGT GTAGTGGTGC GATCACTGCT CACTGCAGCC TTGACCCCCT  28380
GGACTCAAGC TATCCTCGCA CCTCAGCCTC CCGAGTAGCT GGGACTACAG AACATGCCAC  28440
CATGCTCAGC TAATTTTTGT ATTTTTTGTA GAGACAGGGT TTTGCCATAT TGCCTAGGCT  28500
GGTCTTGAAC TCCTAAGCTC AAGCAATCTT CCCGCCTCAG TCTCCAAAGT TCTGGCACTA  28560
CAGGTGTGAG CCACTGTGCC TGGCCTCTTT TTCTCATTTA AATACTTTTC ATACCTTTTG  28620
TAAAACGGGT TCCTTGTTGC CTGTCTATGC CTTCCTCCTC CTTCTTAATG ACACCACGTT  28680
AATTCTGACT GTTTTCCCTT GGCCTGTTGC AGAAGCCTCT TAACTATTAA CCCTTCATTC  28740
TCTCTCTCTG TTTCATCTGA TATATGAGTA CCAAACTAAA TCTTCCTTTA TCATATCTTA  28800
CTTCTGCTTA AATGTTTTTT TTCTAGCTTA GAATTCAAGG CCCTCTATTT ATGAACTTAA  28860
ACTTACTTTT CCCTCTAAGT TACAGAATTT GAAATGGTTT ATCTTACCTG GATTGTTTAT  28920
CACTTGTTGA AGATCCATTT TCAACTTCCA TATATTTATT TACAGTGTTG CTTCTCCTTG  28980
TAGTTTCCTT GATTCCTCAA AACTCCTTTT AAGAATTCTT GAAGATCTCG CTTTATTACT  29040
ATTTCTCGCT TTATTACTGT AAAGACTATG AGAAGGTCTT TCATGATCTT ATCAGCAAAG  29100
TAATTCCTCT CTCTTGAATT CATAGAGGAC TTTCAGATGA ATTCTAAAGA TGCTTCTGTA  29160
GCACTTACCA CACAATNGCT ATATTTTATT TTTTTGTAAT TAGTGGTAAA CAAGTATTAT  29220
TATATCTTNC TAGATTTTAA ACTCCAAATA AAGATACTAG CTCCTTACCT TTTTGTGTGT  29280
CTCCTGTAGC ACCTAGCACA ATGCCTCATA AACAGGAGGT GATCATTAAA TATTTAGAAG  29340
AAATTATTTC CCAAGAATAG TTGCTTGGTA ATTGTATTTG TCTTTTACTT CCTTTTAAAA  29400
```

*Fig. 5G*

```
AATTGTTTCT GTCACTAAAT TGCATCCAAT AGATGTTACT TGAGTGCAGA ATTTTCTAAT  29460
GACATTACAC AGTGCTACAT CTGACACTAA TTCTTTTGTT AAAAAATAAA TATTCTGGCC  29520
GGGCGCTGTG GCTCACGCTT GTAAATCCCA GGACTTTGGG AGGCCGAGGC GGGCGGATCA  29580
CGAGGTTAGG AGATCGAGGC CATCCTGGCT AACACGGTGA AACCCCGTTT CTACTAAAAA  29640
TACAAAAAAT TAGCCGGGCG TGGTGGCGGG TGCCTGTAGT CCCAGTTACT CTGGCGGCTG  29700
AGGCAGGAGA ATGGCGTGAA CCCGGGAGGC GGAGCTTGCA GTGAGCGGAG ATCGCGCCAC  29760
TGCACTCCAG CCTGGGTGAC AGAGCNNNAC TCCGTCTCAA AAAAAAATAA AAAATAAAAA  29820
TAAATAAATA TTCTAAGACC ATACTTTAAT GGAGGTGTTT TTTGTTTTTT TTTGTTTTTT  29880
TTTTTTTTTT TTGGTGATAG AGTTCTCACT CTGTCACCTA GGCTAGAGTG CAGTGGCGCG  29940
ATNCTCNGGC TCACTGCAAC CTCCGCCTCC TGGGTTCAAG CCATTCTCCT GCCTCAGCCT  30000
CCGGAATAGC TGGGACTACA GGTGCGCGCT GCCACCCCCG GCTAATTTTT TGTATTTTAG  30060
TAGAGATGAG GTTTCACTGT GTTGTCCAGG CTGGTCTTGA ACTCCTGAGC TCAGGCAATC  30120
CACCCGCCCC GGCCTCCCAA ATTGTTGGGA TTACAGGCGT GAGCCACAGT GCCTGGCCCA  30180
GAGGAGATAT TTAATGAAAA ATAATAATCA TTAGATAGGC AGATTTTTAG AAGGAGGGCA  30240
TCGAATGGGT TCTTGGATAT TGGACACAAT AAGAAATATT GAGCTAAAAG TCTGAAGGAA  30300
TTGGCAGATA TACTGTTACA GGTAAACACT TTGTAGAAGA AAATAATGAA TGAGACTTTC  30360
TTTTGAGATT TTCTTAGCCT CTTAGTTGTT CCCAGTTAAA GCCTCATATT TTTCCTTTTC  30420
ATGACAATAA AAATAATAAT AAAATCAGTA ATAAAGTGAA TATATGAGAT GTTAACCTGT  30480
TCCTTTATGA CAATGTCCTG TTTACCAATT AACAGTGTGT TTTTGTGGTG ATGGGGGCAA  30540
GACAAATCTT TAAATGGTGG AAAGCAAAGA AAGAAATTAT AAAACATGAT TAGTTGTATT  30600
ATACGTTGTT TTTGGTTGTT GGAAAAACTA TACATTTATT GAGAGAATCA TTAGGAAGCT  30660
GAACATCAGC TATATTGCTG GAGTGATACT GTTCAGTGG TTTCTTGACC TTTTTGTTGT  30720
TGTTGTTGTT GTTGTTAAAC ACAGACCAAC TACGGTTGAA AACGTAAAAA GGATTGATGG  30780
TGTTTCTGAA GGCAAAGCTG CCATGTTGGC CCCTCTGTTG GAAGTCATCA AACATTTCTG  30840
CCAAACAAAT AGTGTTCAGG TAAAATACTG TGGTTTGCAG GAGCTCTTAG AGAATAAGCA  30900
TTTTTTGTAA CCATTTCAAA AGTACCCTCC AGAAGCAACA TTTGCTCACT TTATTTGCAT  30960
TTCCATACTG GACACTTAGA AAATGAATTA AAATTGTTTT TACAGTCAAT CNNTGTTGTA  31020
AAAACATGTC AGTTATCTAC TTTTAAAGAT GATACTAAAA AGTAGTTGTC CAGGCTGCTG  31080
ATGTCTTTCT ATTTCATTGG GAGGTTTTGT TTTTAAATTG GAAACATTAT TTTAGGTTGA  31140
TAAATTATAA TTTTACATTC AAATGTGGTA GTTGGAATTT AAAGCTGGAA AGTTATCCTT  31200
GCTATGAGTT GGTCAGGAGC TCAGCCACTT TCTTTTGGTT TAGCATCTTC TCTAATCTCC  31260
CTCCCCTTCC AGTAATGCTG TCTTTTGATA GTAAGTGGAT TTCATATTAT TCTCTTCAGT  31320
TTTAATAGTG TTTCCTTCAT ATCCTTTTAT TATTGCTTGT TCTGCCCTAA GTGACCATTT  31380
CCAGAAATGT CATTTAGGNA TTTTCTCTAA ACTCCACGTA GCAGACTCTA TAATGCATAC  31440
TCTGCAGAAG GTGAGGCAGT GGGAGGTAGA GGGGAGACTA CTAGACTAGG AGTCACGGAA  31500
TCAGGACTTT AGTTCTTCCT TACAGTTGTT CACCTGGTGA ACCTGCACAT GTCCTTTAAT  31560
TTCCTTGGGT CTCCATTTCC TCAGCTATAC AATGGAAATG ACACTTCCTC CCCCACATCC  31620
AGGAAACAAC AGATGACATT AGAAAATAGA AGACATGGGA TAAGTATAAA ATGTTGAAAG  31680
AGTTAAACAC ATTCAAGGCA ATATTAAGGG ATTATTTTTT ACTTCCAAGA AGCTCCTGGA  31740
AGCTTTGGGC AGGCACAGTT GGATCCTACT TTAGAAAAAT CTTTCTCTAA CTATAAGTAG  31800
AAAACCCTTC TGCTTTTTGA ATGTAGCATT TCCCTCTTTT GATATAGAGT ATCTTTGGCA  31860
ACTTTGAATT TTCTTTTTCA TACTCTTATA TAAGACATCA TGTGAAAATT CTTATTTCTT  31920
ACTGAGTTTT TGGAAATGAA ATTATAATGT CTTAATAGTT TGAGAAAGAA TATCATACCT  31980
ACCAGCGGTA ATTGAGTAAG TTCCCTCTCT TTGACACTT GAAAGTAGTA TCTTCTTTCA  32040
TGAATTAGTG ATATTATTTA ATAATGAATG AGTGATCTCT CCTAACTCCC CTTCAGAAGA  32100
GGAAAATGAA GTAGGGAAAA AGGTAAATTC CCCAAGGGAT AGGTATGAAA CCTTTATGAA  32160
CCTTCTGGAT AGAGAAGATG ACTGCTGATT TCTGTGATTA GAAATTATAC TTGGGTTATT  32220
CTGCAAATTG AAATGAATTA TTTAAAAAAA AACAACTTTA ATGTTTATTA AGCAAGTTTT  32280
GTTATTCATG AGTTTCATTA GCCTTTTATT TTTTTTTTAA ATTTTGAAGT AAAATTTCTT  32340
GCTGTCACAA TACACATTAA AAATTACAAA TATGACACAT ATTAAACACA TTAAGATGGC  32400
CGAATAGGAA AAATATGCTA AAATATTTTT ATATAAATAC ATTTTTTGAG AATTTTGAGA  32460
ATTTCTGGAA CAAAGTAATG ATATAATCCA TAAATGTACA ATTAAAGAGT TTAAGGATAT  32520
CCAAAATACT TGGCAAAGTA ATCTGAAATA ATACTCTTAG GAAGGTAGGG CAAGAATGTG  32580
ATTCTAGTAA GCAAAAATGT AATCAAATCG TATTCTAGTC CCAGCTACTC GGGAGGCTGA  32640
GGCAGGAGAA TGGCGTGAAC CTGGGAGGCG GAGCTTGGAG TAAGCCGAGA TCGTGCCACT  32700
GCACTCCAGC CTGGGCGACA GAGCGAGACT CCATCTCAAA AAAAAAAAAA GACTATATGA  32760
ACTTGTATGG CATAAATATG TACAAATATT ATTTATTTTA AAAAAATTCA GGGGTAGGGA  32820
CAGGGTAGTT AGAAAATATC TAAGGATGTT CATGAAATAA TACTGGCTAT GAATGACAGT  32880
TGATGAAACC GGGTGGTGCC CNATCTTATT CCCTCGACTC GTGTATATGT TTGATATATC  32940
CCACAATAAA CCTTAAAAAA AAAAAGNATG AGTAGTGATA TATAGGAAGA TATAAATAGA  33000
AAAGGCAATA AGGACAAAAG TTGGCAAAGC TTACCTAAGC ACTCTTCAGA TAAAAAGACA  33060
TTTTTGCTAA CTAGATTTGA ATATTATAGT TTAATTGTCA AGGAAAATGC CTCAACTTAA  33120
TCTTTGTTAA GAGACTACTT AAGGCACTAT CAGAAGTTCC CTCATGGCAA GGTGCAATCC  33180
CTCATGCCTG TAATCCCAGC ACTTTGGGAG GCCAAGGCAG GCAGGTTACC TGAGGCCAGG  33240
AGTTAGAAAA CAACCTGGGA AACATAGTGA GACCCGACCT CTACAAAAAC AATTTCTTAA  33300
AATTAGCCAG GCATGGTGGT GCTAGCCTGT AATCCCAGCT ATTTAGGATG CTTAGGCAGG  33360
AGGATTGCTT GAGCCCGGGG ATTTGAGGCT GCAGTGAGCC ATCATTGTGC CACAATACTC  33420
CAGCCTGAGT GATAGAAAAA AAAAAAAAAA GTGTCTTTGT TATATTCCAA ACTTGTTCTC  33480
AACTTTCAGG TGAGCTGGCT TCCTGTATAA CTCTTGTATA GGACAGAACA TACTGGTTGG  33540
GGCAAGTGAA ACTGTCTAGT TGTATGCCTC ATAAATTAAT GAATTTCCTT TCTAATATAT  33600
```

*Fig. 5H*

```
ACACTGATAT TTATACACAC ATACACATAA AACCAAGCTC AATAGATGGG TAGTGCAGCT  33660
CTATTCCCCA AAACCCAACT ACCCTGTAAC AAGACACATT AGACTTTTGA GATTGCAAGG  33720
ATGAGGACTG AAATGCTGGC CTAGACCATG GTGTTGCCAT AGTGGGGTGA CCAGTCTGAA  33780
TAGCCAACAA TGCTTCCTCA GTAAATACCC ATTTTGTCTT GGTGGGATTT CTACAAATTG  33840
CAAAATGCAG CTATTATGAA GCTGTAAAAG AGNAAACANG AAACATGTAA CACCTGGGAC  33900
TGTTTTATTA GGCCCACCGT ATGCTCAGAA CATGAAATCT CCACTGCTAG GGTTATTTGA  33960
TTGAAATTAT CTTTTGTGTT GATGTGAGAG TTTAGCTCTG AGATTCTTCC ACATGTAAAA  34020
TGTAATCCCC CAAAGTATTT GGCAAGCACA TTTTATTGCC TTGGGTCAGA TAATTGAAAC  34080
ATTAGGCATC ATATATATAG CATGTAAAAA GTAAAACAGA AACATTTATG TTTCTCACCA  34140
AGCAGTAAAT TAGTACTCAA CTAATAAATT TCTTAAACTC CCTAATAACA GAATATGAAA  34200
ACAAAAAATA AATCTTTCCA AAAGAAGAGC TCATGGACAC ATTTCCTCAT ATATGTATAC  34260
ATAATATAGT AGAACACATG ATAAATAACC TATAAAAATG ATACCAATAT CATTCATCAA  34320
GAGACGAGGC TCTTCTTTAA ATTATTAATT TCATCTGTTA CAGGTTTTAT TATGACTGTA  34380
GTATGCTGTT TTCATCTACC TTTTATGTGT AGTTAAAAAA ATAGTTTTCT ATCTCTTTAC  34440
CTTTATTTCA GCCTTTAAAA AGATTCCATT ATTTTTTCAT TAATCTTGTT TTTCAGTTTT  34500
TCCCATTTTT TCTTTTAAAC ATTTCTTAAG GAACCATATT TAAGATTTTA TAGAATACTT  34560
AGATTTCTAG TTGGGATGTA TCATTTAAAA TTAGATATGT AGAGAGAGTG TTATGATATA  34620
TTTCCTTACG ATATATTAGT GGTTATAGTA CCTAAATTTG AATAGTGATT CTGTTCATTC  34680
ATTCATTCAT TCATTCAATA TTCACTTCCA GGAGATTGGG GACTTATTTA AAGACAGAGT  34740
AGTTCACATT ATAGTTCCTT TTTTTAGTCC TTCTTATTCG TTAAAGAAAA GACTAGGAAA  34800
TGTTTGTTAT TACAAATATT TTATTAAAAT TTTGTGTGCT CTAGCATTAT TTTACCTTTT  34860
AAAATCAATA TGTAAAAAAT CCAACTTCTT TTTGAGCTCC CCATAAAAAG GGAATTATTT  34920
GTTGCTTATG GGTTTAACTT GTGTTATTTT TTTCTTAATG GCTAATTATC ATACATATAT  34980
TCTATTATTG TATTGATATT ACTGATCATT TGTGCTACAT TAAAAATTCT GTAGACAGAC  35040
CTCTTTTCAA GTACAAAACC TCAAGAAGAA CAGAAGACGA GTCTGGTAGC AAAAAATAAA  35100
ATATGCACAC TTTCACAGTC TATGGCCATC ACATACTCTT TATTCCAAGA AAAGAAGATG  35160
CCTTTGGTAA GTGTGACTTT CATGTTACAG GGAATTTTTT TAGTTTACTT AAACTTGTGT  35220
TTTATCAGCT TTTTAGTATT AAAGTTCTGA CTTGGGATCA ATTTCCTCCA ACCCTACAAT  35280
AAATCTCAGT TTATCTTTAA TTTTAAAAGA GAATGTTGTT TTCTTTTTCT GTTAAGCCTC  35340
CCTGTTAAGT AATAGCAGCA AGTTTAGTTT GGCCATGAAT ATCTTCTAGA GATTGTATCG  35400
GGGTACTGAT AAACACATTT ATAGCTCAGG GATACTGCAT CAGCCATATT TTAAAATGGG  35460
ACTAACAGTT TAAAAACTAT AAATATTCAC AGTGTTAAGA AACAATCTCA AGATGCATTA  35520
AGAAAAAGGA AGGTGCAAAA CAGAAAAACA AACGTAAACG TGTGTGCATA TGCATGCTTA  35580
TATAGTCACA TATTCTTGTA TGTGTACAAA AAATACACAC TGGATCTCTG CAAGCATAGC  35640
CAAGCAACTG GAAATATGTT TTTAAAAACT TGCTTTTCAT TCTATCTCTT CTAGTACTGT  35700
TTTGATGCTC TTTGAAAACA ATCTAATTGC TGTAACAAAT GACCATACGT AGGCCGGGTG  35760
TGGTGGCTCA TGCCTGTAAT CCCAGCACTT CGGGAGGCTG AGGCAGGCAG ATCATTTGAG  35820
GCCAGGGATT TGAGACCAGT TGGACAACAT AGGGAGACCC TGTCTTTACT AAAAATACAA  35880
AAATTAGCTG GGCGTAGTGA CGCATGCCTG TAATCCCAGA TACTTGGGAG GCGGAGACAT  35940
GGGACTTGCA TGAACCCAGG AGGCAGAGGT TGCAGTGAGC TGAGATTGCG ACACTGCATT  36000
CCAACCTGGG CGACCGAGCA AGACGCGGTC TCCAAAAAAA AAAAAAAAAA AGACCATATG  36060
TAATGTTTCT TCATTGTTCT AAGATAAATC TTTAAGGCTG TTGAGGTTTT TTGTATACAA  36120
AATGGAGAGT AAGTTTTAAT GGGATGGGAC AAAATGAGGC TTACAGTTGA GTTTAATTTG  36180
AGTTCACATC CTGTTGACAT TAAGTTGATT TGGAACAAGT GATATGGTCC AATGCCTGCT  36240
TTTCTATTGT CTGTGGTTCC ATCCACTAGT GCCTGTGTTA CACACCTCTT GTTCAGGTTT  36300
TATCATTTAA AATAAATAAG AATAAACAGT CCATAGCTTA TCTTACTTAC TGAATAAATG  36360
CTCTGATTTG ACAGTCATGT TTCTTAAAGT TCCTTACAAA GGCCATTGCC CAAGAAACCA  36420
AATAATTCCA TTATACTATT TTTGAAATAG AACACATAAT AAATGGGAAT TTTAAGTTCA  36480
GTTTCTTATG TAAACAATAA CTTCTATGTA CATGTTAAAT ATGCCTGTAT ATACCTAATT  36540
TGACCATGTA TGTATAGTAG AAATGAAAAC AGTTACTAAG AAAATTTGTT ATTGGCTCCA  36600
AATTTTCTGA ATTAAGTGTA TTNCTAATGC TCAGCCATAA TATGGGGTTT CATGTGTTAG  36660
TTTATGTATT CATGGTTAAA AATGTGAAGA CTGTTATATC TTCATTTGTG TCTTTTGGTA  36720
TTATTTGGTT GTATTTTATT GTGTGATATG GTGGTAATAT TATCCTTACC TCCCAGGAGT  36780
TTGAGAGGGT CTTGCCAGTT AACCGCAGAA TTAAACATGC CTAGGACTAA TTAATCAGGA  36840
GCAATACTAC AATTAATTGG AGGTAATTTG AAACCTGGTT TCAAATAACC CTGATATTAT  36900
GCACACATGG TGCACACTTT TCTAGTAGAC ATTTAATGAA AGTAATTTAA AACCTACCTT  36960
TGAAGGATGA AAAACATTGC CTTAAATGCT CTATTCTGTG AAAGTATCAA CATTTATGCA  37020
AATACAGTCT AAATTCAGAC TTTGAAAATG TATTGAAAGA GAGGATCATG AAATAAGTTA  37080
GAGCTGAGTG ACAAAGCTTT CTGAGTGTTT AAAAGAATGT TTACCTAAT AAATATCTGA   37140
AATGTATTTG GAGCCACATT TGTTTAAAGA ACTGTATAAA TATGTAGCAC TGTTCATGTG  37200
AAGTTCAATA GTAGGAAAAT GCTGACAGCC CTTGTGGAAC TGTGGTTATT ATTATTTTAT  37260
GAATAGAGCC AATTTCAAAC ACCTATTAGA GTCTTCTCAG GAACATTTTA TAGAATGCAT  37320
CTGGAGCCTT ATGTTATCTC TAAGCATTTT AGGATTTGTC TTCTTGGAAA TTCATGTAAC  37380
CAAACCACCA TGTGTTATTT CAAGTGTATA TAGTATTGGG TTACAGTTTA CTATGTTTTC  37440
AGAAGGTTGT GACAACTATT AGACTTACAG AGAATGACTT CTCTGCCACT AACGGCTTTC  37500
TAAAGTGAAT AGAGAGGGGC GAGGATTGAA TTCTTCGGTA AAGCTGGGTG ATTTTGTTTT  37560
ATTCAATACA GTATAATAAG TATAAAAAGT AGAACCTATA GAGAGCTATA ATGGGGGTAG  37620
TTTTAAAGAA ATTCTGAAAA TGAAAAACTT AAGTAAAGGT TTAGTTCATT GTTTATTTCA  37680
CACTGAGCAT TTACTACCTG AATGTTTTGG ACATTTTATT TCCATGACTG GAGTGGACAC  37740
TTTTACAACT CACTGGGTTC TTTGCTGATC TTTCTCTAGA AGAGCATAGC TGAGAGCAGG  37800
```

*Fig. 51*

```
ATTCTGCCTC TCATGACAAT TGGCATGCAC TTATCCCAAG CGGTGAAAGC TGGCTGCCCC  37860
CTTGATTTGG AGCGAGCAGG CCTGACTCCA GAGGTTCAGA AGATTATTGC TGATGTTATC  37920
CGAAACCCTC CCGTCAACTC AGGTGAGAGG CATGGCCTAG CTCTGCACCC TTAATGACTT  37980
GATGAAGTAA ACAAGCAATC CACTATATTT TTCACTGTTA ACAGCATTAA TCCTTTATGC  38040
TATTATGAAA ACCTTACTTT TGTGATTCTT TTTCTTGTTT TAGGAAAACA ATCTTTCTTC  38100
CCATTATCAC TCAGAGGAAA GTATACTGAG AAATTTTTTT GTTTTGTTTT GTTTTTTGAG  38160
ACAGAGTCTT GCTCTCTTGT CTAGGCTGGA GTGCAGTGGC GTGATCTTGG CTCGCTGCAA  38220
CCTCTATCTC CCAGGTTCAA GTGATTCTCT TGCCTCAGCT TCCTGAGTAG CTGGGACTAC  38280
AGGCGTGTGC CACCATGCCC AGCTACTTTT TGTATTTTTT GATAGAGACA GGGTTTTCCA  38340
TGTTGGCTAG GCAGGTCTCG AACTCCTGAC CTCTGATGAT CCGCCCACCT CAGCCTCCCA  38400
AAGTGCTGCG ATTACAGGTG TGAGCCATGG CACCTGGCCA ATACACTGAG AAATTTTTAT  38460
TTTCCTTTTC AGCTTAAGGT TACAACTTCC CCACCATCCA AAACGTGCAC TTTCATTTTT  38520
TTTCTAATTT CTATCTCATC ACTTGCAAAA ACCATATTTT TCTCCACATT CATTCCCAGT  38580
AGCTTCCTGA CTCCTAGTTC TTCCCTAAAT CCTTCTGAGT CCTTGTCATT GGTTTCGCTT  38640
GAGTAGCCTT TCTAATCAAC ACAGTCATTG GTATCAGTTA CTGTGACATG GAAGGGACAG  38700
ACCAAGTTCT GTGGGCCGCT ACGTAGAAGG ATTTCCTGTC ACTTTGCTGC AGAACCTCAG  38760
CTCGCGGAGA GCAAGCCCCT TTGCTTGCCC TGTAGAAATA TTTTAAATTA TTATCCTTTT  38820
TTTTTTNAAC AGAAGTAAAT AGGAGATACG TTAGAGGATT TTCTCTCCTA GATGTGTAAA  38880
TACAAACTTG GGGTCTTATA ACTCAATAAA TCTGATAAAT TTCTTTTGAC TGTTAGGATA  38940
GAGCAGTGGC CATACCAATA GCCTCATCTC CAAAGCTGCA GTGAAGATAC TTTTTACTAC  39000
CTTAAAGTCT TTCCCATTTG TGAACAACTT GTGAACAATT CCCCCCAAGA ATTTGGAAGA  39060
TCACTCTCTG AAAGCACAGT CAATACTGTA CTTAAATGGA TCTGAGCAAA AATAAGTCAC  39120
TTAGAAGACA GGATTATTTC TAGACTTGAG TGTGACTTGA CTGAAGGTCT AAAGAACAAA  39180
CAGCTCCTTC ACTTCCATTG ATCACGGTGG AAGCACAGGG AAAGGACAGA CACGGAGGCA  39240
AGTTGGAGTA GTGCTCATCT AAGTTCCAGG GATGCGGGGG AGTGGCCAGG GGACTTCAGG  39300
TATAGTAAAT AAATAACCTA TTTATAAGTT ATGTCAATGT CATGTTTGAA ATAGAAAACC  39360
AAATACTGCA TGTTCTTACT TACAAGCAGG AGCTAAAGTT GGTGCATATG GATATAAAAA  39420
TGAGAACAGG CCGGGCGTGG TGGCTTGTGT CTGTAATCCC AGCACTTTGG GAGACCTAGA  39480
TGGAAGGATT GCTTGAGCTC AGGAGTTCAA GACCAGCCTG AGCAACATGA TGTGACCCCC  39540
ATCTCTACAA AAAATAAGAA AATTAGCCAG ACGTGGTGGC ATATACCTAT AGTCTCAGCT  39600
ACTTGGGAGT CTGAGTCAGG AGGAGTGCTT GAGCTCAGGA GTTGGGGTT ATAATAAGCT  39660
GTGATCATGC CACTGTGCTC CAGCCTGAGT GACACCCAGA GTGAGAACCT GTCTCAAAAG  39720
GAGAAAAAAA AAAAAGTAAC AGTAGACGCT GGGAACTACT GAGGGGAGGG AAGGAACAAT  39780
GGTTGAAAAG GTGGGAAGGG ACAGTGGTTG AAAAACTACG TGTTGGGTAC TATGCTCACT  39840
ATCTGGGTGA TGGGATCAAT TGTACCTCAA ACCTCAGCAT CCTGCAATAT ACTAATGTTA  39900
CAAACCTGCC CATGTACTAC CTGAATCTAA AGTAAAAGTT ATAATTTAAA AAAATTATAA  39960
TAAAATCAGA AAATAAAGGT CTGAGATGGA AAATTAAAAG ACCAAAGCCA CCCATAAGCA  40020
CAATAAATCC CTCCCCCAA AAAATTATAT CTATTAAAAA AAGGTGTTGC GCCAGGCACT  40080
GTGGCTCATG CCTATTGCCT ATAATCCTAG CACTTTGGGA GGCCAAGACG GGCAGATGAC  40140
TTGACTTGAG GTCAGGAGTT CAAGACCAGC CTGGCCAACA TGGTGAAACC CTGTCTCTAC  40200
TGAAAATACA AAAATTAGCC AGCAGTGGTG GCATGCGCCT GTAATCCCAG CTACTCAGGA  40260
GACTGAGGCA GGAGAATCGC TTGAACTGGG GAGGCGGAGG TTGCAGTGAG CCGAGATCAT  40320
GCCACTGCAC TTCAGCCTGG GTGACAGAGT GAGACTCTGT CTCAAAAAAA AAAAAAAAAA  40380
AAGACCTTGT ACCCTGACAA GTTTTAGTTT GTGCAGGAAT GACACAATCT AGAATGACTC  40440
AAGATTGGAA AAATCTTTAA ATGTTAATTA CACAATAAGG GTAAAAGGAG AAAAATTACC  40500
TAATGTCATC TGAGCAACAA GAAGAAGAAA TGAAGGCAT TAAAAATTGG GAAAAATTTA  40560
TATTTGACAG TATCTTAACA ACGAATTCTG CTTCTATATC ACTTCCTAGC TTTCTGATGA  40620
TAACTTCCCG TGCAGATCTG TATGTAAGGA ATGGACGTAG TAGTCATGCT AATCTGAGTA  40680
TTTATCTGTG TGATACTTAC GAATTAACGA TGTAAGTTAA TAAGTTAGCA TTTCGTGAAC  40740
CTGGTTAATA CCATTTGCTA AGGTTAAATT AGCCAAATCC TGAAGTAAGC TGTAAAACAT  40800
CCAAGGTAGG GTAGAGAGGC ATCTTATGAG AAAGCTGCC AACTCTCCTG GTCACCTTCT  40860
AATCTTCCTA ACTTCAGAAA TCAAGGCAGA GAGAGGAAAA TAGTAATTAC TTTGTAGGAT  40920
TAGATTTATG GTTGTCGAAA CCTTTGTTTC TCCAGTGCAG AATGAGATAG CGTTTTAGGG  40980
AAAGCCAAAG ACTCAGATGT CTTCTTCATG CTCATCGTGT GGAATTTTTC TTCCTTTAGA  41040
AATGTATTGT CTCTCAGGGC TTAAAGCAAT TTGCATTCTT CGATGAGACA TTGAGTAATA  41100
GGCAATATTC TCTGAAATAA TTTGTCAGG CTGGGCACAG TGGCTCACAC CTGTAATCCC  41160
AGCACTTTGG GAGGCCGAGG CGGGCAGGTC ACTGAGGTCA GGTGTTGGAG ACGAGCCTGA  41220
CCAACATGGT GAAACCCCGT CTCTACTAAA AATACCAAAA TTAGCTGGGC TTGGTGGCAC  41280
ACACCTGTAA TCCCAGCTAC TTGGGAGGCT GAGGCAGGAG AATTGCTTGA ACCCCCATGG  41340
AAGGTGGAGG TTGTGGTGAG CCAAGATTGT GTCATTGTAC TACAGTCTGG ACAACAGAGT  41400
GAGACTCTGT CTCAAAAAAA AAAAATAGA ATTTGTGCAG TTCCCCCAC CCCCTTTTTT  41460
TTTTCTGTTG GCATTTTTGC TATCATTTAG CTGCCTTCTT TATATCCTGA AACTTACAGG  41520
TGGTGTTGGT CTAGTCAGTA AGAGCAAAGG CTTTGGGAAT AGATAGATCT GTATTTAGAC  41580
CTTGGCTCTA GCATCTCATT GTTATGTGAC CTCCATCAAG TGACCTAATT TCCCTAATAT  41640
TCAATTTCCT CATCTCTAAG ACAGGGAGTT AATATTGCCT CTCTTATAGA ATTGTGAGAA  41700
ATATAGTCAT GTGTCGCTTG ATGATGGGGA TGAATTCTGA GAAATGTGTT GTTGGGCGAT  41760
TTCATTTTGT GGGAACCTCA CAGGGTGGAC TTAAACAAAC CTAGATGGTA TGGCCTACTA  41820
CACACCTAGG CTGTACGGTA TAGCTCCTGT CTTCAAACCT GTACAGCATG TGACTTTACT  41880
GAACACTGTA GGCAATTATA ACACAGTGGT ATTTGTATAT ATAAACATAG TGAAACATAG  41940
AAAAGGCCCA GTAGAAATAC AGTGTAAAAG NATTTTTTAA AAAAGCTGGG CATGGTGGCT  42000
```

*Fig. 5J*

```
CACGCCTGTA ATCCCAGCAC TTTGGGAGGC CGAGGCAGGC AGATCACTTG AGGTCAGGAG    42060
TTCAAGACCA GCCTGGCCAA CATGATGAAA CTCCGTTTCT ACTAAAAGTA CAAAAATTAG    42120
CTGGGCGTGG TGTTGGGTGC CTGTAATCCC AGCTATTCAG GAGGCTGAGG CAGGAGAATT    42180
GCTTGAACCC AGGAGGTGGA GGTTGCAGTG AGTCAAGATT GTGCCACTGC ACTTCAGCCT    42240
GGGAGACAGA GCGAGACTCT GTCTCNAAAA AAAAAAAAAA AAAAAAGAGA TAAAAAGGTA    42300
CATCTGTACA GGGCACTTAC CACGAATGGA GCTTGCACCC TGGGAGTTGC TCTGGGTAAG    42360
TCAGTGAGTG AGCGGTGAGT GAATGTGAAG ACCTAGGACT GTGCACTGCT GTAGACTTTA    42420
TAAACCCTGT GCACTTAGGC CACACTCACC CCTGTGATAC GAGTCTACCT ACTGTATAAC    42480
GTACCTGCAT ATGTACCCTT GAAACTAAAA CAAAAGTTAA AAAATTTATC TTCTTTTGCC    42540
AATAATAAAT TAACCTTAGC TTACTGTAAT GATTTTTCTT TATGAATTAA AATCTTTTTA    42600
CTCTTTTGTA ATAACACTTG GCTTAAAACA CAAACATATT GTACAGCTAT ACAAATATAT    42660
TTTCTTTATA TCCTTCTTCT CTAAGATTTT TTCTGTTTTT GATTTTGTTA AATTTGTTTT    42720
TACTTTTTAC ATTTTTTTTG TTAAAAACCA AGACAAAAAC CCACACATCA GCCTAGGCCT    42780
ACATGGGCTC AGGATCATCA GTCTCACTAT CTTCCACCTC CACATCTTGT CCCACCAGGT    42840
CTTCAGGGGC AGTCATATGC ATGGGGCTGT CATCTCCTGT GATAACAATG CCTTCTTCTG    42900
GACACCTCCA GAAGGGCCTG CGTGTTTTAC AGTGAACTTC TAAAAAATAA TAAAATGTAT    42960
AGTATAGCAA ACACATAAAC ATAGTAACAT AGTCATTTAT TATCATTTTC AAGTATTATA    43020
TACTGTACAT AATTGTACAT GCTAGACTTT TACACAGCTG GCAGCAAGGT GAGTTTGTTT    43080
ACACCATTAC CACCACAAAC ACATGGGTGA TGCTTTGCAT TGTGATGTTA CGATGGCATG    43140
ATGTCACTAG GTGGTAGGAA CTTTTCAGCT CCATGATAAT CTAATGGATA CTTGTTCCTG    43200
TTGGCTGCCC GTCGTTGACT GCAACATCAT TATGTGGTGC ATGACTGTAA ATTAGATACT    43260
GTCAGAAAG CTTTGGCACA CTGGTAATGA CAAATGGTGG TGGCAAATAT GATGATGATG    43320
ATGATGATGA TTGAAGACAT AGATGGTAAA ATTTTATGGT GTCTTAAAAG TACCCTCTAA    43380
ATATGATTAT TTTTATAGTC TGTCCTTTTG AATAGGCACT TAAGAATGTA TGAACTTAAT    43440
AAGTATATAA GAAAGAATGT TCCCCAAAAT ATATCTTACA GAGGCATACA ATTTAAGAAT    43500
TCAAACAGGT TGTAATGGGG TGTGTGTGTG TGTGCACACG CGCACGCATG CGTGCTCATT    43560
CACACTAAAG AATTCTTGGG CATATGTTCC TGAATGTCCT AAATGGACAT TCTAACATCA    43620
CTTCATTATG GGCAGAGGGA AATGGTAAAG AAAAATTTCA TATTATATTA TTCAGCCACA    43680
TATTGACAGC ATCTGTTTTA TTTGCCTATG GTAAAGAATT GAAGCACTGT TAATTTGCTT    43740
TTTAAATCAT GTAGGCACAA AGTTATCGAA CTTTAGATTT AGAAATGAAA CTGGAAATCA    43800
TTACACTTTC CCTTTCCTAT CCCCACCCTG TTTTGGAGAG AAAGAGTGTG AGGCTTAGAG    43860
AGTTATAAAA CTGTTTTAAT ACCATGTCTA AGATTAATAA CTGAACAAGT TTCTCTTTTT    43920
ACTCGTGTTA AAGTTGTACT GCCAATTAAC TTAAAAGAAA GAAATATGCA ATTTCTAATC    43980
CTGATATAGG ATATGGGTAT ATAAACTCTA ACTTGATGAG TGAAACAAAT TAACTTATTT    44040
ATAATCAGTT TCATATCTTT ATTTATTGAG TGTCTTTAAA TACCCTTAC CTTTAAAGTA    44100
AGAAATATTA AAATCAAGCA GAATATAATA ATGAAAAATT CTTAAGATAT ACTTACTAAA    44160
AACTTATCGT TCGGTTAATA CACTGTATGT AGGTTGTACA TACAATATGA AAAAGTATAT    44220
TTTTGTAGCC TACTTTTAAA TCCAGAATAG AGGAGGTTAA GAAGGTTGTG ATAACCATGA    44280
GCTCTTTTTT TTTTTTTTTT GAGACAAGGT CTTACTCTGT TTCCCAGGCT GGAGTGCCGT    44340
GGCACAATCA TAGCTTACTG CAGCCTTGAA CTCTTGGGCT CAAGCAAGCC TTCCACTTCA    44400
GCCTTCCAAG TAGCTGGGAC CACACCTGGC TAATTTTTAA GTATTTTTGT AGAGATGAGT    44460
TCTCACTACA TTGCCCAGGC TAGTCTTGAA CCCCTAGCCT TAAGCGATCC TCCCACCTCA    44520
GCCTGCCTAA GTGCTGGGAT TACAGGTGTG AGCCACTGAG CCCAGCCCTC TTTTATTTCT    44580
TTTGATAGTA CACTCATAAT CATTAAACTA TCATTTCTGG ATGTGAGATT GTGCTTTTGG    44640
ATTCTTATTT TTTCTTTATA AAATACTTTT TGTTCTCTTA CTGGAGAAAA CATTGTTGGA    44700
TTATAAATGA TATAACAAGG AATGAGGATA TACATACTAT AATAACGATT CAGATATGTT    44760
ATTTTCATAT TTTATTTAAC TGTAGCCATG CCACAATAAT TTAGAGTTTT AAAGAACAAG    44820
TTTGATTGAA ATCTAAACTT TGTACAATCC TGAATTGAGA AGTTTCCTGT ATTTTATTAT    44880
GACACAATAT TTACCTAAAA ATAGGGTAAT TATGAATTGA GAAAACATAG CTATTAATTT    44940
CATACTCTTA TTTGTTAAGT AGATTTTGTC TGGAAAACTG TTCATATTTA AAGGAGCTTT    45000
GTACCTTTGT ATTCTTTTTG TTTTTCCTTG TTTATATAAT TTTAAACTCT GTTTATGGAT    45060
TTGGGATTCT AACTATGCTA AATAATAAAT TAAGGCATTG AATGAAGTAC CTAGACAGTA    45120
TTTTGATTAA TTTTATTCCC CCATTCTTAA TGTGCATGTA ACTGGAAAAT TAAGAGTGGC    45180
TTCCAAGGGA TCTACTACAA AAGTAAGGTT AATATGATCT CTTTTAAAAC ACTGAAGGCG    45240
TGTAGCCAGT GTTGTCATTA ATTCTGCAGT AGATATTTTC AGCACTTATT TACATGGGAA    45300
GTTAGAGCAG AGTAAGATGC ACCTGTAAAG CTAAATGTCCA CTTATTTGCA TATATATAAA    45360
ACGCAGGATG AATTTACCAT AGAAATATAA AGGGTACTTA TAGAAATGTA TTAGAAAAAT    45420
ATATGAATTT TTAACTTATA TCTAGAAGTT AACTTTATAC ATTTAACTTT AAATCATTAA    45480
TAGTGGTTTA ACACCATAAG CGGATGTTTA TGCATCATCA TTTTATGAAC AAAAGACATT    45540
CTAATTTTAG AAATAAAGTG ATTCAAAAGA GAATAAAATA TCTTACTTTT TCTTTTAAAA    45600
TTAATTTGTT TAGCGCATTA CATGATAATA GCTCAAGCTT GTGTGATTTT TCCCTAAAAA    45660
ATTGGTTTAT AAATATTACA TTTATAGTAT GAAGAAATTA ATCATACATA GTTTATTTAT    45720
CTAATTTCTA AATACCCATG GAAGAAAATG AATTTAATGG AATGTAGTTG TGTATTACTT    45780
GGTTTCGAGT GTGGGAAAAT TTATATGGTC TTTCTAAAAC AGCACTGTCA GTAGAAATAC    45840
AATGTGAGCT ACATATGCAA TTTAAAATTT TCTAGTAGCC ACATTTTAAG AAGTAAATGG    45900
ATGCAATTTA TTTTGATAAT ATAATTTAAT TAGTCTACTA TATTTAAAAT TTTATCATTT    45960
CAACATGTAA TCAATATGAA AATTATTAAT GAGATATTTT ACATACTTTT TTCTGTAATA    46020
AGCCTTTGTA ATCAGGTATG TACTTTATAT ATACAACAAA TCTTCTGATG CTAAATTTTA    46080
ACTGGAAATA CTTGATCTGT GTTTAGCTTT TGTAAAATTT ACTGTTGAAC AACGTGGACT    46140
AATGTGCCTA AGTGGTTCCA AACATATTTT AAAATTTGAA GACAAATAAA AGGGAACTCA    46200
```

*Fig. 5K*

```
AAGTAAATTG GGATACATAC ATACAACAGA ATACTGAGCC ATTAAAAAAT GATGAAATAG  46260
TAAAATTGGG GGAATTTTGA TGATACTAGG ATGATATAAT GACCAAGAGA CAAATACAAT  46320
TTTAGTTTGG TTGAGAGATG TGATCATCAC GTTGCTGATT TTACTATGTA TAGAGGTTAT  46380
CTTTTCCTTT CTAAGATTTT GAAACTTTAA TTAGTTAACC CACTTACCTA GTTTCTATTA  46440
GCTGTGTAAC TTTCTCTTCC TGTTTTTTGT TTTGTTTTTT GCTTTTTAAC              46500
TGCAGTATTT TGAGGAGTCT TGGAGTAGCA AGCTAATCTT TGGAAGAAAG GAAAATATAA  46560
ACCTGAAAAC TAATAATTTA AAGAACGTCT TTTCAGGTTG TCATTTGAAA AATANCTTGA  46620
TTTCTGATCN ACNTGATTTG AATTGAGTGT CAAATATTTG ATATGTTTTG TAAATTAGGT  46680
GAAGATGAGT GAGTAGGTTC TAAACTGCTT GGGTTTACCG CACTCTGGAG CATTGCAGGA  46740
GAATGTGATG TTGGAAGGAA GTGCTGAAAC ATAATTATTG GCTTGCCTAT AGGAGGGTGC  46800
TACATAATTT TAGAAGGTGT CAAGAAATTG ACACAGTCTG AATTAGTTCT GTTGAGTTGC  46860
AAAAAATGTA AAGTTTCTTG ATTCTGAAAA TAAGAAATAT GTTCCCAGAA ATCTCATCTA  46920
GTTAATGTGC TTTTAAAATC ATTGATGTCT CTTGTTATTA CAATAATAGC CATTGAAAGA  46980
ATCTTTTTTA TTAGAATGTT ATTTACAGGT ACGATTAGCT TCTATTTAAA TAAATTATTT  47040
TTATACTTGA TCTTAGGCAA AAGGCCAACA AGTGATCAGA ATAAATTATT TTAAGAGNAA  47100
AACTAATTAT AATTGATATT TGGAATTGGA AGCACAATTT CCTTTAGAAC AATTCCACGA  47160
ATGGTTGTTT TGATTCTCAA GGCAGCCCAC AAAAGACAGT TTGAAACACA ATTTATGCAG  47220
TGTCAATAGT ACTGACCTGA CTTTGGATCT TGGAGGCAGG GGCTTCAGGT GATACCCGAG  47280
TGGAGTTTTT ACTCCATTTC CATTCCGTAA GGCTATAGGC ATTTGAAAGA GGAAACTTTT  47340
CTTTGGCAAC CTTCCACCTT CCTTTCTACA GAATATTTCA GTATTTCTAG CTCATAGGTT  47400
TTCTAAAATA TTCTCTGTAA TTTATTTTGA AATGGAGTTT TTTTATCGTT TACAGATATG  47460
AGTAAAATTA GCCTAATCAG AATGTTAGTT CCTGAAAACA TTGACACGTA CCTTATACAG  47520
ATGGCAATTG AGATCCTTAA ACATGGTCCT GACAGCGGAC TTCAACCTTC ATGTGATGTC  47580
AACAAAAGGA GATGTTTTCC CGGTTCTGAA GAGATCTGTT CAAGTTCTAA GAGAAGCAAG  47640
GAAGAAGTAG GCATCAATAC TGAGGTATTA ATTATATATA GAATTTTCAT AAAGTGTCAG  47700
TTTGTTCAAT TTGCATATCC TAGTACTAGA ATGCTGTATT TTTTTGAACT GTTATGAATT  47760
CTGATATGAT TACTTTCTCT ATGTGCTACA TTTCCTTTGC TTTTCATAAA TATGATCTGA  47820
GAAAAGTGAT TAAAAAAAAG ACAGTAAAAG GGAGGTTTAG TCCATCTGTT TAGCTTATTA  47880
TGTAGAATGT CAGCTTAAAT TTTACCTGTA CCTCATATTG ACCGTATAGC CTGGAAAATC  47940
TTTCGGAGGT ATAGTTAATG GATTTAAGCA TATGCAGTT TATGTAGTTA ATGAAAGTGA  48000
AAACAAATTG TATTATAAAT ACCTCCCAAA CTGGTTTATT ATCATTCTAT CATTCTTCAT  48060
GCTCTGTTAG TATGATATTG AATATCTGAG GTACCAGGAT TATTGTTGCT TGTGGCTCTG  48120
AGCATTTCGT AGTGCTTTTG CATGATGAGA GAAAGATTAC AAATTTAGTA TTATGTTAGA  48180
TGGTACGTTT TATTAAAATC AAATGCTTCA AAAATAATTG CTCTGTGTAT GGCATGAGAT  48240
AAATAGCAAT CAGATATATT GTTAATAAT ATGACTCTAT TAAATGATGG CATAAATTTG   48300
AAAATTTGAC CTTCGGTATC TTCCGGGTCT AAAATTATAT GACTCCATTA TAAATATTTT  48360
GGAAATGATT AACTAAAAAA TTGTTTCAAT TCTTAGTTGG TAAATTCAAT GTGGTAGTAG  48420
GTGGTGGTGA TTATTTTGTA TTAGAGAATT AGGAATTACA CTTAGTTCTA AGGTAATCTT  48480
TATAGGATGT CCAGCAATTA AACCCCTACT TTTTTGAATT GCTAAAAAT AAGGGAACTG   48540
ATCTTTTTAA ATTCTGTACT TGAGTTACGT CTGTATATAT AGTCATGTCC TAGATAATCT  48600
AATGGAACTT AATTAGTTGG AAATCTTTAT ATTGTTTATA ACTGAACTAG CTATAAGAGG  48660
AACATTAAAG AAAACATATT TTGAGTGGAG GTAATGAAAT TTAGCTTCTA ATGCTCAGCC  48720
TTTTATTTCT GTAATCTATA CCAGATACCT AAGACCCTCT TATTGTTTCC CAGCTTCAAC  48780
CTGTCAGTAT AGAAAACGGT GTAACTTACT ATTTTTTCTC AATATTGAAG CACATTTGTA  48840
GTGAAATATT ATTTTAACTA TATATTGCCA TTTTTTGCTTT TTCCCTATTT CAGTAACATT  48900
TTTCGCTATT TCAGTAACAT TACATGTCAA CAAGAGAATG GTGGGTATTT TGGGGGGGGT  48960
TGGGTGGGAA GAAATTTTAC TAAGCTTGCT AGATTCTAAA AGGTATACCT TATTTGGCCC  49020
CTTTTCCCCA TTTAGGGGAA CAAGGGTGTT GGGGCTGGGA AGTAGATAAG AGGTGAAGTA  49080
AGTCATCCAA AGCATATGTC TTCATTAGCC TCCCTGTATG AAAAGCTGAT TTCTGTAGAG  49140
TGTTGGAGGC CTACTTTCAG AATCTGTCAT ATGTTAACAT TCATCTTCTC TACTGACCTG  49200
ATTTATATCC CTTAGTCTAT TTCATTTTAT AATTATGACA AAGGATAAAG TCATTAGAAC  49260
AAATTCTTTT TATTAGTTGA CGTATTGTTG TGTTATATC TCTTGTGTTT GTTATTAAGA   49320
TGGAAGCTCA ATCATGTCCT TGTTTAACAG AAAGGTGATG TCTTGGCATT GATAATTCTG  49380
ATTCAATATC CATAGGTACA TGGTGGATTC TTTAAATATT TAGTATTCTT TTATTTCTGG  49440
AAAGTTTTCT TAAATGATAG TTTTTTTAAA ATTTCATTTC TATAAAGTTT TCTTAAATCA  49500
TACTTTTTAG TGTTTTATTC CATTACTTCA TATTTCTTCT TCAGGAACTC CTGCTATACA  49560
TGTATGTTGG ATCTTCATTA CCCAGCTTCA ATATTTTTCA CTTTTCATGC ATTCTTTTTA  49620
TTTCTTCATT TCTCTTTAAA TTTTTTTCTT CCTTTTCACC TTCTATTTCT CTTTTAACAT  49680
AATTGTATTT ATTTCTGTAT TCCACATAGC TTAGTATTCA CTTATTTTAA AATTATTTTA  49740
AAACGTTTTT TAGATTTAAA AATTCTTTTT TTATTTATAT ATACATATTT TATTTTTACC  49800
AAAGGAGCAA CACTATTAAC TGAAGACTTC TATAATTTTT TTCTTTTATT TCTGATTCTT  49860
TCTTCGGTTT TCCCCCTCAG TTTTGAACTT TTCTAATTTT GATTTGTGAT GTCCTTTTGT  49920
ATTTTAGATA ATTTTCCTAA TGTTTTCCAG CTCATTTGGA AAGGCTACAG TTTTATTCTG  49980
TACCTAAGCA AGTCTTTCTG GTGTCAAGGA TTTGACCTTG ATACTTTTCT TTTGCTCATT  50040
TTCGTATGAG ATTAGTTTTC CTGTACTTTC AAAAGAAGGC GTGGTTCAAG ATGGCTTTCC  50100
CAATTTCACA TCTGTCTCTA ATGTTTTTGT GTAATGTCTA AAATATGGAA ACTTGGTTTA  50160
TGAGATCTAC TCTGCCATTT TTATCTGGGC TTTCTCTTCC TTTTGTCTCT GTTGTACCTG  50220
TCCTGCTTGG TTCTGATTTA ACCCCAGTGG TTTCCTGGA ATGTGGAGCC TTCTCCTAGA   50280
AGGCAGCCTC GGCTAGTCCC AGGGTTCAGA GTAGCCAGCT GCTCTCTTCA CCTAAGAGAC  50340
CACTGTGGAT TCCTTGTACT CACTTGCTAT TGGCTTGGAC AAAAGCCCTC CCATTTTCAG  50400
```

*Fig. 5L*

```
ATGCTATTAT CAGATTAATC TCTCATTAAT CTGTCTTTCC AGTGTATGCC TGTGGGCTAT  50460
CTTGGGGTTC TCTTGTTATC AGACACCTCC CTGCTGGCCT CTGCTTTCTC CCGTACAGAT  50520
GTCAGTACTG TGCAGGTCTT AATTGCTGTT GGTGGTTTGC CCCTACATTC TTACAGTTTT  50580
AGTTTCCCAA GGATACCTTT AAACTTGGTT TTATTGTAAA TGTCGACAAT GGATTTTGGG  50640
TTTTACTATC TAGTTCTGTC TTAATTCTGG AATTCAGAAA GATTAAAAGC TCTGTTGTTG  50700
CAGCTGCTGC CACCTCTTCC CAGTACCCTC TCCTCCTATG TCATTTTTTT CTTCTTATTT  50760
TTCTTGACTG TATAAGAGAG AATGTATGAC ATTTCCTGCT TGACCGCTGA GTTTGATTAT  50820
AAATTAAAAT ACACAATATT TTATACAAAT TGTTTTGTAG AAGATTTATT TACAGATGCT  50880
CATTCACAGG TAAAATTGAC TTATGAAAAT AGTTTTCATG ACAAATGTAT CAGGCTCGGT  50940
AACTAAATAT ATGGATTGAT CTTGTTTATA AATGAAATTA AATGTGAATG TAACTTACAT  51000
ATTTCTGTAT TTGCTTACAT CCGTATGTAC ACATATAATC AGCAAATGAG TTGATGTTTC  51060
CTATTCGTAA CTTAATGGTA ATAGCTTGGT AACAGAGTTG GGAGTATTAA AAAGATGTAA  51120
AGAGCCCCTT AAAATTTTGT TGCTGGGAAT TTTAGTGTTC TACTGATGAA GGAAATAGAC  51180
ACTGGAAGGT GTTGTTTCTA TTAGGTAACT TAGATATCAT ACTGAAGACT TCAAATACTT  51240
ATTGTTGACA CTCAAAAGAC ACACTTAGTG TAAGTAAGCA TTTCCCCGCT TTTCCCAATG  51300
AAATAAGATC ATTATTATAA TTCCATTATA AATGCTGATG ATCATATTTA TAGAAATATA  51360
GAAGATAAGA CTTGAAATGA TATTCGCTAC CAATTAATGA GTTGAAGAA GAAATCAGGA  51420
TGTGTTTTGC TATTTTACAT TTATTCTTAT TTAACTCCAA AGAATTCAGT GATGTTATGT  51480
ACTATTATTT CCATTTCTCT GTGAAGACGT TGAAGCTTAA GTAACACGCA TAATAAGGTC  51540
ATACATTTAG CAAGTGGCTC AATTAAAGTT CAAACCTGGT TCTGCCTGGT TTCAAAGTCT  51600
GTGCTACTCC ATGGTATTAG GCTACAACAT GACTTAGGGT TTCTTCCTCT GCTCTATTGC  51660
TGTTCAGATG TACTCCTCTT TTGGCAGAGT GGGAGAAAAT TTTTGCAATC TATGCATCTG  51720
ACAAAGGCCC AATATCCAGA ATCTACAAGG AACCTAAACA AATTTACAAG AAAAAAAAAA  51780
AAACATTAAA AAGTGGGCAA AGGACTTGAT CAGACACATC TCAAAAGAAG ACATTTATGT  51840
AGCCAACAAA CATATGAAGA AAAGCTCAAC ATCACTGATC ATTAGAAAGA TGCAAAATGC  51900
CTTTTCTGTA TGCCACCTTA TATCCCAGT ATTTATTATT TCTAAGTCAT AGTATCTTAC  51960
AGTGTATATA AGTCTCATCC GTTCTCTTC CCTGCTTGCA ATTGGGTACC  52020
TAGGAACAAA GTTGCAATCT TAGCCAGTTT TTTCTTTAGC CTTTGCTGAT GTGTGAAAAG  52080
CCCTTTTTTC TACCCTGGAT TTCTGTACTT AAGCTGGAAC AGCTAAGTTT TTACCTTTTT  52140
TAAATATAAA GTTTCAGAGT CTTCTGCCAA GGATCTTTTG CTGTTTTCCT ACTGTTAAAT  52200
ATTTCAAAGC CTTTTTTAAA CATAGGGAAT ATAATCAAAC ATAGCAAGCA GCTGATGAAC  52260
AATATCTAGA TAGTCTTCAT TATTGAAATG GAATAAATGG TATTTTTGTA TTTTAGGCTA  52320
ACAGACACCT TGTACCTTAG ATAAGGCCAA CCTTCTCATA AAATCCCTCA GTTACTTTTA  52380
TTAATAATAA CCAAATTAAC TCTGGATTCC AGGGTGTACT CATGATGGAA TGATTTCTCT  52440
GTCATGTTAT CCTGAGGATC TAGTACTCTG AGATAACATA AGTGTATGAC ACTTTAGGCT  52500
TATGAAACAC TTAGCTACTT AAATTATTTA ATTTTTTTTC ATGTGCAGAT GGTATTGTAC  52560
CCAAACACTA CCTTTGTGTG TGTGTGTGTG TGNNCGCCTG TGTGTGTGTT TTTGAGACAG  52620
GGTCTTACTC TGCTCAGGCT GGAGTGCAGT GGCGTGATTA TAGCTCACTA CAGCCTTGAC  52680
CTCCTGGGCT CCAGTGATCC TGCCAAAGTG TTGGGATTGC AGGCGTGAGC CACCTCACCC  52740
AGCCTTAAAT TATTTTTTTT TCAAGGATGT TTAACCTGAG GGTTAGAGGC TCTTTGGCAC  52800
GTGAGCTGCT GAAATGTGTG TGAAAGTGTT GTGCACGTGT ATGTTCTCT TTTTTTCTGG  52860
GAAGTGGATC TGTAGTGATT CTTAGATGAG TCTATGAGAC AAGAAACTTT TATTTTTTTC  52920
ATTTATTTAG CGAATGTTTG TTAAGCGTAC TATGCCTTGG CCACTCTACA GGGTGCTGAT  52980
TGGACCAGTC TGTCTACCTA CCGTTGTAGA TGTTAGAAGC TATATTCTTT TCACATGCCT  53040
AATATAACTC TTTGTGTATG TATACATGCC CAGGCATGTT CCTTCCTCAG AACATTAAAT  53100
TCACCATTTT GGTCAACTCA AAGCAAGTAC ACCATGGGAC ACAGATCTGA AATAATGTCC  53160
AGATTTTTAC TTACTGAATG AGGTGTGTTG NAGTGTATAA GACTACATGA TGAGATGGCA  53220
AGTAATTGCC TGAAGAAATG ATGTAGTGAT TTTGTGTGTC TTATATTTAT TTACTTTTTG  53280
ATCCAGAAAT AAATTATATA GATACCACTA TTTTGTTTGG ATGGGGGAGA AAGGATGGGT  53340
GTGTATTCAG GAACTTATGT TACTTTTTTG CAACTAATAC CCCTTCTCAG TAGTACAAAG  53400
ATTTGATTTC TTTTTCTTTC TATTTCCTAC AGACTTCATC TGCAGAGAGA AAGAGACGAT  53460
TACCTGTGTG GTTTGCCAAA GGAAGTGATA CCAGCAAGAA ATTAATGGAC AAAACGAAAA  53520
GGGGAGGTCT TTTTAGTTAA GCTGGCAATT ACCAGAACAA TTATGTTTCT TGCTGTATTA  53580
TAAGAGGATA GCTATATTTT ATTTCTGAAG AGTAAGGAGT AGTATTTTGG CTTAAAAATC  53640
ATTCTAATTA CAAAGTTCAC TGTTTATTGA AGAACTGGCA TCTTAAATCA GCCTTCCGCA  53700
ATTCATGTAG TTTCTGGGTC TTCTGGGAGC CTACGTGAGT ACATCACCTA ACAGAATATT  53760
AAATTAGACT TCCTGTAAGA TTGCTTTAAG AAACTGTTAC TGTCCTGTTT TCTAATCTCT  53820
TTATTAAAAC AGTGTATTTG GAAAATGTTA TGTGCTCTGA TTTGATATAG ATAACAGATT  53880
AGTAGTTACA TGGTAATTAT GTGATATAAA ATATTCATAT ATTATCAAAA TTCTGTTTTG  53940
TAAATGTAAG AAAGCATAGT TATTTTACAA ATTGTTTTTA CTGTCTTTTG AAGAAGTTCT  54000
TAAATACGTT GTTAAATGGT ATTAGTTGAC CAGGGCAGTG AAAATGAAAC CGCATTTTGG  54060
GTGCCATTAA ATAGGGAAAA AACATGTAAA AAATGTAAAA TGGAGACCAA TTGCACTAGG  54120
CAAGTGTATA TTTTGTATTT TATATACAAT TTCTATTATT TTCAAGTAA TAAAACAATAG  54180
TTTTTCATAC TGAATATTAT ATATATATTT TTTAGCTTTC ATTTACTTAA TTATTTTAAG  54240
TACCTTTATT TTTCCAGGAT GTCAGAATTT GATTCTAATC TCTCTTATGT AGCACATGTG  54300
ACTTAATTTA AAACCTATAC TGTGACACAG AGTTGGGTAA ACGATGATTA TTTAACTTTA  54360
AGCAGTTCAC CATCCATTTC AAAGCCTTTG ATTGGCTTTT TTGTAAATAA AAATAACTTG  54420
TTAAGAAACA AATATATCTG TCATAGAAGA ACTAGAAAAT CCAGGGAAGT GAGAAAAATG  54480
AAAATAAAAA NTCATTCATA GTTTTACTAG TAGCTAATCA CAGTCAACCT CTTTTGTGTA  54540
TCCCACCAGA CTTTTTTATA TTCATTTGTT TTTAGGTAAA ATATAAAAGT CTCGTATATT  54600
```

*Fig. 5M*

```
CCCATTTTTC TGCATTGCAT TACCAGAAGG TAGTGGCGCC TATTAAATAT GTGATATGTT  54660
GTTGTCCAGC CATGGCTTCT GCATTTGCAT GCTTTTGTGT GTGCATCGC AATACCCTGT   54720
GAATATCCTG TGTGATGGAG TGGCAAGTAC GCACAGACAC GTCTGCTGCA TGCCTAGGTA  54780
CGAGGCTGTC TCCAGGAGAA GCACTTGTTT GATTATTTGA GTTGCCAATT GAATTTGCTG  54840
CTTTTTTTCA TGGCTTGCCA TTTTCACTGA AAAGAATGAC TAATGAAAAA CGATGATTGG  54900
TTATTAGATT TGGATGTTTG GCAGACATTT TCTCAAAATT GAACTAAGTT GGCCTCTTCA  54960
CGGAAAACAA CTGGTATTTG TTGTGCCAAT GATAAAATTG GAGATTTCTA GCAAAATGTA  55020
TAATTTTGGA AAAGTTGTGT TCCTCCACTG GAAGCTTGAC AGCTTTCCTT AACATAAAGA  55080
CTTCTCTTTC TCTTCGCTTT CACTACTACT ACTACTAATT CTTCTTCTGA TTCTTCTTCT  55140
TCTCCTTCTT CCTTCTTCCT TCCTTCCTCC TCCTCCTCCT TCTTCTTCCT CTTCCTCTTC  55200
TTCTTTCTCT CTTTCCTTCC TTCCCTTCCC TTTCCCTTCC TTCCTTCCTT CCTTCCTGCC  55260
CGTCCGACCG CCCTGCCTTC CTTCCTTCCT TCCTCCCTCC CTCCCTCCCT CCCTCCTTTC  55320
TTTTTCTTTC TTTCTTTCTC TCTCTCTCTC TCTTTCTTTC TTTTTCTTTC             55380
TCTTTTTCTT TCTTTCAAGC AGTCCTCCCG CCTCAGTCCC CCAAAATAGT GGGATTATAG  55440
GTGTGAGCCA CCATGCACAG CCTTACATAA AGCCTTTTCT AATGAGATGG ATAGTAATTA  55500
ACAAATGTGA GTTTTTGATA TTATATAAAG ATTTTTTCTG TGTTTCGAAG ATCCGTATAA  55560
CTCAGTGAAT CAGTATGTTC TGGATGACTA ATATGTGATG TTAAGAAATC ATGACTGAGG  55620
CCGGGCGCGG TGGCTCACGC CTGTAATCCC AGCACTTTGG GAGGCCGAGG CGGGCGGATC  55680
ACGAGATCAG GAGATCGAGA CCACCCTGGC CAACATGGTG AAACCCCGTC TCTACTAAAA  55740
ATACAAAAAT TAGCTGGGTG TGTTGGTGCG TGCCTATAAT CCCAGCTACT CGGGAGGCTG  55800
AGGCAGGAGA ATCGCTTGAA CTCAGGAGGC GGAGTTTGCA GTGAGCTGAG ACTGCGCCAC  55860
TGCACCCCAG CCTGGCGACA GAGCAAGACT CCGTCTCAAA AATAAAAAAA GAAATCATGA  55920
CTGGGTAAAA GATCTGTTCA GAGTACAAGA TGGACCAATG GATTTGATAT ATTTGAATAT  55980
AACAGAGTAT GAAAAAGTTT ATTGATATAG TTTCAGATTA CACACTGCAA CTAATCTTTA  56040
AGAAACTATT ACTTGTCCAC TTTTTGGTAA AATTTCAGAG AACAATGTCC ACCATTATCT  56100
GAACAGGCTA TTAAAATACT CTTCTCTTTT CCAACTACGT GCCTGTGCAA AGTCAGATTT  56160
TTTTCATATA CTTCAGCCAA AACAGCATAT CAAAATGGAT TGAATGCAGA AGTAGATCTG  56220
AGAATACAGC CACTTTTGTT AAGCCAGACA ATGAGATTTG CAAAATGTAA ACAATGCTGC  56280
TGTTCTCAGT TTTTAAAAAT ATGTTTTTTA AAAGTATTTA TGTTAATGTG TACTTGGTTT  56340
ACTACTGCTA TTTTTAAATA AAACAAGAAA CATTTTTAAA TGTCTGTTTT AATTTCTAAA  56400
GTGGTAGTGA TAGATATAAC CCATATTAAT AAAAGCTCTT TGGGGTCCTC AGTGATTTTT  56460
TTTTAAGAGT ATGGAAGGGT TCTCAGACCT AAGAGATTGA GAAATGCTGA TGTAATGTTT  56520
TATTATAAAG GTGTACCATG AATTATGTAC CTTACTTCAT ATTGTTGGAC ATTAAAGTTG  56580
CTTTCAGTTT TTTTGTTTTA AACAGCACTG CTTTGACCTT TTTTAAAAAA TGAGTCAGGG  56640
TCTTGCTGTG TTGCCCAGGT TGGAGTGCAG TGGCTATTCA CAGACATGAT CATAGCATGC  56700
TATAGCCTTG AATTCCTGGG CTCATGTGAT ACTTCTGCTT CAGCCTCCTG AGTAGCTGGG  56760
ACTATAGGCG TGCACCACTA TGCCCAGCTG CTTTGAATAT TCTTGAAATG AAATATGGTA  56820
TAGTCTCATA CCATATCATA GCCAGAGGGG GAGAGAGAGA ATTTTGTTGT TGTTGTTATG  56880
TTATCTGTAG TGGACTTTAT GCCTTCCCAG CATAAATTCT CTCTTTCCCC ATTTTTCGTG  56940
ACCCTTGATT TTTGTTGGGG TTCGTTCCAA GGAGAATAAT TTCCATCTGG ATATTGGATT  57000
GGCACCTGTG ACCTCTTCTG AGCTAGACCC TAGTAACAGC GTTTGGATCT GGGGTAGGTG  57060
TGTGCCAAC TGAGCTGCTG GTTCATGCCT TTCCTGAAAT GAGCCCTACC TCTGAATATT    57120
TCAGAAACAT GGGACATTAA CTTCCCTTTA CTTACGTTAA ACCCCTTTGA ATGAGGAGTT  57180
GTTTTTCACT TCCAGTTGTG TTCAGTTGTC ACAGAAGCAC AGCGATGTGA TTGGTGGAAG  57240
GACCCGTCAA CAGACCCAGA AGATGTAAAG TGTTTTTAAT CTCAAAGGAT GTGGAATCTC  57300
AGAGATAGTT ACACCGAGTA GAGGATGAAG CGGCCTCCTGG ATGGAGGCAG AGGCTTCCTG  57360
GATCTTCAAG TTCTGTATGG GTTGTTGTAT GAGGTTGGTG CAAAAGTGAG GCAGGAGAAT  57420
AGGGTCTGGA GGCAAGGAAA CTAAGGCCGA TTCACACTGA CTTCCTAGAA CTAAATCAAA  57480
AGGAAAACCC CAATTTTCCA GACCTAAATA ACAAAAGTAC CAGATGGCTC CTCCCTTTCA  57540
ACTGCCCTC CCCCACACCT TTCTGCGTGA CACATGGAAA ATTGAAAGTA TCTCTGGTTG    57600
CTTCTGCGTA GGAATGTAAC TTTGTAACCA ATCAGACGGA TCGCAGGCCA AGTCGCCTGC  57660
ATAGAAATGT AACTTTGTAA CTTCACTTTA GCCTCTGATT GGTTGCTTTC CACAACCAAT  57720
CAGATGCTTG CATAGGGTGT ACCTGTTGTG ACTTCACAAA GTGGTGGAAG TGGTGGAAGT  57780
GGTGGAAGGG TGGAAGGGCT ATTTAAATTT TTATTCATCC TCTGATTGGT TGTTTCACTT  57840
AAGCCTCTAA TTGGTTCTTG AGTCCTGGAG CCTGTGAAGG GTACTTTATT TTCAGTAAAT  57900
GCATGCTTTT TTTGCTTCAT TCTTTCCTTG CTTTGTGCAT TTTGTTCAGT TCTTAGTTCA  57960
AGACACCAAG AGCCTGGACA CCCTCCACTG GTAACAAAAG TAACTGGTGT TTTTGCCATT  58020
AGAAGTAATG GCACAGAACA AGTACATGAG AGCGATTTCT TATGGAAAAT TAAATGGCGC  58080
ATAAGTCGTG TGCTCAGGTA AGGGAGCTGG GAACCGGTAG AGGAAGGTCT CCAACCCACA  58140
CCCGTGGGAT CTCTGAGTCT TTGAAAGTCC GTCCTCACCC TTTGTGAAGA ATGGGAGCAC  58200
GGCTGGACTC GTCACCGGGG GTTTTGGGGG GCTGAACTTG TCATTTGAGG GTGTAGGGAG  58260
GTTGGATGAA TCGCAGGGGT GCAGGGAGGG GGCCCACTGG AGCTCCACCA GGACCCCAGC  58320
ACCCTAGATC CAAACCTGGT CATGCTTCCC ATGCTCCAGG GCAAATCTCC CTCCCCTTGG  58380
GGGGCGGAGT CAGACAGAGAC CCCCTCTCCA TCCTTTTCCA GGTCCGGTGG GGGCGGGACT  58440
TTAAAGGTAA AAACAGCAAT TACTTTTGCA CCAACTTATC TTCTAAGTTT CGCTCCCTAC  58500
CACCTGAGTG TGTTTGGAGG CTCTGGCTCA TTGTACCTGC CTGATCACCA GGTGCAAGTA  58560
GCTGGGCCAG AAGGACCTCG GCACGTTACG GAATATTTAC TACAGGAACA GGTGAGCTGA  58620
AGGCGAATTC CCCAGGTGTA GCCTGTGACC ATAGATTCAG ACAAAGCCCT GACTGTTGCC  58680
TGGAATTCAA AAAAGCTGTA GCCCTACCAG ATAGAATAAG AAAAGAATAT AGGATTCTTC  58740
CTATTCAAAT AGGTTGCATA TAATTAAGAG CATGAACGAT CCAATGGAAT GAACTCAAAG  58800
```

*Fig. 5N*

```
TAGTTTTTGA GTGTAATAGA CTTGAAGTGT CTTATGGAAA AGAATTGCAA AACCACAGAA    58860
ACAGTGAAGA AGGTTAGTTA TAGCCTTGAT GGGGTAGCTG ACTTCAGCAG TCTCAGCTAT    58920
CTGAAAAGTT ATTTACCAGA TTTTGGTTGG GAACATAATC CCTAAATCAT TTGAGATAAT    58980
GTACTTGTTT CCTTACTGGG TAAATGTGTT TAAACCTTGA GNAAAATGTA GACATAAGTA    59040
GNAATATANG AATAAATTAA ACCTTTGGTA GTTATGTTTT AGGATTAAGG ACTAATAAGT    59100
ACATATTTGA TATTTAAGCA TTTGTAATGC TTGAGATAAT TTATCCTACT CAAGTAACAG    59160
ATTACTCTTG TGACTCCAAT GTAAAATATA TCATTGAAAA ATTAGTATCT GCTTGTGATT    59220
TTTAAGTAGA AACCCTGCCA TTTGAAAGGT ATTTGCCTTT ATTATTGGAG ATATTTCATA    59280
TGAATGTTTA ACTTTGTTAT TGCATAGAAG TATTTAAACA GATTTCACTT GCAAGAGAAA    59340
GATATCTAAT AGGTTACTCT TAATCAGTAC TAAATTACTA CAATTACTAT ATTCTATTAA    59400
TATCGATTCA TTAAAACCCA GAGCTTTAAT TATGTCTCAG AAAATTAATT AAACTTTAGC    59460
CTCATAATCA GCTTTATTTT CTAACTCAAT GTTTAAAAAT TGACAAGTAT GTATTATACT    59520
TATTTATGTC TTCATTCAGT AAACATTTGC ATTTGTAGCA TGCAAGACAA CATGCTAGAC    59580
ACACGAAAGA TGGAATAAAT GGAAGAAAAT GCAACACAGA TCTCATGCTT AAGAGGGACA    59640
GATTTACTCT GAAGATTCAA TGAAAAAACA TCCACAAACA ACTTTTCTAC AAGAAACAAA    59700
ACATTTTAAA GAAAACATTT ACTTCAGCCG GGCGCGGTGG CTTACGCCTG TAATCCCAGC    59760
ACTTTGGGAG GGCGAGGTGG GTGCATCACG AGGTCAGAAG TTCGAAACCA GACTGGCCAG    59820
TATGGTGAAA CTGTGTCTCT ACTAAAAATA CAAAAATTAG CCTGCGTGG TGGTGTGTGC    59880
CTGTGATCCC AGCTACTCAG GAGGCTGAGG CAGGAGAATC GCTTGAACCT GGGAGGCAGA    59940
GGTTGCAGTG AGCTGAGATC AGGCCATTGT GCTCCAGCCT GGGCAACAGA GCGAGACTCC    60000
GACTCAAAAA AAAAAAAAAG AAAAAAAAAA AGAAAACATT TACTTCACAT AATAAGATAT    60060
GAGAAAAAAT GGACTCTCTG AATGAAAAAA AGAGGAGATC ATGTGAAAGA TTTGCGCTTT    60120
TTTTTTTTTT AAAGTTATGG ACTGAAACAC TCCTAATCAT TAACATTTGT TATTTTAGGG    60180
GAGTGGAATT GGAAAGGTGG AAAGGGCTAT TTACATTTTT ATAATCTCCA TGTCTTTTAA    60240
ATCAATATAT ATTGCATTTA TTCTTTTAGT TAAAATTTTA AGAACTCTAT AAAAAAATAGA   60300
GACAGGGACT CCCTTTGTTA CCCAGGCTGG TCTCAAACTC CTGGGATTAA GTGATCCTCC    60360
CACCTCAATT AGAAGGGTGG AAGGGCCAGC TGTTTAAGTT TCTATAATCT CTGTTAAATC    60420
AAATGTATAT TGCATTTATT ATTTTAAATT TTAAAAACTT TTTTAAAAAT AGAGATGGGA    60480
TCTTCCTATG TTGTCCAGGC TGGTTGTGAG CTCCTAGGAT CAAGTGATTC TCCCGCCTTG    60540
ACCTTTCAAA GAGCTGGGAT TACAGGCATG AGCCACCATG CCCAGCCTAT TTATTTGTTT    60600
ATTTATTTTT AGAGGCAGGG TCTCACTCTC ACTAGACTGA AGTGCAGTGG TGTGATCATA    60660
GCTCACTGCA GTCTCAAACT CCTGGACTCA AGCAATCAAC TAGCCTCAGC CTCTGAGTAC    60720
TGAGATGACA GGCATGTGCC TTCATACCCA GCTAATATTT TTGTAGAGAT GGGGTCTTCC    60780
TGTGTTGCCC GGAAGAGTCT CAAACTCTTG GCCTCAGCCT CCCAAAGCAC TGGGATTGCA    60840
GGCATGAGCC ACAACACATG GCCCTGCTTT TAAAAAATAT ATAGTGGGCC AGGCTTTCTG    60900
GGATGATGGG CAACCATTAC ATTTGCTTTC TCTCCATTCT GAATGTCAGC CTCCATACAC    60960
CTCTCTTGAG CCATCTCTTG ATGCCCAGGA CTGGCAGGCA AGCAGGATGT TAGGGTGCTG    61020
GCTGGAGGGC TGGAAAGCCC CAGGGCAAGG ATATGAACGT GAAGGATTTT AAGGAGATTC    61080
TTGGACCTCA AGGGAACTTT TGGTTCCTGGT TTCCTAGATT ATGTTAGATC TTCTTGGCCC    61140
CCAAAGAATC AAGGAAAAGC TGAATAGGTG GACCGAATCC TTTCCAGCAC TGAGGCTGGG    61200
AGAACTCTAT GACACCAGTG GGTGCTCATC CTGGTGCTGC CATGGACCTG ACTACCTACT    61260
TCCGCTAAAC TCTCCAGCAG CTGAGCCTTC AAGAGAAGAC GTCCTCCACC TTTTCCATGA    61320
GATGAAGAAT CCTTGGGGCC AGGGGATGTG CTCACTAGCT CACACCTGTC TCCATCCTCT    61380
AGACCATGCT TGCAGTACAC AGGACCCCAG AATGCCTGGC CCAAACACTC GTGAGCCTCC    61440
AGGGGCTGCA GGGGCTTCTG GCCTTGTTTC CCCATCTGAT GAGTTCGTTT CTTGGTCTGA    61500
AAGATTGTGA CAGTTACTAC GAGACTGAAT GAAGGGGGAT GAATGCAGAA ATGAAAACTT    61560
AAGACAAAAG TAACTTTTAA TGAGAGGGGC CGAGGGAAGA AGAAGAGGGC TCCCTGCTTC    61620
TAATGAGCAA AGGCAGCCAC CCTGACCTTC TACAGCCTTT CGTATTTATT GAGTAGAAAG    61680
AGCAGGGAGG AGGAGGTAAT GATTGGTCAG CTGCTGGATT GATCACAGGT TCATATATT    61740
GCTAACAGGC TTCAGATGTG CCTGATCACA AGAAACACTT GCGCCTGGGC ATGACTGCCC    61800
TCAGCATTCC TTCTGGGCGG CAGATGCAGT TTGTCAGTTT GCTAACAACC TGCTTTCATG    61860
AGAACAGTTT GCTGCTTACT TACACAGCCA CCAGTGATTT ACTGAGTTGA TCACGACCCT    61920
CACTCTTTCG GCCTCCAACA AAAGACGATC AAAGAATGGT TGTTTGCAGA GGTTATGGAC    61980
AAGACTTGAT GTCCAGGCCG AGTGTCCGTA TGCACAGGAG CCTCTTGGTG GTGCAGAGTG    62040
AAGCCAGAGG AGGAGGAGTG GGTTGTGTCC ATGGGCTGAT TCTCCCTGCA CCAACAGGAC    62100
AGAATCCTAA GGAATCCGAG CATTTGAAAT TCAAATCTGG TCTTACAGGT TGTTATATAT    62160
TTGTCTAGGT AGGAGGCTAG AATGATTGA AATGAGGGTTA GCCTGACATA TTTATATATT    62220
TCATATTTAG GCTTCCATTT GTTCCTTTGT CTTGGGTCCC AAAAATATAT TAGAGGTGGG    62280
CCTGTCTGTT CTCTTGGACA CGAGGACCTC AACGAGTTTC CACTGTTCTC TGAATGTTTC    62340
CTTCCTGGTT TTCTGTGTAT ACAATAATTC CTAGTTTTCT GTTATTTACA ATTTTACTTC    62400
CACTTTTTAA AGACAAAAAT GTATGTTTTT TTAGTCAATA TTGATATAGT GGACCAATAT    62460
ATTTTACCGT TATTTTTGCT TACTGTTTTT GTTTTTTTGC CTTCCTCATC TTCTCACTAA    62520
GTTTGTCTGA CTACAGCCAC ACACCATTCA TTCAATACCA ACTCTTTTTT ATTTTTATTT    62580
TTTGGAGAGA GGGTCTCACT CTGTCACCCA GGCTGGAGTG CAGTGGCATG ATCTTGGTTC    62640
ACTGCAGTCT CAAACTCTTG GACTCAAATG TTCTTCCTGC CTCAGCCTCC TGAGTAGCTG    62700
GGACCACAGG TGCACACGAC CATGCCTGGC TAATTAAAAA CAAACAATT TTTTTTTTT     62760
TAGAGACGGG GTCTCACTAT GTTGCCTAGG CTGGTTTCAA ACTCCTGGGG TCAAGTGATC    62820
CAATACCAAC TCAACACGTG GTGAGACCCA GTGGTCTAGA CAAACAGCCA CATAGCAATA    62880
TGTTTTTCTC CATGATTCAT ATCCATGTTC GTTTGTTACA AAATAACAGG CATGAACATT    62940
TTCTTCAGAG AGGGAGATCC CCACTTATCC ATTAATGACT CATTTGGTGT CCATTCCAAA    63000
```

Fig. 50

```
CTATTAAACT GCAAAAGCAG ACATGAGAAA AGAAACTTAA GTCAATGTTT TTATCACATG   63060
TTGGTGCCAG CCTCCCATAG TGGTGCTAAA TTTATGNAAA TTGCAACAAA ACAAAAACCC   63120
AAACAACCCA ACAACGAAAA GCTATTTAGT GAACACCGTG ACTAACAAGC TTATTAGAAC   63180
TGCTTATCAG AGCTATGTGT GGATTTTGTA GGGGGAAAGA TTTTCTTCCC TCGTAGACAT   63240
TTTGCAAAAT AAAAGTAAAA TATTACCTTT ATGTACGTGG TAGATAGAAT TCCACAAGCT   63300
TCAAATTCAA CGACTCAAAA ATGTTGCTTT TACTTTCCAT ATCTCAGAAG TCACTTTTCT   63360
TTTATTTATT TTTTAGAGAT AGGGTCTCGC TCTGTTGCCC AAGCTGGAGT TGCAGTGGCA   63420
CAATCATAGC TCACTGCAGC CTTGAACTCC TGGGCTCAAG CAGTCCTCTT ATCTCAGCAT   63480
CCTGAGTAGC TGGGACTACA GGCGCATACC ACCACTCCTA GCTGATTTTT AAATTCTGTG   63540
TAGACATAGG ATCTTGCTGT ACTGCCCAGG CTAGTCTTGA ACTCTTGGCC TCAAGTGATC   63600
CTCCCACCTT GGCCTCCTAA AGTGCCGGGA TTGCAGGTGT GAGCCACCAT ACCTGCCCAG   63660
AAATCTCTTA TTTTAAACCC CAATTCCTCC TGATAGTAAA AAAAAAAAAA AAAAAAAAAT   63720
GTCATCTTGG TGTATTTTGG GTAGGCTGGA TCACTTCAAG TTTCCCCCTC CTCCTGAAGC   63780
TCCGACAGAG GCCTGCAAGC CCTGCTGGGA TCTGTCCTCA GTCCCTCTCG GGCTCATCTT   63840
CTACCATCTT GCTGTCACTC CATCTCCCTG TCCTTCCCTT TGCTTCACCC ATACCAGACC   63900
CTGTACTGTT TCTGGAAGAC ACCAGGCATG CTGTGTCTTA GGGGAGAATG TGATTTCACC   63960
AACTAGTGCC GCCCAAGTAA CATGCATTTG CCCTGACTGC TCTTTTCACC TGCTGTGCTG   64020
CTCCCCCAGA TAACCACAGG CAAACCCCGC CAACTCCTAG TTTATTGAAC TATACCATGA   64080
GTAACTTACT TAAAATCTCC ATACCTTGTC CCATTCTCTC TTACCTGTTC CAATACTTAT   64140
TTATGATGTT GATAGATGAT CTCCCTCTAC TAGACTGAAA GCTCCTTGAC AGCGGGGATT   64200
CTTGTCTGTT TTGTTCACTG CTGTGTCTTT AGCACCTGGA GAAATGCCTG GCACACAGCA   64260
GGAACTCAGT AAATAACTGC TGAATAAATA AACATGAATA AATCAATGAA TGGGGATGCC   64320
TAAGTGCTTC GGGATTCTGG TCAAAGCTTT GGCAACTAGG GACGCACAGG GACCCTCATC   64380
ATCTCTGCCT CCTAGGCAGG TATCCACTGA GATCCGCAAT CCCATCTGGT CCTTGGACCA   64440
GTTACCCTTC ATGTTGGCCT CTGTTAAGAT GTCCAGGTTG TATCTGGTCT CCCACACAGC   64500
ATCCCTTTAT TACTACCCCT GGACCTCAGC AGTCAGCCAC ACATTCAGTA AAGGCCACAG   64560
CTCTGCCATC TCCTAGCTAG GGGACTTTGG ACAAATTACT TAGACACTCT GAGCCTCGTT   64620
TGTAACATGC AGAGACGTTG CTGGGATTAG ACACAATGCC TGTAGACCAT TTAACAATTG   64680
CTGTCACACA TGGTTGGTAT TCACTCAGCT GTCGCTATGG AATTAGCAGA CAGAAAAGGC   64740
ACAGCGTCAG TGGCTGGGTG TCCAGAGAGA AGCAGCCTGT CTCTCTAGAT AATACTTGCC   64800
AAAATCACAG CAGTCCGGTG TGTGGCCCTT TACTGACCTT GATTAAAAAT CGGGTGTCAG   64860
CACCCCAAGT GGATCCTTCT TACAGGTGCA GATTCAGACT CATTATCCAA GTTGACAGAG   64920
ACAGAAGTAA ATATTCAACA AATATTTATT GAGCACTTAC TATGTGCCAG GCACTGTTGT   64980
TGTAGGTGCT GGAATACAGC AATGAACAAA AAAAGTGAAA CATTCTTCCT TAGATGGTGG   65040
TAAAGCGATA GGAGGACACA GCAGGGAAGG GGTTTGGACT ATTTCAATTT GGGACAGGAA   65100
ACGCCTTGCT GAGAGAGTGA GGGTTGAGCT CTGGAATTAG CCTGAGTTTG ACCACATGTA   65160
ACTGCAACTT TGAGCAAGTC GATCCACTGT AAGTCTCTTT TATTAACACC ATTGTGTGTA   65220
AGAGGAAATA GAAACTCAGC TAAAGTCGTT GGAGAATTGA ATGTGGTGCA GCATTTAGCA   65280
CAGCGCAGGA ATAATAAAAG CCAGCTGTTC TCATCCTTTG CCCATAGAAA AGCTATCCGG   65340
GAAGCCACAT TATAGTCTGA AGGCTGCCTA CTGGTTTGGT CAAAGAAAGG GCAGTTAGAT   65400
AATTTTCATG TTTAATTAAG GGCACGGGGC TAGATTTCTT GAGGTGCCAG AGTAATGCTT   65460
GCTTTTCATG AACAACGGAT ACAAGATATG GGCATTGCAG AACCTTTAAA GAACATAACT   65520
GGAATAATCA AATAACCGAA AGTTCATGAA ATATTCTGGC TCATGAATTA GTTATCTGGT   65580
AAATCACAGT CTGAAAGTCA CAGAATACAA ATTACTTTAA ATTTCCTCCA AAGCTTACTG   65640
AGTAAGGGGA GGGACATTTA AGATGCGGAG GAAGCGCTGA ACTTGCAAGA GGAACAAGGA   65700
GGACGGTGGC TGCTGGAACT CTGTAACCCT TAGAGAAGAT GTGGGTGGGA TTTGGCAAGC   65760
CCCCTAGACT CTCTTTGTTT TGGGTCTTAA TAGGGACAGT TTATTATTTT TAATGACTCG   65820
CGTGAATTGT ATACTGTTTT AAGCATCCAC CAAAAGCCTT TCGGCTTTTT CCCTAATTAG   65880
ACTCATTCTC ACACAGAGAG GAACTGAACT TTTTACCTCT TTGGTTCAAG AGCACCATCT   65940
ACTGGTCAGA TTTGGTAATT TCGGGTTTAT GGCACTGGAA AATCAAAGAG CATTTTGATT   66000
TGGTTGTGTT TGGTTTTGGT CCATTTATCA ATACAGGTTT TTTGGCGGAC AAAATAATGT   66060
GAAAATCAGG GGAATCAGGT GAGGGCATTG GATGTCTCTG TCACAGACGA TGGGGAGCTC   66120
AGCCGATTTT AAGCTTCTAA CCTCAGCTGG TCTGGAGAAG AGCAAACCTG ACAACCAGCA   66180
CGAAGAAAGT AGCTCTGCCT CTGTGGTGTG CTGGACATTC TGGTTACATA GATGGGAAGA   66240
CGAGGCCCTT TCCGACAAAT ATGCAAATCC CCCACATCTC CAAATTTGGT AGCTCTGGGG   66300
CTTAGGGCAG CTTCTGGAAA CAGAACTCAG ACCTAGCCTG CTGGAGCAGG AAGGGCTTCT   66360
GAGAAGATGA TATCTGGACC ATCAAGGAG TGTAAATAAG AAATAGCCGC CAGGCATGGT   66420
NGCTCACGCC TGTAATCCCA GCACTTTGGG AGGCTGAGGC GGGCAAGTCG CTTGACAAAG   66480
TCAGGAGTTT GAGTCCAGTC GGGGCAACAT GATGAAACCC CATCTCTACA AAAAATACAA   66540
AAATTAGCTG GGTATGGTGG TGCATGCCTG TAGTCCCAGC TACTCTGGAG GCTGAGGTGG   66600
GAGGATCACT TGAGCCTGAG AGGTTGAGGC TGCAGTGAGT CGTGATGGCT GCACTCCAGC   66660
CCGGGCAACA GAGTGAGACC CTATCTTAAA AAAGAAAGAA AAAGGAAGA GGTCAGGAGT   66720
TTGAGACCAG CATGGCCAAC ATGATGAAAC CCCATCTCTA CTAAAAATAA AAAAAAAATC   66780
AGCTGGGCGT GGTGCATGCG CCTGTAATCC CAGCTACTGG GGAGGTTGAA ACTGGAGGAT   66840
TCCTTGAACC CGGGAGGCGG ACGTTGCAGT GAGCCGAGAC CACACCACTG CACTCCAGCC   66900
TGGGCGATAG AGCGAGACTC CACCTCAAAA AAAGAAAAA AGAAAAAGAA AAGAAAAGAA   66960
ATAGCCAGAT GGAGAACAGG GGAAAGGCCA GAAGAGCAGG GGCGTAAAAG GCGTGGAATG   67020
GCATGCGGGG GAGTAACAAG GTTTTTTTTT TTTAAACGGA GTCTCACTCT GTTGCCCAGT   67080
TTGGAGTACA GTGGCGCGAT CTTGGCTCGC TGCAACCTCT ACCTCCCGGG TTCTAGCGAT   67140
TCTCCTGCCT CAGCCTCCTG AGTAGCTGGG ACTACAGGCG TGTGCCACCA CACCTGGCTA   67200
```

*Fig. 5P*

```
ATTTCTGTAT TTTTAGTAGA GATGGGGTTT CATCATGTTG GCCAGGCTGG TCTCGAACTC    67260
CTGACCTCAA GTGATCTGCC CGCCTCAGCC TCCGAAAGTG CTAGGATTAC AGGCGTGAGC    67320
ACCGTGCCCA GCTAGTAACA AGGTATTGAC TGAACCAGCA TGGGGTGTGT CAAGATCGGG    67380
AATCAGCAAG CAGCACAGGG GGTGTCCTGG GTGGGGATCT GGGGCTCAGG TCTTCCTGCT    67440
ATCCTGCTAC CCACCTGCAC ACTTGTTCGT TTTCTTTCCA CTCATTTTTC TCCCTTGCCC    67500
AGACTTCAGG TCTACCAGCT ACACTTCTTG ATTTCTTTGG CCTTCAAAAT TCGGTTCAAT    67560
AAGGAAAGTT TTAGCATTAT TTTCATATAG GTCCTTGACA TTTCTTGCTA AGGTTATCAT    67620
TAGATTTTTT TTTAATGGTG TAATAGTTCA GGCCTTCACT CAAATGTCAT CTCTCTAGAG    67680
AAGCCTTCCT TAACTACCAT ACCAAAAACG GTTCCAGCGC CGCTACCGTC TATCCCAGCC    67740
TATCCTCTCA CGTCCTGTGG TCCTGAGGTT CTGTGATAAT GTTCTATAAT TCTGTGCTGT    67800
CCAATATGGT AGCCACGAGC CACATGTATT CATATCGTCG TTATTGAGCA CTATATAATG    67860
TGGCTAGTGC AATTGACACA CTACAATTTT AGTTGAATGC AATTTAAATT AATTTACATT    67920
GAAATAGCCA CATGTTTGGC TCACACCTGT AATCCCAGCA CTTTGGGAGG CTGAGGCGGG    67980
TGGATCACCT GAGGTCAAGA GTTCGGACC AGCCTGGCCA ACATGGTGAA ACCCCATCTC     68040
TACTAAAAAT ACAAAAATTA GCCGGGTGTG GTGGCACGCG CCTGCAATCC CAGCTACTCG    68100
GGAGGCTGAG GCAGGAGAAT CACTTGAACC TGGAGGGTGG AGGTTGCAGT GAGCCAAGAT    68160
TGCACCACTT CACTCCAACC TGGGCAAAAG AGTGACACTC TGTCCAAAAA AAAGAGAAAT    68220
AGCCATATGT GGCTGGTGGC TATTGTATTG GACAGCACAG CTCTGTTTCT CCCACTAGAA    68280
TGTAATTTGA TGAGGGTGGG GACTTGGACT TATTCACAGC TGAATACCTA GAATGGAACA    68340
TAACTGCTAT GTTTTGAATG TTTGTGTCCC TTCCAAAATG TATGTTGAAA CTTAATCCCC    68400
TATATAAGAG TTGAAGAACC TTTTAGAAGG TAATTAGGCC ATGAGGGCAG AGTCCTCATG    68460
GATGGGNATT AGGGTCTTAT AACAGGACTT GAGTCCTCTA TAANGGAACG GAGAGTTCAC    68520
CTTTNCCTTC CCTTCTGCCN ATGTGNAGGA CACAGCGTGT GTCCCCTCTG AAGGACACAG    68580
CGACAAGCCT CCATTTTGGA AGCAGAGAGC AGCCCTCACC AGACACTGAA CCTACTGGCG    68640
CCTTGATCTT GGACCTCCAG CCTCAGAAC TATGAGAAAT AAACTACTGT TGTTTGTAAA     68700
TTGCCCAGTC TGTGGCATTT TGTTATGAAA ACAGCAAAAA CAGACTAAGA CAAATCAGTT    68760
CTGGCACATA CTAGTAACTC AGTGATTCTT TGTAGAGTGA GCAAACGTGT GAATGAATGA    68820
ATGAATACAT TGTCATGCGC AGCTTTCGTG GGTCGTGAGT ACAAATGAGA AAATACGATC    68880
ATGGTGCCAT TGCAATGGCT TGAAACCCCA GCACTTACTG GCAGGAAGTC TGTCATTTTT    68940
TGCAATTCTC CTTCCCAAGT GTTCCAGAC TCCCGAGAAG TGCACATGTA TATTTAGGAA     69000
TCAGTTCTCA TCTGCTAGAA CATGGGAAGG GAGTTAGTTG ATAGCAGTTC AGCTGCTTCA    69060
AATGCAGTCC TAGCTGACCC TGGAGGATCC AGGTACCTAT GGGTGCCATC ACGGCCACCT    69120
TTGCACTATC CTGTGAGAAA CTCTCTCCCA TCCTTGGTGA TGTCCTCCTG TGGTAACCTC    69180
AGTGAGAGAA CTCCATTGAT TCCCTAAACC AGAGGTCCCC AACCTTTTTG GCACCAGGGA    69240
CTGGTTTTGT GGGAGACAAT TTTTCCATGG ACCATGGGTG GGGAGGGGGG GATGGTTTTG    69300
GAATAATTCA AGTGCATTAT AATACGTTTA TTGTGTACCT TGTTATTATT ATTACATTGT    69360
AGTATAGAAT AATTATACAA CACACAGTAA TGTCTAATCA GTGGGAGCCC TGAGCTTGTT    69420
TTCCTGCAAC TAGACAGTCC CATCTGGGGG TGATGGGACA CAGTGGCAGA TCATCAGGCA    69480
TTAGATTCTC TTAAGGAACA TGCAACCTAG ATCCCTCGCA TACACAGTTC ACAATAGGGC    69540
TCATGCTCCT GTAAGAATCT AACGCTGCTG CTGATCTGAC AGGGGGCGGA GNTCAAGTGG    69600
TAATGTGATG GATGGGGAAC TGCTGTAAAT ACAGTTGAAG CCGCTCACCT CTTGCTTTGT    69660
GGCTGGGGCC TGGGTACCCC TGCCCTAGAC AGTAGACTTC TCAAGGGGAG GGGAAAGAAT    69720
GGGCCAAGGA ACTGTGTCAG TCAAGAGGGC CCCCACTCAA CGGAAACAGA CCAGCCACTG    69780
GTCTCACAGT GCAAGTCAAG GAAGCTGGTC TCAGAGCTGT CCTCAGAGGG GACGCGTGAT    69840
AAGCAGATCA CACCCGGGAA GACTCGGCAT CAAGATGGAG AGGAGGGAAT GCGATGCGCC    69900
TGGTGGCAGC CGTAGGATCT CCTTCCAAGG CCGCACTGGA GGAGAGCTGC CTCCTAAGAA    69960
CAGGAAAGTG AATCAGAGTG AGGCTGTCAT TATAGTAAGA TAAAGAAAGA TGAGTGCTTG    70020
TTTGGGAATC TGGACAGAAT TAGCATCTGC TTGCTTTAGG ATAGTGGCTT CTTTTCTCTC    70080
TTGAACAAAA TACTCTCCTT AATAACTGCA GACCCAGGAT AACATGGAGT CATTGTTCAA    70140
ATTCACCCCG TTGCAGAATT CTCCAGTTAT CAGCATTTGT GTGTGTGTGC GTGTGTACCT    70200
ACATGTGCAC AGATGTATAC ACACACAGAT AAACACACTC CAGGCTTTGG GGAAATCGTA    70260
TTCGTAGATG CCTGTCTCTA CCTTTATTAT GTTAAAGAGA ATTCTGACTC TCAGGTCGTG    70320
GACTTCATTC ATTGTGTTGC TCACATGCAG GAAAAAAAAA AACCAGAATG CAATAAGGAT    70380
AATTCATTGA TTTGTGGGGA AAGAGAAAAT TCATTGTTTT GGGGGGAAAG AGAGAATGTA    70440
TTGATTTGTG GGGAAAGAGT CAATAAGTGA ATGTTTCCTG TTCTAGGACT GGCTTTGCCT    70500
TGTCAATAAT TGATTTTGTT GTTGAAATA CATTTCAAAG CCTTTAAAGC AGTGTGCAGT     70560
TAAGGATGAT ATTTTTGCTT GAAATGACTA CTTTGCATCA TGTAGAAGGA ATAGTGTCTT    70620
TTAAAGGCAA CAGATGCAAG TCTAGGACCC CAGAGCTTTA GAAGGCTCTG GGCTTCGGGT    70680
ATGTGTCTGA TGTGTTGAGA GTTGCAGGGG ACGGGAGGGA TGTCCACTGT GGGCCAGTTT    70740
CTACCAGCCA CCGAGAAGCT GGAATTTGTT TATTCATTTA TAGAGCAACA GGAACTGGAA    70800
TCGAAATCTG TCAGTCCCTA TGTGCAGGGT GTAATTGAAT TGACTTCTCT GCTCTCAATT    70860
GGAACTTCCT TTGACCTGTA GTGAGAACAT TTTATGGCTC CCTCTAATCT AAAAAGGGTT    70920
TTTTTTTTTT TTTTAACTTT CCTTCCTATT CCCTTGTCTG CTAACCAACA GAGAACTCAG    70980
CCCACAGCCT CACAGACAGA ATGAGAGCAA TGCTTAATCC TTGTTCAGTG AATCTCATGG    71040
CCTCCTCTAG TCTTCAAACT TGGATTCCAA GTGCCTTGAA GAGCCAGACA CAGTGGCTCA    71100
TGCCTGTAAT CCCAACACTA TCGGAGGCTG AGGCAAGGGT GGATCACTTG AGATCAGGAG    71160
TTTAAGACCA GCCTGGCCCA CATGGCGAAA CCCTGATTCT ACAAAACATA CAAAAATTAG    71220
CCAGTCCTAG TGGTGCATGC CTGAAATCCC AGATACTCCA GAGGCTGAGG GAGGAGAATC    71280
ACTTGAACCT GGGAGGTGGA GGTTGCAGTG AGTGGAGATC GCACTACTGC ACTCTACTCT    71340
GTCTCAAATA ATAATAATAT ATATTTTTAA GTGCCTAGAA GAAAGAACTG CACTTCTGCA    71400
```

*Fig. 5Q*

```
GAGAGCGCCT CCAAAGCTCA GGGTAAGTGA CATGCTGCTT ACCATCCTAG AATGGAACCA 71460
GGCCACCCAT CCCCAGGTGG GACAACTGCA CTCCCAGGAT AACCCCTGAG TTATGGGCAG 71520
ACTTGTGTCT CTCCCCAGTT CAGATCTTGA AGTCCTAGAC CCAGTGCCTC AGGATGTAAC 71580
TGTAGATTCT TTAAAGAGTG AATTAAGATG AGGCCATTAC TAAAAGCCTA GACCTGACCA 71640
CTATGCAATC TATGCATGTA ACAAAATTGC ACATGTATCC CATCTCTACA AATTAAAATA 71700
AATAAATAAA ACTACGTCAT TACAGTGGGT CCTAATCCAG TATGACTAGT GTTTTTGTGT 71760
TTGTTTTTGT TTTGAGATGG AGTCTCTGTC ACCTAGGCTG GAGTGCAGTG ACACGACCTC 71820
GGCTCACTGC AACCTCCACT TCCCAGGTTC AAGCAATTCT CCTGCCTCAG CCTCCCGAGC 71880
AGCTGGGATT ACAGGCACGT GCCACCACAT TCAGCTAATT GTTTTGTAAT TTTTTTTTGA 71940
AGTTTTTATT TTTTATTTAT TTATTTTTAA TCTTTTTTTA TTTTTTTTTA TTTTTTTACT 72000
TTAAGTTTTA GGGTACATGT GCACAACGTG CAGGTTAGTT ACATATGTAT ACGTGTGCCA 72060
TGCTGGTGCG CTGCACCCAC TAACTCGTCA TCTAGCATTA GGTATATCTC CCAATGCTAT 72120
CCCTCCCCCC TCCCCCCAAC CCACAACAGT CCCCAGAGTG TGATGTTCCC CTTCCTGTGT 72180
CCATGTGTTC TCATTGTTCA ATTCCCACCT ATGAGTGAGA ATATGCGGTG TTTGGTTTTT 72240
TGTTCTTGCG ATAGTTTACT GAGAATGATG ATTTCCAAAT AGAGACAGGG TTTCATCGTG 72300
TTGCCCAGGC TGGTCTCGAA CTCCTGACCT CAAGTGAGTT GCCTGCCTTG GCCTCCCAAA 72360
GTGCTGGGAT TACAGGCGTG AGCCACCACT CCCCGCCTGG TGTTATTAGA AGAAGAGATT 72420
AGGACAGAGA CACAGACACA GAGGAAAGGC TGAGTGAGGA CACAGGGAGA AGACAGCCAT 72480
CTGCAAGCCA AGGAGAGAGG CCTCAGAAGA AACCAACCCT ACTGACATCC TGAGCTTGGG 72540
CTTCCAGCAT CTAGAAACTG TGAAAAAATA AATGTTGCTT GTCTAAGCCA CCCAGCCAGT 72600
GGTATTTCGT TGTGGTAGCC CTAACAGACT AATACATGCT GAGTCTCTCA TTGTTCAAAT 72660
CATCCTGTAA AACTGACTCA ACAGGCTTTT TTTGAGCAGG GTTTTCTATT CATGTACTCA 72720
TTAATTTTCC TTAAATTAAA AGTTGCAAAT ACAATATACA AAATTAAAAG TTCAATTAGA 72780
AAAATGAGTT TCTATAATCA GCCTACTCAG AATTAACCAT GGTTTCAAAT AGGGGTTTTG 72840
CTGGTGTTTT TTGTTTTGTT TTGTTTTGAG AGAAAGTTTT GCTCTTGTCT CTCAGGCTGG 72900
AGTGCAATGA CGTGATCTCA TCTCACTGCA ACCTCCACCT CCGGGTTCAA GTGATTCTCC 72960
CGCCTCAGCC TCCCAAGCAG CTGGGATTAC AGGCAAGCGC CACCATGCCC AGCTAATTTT 73020
GTATTTTTAG TAGAGACGGG GTGATCTGCC CTCCTTGGCC TCCCAAAGTG CTGGGATTAC 73080
AGGCGTGAGC CACTGCGCCC GTTAGCTGTT TTGTTTTGAA ATCAACTTTG AAAAATGTTT 73140
TGATATCTCA TCATGTCCCC AATGCCATTT GTAATGGTCA CACAGCATTC TGTTGTATGA 73200
TGTACCATGC TTTATCTAAC CTGTGTCCTA TTTTTGGATA GTTCGAATTT TCCTATTTCT 73260
TTTCACTATT AGAAGCAAGG CTGCAATGGA CATCCTTTTA AATACTTTTT AAAAACAAAA 73320
ACCTTGGTAC AAGTACCTGT ATATAGACTT GCAGGGTCAA AACTTCCCAT TTGATGGCTA 73380
TTGATATGTA CTAACAAATT GTCCTCAGA AAGTGGTCTT TTCCTCACCC TCATCAGTTC 73440
TTGGTGTTAC CACCTTTTTG CATTTTGCCA AGCTGATAGG TAAAAAAGTG TCTCTTACTA 73500
TTGTATGTAT TGAATTAAAT TTATTTATTT ATTTATTTAG ACAGGGTCTG GTTCTGTCCC 73560
CCAGGTAGGA GTGCAGTGGT GCAATCATAG CTCACTGCAG GCTTCAACTC CTGGGCTCCA 73620
GCAATCCTCC TGCCTCAGCT TCCTAAGTAG CTGGGACTAT AGGTGGGCCC AGCTAATTAA 73680
ATTTTTTTTT TTTTTTTTT TTAAGATAC AAGGTCTCAC TACTTCGCCC AAGCTGGTCT 73740
TGAACTCCTG AGCTCAAGAC ATCCTCCCAC CTCAGCCTCC TGAGTTGCTG GGATTACAGG 73800
CAGGAGCCAC TGTGCCTGCT TATTATATAT TTCAAAATAA CGAAAAGAGT GGAATTGCAA 73860
GTTCCTCACA CAAAGAAATG ACAAATGCTT GAGATAATGA TTATCATAAT TATCCTGATT 73920
TGATCACTAC AACTTGTATG CTTATATCAA AATATCACAT ATTTATATTT TTAAAAATTA 73980
TATTTATATT TATGTGATAT TTTGTAATGA TCATTTTACA TATGAACATA 74040
TTTATACATA TATACAAACC AAATAAACCA TACATATTTA TACATATGCA CCTATGTACA 74100
AACCAAAGAA ATTGGGATAT AGCTATCCCA GTTCTATTAA AAAATTGAGA TTTTTTTCTT 74160
CTCTATTGAT ATTTCCTACT TTTTTTTTGT TTTGAAAAAT AATTTATCCT TGAGTCAGTT 74220
GTGATGATTT ATACCTGTAT AGAGATTACT AGTTTGATCA AAATCATTTC ATTTATTGTT 74280
AAAAATTGTA TAATGATATT ATCTCCTAAC TGAAAATTTT CCTTTATCTC TGTGATTATA 74340
TTCCATTTCT CATTCATCAT ATTTTCATTT CATTCCAGTT TTCCTTGGTT AGACTTTCCT 74400
ATGATTTGTG TCTTTTACTG TTCTTTTCAA AGAACAGCCT TGGTATTTAT TTATCAATTC 74460
TATTTCTTTT TAATTTCACA ATTAATTGTT TTCTGTTTTT ACCATGACTA ATTCCCACCA 74520
CTGCTTTCAT AGATTAATTT TGTGTTCTTT TCTAATTCT TTCAATTAAT TTATTTTCAT 74580
TTTTTAAAAA CTTAATAATA AAAGTTCTTA AAGTCCTAAA TCTTTTCCTG AGTACTGTGG 74640
GATTCTTTCC ATGTGCTTCT GCATGTAGTA TGACTATTGC AATTGGTATA GATGGTATTA 74700
CAGTTCTTAC TCCTTCTTAC ATCCAGGGAT TACTAAGGAG ACTGATTTTA AATTTGCAAG 74760
AAGTTGACT TCTAAAAGTG CCAGGCTCCT TTTTGATGTC AAGTCTCACC TATTTCTTCT 74820
GTTTTTCTCT AGTAACTGAG CTCAGGTTTT GTTGAAGGCA GCAAACTACT GGCTAAAACT 74880
GCTCAATGTT TTCCAGCTAA AATTGCTCAA GTATTTCCTG CAGCTAGTTA GGGCAAGTTA 74940
CCTGGCTCTG TCTAGAGAGA TGGAGGTGCA GGTCCTTGGA GACAGAGTAC CCTCTGAACA 75000
AAAAGGCAAA GACTTACCAG CAGAAAACCC ATTTGCCTTT TCCCTTTCCT CCTCACTGAC 75060
ATGCAAGGGT TATGTCTGGA GGTACGAGAA AAGGAAAGCA TAAGGATAAA ATCTAACAGG 75120
CTAAGAATGA CAGGGCAGAA AGATAGAAAG GATCTGTGTC CCCGATGGCA TCGTTGTACC 75180
AGCAAGACTG ATGATCATGA TGTAAGTCAA ATGAATGCCC AGCTGCTGCT GGCTGTGTTT 75240
TTTGTTATTT GCGGCTGAAT GCATTGCTAA TGTAAACATT ACCTTGCAGC CAGAGAATAC 75300
GGCTTGCCAA AAGTCTAGTT TTGTATGTTA ATCATGATAC ACCAGCCAGA CAGAGTGGCC 75360
CTCAGCTGTA ATCCCAGCAC TTGGGGAGGC CAAGGCAGGC GGATCACTTG AGGTTAGGAG 75420
TTCGAGACCA GCCTGACCAA CATGACAAAC CCCCGTCTCT ACTAAAAATG CAAAAATTAG 75480
CTGGGCATGG TGGCTCCTGC CTGTAGTTCC AGCTACACGG GAGGCTGAGG CAGGAGAATC 75540
GCCTGAATGC AGGAGGAGGA GGTTGCAGTG AGCCAAGATG GTGCCATTGC ACTCCAGCCT 75600
```

*Fig. 5R*

```
GGGCGACAGA GTGAGACTCT GTCTCAAAAA ATAAAAATAA TAATAATAAT GATATGCCAA  75660
CTGCTATAGC ACCTAGACTG CAAAATGTAC ATCACAACAG TCCGATTCTC TGTTCTCTTT  75720
GTTCAGGGGT AAGCATGGAG CTTAATTTTG ATCTATGAGT CAACGTGGGA AGTCCGTTAG  75780
GTTAGAAGTG CTTCTGGTCA AGGTTCTTT GCTTCTAAAA GAGGAATGTG AGGAAAAAGT  75840
CCCTGTCTTG GTGTGGATTT TGGTGTGGGG GGATGTATAT AAAGCCTGTA GCTATTGAAG  75900
CCATCTGGCA AACTTGAAGG GAGCAGCTGA CTCTGAGCTG GTAGAATATA GAAATGGAAA  75960
GGATTTAGAT CTTGATGTGG TTGAGAGGCT GCCCTCCCTT GGGACTTCTT TTTTGTGTGT  76020
GAGTTAACAA GTTTTCCTTA TTGTTAAGTT GCTTTAGTGG GTTGCTATT ACTTGTAGTC   76080
AAAACATTTA TTATGGCATC ATCTACTTTA TTCTATCCTT CTGCTTTCCT TATTACAAGT  76140
ATATTTACAA GCTCATTGTC ATTCATGTCA TCATTTTAAT CAGCACCAAC AACAGCATCA  76200
CCAGTAACAT TTATTGAGTG TTTTTAAGTG CCAGGCCCTG TTGTTGTCAT TTAAATCTTA  76260
CACCAATCCC TACTGCTCAG ATACTATTCT TTTTAAAAAT TATTTTTTT TTAGGCACAG   76320
GATCTTGCTC TGTTGCCCAG GCTGGAGTGC AGTGGCATAA TCATAGCTCA CTGCAGCCTC  76380
AAACTCCTGG GCTCCAGTGA TCTTCCTGCT TCAGTTTCCC AAAGTGCTGG GATTACAGGT  76440
GTGACCACTA CCCCCTGTCC TATTATTATT GATTCAGATT TACAGATGAG GAAAATAAGG  76500
CTTAGGAAGG CTACATAATT TCCTAGATTG CTTATTTAGT AAGCGGCAGA GCCAGGATTC  76560
AAACCCAGAC CTGAGGGACT CCTAGACTAG TCCATGCCAC TGTGATATGG CCTTTCACAT  76620
CTCTTCTTTC ATCCGTCATC ATGATATCTT TCTCCTCTGA GTTCTGGGGA AGTTTCTCAA  76680
GTTGGACTGC CAATTTTCTG CAGGATTTTC CTGTGATATA TAACTCCTTC ATTTACTGCT  76740
TCCATTTTAT TTCATATCAC CTACAATTTC CCTTATGTCT AAAACCAATT GCTCCTATAT  76800
CTAAGATGCA ACGTCCTTCT GAATTATAGT GTTAATGCAA TAGGGTATTT TGAAGGTTTC  76860
TGTATGTTTT CTGTAGAAAA GTTATCTCAA AGGGGGATAT ATACTTCCAT TTCCCAGTGG  76920
TCTACTTCTT TTAAGCCACA AATAGGGCAC TTTCTCTTGT TAGTTTAATC CTACGGGTAT  76980
ATAATTTTCA GTATTTCTAG TGTTAGAATT TGAGATTCAG AGAACTATGA GTCTCTGTTT  77040
TAATCTTTCA GTCCTAGGAA AAGGAGAAAT AGGGCTGCCT ATCTTTTCTG TGGTTTTATT  77100
TTGCCATTTA ATTTCTAATT GACTGTGAGA TGTATCAAGA GATCTGTAGC TCAAGGCAGT  77160
TGAATGTCCC AGAGCTTCAC AGCTGAGCCA AGTGACTTCT TTTCCATGTT TATTGTGGCA  77220
GCCAAGGTCA GCAGATGCCA TGCCTCTTGC TCTGAGTGCC TGGACCACCC CCATTAAGAG  77280
CCTCCCACAG CAACAACTCC ACTTGACCCA CGATAAGTGA GGTTGGCACT GTGTCTCTCT  77340
CTTTGTACAT TTTGTTTTCT AAGTTGCTTG TAGGGCCAAG CTTTGAGTCC TTGTTACCAT  77400
CAGCTTAAGC TCCGGCCTCT CTGAATTGGA GGATTTTGTT TGTGTTTGAT TAGAGCCTGT  77460
TGGCAGAAGC AAGTGCCAAA GTCAGACATA AAACAGAAAA CTCTAATGTG GTGTCAAGTC  77520
TTTTCCAGAT GTTACTGATC CTCTTTCTTT TCCTTCTTT TTTTTTCTTT TTTGTTATTT   77580
TTGATCCCCT TCCTTTTTGC TTCCCTTAGG TTGACCTTTG CTGTCCTACG GGCAGTACAA  77640
AGATTGGGTC TTTCTGTCTC TGCCTCTCCT GCCCTCGGAC TCCTACCATG GGTCTTTTCT  77700
TTTTTTATAG AGATAGGGGT CTCACTTTGT TTATCGTGTT TTTTTTTG TTTGTTTTTT    77760
GAGGTGGAGT CTTACTCTGT CACCAGGCTG CAGTGCAGTG GCGTGATCTT GGCTCACTGC  77820
AACCTCCGCC TCCTGGGTTC AAGCGATTCT CCTGCCTCGG CCTCCTGAGT AGCTGGGACT  77880
ACAGGTGTGT GCCACTATGC CCAGTTAATT GTTGTATTTT TACTAGAGAC AAGGTTTCAC  77940
CATGTTGGCC AGGATGGTCT CAATCTCTTG ACCTTGTGAT CCACCCGCCT CAGCTTCCCA  78000
AAGTTCTGGG ATTACAGGTG TGAGCCACAG CGCTCAGCCT GAACTTTTAC TTTTAAGACA  78060
ATTGTAGATT CAAATCCTGT GTCCTCTCTT ACACAGTTTC CTCCAATGGG GGCATTTTAC  78120
AAATATAATA ACCAGGATAT TGACATTGAT ACATTTGATA CAGTCAAGTT ACATTTTCAT  78180
CACCACAAAG ATCCTGGTGT TACTCTTTTA TAGCCATACC TGCCTCCTTC TCCCTCCCC   78240
CATCCCTCAC GCCGGCAACC ACTAATCTGT TCTCCATTTC TACAATTTTG TCGTTTCAAA  78300
AATGTTATGT AAACAGAATC ATACAGTTTC TCATCTTTAA GATTCGTTCT TTCCTGTTTT  78360
TTTTTCTTT TTTTTCTTT CTTTGTTTT TTGAGATGGA GTCTCACTGT GCCACCCAGG     78420
CTGGAGTGCA CTGGTGTGAT CTCGGCTCAC TGCAACCTCC GCCTCCAAGT TGTGGGTTGA  78480
AGCGATTCTC CTGCCTCAGC CTCCCAAGTA GCTGGGATTA CAGGTGCCTG CCACCACGCT  78540
CGGCTAATTT TTTTTTTGTA TTTTTAGTAC AGACAAGGTT TCACCATGTT GGCCAAGCTG  78600
GTCTCGAGCT CCTGACCTCA GGTGATCTGC CTCGGCCTCC CAACTTGCTG GGATTACAGG  78660
CATGAGCCAC CGCACCCGGC TGAGATTGGC TCTTTCACTC AGCATAATTC CCTGGAGACT  78720
TCATCCAAGT TGTTGCATGT ATCAATAGCT TGTTTCTTTT CATTGCCACC TAGTTTTCAA  78780
TGGTATGAAT GCCGCATTGC TTGTTTCATC AGTCACCTGG TGGAAAACAT CAGGGTTGTT  78840
CCCAGTTTT AACTATTATG AATAAAGCTG CTATGAACAT TTGTGTACAG GTTTTTGTGT   78900
GAACATATTA TCATTTCTCT GAGATGAATC AATGCCAAAG NAATGCAATG GTATGTTGA   78960
TTTTATAAGA AACTGCCAAA CTGTTTTCCA GAGTGGCTAT ATGANTTTTG TATTCCTACT  79020
AGCAGTGTAT GAATAATCTA GTTCTTTAC ATCCTCACCA GCATTTCATG TTCTCAGTAT   79080
TTTTTTTATT TTAGTTAATC CGATATGTAT GTAGTGCAAT ATCACTGTGG TCTTAATTTT  79140
TAGTTCACCA GTGCTAATGA TGTTGAATAT CTTTCATGTA CTTATTTGCC ATCTGTATAT  79200
CCACTTGGTG AAATACTTCA TGTCTTTAAA GAAGACCCAG GATTTCTAAA AAACTGTTGA  79260
GTTTTGAGAA TTTAAGAAAT ATATTCTAGA TACTGGTACT TTGTTGGATA CATGGTTTGT  79320
AAAATATGTTC TCCTAGTTTG TAGCTTGTCT TTTCATATGT GTTAAAGCTT ATCTCCCATT 79380
TTATTATTTG TTTTCTGTTT ACTTTGTTTT TTATTCCTCT ATTCTCACTT TGGGTGGATT  79440
ATTTAAATAT TTTTTAAGGT TTCATCTTGA TTTATTTGTA GCATTTTGGG TACATCTCTT  79500
TGTACACTTT TCTTAGTGGT TGCCCTGGGT GTTACCATAT ACATATGTCA AGAGTCACAT  79560
TCTGCTGGTG TCAGTGTTTT TCCAGTTGAA GGCAAGTGTG GAAAACTTAC CTCCATTTAG  79620
ATTCCTTTAC TCTTCCCATT TTTAAAACAT GTGTCTCAAG TATTCCCTCT ACATTCATTG  79680
ATCAGCACAC TAGAGAGTGT TATTTTGGCT TTAACCTTCA AATATAATTT AAGCACTCA   79740
GGAGAATAGG ATCATCTATT ATGTTTACCC CTGTCTTTGC CTGTTTTGAT GTTCTTCATT  79800
```

*Fig. 5S*

```
CTTTTCTAAA GTTTCAAGCA TTCTTCTGTT ATCATTTCCT TTCTGTTTAA AGAACTTCCT  79860
TTAGTCGTTC TTTAAGGACA GATTTACTAG CAACAGATTC TCAGTTTTCC TTCATCTGAG  79920
AATGTCTTTA TTTCCCCTGC ATTCCTGAAG GATATTTTCA CCTGATATGG AATTTGTGAG  79980
TGATAGTTCT TTTTCCTCTA AGCACTTGAA AAATGTTATG CCACTTTCTG CTGTCTTTTA  80040
TGGTTTCCGA AGAGAAATCC ACTTTCATTC AAACTGTCAT TTCCCTGTAA GTAATGGATG  80100
TTTTCTGTCT AGTTGCCTTC AAGACTTTGT CTTTAGTTTT TACAAGTTTA ATTATGATAT  80160
GTCTTGGTGT GAATTTCTTT GAGTTTATCC TGCTTATGAT AGTTCACACA GCTTTTTGAA  80220
ACTGTAGGTT TATGTCTTCC ACCAAATTTT ACTGAATTTC TTCAGTTTCTA TGGTCTTGCT  80280
CCTCTTCCTG AAGTATTCCA ATGATACCGT GTTCTCTTTT GTTACGGTCC CACTGGTCTT  80340
TGAGACTCTC TGTTCATTTT ATTTCGGTCT TTCTTTTCTC TGTTGTTCAG ATTGGGTAAA  80400
TTCCATTGAT CTACCTTCAA GCCCACTGAT TCTGTCCTCT ATCATCTCTA TTATTGAGCC  80460
CAACCACACA GTTTTAATTT TGATTATTGT ATTTCTCAGT TCTATAATTT CCATTTGGTT  80520
ATTTTTCAAT GACTTCCATT TTTGCTGAAA TTTTCACTTG TTTCAAGAGA ATTTGTAATT  80580
ACTTGTTGAA GCACTTTTAT AATATCTGTT TAAAATACTT GTCATATAAT TCCAGTAACT  80640
AATTCATCTT GGTGTTGACA TCTGTTTATT GCTCACTTAA AAATAAAAAA TAAAAAACAC  80700
CTAGACTTTA TTTTTTATAG CAGTTTAAGG TTCACAGCAA AATTGAGAAG AAAGTAAAGA  80760
GTGTGCCCAG AAAAATAGTA CCCCTATGCA GAACCTCCCT GATATTGTTT GGCTGTGTCC  80820
CCCACCAAAT CTCATCTTGA ATGGTAGCTC CCACAATTCC CACGTGTTGT GGGAGGGATC  80880
CAGTGGGAGG TAATTGGATA ATGGGGGCGA ATCTTTCCCA TGCTGTTCTC ATGATAGTGA  80940
ATAAGTCTCA TGAGATCTGA TGGTTTTATA AAGAGGGGTT CCCCTGCACA AGTCCTCTCT  81000
TGCCTGGCGC CAGGTAAGAA GTCCCTTTGC TCTTCCTTCA TCTTCCATTA TGATTGCGAG  81060
GTCTCCCCAG CCATGTGGAA CTGTAAGTCC ATTAAACCTC CTTTTCTGTA TAAAGTACCC  81120
AGTCTCAGGT ATGTCTTTAT TAGCAGTGTG AGAATGGACT AATACACTCC CTATCAACAT  81180
CCCCTACCAG ATTGGTATGT TTGTTGTAAT CGATGAACCT ATGTCAACAC AGCGTTATTT  81240
CCCAAGCTCC ATAGCTTATA TGAGGATTCG CTCTTGGTGT TTACATTCTG TGAGTATTGA  81300
CAAATGTATG ATGAAATGTA TTGACCATTA TAGTGTCATA CAGAATACAG GATAGTTTCA  81360
CTGTCTTAAA AAATCTTCTG TGCTCCCCTT ATTCATCCCT TCCTTCTGTG TAAGCCCTGG  81420
CAACCACCGA GCTTTTCACT GCCTCCATTG TTTTGCTTTT TCCAGGATGT CATAGAGATG  81480
GACTCATACA GTAGGTAGCC TTTTGAAATT GACTTCTTTC ACTTAGTAAT ATGATTCCTC  81540
CATGTCTTTT CATGGCTTGA TAGCTAATTT CTTTATAGTG CTGAGTAGTA TTCCATTCAC  81600
TTATAATTCC TTGAATTCAT TGTTTGGAAT ATTTTGCAGA TGATATGCTA TTCCCTAACT  81660
TTATGCATCT TCACTCACAG GATTGTTTTT TTCTCACCAA TGCTTATTTA TATAAAAGCC  81720
ATATCAACAA AATTTTACAC ATCAAAAATT TTCAGATTTC TGGTTGCTCC AAAGAAGGAA  81780
TGACCCCATT CTTCTCAGGT CCTCTTCCTC ATGACTAAAA AACTCTGAAC AAAGCACAGA  81840
AAGTTGCGGA AGGCTCTGAA AGGTGAAAGG AGGTGGACTG CCTAGGGACC TCAGGACTTG  81900
GAAAACAACT CAGTGGGGAA TTCCGTGGAT TTCCTTATCA CCTCCCTTAT ATCCTGGACA  81960
CGGAGCTGCA GAAGACTCCA ACCTACAGTC ACCAATGCGC ATAGAAGAAA AAAGCTCCAA  82020
GAAAAGCCTT TTCCTCCTGG CCAGATGACT GGACAAGGGT GGCCTGACAA CAGAAAACCC  82080
ACAACAAGGA ATTACAGGTA ACTCCAGAGA GGATCAGCTT GAGTGGTTAA AACAAGTACA  82140
TGGAAAACAA AAAGAAGCAT TTTTCTTTTT TTGTAAAAGA GCTTGTACTG TAATAACTTT  82200
GATTTTGTTT TTTGTTTTTT GTTTTTTGTT TTTTTTTTGA GACTGAGTCT CACTCTATTG  82260
CCCAGGCTAG AGTGCTGTGG CGCAATCTTG GCTTACTGCA ACTTTTGCCT CCTGGGTTCA  82320
AGTGATTCTC ATGTCTCAGC TTCCTGAGTA GTTGGGATTA CAGGCATGCA CCACCACACC  82380
AACTAATTTT TGTATTTTTA GTAGAGATGG GGTTTGACCA TGTTGGCCAG ACTGGTCTTG  82440
AACTCCTGAC CTCAAATGAT CTGCCCACCT TGGCCTCCCA AAGTGCTGAG ATTACAAGCC  82500
TGAGCCACCG CACCTGGCCA ACTTGGACTT ATTTTTATAA TAAGTAGATA TTGTTCACTG  82560
TAGATATTGA ATCAATTTTT ATTTAATCTT GATTTTTTTT CTTGAGCTGC ATTAGAAATT  82620
CATTACAATA TTTCAATTTA TAAATCTTAT TAAAAATTAC TACTACCTAG ATCTCATTGT  82680
TTTCTTTTTT CTTTTTTGAG ACATGGTCTT GCTCTGTCAA GCAGGAGTGC AGTGGGACAA  82740
TCATAACTCA CTGTAGCCTC CAACTCCTGG GCTCAAACGA TCCTGCTACC TCAGCCTCCT  82800
GAGTAGGTGG GACTATAGGT GCACGCCACC CATGTGTGGC TAATTTTCTT TATTTTTTTT  82860
TGTAGAGACA AGGTCTCACT GTGTTGCCCA AGCTGGTCTT GAATTCCTGG CTTCAATCAA  82920
TCCTCCCGCC TCAGCCTCCC AAGGTGTTGG GATTTCAGAC GTGAGCCACT GCACACCTGG  82980
CCCCATTTTT TTTCCTTGAA TAAAGTGTAC TGGTAAATTT TAGGCTCATG AGGGTATATA  83040
TGCATTATTT TCTTCAAATC AAGCCTGAAT CAAAGAAACT TCTGCTTTAG TTTTAGTGAT  83100
ATTTGTCCCA AATGTTTAAA GACTGTATCA TTCTGATGAA TTGGATATTC CCATTGAGAG  83160
ATATTCAATA GGCCTTGATT GAAATGTTCT TCATTTTCTT TTTAAATTCT ATTTACAGTA  83220
GTCTGCATGT GTTAGAACTT TCAGAAAGGG AGAGATTTCT GTCTGGGCTG TCCCCACCAG  83280
CCAGAAGGGT CTGAGAGGCA CTGACTTGCC CTGGGGTGAT ATTTCTGCAG GACTTTGCTC  83340
CTCTGTAGGA AGACAGCCTA GAACAGAGGT GAAGGATGCC TCGGGCCTGC CTAGACCAAC  83400
AGCCATTCCC TGGTGATGCT GTAGTGTGAA GACCCTTTGT TTTCCCAACA CCTGTGATAG  83460
CTTTCAAATT ATTCTTTTCA GACAAACTTT ATGCCTGTTT CTTTATCTCT ATTTTGCATC  83520
CTAACAGAAA AAGCCAATCA CCTAGAAGGG AAAGTCAGAC TGGTCCCTGC TGCTTTCCCC  83580
ACATCTCCAC TGCCCCCAAT ATTGAATGCC GTGACAATGG AATGAAATTC CAATGTCCAT  83640
GAAATTCTGA GGGGAGACAT TTTGACTCAA GATTATATAC TCAGTGAAGA TGTCCTTTAT  83700
TTATTTATTA AATTAATTTT TTTTGAGATG GAGTCTCTCT CTGTCTCCCA GTTTGGAGTG  83760
CAGTGGTGCG ATCTCGGCTC ACTGCAACCT CTGCCTCCTG GGTTAAAGTG ATTCTCCTGC  83820
TGCAGCCTCC TGAATAGCTG GGACTATAGG TACTCACCAC CACACCTAGC TAATTTTTTT  83880
TTTTTTTTTT TTTTTTTTGG TAAAGATGGG GTTTCACCAT GTTGGCCCGT CTGGTCTTGA  83940
ACTCCAGACC TCAGGTGATC TGCCCGCTTT GGCCTCCCAA AGTGCTGGGA TTACAGGCGT  84000
```

*Fig. 5T*

```
GAGCCACCTT GTCTGGCCAA AGACGTCCTT TAACTAAAGA CTTCTGGTGT ATGTTACCTT    84060
AAAAATATAA ATATAAAAGC ATGAAGAAAA TACAACCTCC ATGGAATTTT TTTGCCAATG    84120
AATCTAGAAA AATAAGAATT GATTCAAAAT AATGAATAGG GAAGCTGTAA TAAAATGACT    84180
TGAGGGTTCA TTGAGTCCAT TTAAATATAT ATCTCTTACT AAAATCACTA AGGGTCATAA    84240
TTAGACAATG AAGTAAGTGC CATAAATCTA AACAATGTAA ATAACAATAT ATCTAAAAAA    84300
AAAAAACTAA GGAGTTTGGA GAGAGGATAC GGGAGGATGT GTTCTTTCAT AGTAGGGAAT    84360
TAGTTAATAT TCTTTAAAAT GGAAACATGT AAGAAAAAAG ACCCTAATGA CTGAAAACTA    84420
AGTTTTCCTC AATCTTTTTT TCATATCCTT TGAAGGCTAT TTTAAGAAAT AATATCTAAA    84480
GAACATCGAT TTGATGTTCA CAATTCCAGT TGATTTTCCT TCTGTGAAAT TCAAATGAAA    84540
TTAAATAAAT ATGTTTTGTT AAAAATGGTG TCATCCCATT TAAGTAAATG TCCTTTCTTT    84600
TACCTATTTA TCCATCTATA ATCTGTATCT ATTCATCCAT CAATGGATAC ATGTGCACAG    84660
ATAAATGGCC CCTTTGGTGA AGGGCTGAGA GGGTATTGTT TTCTAACCCC AACCTGTGAC    84720
GGCTTCCATG AGGCCAATGG AATCATTTTG AAATGTGTTT ACCACAGCAG GGAGACACAG    84780
AAGACTGGGG TCTCACACCT GTGTGGGAAC TCCAGAGGGT GAGAAAGGG CCAATGAACT     84840
GCTCCGGTGA CACAGCAGGG AGGGTGGCTG CCGTGCTGGG TGCGGCCTGC CTTCCTAGAG    84900
AATGTCAGGG AAAGGGATGT GGGGTCATTT CCTGTGGACA CATTTAAGCC AAGTAGGGGA    84960
GAGGTCTGGT ATGGGGTCCT CTTGGGGCCT GTTGGACAGG GTTGACCAGC AGAGAGAGGA    85020
TGCCCAAGGA TTGAAGGAGG AGTGGGTAAG AGGTTCTCTA GGTCATGGGA ACTTCTGAAT    85080
TTCCCATGGA AAGCACCACC ATAATCTGTG TGCAATGAAC AGCCAGACCC ACGTGGGAAT    85140
TCTAGGCCAG CAAGAATCCC TTACTTGCTC ACTGGCTGCC ACGTGGCTCT GACCATGGAG    85200
AGGTCTGGAA CTGTAGCTTC CCAGTGGGGG AGAAGTAGGC TGGGAGAGAG AAGGGGACAG    85260
AGGAACCACA CCCTCCTTCC CCACCTCCAA ACAGAAGCCA GTAAAAATTG AGGGATGGAG    85320
AAAAATATAA GGCTAAATTA AGTTTTGGAA CTTTGGCATG ATCAAGGCTC ACTGCAGCCT    85380
CAACCTCCTG GGCTCAAACA ATCCTCCCTT CTCAGCCTCC TGAGTAGCTG GGACTACAGG    85440
CACATACAAC CATGCTCACC TTTTTTTTTT TTTTTTTTTT GTAGAGATGG GGTATTGCTA    85500
TGTTGCTCAG GGCTGGTCTC AAACTCCTGG GCTCAAGCAA TTCTCCTGCC TCAGCCTCCA    85560
AAAGTGCTGG GATTACAGGT GTAAGCCATT GGCCCTGCCA AGTTTAAGAA CTTTTACAGT    85620
TATAAGAGAC TAGATATTTT AATTATTATT ATTATTTTTT AGACAGAGTC TTACTCCGTA    85680
TCCAGGCTGG AGTGCGGTGG CACAATCTTG GCTCACTGTA ACCTCCACCT TCTAGGTTTA    85740
AGCGATTCTC CTGTCTCGGC CTCCTGAGTA GCCAGAATTA GTAGAGACGG GGATTCGCCA    85800
TGTTGATCAG GCTGGTCTCG AACTCCTGAC CTCAAGTAAT CCACCTGCCT TAGCCTCCCA    85860
AAGTGCTGGG ATTACAGTAG ATATTTTAAT TTTTTTGCAT GGAGGCTATT TTTACTACTA    85920
AAAGTGAATG AAGTATATTT TGTATCTTCC AGGAGTTTGG AAAGTCAAGT CTATTTGCAC    85980
CCAGCCACGT GCCTGCCATG GTGCCCGCGG CCTCTCAATT TTTGACCTTT GTTTATGCTG    86040
CTCTGTCTAC CCAGAATGCT CTCCATCGAG GGAAACCTAC TCTCTCTTCA AGGCCAAATT    86100
CCAGCATCAC CTCCGCCATG AAGCCTTCAT AGATCTACTC AANGTAGAAA CTTCTTAACC    86160
CCTCTAAACT GTCTTAGCAT CTTGGTTGTA GTATTGGTTT AGAATAGCAC AAATTCTACC    86220
CAAAATCTCA CTAAGTCTAT TCTAAGCAAA TCTTGGATAA TTTGCTAACA CTAAAATTAA    86280
ACCTGTTCTC TTTTGGTTTT TTGCTAACAA TGAAACAAAC TTGGTCTTAC TCTTTTGCTC    86340
AAGCTGGAGT ACAGTGGTGT AATCATGTCT CACTGCAGCC AGGAATTCCC GGACTCAAGG    86400
GATCGTCCTA CCTCAGCCTC CTGAGTAGCC GGGACTACAG GTGTGCATAA CCGTGCCTGG    86460
CCAGTTTTAA AATTTTTATT TAGGGACAGA GTTTTGCTAT GTTGTCCAGG CTGGTCTTGA    86520
ACTATTGACC TCAAGTGATC CTCCCACCTT GGCCTTTCAA AGTGCTGGGA TTAGAGGTGT    86580
GAGCTGCCAC ACCCAGCCCC GTTCTCTCTT TTGCATCTAT ATTAGTCTCT GTGCTCTTGG    86640
GAAAAGTGGA CCAATATCAT TTCAAAACTT GATGAAAAAG AAAATTAAAA TCTCATCCTC    86700
GGGAACTGAA ATCACAAACC ACCCAGCAAG GTCCACACCT CTAGGAGACT GGCATTTAGA    86760
AGACAGGACC ACAGTTGAAG CAACGGTTCT TTCTTTACCC TCCCTGCCTG TGACAGACTG    86820
CATGTGCTGA TTATCCCTGC GTTTTCTGCA GAGCTTGCCT TCCTGGTGAT ACAGTACTTT    86880
ATTTTATTCT GAGGGCCCCT TCCTGCCAGG GGATATCTGT CAGGGGATAC ATAAAACTGC    86940
ACAAAATGGA ACAAGTTATA GGTCATATAA AATTTCAGGA CATTGTTGAG AAGGAGAAGT    87000
TGCTAAATTG GAGACACCAT GATGTGAAAT CCCAGGGTCC CAGAATATTG ATGGAACTAG    87060
TATGTTTTTC TTATGTAATA TTTTATGGTG TCTGGGAAAT GGAGTTGCCT AAGTGAACTC    87120
ATTTTTTATG TCTAGGGGAA TAGCAACATA ACTATCATCT AACACTAAAT AAAGAGGAGC    87180
AAAATGTGCT ACATTTAGAA AGTGATGGTA TTATCCCCAG CTGAGGCAGA CTTAGTGATG    87240
GTGTTAGAAA TAAAGTATGG TAGGAGGCTG AGGCAGGTGG ATTGCATGAG CTCAGGAGTT    87300
TGAGACCAGA CTGGGCAACA TGGCGGAAAC CCCATCTCTA CAAAAATCCA               87350
```

*Fig. 5U*

```
GTATAAAGTT AGTAAATGTG AGGCCTCTCT CGATGCCTGG GTCCTGGGCT TTGGTTCTCA    60
GTCCTCCATA AATCATCCTG CTGGAGGAGA AGACCCTTAG ATCTGGCTCT TCTCAGGGGC   120
ATTTTAAAGA CAAATGAAAA TAAA ATG GAA ACC ACT TCA CTA CAG CGG AAA      171
                           Met Glu Thr Thr Ser Leu Gln Arg Lys
                            1               5
TTT CCA GAA TGG ATG TCT ATG CAG AGT CAA AGA TGT GCT ACA GAA GAA     219
Phe Pro Glu Trp Met Ser Met Gln Ser Gln Arg Cys Ala Thr Glu Glu
 10              15              20              25
AAG GCC TGC GTT CAG AAG AGT GTT CTT GAA GAT AAC CTC CCA TTC TTA     267
Lys Ala Cys Val Gln Lys Ser Val Leu Glu Asp Asn Leu Pro Phe Leu
                 30              35              40
GAA TTC CCT GGA TCC ATT GTT TAC AGT TAT GAA GCT AGT GAT TGC TCC     315
Glu Phe Pro Gly Ser Ile Val Tyr Ser Tyr Glu Ala Ser Asp Cys Ser
             45              50              55
TTC CTG TCT GAA GAC ATT AGC ATG CGT CTG TCT GAT GGC GAT GTG GTG     363
Phe Leu Ser Glu Asp Ile Ser Met Arg Leu Ser Asp Gly Asp Val Val
         60              65              70
GGA TTT GAC ATG GAA TGG CCG CCC ATA TAC AAG CCA GGG AAA AGA AGC     411
Gly Phe Asp Met Glu Trp Pro Pro Ile Tyr Lys Pro Gly Lys Arg Ser
     75              80              85
AGA GTC GCA GTG ATC CAG TTG TGT GTG TCT GAG AGC AAA TGT TAC TTG     459
Arg Val Ala Val Ile Gln Leu Cys Val Ser Glu Ser Lys Cys Tyr Leu
 90              95             100             105
TTT CAC ATT TCT TCC ATG TCA GTT TTC CCC CAG GGA TTA AAA ATG TTA     507
Phe His Ile Ser Ser Met Ser Val Phe Pro Gln Gly Leu Lys Met Leu
                110             115             120
CTA GAA AAC AAA TCA ATT AAG AAG GCA GGG GTT GGG ATT GAA GGG GAC     555
Leu Glu Asn Lys Ser Ile Lys Lys Ala Gly Val Gly Ile Glu Gly Asp
            125             130             135
CAG TGG AAA CTT CTG CGT GAT TTT GAC GTC AAG TTG GAG AGT TTT GTG     603
Gln Trp Lys Leu Leu Arg Asp Phe Asp Val Lys Leu Glu Ser Phe Val
        140             145             150
GAG CTG ACG GAT GTT GCC AAT GAA AAG TTG AAG TGC GCA GAG ACC TGG     651
Glu Leu Thr Asp Val Ala Asn Glu Lys Leu Lys Cys Ala Glu Thr Trp
    155             160             165
AGC CTC AAT GGT CTG GTT AAA CAC GTC TTA GGG AAA CAA CTT TTG AAA     699
Ser Leu Asn Gly Leu Val Lys His Val Leu Gly Lys Gln Leu Leu Lys
170             175             180             185
GAC AAG TCC ATC CGC TGC AGC AAT TGG AGT AAT TTC CCC CTC ACT GAG     747
Asp Lys Ser Ile Arg Cys Ser Asn Trp Ser Asn Phe Pro Leu Thr Glu
            190             195             200
```

*Fig. 6-1*

```
GAC CAG AAA CTG TAT GCA GCC ACT GAT GCT TAT GCT GGT CTT ATC ATC    795
Asp Gln Lys Leu Tyr Ala Ala Thr Asp Ala Tyr Ala Gly Leu Ile Ile
            205                 210                 215
TAT CAA AAA TTA GGA AAT TTG GGT GAT ACT GCG CAA GTG TTT GCT CTA    843
Tyr Gln Lys Leu Gly Asn Leu Gly Asp Thr Ala Gln Val Phe Ala Leu
            220                 225                 230
AAT AAA GCA GAG GAA AAC CTA CCT CTG GAG ATG AAG AAA CAG TTG AAT    891
Asn Lys Ala Glu Glu Asn Leu Pro Leu Glu Met Lys Lys Gln Leu Asn
            235                 240                 245
TCA ATC TCC GAA GAA ATG AGG GAC CTA GCC AAT CGT TTT CCT GTC ACT    939
Ser Ile Ser Glu Glu Met Arg Asp Leu Ala Asn Arg Phe Pro Val Thr
250                 255                 260                 265
TGC AGA AAT TTG GAA ACT CTC CAG AGG GTT CCT GTA ATA TTG AAG AGT    987
Cys Arg Asn Leu Glu Thr Leu Gln Arg Val Pro Val Ile Leu Lys Ser
                270                 275                 280
ATT TCA GAA AAT CTC TGT TCA TTG AGA AAA GTG ATC TGT GGT CCT ACA    1035
Ile Ser Glu Asn Leu Cys Ser Leu Arg Lys Val Ile Cys Gly Pro Thr
            285                 290                 295
AAC ACT GAG ACT AGA CTG AAG CCG GGC AGT AGT TTT AAT TTA CTG TCA    1083
Asn Thr Glu Thr Arg Leu Lys Pro Gly Ser Ser Phe Asn Leu Leu Ser
            300                 305                 310
TCA GAG GAT TCA GCT GCT GCT GGA GAA AAA GAG AAA CAG ATT GGA AAA    1131
Ser Glu Asp Ser Ala Ala Ala Gly Glu Lys Glu Lys Gln Ile Gly Lys
            315                 320                 325
CAT AGT ACT TTT GCT AAA ATT AAA GAA GAA CCA TGG GAC CCA GAA CTT    1179
His Ser Thr Phe Ala Lys Ile Lys Glu Glu Pro Trp Asp Pro Glu Leu
330                 335                 340                 345
GAC AGT TTA GTG AAG CAA GAG GAG GTT GAT GTA TTT AGA AAT CAA GTG    1227
Asp Ser Leu Val Lys Gln Glu Glu Val Asp Val Phe Arg Asn Gln Val
                350                 355                 360
AAG CAA GAA AAA GGT GAA TCT GAA AAT GAA ATA GAA GAC AAT CTG TTG    1275
Lys Gln Glu Lys Gly Glu Ser Glu Asn Glu Ile Glu Asp Asn Leu Leu
            365                 370                 375
AGA GAA GAT ATG GAA AGA ACT TGT GTG ATT CCT AGT ATT TCA GAA AAT    1323
Arg Glu Asp Met Glu Arg Thr Cys Val Ile Pro Ser Ile Ser Glu Asn
            380                 385                 390
GAA CTC CAA GAT TTG GAA CAG CAA GCT AAA GAA GAA AAA TAT AAT GAT    1371
Glu Leu Gln Asp Leu Glu Gln Gln Ala Lys Glu Glu Lys Tyr Asn Asp
            395                 400                 405
GTT TCT CAC CAA CTT TCT GAG CAT TTA TCT CCC AAT GAT GAT GAG AAT    1419
Val Ser His Gln Leu Ser Glu His Leu Ser Pro Asn Asp Asp Glu Asn
410                 415                 420                 425
```

*Fig. 6-2*

```
GAC TCC TCC TAT ATA ATT GAA AGT GAT GAA GAT TTG GAA ATG GAG ATG    1467
Asp Ser Ser Tyr Ile Ile Glu Ser Asp Glu Asp Leu Glu Met Glu Met
                430              435                 440

CTG AAG TCT TTA GAA AAC CTA AAT AGT GAC GTG GTG GAA CCC ACT CAC    1515
Leu Lys Ser Leu Glu Asn Leu Asn Ser Asp Val Val Glu Pro Thr His
                445              450                 455

TCT ACA TGG TTG GAA ATG GGA ACC AAT GGG CGT CTT CCT CCT GAG GAG    1563
Ser Thr Trp Leu Glu Met Gly Thr Asn Gly Arg Leu Pro Pro Glu Glu
                460              465                 470

GAA GAT GGA CAC GGA AAT GAA GCC ATC AAA GAG GAG CAG GAA GAA GAG    1611
Glu Asp Gly His Gly Asn Glu Ala Ile Lys Glu Glu Gln Glu Glu Glu
                475              480                 485

GAC CAT TTA TTG CCG GAA CCC AAC GCA AAG CAA ATT AAT TGC CTC AAG    1659
Asp His Leu Leu Pro Glu Pro Asn Ala Lys Gln Ile Asn Cys Leu Lys
490             495              500                 505

ACC TAT TTC GGA CAC AGC AGT TTT AAA CCG GTT CAG TGG AAA GTC ATC    1707
Thr Tyr Phe Gly His Ser Ser Phe Lys Pro Val Gln Trp Lys Val Ile
                510              515                 520

CAT TCT GTA TTA GAA GAG AGA AGA GAT AAT GTT GTT GTC ATG GCA ACT    1755
His Ser Val Leu Glu Glu Arg Arg Asp Asn Val Val Val Met Ala Thr
                525              530                 535

GGA TAT GGG AAG AGT CTG TGC TTC CAG TAT CCG CCT GTT TAT ACA GGC    1803
Gly Tyr Gly Lys Ser Leu Cys Phe Gln Tyr Pro Pro Val Tyr Thr Gly
                540              545                 550

AAG ATT GGC ATT GTC ATT TCA CCT CTC ATT TCC TTA ATG GAA GAC CAA    1851
Lys Ile Gly Ile Val Ile Ser Pro Leu Ile Ser Leu Met Glu Asp Gln
                555              560                 565

GTC CTC CAG CTT GAG CTG TCC AAT GTT CCA GCC TGT TTA CTT GGA TCT    1899
Val Leu Gln Leu Glu Leu Ser Asn Val Pro Ala Cys Leu Leu Gly Ser
570             575              580                 585

GCA CAG TCA AAA AAT ATT CTA GGA GAT GTT AAA TTA GGC AAA TAT AGG    1947
Ala Gln Ser Lys Asn Ile Leu Gly Asp Val Lys Leu Gly Lys Tyr Arg
                590              595                 600

GTC ATC TAC ATA ACT CCA GAG TTC TGT TCT GGT AAC TTG GAT CTA CTC    1995
Val Ile Tyr Ile Thr Pro Glu Phe Cys Ser Gly Asn Leu Asp Leu Leu
                605              610                 615

CAG CAA CTT GAC TCT AGT ATT GGC ATC ACT CTC ATT GCT GTG GAT GAG    2043
Gln Gln Leu Asp Ser Ser Ile Gly Ile Thr Leu Ile Ala Val Asp Glu
                620              625                 630

GCT CAC TGC ATT TCA GAG TGG GGC CAT GAT TTC AGA AGT TCA TTC AGG    2091
Ala His Cys Ile Ser Glu Trp Gly His Asp Phe Arg Ser Ser Phe Arg
                635              640                 645
```

*Fig. 6-3*

```
ATG CTG GGC TCT CTT AAA ACA GCG CTC CCA TTG GTT CCA GTC ATT GCA    2139
Met Leu Gly Ser Leu Lys Thr Ala Leu Pro Leu Val Pro Val Ile Ala
650             655             660             665

CTC TCC GCT ACT GCA AGC TCT TCC ATC CGG GAA GAC ATT ATA AGC TGC    2187
Leu Ser Ala Thr Ala Ser Ser Ser Ile Arg Glu Asp Ile Ile Ser Cys
            670             675             680

TTA AAC CTG AAA GAC CCT CAG ATC ACC TGC ACT GGA TTT GAT CGG CCA    2235
Leu Asn Leu Lys Asp Pro Gln Ile Thr Cys Thr Gly Phe Asp Arg Pro
        685             690             695

AAT CTG TAC TTA GAA GTT GGA CGG AAA ACA GGG AAC ATC CTT CAG GAT    2283
Asn Leu Tyr Leu Glu Val Gly Arg Lys Thr Gly Asn Ile Leu Gln Asp
    700             705             710

CTA AAG CCG TTT CTC GTC CGA AAG GCA AGT TCT GCC TGG GAA TTT GAA    2331
Leu Lys Pro Phe Leu Val Arg Lys Ala Ser Ser Ala Trp Glu Phe Glu
715             720             725

GGT CCA ACC ATC ATC TAT TGT CCT TCG AGA AAA ATG ACA GAA CAA GTT    2379
Gly Pro Thr Ile Ile Tyr Cys Pro Ser Arg Lys Met Thr Glu Gln Val
730             735             740             745

ACT GCT GAA CTT GGG AAA CTG AAC TTA GCC TGC AGA ACA TAC CAC GCT    2427
Thr Ala Glu Leu Gly Lys Leu Asn Leu Ala Cys Arg Thr Tyr His Ala
            750             755             760

GGC ATG AAA ATT AGC GAA AGG AAG GAC GTT CAT CAT AGG TTC CTG AGA    2475
Gly Met Lys Ile Ser Glu Arg Lys Asp Val His His Arg Phe Leu Arg
        765             770             775

GAT GAA ATT CAG TGT GTT GTA GCT ACT GTA GCT TTT GGA ATG GGC ATT    2523
Asp Glu Ile Gln Cys Val Val Ala Thr Val Ala Phe Gly Met Gly Ile
    780             785             790

AAT AAA GCT GAC ATT CGC AAA GTT ATT CAT TAT GGT GCG CCT AAG GAA    2571
Asn Lys Ala Asp Ile Arg Lys Val Ile His Tyr Gly Ala Pro Lys Glu
795             800             805

ATG GAA TCC TAT TAC CAG GAA ATT GGT AGA GCT GGC CGG GAT GGA CTT    2619
Met Glu Ser Tyr Tyr Gln Glu Ile Gly Arg Ala Gly Arg Asp Gly Leu
810             815             820             825

CAG AGT TCC TGT CAC TTG CTC TGG GCT CCA GCA GAC TTT AAC ACA TCC    2667
Gln Ser Ser Cys His Leu Leu Trp Ala Pro Ala Asp Phe Asn Thr Ser
            830             835             840

AGG AAT CTC CTT ATT GAG ATT CAC GAT GAA AAG TTC CGG TTA TAT AAA    2715
Arg Asn Leu Leu Ile Glu Ile His Asp Glu Lys Phe Arg Leu Tyr Lys
        845             850             855

TTA AAG ATG ATG GTA AAG ATG GAA AAA TAC CTT CAC TCC AGT CAG TGT    2763
Leu Lys Met Met Val Lys Met Glu Lys Tyr Leu His Ser Ser Gln Cys
    860             865             870
```

*Fig. 6-4*

```
AGG CGA CGA ATC ATC TTG TCC CAT TTT GAG GAC AAA TGT CTG CAG AAG    2811
Arg Arg Arg Ile Ile Leu Ser His Phe Glu Asp Lys Cys Leu Gln Lys
    875             880             885

GCC TCC TTG GAC ATT ATG GGA ACT GAA AAA TGC TGT GAT AAT TGC AGG    2859
Ala Ser Leu Asp Ile Met Gly Thr Glu Lys Cys Cys Asp Asn Cys Arg
890             895             900             905

CCC AGG CTG AAT CAT TGC ATT ACT GCT AAC AAC TCA GAG GAC GCA TCC    2907
Pro Arg Leu Asn His Cys Ile Thr Ala Asn Asn Ser Glu Asp Ala Ser
            910             915             920

CAA GAC TTT GGG CCA CAA GCA TTC CAG CTA CTG TCT GCT GTG GAC ATC    2955
Gln Asp Phe Gly Pro Gln Ala Phe Gln Leu Leu Ser Ala Val Asp Ile
        925             930             935

CTG CAG GAG AAA TTT GGA ATT GGG ATT CCG ATC TTA TTT CTC CGA GGA    3003
Leu Gln Glu Lys Phe Gly Ile Gly Ile Pro Ile Leu Phe Leu Arg Gly
        940             945             950

TCT AAT TCT CAG CGT CTT CCT GAT AAA TAT CGG GGT CAC AGG CTC TTT    3051
Ser Asn Ser Gln Arg Leu Pro Asp Lys Tyr Arg Gly His Arg Leu Phe
    955             960             965

GGT GCT GGA AAG GAG CAA GCA GAA AGT TGG TGG AAG ACC CTT TCT CAC    3099
Gly Ala Gly Lys Glu Gln Ala Glu Ser Trp Trp Lys Thr Leu Ser His
970             975             980             985

CAT CTC ATA GCT GAA GGA TTC TTG GTA GAA GTT CCC AAG GAA AAC AAA    3147
His Leu Ile Ala Glu Gly Phe Leu Val Glu Val Pro Lys Glu Asn Lys
            990             995             1000

TAT ATA AAG ACA TGT TCC CTC ACA AAA AAG GGT AGA AAG TGG CTT GGA    3195
Tyr Ile Lys Thr Cys Ser Leu Thr Lys Lys Gly Arg Lys Trp Leu Gly
        1005            1010            1015

GAA GCC AGT TCG CAG TCT CCT CCG AGC CTT CTC CTT CAA GCT AAT GAA    3243
Glu Ala Ser Ser Gln Ser Pro Pro Ser Leu Leu Leu Gln Ala Asn Glu
        1020            1025            1030

GAG ATG TTT CCA AGG AAA GTT CTG CTA CCA AGT TCT AAT CCT GTA TCT    3291
Glu Met Phe Pro Arg Lys Val Leu Leu Pro Ser Ser Asn Pro Val Ser
    1035            1040            1045

CCA GAA ACG ACG CAA CAT TCC TCT AAT CAA AAC CCA GCT GGA TTA ACT    3339
Pro Glu Thr Thr Gln His Ser Ser Asn Gln Asn Pro Ala Gly Leu Thr
    1050            1055            1060            1065

ACC AAG CAG TCT AAT TTG GAG AGA ACG CAT TCT TAC AAA GTG CCT GAG    3387
Thr Lys Gln Ser Asn Leu Glu Arg Thr His Ser Tyr Lys Val Pro Glu
        1070            1075            1080

AAA GTT TCT TCT GGG ACT AAC ATT CCT AAA AAA AGT GCC GTG ATG CCG    3435
Lys Val Ser Ser Gly Thr Asn Ile Pro Lys Lys Ser Ala Val Met Pro
    1085            1090            1095
```

*Fig. 6-5*

```
TCA CCA GGA ACA TCT TCC AGC CCC TTA GAA CCT GCC ATC TCA GCC CAA        3483
Ser Pro Gly Thr Ser Ser Ser Pro Leu Glu Pro Ala Ile Ser Ala Gln
        1100            1105            1110

GAG CTG GAC GCT CGG ACT GGG CTA TAT GCC AGG CTG GTG GAA GCA AGG        3531
Glu Leu Asp Ala Arg Thr Gly Leu Tyr Ala Arg Leu Val Glu Ala Arg
    1115            1120            1125

CAG AAA CAC GCT AAT AAG ATG GAT GTA CCT CCA GCT ATT TTA GCA ACA        3579
Gln Lys His Ala Asn Lys Met Asp Val Pro Pro Ala Ile Leu Ala Thr
1130            1135            1140            1145

AAC AAG GTT CTG CTG GAC ATG GCT AAA ATG AGA CCG ACT ACT GTT GAA        3627
Asn Lys Val Leu Leu Asp Met Ala Lys Met Arg Pro Thr Thr Val Glu
            1150            1155            1160

AAC ATG AAA CAG ATC GAC GGT GTC TCT GAA GGC AAA GCT GCT CTG TTG        3675
Asn Met Lys Gln Ile Asp Gly Val Ser Glu Gly Lys Ala Ala Leu Leu
        1165            1170            1175

GCC CCT CTG TTG GAA GTC ATC AAA CAT TTC TGT CAA GTA ACT AGT GTT        3723
Ala Pro Leu Leu Glu Val Ile Lys His Phe Cys Gln Val Thr Ser Val
    1180            1185            1190

CAG ACA GAC CTC CTT TCC AGT GCC AAA CCT CAC AAG GAA CAG GAG AAA        3771
Gln Thr Asp Leu Leu Ser Ser Ala Lys Pro His Lys Glu Gln Glu Lys
1195            1200            1205

AGT CAG GAG ATG GAA AAG AAA GAC TGC TCA CTC CCC CAG TCT GTG GCC        3819
Ser Gln Glu Met Glu Lys Lys Asp Cys Ser Leu Pro Gln Ser Val Ala
1210            1215            1220            1225

GTC ACA TAC ACT CTA TTC CAG GAA AAG AAA ATG CCC TTA CAC AGC ATA        3867
Val Thr Tyr Thr Leu Phe Gln Glu Lys Lys Met Pro Leu His Ser Ile
        1230            1235            1240

GCT GAG AAC AGG CTC CTG CCT CTC ACA GCA GCC GGC ATG CAC TTA GCC        3915
Ala Glu Asn Arg Leu Leu Pro Leu Thr Ala Ala Gly Met His Leu Ala
        1245            1250            1255

CAG GCG GTG AAA GCC GGC TAC CCC CTG GAT ATG GAG CGA GCT GGC CTG        3963
Gln Ala Val Lys Ala Gly Tyr Pro Leu Asp Met Glu Arg Ala Gly Leu
        1260            1265            1270

ACC CCA GAG ACT TGG AAG ATT ATT ATG GAT GTC ATC CGA AAC CCT CCC        4011
Thr Pro Glu Thr Trp Lys Ile Ile Met Asp Val Ile Arg Asn Pro Pro
    1275            1280            1285

ATC AAC TCA GAT ATG TAT AAA GTT AAA CTC ATC AGA ATG TTA GTT CCT        4059
Ile Asn Ser Asp Met Tyr Lys Val Lys Leu Ile Arg Met Leu Val Pro
1290            1295            1300            1305

GAA AAC TTA GAC ACG TAC CTC ATC CAC ATG GCG ATT GAG ATT CTT CAG        4107
Glu Asn Leu Asp Thr Tyr Leu Ile His Met Ala Ile Glu Ile Leu Gln
        1310            1315            1320
```

Fig. 6-6

```
AGT GGT TCC GAC AGC AGA ACC CAG CCT CCT TGT GAT TCC AGC AGG AAG      4155
Ser Gly Ser Asp Ser Arg Thr Gln Pro Pro Cys Asp Ser Ser Arg Lys
            1325            1330            1335
AGG CGT TTC CCC AGC TCT GCA GAG AGT TGT GAG AGC TGT AAG GAG AGC      4203
Arg Arg Phe Pro Ser Ser Ala Glu Ser Cys Glu Ser Cys Lys Glu Ser
            1340            1345            1350
AAA GAG GCG GTC ACC GAG ACC AAG GCA TCA TCT TCA GAG TCA AAG AGA      4251
Lys Glu Ala Val Thr Glu Thr Lys Ala Ser Ser Ser Glu Ser Lys Arg
            1355            1360            1365
AAA TTA CCC GAG TGG TTT GCC AAA GGA AAT GTG CCC TCA GCT GAT ACC      4299
Lys Leu Pro Glu Trp Phe Ala Lys Gly Asn Val Pro Ser Ala Asp Thr
1370            1375            1380            1385
GGC AGC TCA TCA TCA ATG GCC AAG ACC AAA AAG AAA GGT CTC TTT AGT      4347
Gly Ser Ser Ser Ser Met Ala Lys Thr Lys Lys Lys Gly Leu Phe Ser
            1390            1395            1400
TAANATGACN ACGATGGAAC AGTTTGTGTG TCCTACATCT TCATTCCTAT AAAGAATGAA    4407
NAGAAATATT TTAACCTCAA AATTATTTAA AGTCCAAAGT GAAGCTCACC TAAACGTCGA    4467
GCCATAGAGT CTTTAATTGN CCGTTGGCAG TTGAGCTACA GTATCTGAAC CTTCTGAGAC    4527
CCGGAGTGCA GCATAGACTG TGAAGTCGGC TTCCTTTCCG ATTGCCTTCC GAACCCGTGT    4587
CACTGTCAGG TTGCAGTCTT TCTCTTCTTG CAGCAGTGTG TGTTGGAAAT GGAGGCTGTG    4647
TCGCTTTGAC ATATAGAACA GATCAGTANT TGCATAGGGA CAGATATGAA GATNCAGCCG    4707
GTCTTTGCTT TCTTATGCAG ATGCCTGTAT GACAGTATCA GTGCACCAGC CCAGCCAGGG    4767
AGACATCAGC TTCCATTTAA AAAGG                                          4792
```

*Fig. 6-7*

Genomic sequnce
>01459     01459

```
TGAGGTTATT CTTTGAAGGG GACAGAATCC CATTTCACTT TTACTAGATA AGAATTTAGA     60
ACCTAACATC TGCCACCGTA GACTCTGAGT TATTAAATTG AGAGGAAATG GCCAAAGTGT    120
ATCCTGTAAT GAAATAATCC TCATATGAAA TTGTTCTTAT ATGACATTGG AAGACCTGTC    180
TTGCTCTGTC TTTTCAGTTT TGGATACATT TTCTTGACAC AAACCGGTAT CAGAGCCAGA    240
CTCTTTTCTG CTCTAACATC TTGCTTCTGT ACGTTATAAT CCTCAGTCCT CAAGCGGTCT    300
CTAACATCTT GCTTCTGTAC GTTATAATCC TCAGTCCTCA AGCGGTCTTC GGCGACGTCA    360
GCTACTCTTT TTTTGTACAG AGTGATGGTT ATAAAGTCTT CTTGTTGAAA ATCACTGTGA    420
ACTTAGTAGC TATAGTAAAA TTTTCATAAA GATCCGTAGA AATTAAAATT ATAGCATAAA    480
TATACAACTA GCTTTTTCTA ACATTTTGTT ATCAGATTTC AGAATAATCA TACATTTTTT    540
ACATTTTTAC TAAAAAATGA GTATTTACAT ATTTGACCAA AATAAAATTG AACCATTTTA    600
GATAATTATT GAAACAATTT CCACATTAAG CAGTATAACT GCCAATTAGT TAATTGCTGA    660
ATGATTACAT ATTAGTTATT AATATTGTCT AGCAACAACT TTATCTTATA CTCAAAATGA    720
TTATATTGGC CATTTAACTT AATTAAGTTT CTCGCTTTTT TAATGCTTTT AGAAAAGATT    780
GGGATGCCTT ATTTAGTTTA GCCCTCAAGC AATTAGGTGA GGCAATTACC ATGGTAACAG    840
AAGGTATTCA TTTCCTTACC TTAGCTAAAG GTTTTGGGAA CAAAGAAACC TCTCAGCTCA    900
TCCATTGAAA CCCAACTTTC TCCTGAGCCT GGCATTAAGT GTTTGTTCTC TAAAAGAGGA    960
CTTAATTTTA AGTGGGGAAA ACATGCCCCT GAGCTGAGTC TCTTTGTCAT AGGGCGATTA   1020
AAAAGCTACC TCTTCTTAAT AGGAAGTGTG GTCTTAACTT TTATATTTCA CATTTTATAT   1080
TGAGAATTTC TACACTCATA TAATGTTTTG ATCAAACTTT CCCTTTAAAT CCTTGCCTTC   1140
CCTATCCTCT TTCTTCCTTT GTTTCCTTCT TTGTTTGTTT CTCTCTCTCT CTCTCTCTCT   1200
CTCTCTCTCT CTCTCTCTCT CTCTTTCTTT CTTTCCTTCA AATGCCCTGA ACGTCCTTAC   1260
GCTGCTTCTC GCTGCATGAG TACAGGATCA CCTGAGATAC CTACCTAGCT GTCAGGAACC   1320
ACATCCTGAA GAAGACAGAC CCTTGCTTCC CCAGTGGCTG GCTATCTGTT GCCAATACTG   1380
TAGGCTTCAT GAGCTTCCCC TCAGTGCACG CTGAGATTTG GCTGGCTTGA TTTTTTTGCA   1440
TGCAGACATA GCCTCTGAGA TGGACAATAA TCCTGCCAAC AGTCTTCCTG CCCCTCTTCT   1500
GCAATGATTC CCAAGCCTTG TGACATGGGA GTCACATTTA GAGCTGGTCA GTTTTTGTTC   1560
TTTTTTCTTT TGTTTTGAAT TAAACTCGAA ATCTCATTGG TATGCTCTCT TTTGACAAAA   1620
GGATACCAGA CCACCTCTCC TAACGGTCTA ATTGCTGTCA AATAAAATCA CTTAAGGTGT   1680
ATTTTTCAAC ACATAATTTA TAGTTTTTGA CAGGTAATTT ATTAATATTT ATTTGGCTAG   1740
TTCTACCATT CCCAAGCAGA AAGTCTACTT ACTAAATTAG CTATCATGAG GCAAATTTTG   1800
TAACTAATTT ATCAAAAATT CTGGTCATGG TGGTGCATAT CTATAATCCT ATCACCCAGG   1860
ATTGTGGTTC AAGGCCAATC TCAAAGGAAA CTTTGTCTCA AAACAAACAA ACAAACAAAC   1920
AAACAAATTA ACATGAAACA GAACACATTA AAAAAACCCA GGGTTTTTAC CAGAAAATTTA  1980
ATTATTAAAT ATATCTTGGA AATTAAAACC AGACAACAAC AACAACAACA TCAACCCACC   2040
CTGAGTATGC TGTTAAAAAT ACCAGTACTA GAGGCCTGGA GACATTGCTC ATGCTTGAGA   2100
CTATTAAGCA TTCTTACAGA AGAATGGGTT CTGTTTCTTG CAACCTCATG GTGGCTCACA   2160
GCTCCCAGTA TATGGACATC TGAGACTGGA AATGATAGGA AGAATTAAGG CTTTACACAA   2220
ATATCTGTCT AAAAACACGC ATGCGCCAGG CTGTCTATAT ACAGCGACTC CTGAATATTC   2280
ACACTTGCAT TTAATTTGAA TTCTGCATTG TGATGCCATA TAAACTGTTA AGTGCAGTGG   2340
AATTCAGGAA CTTGTGGTAC TTTCTGTTTA GTTTAAGATT AAAAGTGCAG TTACTATGTA   2400
GTGGGTAAAG GTGCTTGCTT TGCAAGCCTG ACAGCCTGGC TCAGGGTTCA GCCTCTGTGT   2460
GATGTAGGAG AGAAGCACAC CAGAGCATCA GTAACACTGT CAGGCATTGG TGCCTCTCAT   2520
GAGCTGGATC CCAAGTTGGG CCTGTCATTC CTGTTCCCCA GGCTCTTCTC CATATTTTTC   2580
CCTGCAGTTC CTTTAGACAG GAACAATTCT GAGTCAGAGT TTTTGACTGT GGGATGACAA   2640
CCCCATCCCT CCACTTGGTG CCCTGTCTTT CTATTGGAGG TGGACTCTAC AAGTTCCCTC   2700
TCCCCACTTT TGAGCATTTC GTCTAAGGTC CCTTGCTTTG AGTCCTGAGA GTCTCTCACC   2760
TCCGAGGTCT CTGGTACTTT CTAGAGGGTC CCCCCATTTG AGGGCAACTG ACAGTGCATT   2820
GAGCTTACCA AATATTTTGT AAACTTCTTG TTGTTCAGAT TTAATTACAT CTTTAAAGAG   2880
TTTTGTCCCT AGCTATCGTT CTCGCCGGCA AGAACACACG CGGACAACCG GATTCTTCTG   2940
CGGCAAGCTT TATTGCTTCT TAAGGAGGGA AGACCCAGAC CCTGGAAAAT GGTGCTGCTT   3000
ATATAGCCCT CAGCGTGGCG TTTCAGCACC TGATGTGGCA TGTCACCTCC TGATTTGTTG   3060
CTCGCCCATC ACTTCATTAC TATGCCCCGA GATGGGCAGT GACTAGGCGT GAGTTCACTC   3120
TTGCACTTGC GCACAAGGCT TGTTTATTAG GCACAGCGGA AGCCAGCGCC ATCTTATAAT   3180
```

*Fig. 7-1*

```
GGTGATTACT CGCGGCACGG CTCTCCACAG AGTTTACCAG AAAATGTATT CATAAAATGA    3240
GTGTTATATT ACTTTCCTGT TATATTTATT CCCAATAATA TTGTTTATTT TATTGTATAG    3300
CTTTTTGCTA TTGTAAATAT AATTTTGACT CTGCCCTAAT TTCTGAGGAT GCATTGTCAT    3360
ATCAGAAAAA GTTTTATTAT AGTTTCTATT GTGTTTCTAT AGTTTTTATT ATAGTTTCTA    3420
GTTCAAACCA TATTACTGTT TTCTTTATCA ATTGAAAAAG AGCTACTTTT TAAATTATAG    3480
GCTCCTTGGT TCTCTGGTTA TAAACAATGG TATGCAAAAT AAAACCATTT ACCACTGTGT    3540
CTCTTAAAAA GAAAGTAGGA GATAACTGAC TTCACAAAGT TGCTCTGTGA TCCCCCACGC    3600
ATGTGTCATG GTGGGAGCTT GCTGGCATTC AAACATAAAC ATATCACAAA CGCACACACA    3660
TGCACACATA CTCTCTCTCT CTCACACATG CACACACACA CAATTTGTTA TTTCACTATT    3720
GAAGTCTTGA GAGACCAAAA GAAGGTTTTA CACTAAAAGG AACATTTTTA ATTATCCCCT    3780
CTGTTTCCTT TTTGAAGACT TGTAATATAA TTACATTATA GTTAAAACTG TAGCAATCAC    3840
AGATCACAGG GAAGATGCCC TGATAGCCCA GAAGTAGTAG CATGAAACAA TGTTTAATTA    3900
ATGCTGTCTG ACTCTCAAAT AATAACTAAT AGTACTAACA GAGCAGATGA GAGCTTTTAA    3960
TAGTATTTTG AAAATATTTT ATATAAAATT TAGTCATATT CAAAGCTGTC TATATGATTG    4020
GAAGGAATTA ACATGTCTCC TCTTTAAGGA AACAGAGACT CTCTTAGCTT TAAGGGCTTT    4080
GTGCCCTTGG TAATCCATGT AAGGGGCCTG AACTGCTGCA CAGCAGTTGG TTGTAAAGAA    4140
GTTTTTAGAC TGCCAAGCGA GACACTCCTC CTGCTGTTTG CTACCACTTG ATTAGAAAAT    4200
AGTTTGTGTG GTGGTTGTTA AATAAAATTC AAGTCATGAT CAAAAGTAAG CATAAAGTCC    4260
AATATATAGT AACCTTAATA ATGGGGGGAG GAGAGTGAGT ACTTGTCGAG TGTTCAAGAA    4320
GTCTCAGGTT CCGTCCACAG TCCCACATAC ACCAGGCACA GGGGCACAGA CCTGTCATCT    4380
CATCTCAGTA CGCGGGCAAG AAAATCAGGA GTTCAAAGCC ATCCTTGGCT ACATAGCAAG    4440
TTTGAGGCCA GCGTAGACGT CATGACATTC TGTCTCAATA AAACAAGCAA CAACAAGAAC    4500
ACTCCCCAAA CAACAACCTT CCCTCAAGTC CAAAGAAGAC TGAGACATGC GAGATGCACA    4560
GTAAACTAAG GTCATCAGGA GTGTGAGGGG CTTAGAGAGG ATGGGTGGGG GGGACTACAC    4620
TGTATGAAGC TGTCACAAAG ATGCACACTA GACAAGGGAA AATGTCTTTA AAATGCAGAC    4680
ATATAATCTT ATTTATTATT GTGTGTGAGT GTGGGTAGAC ACATGCCATG GCATGCATGT    4740
CAACTTTGTG GAGTTGCTTC TCTTTTTCTA CCTTTCCATG GATTCTGAGT CTCCAATTCA    4800
GGTCACCACA CCTGTGGAGT TAATACCCTT ATCTGCTGGG CTGTCTCATC AGCGCCAAAG    4860
AACTTGTTTT TAATACTGCC TGTGAATGAG ATGAATGGCA CTACTGAAAA ACTGTAAATT    4920
AATATAAATT ATGCTGATCC CTGCTTAGCC TCAAATGAAT GAGACCCAAA CTATAATTTA    4980
TTTATTGGGC TCTGCTCAAT TACCTCGGGA TGACCCCAAA TCTATTCTCT AATGCTAGTC    5040
TGGCTACTTC CCCAACTGTG CTCCCCAAAT ACTTGCCGTC TGAATCTTCC TGGGTGATTC    5100
CTGCTCTAGC AGCCTGGTGT CCCAGGAAGG CATTTCACTC AGGCAGTGCT GCTGGTCCAT    5160
CAGGACTAAT GGAGATCTCC TCTTTTCTAT GTCTTCTTCC CCATTCCCAC CCCACCCTTG    5220
TAATTGGTTG TTGCCAGTTT TACTTAACTA ATAGTTTTAA ATTGGATAAG TTTGCACAAC    5280
AAAGGTGGGT TGTAACTAGG GATTTGCTTG TCTTGGCGCA ACCAGATCAT GGAGTACAGA    5340
ATTTAACATA TGGATACAAG TAGCACCAGA CCAACCCACA ATAAAAAACA GACAAAAAAA    5400
AAAAAAAAAA AAAAAACCAG CAAAAAAAAC CCCCATAGAC AGTCTTTAAA TGATAAGAGC    5460
GGAAAAGTTG TAGGTGGTAA TAGATGGTTA GACAGGATAA TTTCAGGGAA GATTTAAGTT    5520
ATTTAAAAAA AATCTATTTA TATATGCATG CAATTGTGTG TGAGTGTGTG TGTGCGCACG    5580
TGATTGTATG AGTATGTGAT GGCCAGTGCT CTTGGAGGTC AGGGTGTCAG ATCTGGTAGC    5640
TGGAGTCTCA ACTTGGGTAG AAACTTTTAA CCTCTGAGCC ATCTTTCTAG CCCCAAGATA    5700
CTGGTTTTGT AAATAAATTT ACCTTTAAAT TCTCTTCCTG GGGGTATCT AGATCCAATT    5760
TTGTACGTAA GCAGATATTT CAAATTAAAA TGATGCTGGT GTCACACAGC TGCCGATTAG    5820
TTACTGAGAT TTACGTTTGC TTCAACATTG TGCTGAACTA CATGCATAGC TTTTGTAAAA    5880
GGTTATTTGC TGAAACTAGC TTTCTGGTAT TTCACCAGTA ATATACTCTG GGCACAGAAC    5940
AAACTTGTTT TCTGACTCAA TATAAATATA TTGCGTGTGT GTGTGTGTGT GTGTGTGTGT    6000
GTGTGTGTGT GTGTGTGTGC ATGTTATAAA ATCCTGTCTT CTGCTCATGA CATAGCTGTT    6060
TCATTAACTC ACAGCAGTTT GTATTTGCCT GCATGAGACC TATATAAGAT CAAGCCAGTC    6120
TGAATCCCAG CATGCAAAGG GGAGATGCTA TCTGGGACCC ACCCTTCATG GGAGATACAG    6180
GAATTGGTGG CTCCTGGGGG AGGGAAGAGT AATTTTTCTT TGGGAGTGTG GCCATTGTCA    6240
TCTTGTCCAT GTTCCAGTGG ATAGCCCTAC ACTCATACAC AGAAGCAACA GTAACTGGAC    6300
TTAGTGGGTT ATAAAAAATA TTAGAAATGG AATTTGTATA CAACCGAGCC GTATCACTCC    6360
TGATCATATA CCCAAAGGAC TTTACCATAC AATAGAAGTA TTTGCTTAGC CATGTTTATT    6420
GCTAATCTTT TCATAATAGT GAGTATGTGA ATAAGTGGAT GAGTGGATAG AGAGTCTGGA    6480
```

Fig. 7-2

```
ACTAGGTAGG AGACCATGAA CGGGAACAGT AGGTGTTGAG AAGGGGCAGG AGCAGAAAGC   6540
AAAAGGTCAC ATTGGGCATT GTCTTAGTTA GGCTTACTAT CGTTGTGACA AAACACAAAA   6600
TAAAATCTCC AAAAGCAACT TGGGGAGGAA AAGATTAGAA TTTACGACTC TTGAGTTCAT   6660
ACTCCATCAC TGTGGGAAGT CAGAGCAGGA ACTCTAGGCA GGAACTGAAG GAGAGGCCAA   6720
GGAGGAACAC TGCTTACTGG CTTTCTCTTC ATGGCTTGCT CAGCCTGTTT TCTTAGACAC   6780
CAAGAACAAC CTGCCCTGGG GTGACATCAC TTACTGTAGA CCAGGCCCTC CCACATTAAT   6840
CATGTGTCAA GAAAATGTCC CACATGCTTT CTTTAAGGCC AATCTTATAG AGCTGTGGGA   6900
AGCCACATGT GCCGTTGCAG AGTGGCACCG GCTACTGCTG GCTACCACGC ATAAGTTTGG   6960
ACAAACAACC AATGTGTACA TATGCAGTAA AGCTTTTTGC CAAGTCACTG CCTGGCCCCG   7020
GCATGTTAAT GAGGTACTGA GAATATAACC AATCAGATGT GAGACATGCA AATGAGGTAT   7080
GATAATGAGG TTCTGTGAGG TACTGAGAGA GAGTAGCCAA TCAGATGAGG AACATGCAAA   7140
TGAGGCATAG TGCATAACCA ATCCGTGTGT GAGACACGCC TCTCCTAGGC CTATATAAGC   7200
AGCACCAGTT CTGGGCTCAG GGTCTCTTTG CCTCTGCAAT CAAGCTCTCC CAGAAGGATC   7260
CTGTTGCAGC GTCGTTCTTG CTGGTCAAGT CGGGCGAGCA CAAAATAGAG CCTTTTTTTT   7320
TTTTTAAATT GAGAGTCCCT CCTCCCAAAT GACTCCCGCT TGTGTCAGGT GGACAGTAAA   7380
CTAGCCAGGA CAGATGACCC CCTTGTCAAC TTGGCACACC AGTACTTATT ATGAAAACAT   7440
AACCTTTCCC TTTTTGTTCA TTTTTAAGGT CTCATATTAA TATTATAATA TAAGCTATAA   7500
ATAACTTTAA AAGTTTCATA TTCTTTAAAA ATTCAAAAAA TTTACAAGTT AAGTCTCTTT   7560
AAAATATCCA AAATTTCTCT AAAATTACCA AGTTTCTTTG AAATATCCAA GGCCTCATAA   7620
ATGGATGTTT CTGTAAAATT AAAATAAATT ACTTTCTTAT TCCAAGAGAG AAGAAGCAGG   7680
GCACAGCCAC AGAAAATTCT GAGTGCACAT TAATAACTAA GTAAGATAAT GCCCCATAGG   7740
GTTGTCTTCT GTCGGCCTGT CTTACAGAGG CAATTTCTCA ATTATGCTTC CCTTTTCTCA   7800
GACAACACAT ACTTGTGTCA CATTGGCAAA AATCTAGCCA ACAAAGGCTT GAAAGCAGAA   7860
GGCTACTGGG GATGGCAGGG CTCAAGGACT GGGGACTTGG TGATTAGGGA GAAATAGGGC   7920
ATAGGAAGAG AAACCGCAAA AACAAAAATT TCTTGTAAAA ATGCTACAAT GAAACCTAAT   7980
CATCTGTATA TAATAAAAAG TGAATAGAAC AGATTGTACA TCTGTAATTT GCTATCATCT   8040
TTTGACTTCT GTTAGTGGTT TTGAAATCTT GGCAAAAAGC AACTTAACCA TTAACAGTTC   8100
TAAATTGCTT TAGGGTTTAT AAAACCTGCA TTTTCACATG AGATTGTCTT ATTACATTAA   8160
AGTTGGGTGG ATCTGGGAAG AGTTACACTA TGTATGCAAT TCTCAAAGAA CCGAGGAAAG   8220
GAAGATAAAA TTTCTTTATA TTATTTAATA GTGCTGAGTG TAGTAGGCTG TTCCTCCATC   8280
TTAAATGCGT GCTCTGATTT CTTCATGGTA ACAGAGGTTT CATCAGGAGA CTCTTCCAAA   8340
ACATATTTAA AACTTTACTC CCCACAAGAC ATTTGGGTAA CAGGAACTTT CCGGANGTGT   8400
GAGGAGTTTA TTACTTGGCT TTAGTATAAA TCATGTAGGA GCATGGATGC ATTTCATTAT   8460
TGAAAAAATA ATATATTTGG AGTCTCATAC TTGAAGTCTG GGTTATATTC CAGAGAGCCC   8520
TCAAAACTAG TAACAGCTTA AGAGAAAGAT CATCCAAGAA ACCCTTTCTT TTTAGGGAAG   8580
TGTCTCTTAC TCAGCCAAGA GCACAGTGAA AGGGCTTAGT ATTGGACAGC TATTATATCT   8640
TCAAAACTAG GTCTTTATTT TATTTTACGA ATAAATCCAG TAGTTGCTCT GAGTCAGCTT   8700
ATACCTTATG AGAGATGATA ATTATACAGA AAATCAAAGA TGCTGAAAAT GTAATACCTC   8760
ACATACTGAG GGATCCTGTT CATTAAGGAG ATAAAAATTA TTCTTTTGAA GGAGCAAAGC   8820
TATACACATA ACATATTAGA ATTTTGAAAC AGCCACAATC ATAGAACTTA ATTTGTTATA   8880
AAAGGAAGAA GTAATGTATA GTTAATAAGT GGTTAAGCC TTGTCCTTGA GGCTAGATGT   8940
TATAACTCAT ACTAAATATG TATGTTTGTT TCAGGCTAGG TATCATATCC TACACGAAAT   9000
ATGTATGTAT GTTTCAGGTT AGATGCTATA TCCTACACTA ATTATATATG TTTGTTTCAT   9060
TTTCAGTCCT ATCTATGGAG CTGTCTCTGA GCTTTCTATC AAATATTTGT CATATTTATT   9120
CATAGATATT GTTTATTGGA ATTTGCAAAC AGGGCATTTT AAAGACAAAT GAAAATAAAA   9180
TGGAAACCAC TTCACTACAG CGGAAATTTC CAGAATGGAT GTCTATGCAG AGTCAAAGAT   9240
GTGCTACAGA AGAAAAGGTA ATTGTTCATT GATTATTTGT CTAAATGGGC AATCTTGTTT   9300
GAGTTTGACT ATGCAGTGAG TCACATCATT GCTTGTGAGC TTTGGGTCAT TGTTGAGGTA   9360
AAACTTTCTG TTGTGTGAAT GAACCAGAAC TAAGTTGTTC AAAGGTAAAT GAGACTCAAT   9420
TTTATACATG TTTTATAAAA TGAGATTCCC TAGAGTATAT TCTTTCTTTT TATAGTTAGC   9480
ATTCTTAGTT GAAGTTATTG GTTTGTTCAA ATTCAAGTAA TAATTTATAC AATATTAATG   9540
TTGGCATTTT TTGGTTAAAA TAGTTTGAGT CCTTAGAGGC TTAAGATCTG ATAATTAGCC   9600
ACCAACATTT TTTTGTTTTC TTTTTCAATA TTTTATTAGA TATTTTCTTC ATTTACGTTT   9660
CAAATGCTAT CCCGAAAGTC CCTTATACTC CCTCACTCCA CCCACTCCCC TACCCACCCA   9720
CTCCCACTTC TTGGCCCTGG CGTTTCCCTG TACTGGGGCA TATAAAGTTT GCAAGACCAA   9780
```

*Fig. 7-3*

```
GGGGCCTCTC TTCCCAATGA TGGCTGACTA GGACATCTTC TGCTACATAT GCATCTAGAG   9840
ACATGAGCTC TGGGGGGTAC TGGTTAGTTC ATATTGTTGT TCTACCTATA GGGTTGCAGA   9900
TCCCCCCAGC TCCTTGGGTA CTTTCTCTAG CTCCTCCATT GGGGGCCCTG TGATCCATCC   9960
TATAGATGAC TGTGAGCATC CACGTCTGTG TTTGCCAGGC ACTGGCATAG CCTCACACGA  10020
GACAGCTATA TCAGGGTCCT TTCAGCAAAA TCTTGCTGGC ATGTGCAATA GTGTCTGCGT  10080
TTGGTAGCCA CCAACATTTT AAGGTTACAT TATTGCATCT AGCATGCTAA TATAATTATG  10140
AGGAAAAAAC AAGTAAATTA AGTGACTTCA CAAAAGAAAG ATTGGATGTT TGAAAATAGA  10200
ATTGTGTGGA AAAATAACTT TATGTTTACC CTTGTTAATC TGACCTTATG AATTCTTACT  10260
CTATAATATA AAATGTAGTG CTATAAATTT CTTCAGTGAA CTTTATTATT TCAGTTAACA  10320
CTACAACTTA CTGTGATATT TATTTGTGCC TGTTTTGAAT TTTGCTCAAC TCAAGGCCTG  10380
CGTTCAGAAG AGTGTTCTTG AAGATAATCT CCCATTCTTA GAATTCCCTG GATCCATTGT  10440
TTACAGTTAT GAAGCTAGTG ATTGCTCCTT CCTGTCTGAA GACATTAGGT AAGGGATTGG  10500
AAGTTCTTAC CATTAAGTTT GTACCCGTAA GAAATAGCGA TATTTATGAG TGCCTAGTTT  10560
TACAATGGAA GTATATCTCA GAAGTATATT TACATACATC ATATCACAGT TGTATTCTAC  10620
TTTTTAAAAT ATAAAATAAA CTCACTAAAT TAAATTAGTA AGGTTCCTAT TTGTTAATTA  10680
GTAACCTTTT CTACTTTATT AGATACTTTT TTTTTCTTTT AGTGCTTTAG ATGTAAATAC  10740
AGGTAAAACT ATTGAAGACA ACTGTTTACC AATTTAGGAA AAAATGGAAA ATGTTATTTA  10800
ATGTCGAACT ATTTTCATAT CTTAAAACAT CAATGTATTA AGTAATGTTT ATGATTCTCT  10860
GTTTTATTTT TTTTAATTTA TTTTTAGCTT TTAAAATTGT GTTAGGATGC CTCCTCTGCG  10920
TGTATGTTTG TATACCACAT GGTTACGGTG TCCACAGAGG CCAGGAGAGG GCTTTGGATC  10980
CCCTTGAACT GGAGTTGTGA GCGATCTTAT GGGTGCCGGG AATCAAGCCT AGGTTCTCTG  11040
GAAGAGCAGC CAGTGCATTC AGCTGCTGAA CCATTTTAAA AGATAGTGAT AGTTCCTGCA  11100
AATGGTCCAT GAAAAGAGCT TTAGCAATGA CTGTTGGTAC TTTAAGAGTT GCCTGTCTTT  11160
GTTTTTCTAA GGCTATAACA AAATCCATGG CCTGAGTAAA TTATAAAAAA ATACATATAA  11220
GTAAATTCAT AAATAAATTT ATTCCTTACA GTTTTGGAGG CTATAGAGCC CCCAGAGAAT  11280
GGGATTGGCA TTTGTAAGGG GACCATTTTT TTTTTTAAAT TGGATATTTT CTTTATTTAC  11340
ATTTCAAATG TTATCATCTT TTCTGGTTTC CTTCCCTCCT GGAAACCCCC TATCACATCC  11400
TCCGTCTCTC TGCTTCTGTA AGAGTGTTCC TCTACCCACC CACCCACCCA CCCACCCACT  11460
CCCACCTTCC TGCCCTTGAT TCACCTACAC TGATGCATCT ATTGAGCCTT CATAGGACCA  11520
CGGACATCTC CTCCCACTGA TGAATGACAA GGCCATCCTC TGCAACATAT GCAGCTGGAG  11580
CTATGTGTAC TCCTTGGTTG ATGGCTTAGT CCCTAGTTTT CTGGGGGTGG GGGAGGTGTG  11640
ATCTGGTTGG TTTATGTTGT TGTTCTTCCT ATGGGATTTC AAACCCTTTC AACTCTTTCA  11700
GTCCCTTCTC TAACTCCTCT ATTAAGGACC CTGCGCTCAG TCCAATGGTT GGCTGTTAAC  11760
ATCCACCTCT GTATTTGTAA GGCTCTGGCA GGGCCTCTCA GGAGCAGGCT CCTTTCAGCA  11820
TGCACTTCTT GGCATCCACA ATAGTGTCTG GGTTTGGTAA CTGTATATGG AATGAATCCC  11880
CAGGTGAGAC AGTTTCTGGG TGGTCTTTCC TTCAGTCTCT GCTCTTCACT TTATCTCCAT  11940
ATTTGCTCCT GTGAGTATTT TGTTCTCCTT CTAAGAAGGA CCGAAGCACC CCCACTTTGG  12000
TCTTCTTTCT TATTGACCTT CATGTAGTCT GTGAATTGTA TCCTGGTCAT TTGGAGCTTT  12060
TGGGCTAATA TCCACTTATC AATGAGTGTA TAATATTTGT GTTCTTCTGC GATTGGGTTA  12120
CCTCACTCAG GATGATATTT TCTGTCCATT TGCCTAAGAA TTTCATGAAT TCATCATTTT  12180
TAATAGCTGA GTAGTAAGTA CTCCATTGTG TAAATGTACC ACATTTTCTG TATCTATTCC  12240
TCTTTTGAAG GACATCTGGC TTCCTTCCAG CTCCTGGCTA TTATAAATAA ATATATAAAC  12300
ATAGTGGAGC ATGTGTTCTT ATTACATATT GGAACAGAAA GAGCAATTTG CAAATTCATT  12360
TGGAATAACA AAAAAAAAAA AAAAAAAAAC CCAGGATAGC GAAAACTATT CTCAACAATA  12420
GAAGAACTTC TGGGGGAATC ACCATCCTGA CCTCAAGTTG TATTACAGAG CAATAGTGAT  12480
AAAGACTGCT TGGTAATGGT TCAGAGACAG GCAGGAAGAT CAATGGAATA GAATTGAAGA  12540
CCCAGAAATG AACCCACACT CATATGGTCA CTTAATCTTT GACAAAGGAG CTAAAACCAT  12600
CCAGTGGAAA AATGACAGCA TTTTTAACAA ATGGTGTTAG TTTAACTGGT AGTCAGCATG  12660
TAGAAGAATG CAAATCGACC CATTTTTTTC TTTTCTTTTC TTTATTTACA TTTCAAATGT  12720
TATTCCCTTT CCTGGTTTCC CCTCTAACCC CCCCCCCCCC CCACACACAC ACACACACAC  12780
ACCAACCCAC TGGCTTCCTC TTCCTGGCCC TGGCATTCCT CTATACTGGG GCATAGAGCC  12840
TTCAAAAGAC CAAGGGCCTC TCCTCCCATT GATGACCAAC TAGGCCATCC TCAGCTACAT  12900
ATGTAGCTGA AGCCATGAGT GTGCTCTTTG GTTAGTGGTT TAGTCTCTGA GAGCTCTGGT  12960
GGTACTGGTT AGTTCATATT GTTGTTCCTC CAATGGGGCT GCAAACCTCT GCTACTCCTT  13020
GGTTACTTTC TCTAACTCCT TCACTGGGGA TCCTGTGCTC AGTCCAATGG ATGGCTGTGA  13080
```

Fig. 7-4

```
GCATCCATTT CTGTATTTGA AGTTGACCCA TTCTTACCTC CTTGTACAAA GCTCAAGTCC   13140
AAGTGGATCA AGGACCTTCA CATAAAACCA GATACACTGA AACTTATAGA GAAGAAAGTG   13200
GGGAAGAGCC CCAAACATAT GGGCACAGGG GAAAAATTCC TGAACAGAAC ACCAATGGCT   13260
TATGCTGTAA GATAAAGAAT CAACAAATGG GACCTCATAA AATTGCAAAG CTTCTGTAAG   13320
GCAAAGCACA TTGTCAATAA GAAAAAAAGG CCACCAACAG ATTGGGAAAA GATCTTTACC   13380
AATCCTACAT CTGATAGAGG GCTAATATCC AATATATTCA AAGAACTCAA GAAGTTAGAC   13440
TTCAGAGAAC CAAATAACCC TATTAAAAAT GGGGTTCAGA GCTGTCTTAG TCAGGGTTTC   13500
TATTCCTGCA CAAACATCAT GACCAAGAAG CAAGTTGGGG AGGAAAGGGT TTATTCGGCT   13560
TACATTTCCA TATTGCTGTT GATCACCAAA GGATGCAGGA CTGGAACTCA AGCAGGTCAG   13620
AAAGCAGGAG CTGATGCAGA GACCATGGAG GGATGTTCTT TACTGGCTTG CTTCCCCTGG   13680
CTTGCTCAGC CTGCTCTCTT ATAGAACCCA AGACTACCAG CCCAGAGATG GTTCCACCTA   13740
CAAGGGGCCT TTCCCCCTTT ATCACTAATT GAGAAAATGC CTTAGAGTTG GATCTCATGG   13800
AGGCATTTCC TCAACTGAAG CTCCTTTCTC TGTGATAACC CCAGCTGTGT CAAGTTGACA   13860
CAAAACCAGC CAGTACAAGA GCTAAACAAA GAATTTTCAA CTGAGGAATA CTGAATGGCT   13920
GAGAAGCACC TAAAGAAATG TTCAACATCC TTAATGATCA GGGAAATGCA AATCAAAACA   13980
ACCATGAGAT TCCACCTCAC ACCAGTCAGA ATGGCTAAGA TCAAAAACTC AGGTGACAGC   14040
AGATGCTGGC AAGGATGTGG AGAAAGAGGA ACACTCCTCC ATTGCTGGTG GGATTGCAGG   14100
CTTGTACAAC CACTCTGGAA ATCAGTCTGG CGGTTCCTCA GAAAACTGAA CATAGTACCT   14160
ACTACCTGAG GACCCAGCTA TACCACTCCT GGGCATATAT CCAGAAGATG CTGCAACATC   14220
TAAGGGAACT TTGTACTGCG TCTGTATCAG GGTAGAGGCT AAGATGGGTT GGGATTAAGC   14280
CAGTTCTCTG GATACCTGTT CTGGGAGTGG AGCCCTGATG AGCCAAACAC TTGTGTTTAG   14340
GCCCCACCTC CACGCCCTGC TCCATTAAGG ATTCCATTTT AACAGGGACT ATGAATAGGA   14400
TATTCATGAC CCAGCACCTT GTGTAATTCG GGTTCTGGAG TAATGCAATC TAAGCCTCTT   14460
GATGCAACTT ACACTGAGAA GTAGTAAATC AATTCAGATC ATTGAAATGA CTGCGTGTGT   14520
CCTTTTGGTT TTTAACTATT TTCATGAAAA GCAGAAGTGA ATAAAGTTGT TCATCAGTGC   14580
CCTCCTGGTG GTTGGTAAAT GTGATCTAGA AGTGGCATTT AGGTATCTTT ACTTCCACTG   14640
CATTTACTGG TTATGTGTGG GCTTCATTTT GCTGAACTAA AATTAGACTT ACAGAATAAG   14700
TAAATCTATT ACACACGGTT ATATATTGTC CTCACCATGT TACCTTTGTC TTCCTACGGT   14760
ATGACATGTG TTTTATTAGT CAGAGGGTTT TTTTTTTTTG GTTTGTTTGT TTATCTTTTG   14820
TTTTTAAAGG AATAGAACTG GCAGAATGAA CGTATATATA TATCAAACAG GGATTTATTA   14880
GTGTGGCTTT GCAGACTGAG GTCTCTTGTC CAACAATGGC TGTGCCTCAT CAAAGCCAAG   14940
AATCCTTTTT TCTCGTAGTT GTTCATTCGA GGAGCCTGGG TGTCTAAGTC AGTCTTCAGT   15000
CTGCATGGGC TTCCTGAAGA AGGAATTTCT AACACCAGCT AAGTAGTGCC TTAGTAGCAA   15060
GACAGACGAA CTTGCCAGCC AGACTGAGGA CAGGCTGACA AAAAGCCAAA GCTTCCCTCT   15120
TCCGTGCCCC TTCAGAAGTG GGCCGCCATC AGAAAGCGTA ACCTAGATTT AGGATGCTCT   15180
TCTCCTGTCA CATAATCTAA TCAAGAAAAG CCCTCATAGG TGAGCCCAGG GCTTATATTT   15240
TAGATGATTC CAAATGGAGT CAGGTTGCCA GCCAAGATCA GCTCAGCACA GTAAGTTGAA   15300
GTGGTCTGAA TGAAGCTCTG TGTTCATTTT GAAGTGCAAG ACGGGCTTGG TTTGCTTTGC   15360
ATTACTTTTC ATATGGCCAC TTTGGAGATC CTCGCATCAG GGGCTGGAAA CATGGCCCCC   15420
CATTAAGAGC AGGAAGCGCT ATTGCAGAGG ACCCCAGTCT GGTTCCCAGT ACCCATAATG   15480
GTGGCTCACA GACCTCTGTT TTCTATGACT CCAGCTCCAG GGTGCTGAGT CCCTCTTCTG   15540
CCCTCTACAG GCACCTGTGC TTATGTGCAC ATATGTACCC CTCTTCCCAT ACACACCTGG   15600
TTAGAAAAAT AAAAATCTTA AAGAATATTT TTACACCAGG GCCAGTGACA TGGCTCAGCG   15660
GGTAACAGGG CCTGCCACCA AGACTGGAGA TCTGAGTTCT AATCCCATTT CAACCTCAGA   15720
GGCTCATGGT GGAAGCCAAG AGCTGATCCT GAATTCAACA TGCATGGGGC CACCAAAAAA   15780
GAAAGAAAGA AAGAAAGCAA TTTAAAAAGA TGTTTACCCC ATGGGGTTTC AACAGTTTGA   15840
TATGACATAC CTTTGTGTGC TGAAGTTTGT GCTGATCCTG CTTGGGGACC ATCGACCTTT   15900
TTTTTTTTTT TTTTTAAATT TGTGGGTTTA ATAGTTTTTG TCCAATTTGA AAATCATCTT   15960
CAGTTTTTAT TTTTTTCAGT ACTGTGCTTT TCTGGGACTC TGATATACAT ACACTAGGTT   16020
GCTGGATACT ATGTCTTAAC TTCTTTTCTC TTTTTGTTTA TGCTTTGGTT TGAATGTTTC   16080
TTCTGCTGTG TCTTTAAGTT AATCACCTAT ATTTCTTCTG TAGTGGCTGA TCTACTGTAT   16140
ATCCTCCCTG TGTATTTTTA ATTTTCATTG TGTTTTTCTC TTTTTTGTTA TTGAAAATGA   16200
TTTTTTTAAA AATACAACAC ATTTGGACTG TGGTTTCCCT TTCCACAACT CACCCCAAAT   16260
CCTCTCCACC TCAACAGAAA AAGAAAGGGC CAGAGAAGAA GCACAGGAAA CACATACAGA   16320
TGCAGGCCAC ACACGTGTAC ACACAGGAAT CTCATAAGTA CACAAAATCA GAAACCAGAT   16380
```

*Fig. 7-5*

```
ATATAAAAAT TATATAAGCA AAAGACTTGC TAGATTAACA AAATAAAGGT TCATTCTCTG    16440
TTGGCCATTT ACTGCTGGGC CTAGGGCCTG CTGGTGAGTG TGGTTTGTAT ACCCAGTGAG    16500
TCTGGTGGAG AAACTAGTTT TTCCTTTGTG AGTGGTTATA AATAGGAGAT AATTTCTGGG    16560
TGAGGGATAG GATCGGCGCT GGGACTTTAT CTGGTTAGAC CTGGGTAGAC CCTGTGTGTG    16620
CTCCCACATG AAAGCTCTTC TGTGCTTTAT CAGCCCTGCT GTGTCTTGAA GGGCTTCTTG    16680
CCTTGGTGTC TTCCATCCCA CTGGGTCTTA CAACCTCTCT GCCCCCTCTT TTGCAAAGTT    16740
CCCTGAGCCA TGCGGGGAGG GGTCTGTCAT TGTTCCCATC TCCTGCAGGA GGCAGTGTCT    16800
CTGACATTGG CTGGGCAAGA CACTGAGCCA TGAGCATAAA AAAACCCTGC CAATTTGCTA    16860
TTCATTGTGT GCATGCTTTC CTTTAAATTC CTGAACATAT TTACAATTTA TAATAGTTTT    16920
CGTTTGTCTT GTTTTGAGCA GGGGCTTATG TAGCCTAGGC TGGCCTTGAA TGTACTCTGT    16980
CGCCAAGGCT GATCTTAGTT CCTGATCCTA TTGCCTATGC CACCAAGTGC TGGGATCACT    17040
GACTTGTGCC AGCAGGCCCT GCTGTGACCA TAATGCAAAT TTCAGTGATA TTTTAGCTCT    17100
ATTTTTGCCT CTATTGAGTG ATCACCCCGC CAACTGATTA TGTTTATGTT TGATATGTGT    17160
CAGGGCTGTT GAGGTTTTTT TTCTTTTTCT TTTTTTTTTT TTTTTTTTGG TCTGCTGTTG    17220
TGATTTTACC TTGCTCAATA TATATATATA TATATATATA TATATATATT TTTTTTTTTT    17280
TAGTTTGCTT TCTAAGAAAA GAGGTTTTGC CAGAGGGCTC ACCCAGAGAT GGGTTTTGTA    17340
TTCGGAGGCT TGCTTTTAGA CCTCATTAGG CCGGCAATTG CTTTTCCTCC AAAGGTAATT    17400
TAGTTCTCTC AGGTGCGATC ATAAGGGAGG CTGCTGCATG TTCCTAGAGT TCAGCAAGAA    17460
TGTCTGCTGG GACTTGGGAA CTTACGCTCT TACCTCTGTC TGTGTCCCCA CCTCAGGGCT    17520
GTCCTTTCTC TGTTGTCTGT AAGGCATTCT AGGAGAACCA GGGACAACGA CAGAGACTGT    17580
CCTCTTGTTC AGAGAACAGT AAATTTAGAC GTGTTTGTAC AATTTATTGT TTCTTTTTAG    17640
TGGAAAAAGA AGTACTTGTA AATTTTATCT TAGCCTGAGG TATTAGTTGA TATTCTTTTA    17700
TGTTTGTAAT AAATTTTTAA TCAAAACTTG TGAACTAGGC ATAGAAACAA TAGTAAACAA    17760
AACCGTATCT TCTTATTTAA TTATATCAAA TCTTTATTAT TTAGTGTGTA TGTGTGTGTG    17820
CTCATGTATG TAGATATATA CTTGGTCAGA GGACAACTTT CAGGAGTAGT TTTCTTCTAT    17880
TATTTATGTC TAAAATTAAA TAGAAAATAA AAGCTCATGT ATACCCTTTT TAATTTATTT    17940
TCTTCCAACC CCCGTGCTAC TTTAAATAAC ATGTCATGAA TTTAGTATTT ATCATTTCTT    18000
TATATTGTGT TATTTGCCAA CTTAGAAACT ATATGGTTTT CCTGAAGCTT GTCTTTTTCA    18060
CTCAAGTTTT GAGAATTTTT CATTTTGATA TATGTAGTTC CATTATTTTA TATGCTATAT    18120
TATGTTTTGG CATGCCACAA TTTCTTTATT TTTTTGTTTT ATGGAAACAT AGTTTTTCCA    18180
ATTCCCCCGT CTGCAAAAGG ATCAGGGTTG TAGTGAACAT TCTTTCTTTG CTGTGTTGGT    18240
TAGTGTTTCT TGTCCATTTG GCACAGCCTA GAGTCGTCTG AGGCTAAGGA ACCCAACTGA    18300
GAGAATGCCC CATCAGATTG GTGTATAGGC AAGCGTGGGA ATAGGGTTTT CTTGACTGAT    18360
GATTGATGTG GGAGGGACCA GCTCACCTTG GGCAATGTCA TCCCTTGGGA GTTGGTCCTA    18420
CCTTGTATAA GAAAGCAAAC CTAGCAAGCC AGTTAGCAGT GTTTCTCCAT GGCCTCTACT    18480
TCCGCTCCTG CTTCTAGGGA CCTGCCTTGA GTTCCTGCCC TGACTTCCTT TTCTTCCCAA    18540
ATTGCTTTTG GACATGGTGA TGATCACAGC AATAGATGGC AAAACTAAGAC ATTAATCAAT    18600
TGAGCTGTCT CACCTTTTAG AGTGGTTTGA ATAAGCATGG CCCTCAAAGG CTCATATATA    18660
GAATGGCTAA TCACCGAGGA GTGGAACTCT TTGATAGGAT TGGAACAGTG GTTCTCAACT    18720
TGAGAGTCTT GATGTCTTTG GACATTAAGC GACCCTTTCA CAGATATCCT GAATATCAGG    18780
TATTTACATC GTGATTCATA GCAGTAACAA AATTACAGTT ATGAAGTACC AATGAAATCA    18840
TTTTATGGTT GGCGTCATTA GGAAGGTTGA CAACCACTGG ATTAGAAGAA TTAGGACTTA    18900
TGACCTTGTT GGGGGAAGTG TGTCACTTGG GGTGGGCTTT GAGGCTTCAA AAGCCTAGAC    18960
TTTGAACAGA CCTTTTGCAC AAGAACAGGC CTCTTGTTCT CTCTACTGCT GCTCAGGGTA    19020
TAGCTCTCAG CTGCTGCCGC AGTGCCGTGC TTTACACCAT GATAATGGAC TAAGCCTCTG    19080
AGCTGTAAGC CAGCCACCAA TTACATGCTT TCTTTTATGA GAGTTGCCAT GGTCATGGTG    19140
TCTCTGCAGC AGTACAACAG TGACTAAGAC AGAAGGAAAC ATAGAAACAT TCACGCAGTT    19200
AATCCACACA ATTTTTCCTT TGATAGCATG CGTCTGTCTG ATGGCGATGT GGTGGGATTT    19260
GACATGGAAT GGCCGCCCAT ATACAAGCCA GGGAAACGAA GCAGAGTCGC AGTGATCCAG    19320
TTGTGTGTGT CTGAGAACAA ATGTTACTTG TTTCACATTT CTTCCATGTC AGGTTGGTAT    19380
CTCTGCTTCA TTGTCATATG GCCATCAATA ATACCATATC AACTTTCTTC CTGCAAAGTT    19440
AAGTTCTTTC ATTAGCAGGC CTTCTTTCAT GATCTTGTAT TTGTTTAAGT ATTTATATTT    19500
TTACTTGATT TTTATACCTT TTCCCTTGGT TAGAGAAATG AGAACTGAAG TTTAGAGGTG    19560
TAAATGACTA GGAATAAATAC CCTATTACTG TTACTACAGG TGGCGTTCGA ACTCATTCTA    19620
TCTAGTCAAA TTTCAGTCTG GACTCTGCAT TAGCTAAGAA AAGAGATAGT TAAGGTGAAT    19680
```

*Fig. 7-6*

```
GTGATTCTAA ATTTAAGCTT AATATAAACA GTTTACCACA CATTCCGTGT GCATTAAAAT    19740
AGTAAATCCA TTATATTAAA GAGTTTTATG GAAATAATAA TGAAATGTTT TAGTTTTCCC    19800
CCAGGGATTA AAAATGTTAC TAGAAAACAA ATCAATTAAG AAGGCAGGGG TTGGGATTGA    19860
AGGGGACCAG TGGAAACTTC TGCGTGATTT TGACGTCAAG TTGGAGAGTT TTGTGGAGCT    19920
GACGGATGTT GCCAATGAAA AGGTAGGCGT AATAAATGCA GTATTTTAAT AAACATGATA    19980
ACCTGAGTTT CATAGAATGT GCATTTTCAT CTAAATGTTA AGTTTCTTTT TTTTTCCATT    20040
TTTTATTAGG TATTTAGCTC ATTTACATTT CCAATGCTAT ACCAAAAGTC CCCCATACCC    20100
ACCCACCCCC ACTCCCCTGC CCACCCACTC CCCCTTTTTG GCCCTGGCGT TACCCTGTAC    20160
TGGGGCATAT AAAGTTTGCA AGTCCAATGG GCCTCTCTTT CCAGTGATGG CCGACTAGGC    20220
CATCTTTTGA TATATATGCA GCTAGAGTCA AGAGCTCCGG GGTACTGGTT AGTTCATAAT    20280
GTTGTTCCAC CTATAGGGTT GCAGATCCCT TTAGCTCCTT GGCTACTTTC TCTAGCTCCT    20340
CCATTGGGAG CCCTATGATC CATCCATTAG CTGACTGTGA GCATCCACTT CTGTGTTTGC    20400
TAGGCCCCGG CATAGTCTCA CAAGAGACAG CTACATCTGG GTCCTTTCAA TAAAATCTTG    20460
CTAGTGTATG CAATGGTGTC AGCGTTTGGA TGCTGATTAT GGGGTGGATC CCTGGATATG    20520
GCAGTCTCTA CATGGTCCAT CCTTTCATCT CAGCTCCAAA CTTTGTCTCT GTAACTCCTT    20580
CCATGGGTGT TTTGTTCCCA AATCTAAGGA AGGGCATAGT GTTCACACTT CAGTCTTCAT    20640
TCTTCTTGAG TTTCATGTGT TTAGCAAATT ATATCTTATA TCTTGGGTAT CCTAGGTTTG    20700
GGGCTAATAT CCACTTATCA GTGAGTACAT ATTGTGTGAG TTTCTTTGTG AATGTGTTAC    20760
CTCACTCAGG ATGATGCCCT CCAGGTCCAT CCATTTGGCT AGGAATTTCA TAAATTCATT    20820
CTTTTTAATA GCTGAGTAGT ACTCCATTGT GTAGATGTAC CACATTTTCT GTATCCATTC    20880
CTCTGTTGAG GGGCATCTAG GTTCTTTCCA GCTTCTGGCT ATTATAAATA AGGCTGCTAT    20940
GAACATAGTG GAGCATGTGT CCTTCTTACC AGTTGGGGCA TCTTCTGGAT ATATGCCCAG    21000
GAGAGGTATT GCTGGATCCC CCGGTAGTAA ATATGTCCAA TTTTCTGAGG AACCGCCAGA    21060
CTGATTTCCA GAGTGGTTGT ACAAGCCTGC AATCCCACCA ACAATGGAGG AGTGTTCCTC    21120
TTTCTCCACA TCCACGCCAG CATCTGCTGT CACCTGAATT TTTGATCTTA GCCATTCTGA    21180
CTGGTGTGAG GTGGAATCTC AGGGTTGTTT TGATTTGCAT TTCCCTGATG ATTAAGGATG    21240
TTGAACATTT TTTCAGGTGT TTCTCTGCCA TTCGGTATTC CTCAGGTGAG AATTCTTTGT    21300
TCAGTTCTGA GCCCCATTTT TTAATGGGGT TATTTGATTT TCTGAAGTCC ACCTTCTTGA    21360
GTTCTTTATA TATGTTGGAT ATTAGTCCCC TATCTGATTT AGGATAGGTA AAGATCCTTT    21420
CCCAATCTGT TGGTGGTCTT TTTGTCTTAT TGACGGTGTC TTTTGCCTTG CAGAAACTTT    21480
GGAGTTTCAT TAGGTCCCAT TTGTCAATTC TCGATCTTAC AGCACAAGCC ATTGCTGTTC    21540
TGTTCAGGAA TTTTTCCCCT GTGCCCATAT CTTCAAGGCT TTTCCCCACT TTCTCCTCTA    21600
TAAGTTTCAG TGTCTCTGGT TTTATGTGAA GATCCTTGAT CCACTTAGAT TTGACCTTAG    21660
TACAAGGAGA TAAGTATGGA TCGATTCGCA TTCTTCTACA CGATAACAAC CAGTTGTGCC    21720
AGCACCAATT GTTGAAAATG CTGTCTTTCT TCCACTGGAT GGTTTTAGCT CCCTTGTCGA    21780
AGATCAAGTG ACCATAGGTG TGTGGGTTCA TTTCTGGGTC TTCAATTCTA TTCCATTGGT    21840
CTACTTGTCT GTCTCTATAC CAGTACCATG CAGTTTTTAT CACAATTGCT CTGTAGTAAA    21900
GCTTTAGGTC TGGCATGGTG ATTCCGCCAG AAGTTCTTTT ATCCTTGAGA AGACTTTTTG    21960
CTATCCTAGG TTTTTTGTTA TTCCAGACAA ATTTGCAAAT TGCTCCTTCC AATTCGTTGA    22020
AGAATTGAGT TGGAATTTTG ATGGGGATTG CATTGAATCT GTAGATTGCT TTTGGCAAGA    22080
TAGCCATTTT TACAATGTTA ATCCTGCCAA TCCATGAGCA TGGGAGATCT TTCCATCTTC    22140
TGAGATCTTC CTTAATTTCT TTCTTCAGAG ATTTGAAGTT TTTATCATAC AGATCTTTCA    22200
CTTCCTTAGT TAGAGTCACG CCAAGATATT TTATATTATT TGTGACTATT GAGAAGGGTG    22260
TTGTTTCCCT AATTTCTTTC TCAGCCTGTT TATTCTTTGT ATAGAGAAAG GCCATTGACT    22320
TGTTTGAGTT TATTTTATAT CCAGCTACTT CACCGAAGCT GTTTATCAGG TTTAGGAGTT    22380
CTCTGGTAGA ATTTTTAGGG TCACTTATAT ATACTATCAT ATCATCTGCA AAAAGTGATA    22440
TTTTGACTTC CTCTTTTCCA ATTTGTATCC CCTTGATCTC CTTTTCTTGT CGAATTGCTC    22500
TGGCTAATAC TTCAAGTACT ATGTTGAAAA GGTAGGGAGA AAGTGGGCAG CCTTGTCTAG    22560
TCCCTGATTT TAGTGGGATT GCTTCCAGCT TCTCTCCATT TACTTTGATG TTGGCTACTG    22620
GTTTGCTGTA GATTGCTTTT ATCATGTTTA GGTATGGGCC TTGAATTCCT GATCTTTCCA    22680
ACACTTTTAT CATGAATGGG TGTTGGATCT TGTCAAATGC TTTTTCTGCA TCTAACGAGA    22740
TGATCATGTG GTTTTTGTCT TTGAGTTTGT TTATATAATG GATTACATTG ATGGATTTTC    22800
GTATATTAAA CCATCCCTGC ATCCCTGGAA TAAAACCTAC TTGGTCAGGA TGGATGATTG    22860
CTTTAATGTG TTCTTGGATT CGGTTAGCGA GAATTTTATT GAGGATTTTT GCATCGATAT    22920
TCATAAGAGA AATTGGTCTG AAGTTCTCTA TCTTTGTTGG GTCTTTCTGT GGTTTAGGTA    22980
```

*Fig. 7-7*

```
TCAGAGTAAT AGTGGCTTCA TAAAATGAGT TGGGTAGAGT ACCTTCTACT TCTATTTTGT  23040
GAAATAGTTT GTGCAGAAGT GGAATTAGAT CTTCTTTGAA GGTCTGATAG AACTCTGCAC  23100
TAAACCCATC TGGTCCTGGG CTTTTTTTGG TTGGGAGACT ATTAATAACT GCTTCTATTT  23160
CTTTAGGTGA TATGGGACTG TTTAGATAGT CAACTTGATC CTGATTCAAC TTTGGTACCT  23220
GGTATCTTTC CAGAAATTTG TCCATTTCGT CCAGGTTTAC CAGTTTTGTT GAGTATAGCC  23280
TTTTGTAGAA GGATCTGATG GTGTTTTGGA TTTCTTCAGG ATCTGTTGTT ATGTCTCCCT  23340
TTTCATTTCT GATTTTGTTA ATTAGGATTT TGTCCCTGTG CCCTCTAGTG AGTCTAGCTA  23400
AGGGTTTATC TATCTTGTTG ATTTTCTCAA AGAACCAGCT CCTCGTTTGG TTAATTCTTT  23460
GAATAGTTCT TCTTGTTTCC ACTTGGTTGA TTTCACCCCT GAGTTTGATT ATTTCCTGCC  23520
GTCTACTCCT CTTGGGTGAA TTTGCTTCCT TTTTTTCTAG AGCTTTTAGA TGTGTTGTCA  23580
AGCTGCTAGT ATGTGCTCTC TCCCGTTTCT TCTTGGAGGC ACTCAGAGAT ATGAGTTTTC  23640
CTCTTAGAAA TGCTTTCATT GTGTCCCATA GATTTGGGTA CGTTGTGGCT TCATTTTCAT  23700
TAAACTCTAA AAAGTCTTTA ATTTCTTTCT TTATTCCTTC CTTGACCAAG GTATCATTGA  23760
GAAGAGTGTT ATTCAGTTTC CACGTGAATG TTGGCTTTCC ATTATTTATG TTGTTATTGA  23820
AGATCAGCCT TAGGCCATGG TGGTCTGATA GGATACATGG GACAATTTCA ATATTTTTGT  23880
ATCTATTGAG GCCTGTTTTG TGACCAATTA TATGGTCAAT TTTGGAGAAG GTCCCGTGAG  23940
GTGCTGAGAA GAAGGTATAT CCTTTTGTTT TAGGATAAAA TGTTCTGTAG ATATCTGTCA  24000
GGTCCATTTG TTTCATAACT TCTGTTAGTT TCACTGTGTC CCTGTTTAGT TTCTGTTTCC  24060
ACGATCTGTC CTTTGAAGAA AGTGGTGTGT TGAAGTCTCC CACTATTATT GTGTGAGGTG  24120
CAATGTATGC TTTGAGCTTT ACTAAAGTGT CTCTAATGAA TGTGGCTGCC CTTGCATTTG  24180
GTGCGTAGAT ATTCAGAATT GAGTGTTCCT CTTGGAGGAT TTTACCTTTG ATGAGTATGA  24240
AGTGTCCCTC CTTGTCTTTT TTGATAACTT TGGGTTGGAA GTCGATTTTA TCCGATACTA  24300
AAATGGCTAC TCCAGCTTGT TTCTTCAGTC CATTTGCTTG GAAAATTGTT TTCCAGCCTT  24360
TTACTCTGAG GTAGTGTCTG TCTTTTTCCC TGAGATGGGT TTCCTGTAAG CAGCAGAATG  24420
TTGGGTCCTG TTTGTGTAGC CAGTCTGTTA GTCTATGTCT TTTTATTGGG GAATTGAGTC  24480
CATTGATATT AAGAGATATT AAGGAAAAGT AATTGTTGCT TCCTTTTATT TTTGTTGTTA  24540
GAGTTGGCAT TCTGTTCTTG TGGCTTTCTT CTTTTTTGGTT TGTTGAATGA TTACTTTCTT  24600
GGTTGTTCTA GGGCGTGATT TCCGTTCTTG TATTGCTTCT TTTCTGTTAT TATCCTTTGA  24660
AGGGCTGGAT TCGTGGAAAG ATATTGTGTG AATTTGTTTT TGTCGTGGAA TACTTTGGTT  24720
TCTCCATCTA TGGTAATTGA GAGTTTGGCC TGGTATAGTA GCCTGGGCTG GCATTTGTGT  24780
TCTCTTAGTT TCTGTATAAC ATCTGTCCAG GCTCTTCTGG CTTTCATAGT CTCTGGTGAA  24840
AAGTCTGGTG TAATTCTGAT AGGCCTTCCT TTATATGTTA CTTGACCTTT CTCCCTTACT  24900
GCTTTTAATA TTCTATCTTT ATTTAGTGCA TTTGTTGTTC TGATTATTAT GTGTCGGGAG  24960
GAATTTCTTT TCTGGTCCAG TCTATTTGGA GTTCTGTAGG CTTCTTGTAT GATCATGGGC  25020
ATCTCTTTTT TTATGTTTGG GAAGTTTTCT TCTATTATTT TGTTGAAGAT ATTAGCTGGC  25080
CCTTTAAGTT GAAAATCTTC ATTCTCATCA ATTCCTATTA TCCGTAGGTT TGGTCTTCTC  25140
ATTGTGTCCT GGATTACCTG GATGTTTTGA GTTAGGATCC TTTTGCATTT TGTATTTTCT  25200
TTGACTGTTG TGTCGATGTT CTCTATGGAA TCTTCTGCAC CTGAGATTCT CTCTTCCATT  25260
TCTTGTATTC TGTTGCTGAT GCTCGCATCT ATGGTTCCAG ATCTCTTTCC TAGGATTTCT  25320
ATCTCCAGCG TTGCCTCGCT TTGGGTTTTC TTTATTGTGT CTACTTCCCC TTTTAGTTCT  25380
AGTATGGTTT TGTTCATTTC CATCACCTGT TTGGATGTGT TTTCCTGTTT TTCTTTAATG  25440
ATTTCTACCT GTTTGGCTGT GTTTTCCTGC TTTTCTTTAA GGGCCTGTAA CTCTTTAGCA  25500
GTGCTCTCCT GTAATTCTTT AAGTGACTTA TGAAAGTCCT TCTTGATGTC CTCTATCATC  25560
ATCATGAGAA ATGTTTTTAA ATCTGGGTCT AGATTTTCGG TTGTGTTGGG GTGCCCAGGA  25620
CTAGGTGGGG TGGGAGTGCT GCGTTCTGAT GATGGTGAGT GGTCTTGATT TCTGTTAGTA  25680
GGATTCTTAC GTTTGCCTTT CGCCATCTGG TAATCTCTGA AGCTAGCTGT TTTAGTTGTC  25740
ACTGTTAAGA GCTTGTTCTT CAGGTGACTC TGTTAGCCTC TATAAGCAGA CCTGGAGGGC  25800
AGCACTCTCC TTAGTTTCAG TGAGCAGAGT ATTCTCTGCA GGCAAGCTCT CTTCTTGCAG  25860
GGCAGGTACC CAGATATCTG GTGTTCGAAC CAGACTCCTG GCAGAAGTTG TGTTCCACTC  25920
ACTAGAGGTC TTAGGATCTT GTGTGGAATC CTGTGTGGGC CCTTGCAGGT GTCAGGCGAC  25980
TCTGCTGGCA AGGTAGCCCG GGGCTCGAGT CGAGTGGAAG GGACTTGTGC CCCAGATCAG  26040
GCCCGGGTAG CCTGCTTCCC TATGTACTGC AGTCTCAGGT TCCGCGCGAT TGGATTGGGG  26100
CAGGCACTGT GTTCCACTCA TCAGAGGTCT TAGGATCCTG TGGGGGGTCC CGTGTGGGCC  26160
CTTGCGGGTG TTGGGCAAAC TCTGCTGGCA AGGTAGCCCT GGGCTCGAGT CGAGCGGAAG  26220
GGACTTGTGC CCCAGATCAG GCCAGGGTAG CCTGCTTCCC TATGTACTGC AGTCTCAGGT  26280
```

*Fig. 7-8*

```
TCCGCGCGAT TGGATTGGGG CAGGCGCTGT GTTCCACTCA CCAGAGGTCT TAGGATCCCG  26340
TGGGGGGTCC CGTGTGGGCC CTTTCGGGTG TTGGGCAAGA CTCTGCTGGC AAGGTAGCCC  26400
GGGGCTCGAG CTCTTTTTTT TTCTTTAAAA AAAAATTTTT TTTATTAGGT ATTTTCCTCA  26460
TTTACATTTC CAATGCTATC CCAAAAGTCC CCCATACCCT CCCCCTGACT CCCCTACCCA  26520
CCCACTGCCA CTTCTTGGCC CTGGCGTTCC CCTGTACTGA GGCAGATAAA GTTTGCACGA  26580
CCAATGGGCC TCTCTTTCCA CTGATGGCCT GCTAGGCCAT CTTCTGCTAC ATATGCAGCT  26640
AGAGACAAGA GCTCCAGGGG GTACTGGTTA GTTCATATTG TTGTTCCACT TATAGGGTTG  26700
CAGATCCCTT TAGCTCCTTG GATACTTTCT CTAGCTCCTC CATTGGTGCC CTGTGATCCA  26760
TCCAATAGCT GACTGTGATC ATCCACTTCT GTGTTTGCTA GGCCCCGGCA TAGTCTCACA  26820
AGAGACAGCT ATATCAGGGT CCTTTCAGCA AAATCTTGCT AGTGTATGCA ATGGTATCTG  26880
TGTTTGGCGG CTGATTATGG GATGGATCCC CGGATATGGT AGTCTCTAGA TGGTCCATCC  26940
TATTGTCTCA GCTCCAAACT TTGTCTCTGT AACTTCTTCC ATGGGTGTTT TGTTCCCAAT  27000
TCTAAGAAGG GGCAAACTGT CCACACTTTG GTCTTCATTC TTCTTGAGTT TCATGTGCAT  27060
TGTATCTTGT ATCTTGGGTA TTCTAAGTTT CTGGGCTAAT ATCCACTTAT CAGTGAGTAC  27120
ATATCATGTG AGTTCTTTTG TGATTGGGTT ACCTCACTCA GGATGATGCC CTCCAGGACA  27180
ATCCATTTGC CTAGGAATTT CATAAATTCA TTCTTTTTAA TAGGTGAGTA GTACTCTGTT  27240
GTGTAAATGT ACCACATTTT CTGTATCCAT TCCTCTGTTG AGGGGCATCT GGGTTCTTTC  27300
CATCTTCTGG CTATTATAAA TAAGGCTGCT ATGAACATGG TGGGCATGT GTCTTTCTTA  27360
CCAGTTGGAA CATCTTCTGG ATATATGCCC AGGAGAGGTA TGTCGGGATC CTCTGGTAGT  27420
ACTATGTCCA TTTTTCTGAG GAACCGCCAG ACTGATTTCC AGAGTGGTTG TACAGCTTTC  27480
AATCTGACCA GCAATGGAGG AGTGTTCCTC TTTCTCCACA TCCTCACCAG CATCTGCTGT  27540
CACCTGAATT TTTGATCTTA GCCATTCTGA CTGGTGTGAG ATGGAATCTC AGGGTTGTTT  27600
TGATTTGCAT TTCCCTGATG ATTAAGGATG CTGAACATTT TTTCAGGTGC TTCTCGGCCA  27660
TTCGGTATTC CTCAGGTGAG AATTCTTTGT TTAGCTCTGA GCCCCATTTT TAATGGGGTT  27720
ATCTGATTTT CTGGAGTCCA CCTTCTTCAG TTCTTTATAT ATATTAGATA TTAGTTCACT  27780
ATCTGATTTA GGATAGGTAA AGATCCTTTC CCAGTCTGTT GGTGGCCTTT TTGTCTTATT  27840
GACGGTGTCC TTTGCTTTAC AGAAGCTTTG CAATTTTATG AGGTTCCATT GGTCAATTCT  27900
AGATCTTACA GCACAAGCCA TTGCTCTTCT ATTCAGGAAT TTTTCCCCTG TGCCCATATC  27960
TTCAAGGCTT TTCCCCACTT TCTCCTCTAT AAGTTTAAGT GTCTCTGGTT TTATGTGGAG  28020
TTCCTTGATC CTATTAGATT TAACCTTAGA ACAAGGAGAT AGGAATGGAT TAATTCGTAT  28080
TCTTCTATAT GTTAACCACC AGTTGTGCCA GCACCATTTG TTGAAAATGC TGTCATTTTT  28140
CCACTGGATG GTTTAGCTC CCTTGTCAAA GATCAAGTGA CCATAGGTGT GTGGGCTCAT  28200
TTTTGGGTCT TCAATTCTAT TCTACTGGTC TACTTGTCTG TCACTATACC AGTACCATGC  28260
AGTTTTTATC ACAATTTAGG TCAGGCATGG TGATTCCACC AGAGGTTCTT TTATCCTTGA  28320
GAAGAGTTTT TGCTAACCTA GGGTTTTTGT TATTCCAGAT GAATTTGCAG ATTGCTCTAA  28380
TTCATTGAAG AATTGAGTTG AAATTTTGAT AGGGATTGCA TTGAATCTAT AGATTGCTTT  28440
TGGGAAGATA GCCATTTTTA CTATATTGAT CCTGCCAATC CATGAGCATG GGAGATCTTT  28500
CCATCTTCTG AGATCTTCTT TAATTTCTTT CTTCAGAGAC TTGAAGTTTT TTTTCATACA  28560
GATCTTTCAC TTAGTTAGAG TCACACCAAG GTATTTTATA TTATTTGTGA CTATTGAGAA  28620
GGGTGTTGTA TCCCTAATTT CTTTCTCAGC CTTTTTATTC TTTGTGTAGA GAAAGGCCAT  28680
TGACTTGTTT GAGTTAATAT CCAGCCACTT CACCGAAGCT GTTATCAGG TTTAGGAGTT  28740
CTCTGGTGGA ATTTTTAGGG TCACTTATAT ATACTATCAT ATTATCATCT GCAAAAAGTG  28800
ATATTTTGAC TTCTTCTTTC CAATTTGTAT CCCCTTGATC TCCTTTTCTT GTCGAATTGC  28860
TCTGGCTAGG ACTTCAAGTA CAATGTTGAA TAGGTAGGGA GAAAGTGGGC AGCCTTGTCT  28920
AGTCCCTAAT TTTAGTGGGA TTGCTTCCAG CTTCTCACCA TTTACTTTGA TGTTGGCTAC  28980
TGGTTTGCTG TAGATTGCTT TTATCATGTT TACGTATGGG TCTTGAATTC CTGATCTTTC  29040
CAAGACTTTT ATCATGAATG GGTGTTGGAT TTTGTCAAAT GCTTTCTCCT CTTCTAACAA  29100
GATGATCATG TGGTTTTTGT CTTTGAGTTT GTTTATATAA TGGATTACGT TGCTGGATTT  29160
CCATATATTA AACCATCCCT GCATCCCTGA AATAAAATCT ACTTGGTAAG GATGGATGAT  29220
TGTTTTAATG TGTTCTTGGG TTCGGGTAGC GAGAATTTTA TTGCTTATTT TTGCATCAAT  29280
ATTCATAAGG GAAATTGGTC TGAAGTTCTC TATCTTTGTT GGATCTTTCT TTGTTTTAGG  29340
TATCAGAGTA TTGTGTCTTC ATAGAATGAA TTGGGTAGAG TACCTTCTGC TTCTATTTTG  29400
TGGAATAGTT TGTGCAGAAC TGGAATTAGA TATTCTTTGA AGGTCTGATA GAACTCTGCA  29460
TTAAACCCAT CTGTCCCTGG GCTTTTTTTG GTTGGCAGAC TATTAACGAC TGCTTCTATT  29520
TCTTTAGGGG ATATAGGATT GTTAGATCA TTAACCTGAT CTTGATTTAA TTTTGGTACC  29580
```

Fig. 7-9

```
TGGTATCTGT CTAGAAACTT GTCC                                              29604
>00109     00109
TGTTCTTGTG GCTGTCTTTT TGGTTTGTTG AAGGATTACT TTCTTATTTT TTCTAGGGCG          60
TGGTTTCTAT CCTTGTATTG GGTTTTTTTT TTTTTTCTGT TATTATCCTT TGAAGGGCTG         120
GATTCGTGGA GAGATAATGT GTGAATTTGG TATTGTCATG GAATACTTTG TTTTCTCCAT         180
CTATGGCAAT TGAGAGTTTG GTTGGGTATA GTAGCCTGGG CTGGCGTTTG TGTTCTCTTA         240
GGGTCTTTAT AACATCTGTC TAGGATCTTC TGGCTTTCAT AGTCTCTGGT GCAAAGGTCT         300
GGTATAATTC TGATAGGCCT GCCTTTATAT GTTACTTGAC TTTTTTCCCT TACTGCTTTT         360
AATATTCTAT CTTTATTTAG TGCACTTGTT GTTCTGATTA TTATGTGTGG GGAGGAATTT         420
CTTTTCTGGT CCTGTCTATT TGGAGTTCTG TAGGCTTCTT GTATGTTCAT GTGCATCTCT         480
TTAAGTTTGG GAAGGTTTCT TCTATTATTT TGTTGAAGAT ATTTGTTGGC CCTTTAAGTT         540
GAAAATCTTC ATTTTCATCT ACTCCTATTA TCCGTANGTT TGGACTTCTC ATTGTGTCCT         600
GAATTTCCTG GATGTTTTAA GTTAGGATCT TTTTGCATTT TGCATTTTCT TTGATTGTTG         660
TGCCTATGTT CTCTATGGAA TCTTCTGCAC CTGAGATTCT CTCTTCCATG TCTTGTATTC         720
TGCTGCTGAT GCTTGCATCT ATGGTTCCAG ATTTCTTTCC TAGGGTTTCT ATCTCTAGCG         780
TTGCCTCATT TTGGGTTTTC TTTATTGTGT CTACTTCGCT TTTTAGGTCT ACTATGGTTT         840
TGTTCATTTC CATCACCTAT TTGGATGTGT TTTCCTGTTT TTCTTTAAGG ACTTCTACCT         900
GTTTGGTTAT TTTTTCGTGT TTTTCTTTAA GGACTTGTAA CTCTTTAGCA GTGTTCTCCT         960
GTATTTCTTT GAGTTATTAA AGTCCTTCTT GATGTCCTCT ACTATCATCA TGAGATATGC        1020
TTTTAAATCC GGGTCTAGCT TTTCGGGTGT GTTTGGGTGC CCAGGACTGG GTGAGGTGGG        1080
AATGCTGCAT TCTGATGATG GTGAGTGGTC TTGGCTTCTG TTACTAAGAT TCTTACGTTT        1140
GCCTCTCACC ATCCAGTAAT CTCTGGAGTC AGTTGTTATA GTTGTCTCTG GTTAGAGCTT        1200
GTTCCTCTTG TGATTCTGTT AGTGTCTATC AGCAGACCTG GGAGACTAGC CTTCTCCTGA        1260
GTTTCAGTAG TCAGAGCACT CTCTGCAGAT AAGCTCTCCT CTTGTAGGGA CGGTGCCCAG        1320
ATATCTGGCA TTTGAACCTG CCTCCTGGCA GATTTTGTGT TCCACTCACC AGAGGTCCTA        1380
AGATCTCGTG GAGAGTGTTC TGGGTACCTT GGGGGTGTCC GACAACTCCG TGTCCGACAA        1440
TTCTAGTGCT GGGGCCGACT GGAAGGGACC TCTTTTTCTT TTATAAAGTA ATGAAAGCTA        1500
TGTGTTGATT TTGGTGGCAA AAGAGAAGTT CAAAGTGCAA TAATGAAACC CTCCATTTCT        1560
GAAACTCCAT CTCAGCGTCC AGTTGCCTGA ACTAACGCCC GTTCATCTTT CCTGCCAACC        1620
TTAGTATTTT GTATATTGCA CACTTGAATG TTTATTGTAT CTAACGGATT TATTCCAATA        1680
GCACGTCTTT GGAAAAGATG ACTACAGGGC AACTCTCAAT ATAGAATGTT GAGTGTCTGT        1740
TTGACCTTTA ACATCATCAC CTATGTTTCC ATCATTTTAT TGATGAGATG ATTACATCCT        1800
TATATTCAGC CACGTATTCA TTTGGTTTTG AGATCAAAAC CATTCTTGCC TATTCCGCTG        1860
CCTTCTAGGA ACAGCATCTT TAACGTTTCA GCCCTTTGAT ACCCACATTA TGGAACCTCG        1920
GAGTTAAATT CCTACTGTCC ACTATGAATG AGGTCTCAGA TGGGAGGCTT GTTTTTTTTG        1980
TGGTCCCTGG GGACAGCTGA CTATGACTGT GAATGTTTGC TCTGTCCCCC TTTCACTCCT        2040
TCCAGTTGAA GTGCGCAGAG ACCTGGAGCC TCAATGGTCT GGTTAAACAC GTCTTAGGGA        2100
AACAACTTTT GAAAGACAAG TCCATCCGCT GCAGCAATTG GAGTAATTTC CCCCTCACTG        2160
AGGACCAGAA ACTGTATGCA GCCACTGATG CTTATGTATG TATTTAAAGA CCTTTAATAT        2220
GACATCATTC TCATTTCTCG GACCAAATCA CTTTAGTAAA AATGTATTGG GGTTATGTCC        2280
TTAGCTGAAA TATTTTATTA TAGTTTGGCA TTAAAATTTG CTTAGGAATA CATCAAGTGA        2340
AATTCTTCAT GTTAATTAGA AAATACCAAT TAATAGGTTG TTTAGCAGTA GTTATTTCTA        2400
CTATTACGAT GTAAAGTGAT GTCCAATTCC TGTGTAAAAG AATGTGAAACT TACTGAAAAC        2460
ATGAAAGGCT TTGAGCTTAG CAGGCACAAA TAGTTTGATG ATGTATTTTG TATATAAGCA        2520
ACTCAGAATC AGAAAAATCA CAGGCTTTCC ATATTTAAAC TAGCCTTATT CCCTACATTT        2580
ATATTTAAAA TGTGGAAATT TAGATAAATT GCCTCCAAAT TTAGTTGCTG CTGTTCTTAG        2640
ATGTATTTTC ATATGTGTAA TCTGTACATA CTGGCATCTA GGCTTGTCTT TATATATAGT        2700
ACTGTGGTCT GTGTGTGCTT TACCTTAAGA AATGTTTCTT TTGTAAATTT CTTTGCCCTA        2760
GATCATACTT ATTGCTCATA TTTAAATAGT ATTTATTGAT AAATATCTTG TTAATTTTCC        2820
ACCTTACATT TATTTTTAAG ACATCGATAC TCTAACTTTT AGCCAGAAAA ACAAAGGAAA        2880
ACCAACTGTC TTAGTCAGGG TTTCTATTCC TGCACAAACA TCATGACCAA GAAGCAAGTT        2940
GGGGAGGAAA GGGTTTATTC AGCTTACACT TCCATACTGC TGTTCATCAC CAAGGAAGTC        3000
AGGGCTGGAA CTCAAGCAGG TCAGAAAGCA GGAGCTGATG CAGAAGCCAT GGAGGGATGT        3060
TCTTTACTGG CTTGCTTCCC CTGGCTTGCT CAGCCTTCTC TCTTATAGAA CCCAAGACTA        3120
CCAGCCCAGA GATGGTCCCA CCCACAAGGT GTCTTTCCCC CTTGATCACT AATTGAGAAA        3180
```

*Fig. 7-10*

```
ATACCCCACA GCTGGATCGC ATGTAGGCAC TTCCTCAACT GAAGCTCCTT TCTCTGTGAT   3240
AACTCCAGCC TGTGTCAAGT TGACACAAAA CTAGCCAGTA CAGCAACAGA TGCTTTTTGT   3300
CAGGAGAACA GCTGGATGAG TTGGGATGTG CTGTTGTTCC TTTGGCTTCC TTTGCTTCCT   3360
TGCTTACTTG CTTTAAAAAA AATAACAGAC TCTCTTGCAG CTTATTCCAC TCTTGAACTG   3420
TTCATGCAGC CGAGGCTGCC CTTAATGTCC AGATCCTCTT GCCCCTGTTT CCTTGCTATG   3480
GAGATTACAG GCTGTAGTGT CTATATTCTT GACAGTTTGT ATGACTTGAT CAAGTCTGTG   3540
AAAAATACCC AGCATGCATT GTTGTTCATA CACTGACCAG CATTCTCAGT TGGTTTAATG   3600
AAATCTCAAG AATTGGATAG GATCTGTCAC CAAAACAGAT GTTTCTTACT AGATGGTAGT   3660
TATTAGATTT TGTTTACAGA TCATTTCATT TGGATACCTA TTTACAATAC TGAAAATTAG   3720
TAAGTGAAAA TTTAAAGCTG TATTTTATAG CCTAGGCAGC TTTTGTTTCC CCATTGGGTA   3780
GTGCTTACAT GAAGACCCGA GTCTTTGCAT ACTGAAATAG TTTTACTTCA TTTTTGGAGA   3840
GTATTTTGGA AATCATTCTT GTAGATGTTG CTTGAGATAT CACATATATA TATTTATTTT   3900
GGTAATCTTT AACTTGCACT TTGTTTTTCT TTTGTCTTTT TATAGGCTGG TCTTATCATC   3960
TATCAAAAAT TAGGAAATTT GGGTGATACT GTGCAAGTGT TTGCTCTAAA TAAAGGTATG   4020
TTGTGGCCTA AAATAAAAGA TAAAAATATG AATTTGCTAT TTTGTGAGAT TCATTTAAAA   4080
AAGTCAAAGT ATTATGTATC TTTGCAAAGT ATTATGGTAC TTCTTAAATG TCTGAGCAGT   4140
GTTGCTGTAA AGGTGACATC CATCAGGATC AGAAATTAGA GTTGTAGATC TTCCCTTGTG   4200
AAAAGCAGGG ATTCCATTGC TAGTTTGATA GTGTTGCTGC TCTTCTTGTC CATGGAGTGG   4260
CCATGTTATT GTCCTTGATA ACATCAGTTA GCCAGCCAGC TGCCTCTTGG CTGGTAACAT   4320
CCACATTCTT TCTACACTTG TTTAAAACGG ATTTGCCTCG ACTATTCCTG TGTATATGGT   4380
GCACTGTAGT GTTCTGCCTT TCTGTGTTCG GTTGCTGTTT TCTTCACTCA GCTTCATTGA   4440
CCTTGTCAGA TGCTTTGATC TGTTAGTGAT TACAGGCAGA GTCAGCCAGT AGGTGGATAA   4500
GCACCAGCTT TTGTGCTGCA GAACCTCTGT GGTGGAGCCT TAGCCATCTG ACCTGTAAGA   4560
TGTCCCTTTC CCCATGCTTG TAATGTGGAC AATAGATAAG TGTCTATCTC ATGGATTGGT   4620
TGTGACCACT AAAGGGACAG ATGTTCAAAG TAAGATGGTC AGAGAAAATT GTTAAATAGA   4680
TTGAACAGTC CTATAATACA TGATCTGAAA TGCTTTGAAA TCGGAAACTT TTTGGTGATA   4740
ACATGATTTA CGTATTCATT AGTATATTTC ATTGAAAATA TTTCCTGGAA GAAGCAATAC   4800
TTGAGAAGCC TGAAATAGGA ACAGAAATTT GCCAGCCAAA GCCAGAGGGA AAGTGATAGA   4860
CAGGTACAAA GCCTCAGAGG GCAGCTCTCT GGAACTTATG CAGTGTAAGG AAACTGTTGA   4920
CTGTGACAGT GTAATGTAGG AGAAGCAGAA AAATGAGACA GGCCTCACTA AAGAGGTTAC   4980
ATGTAGCCTT CCAAAGAGCA AATTGAAGCT GTTATTGACG GTTCTAAATG TGGAAGTGAA   5040
ATGCGCTGGA TTGAAAACAA GCTAACAAAA CAAGCTGTAG AATAAAACAC ACTAACTAAG   5100
CGAGCCACAG AGAAAGAAAG TGGATCTTAG GATTACAAAA GAATGGTGGG AAAGGCTTTT   5160
TGGAGGCTAT GATGGTAAGC CAAGAAAGAG GAATTGGTAC CTTGAATTGG TTATTTGTGT   5220
CAAGGGTCGG CACAGTGGGT AGCGTCANCC TACATTTAAT GGAGGCAACA GAATCTGCTG   5280
TAATGACAGG CACACGCCAA GGATCCTCCT GGCTTTTGGC TGCACGACAG ATTAAAATCC   5340
AGGGTAAAGA CTCACTTTAT ATAGACCAGG CTGGCCTAGA ACTCAGAGAC CTACCTGCCT   5400
CTGCCTCCTG AGTGCTGGGA TTAAAGGTGT GCACCACCAC CACTCAGCTG GAAGTAAAGT   5460
TTTATAGTTG TTTTTTTAGA CATGTTCAAG GAGAGTAACA TCTCAGGTAG CAAGAGGGTT   5520
GTAGCCTGTG GACACCTAGA TATGTAGGTT GTATCTCAGA AGACAGTTTG TCTGAGATAA   5580
AATGTAAGCA CTAAGTGTCC TAAGAAACTG CTGGCGTCTA ATCTTTGTGT GGGGGAGGGG   5640
ACCCTATAGG AGTTGCCCTG GGTGTGGAAG GAGATGAGAA AGTGCTGGAC AATTCAAGTA   5700
CCAGTGTGCT GAAAGTCAAG GGAGGGCTAG GTTTGAGGGA GGAGGATGTT ATCAACTGCT   5760
TTGAATTCTG CTGAGATTTT GGCAAAGTGA AGGCTTGTAG GCAATCATCA GATTTGGCAC   5820
AATGGCCACT ATCATTTGTA ACCTTCTACA CCAGTGGTTC TCAACCTTCC TGTACTGTGA   5880
CCCTTTAATA CAGTTCCTCG TGCTGTGATG GCACCAACCA TGACATTATT TCCTTTGCTA   5940
CTTCTTGACT GTAATTTTGC CACCGTTATG AATTGTGATG TAACTATCTG ATATACAGGA   6000
TGTTTGATTT GTAAACCCTG TGAAAGAGCC ATTTGATCAA TCATTGTTCT GTGCTCTACT   6060
TCTGGTGTCC TGGGTGTTGA CAAAAGAGTA TTGCAATCAG AGGGTGAACT TCTAGAGCAG   6120
ACAGGGTCCA GAGGCTTTGG TAGTATAAAA ATATTTATAGG CATAGCAAGA ATAAAGTAGT   6180
TTAATGAGGT AGGTAGAAAC CAGTACTAAA ATTATATCAA TCATATTACT GCAAATAGTG   6240
GAGAAAGATG TAAGGAATTG ATTTTAAGTG TATATAAATA ATATTTTTTA AAGACTTAAT   6300
TTAGAAAGGG AACGTTCATA AAACACAGGT TTGTCTAGTG TTTGCTATAT TTTAGTGTTC   6360
ATTATGTATT GATTTTATTT GACAAGCAAG GTAACATGCT ATTTGGCTCT CTGAAGGAAG   6420
AGAGCCAAAT GCTTAGAGCT GAGAAAGTAC AAAGCCACTG AGGGCAACTG CTTCCCTAGT   6480
```

*Fig. 7-11*

```
GTAAGGAACA GAAATATAAC CAAAGAGAAA CGAGTGTGAG GGAGACTTGT AGGAAACAAG    6540
GCTGGAAAAG AGGCTTGGGG CCAGTCAGTT AGGGCATCAG ATTGTGTGAA TTGGACTTGA    6600
TGTTTTAATA CTCAAAACCA TCAACAACCA CGGTACAACG ATGGCCAATA GGAAACCCTT    6660
AGTTTGGGTG TGTGGAGCAG CAGAGTAAAA TGATCCAGAT TTTGTCTTAA AGTGTTTTTT    6720
TTTTCTCACT GCTGTAAGAA GGTCAGGAAG TTAGATAGGA GGCTTTTTCA ATTGTCCAGA    6780
AATAGAAGAT AGTTGTACTG GGCCAGTGGA GGTAGCAAGA AATGTAAATG CAGTAGGTAT    6840
TCTGAAGGCA TACACTGAAG AATTCTAGGT GAATTCCTTA TAAAGGGTGA GGAAAAGACT    6900
GCTAGGATGG CCAAGGTATT TTTCTTTTCT TTTCTTTTTC AGTTTTTCGA GACAGGGTTT    6960
CTCTGTGTAG CCCTGGCTGT CCTGGAGCTC ACTCTGTAGA CCAGGCTGGC CTTGAACTCA    7020
GAAATCTGCC TATCTGCGCC TCTCAAGTGT TGGGATTAAA GGCGCCCGGC TTAAGGTATT    7080
TTTCTTGAAT GACCTGATGA CTGGCAGTGC AGGATGATAT GAAGAGTATG TTTTGGTTGG    7140
AAAAAATCCA CCAAAGTTGC AACGTGGACA TGAAAAAAAA CTAGAGGTGG ATTTTGATAT    7200
CCACGAACGG CTCCATACTA GTTATTTTCT GTTACTGTGA TAAAACACCG TGACCAGAGA    7260
GGTCTTTAAG GAAAGGAGTT TCTTTTTGCT CACAGTCCCA GAGGGAAGTC TTCAGTGGCT    7320
CTGCGGGAGC ATGGCAGAAA GCAGCCGGCT TGGCAGTGGG GCAGGAAACT GTTAGGTCAC    7380
ATCTTGAACA GCAGTCTTGA AGCAGAGAGA GCAAACAGGA AGTAGGGTGA AGCTGTGCAC    7440
TCTCAAAGCC ACCCCCAGTG TCAAACTTAC TCCCGGAAGG TTGCACCACC TAAACCTCTC    7500
CAAATGGAGT CACCAACTGA GCATCCAGTG TTCCACTGCC CGCGACCCTG TGGGAAATAT    7560
TTCCCACCTA ACCACCACTG CACTGTGAGA AATGGAATTC CAGAGTACAC GGCGGAAGTT    7620
GGGGTTAGAA ATATAGATTG TCCAGTGGTG AAACTGGAGA TAAAACTGGG AGTGAATAAA    7680
CTGAAGAATA TAGGTGGTGT CAGCTTCAAG GTCACACTGA CATTTAGAAA ATGAGAGTGG    7740
CTTGAGGGCG GAGACGGGGC ATCAGTGAAT GAGGAGGGGG GCGAAGGACA TGCTTTAAAT    7800
AGGAAGGAGA CATCAGCCCC TTAAACCTCG GAGGAGTTGA ACGATGCACA GATCGTGGAT    7860
TAACTATTAG GGTTGATAAT GTGGTAGCCT TCCCAGAGGA AGCTGTGCTG CTGAGGGCAA    7920
AACTCTTGAG TTGGAGTTAG TTTAGGAGAA AATAAGAGCA GAACATTCGA GGATGAGCAG    7980
CAGGCGTTGG AAACGTAAAA GAGAAAGAAG AGGTGTAAAA TTGTCATCTT AAGATAAGCG    8040
GGGTCTGCGT CATGAGTTTA AAACTAAACC GGCCATTATC ATTTTGTTTT AATTTCAAGA    8100
ATGTCCAGCT ACTTAGGCAC CGATTAGCTA AAGAAGTTGA GTATGATTAG AGTAGATTTT    8160
GCCCCGTGAG TTCCACGGAG TTGGGTAAAG AAGGCAGAAG TGGAGAGTCT GTATCAAATG    8220
AATGGCTAAG AAAGGAAAGG AGACCAGGTA GGGAGAGTAG GAGTGGGTGC TGGAGGGGGC    8280
GGATTCAACA GGTTTCATTC TGAAGTGTTA ACTCACTGAG CTGGGGTAAG CAAGCCAGAA    8340
AGAGCGGTGG GATGGCTCTA TTTATGGTGG AAAGTGTTTG TAATAGAAGG TTTGGGTGCA    8400
GTGGAGGTTT TATTGGGCAG TTTTAAGGTC GAGAGTCTGA TTGTGGGAAT GAGTAGCTCA    8460
GATTAGATGA GGAAGATTGT TGGAATGAAG GGTGACCCTT GGGCAAGGGT TCCAAACGGT    8520
GTTAAGTTTG AACGTGCCTG GATTGGGGCT TACTGACTTC CAAGTCAGAA ACAGTGTCGG    8580
GTGAGTTTAG AGTCCCAGGC TTGTCCTCTG GCCCAGGTCA GTAACATTTA GATTGGATAA    8640
TGTATACATT TGGAATTCAC TCTAAATTTC AAATAGCAAA AATTTGAAAG GAACATTAAA    8700
ACAAGGGAGT AAAGAGGAAA GTGATTTAGA GATCCGAGAG GGAAGTGTTC TGTTAGAATT    8760
CATTGTGCGA ATAGATGAAA ATCTGGATAC TAATACTATG CTGTGATGTG GTTAAATAAA    8820
ATCTCTGCTT TCTAATTTTA ATATTAATCT TTTCTCTCTC TCTCTCTCTC TCTCTCTTTC    8880
TCTCTCTCTC TCTCTCTTCT TTTATTTAGC AGAGGAAAAC CTACCTCTGG AGATGAAGAA    8940
ACAGTTGAAT TTAATCTCCG AAGAAATGAG GGATCTAGCC AATCGTTTTC CTGTCACTTG    9000
CAGAAATTTG GAAACTCTCC AGAGGTTAAA TATTGTGCTT TTTAAAATAT TTATTTTATT    9060
TTTAATTGTA TGTGTATGCG CGTTCAGTCA CCTTTTATGC TATTTTCTTA AACATGGAAT    9120
TCTGATTTTT ACAGAATGCC TGCTTGTTAT AAAATTACATA TACCTACAGC TTGGCTTTAT    9180
AACAGCAAGT TAAGTAGGAT TTATTAGCAT CAAGAACTCA CAACAGAGTG GTTTGAAGTT    9240
TATTGTAGGA AGGAACAGTT GTTTTTGTCT CAGAGGACCC TAATAGAATC GATGTGATTT    9300
AGTATTGTTT AGTCATTTAT TTACATTCAG TGTGCTGCGG TGTTGCTGCA GTGTGATTAG    9360
CACTCTACTG GCTGTTGAGC TTGTCTGCTG CTAACTAATG AGCAGGATAG AAATCTTAAG    9420
GAAGGAAATG TGCATGCCAC CATGTATGCC TTCCTAGTCC AGCCTTTAAC GTTAGAGTAA    9480
GTGGTTATGT CTTACTCTGA TGTGAGTGCT TGGTAAATAA GATATTATAA TAGTATCACT    9540
GTTGCTATAG CAACACATTT ATTTCACAAT TAAATTGAAT CATAACTTCT CATACCATAT    9600
TATTTATACA CAGTTGTTAT ATATAAGCAG TATATGTATA TACATATAAT TATATACTGT    9660
GTATGTAGTA AAATTTACAA AATTGCCAGG CACCACGGTA CATACCTGTA ATCTGTGCAT    9720
TCAGGAGGCA GAGGCAGGAG AATTCCAAGC TCAAGGCCAG CCTGACTAAT AAAAAGCTTT    9780
```

*Fig. 7-12*

```
ATAAATTTTT ATTATTTTAA AATAACTTGT TATTAGATTT TGAATTTAGT TAATAGTTTT      9840
AAAAGTTTTT TTTTTGTATC ATTTTATGTG TATGGCTGTC TTTGCCTGCA TGTATGTCTC      9900
TGTACAACTT ATGTGATGTA TTCCTGAGAG GTGCAGAGGA GGGTATTGGA TCTTCTGGAA      9960
CTGGTGTTAC ACACAGTTGA AAGCTGCCAT GTGGGTGCTG GGAATCAAAC CTGGGTCCTC     10020
TAGAAGAGCA GCCAATGCTC TTAACTGCTG AGCTATCTTT CCAGCCCTGA ATTTAATTTT     10080
GATCTTGATT TTTGCTTATG TTAATATAGA CTTTGACAGT TTAAGGTTGA GCTAAAGTTG     10140
GGAGAGTTGA TAATTGTGTA GTTTTGTTTT TTTGAGTATT TTTGTACATT TTATTATGAT     10200
CATAATTACT TTCCATTACA CTCTCTTATC CCCCTGATTC CTGCTGACTC CCTCTTACTT     10260
AAGTAGCTCC TTTCCTTCTT TCACGTCTCA TGTGTGTTTG TGTATTTGTG TGTGCATGTG     10320
TGTGCATGTG TGTGTGTGTG TGTGTGAGTG TGTGTGAGTG GCACTGTGTT TATTTAGGAG     10380
TATTTGTATG AGCATGGTTA AGAGGCTGCT GACTAAGCAC TGGCAACTTT ACCAGTGACT     10440
ACTGAAGAGA ATGATGACTG TTTGCCTAGA AGCCAAGCAA AAGCTCCCTA GGGAAGGATG     10500
GGGTGGGTCA CTTTTGAGCT TCACCATCCA CGTGGGAGCG GCAGAAGGCC CTGTGTTTTG     10560
TGGGTTTTAT GCAGATATCC ATAGCTGCTG CGTGTTTATG ATTTCAGTAG CCATGCAATG     10620
TCTACATGGC AATGTTTCAC AGCACTCCCC CACATCGTCT GACTCTTACG GTTTGTCCAT     10680
CCATCCTGTT ATGTCCACTG GGCCATTGAA GGAGTTTTAT GTACAGGCTG GTCCCAATTC     10740
AGGCAGAGCA CCCAGTATTC ATTTATGCTC AACACTTTGA TCATTGTGAG TCTTCTTTAG     10800
CCAAAAGCTT CTTTGACCAA GACTGAGAGT AGCACTCTGG ATAAGAACAA GAGTTCGAAG     10860
GCAATATGAT ATGTGTCTAT CTAGCAATGT GTCAGCAGTT GGTACCCCTC TGCTATGGCC     10920
TGTGATCTCC CCAGCCAAAG GCTTCTGACC AGATTTATAC TTCCAGTCAC GTATTCCCTC     10980
CTGAAGGTCC AGGCTTCAAA TGCCTCGATT GCTGATTGAT GTGACCCACC CCCAGTCATG     11040
TCATTGGTTC TCCAGCAGAC ATACCTTGCC TGGCAGGTTG GTACTGTAGC ATGCAGGGTA     11100
CAGAGTTGGG TAAGACCCTT GATGACCATC GCCACCCCTC CCCCCTGGCA GGTGGCATAG     11160
TACCTTTTCC AAGTATGAAT GCTGACTGGC AGGATGAAAC TGAAGCATCC GGTCAGTTCC     11220
AGTTTGATTT TTCTGTGTCT TGTAAGAATG AGCTCCCAGT GTAGGACCAA CCCCTGGACA     11280
AACTCAGACT TTGATGGTTT ATTCTCATAG AAGAGCAGAG TTTCATCTGA ACCATTAAAA     11340
TAAAAATTAG CTGGAACTAC CTGAACATTT CTGGTTTTAT AAATCATTGA GTTAAATATT     11400
GGAAAATTAG AATACATAGT CCAAAGCACT TATTACATAA CAACATACGT CTCTTTGTTT     11460
ATTACCATCT TTTGTCTTTC TCTAATTTCC TCACTTATTT AGGTAATTTT TCTTTCTTTA     11520
GTGCTGAGGA TTGAGCTTGA AGCCTTGTGC ACTCCAGGCA AGCATCACAG AGTTGTCTTT     11580
AAAGTAGTCC TGTTGTTTGG TGTTCTGCAC AGTGTTTCTT ATTTACACTA CGTTCAGAAT     11640
GTATTACCTA CAATTTCTAC TTTTAGTTTC TTTAAAGTGG AATGATAATT CAATATACTT     11700
GAAGTCATGT GACTACAAAG TCCTAAGAAT TTTTAAGTTT TTTTCTTATG AGCTTTTGCA     11760
GTTATTTTGA CTATGGGGCA TAATTTTTTG ATTATAATTT TTATGTAATA GATAATTATA     11820
TTTTTCCTAT CCCCCAACCC TTTCCAGATC CTAACCACCT CCCTATCCAC CCAAGGTTTG     11880
AGCCCCTTTC TATCAACAAT GAACAATCTA ACAAAGAAAA ATCAGAACAA AAAACCAGTA     11940
AGGAAAAACA GATACCTCAA CAAAATGAAA TTAAAAGCCT ACAAAAAAAA AAAAAAAAAA     12000
AAAAACCAAA ACAAAACAAG GCGTTCATTT TGTGTTGGTT ATCTTCTCCT GGGCATGGGG     12060
CCTGCCCTGG ACTGTTGCCA ATACATCCAG TGACACGTAA TTAGAGAAAG CAGATTTTTT     12120
TTCTTTCCCA GCTTTTGCAA AGAAGTTTTT AGTTAGGAGT GCTGGGATTT TGTCTAGATT     12180
GAACCTTTGC TATTCATGTG CAAGCTACCA CAGTCTCTGG GAGTTCATAT GTGCATCAGT     12240
CTTGTGTCTG GAAGACAGTG TTTCTGTGTC ATTTTATTGT AAAATTTACT ACTTAACTGA     12300
GAGTTATCAA TAATTTTTTT TTCTTTTTTA GTTTTGTTTT TTGACTTTGT TATTTTGTGG     12360
TTAAAGTGTG GCTTGCTTCC TCCTCTTCTG ATTTACTGGT CTGGGATTGT TCCTTCTGTT     12420
TTCTTGGATG TGATTAACTG CTTCAGACTA AAGTTTTCCT TCTAATGCCT TCAGTAGTGT     12480
TGGTTTAGTA GACTGATATG CTTAAAATTG GTTAATCAC AGAATGTCCC CCTCGCCCCC      12540
AAGCTACTGT GATTGATAGT TTTGCTGGGT ATAGTAGTCT GGGCAGGGAT TTGTGATCTT     12600
TCAGAGCTTG TAGACTATTT GCCCAGGTCC TTTATGGGTT TTTAAAATCT CCATTTAAAA     12660
GCCAGAAGAT ATTTTAATAG CTCTGCCTTT ATATGTTATA TGGTCTTTAA ACCTTGTAGC     12720
CTTTAATATT CTTTCTTTCC TCTGTATGTT TAGTATTTTG ATTATGTGGC GAGGGATTTC     12780
TATTCCTATC TATTTTGTTT TCTGTATACT TCTTGTACCT TAAAACGCAT TTCCTGCTTT     12840
AGATTGGGAG AAATTTCTTG TATGGTTTTG TTAATAATAT TTTCTGTGAC TTTACATGGA     12900
TTTCTTCTCC TTCCTTTATA TCTACTTTTT ATAAGTTTGA TCCTTTCATT GTATTACAGG     12960
ATTTCCAAAT GGCTTGTGCC TGCGTCTTTT TAGATTTAAC ATTTTTTGAC TGAACTGTAC     13020
ATTTTTTTCT ACCTTGTTTT TAAGACTTGA ACTTCATTCT TCCATGTTGT GTGATATGTT     13080
```

*Fig. 7-13*

```
GATGACACTT ACCTCTCAAG TTTTTCTTTA ACACCCTGAG TTTTTCATTT TAGAAAATTT    13140
ATTAACAAAT AACAAATTTA CGAACAGAAC TTTATTGGCT TTTCCCATGT GTTTAGTCCA    13200
GAATAGAATG AAATAGTTTT TGCTTTGTTT TTTGTCATAT CTTATTGCTG CAGTTTACAT    13260
TTCATTAAAT TAATTATCAA AAAGGGCCAT CTGGCATAAA GGGGATGGGG ACTCAGAGTT    13320
AGTAAACTCT GAGTGAGTAT GCAAGGCTAC TTCTACAATG AGAAGCACCT GATCACACAG    13380
GCAAGTTGGC TGTTACTCAT ATTCACGTGT GGCCACATGG AAATAAGGAA CAGTTTTAGT    13440
CCCAATGGGT CTCCTCAGTA AGCCTTCGTT CAGTAAGAAC TTTTAAAGCT CATCTTTACA    13500
ATGAATAAAA TTAGAGCTGA ATAATGCTTA TTGAATTTTT TTTAGGGTTC CTGTAATATT    13560
GAAGAGTATT TCAGAAAATC TCTGTTCATT GAGAAAAGTG ATCTGTGGTC CTACAAACAC    13620
TGAGACTAGA CTGAAGCCGG GCAGTAGTTT TAATTTACTG TCATCAGAGG ATTCAGCTGC    13680
TGCTGGAGAA AAAGAGAAAC AGATTGGAAA ACATAGTACT TTTGCTAAAA TTAAAGAAGA    13740
ACCATGGGAC CCAGAACTTG ACAGTTTAGT GAAGCAAGAG GAGGTTGATG TATTTAGAAA    13800
TCAAGTGAAG CAAGAAAAAG GTGAATCTGA AAATGAAATA GAAGATAATC TGTTGAGAGA    13860
AGATATGGAA AGAACTTGTG TGATTCCTAG TATTTCAGAA AATGAACTCC AAGATTTGGA    13920
ACAGCAAGCT AAAGAAGAAA AATATAATGA TGTTTCTCAC CAACTTTCTG AGGTACTGAA    13980
TCAAGAGGGA ATAATATATT CATCAGTGGT TGGTTTACTT TGTTGTATAA ATGCACAAAG    14040
AACAAATATT TTAGTTTTTG TGGGATGCAT GGTCTCTGTT GTACCTATCC AGTTCATCCG    14100
TTGTAAAGCT GCCATAGACA CATGCAAGCA GTGGTACCTG TGTGCTTCAG TAAAACTTTA    14160
TTTAAAAATA CAAACAGAGG GCCATGTTAA CTTGTGAGAT CCACTTAATA CAATAAGTAG    14220
AATTGTATAA GTGAAAAATT TTGCTGCTTT ACTATTTATG TTTTTTATAT GATAGGTAAT    14280
AGTTTTTTGG TGGATTCTTC CTAAGTATTT ACTCATTCAA ACTTGATTTG GGGGGTGGGT    14340
GGGTTTTATT CCTTCAAATA GAAATTATTT GTTAGGGTGA AAGGGTCCTT TGATTTACAG    14400
GCATCCATAC TGTGACCTGG AGAGCCAGGA AGCTCTTGTC TCCTTCCTAA TTCTTATTAG    14460
CTTGCAAATT ACTGAAGACA TTTATCATTT CTGGGAGGTT TTTCTTTTTC TTTTCTTTTC    14520
TTTTCTTTTC TTTTTTTTTC TTTCTCTTC TCTCTTTTTT TTTGCAATAA CAAATTTCAT    14580
TTTAGATTTT GAAAAGATTG TATAGGTTTA AACCTCTCAA TTTCATTACA GAAGTGGAAA    14640
CCCAGTCTTA TATACAATTC TTTGATTTTT TTTTTACAGG AGTTTTTCAA TTGTTTCTAT    14700
TGAGTATATA AATGTAAATT GTTTTAAAAA TTTCAAAATA TTCTCATTCT AATTTTTTGT    14760
GAACCAGATT CCCTCTCTAG AAAATGCTGT CTTTCACTTA CATGTGCATC ATTCTAATTC    14820
TGTAGAAATT TCTAATTAGA TCTGCACTTT CATATTTTTA TATATTAGAG AATTATGCTC    14880
ATGAGTTTGA TTTGACTGAT ATCTTTTATA TCAATTATTG CCATTTTATT ATGTAATGAT    14940
TAGCATCATT TTTATTATTT AAGACTGCGT TTAGAAGTCA AGAAAACCTT ACTCAGTTAA    15000
AAGTGTACTT TAATACATTT TAATAGCTTT AAATTAGCAT GTTAATTAAG GCTATTTTCA    15060
TTTTCCCATT AACAAATTAA ATATGAAGCA TTTGGGGAGA TATTCCTTCA AGTTTCTTCT    15120
TGATTTGTGT GTGTGTGTGT GTGTGTGTGT GTGTGTGTGT GTGTGAAGGG TAGATTTGCA    15180
GCTTGTTAGG CACCCGGTTC CTTGGGATTG CCAAATTATT GTAAAGATTC TTCATATCCA    15240
AACATCAACA ACAGATCAAG AAAATAATAT ATTTAGTATT TTTTCAAATA GATGGTCTTT    15300
GTAAAACACT AATTTATTGA AAGATTATTA TGTATTAGTC TTTGGTATTT TTAAGTCAGT    15360
GTATGTAAGA AAACCATTGA TTTTCTTGGT TTGTACAGAC TTTTTTCAAC ATTGATTAGA    15420
ATGCCATCTA TTGGAAAGTT GGGGAGACCC AGGTTGACCT GGTTGACCTT CAACTTGCAC    15480
TTTCTCTTCT TTTGCATGTA GATTCTACTT GACGTCTGTT TATCTAACTT GCCTGTCTTT    15540
TTAATTACGC TCTCTCTCTC TCTCTCATTA TTTGAAGATT AAAACACTCA TTCTCCTTTC    15600
TCTCCCGTCC TCTCTGTGCT CATGCTGTGA ACATATAAAT ATGCTTTAAA CATCTGCCTA    15660
TTAAAGAAGA GGAAGATGTC TAAATACTTC AGTGAAAGCA GCTGAGAGCA TAGTGTCACT    15720
CTCGCAGAAC GTTAATCTTT GAAATCCTTT TCTTTAAAGC ATTTATCTCC CAATGATGAT    15780
GAGAATGACT CCTCCTATAT AATTGAAAGT GATGAAGATT TGGAAATGGA GATGCTGAAG    15840
GTATGTTTGA ACACAAGAGA AAGTTACTTC AAGTTTTTAA AAGAACACTT TAATAATTAA    15900
AATATTATCC ACTTCCAAAT CAGATGCCAC CACAATGATA TTCATACCCA TTATTTAATG    15960
TTAGACTTTA AGTTTTCAAT TTACATGTCC TCATCTGTAA GTAGTCTTAG GTGTAACGTT    16020
GGGAGTTCTC ACGGGAGTTC TGTGTCCTCA TACGTCTCTC TCTCTGGAAA CTGGGCAGTA    16080
ACTAAGCACT TGAGCAGGAA ACTCATTATT TCTTCTTCTT CTTCTTCTTC TTCTTCTTCT    16140
TCTTCTTCTT CTTCTTCTTC TTCTTCTTCT TCTTCTTCTT CTTCTTCTTC TTCTCCTTCT    16200
ACTCCTCCTC CTCCTCCTCC TCCTCCTGCT CCTGCTCCTC CTCCTCCTGC TCCTCCTGCT    16260
CCTCCTCCTC CTGCTCCTGC TCCTCCTCCT GCTCCTCCTC CTCCTCCTGC TCCTCCTGCT    16320
CCTCCTCCTC CTCCTGCTCC TCCTGCTCCT GCTCCTCCTC CTGCTCCTGC TCCTGCTCCT    16380
```

*Fig. 7-14*

```
CCTCCTCCTC CTGCTCCTGC TCCTCCTCCT CCTCCTCCTG CTCCTGCTCC TCCTCCTGCT    16440
CC                                                                    16442
>00275    00275
GCTCCTCCTC CTCCTGCTCC TCCTGCTCCT GCTCCTGCTC CTCCTCCTCC TCCTGCTCCT       60
GTTCCTGCTC CTGCTCCTCC TCCTCCTCCT CCTCCTCCTC CTGCCCCTCC TTCTCCTCCT      120
TCTCCTTCTC CTCCTTCTCC TCCTCCTCCT GCTCCTCCTC CTCCTCCTGC TCCTCCTTCT      180
TCTCCTCCTC CTCCTCTTCC TCCTCCTCCT CCTGCTCCTC CTCCTCCTCC TCCTCCTCCT      240
CCTCCTCCTC CTCCTCCTCC TTCTTCATGT ATTTGTTGTG TTTTAGACAT TCTGTGTTTT      300
ACTCATTCAA TCATTTACAG GGTCTGGATT TTCTTATTGT GTGTTTTTTT TTTTTTAAAT      360
ACTGATTATA TATAATGGCT GTTTACTCTG TTATCAAAGC TGAAGTATGG ATCTGTGCAT      420
TTCTATCCTG TCACTCATCC TCCAGCTTAT CAAGTGTCGT AAGCCATGTG CAGACAGAAA      480
AATCCAGACT GAGAGAGTAA GGGAAAGCAC AGTTTAGTTA AATCAAATGA AAAATAAAAA      540
GAAATAGAAG TATGCTTTTG TGTCTGCCTT TTAAGCTGCC ACCTGTAGGT TAGTGTGCTT      600
TTTCTTTTCA TTAAATGAGA GTAATTTTCT AGTTCTTTAG TTTTGAGTTT TAGATAAATA      660
AGGATAAATA AAGATGTGGA TTCCTAATTG AATGTAGACC TGAGTCCTCC CTTCCCCATT      720
GGTGTCCATT GCTAACATCA CAGTTTACCA GGGAGCCTGT CTCCTATTTA AGAAATATGA      780
GCTAAATCAC AATCTATTCA CTAGGTATCC ATTTTTCTAG TGCATTCAGT TCAAGTGGTA      840
CCAAGTGTAG GATGCTTGTA GACATCTGTA CCATATATTA TACACTGGAC ATCTCTGTTC      900
TCTGGATATG TTGGTAGAGT TAAAGAAATA TCATCACCTC TTTTTTCCCC TCATTTTTCT      960
TTTATAGGAC GGAAATATTA TACTTTAAAG GACATTCTTA AAACCAAACT AAAAAATAGA     1020
ACGCCTCATA AAAAGTGAAG ATAACTTGTG TTAAATGAAT AGTCTATGTA ACTCCTTAGT     1080
AAAAAGTTTT ATAGATACAG CGATTTGAAA TATACTAATA TTTTTGAAAT AGTGGAGAAA     1140
ATACATATCA AAACACCTTT TTTTCACATC AGTAATATTT CTTTCCTAAA ATTATTTGAA     1200
TCCTTTTTTA CAATTCCAAA ACACATTTAT TGCTTGCTCA TAATTTAAGC ATCATCTTTA     1260
CTCAAGAAAA ATGCAATTGA CATGTAACAT AGAGAAATCT ATGATAAAAA TAGCATTAAA     1320
ATGTTTCATT TTACCACTTA GAATTCTAAA ACGTTGAAGT CCAATAAGAA AAACTGGTTA     1380
AATTATGCAA ATTTTAAATT TACGATACGT TTCCCAGAGG CCGTTCATTA TGTGCTATTA     1440
CTGAACCTTG TTTATGCTGG CCATGCTCCA TCCTGGCCTC GTGCCTTGGA GCATCTTCAG     1500
CACGTATTTA TAGAGGAGCA CACATGTTCT TTTGTGCTGT TGTTTGCACA TCTGCCGGTT     1560
TTCAACCAAA TTGTAGGCTT TGTTAATAAC CCTCCTTTTG TACTCAGTAA AAAGATACTG     1620
TATTGTCAGT GTTCTGCCTC AAATTTCTTT TAAACTTCCA GTCTTTAGAA AACCTAAATA     1680
GTGACATGGT GGAACCCACT CACTCTAAAT GGTTGGAAAT GGGAACCAAT GGGTGTCTTC     1740
CTCCTGAGGA GGAAGATGGA CACGGAAATG AAGCCATCAA AGAGGAGCAG GAAGAAGAGG     1800
GTAAGAATCA GGGTGGAAAC AAACTCACCT TTCATGGATT TCGTGTCAGT TTTCCCGTGT     1860
TTGGAAGTTT AACAAGTTGG TGGCACGTAG TTACTTATCC AGTCTATAAA CCAACCACTT     1920
AAGTCCTTAG TGCTCCTGTC TCTCGGGAAC TGTGGATGAT GAAACCTTTA ATCCTGAAGT     1980
GAAAGATTTG GTTTGGGTCC CAATGACAGT GGTGAAATAG TTTACTAATT GTTCATATTG     2040
AATGCCCTTG TTGGTGATAC AAATACATGC AGTCTGCTAC CCACCAGGAG CTTATGGTTT     2100
AAACAAGTGC CACACCTAT GTTCAATTAA ATGTATAGAA TAGTAAATGA GTGTGCAAGT      2160
GATAGAACTG TCATCTACGT GTAACCAATC ATGGTCATTC GGTCAACTTT GTAGTACTAT     2220
CACTATACTT ACAATATATT GTGGTGGGAA AATGTGGGCA TTTCAAAATC ATTTTGTAGG     2280
TAGAAGGTAC TTATAAATGT ATTGATGAGT TATTCTCCTT TGTTTCCTTT TATTAAGTGT     2340
AGCCATCTGT TTGTTAAGAT GTGCCATAGC ACTTATTTTT CATGTTTAAT GATAGCTTAT     2400
CTAGAATCTG TGTTTTATCC TTTCTTGGCT GCTTGTGAAT CTTTGCATCA ATGGACAGAC     2460
AGTGGTGGGA CTTAGGGAGA GCTAACATAG TCCACCATGT GGTACCATTA AAATTTTTGG     2520
CTAAAGATTT AAGTAGCTAT ATTAACCTAA CTAAATAGGA TAGGTAGCTA AATTAGATCC     2580
AGGTAACTTA ATTTATATAA CTAGATTTAG TTTTAAACAG CTAAATGAAA ATTTTATTTT     2640
TTTTCTGTAC ACTTAATTTG GGATACTAAT ATAATTCATG TTTATCATTA ATTGAAAATT     2700
ACTTCTAATA TAAAATTTTT ATCGGCATTT CTATTGTTTG CTTGGTTCGC TTCATTCTGG     2760
ATTGTAGATC CTGCAAGTTT CCCAATTACA GGATGTTGGG CCTCTTCTTA CCACTATTGC     2820
TAAAGCGGGC CACAAGGATA GGTCTAGTTT GTAAGTAGTG ATCAGAGGAT TTGCCTGGTG     2880
TCATGCTAGA TATCTGTAGA GTCAAGTGTG ACTGGGATGG AAACAGTGGA TGTCACCCAT     2940
CACTCTGTTC TTTATCACAG CAATGGAATG AACATTTTCC TCTTCTTGCA TAGCATATTT     3000
GCTTTTGAAC ATAAATGTCA ATTTTATTAT TTTATTTATT TTAAGACCA TTTATTGCCG      3060
GAACCCAACG CAAAGCAAAT TAATTGCCTC AAGACCTATT TCGGACACAG CAGTTTTAAA     3120
```

*Fig. 7-15*

```
CCGTGAGTAT GATCTCAATT AACTATATTA TGTACATATT TTTTTTTCAC AAAGAGAAAG   3180
AGTAAATAAT CCATCCCCAT ATCCTAACAG CAGCAGCCTA ATTTTATTGT AGGCATATAT   3240
GTCAGGTATA GATTATATAC AACTGTAAAA TTATTGGAAA TATTAATTAC ATAAGTTTCT   3300
TTGTCCTTTT AATAGGAAAG GAAGCGGTTC TATTTTTCTT TAACTGAGTG CTTCTATGCA   3360
AAAACTATAT AATAATAAAA AAAGAATTTT TCTCACTGCT GAGTTATCTT TTATTGAGTA   3420
TGAATTCAGA GGAAAGGCAC ATTGCTTACT GCTTTCTGCA GGTGTTGCAA GGCACACTGT   3480
TGTGAGTCTC TGAGAGAACA GTTTGAGAAG CTGAAGGTTT ATTGTTTTAA CATTTCAAAA   3540
TATATTTCCA TCTAAAGGGC TGTCTTAGTC CATGTCCCAT TGTCGTGAAG GGACACCATG   3600
ACTACAGCAA CTCCGATAAA GGAAAACATT TGATCAGGGC TGGCTTACCA GTTCAGAGGT   3660
TTAGTCCATT ATCATGGAAG GCATGGCAGT GTACAGGCA ACATGGTGCT GGAGAAGGAG    3720
CTGAGAGTTC TACATCCCAA TTGGCGGGCA GGAGGAAGAG AGAGTGAGAC ACTGGTTGTG   3780
GCTTGAGCTT TTGACACCTC AAAGCTCACA TCTGGTGACA TACTTCCTCC AACAAGGCCA   3840
CACCTGGTCC AACAAGGCCA CACCTCCTAA TCTGTTCAGA TACTGCCAAT CCCTGTGAGC   3900
CTTAGGGGAG TGTTTTCATT CCAACCATCA CAAGGGCACA CTAATAACTA GAAACAATGA   3960
GATGAACACA AACGAGATTA GGAACAAGTG CATTTGAATA AGACCAGTAA GTAACTAACA   4020
ATCTAGACAG GGTTTTTTCA ATTTTTTTTA TAACTTTTTT TTGGGGGGGG GTGCGTGTTT   4080
CGAGACAGGG TTTCTCTGTG TAGCCCTGGC TGTCCTGGAA CTCACTCTGT AGACCAGGCT   4140
GACTTTGAAC TCAGAAATCT GCCTGCCTCT GCCTCCCAAG TCCTGGGATT AAAGGCGTGC   4200
ATCACCACTG CCCGTTTTTT GTTTTTTTTT TTAAATAACT TTAAAAAGAA TTCATCGGAA   4260
CATTTTTCCT TCTTTTAATA AACTATCACC TCCAGTTGAT TTCACCTTAG TCCATCACTT   4320
TACACAGGTC TCATTTCAAA CCTATAGCAG TCCTCTTATT TATTCTAAAA TATTAACTTT   4380
TCGGTCTATA GTACAAAGCT GGGTATTTGT TTTATACTTT AGATATATGT AATAAAATTA   4440
CATATACATA CTATATGGCA ACTCATGGTT ATTCAGTCAG TCTGAATGAA AAGTTAATCA   4500
AATGATCAAA TTTTTTCTCT CAAATTTCTA GGATTTGAAT ATATTTTTAT AGGTAGCTCC   4560
AAAAAAAAAT CTGAGTTTAT TGGAGAGAAG TTAAATAGAT TTGAACTTGT GCTTTGGATG   4620
CTATTGATAA AACATTTTAC TTTGTACCTT CAAGGGTTCA GTGAAAGTC ATCCATTCTG     4680
TATTAGAAGA GAGAAGAGAT AATGTTGTTG TCATGGCAAC TGGTAAGCTA TACTTAAAGT   4740
AAATAATTTA ATCATCTAAA AGTCATAAAG GGTCTAAAGT GCTTAATCTT TCAGAAACTT   4800
ATAAAATATA GGAAGGAATG ATTGGGGGAA AAGCCTTCAA ACTTATGCAT GAATTACCAT   4860
GTCAGTCCAC TTATTCTGCT ATATAAGCAC ACTGTAAGAA GAAAGTAAAG CATCAAGAGT   4920
TTCTTTTTAT TTTTTTGTGT TATTTTTTTT TTATTCAAGG ATATGGGAAG AGTCTGTGCT   4980
TCCAGTATCC GCCTGTTTAT ACAGGCAAGA TTGGCATTGT CATTTCACCT CTCATTTCCT   5040
TAATGGAAGA CCAAGTCCTC CAGCTTGAGT AAGTAATGCT TGCACTGCTG CAGCGTCGCC   5100
TTGGATAAGC AAGTGGAAAG AACATGGCAA GGCAGGATCT TACTACACAG GCTTAGCTAG   5160
GCTCTTCTCT CAGTGCAGTG GCCCTTTGCC CAGTTGTCCC TCTCTGTTCT ATCGATGAAA   5220
TATCAGAAGA TGAACGTGAA TCTAGGTCAC AGGATTACGT TTTGGGAAGT AACTTGATCT   5280
TCTTTATTTC TATTTTTAAT TTTTGAGATA GGGTCTTGAT ATATATATAG TCCAGGGTGG   5340
TGTCGCTCTG GCCTCTTGCC TTGCCCTTCA TGCCTTGGGC TCACAGAGCA TGCACTAGCA   5400
CCCCTGGCTG CATTCATTAG TAGCAAACGA AGTGTTAGTG GAAGAGTTTA CATTCATTCT   5460
TGAGGTCTCC AATGCAAGGC TACCTGTTTT CTCTGATCAG GGTTTAAAAG GACTGATTGC   5520
TTTATGCTAG TTAGCTGTCT CAAATTCTTT TTTTTTTGTT CTGCTCTCTG GGCTCCCAAG   5580
CTTGCAATGA GATATATATA AAAGTTTACT TTTTAAGATA TGTTTTTATT AGTTCTTTGA   5640
AAATCTCCTA CATGTTTTGA TTATAGTCAC CCCTCTTCTA ACCCTAAGTT CACCTTTCTA   5700
TTCCTTCTTG AAAGATCCAC ATTAAAGACT TGCCTCCTCA TCAGGCTTTT GAAGGAATAT   5760
ATCAAGTTAT ATAGACACAA AAAGGAAGAA CATTAGAAAG ATGAGGAACA TAGGAGGTTC   5820
ATGTTTATGT GTGTATTCAT CAGAGCGTTT GTCTCTTGTA GGCTATCCAA TGTTCCAGCC   5880
TGTTTACTTG GATCTGCACA ATCAAAAAAT ATTCTAGGAG ATGTTAAATT GTGAGTAACT   5940
TATATCATGT CACATAATAT TGTAAGATGT ATATAGAGTA AGAGAATTTT GTATATATGT   6000
TTACTTATAT GAGTAAATTG CCCATATTTG AAAACATACT TTAAAAAGCC TTATTTCTGA   6060
AATAATAACA TAGTTCCATT TCTTCCTTTC CTTTCTTCCT TCCAAACTCT GCCAAACATC   6120
CTTCCTTGTT CTCTTTCAGA TTGATGGATT TTTTTCCCAT TAGTTGTCAT TACATGGATC   6180
CATGTTTATA CATATGTATT ACCAAATGCC CCGTTTTTTC TCAGCAGAAG TCATGTAAAA   6240
CTCCTTTATC CTTAAGATAA ATATTCACTT TTGGGGGGCT GGTAAGATGG CTCAGTGGTT   6300
GAGAGCATAC TGAGTGCTTT TCTGGAGGTT ATGAGTTCAA ATCCCAGCAA CCACATGGTG   6360
GCTCACAACC ATCTGTAATG AGAAACAAAT AAAAAAAATC CCTATGGGCC AGAACGAGTG   6420
```

*Fig. 7-16*

```
GGGCCCCGGA GTGAGTGGGG TCAGAGCAAG AGGGAGAGAA AGGGAAGTGG ATTTTTATTC    6480
ACTTTTTGTT TAAATTATTA TTGTATTTGT ATTATTAACT TGTCTTCCAT TATCTTATTG    6540
TATCATATCT AGTATTATAT GTTATACATA TATATCGTAT ATATGTATTT ATATGTATCA    6600
TACTTTATAT TATATGGTTA ATTTGCTATT ATGATAATTT TTATAAAAGA AGGCTAGAAA    6660
TTACTTATGG CATGTCTCTA CCATATAAAA GCAGATAAAA TTAAATTAAA AATTTTAATA    6720
TAAAAGTTCT TTAAGTTTTT AATTTATCTA TTCCACTAGT ATTTTAGTGT CTATTACATG    6780
CTAAACATTA TGTTTTCACT AGTAATTTAT TAGGCATGTA ATAAATTTTA TCGTATCTCC    6840
AGGAAATTGA TGCAGTTTTC TAATTACTGT AAGAAACAAT AAAAATAATG AAGGCTAACA    6900
TCACTGTACC CAGGTTTGGA ATCAGTTCTC CGTCCGACTA GGAAACTGAT CTGAGATGAG    6960
CCAGTCAACT CCAGTGTATC CCAGTTTCTT GAAAATTAGC TGTTTACTTA CAGAGACAGA    7020
CTTAGGACAT CTCAGTTAAG AAACGGACAC TGGAACCTTC ATGGAACCAA AGAGCAGCCA    7080
GGAAAACTAA CACACCCCTG AAAACAAAGA GCATAACTGG GGGCTTGTCA TCGAGACTTG    7140
CAGGCTTTTA CTGTAGCTAC AGCAGCCAAC ACAGGCAGAC GGAGCCACAG AAGCAGATCT    7200
CAGCAAGGAA TCTGCACATG CCTACAAAGC TCATCATCTG AGAAAGGCTC AAAGGTGATC    7260
CAGTGGAAAA GAGACAATCC AGAATAATGG CTTATATGAA AACAATGGCC TTATAAGAAA    7320
AACAAACCAA ACAAACCAAA CCAAAACAAA CAAAACCCCC CAAACTAATA CACCACACAA    7380
TATAAACATT TTTTGCTAAA AGCGAATTAT GCGTCCAAGC ATAAAATTGT GAAATGTTTA    7440
AGGAAAAGCA TGCCATCTTT ATAACCTTCA GTTAGGGAGA CTTCTTAAAT ACCCAAAGCA    7500
AAATCTATAG GAACAAACTA GCAGCTGGAC TTTTACAAAC TGAAAACCTA CTTCTCTTCA    7560
AAAGAATTAT TGAAAAAGGA AGAAAGGCCA TAAACTAGCA AAGTATATGC AAAGTACATA    7620
TCCATACAAG ATTTCTACCT ATAATATAGA AATTACCACC AAAAGAGAAT TAAAAAAAAT    7680
TAAAGTGTCA AAAGATTGGA ACAGACACTA GCACAAAGAT ATACAAACAG CAATAAGTAT    7740
AAGATGCTTA TATAATTGGT CACCAGGCAA AAACAAATTC AAGGTACAGT GAGATTCTTT    7800
CCAAGTGGCT AAAGCCAATG ACTGGCTAAG AAATGTCAGG GGTAGTGAGC AACAAGACTT    7860
TTCACACACC ACTTCTAGGG ATGAGAGATG GTAGAATGTT TGTTTGGGGA GTAGACTGTT    7920
AGAAACCATA ATTTGGCTTA TAATTCCAGC TTAGTGGTGA ATCCTACACA TCAAGAATTG    7980
TTATATTTTA TTTTGGTGAA TTGAAGATAA ATGAAAGGAC TAACATCTGA ATTATGTATA    8040
TATATAAAAT ATTCCTTTGG ATTTTAATAA TCAGCATGAT GCATTACTTA AAAACCTATT    8100
GAATGCTTCT TTCCAGTCTA GGGCAGGGAC CTTAGCTGAC CTTGGGTGCT AACTCTGCAC    8160
CCAGCCCCAC AATACCCAAA GGAAGCTCCA CTTCTAGGCG CTCTAACACG CCAAGTCCGC    8220
AGGATTCCAG GATCCCAGGA ACTTGGTCAC ACCAGGATCT CAGGGTTTTA GAGGAACCTT    8280
GGCTCCCAGG AGCTCTGACA CACCCAGGAT CTCAGGATCA CAGGATCACA GAGACAGCTG    8340
AACTCTGAGA AGGTCTGACA CGACCAGGAT CACAGGAAGG ACAGGCTCCA GTCAGATATA    8400
GTGAAGGCAG GTAGCACTAT AGATAACCAG ATGGTGGGAG GCAAGGGGAA GAACATAAGC    8460
AACAGAAACC AAGGTTACTT GGCATCATCA GAACCCAGTT CTCTCACCAT AGCAAGTCCT    8520
GGATACCCCA ACACACTGGA AAAGCAAGAT TCAGATCTAA AAATCACTTC TCAGGATGAT    8580
GATAGAGGAC ATTAAGAAGG ACATCAACAA CTCCCTTAAA GAATACAGGA GAACACAAGT    8640
AAACAACTAG AAGCCCTTAA AGAGGAAACA CAAAAATCTT TTAAAGAACT ACAGGAGAAC    8700
AAAATCAAAC AGGTGAAGGA AATGAACAAA ACCATCCAGG ATCTAAAAAT GGAACTAGAA    8760
ACAATAAAGA AATCACAAAG GGAGACAACG CTGGAGACAG AAAACCTAGG AAAGAGATCA    8820
GCAGTCATAT ATACAAGCAT CACCAACAGA ATACAAGAGA TAGAAGAGAG AATCTCAGGT    8880
GCAGAAGATA CCATAGAAAA CATTGACACA ACAGTCAAAG AAAATACAAA ATGCAAAAAG    8940
CTCCTAACCC AAAACATCCA GGAAATATAG GACACAATGA GAAAATGAAA CCTAAGGATA    9000
ATAGGTATAG AAGAAAGTGA AGATTCCCAA CTCAAAGGGC CAGTAAATAT CTTCAACAAA    9060
ATTATAGAAG AAAACTTCCA TAACCTAAAG AAAGCGATGT CCATGAACAT ACAAGAAACC    9120
TCCAGAACTC CAAATAGACT GGACAAGAAA AGAATTCCTC CTGTCACATA ATAATTGAAA    9180
CATCAAATGC ATTAAACAAA GAAAGAATAA TGAAAGCAGT AAGGGAAAGA AGTCAAGTAA    9240
CATATAAAGG CAGACCTATC AGATATAGGA CTAGCTTCT CACCAGAGAC TATGAAAGCT    9300
AGAAGATCCT AGGCAGATGT CATACAGACC CAAAGAGAAC ACAAATGCCA GCCCAGGCTA    9360
CTATACCCAG CAAAACTCTG AATTATCATA GATGGAGAAA CCAAGATATT CCATGACAAA    9420
ACCAAATTTA CACAATATCA TTCCACAAAT CCAGCTCTAA AAGGATAAT AGATGGAAAA    9480
CACCAACACA AGGAGGGAAA CTACACCCTA GAAGAAGCAA GAAAGTAATC TTTCAACAAA    9540
CCCAAAAGAA GATAGCCACA CAAACATAAT TCCACCTCTA ACAACAACAA AAATAACAGG    9600
AAGTAACAAT CACTTTTCCT TAATATCTCT TAACATCAAT GGACTCAATT CCTCAAAAAA    9660
GGACATAGAC TAACAGACTG GATGTGTAAG CAGGACCCAG CATTTTGCTG CATACAGGAA    9720
```

*Fig. 7-17*

```
ATGCACCTCA GTGACAAAGG CAGACACTAC CTCAGAGTTC AAGGTTGGAA AACAATTTTC    9780
CAAGCAAATG GTTGTTTCCC AAGAAACAAG CTGGAGTAGC CATTCTAATA TGGAATAAAT    9840
TCAACTCTCA ACCAAGTTAT CAAAAAAAAA AAAAGATAAG GAAGGACACT TCATACTGGT    9900
CAAAGGAAAC ATCTGCCAAG ATGAACTCTC AATTCTGAAC ATGTATGCTA CAAATGCAAG    9960
GGCACCCACA TTCATAAAAG AAACTTTACT AAATCTCAAA GCACACATCA CACCCGATAC   10020
AATAATAGTG GGAGATTTCA GCACCCCACT CTCAGCAATG GACAGGATCA CGGAAACAGA   10080
AACTAATCAG AGACACAGTG AAACTAACAG ATGTTATGAA CCAAATGGAT CTAACAGATA   10140
TTTATAGAAC ATGTCATCCA AAAGCAATAA ATATACCTTC TTCTCAGCAC CTCATGGAAC   10200
CTTCTCCAAA ACTGACCATA TAGCTGGTCA CAAAACAGAC TTCTACAGAT TCAAGATGAT   10260
GGAAATCATC CCATGCACCC TATCATCAGA CCACCACGGC CTAAGATTGG TCTTAAATAC   10320
CAACACAAAC AACGGAAAGC ACACATACAT ATGGAAGCTG AACAGCGCTC TACTCAATGA   10380
TACCTTGGTC AAGGCAGAAA TGAAAATGAA GACACATCAT ACCAAAACTT CCGGGACACA   10440
GTGAAAGCAG TGGTAGGAGG AAAACTCATA GCTCTAAGTG CTTCCAAAAA GAAACTGAAG   10500
AGAGCTTACA CTAGCAGCTT GACAGCTCAC CTGAAAACTC TAGAACTAAA AGAAGCAAAA   10560
ACACTCAAGA GGAGTAGACT GCAGGAAATG ATCAAACTCA GGGCTGAAAT CAACCAAATA   10620
GAAGCAAAAA GAACTATACA AAGAATCAAC AAAACCAGGA GCTCGTTCTT TCAAGAAATC   10680
AACAAGATAG ATAAATCCTT AGCCAGAGTA ACCAGAGGGT ACAGAAACAG TATCCAAATT   10740
AATAAAATCA GAAAGGAAAA AGGAAACATA ACAACAAAGT ATATCTTAAA ATAACTATTC   10800
TGTTTGTTGA ATATCAATAG TTGAAAATAT TAAAATCATG TTCTACAAAC ATCATGGAAA   10860
TATTATTGAT AATTTTTCTC ACTGTGCTTG AAATTAGCAT TTTCTTAATG TTTATGTCAA   10920
AGTGTTTTTG CTATTTTGAA ATGTTAAAAA TATACTTACT GATAAAATAA TTTCTCTCCT   10980
AGAAACACTG ATAATCTTTT TTCTGTAAAC TGATTTTTGG ACAATGTACA CAGATATAAA   11040
ATGTGTTTTA AATACTCTCT CACTATGTCA GGTGTTATTA TATAAAGGCT TTCAAATATA   11100
TTTCTTAGTG ATTCTTTTTA AATATTTTAT GCTCTTTTAC TATGCCTAGC TCCCAAAGAA   11160
TATTCTGTAT GTTTTGAAAC AATTTAGTAT TCAATATTAG GTACAGGATC CTCAGTTATG   11220
GATAGTATTA AATATTAATT AATGATATTT TTAGGATATG AAAGGATATG AATATAAAAG   11280
TTGGACAAAA TTTTAAAGTA TTATCTGATA TCAAAATACT CAATATTATT GATATGTTTG   11340
ATGTATAAAA TACATTTAAA TAATAAGTTT TAAAAAATGT CTATTGAACA TTTTGATTTT   11400
GTTATCATTC ATTGACTGCC TTTTTTTCCT ATTAGAGTGT TTCAATTTAT GTTTCTATTT   11460
TTGTTTGTCT TTACAGAGGC AAAATATAGGG TCATCTACAT AACTCCAGAG TTCTGTTCTG   11520
GTAACTTGGA TCTACTCCAG AAACTTGACT CTAGTATTGG TAAGTAATGA AGTAGGACTT   11580
CGGTGAATAC AAAGTAACCC ATTTATGGTT GAAGACCAGA TTCCAGTTTT GTTAAAGGCT   11640
TATTTCAAAC ATTTGCTCCT CTAGGAAATT TCTAATCAGT TTTACATTTG TCCCATTTTA   11700
CAATGCTGTA TAATTCCTCA TTCCATAGAG GTGGTACTCC TGGGTGGGTG TCATATTTGT   11760
ATATAAGCAT GTATGTATCC CTGTCACACT CAACCCTTTT GAGGCTTCTC TGCTCTTACT   11820
GGCCTCCCAA CTCCTTCATG CAGGATGTGG CACACAGTTG TCTATCCTGT GCATTGCTGC   11880
ATGAACGCTG AGTCTTGTTT CATATTCTGA GTCTAAATGA AATCAGTGTG TGGTTCCTCA   11940
TTCTTGCTCG TCAGAATCGC CCTTCAAGCT CTAGAACAAT GCTGTTAAAT GGCGTATTTC   12000
TTAGAAAAAT AAAATATAAA ATAGGTTAAA TGCTGTGATA TTGTTTATGC TGAAACTTTT   12060
GTTTTTTGGT GGTGGAAGTG TGGTCAGGTT TAGCTAAGAG CTCCAAAGGA AACAAACATT   12120
ATCCATATTC AAAACTTTCA TTTAAATTTT ATCCAACTTA TCAGATAAAA TTGTTTTCCC   12180
AATTTGTGGG ATTTTCGTTT TTGAAGAATT AGGTATTAAG TAATTTCATA TAGGTTAAGT   12240
TTTCAGTATT GTACTGGACT AGCTAGTGGA GTGTCAACTT GATTTAAGCT ATGGTCTTCA   12300
AAGAGGAGGA AACTCAGTTA AGAAAATGTC TCCTTAAGTC AAGATGAAGG CAATCCTGTA   12360
GAACATTTTC TCAATTACGG ATTGATGGTA GAGGGCCATT GTGGATGGTA CTATCTCTGG   12420
CCTGGTGGTC TTGGGTGCTA TAAGAAAACA GGCTGAACAT GCCATGGAGA GCAAGCCTGT   12480
AAGCAGCATC CCTCCGTGGG CTCTGCATCA GCTTGTATTG ATTGGTGTTG CTTGTTGGTG   12540
CCACAGTAGA GAGAGGAGCT CACCAAGTTC CTAAGCCATC CTTTTTGGAA GGAGCAGAGG   12600
GGTTCAGCCT TCCTGGGAAG GCTCACTCCA GTTACTTTAT TCAAGCATTG TTCAAGGTTA   12660
ATTGGGGCTG GGAAAGGTTT CAACCACCAC AGTTGTTATC TTGTGTTTGC TGCTCAAGAG   12720
ACAACATGAC CCACACAGAT CTTAGTCCCT TTTGACCATG GCTAGGCATA ATCAAAGGTA   12780
AGAACTCCAG GTTTGCCAGG AGTGTCTTAG GACCAAGGTT GATGCAGCTG CAGGCCTTCA   12840
GGTAGTACTG AGTGCAGACT TTGCAGGGAG ACAACATTTC TTCAAATAAT CTCAAAACAA   12900
TTTCTCAGCC TCTACTCATT AACCCAAACA CAGCAGAGGC TTCGCTGAAA CATTTCACTC   12960
AAAGCTAGGC ACAAAGGCTT CACTGAACAT TTCACTTCAG GCTCCTGCCT CCAGGTCGCT   13020
```

*Fig. 7-18*

```
TCCCTGCTTG AGTTCCCACA TTGGCTTCCA TCAATAATGA GGATGATGTG GAAGTGTAAG    13080
CCAAATAAAC CCTTCCTCCA CAAATCGCTT TGGTCATGGT AACAAAGACA TGTACCCTAT    13140
CACTTAATAG TATTTCTCTT ATCAGGCATC CATGGGAGGA GGGGCCCTTG GTCCTGTGAA    13200
GGCTCCATGC CCCAGTGTAG GGGAATTCGA GGCTAGGGAG GCAGGAGTCG GGGGTGGGGG    13260
GAACACCCTT ATGGAGGCAG GGGGATGGAG AATGGGACAG GGGATAACAT TTGAAATGTA    13320
AATAATGAAA ATATCCAATA AAAATAAATA AATAAATAAA TAAATAAATA AGGAAATTGA    13380
AAAAAAAAAC AAAACAAAAA GAGAGTAGAC TTTTATATTT CAGTATGTGT TGAAAGCAGC    13440
AAAGAATGAG GACCTACATT AATATTTATG GAAATATATT ATCACAGTGT ACCTATGCTC    13500
TCTCTCTGTT AGCTCTCATT GCCATGTTTT TGCCTGTAAT GGAAAACAAG TTTGATGTCC    13560
AGTCTGTAAT AGCTGGAAGG TGTTCCTTCA AGCATCTCTC TATGGGTTTA GCCTTATAGA    13620
TTTACCTTAT AGATCTATAG CCTTATAGAT CTACCTTATA GGTCAATTTC ATGGTTGGAT    13680
CTAAAAACCT GGTTATCAGT AACTCTGTAT TCTGAGTATA TTTTTTTCCA CTTTCAGTGT    13740
TTATTTGTTT TAATTTATAA TGATGTTAAA TTAATAACTC CTGTAAGTAA ATAAACATTA    13800
AGAGCCTTTG ACAAGTAGTT ATAACTTTTT ATGAGGTAAA TGGTCATTGC TGCCGAGCTG    13860
AGGACACTGT TCAATGATTC TGTTTGCCTA GCATGTTCCA GGCCTGGCTT CAAACCTCAT    13920
TCAGTTTCAC TTATTTTTGT TTTTACTCCA TGTGTTGGTG TTTGTGGTCA CAGGGTAACT    13980
TGAAGGAGAA GGGGAGATGG TCCTCTCCGT CAACCATGTG GGTTCTGGGC ATTTGCTGTT    14040
ATGCCAAAGG GAAGTGGTTT TACCCACTCC CTCTTGCTCA CCTTAGACAC TGTATGTTTT    14100
GTTTATTGTG CTTTTCTCCC CCCCCCCCG TGAATCAGTT TAGGAGAATG ATACAGGAGG    14160
ATCAGATAGT CTGACCTCCC TTCTGTTTTA AAAACATACA CACAAGTGAG CAAACAAAAC    14220
CAGATAACAC GTGTAAGTTT TTCATCACTA GAGCAGAATT GTTTGCTTTT AATAGATAAA    14280
AATATTTCCC TGGGTGATTT AGAAAAAGGG ATAAGGAAAA TGAAAATTAT TTTTTTTAAA    14340
TATTTCCACT GGCTTTTGTT TGCAGGAAAC AGTAAAAAGT CTACAAAAAT GAATATACTT    14400
GGGATGTTAT TTGTACAGTA GTCTGACATT TAACTAATCA GATTTGTCAT TTTTAGGTAA    14460
ATGTTACATT TTTTTTTAAA GTAGTCCGGG TCTATAACAG AAATAGCAAG CATACTTCAT    14520
GGGGTGCCTT CCCAGGCGTA CTTGTGATTG TCTTTTAACT TTGGGAATGA GACTTGAATG    14580
GCAGATGCCT AAATGAAATC TCTACAGGAC CTTGGAAGAC CCTTGAACTT TTGCATTCAG    14640
AGTGAATTTT GCCAAAGCTT GTCTGAACTA ACTGTGTAGG TGAAAGTTCA ACTCTATTAA    14700
CTGCTTGTCA GATCTCTTTT AACTTAAAGT CTAGCCATGT TAATTTCTAC ATTCAGAATA    14760
AGTGTATGAG TGACACTGGA ATTTCCGCAG TCACTCAGTG GTATAAAGTC AGCGTTTGCC    14820
TCTTCGCTTC CTTCCTTCTC GCAGTCTGAG GACATTGGTG TAATCTCAAT GAGTTGCTCT    14880
TGTTTCTTTT GTTCCTCTC TGGATTGTGA GACCCTTGAG GTCAAGTATA CTTTGGTTAC    14940
CAAGAAAAGG GTTAATTCAG TTTTCTTATT TAGATAGAGC CTCCAGCAGC TCAGGCCGGT    15000
CTTGAACTTT CTATGTGGCT GAAGAGAGCC TTGAATTCCT GATCCTGAAT TACATGCGTG    15060
TGGCTCTTAA AAGGGCTTTA AATCATAATG ACCATGTAGT AATAACCGCT GAAGTATATT    15120
TTTATTAAGC TCTTTTTGGG CCCATCCTTA TCTGAGTGTT TTATGTGAAT GTTCTAATTT    15180
AACCTTAGAG GAGTAAGAAG TATTAGGTGC TGTTACTACC TACCGTGTTT TATTTTTGCT    15240
TACGATGCTG TTTGTGCTGC TGGTGCTGCT GGGGGTGATG GTGGTGATGG TGATGGTGAT    15300
GGTGGTAGTG GTGGTGATGA TGTTTGTGGT GGTAGTGGTC AGTGTGTGTG TGTGTGTGTG    15360
TGTGAAATAC CACAGTGTGT TTGTAGAGGT CAGAGAACAC CTGTGTAAGT GGGAGACAGT    15420
TCTCTCTGTG GTTTCTGAGG GTTGAACTCA AGTTCTCAGA CTTTTACCCA CTGAGCCTTC    15480
TCAGCAGGTC CACGATGTAG TTTTGAGGAA ACTGAGAACT GAAAAGATTT GTAGCTTGCT    15540
CAAGGCTTTG TGTACAGCTA ATCTAATTCT AAAGCACATG TTTTAAATCA TCTCACTGAT    15600
AGGGTATATC AGCAAATAAC AGAAGGTTAT TTTTCTCTTA AAAGTACTAA TTTGATAAGG    15660
GTAAAGGCAT TACTAGTCAG TTCTTTGAAA TGTCTGAAGA TGTCATGATG ATTACATAAT    15720
GAAGCCCTTT CAGATGCATT AAGACACCAT TGATCTTGTA TTAGTGTGTG GTGTGGGGCC    15780
CCGTGGAGGG TTATGTTCTT TTTCACTACT TACTTTGCAC ACGGTGGGAA TTAGTTCTCC    15840
CCAAGCCGTT TTATGTTAGC CAATGTGGAT GTCATCTCGT CTTCAGTTAT TGGCATTTCA    15900
GAGGAACTTC CTGTAATATG ATATGTGCCG GATTGCAGAT AACGATGTAC TTAATCTCAG    15960
TAGAAATGTG CTGACTATTT GTCTCCGTTA ATAGCTAATC TATGAGATAA GATTAACATT    16020
ATTGCCAAAA AGAAATGGAA CAATTCTTTT GAAAGGATAT TGTTGTAGAT GTTATAAGTG    16080
ATAATTTTGG GACACAGTAA TAATAAGCAA TTTATGTCTT TGAGGAATAG TAATGAAAAC    16140
TGAAAGATAG TGTGTTGTTT CAATTACGAC GTAAATATTT CCTGTATGCG AACCTCTTTT    16200
ATTCATTTCT CCTCTTACCT CCTATTCTGC CTTCGGAAGT TTGATGTTAT CTGGTATTAT    16260
TTATGCTTCT TATATGTGTG TGTGTTTGAG CCCAATACTT TGATTTGACT TATACTTTCT    16320
```

*Fig. 7-19*

```
GTGAGGTATA TGTTCTAATA GGAACAGACA ATATTGACTT AGCTAGCATT TTCCTTCTGA    16380
GCCTTATTTC TCCTGTATAT TTTCTTCTGT GTAGGCATCA CTCTCATTGC TGTGGATGAG    16440
GCTCACTGCA TTTCAGAGTG GGGCCATGAT TTCAGAAGTT CATTCAGGAT GCTGGGCTCT    16500
CTTAAAACAG CGCTCCCATT GGTAAGCCTT GCCAGATCTC ATGCCCCAC CCCACCCATC     16560
TCAGCTGAGG ACTGACCCCA GGGCTCCTAC CACCAGGCTA GACCCTCAAT CCCGAATTTA    16620
CTGAAGTGAC ATTTTCATCA AGGCCTTTCC AGGACTGGGT AATGTCCACC CATCTCAAGA    16680
CTTCTCTATA AAAGGGATCA GATGTGAGCA ATGGGGCATA TTTAGTTTTA AAATTTTTTA    16740
AATTCTCACG CTGGCTTCCT TTTGAGGTTG ACGTGTAGCT TACTAAGGAA TACTCTTAAC    16800
AGGAGTGTCC AGGCTGTGAC ATTGAGCTAC TCCAGTGTCA TCTTCAAGGT TCTCCCTCAA    16860
GAACCACAAA ATTGTGTTAT TCAAAGACAT CACAAAGATG CCTCTGTTTT AGTTCACGTG    16920
TGACTTTGTG TTGTGCCACA TTCCTACTGT CAGGGCACGG GCTGGATGCT CTTCACTAGG    16980
ACAAGAGCTG GAAAACAAGT TTTGAACATG GCAGATAAAA ATGGCAGTTA CTATTCCTTA    17040
GTGAAAGGGG ATACAGTTTC AAGAATCCGT GGATGCCTGG AAACACCCCC TCAGTGTAAA    17100
TTATGCACAG TAGAAGAATT TTTAAAATGA CTATCTGTGA CAATATACTA TAGCAAAAAT    17160
GACCACAGTC ATTATTCTTG ACCGCGTGGC TCATGATTAA GTAGAGTAGG TAGCACCCAA    17220
CCACAAGCAC TTCCTAGTCT CCTAACTGAG ATGGTTAGTC AGTAGGTAAT GGGGGAGGCT    17280
GTGGATTGTG TGGAAACTTT GGACCAAGGG GAGAATGGGG TGATATCTTT GAGAGTACAG    17340
TGCAGAATTT CATCATGTTA CTCAGCACGC CTTTAATCCC AGCACTCGGG AGACAGAAGC    17400
AGGTGGATCT CTGAGTTTGA GGCAGCCTAC TTTAGTCCTG TCTTAGGAGA AAGATAAAGG    17460
AAAATGTAAG TTGGGTTTTA GGTTTTTTTG GTTTTTTTTT TTTTCTATTT GTTTGTTTTT    17520
GTTTTGTTTT TTGTTTTTTG GTATAACTTT TCATTTAGTA TATTCAGATT TGGTTGTTCA    17580
CAAGAATCTG AAATCAGAAA ACGCCATTGT GGATAGAGAA GGTGGGTGTG AAGTGGATGA    17640
GAGGGCGGGT GTGTGGTGGA TAGAGATGGG AGTGTAGTAG ATGGAGGGGG CGGGTGTGTG    17700
GTAAATGGAA AGGGCGGTGC GTAGTATAGT ATGGCTTTCA CATACAGTTC TCTTTTCTTA    17760
AATAGTCCAT AAAAAAATGTA GTTACCTGGT GTTCCTCACT AATGGCCTCT GTAAAATGGG    17820
CTGGGGACTG CGATAGTTCT ACTTATCACA GTTTGTAGAA ACTTTTAGGT TGTTTGTTGG    17880
AGTTAGGATA TTATGAATGG GGATACTGTA AACATTTGTC TATAGTCCCA GGGTCCAGGT    17940
CAGCGGTTAC AAAGTTTGTG AACATAAGTT TTAGTTTTCT GGGATAAATG ATGTTCTGGG    18000
TTCTATGGGA AGTGCTGGTT TCACTTTTAG GAAGACCCCA GTGCTACTCT CTAGACTGGC    18060
TGCTCTGTTT TGTATCGTCC CCTCCCCAGC AGCTTAGGAA CAATAGCTTC TTCTCTTTTT    18120
TGCCACTGTT TAGTCTTATT ACTATGTAGT ATTTTAGCAA TTATGATACG AGTGGAGTGG    18180
TAGCTTGTGT TTTCAATTTG CATTTCTCTA ATAGCTAGTG GTGTTGAACA TCTTTTGTGA    18240
GCTTCTTATT TGGTTAAATG CCTAGTTTAA TTGGGTTGTA TTTTTTCTGT TAAGCACATG    18300
GGGGAGGTGG AGGGAGAGAA AGGGAGGGAG AGGGATAAGG AAGGAGAGGA GAGAGAAGGA    18360
AGGAGAGAGG GAGGGGGAGG GTTGTGCTTA TGCACATATA CCTCTGCGGT GTGCTCTACA    18420
GTGCAGCCCC TGCAGGCGCC AGATGTTGAC GCTGCTGTCC TCCTCTGTTA CTCTCTACCC    18480
CATTTTATTT GAAACACAGT CTCAGTAGCC AGGGAGCTCC TCATTTGTGC TAGACTAGCA    18540
GGCCACCAAG CCCCTGGGCT CTTCCTACTT TGGAACATTG GGCTCCTAGG TGTGCACGCT    18600
GTGCCTGGCT TTTCTGTTGG TTCTGGGAAT CCTTGCTCAT GTCCTGATAC TCACTGAGCC    18660
ATCTCTTCAG TCCCTCTGTT AACTGCTAAG AATTAAATGT TTATAAGTGT GAGTTATTGG    18720
TTGGATATTG AGCTTGTAAA TATTTCTTTG TAAATTTTAT TTTTTTCTCC TATTTTCACA    18780
ATCTTTTATA AAAAATATTA TAAGTTGGGT AAAATTCAGA ATATTTTTTT TCCTTTATGG    18840
GCTTTCTTTC TCAGTCTCAG ATCTTGAAAG TTTGTCCCTG TAGTTTTTCC TAAAATGTAA    18900
ATGATGTAAA TTTAGGTCCG ACAGGGTACA GAGATGTCAT GGCAGGTAAA GAGCTTGCCG    18960
TGCAAGTGTG AAGACATGAG CTTGAGTCTG TGAAGTACAG TGACATGTGC CCCATCCCAC    19020
ACTATATGGC AGAGGAGACC CAAGGGCCCA CTCCTCCCCT AACTGGGTAA AAAGAGGGCT    19080
TTTTATCTAC TTAATTGCTT TTGCCTCTTT GTTGAGAAATC TTTTGAGTGT GTTTTGTCAG    19140
CCTGTTTCTC TGGGCTGTAG TCATTTGGAT TGAATTAACG AAGCGGCCTA TATTTAGGTC    19200
CTGGTGCTAG AGAGACGGTG TGCACAAGCC TCACAGTTAA ATGGGTCAAA CCAAGAGGAG    19260
CATTCAAAGT TCTTATCCTT TTGGCGAGAT TGTCTGACTT AGTTCCCTTA ATCATCAATC    19320
TTACACATTA ATAGCAAATT GCTATGTTTA AAATGACTTC TTTCTGTTCG GGTTTTCTCG    19380
TCAAGATTTG ATTGAGCAGT GATTAAGTAA GTCAAAAACA GTAGGAGACA GGTAATGCTA    19440
CAGCTAGCAG ATACTACATC AAAGGAAAAG AAACTAATGT ATTTGGGGTC TAAGTATGCG    19500
TCTGGCCTTG GGTCAGACAC TCTTGTCTCA GTCTTCAGGA CTGTTAATTA AGTTAGCTTT    19560
AATGCCATCA TATTTCATCA TTTGTCAAAG GACAGCTCAT TCCCCTTGCT TTCTTTCCCA    19620
```

*Fig. 7-20*

```
GCATAACCTT CTCCTCAAGT CTCTTCTGTT CCTTTGTACC TTCTTGTTTT ATTAGGGTTG   19680
GTGTCCTGGT CCCTGTTTTA GACTTACTCT CTCTCTCTTC TGTGCTCTCT TTTCTGTGCA   19740
TAATTGGATA CCATCCATCC CATTATGGAG AACCCTCAAA TCTACAACTT GGATTAGTAC   19800
CAGATGTGAC TGAGTTCCTC CGCCTACTTA CCGGCACTTG CTGTTGTACT ACATTTTGTT   19860
TTAGCAATTT TATTGCATAT AAATCACACA TATTATAGGG GATTTATAGG ATATGTATAT   19920
ATACACAATT GTCAACTTGA GGGTTTGCTC TTTGGGTTCC TAATAGGTAT CTCAAACTTA   19980
ACCCCTCCAA AACTGGCTCC TGATGTTCTT CGCACTCTGA GTGCTTTTCC CGCAGACTCC   20040
ATCACCTTGT TTAATAGCAG CACCAGAGTG TTTTGCTATG CAGCCCGGAC TAAACAAGAG   20100
ATCCTCCTGC CTCAGTGTAC CCAGTTGCCT GGAATGCAAG TGTGTACTAC TCTGCCTGGG   20160
AGCTTGATTA TTGTTACCAC TCTGCAGCAT ACATTTCACC AGTAAGGAAA GCCTGTGAGT   20220
GATCTTCCGA GCCTATACAG CTGCTAATCG CTTCCCTCTT GATCCCTGCC GTAGCCCCGG   20280
TGCTGGCTTA CATCTTCCTT CATGTAGGCT GTTACAATAA TCGCCTGGTT TCCACCTTTA   20340
GTCTATTTCT ATACAGCGTT CAAAGTGATA CTTCTGAATC TGTCCCCTAG TTCTGTGTCT   20400
TCTGTGCAGG ATGTGATGGC ATCGCCCCTC ACTGAGGTTA TGCTATGTCG TCTTTCACTT   20460
TCATGCCCGA ATGGTGATGT TAGCTTCTTA ATGCAATCCA TCAGTGAATT AAGTCTTTGG   20520
GTCAGGTTAC AGCCATCGTT ATCTAATCAC CTCTCCGTGG TTGGGTCTGT GACTTGGGGA   20580
TTTTCACCCT TCTACACACA GAGAGGGCAG TTTGTATCTA AACCATAACA AGAGGGAGTT   20640
TTTCTTTTTC TTTTTGTTTA TATAAGCAGG GGTACTATCT GACTCATAGC AGTTGCTTAA   20700
TAATTACACG AATCAATTAA TTCTGGTCAG AAAGCTGGGA ATTAGCGAAG TAACTTTCCT   20760
ATATAGGTAG TTATAAAAGA GTTGGGTAAT AAATAGCTAT ACCATAATAT ACTGTGCCGA   20820
TTTCAACACA AATGATTTGA AAGAGACAAG CTATATTTTC TACCCTTAGG TAGTTCATAG   20880
CCCCGAGAGG GAGTTGAGAT CCACATCCAG GAAAGTAGAG GCAATAGAAA CAAACTGTGC   20940
ACCATGCATG GAAAGATGAG TAGTGCCCAT AGCACAGTCG CACATGGGAG GGCAAGTGAA   21000
GGTGTCCCAC AGTGCAGTCA CTGAGCGCTG CTCTGAAGGA CTGGTTCCCA CTGACTTAGG   21060
AAGATTTAAT GAGACAGAGC GAGCTGTGGA ATTGAAAAGC AAGAGGATGC TTGTGTAAGC   21120
CTTTCTTAGG CCTTTGATTC TAGGATTGCG TTAAAGGAGT TTTAAATAAT TTAAGTGGTT   21180
CTCAAATATT CTTCAGGTGG AAAAAAAAAG AATTAAATCT TTTATTATAT CTAACTCTGG   21240
ACATAATGAG ATCGCTTTCA GTTCTTGCAG TGATGAAACA GCGTATTCCT TCAGCTGAGA   21300
GTCTTGGCAG GTTGTTCCTC CTGCAGAGGC CGAGGATCCT TAGCCCCTGT GCTTTTAAAG   21360
ATGGACTCTG TTGGGGGTGG TAAGAAACGC CACCTGGTGG ATATTCCTTT TCTTATTGAC   21420
CTTGATCTTA CTGTTTTAAC CCTGTTATGC TGGGATTACT GTTGGGTTCA TTACACCAAA   21480
TTAGTATAGC AAATCTAAAA GTGCTGGAAA CCACCAAACA ATTAACACAG AGGACCCATT   21540
TGGAAGGAAT CACAAAAGTG AGCCCAGAGA GGTGAAAGCC AGGTGAAAGT TCTGCATAGC   21600
CGTCAAAGTT TATATCTAAC CAGGAGGACG GACTTTTGAA GACTATGAGG TATATTGACT   21660
CTTCCCACTA ATTTGTCGTA AGGACCCATT AAAAAGATCA GAATAGTAGA CACTAAATAA   21720
CTGGAAGAAG AGATTAACTA AAATCTGTGT GCAGAGTGTG AAGTAGTTAT GTCATCCAAT   21780
TTAGAAAAAA GATTGTTATG TTTTCTTTCA ACCGTTGTTT CATGGAGCAT GTAGTTAAGA   21840
TTCATCTCAA TGTACAGTGT CATAAGATTA ATCTGCATTA TATATTCATT GGGTTTTGTT   21900
GCTTACTTTG TCAACAACTG GTGTCTCTTA CCAAGGAAAT CAAGGCAGGC AAACTTAAAG   21960
AACAAATTCC TGGTGCTAAG TGCTTGATAT ATGTAGACAC CAGTATAATT CAGCACATGA   22020
CCAGCTTTCT TCTCAAACAG GTTACACTAT TTATAATTGT GCTGTAGCCA CAAAAACGAC   22080
CTGGAAATAG CCCATCCAAC AAGGGCATAT GGTCCCATTT CTCAGTACTG ACCCATGTGC   22140
TATTTGTAAG CATTGTCCTT GACTAAAATT TTCACATTAT AAAATGCTGC AGACTTCTGA   22200
GGGATCCGTT CTAGTCACAT TCATTTTCAT GAAGACTGTT ATTTTTTATT CTACTTTTTA   22260
GTTGGAAGAG CAGTATTCCT CTCTGTGTCT TTGGAATGTT GTAGTGAGTT TACAATATTT   22320
TCCCTGCTAG CAGTCTGCTT GACTTTTTGA GGACCTTATA AGAAAAATGA AAATTTTTAC   22380
TAAAAGATCT ATCAATCTTG TAGCTCTGTG TCTCTCACTT CACTTTTCCT TAAGTTGAGC   22440
CCTTGCTGGA GTCAGTGGGG AATGCGCTAG CATTTGAAAT TCTCCACCAT TGACATTTCC   22500
ATGCAGAAAG AAATGTCTTC TGTTGTTTTG TGACTGCACT AGTTATAAGG AACATTTTAG   22560
GTGCTGGCTC TAATACCCTG AATAGAATTA AGCACTTAGC ATGCTTTTGT AGATATGTTT   22620
ATGTGTTTTG TGTGGAGTCC AGGTGTGTAT AAAGACTACA GGTCATTCTT GGGTGTTGTT   22680
CCTCAGGTAC AATCCACATT GTCTTTGAGA AACAGGATCT TTCACTGGCC TGGAGCTAGC   22740
CAAGTAGGAT GGAGTGACTG GCCCTAGAGT CCTGGGAACC TCCATATTTC TTTTATATTT   22800
GGCATAAGAC CGCTGTCCTT TTTCTTTGAT TCTTAAAATA TTGTTCAGCC TCTTTGCTTA   22860
TGCAAAGGCG ATCTATCAAT CAGTAAAGTT CTGGCCTGAG AAGTCTGTTC AGGAAGACAG   22920
```

*Fig. 7-21*

```
GCCATTGGCT GAGATCATCT ACCCAGTGCC GGTATTACAA ACTGGAATTT CAAGTGTGTG  22980
TCACAACATC TAGGTGTGTG TGTGTGTGTG TGTGTACACA TATATATGTA TATATGGTGA  23040
TGCCCAGCGT CCTGAAGGCG CTGTTTGACA AAGTTCCAGT TCTTGGACCA AGCCTTCACT  23100
GCCCTTGGTG GATATTCGCT GCACACCTCT TGCTAGTCTT ATGTTTCTCA CTGTTAAAGG  23160
CCTCTCTCTG AAAGCTAGAG GTGGGATAAC AAGAAGCTAG TGTAAACAAG AATCAAGTTA  23220
ATTAAAGTTC CCTGGGGGGG GGGAAGTTAT GCAGAAAATT GAGTCTCTTC TAAGAAGTTA  23280
TTTCTTAAAT AAACATTTAG ATCATTAATG AATGTTGTTA GTAAGCATGA GATAGAAGAT  23340
TTGAGAAGAA TTATTAAAGA AGTAAAACTT AGGGAGAACT TAGAAGTTGA GAAGTTGTAT  23400
TTGGATTGCT AGGTTTTTAA GGTTCAACTT GAGAAACGAG CAGTTTGTAT GTATAGGACG  23460
GGATTGGAT CATGCAGGTT TATGACAAGC CTCGGTGCCT TCCTGAAGGC AAAAGTAAGC  23520
AGGTTTAGGA ACCCTGATGT TCTTCTGTTC TTCACAGAAT TGTTGTAAAG ATAGGGATTG  23580
TATTGAAACA AGGGTTCAAG ACAGAGACAC AGAAGAAGGC ACTCTGGCTC AGTGAACTAC  23640
CTGCCTTCCT GAACATGTAA GGTTAAAAAT GTAAATTCCT AGGAAACTGT TATATTTCTT  23700
TTTAAAATGT TAGGTTTTGT TTGTTTGTTT GTTTGTTTTG TTTTTTAGTT TTAGTTTTAC  23760
TTTTTTTTAG ACAGGGTCTC ACTGTGTAGC TGGGGACAAG CTCCACCCCT GTTCCCCTTT  23820
TCCTCACCCT CCTGAGTGCT GGGATCACAG GCGTGTGCCA CCACCCCTGT CAGGGTCCTC  23880
TACACACCCA GGAGTCCTTA CTGTCAGGCT GTGTCTGTTA TCGTATCTTA TATCAACCAC  23940
TAATCAACCA TTGTAATGCT TGATTAGAGA ATCTGATTTC TTCAAAACAA CAAGGCTCT   24000
GCATGACTTA ATCACTACAT ATACATTCCT AACGCAGAGA GCAGTCGGAT TATTGGCCTG  24060
AAGATTAATG TGGGGTTACA TTTTAAAGTG GTTCACAAA TTTAAAAATA GACAATACAA   24120
AAAATTATCC TAATTACTTG GTTTCATTGA GTTTATTTTT GTATGACTTT GGATAGGTTT  24180
TAATCTAATT AAGTTATTTT AATCGTAAGA GTAGCTGTTT CTTAATTAAT TTACTGCTGA  24240
AGACCAAACC CAAGGCCTTG ACAGGCTCGT ACATTCCCAA TGAGCCATGC CTTCAGCCAC  24300
TTAACTATTC CTTTCTGTGT GTGACTGAAA ATAAGCTTTA TTTTTCTAAG CCAACAAAAA  24360
TGAAATAATG CTTGAAGCTT TGTCCAAGTC TATATTATTT TATGGGTAAT ATTTATTTTA  24420
TATTGAACAC TTTTATTTTT TAACTATGAA GGTCTTTTAT TTTCATAGAT ATCTATTGCG  24480
GTAAAAATTT AAAGGTAATA AACTATGATA AATTGAGCTA AAGATGTGGC TCAGTGGTTA  24540
GATGTTCATA TTGCTCTTAC ATGAGAGGAG AGTTCAATTC CGATCACCCA CATTAGGTGG  24600
CTCACACCTA ACCATAACCC CAGCTCCAGG GGTGTCTGAA AGCTCTGGCC TTTGAGGAGG  24660
ACTTCACACA CACACACACA CACACACACA CACACACACA CACACACAAA GTAATAAATA  24720
AAAATGATCC CTAAGTACAT AAATCATAAT TGAAGTAACA TTCAATGTTG TTATGGAGGA  24780
TCAGCTTATT GGGAGGTTAT GTAACTATAA TATTTACATT TTAAAGAAT AGAAAAAATC   24840
TATTTCTATA ACAAAGCTAA CTGAAACAGT AGAATATAAA AGGCAAAAAC ATTGATATTA  24900
ATATTTTGTG AAATTTAAAT AAAAACCAGC AATCAACTGA AACTGAAAAT ACCATAAATG  24960
ACAATGCTCT TTCTTAGGTA TTTCTTAGTA GTTTTGTTTC GCATTCTTAA TTTACATTGT  25020
TGTATAAAGA AGAATAAACC GAGTTACTGA ACAGAGCAGC AAAGCTTGTA ATCTAAAATT  25080
TAAAGATGTT TATGTTTTAG TTTTCGAATT AACAATTTAT AATTCTGAAG ATAATTTTTT  25140
CTTAATTTGT TTATTATCTA AATGCATTTT ATACATCAAC CATATTAATA ATATTGAACA  25200
TTTTGAGACT CAAATAATAC ATAAAAAATT TGTTCAACTT TTATTTTCAT ATCCTGAAAG  25260
TATCATTAAT GAATATTTAA TACTATCCAT AACTGAGGAT CCTATATCTA ATGTTAAATA  25320
CTAAATTGTT TCAAAACATA CAGAATATGC TTAGGGAGTT AAGCATAGTA AAAGAGCATA  25380
GAATATTAAA AATGAATCAT TAAAAAATAC ATTAAAAAGC CCTTATATGA TACCACATGA  25440
CATAGTGAGA GAGTATTTAA AACGCATTAT ATATCTGTGT GCATTGTCTA ACAATCAGTT  25500
TACTTAAAAA AGATTATCAG TGTTTCTAGG AGAGAAATTA TTTTATCAGT AAGTATATTT  25560
TAAAAATTAC AAAATAGCAA AAACTCTTTG AAGTTAACAG TAAGAAAATG CTAATTTCAA  25620
GCACAGTGAG AAAAATTATC AATAATATTT CCATGATGTT TGTAGAACAT GATTTTAATA  25680
TTTTCAAATG TTGATATTCA ATAAACAGAA AAGTTATTTG AAGATATATT TCATTGTTAT  25740
GTCTCCCTTT TAATTTTTGA TTTTATTAAT TTGGATACTG TCTCTATGCC CTCTGGTTAC  25800
TCTGGCTTAG GGTTTATCTA TCTTGTTGAT TTTTTTTTCA AAGAACCAGC TCCTAGTTTT  25860
GTTGATTCTT TGTATAGTTC TTTTTGCTTC TATTTGGTTG ATTTCAGCCC TGAGTTTGAT  25920
TATTTCCTGC AGTCTACTCC TCTTGAGTGT TTTTGCTTCT TTTAGTTCTA GAGTTTTCAG  25980
GTGAGCTGTC AAGCTGCTAG TGTAAGCTCT CTTCAGTTTC TTTTTGGAAG CACTTAGAGC  26040
TATGAGTTTT CCTCCTACCA CTGCTTTCAC TGTGTCCCGG AAGTTTTGGT ATGATGTGTC  26100
TTCATTTTCA TTTCTGCCTT GACCAAGTTA TCATTGAGTA GAGCGCTGTT CAGCTTCCAT  26160
ATGTATGTGT GCTTTCCGTT GTTTGTGTTG GTATTTAAGA CCAACCTTAG TCCGTGGTGG  26220
```

*Fig. 7-22*

```
TCTGATGATA GGGTGCATGG GATGATTTCC ATCATCTTGA ATCTGTAGAA GTCTGTTTTG    26280
TGACCAGCTA TATGGTCAGT TTTGGAGAAG GTTCCATGAG GTGCTGAGAA GAAGGTATAT    26340
TTTTTGCTTT TGGATGACAT GTTCTATAAA TATCTGTTAG ATCCATTTGG TTCATAACAT    26400
CTGTTAGTTT CACTGTGTCT CTGCTTAGTT TCTGTTTCCG TGATCCTGTC CATTGCTGAG    26460
AGTGGGGTGC TGAAATCTCC CACTATTATT GTATCAGGTA TGATGTGTGC TTTGAGATTT    26520
AGTAAAGTTT TTTTATGAAT GTGGGTGCCC TTGCATTTGG AGCATACATG TTCAGAATTG    26580
AGAGTTCATC TTGGCAGATG TTTCCTTTGA CCAATATGAA GTGTCCTTCC TTATCTTTTT    26640
TTTGATAACT TGGTTGAGAG TTGAATTTAT TCCATATTAG AATGGCTACT CCAGCTTGTT    26700
TCTTGGGAAA CAACCATTTG CTTGGAAAAT TGTTTTCCAA CCTTGAACTC TGAGGTAGTG    26760
TCTGCCTTTG TCACTGAGGT GCATTTCCTG TATGCAGCAA AATGCTGGGT CCTGTTTACA    26820
CACCCAGTCT GTTAGTCTAT GTCTTTTTTT GAGGAATTGA GTCCATTGAT GTTAAGAGAT    26880
ATTAAGGAAA AGTGATTGTT ACTTCCTGTT ATTTTTGTTG TTGTTAGAGG TGGAATTATG    26940
TTTGTGTGGC TATCTTCTTT TGGGTTTGTT GAAAGATTGC TTTCTTGCTT TTTCTAGGGT    27000
GTAGTTTCCC TCCTTGTGTT GGTGTTTTCC ATCTATTATC CTTTTAGAG CTGGAAAGAT    27060
ATTGTGTAAA TTTGGTTTTG TCATGAAATA CCTAGCAGCT TGACAGCACA CCTGAACACT    27120
CTAGAACTAA AAGAAGCAAA TACACCCAAG AGGAGTAGAC TGAGATTGGG AGTTTTGCCT    27180
GGGCTGGCAT TTGTGTTCTC TTAGGGTCTG TATGACATCT GCCTAGGATC TTTTAGCTTT    27240
CATAGTTTCT GGTGAGAAGT CTGGTGTAAT TCTGATAGGC CTGCCTTTAT ATGTTACTTG    27300
ACCTTTTCCA TTGCTGCTTT TAATATTCTT TCTTTGTTTA GTGCATTTGG TGTTTTGATT    27360
ATTATGTGAC AGGAGGAATT TCTTTTCTGG TCCAGTCTAT TTGGAGTTCT GGAGGCTTCT    27420
TGCATGTTCA TGGGCATCGC TTTTTTTAGG TTAGGGAAGT TTCTTCTAT AATTTTGTTG    27480
AAGATATTTA CTGGCCCTTT GAGTTGGGAA TCTTCACTCT CTTCTATACA TATTATCCTT    27540
AGGTTTGGTC TTCTCATTGT GTCCTGGATT TCCTGGATGT TTTGGGTTAG GAGCTTTTTG    27600
CATTTTGTAT TTTCTTTGAC TGTTGTGTCA ATATTTTCTA TGGTATCTTC TGCACCTGAG    27660
ATTCTCTCTT CTATCTCTTG TATTCTGTTT GGTGATGCTT GCATCTCTGA CTCCTGATCT    27720
CTTTCCTAGA TTTTCTAACT CCAGGGTTGT CTCCCTTTGT GATTTCTTTA TTGTTTCTAG    27780
TTCCATTTTT AGACTCTGGA TGGTTTTGTT CATTTCCTTT GCCTGTTTTA AAGTGTTTTC    27840
TGGTAATTCT GTAAGGAATT TTTGTGTTTC CTCTTTAAGG GCTTCTAGCT GTTTACCTGT    27900
GTTCTCCTGT ATTTCTTTAA GGGAATTATT TGTGTCCTTC CTAACGTCCT CTATCATCAT    27960
CATGAGAAGT GATTTTCGAT CTGAATCTTG CTTTTCCAGT GTGTTGGGGT ATCCAGGACT    28020
TGCTATGGTG GGAGAATTGG GTTCTGATGA TGCCAAGTAA CTTTTGTTTC TATTGTTTAT    28080
GTTCTTCAGC TTGCCTCCCG CTATCTGATT ATCTCTAGTG CTACTTGCCC TCGCTCTGTC    28140
TGACTGGAGC CTGTCCTTCC CGTGATCCTG GTTGTGTCAG AACTCCTCAG AGTTCAGCTG    28200
TCTCTGGGAT CCTGTGATTC TGGAATCCTG TGATCCTGAG ATCCTGGGTG TGTCAGAGCT    28260
CCTGGGACTC AAGCTGCCTC TAGGAACCTG AGATCCTGGT GTGACCAAGC TCCTGGGATC    28320
CTGGGATCCT GGGATCCTGT GGACCTGGGT GTGTTAGAGC TCCTGGGAGT AGAGCTTCCT    28380
TTGGGTGTTG TGCTACTGGC TGTGGAGTTT GCTCTCAAGA TCTGCTCTGG GCAACGGCTC    28440
AGAGTGGATG GGACCTGTGC CGCTGGTCAG GTGGAGTTCC TGGGTGCCTG GGTTCCACTG    28500
CTCCCAGTTA CTCCCGGTGT TGGGGCAGAT GTTGTGCCCT CCTCACCTCT GATCCTATGA    28560
TCCTGGGAAT GTTAGGGCA CTTGGGAGTG AGCTTCCTCT GGGTGTTGTG GGACTGGCTG    28620
CGGAGTTAAT GCCCAAGGTC TCTGCTCAGG GCACTGGCCC TGACTGGAAG GAACCTGTGC    28680
CAGTGGTGGG GCGGATTTCC TGGGCACCAG CCCAGACTGG AACAGAACAC TTTTATTTTT    28740
ATTCATTTAT ATTGTTCAAA ATAATGAGTT TCGTTTCATT TCCATAACAT ATTTAATGTA    28800
CTTTGGTCAT ACTTATTCCC TAAGAGATCG TATTTTGTTT TAATTTTAAG TCAAATTATA    28860
TACATATTTC TTTGTAAATT AGCAAACTGC ATACACATTT ATACTTAGAT ACAAGATAAA    28920
TGCTTAAATT ATTTTATGAG GTATTTACCG TTATGTTTGA ATAATTTTAT TAGGATGTTG    28980
TTTCCTCTAT CTGTAACAGG TAATAAAATA AAAAATTGAA TTCTTAGCAA TAGAATAGCT    29040
AATGATTTAG AAATAAATTT TAAGACAGCC TTTTTCTTTT CTGATAATGA AATGGTTGAG    29100
TACCCTGGTT GAGTGTGTCC CCATTGTAAT AGTTATAAAA CATGAGCCAT CTACATGGAA    29160
GATACCTTGC TCACCTACAT GTGAATTTCT GAACGAAATA TTCATGGTCT TCCTGCCTCC    29220
TATTGTGCCT CTTGATTTTG ATGCTCACCC TATGGAGAAA TGCTAGAAAA TAGCCTATGA    29280
GTCAGTTGCT TAAAGAATCG GGTAGTCATA CATGTCTCAC TTTCTACATA TTGATTACAT    29340
CCAGAAATGGC ACTGAGAACT CAGTAAGACA GGAGAGAGGT TGTAATGGCT GTTGGAGAC    29400
TTGCTTCCAC AGCTGGAAAG CCACATGCCA ATATAATTTT GAAGAACGCT TCTCACAAAA    29460
TAAAAGATAA ATTGTTTTAT GTAGCTAGGC TATTAATTTA TAACCCTGCC AGGGCTTATG    29520
```

*Fig. 7-23*

```
TATTGCAAGT TACAGATTAT TAAAAAAGAA CGAGATGTAT TAATCCCCAC TTCTATTAGC    29580
ACTAAAGTAT AAATGGCTAA TAAGTAGTTT TAATTTAGTG GGACAAGATA AATTGCATTG    29640
AAATCTCATG ATTTAGTGTT TGATTTATTA AGTAGGAGAT AACTTTTCTC GTTTAAAAAC    29700
ATTTTTTTTT CTCTTTACGT AGGGCTCGTA GCTTGGTGGT AGAGCACCCA CTAAGCATGC    29760
CCAAGGTCCT GGGTACCATC CCCAACATGA CAAAAAGAAA TAAATATTCT AATAAACCAA    29820
AACGTTAGCA TGTGTGTCTT GGCCATGGTT CCTGTATGGT TGTGACTGTG GATGTGTCAG    29880
AAGACAGTGA GAAGTCAATG CGCCTTTTAA ACGTCCGTTT GTATTGGATT TCCCCCCAGG    29940
TTCCAGTCAT TGCACTCTCC GCTACTGCAA GCTCTTCCAT CCGGGAAGAC ATTATAAGCT    30000
GCTTAAACCT GAAAGACCCT CAGATCACCT GCACTGGATT TGATCGGCCA AATCTGTACT    30060
TAGAAGTTGG ACGGAAAACA GGGAACATCC TTCAGGATCT AAAGCCGTTT CTCGTCCGAA    30120
AGGCAAGGTA AAGATAGGAC GCTAGACGAA AGGATCTTTT AAAGAAGTTA TTTTATTTTT    30180
TTCTATTTCT TTTTTTGATA TATATTTAAT GTCTCAAATT TTATGTAGCC TTGGCTCAAA    30240
TGAGTGTAAT ACTACATAAT CAATTCAGTG ACCAATATGA AACCACTAAA AGAAATATTT    30300
CCATTCATTC TTTTAGAATT TCATATAGTA TACTTTGATC ATATCCACCC CTTATTACTT    30360
TCCCAACTTC TCAACGGAAA CTAGCTCTCC CTCTCCCAGA AGCTATCAGC TGTCTACAGT    30420
CTACTGCTTG GTTAGGGGTA GGGGCTTGGT CTAGTGTAGA CAAGGGTTCA TGAGCGCAGT    30480
GGTCCTGCCA TGACCAGGAC ACATGGCTTT GCTTCAGTTT TCTCTGACCA TTGGCCTTTG    30540
TGTTCTATTT GTCCACTCTC CCATGGTGTT CAAAGCATTT GTATTTTGCA AGGGCAGAGG    30600
AGATGTGGCC AGGAACTAAT TTGTCTAATA TTATTTTTCT TTTATATTGT TATTCAAATA    30660
AGAGATATTC TTTTAATAAT TTACAACTAA ATGAACAAAT ATGACATGAG CATTTCTTAT    30720
GAGTTCTGTC TGCTTTCATA TTTAGATGAT CTACCTCTGC TGGAGGGGCT TTTTAATAGT    30780
CAGTATAGAG TCTGTCCATG TTCCAAGGAC TGTCCTAGAT GCTTTATACA AGTGATCTTG    30840
TTAAATCCTC TAGCATAAGG AAGTTCCTGT GTACATCTAT ATTTTACTGA TGAAACTGTC    30900
CATTACACTT CTAAGATTTG TATTTTAAAA TATACTTTAT GCTTTATTTT GTATGCGAAG    30960
AACCTTTGTA ATGCCATTAT TCTCTGTCCT GCCTGCTGAG TTAAAAGTTG ATATTTTCCT    31020
TATATTAAGT ATTCTGAATA ATGAAAAATA ATTTTCTCCT ACCAATACCA ATGCAAACCA    31080
AGTCCAAGCA AGAAAGAGCT GAGAGCATTG TTAGTGTTTT CCTCGTCCAG AAAGGATGTA    31140
AATGGGAAGA GAGATCCTAG GTTAAGGAAG TGATAGTGTT TGTTGTAGAT ACTAGGAAGT    31200
AGTTTAAGTA CCACCTGAGA AGTGCTCGCT ATTCCGAGTA GAATAGGAAG ATGGGGAATG    31260
TATTGATAGG GTTTTGCTGC TCAAGCTGCC TCCTTGAACC TGCTGTTCCA TGGTCCTTTC    31320
CAGTAAAGGA AAAGTTCTCT TGTCAAAGGC TTCTTCTAAA CTGGATGTTT CTACACTCAT    31380
GTCATTACTA ACCCCTGATC TTTTAGTTCT TGTCAATGCA CATTATTTTT AATATCTATG    31440
GCTAATTTTT ATAGTGACCC TCTTCTTTCA TATGTATATG TGTGTGTGTG TGTGAGTGTG    31500
TGTGTGTGTA TGTATATATG TGTGAGTGTG TGTGTATGTA TGTATATGTG TGTGTGTACG    31560
TGAGTGTGTG TGTGAGTGTG TATCTGTGTG TGTGTGTGTG TATGTGTGTA CACACACGTT    31620
AAAGTGCCTT CCCCCATCTT TTCTTGTGAT GTTTTGTTTT CCCATTTTTG GCATCATTTG    31680
CCTTACAATA TCTTATGCAA ATGCCTTCTT CCCAATTTAT ATTGATATTC TGGTAACGAT    31740
GATTAATTTA ATTTTTAGCC CAGATTTTTC TGATCACTCA TAACACATCT ATATCCTCGG    31800
TGCTACTTGA TATATTCCAC AGATAACTTT CAGGTTTATC ATCTGCAGAC ACGTCCTTAA    31860
ACCTTGGAGT AAAATTTTAT TTTTAAACCT TGTATAATAT TTTATGCAAC AGTGAAATTA    31920
TTCTCTCACC TCTTAAATAA GAATAGATTA ATCTATTGTG CTGCCTTTCT AGACTCATTT    31980
TTATCCATAC CTTGTAAGTT TTAGAATCAT TTTTTTCCTA AAACAAAGTG ATTCCTGGTT    32040
TTAACTTTAA TTTGGGCCAA TGTTGAGTGC CAGAGTTTTG CTTTCACACA ATACGTTTCT    32100
ACGTTTGTCT TTCCAGAATG TTCTGGAGTT TCAGGGAGTT GAAGTGTTTT TCAGTCTGCT    32160
GACTTCTTTA AGACTTTTGC TTAGTGAAAG CAAAGATTAT GAAAGATGAA TCCCAAACTG    32220
CGATGAAACA TACATGTAAC AGGCGTGTTT GCTTTCTCTG TCTCCCTACC TCTTCCCCAC    32280
CCTTCCACAG TTCTGCCTGG GAATTTGAAG GTCCAACCAT CATCTATTGT CCTTCGAGAA    32340
AAATGACAGA ACAAGTTACT GCTGAACTTG GGAAACTGAA CTTAGCCTGC AGAACATACC    32400
ACGCTGGCAT GAAAATTAGC GAAAGGAAGG ACGTTCATCA TAGGTTCCTG AGAGATGAAA    32460
TTCAGGTGTG CAGAGCAACC ATCTTTCTCT GAATTCTTCA CAGGAAGTAT ACGTATCTGT    32520
CAAACATTTA TGTCACCAAT TTTTTTTTTA AAATTGTTGT ATTAAGCACA GTTTCACCAC    32580
TCTGATAAAG GTAATGACTG TATAGTGAAA TTGGATTAAA TAAACCCTAC AGCTTAGTGT    32640
AAATAGCAAA GACTGTCATC TGTTACTGGG CTACACAGAG AATCAACACC AGTTCTGTCA    32700
GAGTAGGTTA TGTAATGAGA GTGGTCATCA GGAAGCTGAA ATCTGAGAAG AGTCTTAAGT    32760
ATGTCAAGTT TACCAGGTCA GTAGGTAACG AGGGCTGTAG AGTCCCAGGA AGCAGCAGCA    32820
```

*Fig. 7-24*

```
GGTGCAGAGA CACACGTTGA GTGCATCCTG GGCTCAGAGA GGAAGAGCCT GAGGTGATCG  32880
GAGGAGAAGA TGAGCGGTAG GAATGGCACA GTCAGGGGAC ACAATGAGAA GGTTAGACAC  32940
TCTCAGGAAG GCTGCGTTGG ATGGTTGGCC AGCTTAAAGA TGAGAAGGAT CCCTGGTTAA  33000
TGGTGCTCGC CCCCTACCAG AAAGCATCTA TTGTCACTCT TCCTGTAGGA ACGGCACTAA  33060
TGCTTATGAG AGGTTGTTGT GCACACTTAT TAATACTTTT ATTACTTTAG CGACTGGGTC  33120
CTTTGGATGC ATCTGGCATA CTGCCTGTCT TAGGTACTTT TCTGTTCTAC TACTGACTGA  33180
GGCAACTTAC AGAAGAAATA GTTTATTGGG GCCTACAGTT TCAGAGAGGG GGTCTGTGGT  33240
CACTGTGGAG AGTGTGCAGC AAGCAGATAG GCATGGTGCT GGCGCAGCGG GTAGGCAAGG  33300
TGCTGGAGCA GCGGGTAGGC AAGGTGCTGG AGCAGCGGGT AGGCAAGGTG CTGGAGCAGC  33360
GGGTAGGCGT GGTGCTGGAG CAGCGGGTAG GCGTGGTGCT GGAGCAGCGG GTAGGCGTGG  33420
TGCTGGAGCA GGAGCTGGCA GCTTGAGCAC CAAGAGAGAG AGCTAGCTGG AATGGCACGG  33480
ACCTTTGAAA TTTCAAGGCC AGCCTTTAAA GCCTGCTCTT CCCCACAAGG ACACACGTCC  33540
TAACTCTTCC CAAACAGTTC TCTCACCTAT GGATCAGCGT CCAAACATAT GAACCTATCA  33600
GGGCCATTCT TGTTCAAACC ACCACACTGC CAATGTATAA CTTGATTGAA GCATTAAATT  33660
TATATATATT AGTTTTTTGA GACAGGGTTT CTCTGTATAG CCCTAGCTGT TCTGTGGAAG  33720
TATTAATATT TTAAAAGAAG GCTTAAAAAT CTTTAGTGAT CTTTCATTAC AGTTAATTTT  33780
GAAGGTTATC TATCTACCTA CCTACCTACC TACCTACCTA CCTACCTACC TACCTACTTA  33840
TCTACCTACC TACCTACCTA CCTACTTACC TACCTATCTA TATTTTGCAT GCCCTGCTGA  33900
ATTTTCTCTT TCTAGTACAG GAAGTCATCA ATTCGAATCC ATATTATAAA AATTAAAGTT  33960
TAGATGAATA GTTGCATTCT AGGTAGCCCG AGGTAGTGTT TTGTCTAACA GCTGAACCGA  34020
TAGACTCCTT CCTGGTCACA ATTCAGAAGC CTGGCATATG CTTCGAACCT TCCCCTTTCT  34080
TAGCACAGTG AAAGGCATGT TGTCATCAGT GTAGACTTAT CTGGACTCTT AGAGCTGATT  34140
ACTTTTTGTT GGGTGTTCGT TGAGTGCCGA CTGAATTCAT AAATGTAATG ACTTCTAGAT  34200
AGCTACTTCC TGACCATTTT ACAGTGGATT TTTACTGTAT GGCAGGCACA GAGGCTGACC  34260
TCTGTAGCTC TTCATATGTT AGACTGATGC ATAAAGCCAT TTTCTGTTTT ACAATTTTAG  34320
AAACAAAGGG AATTTCCTTT ATGTCATATA TACTCAAATC CCATGCACAT TAGCTTTCCA  34380
TGATTTGTTT ATAACTGTCT GTTCTCAAAT TTTATCCCAA CCCTTAGTTT CGTCCTTCCT  34440
ACATTTGCCA TTTTAAGGTG GCTTTTTAAA AAATGAAATG ATGAATAACT TATTTGGTAG  34500
AATAGTTTTC ATTTATATCT AAAAGTTTAT AGGGACAGTG TGAAAATCTG GTTAATAGAA  34560
TAGTTAACAT CAAATGAAAG AATAATCCGG TGAAGCTTAG AATTCCATTG GTTATTGACT  34620
GCTAGCTGGA CTGAGCTGTT AGAATTCCAT TGGTTATTGA CTGCTCGCTG GACTGAGCTG  34680
TTAGAATTCC ATTGGTTATT GATTGCTCGC TGGACTGAGC TGTTAGAATT CCATTGGTTA  34740
TTGACTGCTA GCTGGACTGA GCTGTTAGAA TTCCATTGGT TATTGACTGC TAGCTGGACT  34800
GAGCTGTTAG AATTCCATTG GTTATTGACT GCTCGCTGGA CTGAGCTGGC TTCTTGCACC  34860
AAAGCTTTTG CTTCCCACGT CTGTGCCGTT ATCCCCGCTC CCTCACCCCT CACCCATCCT  34920
TTGCGTGTTT CCTATGCTCT TCCTTTCTCC TTTCTGTCAA TCTCCTGGGC CATCCTAGAA  34980
CATACCCTAT GAGCTTATTT TACTGTTGTC TCTTCAATGA GGCGTCTTCT CCCCTCCCCT  35040
CTCCTAAGCC TTCGATCTGA CTTTGGAGGT GTTTATTGCT CTACCCTGAC ACAATTTACT  35100
TATACTGCTA TCTTAATTTA TTGTCAGTTT TTATGATTCT CTATTGATTC CCCACTAAAA  35160
ATGCCGGAAA TTCACCAGCC TTTCCTCTGT GTTCCTGCAG CCCTGGACCC CTTTCCCTTT  35220
GCCTGTTGGT TTATATCTTA ATTCTGCTTA AATGTCATAT GGTTATCAAC TTAAGCATCT  35280
TACCTTTAAT TTTTATAATA TATGGTTATA GTTCTCACAT ATATTTTTGT ATTCTTGTTA  35340
TTAAAGGATT TTTTTTCTGA GTATTTGTCC CTAATTCTCC TGTGAGTTTT TTCCAACCAT  35400
ATGAACTTTA TTTTGTTAGG TTCATTCACA TTAGGTCATT TGACAGTTTT ATCCTCTTGG  35460
TATTATACCC GTCTTTTTTG TTTTTGTTTC TGTTTTTGTT TTGTTTTGTT TTGTTGTTTT  35520
CTATTGTACC CATCTTAATG ATGCTTCATT AGCTGTATTT CTCTTTGCAG TAGTGAATGG  35580
TATTATACTT AGATTCTGTC ATCAGGAGAG GACATTCGAA ACTTGATAAT AATACAATAG  35640
TTTTATTCAC TACAGTAACT GTTTCTCATA GCTTCGGGTC TCCAGAGAAA CTCCTTTATT  35700
TGCTCCTTTT TATAGAGATG AAGAGAAGTC ACATTTTTTT TTTTAAAGAC AGGGTTTCTC  35760
TGTATAGCCT TAGCTGTCCT GGAACTCACT CTGTAGATCA GGCTGGCCTC AAACTCAGAA  35820
ATCCGCCTGT CTCTGCCTCC CAAGTGCTGT GATTAAAGGC GTGCACCACC ACTGCCCGGC  35880
CAGAAATCAC ATTTTTATAG CCACTATTTA TCCAAATCTG TATTTGGATA GATTATCTTT  35940
TAGTCTGTAA GTAAAGTTAT ATTTAATTTA GTTTTACACT GGCGGGCAAG CTGCTGTTTT  36000
ATTTTGTAAG TTTTAGTTAA GTTGAAATGT GATTCTTACT CTGCGTTGTT GTTCATTCTC  36060
AGTGTGTTGT AGCTACTGTA GCTTTTGGAA TGGGCATTAA TAAAGCTGAC ATTCGCAAAG  36120
```

*Fig. 7-25*

```
TTATTCATTA TGGTGCGCCT AAGGAAATGG AATCCTATTA CCAGGAAATT GGTAGAGCTG  36180
GCCGGGATGG ACTTCAGAGT TCCTGTCACT TGCTCTGGGC TCCAGCAGAC TTTAACACAT  36240
CCAGGTATAA ATGCTTATTG TTTTCACCTT ACAAATTCCT TTTTCCTTTC CAAGAAAGTA  36300
TTTGAGGGAG TATCCAAAAT ATCAAGTGAC CCCTGAGTAT ATTTAAAGGG GTCGCCACCG  36360
GAAAGTGAGC AAAATGAACA GAATATCCCT GAAGAGTGTT TTTGGTAAGT CTTCCCACAT  36420
AGCAGGTGAT CCAGTTGGAG TTAACAAGAT CGGGACTGCA CTTGGACGTA TAACATAGGT  36480
CTTATGGCAT CCTGTCCTAT TGTGCAGCAG TAAGCAGTTC CCACATTTTA AATCCTCCAG  36540
TCATATGGCT CTAGGTTTAA GTAAGTACCA TGTGTCCAGT GCTATAATGG TGGTTATTCT  36600
AAAAGATGTA TCCAATTCTT GTTTAACTCT CTTTACTATT GTTTCTGTGA TTAGTTCCGT  36660
AAGTGCATGC CACTGCTCAT AGACTGAAAA CTCACCTGGT TGATAGTGCC TAAATAATGT  36720
AACAGCGTAG TGTTAGAGTG CTGTCATAAA ATAGTATATG TTCGTGGTTT AAATTCAAGG  36780
AAAGGGAAAC TGCCTACTTA AATGCTAACT AAATTGTAAC TTACATCCTG CCAGATTATA  36840
TTAGAAGCAA CAGCTTCAAT TTCCAAAATC ATAGGGACAT TATTTACCAG TTATCTATCT  36900
ATAGGGAACC AGGAAAAGAA GCCAGTGCAG CCCAGCCAGT GAACGTGCCA ACATAAAGGA  36960
CCTTTCAGTG CTCCTCCAGG CTGATGAGTA AGCTAGACAC TGGTAGCTAA AAGAGTAGGA  37020
TTAGATAAGT AAAAAGGGTT GTTACAAAAT CTAAGATCTT GCTAGGAATA GTCAGTATAT  37080
TTTACTTTGT AATAAGTAGA GCTGAACTCT GATCCCCTGA AAGCAAGCAT TCTTAGCCAC  37140
TGAGCCATCT CTCCAGACCA GGCGCCAGAG TCTTTACCCA GCCTTTTAAA AACCAATTTA  37200
AAGTAAGTTG GATAGAACAC ATCTCTGCAA GCTACTATTA AATTTGGAAT ATATCAAATA  37260
TCACTTGGTT AAGACCAGAT CTTATTTTAT TTGTGTATTA TGCTAACATG CTGGAAACAT  37320
TATAGGCCTG AGTTGTATAA TGCAATCTCA CCCGTGGATA TAGTGTTGAT TTATGTGGGT  37380
TTTGAAAGAT ATGCTGAGTG GTTTATCTCA TTAAGATTGA TCAGGAAATA ATAGTTGTGC  37440
CAGAATACCC GTGCAATTGT TACTTAGTAT CCATGGTGAC TGGTTCTGAG TTCCTTAAGA  37500
TAGAAATAAA TAAATAATCT CCCTATACAT GAGGCTCTTA TACAACATAG TATTTGTATA  37560
CAGGCTGTGT ACTCTTCTAC ATACTATCTT CCTAGCTCAC ATATAACATC TATTATAAAG  37620
TAATTGATGT GTAAGCATTT AGTTTTACAC TGTAATCTTT AGAGAATAAC AATAAGAAGA  37680
ATGTCTCAAT GTGTTTAGTA CAGATGCAAC TACTGTAAGC CTAATTGGGG TTTAACTTGG  37740
GGTTGACCGA CTCTCAAGTG CTGAACTAGT GGGTGCAGAG CTGAACCACT CGCTCTTTTA  37800
GTACAGATAG GCTACTCTGT GTATCAGAGA CAAAGGAGAA AAACTGTAAA AGGATAAACA  37860
GGAGAGAGCC AAGGATTAAG GGTGAGTTTG TACCATCGAG ATCTTGAAGC AGAAGAAAGC  37920
AGTGAGATTC TGGGTCTCAG CTCTAAGGGT CATTGTAACT TATAAAGTTG TAGTCTCGCG  37980
TATGCTAAAA TTCTGTGACA AGGGAAGAGT CTTGTTTGAG GGATCATGCC GTGATTTTAA  38040
CTAACTAATG TTTATTTGTT AGTTTTGTGA TGCTGGGTAT CAAATCTGGG CCACCCTCAT  38100
GCTAGACAGC CTATGTAAGC CACATCCTCA GAGACGATTA TGTAGTTTTA TGTTCCCTTA  38160
TTGTGTGATT TTTGTGTTTC TTACTGCCGA GCCGTAACAA GGCAGTGTCC CAGTGATTAT  38220
GTTTATTATA TTTGTAGTCA TACCCAGTAG TTACTGCCAT CTTTTGTTTC AAAGTGAAGA  38280
ACTTAGAGAA TAATCTCTAA TAAATCTTTG AATTCTCTTA AAGTTAATGA ATTGTTAGAA  38340
TTTATGGTTT TTTTGGTGAA ATAAGTTGTA TTGCGCATTT AATAGTAGCA AAAGAAGAAT  38400
AAACTAATAA ATATTTAATT GAGTTTCTTT TTCTCAAATG AACATGTAAA TGAGCATGGA  38460
TGAAATCAAA TAAATATATT TCATCTCAAT CCAATATACT AAGATATAGT TCTGAGTATT  38520
GTTGACTTTA TCTCTGAAGG ACAAGGGAAC TAAATGAAAC TGATTTTTTT ACAAATCTAT  38580
GATCCATTAA GTATGGGCTT GGATAATAGC TCAGGTTAGT ATTTTTAGTT CAGGGTATTT  38640
GGAGGAGAAA ATTCATGTGA AGGGTGTTAT CCATTGAGAA CATATCTTTG AATAATGGAT  38700
CATTTGTACA TTCAAATTTT CTAGAATAGA GATTGTATAC AGATATTTTG ATTAATCAGA  38760
AGGCTGGATG TTACAAACAT TAGTGAGCAA AGTCCCTAAT GATGAAGTTC AGTATTATCA  38820
TTTAGTTCTT GTATATTAAA TCAGAATGTT ATATTGCAAT ATCTAAAATT CATTTCATGC  38880
AGGTTTTTTT TTATTATTAT TCTTGGAAAG ATGTGGAACA CTGCCTGGAA GATTTCATGG  38940
CCTAATGCAA TAGCACTGAT GTTAAAGAT AAAAACAAAC ATACTGGTAC TGTTATTTCA  39000
CAATTATAAA CAACTTCATT ATTGTGACCA AAAAAATTCA TTACAACTCA CCAAGGAAAA  39060
CACTCAATTC TAATACTTTA CTCCTGTCCT CAAGGGCTTC GCAATACAGA GGGACAGCTT  39120
TGGAGCTGAG CTGTCCTCTG AAAAGCCAGT AGGAGTAGAT GAAGGTTCAG ACTGGAGTGA  39180
CGGGGATGGA GACTAGAGCG ATGGGGATGA AGGGTCATAC AGACTAATGA GCCTCTTTCA  39240
GTTTTCCTTA CATAGATATT TTAACTTTCT CAGAGAACAT TTATTAAAAT AAAAGATGAA  39300
TTTCCAGTGA AAGGTCCAGG ATCCATGTGC TAGAAGGCTT ACTAGAAACT GTGATGAATG  39360
AGGTCTGTAA ATCAAAAGGA AACCTTGAAA GTTATCAGTG GAACTCTCTT GTCCAGGGCA  39420
```

*Fig. 7-26*

```
TGATTAGGAA GAATGCAGGC ATTTGGGGGA GCAAAATAAT AAAATTAACA GTATAATTTT    39480
AGATATTCTT GTGATTTTTC CATTGGCAGG AATCACCTTA TTGAGATTCA TGATGAAAAG    39540
TTCCGGTTAT ATAAATTAAA GATGATGGTA AAGATGGAAA AATACCTTCA CTCCAGTCAG    39600
TGTAGGCGAC GGTATGTATT ACCTGCTTTT TCCAATTGGA AGCATAGGTC TTTAGCTGGT    39660
ACTTTTTTTG TTGTTTGTTT TTTTGAGACA GGGTTTCTCT GTGTAGCCCT GGCTGTCCTG    39720
GAACTCACTC TGTAGACCAG GCTGGCCTCG AACTCAGAAA TCTGCCTACC TCTGCCTCCT    39780
GAGTGCTGGG ATTAAAGGCG TGTGCCACCA CTGCCCGGCT AGATGGTACT TTTTTTTTT    39840
TAAAGTTAAT TAAAAGTGTT TTTAAAGAAT GTTTGCTGTA TACATGCTGA ACTTTAGGGC    39900
AGGCTTATTT CTGTTTAAAT AAATTAATAT GAAATAATGC TGAGACAAGT AAATACAGTA    39960
GTGGTACTAT CGTGTCATTT TGGGTGGTGG GTGTAGTATG TCTATATTTG TTCTTTAATT    40020
TAAGATTTTC CCTTCATCAG AATCATCTTG TCCCATTTTG AGGACAAATG TCTGCAGAAG    40080
GCCTCCTTGG ACATTATGGG AACTGAAAAA TGCTGTGATA ATTGCAGGCC CAGGTAAAAA    40140
TATCTTCCTG ACGAACCTTC TAGAAACTGT CGATTCTCTT TCTGTTCAAC TCCTGCTTCA    40200
TTAAATTTTT GTTTAATATA AGTATTTTAG GTTTTGTTTT GTTTTGTTTT GTTTTGTTTT    40260
TTTCGAGACA GGGTTTCTCT GTATAGCCCT GGCTGTCCTG GAACTCATTT TGTAGACCAG    40320
GCTGGCCTCG AACTCAGAAA TCCACCTGCC TCTGCCTCCC GAGTGCTGGG ATTAAAGACA    40380
TGCTATTTTA GTTTTTTTAA ATGACATAGT TACTTTATTT AAAATAAAAC AAAGTGAAGA    40440
GGTTTACTTT TATACAATAA AGTCTTAAAA CGGTAGGCCT AGTTAGTCAA TAGTTGCGTT    40500
TCAATATGAT TAGCCTAAAA ATACTCATTA AAGGCATAAT TTATCAAAAT TGATTTGAAA    40560
GGCATTCTAC TTGATGTTTA CCATAAGGGC AAGTACAATT ATGTAGATAG TTTTAAAAAA    40620
TGAAATAGAA AACACTGCAA AAACACTAGC CAAAAGAAAC CGTACGTTAC TGTTTTAGTA    40680
TTTAGTGGTA TGGACTTTGG AGCAAAGCAT GCTATCAGGG ATGAATCAAG ACACCGACCA    40740
GTGTGAAGTA TCAGCGTTCT GCAGAGAAGT GGCACCAAGG AGAGAGCAAG AGGGGCAGGA    40800
GAGGTGTGGG ATGGAAAGAA CAGGACAGAG GTGACAGGCA TCAGTGAGGT GGCAAATCTT    40860
AAAACTTGTA GCCAAGTTTT GGTCTGAACC CTGCGTCAGG CACACGCTAA TGTTAGTGTT    40920
GAAACAAAGT TTATTGCCCA GCAAGCTTGT TTGTATTAAG GCTTTCAACC CAAAGAGGGT    40980
AGTTATTGGG CATGATTTCC ATTGTTGAAG TCGTCTCATC ATAAGTAATA TTCACATCTA    41040
CAAAATACAT TTGCTGTGGC ATCTAAATTA TTTTCTGATC AAACAACAGC CCCACTTTGA    41100
CATGCAAGCT ATACAGCCCA GAAGACATAA TCCCAAGTGG GCACATAAGA ACCTGCACAT    41160
AAGAACCTGC ACATAAGTAC CACAGAAGCA GAAGGCGGGG GGATCAGAAA CCCACGTGTA    41220
TTAGGTGACG TCGGCGTCTG CTTACAAGGC AGTGGAATTA ATGGACAAGA ATGAGTAGGG    41280
CTGCGGGGAG CGATGGGCGT GTCTGCAATG GCAAATTCAG AGGTTCAGAC GGGAGATCAA    41340
GAGACTGAGA CCAGCCTGTG ATGCAAGTGA TCTCAAAAAG AACCCAGGTC CCATAGTGAG    41400
ACTGTGTCTC AAGATCCCGA GAACAAAAGC AAGCGTAAGA CTCAACAGCA AGCATGACCC    41460
ACCCCAAAGC CCCCAAACAG CCCCCTACCC CCACCCCACT GACTCTATGA GGAGATGAAG    41520
GAATGAAGAG GGTGTCAGCA AACCAGTTCT AATTAATTTC TTGAAAGCAT TTCAGCCACT    41580
TGTTCCAATG GCGGCTTATA CACACATGTT TACATAAAGC TAACCTTGAC AAATGAGGAA    41640
CTATTCGATT TGGATCAAGT ATGCTTTTTG CTTTAATGGC ATCAATCTAG AAAGCAGCAG    41700
TGGGAAGAAA AGAGAAATCT CCAAACCCTT AGAAACCGTA CCTCCAAATA ATCTTACAGC    41760
CACTCAGAAA ATGATCTGAA CCGACGAAGA AGAATATGAA GTACCTGGGA TACAGCTAGA    41820
ATGACTCTGC AAAGATAATT TATAGTGTTA ATACAACATG GAAGAGCACA GGCTTCAGAC    41880
ACATAACTAG CATTCACTTT AAGAAACGGG CAGAGCCGGG CGTGGTGGCA CAAAACAAAC    41940
AAACAAACAA ACAAACAAAA AACAAAAAAC AAAAACAAAA AAGAAATGGG CAAATATGAG    42000
GAAGATGAAC AGGAAGGGAG TTAAAAAGAG AAGTGCGTAG ATCAATGCCG TAGACGACAA    42060
AGCCAATAGA GGGGAGTCGG CGAGCTCACA GGCTTCATAT TTTCCAAGAC TGGTGGGGAA    42120
AGGGGAGGAC AGTACCAATA TCAAAATGAA GGAATTTCAC TGCAGACCCC ATGAATGCTC    42180
TGAACAAGCC AGGTTACTGG AAATGCAGTA AAACTGATCT AATAGACCAG TTTCTTAGTG    42240
GGCTCTAATT GACAGTGCTC AGGCATGGTG AAACTTAGGA AGAATACTCC TCTAACTGTT    42300
ATAAGGATTG AGTTCTTCCT TAAAAAACCT CTGAAAAGAG AACTCTCTAG CCCACCTGGC    42360
TTTAGTGACA AATTCCAGCA CCAGAAGAGG ACATCAAACT CATTACAGAT GGTTGTGAGT    42420
CACCATGTGG TTGCTGGGAT TTGAACTCAG GACCTTCAGA AGAGCTGTCA GTGCTGAACC    42480
ACTGAGCCAT CTCGCCAGCC CTCCAGCAAA CATTTAAATG AGGAGATATC CCTGCTTCTG    42540
TAGTGTGGCT GCACATGCAC ACTCTCTGAA AGGCAGAGCT GTAGGGAAGA TCAGCCGCTG    42600
GCAGAGGTTA AAGGCAGGCA GAATAGATCT GAGAGCAGGG CATTCAGTGG GTCTTGAGTG    42660
TGACGAAGGT TCGATGGGTC TGCTTATAGG GATATGTACG CTTTATTATA CTGTAAATAA    42720
```

*Fig. 7-27*

```
AATAAGTATA AGTGGTGCCT CTTTGAGTTA ATCGTGTCTC TAGGTACAGT AGCTGTATGC   42780
CAGAAGCAGC GCTGTTAGAG ATAGAAATCT AAAGATGTTT GGAAATTAGT GATAACCACA   42840
ATAACATATA TTTAAGGTGG TAAGATAATA TGTATAGGTC ATACTTCATG GGAACTTGAT   42900
AACTTTAAAT TCTCTGAAGA AAGTCACCTG AGCATCCTAC TAAAGAGGTA AATGGGAGAA   42960
TAAACCTAAG GCAGGGGATT TCTTCTTTAA ATCAAAACAT AATGGCTTTA ACTGGAATAC   43020
TGACTGCATT CTTATTGCTA CTTTAAAGAT ATATGTGATG TGGAAAGTAG TTGAATTTCG   43080
TAATTGAATA TATTAGTTGA TAGTCTCTAA GGACTTCTTT TGTTCTCAAG CTAAAAAAAA   43140
AATCCTCATT TACACCAATG ATAATTTTAC ATCTACTTGG AGGATGACTA AGGAATTTAA   43200
CTGCTGAATG TACCAGCAGG ACAAGCTTAT AGGCTCGGTG CTCTGTTGTA AAATTATTAG   43260
GGTTCAAGCT AACATGTTAC TGCATAGCAG CTTTTTACTT AAAACCAATT TTACCCTTCC   43320
TGGTGTAACG TAGCACAAGC TTCCGTATTT ATATAACTGA TCGTGTGGAG CTGCCCTAGC   43380
CGGGATGCTT TCCTTGAGCC TGGCATCTTC CCAGCGCCTC CATAACATTT AGCTTCTGGG   43440
TGCCACAAGA AAGCGCTGTC TGTAGTGCCG TATTTGTTAT TTGTGTCTCA TACGCATAGA   43500
TCACACACAT GCCCTTGATT GTAATAAGCT TTATGTGTAG AGTTGGAAGT GTCAGACACA   43560
TTTGAGAATT TTTTTTTTTA CGTGGTCTAT GTTTGTATCT TTCTATTTCT AAGGGAGCAT   43620
GCTTTTGTCA GTGTTTTCTT AGGCTGTTCT TACTTTCCTT CAGGCTGAAT CATTGCCTTA   43680
CTGCTAACAA CTCAGAGGAC GCATCCCAAG ACTTTGGGCC ACAAGCATTC CAGCTACTGT   43740
CTGCTGTGGA CATCCTGCAG GAGAAATTTG GAATTGGGAT TCCGATCTTA TTTCTCCGAG   43800
GATCTGTGAG TGTATCTGTG ATAGCTCCTG GGACTGTTTC TGACAGTGCT TTCCACTGTG   43860
TGGCTATGGC TTTGGCTTTC TTTAGATGGC TAACTAGCAA CCCGTGTTAG CAACACCTTG   43920
AGTTCCATCC TAACCCTGCA TTCATTGTCT TGGACAAATC TTGTCTCACG TCAGACGCTG   43980
TTTTGCTATG TTGGATGCTG GCGGTCAGCT GTGTGCTGCA GTCGAAAAT AGCCTATTCG   44040
TTTACCACAC TGCAATTGCA TTAATCCCTA GACTGGTTTT TCTTAGGATA ATTAGGGAAA   44100
GTTAACTCCC AGTGTGTCAA GGGACTGGTA GAACAAAGTT GCAGCTTCTG GTGCCCAGAT   44160
ACGATTATGT TCTTTGCGCA AAACTTGAAT TTCAGGGATT ATGTTGTCAG AGGCTGGGTT   44220
CAGCAACAGT GTACAGCAAC ATAGTCTCCC TCCGATGGTG TTTTATGTCA GAAGTACTTA   44280
ACATGCTAAG AAAGGGCTTT TGCTTGTTTT AGTGGTTTAC CAGTGAATAC CTGATTTAAC   44340
TGGACTCCTT TCTGTTTTGA GTGATTCATG TGGCCTCATT ATGCTGCCAA ATGTCACTTA   44400
CAAAGTGACA ATAATAAGGT ACAAATACAC ATACAGAGCT GGTTTTCTGT AGTCCTTCTG   44460
CTTTTATGAT AATTTTATTT CTGAATTAAG AGTCTGTAAA TTTAAGAATT GTATATTAAT   44520
ATCACTTAAA TAAACCAAGA GTAGAAGAAG GCAGAGTACT TTGTAGATGG ATCTATCTGC   44580
TTATTTAAAA CATGCTTTAG AGTAGAGGCT AAATGTTCAT TTTGTATATA GAATTTTAAA   44640
ATAATTTAGG TAAGCTTTTG CTGCTTAAAT ACTCAAGAGC TTCATGTAAA TGCATTTGCT   44700
TGTGCTTGCT TGTGCTTAGA AAGTAATCTA TGGAGTTAGT TATGAAATAT TTTTAATGAA   44760
ACACATTGAA AACTTGTACT ATCCTTTCAA GTGTCAGTGC TTTCAAGATA ATAGAGTTTA   44820
AATTTTTGGT TTTAAATGGC AAAAAAGCAT ATAAATGTAA CAATAGAAGT GTTACTTAAG   44880
CAGTTTTTAT TTCTATCAGC TCTGCAAGAA ATCTCAAATG CCACTGAAAT CCGTACATTC   44940
GTTTTCTATC TTTGTCACCT TTAAAATCCC TGTAGCCAGT GTGAGTATTT AATTTATGAA   45000
AAGTGTCCTT GTTTGGTTT GGTGCGATCT AGCTGTATCC AATATCAATA AATAAGTTTG   45060
TTTCTCGTCA AACTTTCAGT GGTCACAGGA GGGATCAGGT TCACTTATT ATTTGAAAAC   45120
CAAGTCAGAC GTCCTCTACC GGCAGTGTCT TCTGGGAGTC CTCAAATTAA GCAGTTCATC   45180
CTTAGTGAAA CTTTATACTA CCCTTGCTAG CGCAACGTGT AAAGCTTTTA AAAAGTATCA   45240
CTTAATGAAA ATGTGTAGAT GCTAACAATA GTGAAAATAA GACAGGCTTC CTTTCTCTGC   45300
TTTCAGTGAC TTTGATATCT ATTGGGATAT CGGTGAAAAA GTATGACTGT AATTCTCTTG   45360
AGAACTGAGC AAGTTGTTCC CCTTAACCAA TTTAGGACAA GCTAATACCT TTGTAATTTT   45420
AATTTGTAAG ATGATATATC AAACTGTCTT GGAGTTATTT TGAAGAGATA ATTTTTATAA   45480
GCATAAATTC GGTTTTGGTA GTGCTTGATT CTCTCCTACA TGTTTTTTTA ATATTATAAA   45540
CACTTAATTT ATCCATAAAT TTGTTAAATT TAGTTTAAAA ATTTGTTTTA ATGTGTCTAA   45600
TTAGAAAGTA ACCAAGATTG TCTAGAGAAC TTTGTTTTAA CTGACTAAAC AGTTCACCAT   45660
GTTCAGCAAT CTTTGACATT GCTCAAACGT GTCATAACAT AATCAATAGC CATAATTTAA   45720
GGGAAAAAAA CCACATTGAT CATTTGCATA CCAAGATTAG CATCTTCCCA AATGCCTTAT   45780
CCAAGTGCTA ATCTTTATCA TGGCCTCAGG AGTAGGTACC ACTTAATATT TTAGGATGTG   45840
TGTATATGCA CGTGTTCAGG TGCTCTCACA TCTGTGTGTG CATATGAACA CCAGAGGTGG   45900
ACATTGGATG TCTCCCTCTG GTACCCTCCA TTTCATTCGT ACTCTTTTGA CCCAGTTTGT   45960
CACCGAACCA GGAGCTCAGT GTCTTGGTTA GACTGGCTTG CCATTAGTCC CTGACATTCT   46020
```

*Fig. 7-28*

```
CCTGCCTCCG TTTCCTGCCA GCCAGCTGAC ACTGTAGTAA CAGCACCCAG CTTGTCTTCT    46080
TAAATTATAG TTTACTGGCG TTTCAAGAAC ATCATAACGG ATGCAGTGTA TTTTGGTTAT    46140
AATCAACCTC AGTATTCTCC CAGCTCTTCC CAGACTGATC CCACTGCCTC TTCACCAATC    46200
CCAACTTTAT GACCTCCCCC GCCCAACTTC CCAGCCATG GGTATGGGCA TCTGTTAGAA    46260
TGTGGTCAAC CTATCAGGAG CTATGCCCGT AAAGAATGAC GATCTCCCTG AAGAGCCGTC    46320
AGCTGTGAAT AGTTGTTCCC CAGGAGCTCC TGAACCCTTT TCTCCATCCC TTGATGAAAA    46380
TTTTGCTAAC TTGGTTCTGT GCAGGCAGCC ACAGATGCTG TGGGTTAACG GGTGCAGTGG    46440
TCTGTCATGC CCAAAAGACA CTGTTTGGTT CTGGTTCTAC ATGACCTCTG GCTCTAACAA    46500
TCTCCTTTTG GGACGAACCC TGAGCCTTGA GGGAAAGGAG TGTGACCCAG ATCTCCCATT    46560
TGTAGATGAA CACTCTATAT AGACAATATC CTCTGTGCTG TGCTTTGACC AGATGTGAGA    46620
TTCTGCGTTA ACCGCCATCC ACTGCACAAA GAACCTTCTC TGATGAGGCT TGAGAGTGGG    46680
ACCAATCTAT GGCTATAGGA ACAGGAACTT AGAGACAAGT ATAATTCTAT GTCAGTTTAG    46740
CAAAATAATA GTAAGAAATA TACTGCTGGG GCCGTGAGCT CCTTGACCAA ATGTTCTGGC    46800
CAGATTTACA GCATCCTGTA TGGAATGGGT GTGGGAACGG TAGGGAGAGG ATGGTACTTC    46860
TTAAATCCTG TCAGAAAGTG CTATGATATT GAGGCCACTT TTGCACCCAT GGGCATATCT    46920
GCCATGCTGG TTGTCATTTT AGTGTACAGG GTTAATAACT GGAGGAGAAA TTGACTTTTT    46980
CTTCCCCAGT AGCCTGCATA GCACCTTCTG GTATTGTGAA AGCTAGCCAG CAGAAAGGAA    47040
ACTTCTGGGC CAGGACCAGC GTGATTTCTC CATGTTCTAT GGCCAAAGCA GGTGGTGTCT    47100
TCAGCAATAC AGCCTTACCA CTAAGTTCTG ATGAGAAACC AAGAACAGTA GCGGTGACCT    47160
GTATTATTTG AGGTGGGGCA TCTGTAGGAA AAACTGAGCA ACAGTTTGAG AGGAGGTATC    47220
TCACACTGGA CTATTTGTTT GGTGACCTGT GGCTTCCTTG AGTAACATTA GCTTTTATGT    47280
AGCCTGATTC CAATTAAACT CTTATATAAG TGTGTGTGAG TTTAGGAAGC TTATAAATAG    47340
TAAGTTTCCA TATGGGTTTT AATTTTTTTT TAATTTTATT TTGTGATTTT ACTAATTCGC    47400
TTTACATCCC GCTCACTGCC CTACTCCTGG TCACTCCCTC CCACAATCCT TTCCTTATCC    47460
CTCCTCCCCC CTTCTCCTCT GAGAAGTTGG GCCCCCCTGG GTATCCCTCC ACCCTGGCAC    47520
TTCAAGTCTA TGCGAGGATA GGGTCTTCCT CTCCAATTGA GGCCAGACAA GGTAGCCCAG    47580
CTAGTAGAAC ATATCCCACG TACGGGCAAC AGCTTTGGGA TAGCCCCCAC TCCAGTTGTT    47640
TGGGACCCAC ATGAAGACCA AGCTGGACAC CTGCTACATA TGTGTAAGGA AACCTAGCTC    47700
CATATGTTCT TTGGTTCGTG GTACAGTTTC TGAGAGCTCC AAGGGTCAGG TTAGTTGGCT    47760
CTGTTGGTTT TCCTGTGGAG TTCTATCCCT TTCTGGGCTG CAATCCGTCT TCCTAGTTTT    47820
CCAAGAGTCC CCAAGCTCCA TTCACTGTTT GGCTGTGGGT GTCTGCATCT GTCTAAGTCA    47880
GCTGCTGTGT GGAGCCTCTC AAAAGACAAC ATGCTCCTGT CTGCAAGCAT AACAGAATAT    47940
CATTAATAGT GTCAAGGATT GGTGCTTGCC CATGGGATGG GTCTCAAGTT GGACCGGTTA    48000
TTGGTTGGCC ATTCCCTCAG TCTCTGCTCC CTCCCCTGTG CCTATATTAC TTGTAGACAG    48060
GATAAATTTT GGGTTGATAA TTTTGTGGGT GGGTCAGTGT CTTTATTGCT CTACTTGGGT    48120
TGCTGCCTGG CTACAGGAGG TGGCCTCTTC AAGTTCCATA TCCCCAGTGT AGTAAGTCAC    48180
AGCTAAGGTC ACACCTATTA ATCCTTGGAT GCCTCCCTTA TCCCAGGTTT CTGTCTCATC    48240
CTGTAAATGC CACCCACTTC CCCACTTTTC CTCTGCAGAT TTCCATTCAT TCTCATTACA    48300
TCTAGCTCTC TCCCTGCCCT TCCCTACACC CAATCCTGAA CTCCCATCTC CCTCCGCATC    48360
CCCCGTCCTA GTTCCCTCTT TCCATGTGCC TCTTATAACT ATTTTATTCC CACTTCTAAA    48420
TGAGATTCAA GCATCCTTCT GCCTTCCTTC TTGTTTAGCT TCTTTGGGTC TATGGAGTGT    48480
ACCATGGTAC TTGTATGTTT TGGCTAATGT CCGCTTATAA GTAAGTACAT ATCATGCATC    48540
TCCTTTTGGG GTTGGGTCAC CTCACTCAGG ATGATATTCT CAAGTTCCAG CCATTGGCTT    48600
GCAAAATTCA TGATGTCTTT CTTTTTAATA GCGGAATGGT ATTCCATTCT GTAGATGTAT    48660
CACATTTTAT CCATTCTTCA GTTGAGGGAC AGCTAGGTTG TTTCCAGCTT CTGGCTATTA    48720
TGAATAAAGC TTTAGGAACA TAGTTGGGTA TGTGTCTTTA TGGGATGTTG GAGCATCTTT    48780
TGGGTATGTG CCCAGGAATG GTATAGCTGG GTCTTGAGGT AGGACTATTC CCAGTTTTCT    48840
GAGAAACTGC CAAAGTTTCA AGTGGTTGTA TAAGTTCCCC TCACTCCACA CCCTTGCCAG    48900
CCTGTGTTAT CTTTTGAGTT TTTGATCTTA GCTATTCTGA TGGGTATAAG ATGGAACATC    48960
AATGTTGTTT TGATTTGCAT TTCCCTCATG ACTAAGGACT TTGAACATTT CTCTAAGTGC    49020
CTTTCAGCCA TTTGAGAGTC CTCTTTTGAG AATTCTCTGT TTAGCTCTGT TTCCCATTTT    49080
TAAATTGGGT TATTTGGGTC ATTGTTGTCC AACTTCTTGA ATTCTTCGTA AATTTTAGAT    49140
ATTTGCCTTC TGTCCGATGT AGGATTGGTG AAGATTCTTT TCCAATCTGA AGATTGCCTT    49200
CTTGTCCTAT TGACAGTGTC CTTTGCCTTA CAGAAGCTTT GCAATTTCTT GGGGTCCTAT    49260
TTATCAGTTG TTGATCTTAG AGCCTGAGCC ATTGGTGTTC TGTTCAGGAA CTTGTCTTCT    49320
```

*Fig. 7-29*

```
GTACCAATGC ATTCAAGGTA TTTCCCTCTT TCTCTTCTAT GATATTTAGT GTATATAGTT    49380
TTAAGTCGAG GTCTTTCATC CACTTGGACT TGACTCTTTT AATAAATGTG TGTGTGTGTG    49440
TATGTGTGTG TTTAGGAAGC TTATAAATAG TAAATTTCCA TGTGTTTTTT TTAAACTTTT    49500
TTTTTTACCT CTCTCTCTCT CCCTACCTCT CCACTCTGCC CTCGCATCCC ACTCTACACC    49560
TTAAACCTCT TCCCCCTTTA TATCACATAT TGTTCCAGTA TCCCCGTCAT AATGTTTTTT    49620
TCTTTCACCT ACCTCTACCA ATAAATGGTC CCTTTCTAGT TTCTTGGATT CTTCAGGCAC    49680
TCCAAGTTAA ACACACTATG TGAAACATTC AATGGTAGGA TCACATGTGC GAACATGTGA    49740
TGATGTTTGT CCTTCTGGGT CTGGGTTCCC TGAATCACTA TTGTTCCCCA GCTCCATCAG    49800
TTTCCCTGCA AATTGTTATG ATTGTAGTTT TCTTTATAGC CAAATAAAAC GGCATTGTGT    49860
ATAGGTGGTC CCACACTTTC GTGATCTATT TTGTAATTTA ATGGCTGTTT TCATGTCCTA    49920
GCAGTCATGA ACATAGCAGC TAGACCATGG CTGAGCATGC ATCTCTCTGG TAGGAAATAG    49980
AGGCCTTTGG TTATATACCC AGGGGTGATT TATGTGGGCC ATCGGATTCA TCATTTTAGC    50040
TGTTTGAGGA TTCTCTTTAC TGATTTCGAA GGAGCTGCAC CAGCTTTCTG TCTCACCAAC    50100
GGTGCACAGG GGTTCCCCAG ATCATCACCT GCATTTCTTG TCTTTTATGT TTTTTAATCT    50160
TATCCTCGAA GTAGTTTCAA CTTGAGTTAA GGATGGTAAA CTCTCCTGAA AGCATTTCAT    50220
TTCCTAGGCA CCTGCATTTC TTCTTCTGCA ACTTCTGTTT CATTCTATAA CTCACTTTTT    50280
GTTTTTAGTT TTTTCAACTC TTTTTTGTAT TCTGTAGACT AACCCTCTGT CAGATGTGTA    50340
GCTGGAATTA TACTCTAGGC TGCTCCTTTG GTCATGTAAT GGTTTCTTTC TTAGTAGCAC    50400
CTTTTCATTT ATAAAATTCT ATTTGTTGAT TAGTGGTCAT ATTTTGTAGA TGACAGGGCT    50460
CCTTTTCAGA GTCCTTACCT GAGCTGGTAT ACTGAGGCAT ACTTCACATT CTTCTGGGAG    50520
TTTCAGATCT AGCATTGAAA CCTTTGATTT CATTTGGAAT TTATTTGCCA TATCTTACAG    50580
GTCCTGGGGA TCCAATCTCA GGTGCTTATA TTTAGACATA GAGCCCTTTG TCTCATGAGC    50640
TATCTCCCCA ACCCAGATAA TGCTTTTAAG AAAAGATTGG ACCTATTCAG CTGTTAGAAC    50700
TGTTGATAGA TTTGTGTGTG TATGTGTGTG TGTGTGTGTG TGTGTGTGTG TGTACATGTG    50760
TGTACCTATA TGCACACATC TGTATGTATC TATTTTAAAG ACAAGATCAT GCCTAGGTTG    50820
ACTCTCACTC AACTGGAAAT TCTCCTGTCT AAGCCTCCTG ATTACAGCAG TAGGATTACA    50880
GGCATGTACT ACTATAGTCA ACGGCAATTG CTGTAGTTCT AATCACTCTC CAAAGTTATA    50940
AGAACATGTA GCTGGGGTGG GCTATTTCGT TTAATTTTCT AGACAAATAT TGAGTCTGAT    51000
AGAAATATAT TACTATGGGT TAGGTCTGCT TTTCAGGACT AAAGAACTTG GCTAAATGCA    51060
CAAGGCACTT GGTTCATGAA GAATTACCTA TTGAACCCCT GAAATGGCAG CTGGGACTAT    51120
CTCTGGACTA TAGGAGCTGG AAAGGGGCAG GGCTGGTGGG AGGAGAAGGT GGAGAGGGTA    51180
GCTAGGAACT TAAATGTCTT TGAGCTATTG AGCATCTGTT TTTATGTAAG GCATGACATT    51240
GATTTTGTAG AGGATACAC                                                 51259
```

*Fig. 7-30*

```
            1                                                    50
MOUSE   ......METTS LQRKFPEWMS MQSQRCATEE .KACVQKSVL EDNLPFLEFP
HUMAN   MSEKKLETTA QQRKCPEWMN VQNKRCAVEE RKACVRKSVF EDDLPFLEFT 51                                                  100
MOUSE   GSIVYSYEAS DCSFLSEDIS MRLSDGDVVG FDMEWPPIYK PGKRSRVAVI
HUMAN   GSIVYSYDAS DCSFLSEDIS MSLSDGDVVG FDMEWPPLYN RGKLGKVALI 101                                                 150
MOUSE   QLCVSESKCY LFHISSMSVF PQGLKMLLEN KSIKKAGVGI EGDQWKLLRD
HUMAN   QLCVSESKCY LFHVSSMSVF PQGLKMLLEN KAVKKAGVGI EGDQWKLLRD 151                                                 200
MOUSE   FDVKLESFVE LTDVANEKLK CAETWSLNGL VKHVLGKQLL KDKSIRCSNW
HUMAN   FDIKLKNFVE LTDVANKKLK CTETWSLNSL VKHLLGKQLL KDKSIRCSNW 201                                                 250
MOUSE   SNFPLTEDQK LYAATDAYAG LIIYQKLGNL GDTAQVFALN KAEENLPLEM
HUMAN   SKFPLTEDQK LYAATDAYAG FIIYRNLEIL DDTVQRFAIN KEEEILLSDM 251                                                 300
MOUSE   KKQLNSISEE MRDLANRFPV TCRNLETLQR VPVILKSISE NLCSLRKVIC
HUMAN   NKQLTSISEE VMDLAKHLPH AFSKLENPRR VSILLKDISE NLYSLRRMII 301                                                 350
MOUSE   GPTNTETRLK PGSSFNLLSS EDSAAAGEKE KQIGKHSTFA KIKEEPWDPE
HUMAN   GSTNIETELR PSNNLNLLSF EDSTTGGVQQ KQIREHEVLI HVEDETWDPT 351                                                 400
MOUSE   LDSLVKQEEV DVFRNQVKQE KGESENEIED NLLREDMERT CVIP.SISEN
HUMAN   LDHLAKHDGE DVLGNKVERK EDGFEDGVED NKLKENMERA CLMSLDITEH 401                                                 450
MOUSE   ELQDLEQQAK EEKYNDVSHQ LSE....... .......... ..........
HUMAN   ELQILEQQSQ EEYLSDIAYK STEHLSPNDN ENDTSYVIES DEDLEMEMLK
```

*Fig. 10-1*

```
         451                                                   500
MOUSE    HLSPNDDEND SSYIIESDED LEMEMLKSLE NLNSDVVEPT HSTWLEMGTN
HUMAN    HLSPNDNEND TSYVIESDED LEMEMLKSLE NLNSGTVEPT HSKCLKMERN 501                                                   550
MOUSE    GRLPP.EEED GHGNEAIK.E EQEEEDHLLP EPNAKQINCL KTYFGHSSFK
HUMAN    LGLPTKEEEE DDENEANEGE EDDDKDFLWP APNEEQVTCL KMYFGHSSFK 551                                                   600
MOUSE    PVQWKVIHSV LEERRDNVVV MATGYGKSLC FQYPPVYTGK IGIVISPLIS
HUMAN    PVQWKVIHSV LEERRDNVAV MATGYGKSLC FQYPPVYVGK IGLVISPLIS 601                                                   650
MOUSE    LMEDQVLQLE LSNVPACLLG SAQSKNILGD VKLGKYRVIY ITPEFCSGNL
HUMAN    LMEDQVLQLK MSNIPACFLG SAQSENVLTD IKLGKYRIVY VTPEYCSGNM 651                                                   700
MOUSE    DLLQQLDSSI GITLIAVDEA HCISEWGHDF RSSFRMLGSL KTALPLVPVI
HUMAN    GLLQQLEADI GITLIAVDEA HCISEWGHDF RDSFRKLGSL KTALPMVPIV 701                                                   750
MOUSE    ALSATASSSI REDIISCLNL KDPQITCTGF DRPNLYLEVG RKTGNILQDL
HUMAN    ALTATASSSI REDIVRCLNL RNPQITCTGF DRPNLYLEVR RKTGNILQDL 751                                                   800
MOUSE    KPFLVRKASS AWEFEGPTII YCPSRKMTEQ VTAELGKLNL ACRTYHAGMK
HUMAN    QPFLV.KTSS HWEFEGPTII YCPSRKMTQQ VTGELRKLNL SCGTYHAGMS 801                                                   850
MOUSE    ISERKDVHHR FLRDEIQCVV ATVAFGMGIN KADIRKVIHY GAPKEMESYY
HUMAN    FSTRKDIHHR FVRDEIQCVI ATIAFGMGIN KADIRQVIHY GAPKDMESYY 851                                                   900
MOUSE    QEIGRAGRDG LQSSCHLLWA PADFNTSRNL LIEIHDEKFR LYKLKMMVKM
HUMAN    QEIGRAGRDG LQSSCHVLWA PADINLNRHL LTEIRNEKFR LYKLKMMAKM 901                                                   950
MOUSE    EKYLHSSQCR RRIILSHFED KCLQKASLDI MGTEKCCDNC RPRLNHCLTA
HUMAN    EKYLHSSRCR RQIILSHFED KQVQKASLGI MGTEKCCDNC RSRLDHCYSM 951                                                  1000
MOUSE    NNSEDASQDF GPQAFQLLSA VDILQEKFGI GIPILFLRGS NSQRLPDKYR
HUMAN    DDSEDTSWDF GPQAFKLLSA VDILGEKFGI GLPILFLRGS NSQRLADQYR
```

*Fig. 10-2*

```
              1001                                                    1050
MOUSE   GHRLFGAGKE  QAESWWKTLS  HHLIAEGFLV  EVPKENKYIK  TCSLTKKGRK
HUMAN   RHSLFGTGKD  QTESWWKAFS  RQLITEGFLV  EVSRYNKFMK  ICALTKKGRN 1051                                                    1100
MOUSE   WLGEASSQSP  PSLLLQANEE  MFPRKVLLPS  SNPVSPETTQ  HSSNQNPAGL
HUMAN   WLHKANTES.  QSLILQANEE  LCPKKFLLPS  SKTVSSGTKE  HCYNQVPVEL 1101                                                    1150
MOUSE   TT.KQSNLER  THSYKVPEKV  SSGTNIPKKS  AVMPSPGTSS  SPLEPAISAQ
HUMAN   STEKKSNLEK  LYSYKPCDKI  SSGSNISKKS  IMVQSPEKAY  SSSQPVISAQ 1151                                                    1200
MOUSE   ELDARTGLYA  RLVEARQKHA  NKMDVPPAIL  ATNKVLLDMA  KMRPTTVENM
HUMAN   EQETQIVLYG  KLVEARQKHA  NKMDVPPAIL  ATNKILVDMA  KMRPTTVENV 1201                                                    1250
MOUSE   KQIDGVSEGK  AALLAPLLEV  IKHFCQVTSV  QTDLLSSAKP  HKEQEKSQEM
HUMAN   KRIDGVSEGK  AAMLAPLLEV  IKHFCQTNSV  QTDLFSSTKP  QEEQKTSLVA 1251                                                    1300
MOUSE   EKKDCSLPQS  VAVTYTLFQE  KKMPLHSIAE  NRLLPLTAAG  MHLAQAVKAG
HUMAN   KNKICTLSQS  MAITYSLFQE  KKMPLKSIAE  SRILPLMTIG  MHLSQAVKAG 1301                                                    1350
MOUSE   YPLDMERAGL  TPETWKIIMD  VIRNPPINSD  MYKVKLIRML  VPENLDTYLI
HUMAN   CPLDLERAGL  TPEVQKIIAD  VIRNPPVNSD  MSKISLIRML  VPENIDTYLI 1351                                                    1400
MOUSE   HMAIEILQSG  SDSRTQPPCD  SSRKRRFPSS  AESCESCKES  KEAVT.ETKA
HUMAN   HMAIEILKHG  PDSGLQPSCD  VNKRRCFPGS  EEICSSSKRS  KEEVGINTET 1401                                        1440
MOUSE   SSSESKRKLP  EWFAKGNVPS  ADTGSSSSMA  KTKKKGLFS*
HUMAN   SSAERKRRLP  VWFAKGS...  ..DTSKKLMD  KTKRGGLFS*
```

*Fig. 10-3*

```
                          SEQUENCE LISTING (1) GENERAL INFORMATION:

(iii) NUMBER OF SEQUENCES: 209

(2) INFORMATION FOR SEQ ID NO: 1:

(i) SEQUENCE CHARACTERISTICS:
         (A) LENGTH: 22 base pairs
         (B) TYPE: nucleic acid
         (C) STRANDEDNESS: single
         (D) TOPOLOGY: linear (xi) SEQUENCE DESCRIPTION: SEQ ID NO: 1:

CTGGCAAGGA TCAAACAGAG AG                                                  22

(2) INFORMATION FOR SEQ ID NO: 2:

(i) SEQUENCE CHARACTERISTICS:
         (A) LENGTH: 23 base pairs
         (B) TYPE: nucleic acid
         (C) STRANDEDNESS: single
         (D) TOPOLOGY: linear (xi) SEQUENCE DESCRIPTION: SEQ ID NO: 2:

CTTTATGAAG CCAATTTCTA CCC                                                 23

(2) INFORMATION FOR SEQ ID NO: 3:

(i) SEQUENCE CHARACTERISTICS:
         (A) LENGTH: 22 base pairs
         (B) TYPE: nucleic acid
         (C) STRANDEDNESS: single
         (D) TOPOLOGY: linear (xi) SEQUENCE DESCRIPTION: SEQ ID NO: 3:

TGGCAAATTG GTAGAAGCTA GG                                                  22

(2) INFORMATION FOR SEQ ID NO: 4:

(i) SEQUENCE CHARACTERISTICS:
         (A) LENGTH: 26 base pairs
         (B) TYPE: nucleic acid
         (C) STRANDEDNESS: single
         (D) TOPOLOGY: linear (xi) SEQUENCE DESCRIPTION: SEQ ID NO: 4:

AAATAACTAT GCTTTCTTAC ATTTAC                                              26

(2) INFORMATION FOR SEQ ID NO: 5:

(i) SEQUENCE CHARACTERISTICS:
         (A) LENGTH: 22 base pairs
         (B) TYPE: nucleic acid
         (C) STRANDEDNESS: single
         (D) TOPOLOGY: linear
```

(xi) SEQUENCE DESCRIPTION: SEQ ID NO: 5:

CTCCCGTCAA CTCAGATATG AG                                    22

(2) INFORMATION FOR SEQ ID NO: 6:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO: 6:

CTGTTTGTAA ATGTAAGAAA GCATAG                                26

(2) INFORMATION FOR SEQ ID NO: 7:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 7:

GAGCTATGAT GACACCACTG C                                     21

(2) INFORMATION FOR SEQ ID NO: 8:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 8:

ACTGAGCAAC AGAGTGAGAC C                                     21

(2) INFORMATION FOR SEQ ID NO: 9:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO: 9:

GGATCTGGTC TCACTCTGTT GC                                    22

(2) INFORMATION FOR SEQ ID NO: 10:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO: 10:

TTGCCTAGTG CAATTGGTCT CC                                    22

(2) INFORMATION FOR SEQ ID NO: 11:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO: 11:

AGTGCAGTGG TGTCATCATA GC                                              22

(2) INFORMATION FOR SEQ ID NO: 12:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (xi) SEQUENCE DESCRIPTION: SEQ ID NO: 12:

CCTATTTAAT GGCACCCAAA ATGC                                            24

(2) INFORMATION FOR SEQ ID NO: 13:

(i) SEQUENCE CHARACTERISTICS:
         (A) LENGTH: 23 base pairs
         (B) TYPE: nucleic acid
         (C) STRANDEDNESS: single
         (D) TOPOLOGY: linear (xi) SEQUENCE DESCRIPTION: SEQ ID NO: 13:

CAGTCTATGG CCATCACATA CTC                                             23

(2) INFORMATION FOR SEQ ID NO: 14:

(i) SEQUENCE CHARACTERISTICS:
         (A) LENGTH: 22 base pairs
         (B) TYPE: nucleic acid
         (C) STRANDEDNESS: single
         (D) TOPOLOGY: linear (xi) SEQUENCE DESCRIPTION: SEQ ID NO: 14:

ACCGCTTGGG ATAAGTGCAT GC                                              22

(2) INFORMATION FOR SEQ ID NO: 15:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (xi) SEQUENCE DESCRIPTION: SEQ ID NO: 15:

GAGAAGAAGT CTAACTTGGA GAAG                                            24

(2) INFORMATION FOR SEQ ID NO: 16:

(i) SEQUENCE CHARACTERISTICS:
         (A) LENGTH: 23 base pairs
         (B) TYPE: nucleic acid
         (C) STRANDEDNESS: single
         (D) TOPOLOGY: linear (xi) SEQUENCE DESCRIPTION: SEQ ID NO: 16:

TTCTGGTGAC TGTACCATGA TAC                                             23

(2) INFORMATION FOR SEQ ID NO: 17:

(i) SEQUENCE CHARACTERISTICS:
         (A) LENGTH: 23 base pairs
         (B) TYPE: nucleic acid
         (C) STRANDEDNESS: single
         (D) TOPOLOGY: linear (xi) SEQUENCE DESCRIPTION: SEQ ID NO: 17:

CCAAAGGAAG TGATACCAGC AAG                                                    23

(2) INFORMATION FOR SEQ ID NO: 18:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 18:

ACAGCAAGAA CATAATTGTT CTGG                                                   24

(2) INFORMATION FOR SEQ ID NO: 19:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO: 19:

GAACTTTGAA GTCCATCACG ACC                                                    23

(2) INFORMATION FOR SEQ ID NO: 20:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 20:

GCATTAATAA AGCTGACATT CGCC                                                   24

(2) INFORMATION FOR SEQ ID NO: 21:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 21:

CATTACGGTG CTCCTAAGGA CATG                                                   24

(2) INFORMATION FOR SEQ ID NO: 22:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO: 22:

GATGGATTTG AAGATGGAGT AGAAG                                                  25

(2) INFORMATION FOR SEQ ID NO: 23:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO: 23:

TGAAAGAGAA TATGGAAAGA GCTTG                                                25

(2) INFORMATION FOR SEQ ID NO: 24:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO: 24:

GTAGAACCAA CTCATTCTAA ATGCT                                                25

(2) INFORMATION FOR SEQ ID NO: 25:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO: 25:

AATTTGCGTG TCATCCTTGC GCA                                                  23

(2) INFORMATION FOR SEQ ID NO: 26:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO: 26:

TCCTAGTCAC CCATCTGAAG TC                                                   22

(2) INFORMATION FOR SEQ ID NO: 27:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO: 27:

CATGAAACTT GCTTCTAGGA CAC                                                  23

(2) INFORMATION FOR SEQ ID NO: 28:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 28:

CCCAGGAGTT CGAGACCATC C                                                    21

(2) INFORMATION FOR SEQ ID NO: 29:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO: 29:

TTACAATCGG CCACATTCAT CAC                                23

(2) INFORMATION FOR SEQ ID NO: 30:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO: 30:

TGTAATCCCA ACACTTTGGG AGG                                23

(2) INFORMATION FOR SEQ ID NO: 31:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 31:

AGTGGAAGAA TTCATAGTGG ATGG                               24

(2) INFORMATION FOR SEQ ID NO: 32:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 32:

TAGCTTTATG AACCAATTTC TACC                               24

(2) INFORMATION FOR SEQ ID NO: 33:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO: 33:

AATCCAAAGA ATCAATAGAC AAGTC                              25

(2) INFORMATION FOR SEQ ID NO: 34:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO: 34:

GCTTGAAGGA TGAGGCTCTG AG                                 22

(2) INFORMATION FOR SEQ ID NO: 35:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO: 35:

TGTTCAGAAT GAGCACGATG GG                                    22

(2) INFORMATION FOR SEQ ID NO: 36:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO: 36:

CTTGTGAGAG GCCTATAAAC TGG                                   23

(2) INFORMATION FOR SEQ ID NO: 37:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO: 37:

GGTAAACAGT GTAGGAGTCT GC                                    22

(2) INFORMATION FOR SEQ ID NO: 38:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO: 38:

GCCATTTTCT CTTTAATTGG AAAGG                                 25

(2) INFORMATION FOR SEQ ID NO: 39:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO: 39:

ATCTTATTCA TCTTTCTGAG AATGG                                 25

(2) INFORMATION FOR SEQ ID NO: 40:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO: 40:

TGAAATAGCC CAACATCTGA CAG                                   23

(2) INFORMATION FOR SEQ ID NO: 41:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO: 41:

GATTAATTTG ACAGCTTGAT TAGGC                                              25

(2) INFORMATION FOR SEQ ID NO: 42:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO: 42:

TGAAATATAA ACTCAGACTC TTAGC                                              25

(2) INFORMATION FOR SEQ ID NO: 43:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 43:

GTACTGATTT GGAAAGACAT TCTC                                               24

(2) INFORMATION FOR SEQ ID NO: 44:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO: 44:

GATGTGACAG TGGAAGCTAT GG                                                 22

(2) INFORMATION FOR SEQ ID NO: 45:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 45:

GGAAAAATGT GGTATCTGAA GCTC                                               24

(2) INFORMATION FOR SEQ ID NO: 46:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO: 46:

AAGTGAGCAA ATGTTGCTTC TGG                                                23

(2) INFORMATION FOR SEQ ID NO: 47:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO: 47:

TCATTAGGAA GCTGAACATC AGC                                              23

(2) INFORMATION FOR SEQ ID NO: 48:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (xi) SEQUENCE DESCRIPTION: SEQ ID NO: 48:

GTTGGAGGAA ATTGATCCCA AGTC                                             24

(2) INFORMATION FOR SEQ ID NO: 49:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (xi) SEQUENCE DESCRIPTION: SEQ ID NO: 49:

TGTTGCTTAT GGGTTTAACT TGTG                                             24

(2) INFORMATION FOR SEQ ID NO: 50:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (xi) SEQUENCE DESCRIPTION: SEQ ID NO: 50:

TAAAGGATTA ATGCTGTTAA CAGTG                                            25

(2) INFORMATION FOR SEQ ID NO: 51:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (xi) SEQUENCE DESCRIPTION: SEQ ID NO: 51:

TCACACTGCG CATTTACTAC CTG                                              23

(2) INFORMATION FOR SEQ ID NO: 52:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (xi) SEQUENCE DESCRIPTION: SEQ ID NO: 52:

GTAATCATAT CAGAATTCAT AACAG                                            25

(2) INFORMATION FOR SEQ ID NO: 53:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (xi) SEQUENCE DESCRIPTION: SEQ ID NO: 53:

CTTTGGCAAC CTTCCACCTT CC                                        22

(2) INFORMATION FOR SEQ ID NO: 54:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 54:

GCAAAGGAAA TGTAGCACAT AGAG                                      24

(2) INFORMATION FOR SEQ ID NO: 55:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO: 55:

AGGCTATAGG CATTTGAAAG AGG                                       23

(2) INFORMATION FOR SEQ ID NO: 56:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 56:

GTAGGCTCCC AGAAGACCCA G                                         21

(2) INFORMATION FOR SEQ ID NO: 57:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO: 57:

GAAAGGATGG GTGTGTATTC AGG                                       23

(2) INFORMATION FOR SEQ ID NO: 58:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 58:

TTTTAATAGG GTAGAAA                                              17

(2) INFORMATION FOR SEQ ID NO: 59:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 59:

TTTTAATACG GTAGAAA                                                      17

(2) INFORMATION FOR SEQ ID NO: 60:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 60:

GAAGCTAGGC AGAAACAT                                                     18

(2) INFORMATION FOR SEQ ID NO: 61:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 61:

GAAGCTAGGT AGAAACAT                                                     18

(2) INFORMATION FOR SEQ ID NO: 62:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (xi) SEQUENCE DESCRIPTION: SEQ ID NO: 62:

TTGGAGCGAG CA                                                           12

(2) INFORMATION FOR SEQ ID NO: 63:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (xi) SEQUENCE DESCRIPTION: SEQ ID NO: 63:

TTGGAGTGAG CA                                                           12

(2) INFORMATION FOR SEQ ID NO: 64:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 64:

AAGAAGTTTC TTCTG                                                        15

(2) INFORMATION FOR SEQ ID NO: 65:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 65:

AAGAAGTTGC TTCTG                                                        15

(2) INFORMATION FOR SEQ ID NO: 66:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (xi) SEQUENCE DESCRIPTION: SEQ ID NO: 66:

CCTTCATGTG AT                                                           12

(2) INFORMATION FOR SEQ ID NO: 67:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (xi) SEQUENCE DESCRIPTION: SEQ ID NO: 67:

CCTTCACGTG AT                                                           12

(2) INFORMATION FOR SEQ ID NO: 68:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 68:

CTGTAGACAG ACACCTC                                                      17

(2) INFORMATION FOR SEQ ID NO: 69:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (xi) SEQUENCE DESCRIPTION: SEQ ID NO: 69:

CTGTAGACAC CTC                                                          13

(2) INFORMATION FOR SEQ ID NO: 70:

(i) SEQUENCE CHARACTERISTICS:
        (A) LENGTH: 5208 base pairs
        (B) TYPE: nucleic acid
        (C) STRANDEDNESS: single
        (D) TOPOLOGY: linear (xi) SEQUENCE DESCRIPTION: SEQ ID NO: 70:

TGTGCGCCGG GGAGGCGCCG GCTTGTACTC GGCAGCGCGG GAATAAAGTT TGCTGATTTG        60

GTGTCTAGCC TGGATGCCTG GGTTGCAGCC CTGCTTGTGG TGGCGCTCCA CAGTCATCCG       120

GCTGAAGAAG ACCTGTTGGA CTGGATCTTC TCGGGTTTTC TTTCAGATAT TGTTTTGTAT       180

TTACCCATGA AGACATTGTT TTTTGGACTC TGCAAATAGG ACATTTCAAA GATGAGTGAA       240

AAAAAATTGG AAACAACTGC ACAGCAGCGG AAATGTCCTG AATGGATGAA TGTGCAGAAT       300

AAAAGATGTG CTGTAGAAGA AAGAAAGGCA TGTGTTCGGA AGAGTGTTTT TGAAGATGAC       360

```
CTCCCCTTCT TAGAATTCAC TGGATCCATT GTGTATAGTT ACGATGCTAG TGATTGCTCT      420

TTCCTGTCAG AAGATATTAG CATGAGTCTA TCAGATGGGG ATGTGGTGGG ATTTGACATG      480

GAGTGGCCAC CATTATACAA TAGAGGGAAA CTTGGCAAAG TTGCACTAAT TCAGTTGTGT      540

GTTTCTGAGA GCAAATGTTA CTTGTTCCAC GTTTCTTCCA TGTCAGTTTT TCCCCAGGGA      600

TTAAAAATGT TGCTTGAAAA TAAAGCAGTT AAAAAGGCAG GTGTAGGAAT TGAAGGAGAT      660

CAGTGGAAAC TTCTACGTGA CTTTGATATC AAATTGAAGA ATTTTGTGGA GTTGACAGAT      720

GTTGCCAATA AAAAGCTGAA ATGTACAGAG ACCTGGAGCC TTAACAGTCT GGTTAAACAC      780

CTCTTAGGTA AACAGCTCCT GAAAGACAAG TCTATCCGCT GTAGCAATTG GAGTAAATTT      840

CCTCTCACTG AGGACCAGAA ACTGTATGCA GCCACTGATG CTTATGCTGG TTTTATTATT      900

TACCGAAATT TAGAGATTTT GGATGATACT GTGCAAAGGT TTGCTATAAA TAAAGAGGAA      960

GAAATCCTAC TTAGCGACAT GAACAAACAG TTGACTTCAA TCTCTGAGGA AGTGATGGAT     1020

CTGGCTAAGC ATCTTCCTCA TGCTTTCAGT AAATTGGAAA ACCCACGGAG GGTTTCTATC     1080

TTACTAAAGG ATATTTCAGA AAATCTATAT TCACTGAGGA GGATGATAAT TGGGTCTACT     1140

AACATTGAGA CTGAACTGAG GCCCAGCAAT AATTTAAACT TATTATCCTT TGAAGATTCA     1200

ACTACTGGGG GAGTACAACA GAAACAAATT AGAGAACATG AAGTTTTAAT TCACGTTGAA     1260

GATGAAACAT GGGACCCAAC ACTTGATCAT TTAGCTAAAC ATGATGGAGA AGATGTACTT     1320

GGAAATAAAG TGGAACGAAA AGAAGATGGA TTTGAAGATG GAGTAGAAGA CAACAAATTG     1380

AAAGAGAATA TGGAAAGAGC TTGTTTGATG TCGTTAGATA TTACAGAACA TGAACTCCAA     1440

ATTTTGGAAC AGCAGTCTCA GGAAGAATAT CTTAGTGATA TTGCTTATAA ATCTACTGAG     1500

CATTTATCTC CCAATGATAA TGAAAACGAT ACGTCCTATG TAATTGAGAG TGATGAAGAT     1560

TTAGAAATGG AGATGCTTAA GCATTTATCT CCCAATGATA ATGAAAACGA TACGTCCTAT     1620

GTAATTGAGA GTGATGAAGA TTTAGAAATG GAGATGCTTA AGTCTTTAGA AAACCTCAAT     1680

AGTGGCACGG TAGAACCAAC TCATTCTAAA TGCTTAAAAA TGGAAAGAAA TCTGGGTCTT     1740

CCTACTAAAG AAGAAGAAGA AGATGATGAA AATGAAGCTA ATGAAGGGGA AGAAGATGAT     1800

GATAAGGACT TTTTGTGGCC AGCACCCAAT GAAGAGCAAG TTACTTGCCT CAAGATGTAC     1860

TTTGGCCATT CCAGTTTTAA ACCAGTTCAG TGGAAAGTGA TTCATTCAGT ATTAGAAGAA     1920

AGAAGAGATA ATGTTGCTGT CATGGCAACT GGATATGGAA AGAGTTTGTG CTTCCAGTAT     1980

CCACCTGTTT ATGTAGGCAA GATTGGCCTT GTTATCTCTC CCCTTATTTC TCTGATGGAA     2040

GACCAAGTGC TACAGCTTAA AATGTCCAAC ATCCCAGCTT GCTTCCTTGG ATCAGCACAG     2100

TCAGAAAATG TTCTAACAGA TATTAAATTA GGTAAATACC GGATTGTATA CGTAACTCCA     2160

GAATACTGTT CAGGTAACAT GGGCCTGCTC CAGCAACTTG AGGCTGATAT TGGTATCACG     2220

CTCATTGCTG TGGATGAGGC TCACTGTATT TCTGAGTGGG GGCATGATTT TAGGGATTCA     2280

TTCAGGAAGT TGGGCTCCCT AAAGACAGCA CTGCCAATGG TTCCAATCGT TGCACTTACT     2340

GCTACTGCAA GTTCTTCAAT CCGGGAAGAC ATTGTACGTT GCTTAAATCT GAGAAATCCT     2400

CAGATCACCT GTACTGGTTT TGATCGACCA AACCTGTATT TAGAAGTTAG GCGAAAAACA     2460

GGGAATATCC TTCAGGATCT GCAGCCATTT CTTGTCAAAA CAAGTTCCCA CTGGGAATTT     2520

GAAGGTCCAA CAATCATCTA CTGTCCTTCT AGAAAAATGA CACAACAAGT TACAGGTGAA     2580

CTTAGGAAAC TTAATCTATC CTGTGGAACA TACCATGCGG GCATGAGTTT TAGCACAAGG     2640

AAAGACATTC ATCATAGGTT TGTAAGAGAT GAAATTCAGT GTGTCATAGC TACCATAGCT     2700

TTTGGAATGG GCATTAATAA AGCTGACATT CGCCAAGTCA TTCATTACGG TGCTCCTAAG     2760
```

```
GACATGGAAT CATATTATCA GGAGATTGGT AGAGCTGGTC GTGATGGACT TCAAAGTTCT    2820

TGTCACGTCC TCTGGGCTCC TGCAGACATT AACTTAAATA GGCACCTTCT TACTGAGATA    2880

CGTAATGAGA AGTTTCGATT ATACAAATTA AAGATGATGG CAAAGATGGA AAAATATCTT    2940

CATTCTAGCA GATGTAGGAG ACAAATCATC TTGTCTCATT TTGAGGACAA ACAAGTACAA    3000

AAAGCCTCCT TGGGAATTAT GGGAACTGAA AAATGCTGTG ATAATTGCAG GTCCAGATTG    3060

GATCATTGCT ATTCCATGGA TGACTCAGAG GATACATCCT GGGACTTTGG TCCACAAGCA    3120

TTTAAGCTTT TGTCTGCTGT GGACATCTTA GGCGAAAAAT TTGGAATTGG GCTTCCAATT    3180

TTATTTCTCC GAGGATCTAA TTCTCAGCGT CTTGCCGATC AATATCGCAG GCACAGTTTA    3240

TTTGGCACTG GCAAGGATCA AACAGAGAGT TGGTGGAAGG CTTTTTCCCG TCAGCTGATC    3300

ACTGAGGGAT TCTTGGTAGA AGTTTCTCGG TATAACAAAT TTATGAAGAT TGCGCCCTT    3360

ACGAAAAAGG GTAGAAATTG GCTTCATAAA GCTAATACAG AATCTCAGAG CCTCATCCTT    3420

CAAGCTAATG AAGAATTGTG TCCAAAGAAG TTTCTTCTGC CTAGTTCGAA AACTGTATCT    3480

TCGGGCACCA AAGAGCATTG TTATAATCAA GTACCAGTTG AATTAAGTAC AGAGAAGAAG    3540

TCTAACTTGG AGAAGTTATA TTCTTATAAA CCATGTGATA AGATTTCTTC TGGGAGTAAC    3600

ATTTCTAAAA AAAGTATCAT GGTACAGTCA CCAGAAAAAG CTTACAGTTC CTCACAGCCT    3660

GTTATTTCGG CACAAGAGCA GGAGACTCAG ATTGTGTTAT ATGGCAAATT GGTAGAAGCT    3720

AGGCAGAAAC ATGCCAATAA AATGGATGTT CCCCCAGCTA TTCTGGCAAC AAACAAGATA    3780

CTGGTGGATA TGGCCAAAAT GAGACCAACT ACGGTTGAAA ACGTAAAAAG GATTGATGGT    3840

GTTTCTGAAG GCAAAGCTGC CATGTTGGCC CCTCTGTTGG AAGTCATCAA ACATTTCTGC    3900

CAAACAAATA GTGTTCAGAC AGACCTCTTT TCAAGTACAA AACCTCAAGA AGAACAGAAG    3960

ACGAGTCTGG TAGCAAAAAA TAAAATATGC ACACTTTCAC AGTCTATGGC CATCACATAC    4020

TCTTTATTCC AAGAAAAGAA GATGCCTTTG AAGAGCATAG CTGAGAGCAG GATTCTGCCT    4080

CTCATGACAA TTGGCATGCA CTTATCCCAA GCGGTGAAAG CTGGCTGCCC CCTTGATTTG    4140

GAGCGAGCAG GCCTGACTCC AGAGGTTCAG AAGATTATTG CTGATGTTAT CCGAAACCCT    4200

CCCGTCAACT CAGATATGAG TAAAATTAGC CTAATCAGAA TGTTAGTTCC TGAAAACATT    4260

GACACGTACC TTATCCACAT GGCAATTGAG ATCCTTAAAC ATGGTCCTGA CAGCGGACTT    4320

CAACCTTCAT GTGATGTCAA CAAAAGGAGA TGTTTTCCCG GTTCTGAAGA GATCTGTTCA    4380

AGTTCTAAGA GAAGCAAGGA AGAAGTAGGC ATCAATACTG AGACTTCATC TGCAGAGAGA    4440

AAGAGACGAT TACCTGTGTG GTTTGCCAAA GGAAGTGATA CCAGCAAGAA ATTAATGGAC    4500

AAAACGAAAA GGGGAGGTCT TTTTAGTTAA GCTGGCAATT ACCAGAACAA TTATGTTTCT    4560

TGCTGTATTA TAAGAGGATA GCTATATTTT ATTTCTGAAG AGTAAGGAGT AGTATTTTGG    4620

CTTAAAAATC ATTCTAATTA CAAAGTTCAC TGTTTATTGA AGAACTGGCA TCTTAAATCA    4680

GCCTTCCGCA ATTCATGTAG TTTCTGGGTC TTCTGGGAGC CTACGTGAGT ACATCACCTA    4740

ACAGAATATT AAATTAGACT TCCTGTAAGA TTGCTTTAAG AAACTGTTAC TGTCCTGTTT    4800

TCTAATCTCT TTATTAAAAC AGTGTATTTG GAAAATGTTA TGTGCTCTGA TTTGATATAG    4860

ATAACAGATT AGTAGTTACA TGGTAATTAT GTGATATAAA ATATTCATAT ATTATCAAAA    4920

TTCTGTTTTG TAAATGTAAG AAAGCATAGT TATTTTACAA ATTGTTTTTA CTGTCTTTTG    4980

AAGAAGTTCT TAAATACGTT GTTAAATGGT ATTAGTTGAC CAGGGCAGTG AAAATGAAAC    5040

CGCATTTTGG GTGCCATTAA ATAGGGAAAA AACATGTAAA AAATGTAAAA TGGAGACCAA    5100

TTGCACTAGG CAAGTGTATA TTTTGTATTT TATATACAAT TTCTATTATT TTTCAAGTAA    5160
```

-continued

TAAAACAATG TTTTTCATAC TGAATATTAA AAAAAAAAAA AAAAAAAA     5208

(2) INFORMATION FOR SEQ ID NO: 71:

(i) SEQUENCE CHARACTERISTICS:
        (A) LENGTH: 1432 amino acids
        (B) TYPE: amino acid
        (C) STRANDEDNESS: <Unknown>
        (D) TOPOLOGY: linear (xi) SEQUENCE DESCRIPTION: SEQ ID NO: 71:

```
Met Ser Glu Lys Lys Leu Glu Thr Thr Ala Gln Gln Arg Lys Cys Pr
1               5                   10                  15

Glu Trp Met Asn Val Gln Asn Lys Arg Cys Ala Val Glu Glu Arg Ly
            20                  25                  30

Ala Cys Val Arg Lys Ser Val Phe Glu Asp Asp Leu Pro Phe Leu Gl
        35                  40                  45

Phe Thr Gly Ser Ile Val Tyr Ser Tyr Asp Ala Ser Asp Cys Ser Ph
    50                  55                  60

Leu Ser Glu Asp Ile Ser Met Ser Leu Ser Asp Gly Asp Val Val Gl
65                  70                  75                  80

Phe Asp Met Glu Trp Pro Pro Leu Tyr Asn Arg Gly Lys Leu Gly Ly
                85                  90                  95

Val Ala Leu Ile Gln Leu Cys Val Ser Glu Ser Lys Cys Tyr Leu Ph
            100                 105                 110

His Val Ser Ser Met Ser Val Phe Pro Gln Gly Leu Lys Met Leu Le
        115                 120                 125

Glu Asn Lys Ala Val Lys Lys Ala Gly Val Gly Ile Glu Gly Asp Gl
    130                 135                 140

Trp Lys Leu Leu Arg Asp Phe Asp Ile Lys Leu Lys Asn Phe Val Gl
145                 150                 155                 160

Leu Thr Asp Val Ala Asn Lys Lys Leu Lys Cys Thr Glu Thr Trp Se
                165                 170                 175

Leu Asn Ser Leu Val Lys His Leu Leu Gly Lys Gln Leu Leu Lys As
            180                 185                 190

Lys Ser Ile Arg Cys Ser Asn Trp Ser Lys Phe Pro Leu Thr Glu As
        195                 200                 205

Gln Lys Leu Tyr Ala Ala Thr Asp Ala Tyr Ala Gly Phe Ile Ile Ty
    210                 215                 220

Arg Asn Leu Glu Ile Leu Asp Asp Thr Val Gln Arg Phe Ala Ile As
225                 230                 235                 240

Lys Glu Glu Glu Ile Leu Leu Ser Asp Met Asn Lys Gln Leu Thr Se
                245                 250                 255

Ile Ser Glu Glu Val Met Asp Leu Ala Lys His Leu Pro His Ala Ph
            260                 265                 270

Ser Lys Leu Glu Asn Pro Arg Arg Val Ser Ile Leu Leu Lys Asp Il
        275                 280                 285

Ser Glu Asn Leu Tyr Ser Leu Arg Arg Met Ile Ile Gly Ser Thr As
    290                 295                 300

Ile Glu Thr Glu Leu Arg Pro Ser Asn Asn Leu Asn Leu Leu Ser Ph
305                 310                 315                 320

Glu Asp Ser Thr Thr Gly Gly Val Gln Gln Lys Gln Ile Arg Glu Hi
                325                 330                 335

Glu Val Leu Ile His Val Glu Asp Glu Thr Trp Asp Pro Thr Leu As
            340                 345                 350
```

```
His Leu Ala Lys His Asp Gly Glu Asp Val Leu Gly Asn Lys Val Gl
            355                 360                 365

Arg Lys Glu Asp Gly Phe Glu Asp Gly Val Glu Asp Asn Lys Leu Ly
        370                 375                 380

Glu Asn Met Glu Arg Ala Cys Leu Met Ser Leu Asp Ile Thr Glu Hi
385                 390                 395                 400

Glu Leu Gln Ile Leu Glu Gln Gln Ser Gln Glu Tyr Leu Ser As
                405                 410                 415

Ile Ala Tyr Lys Ser Thr Glu His Leu Ser Pro Asn Asp Asn Glu As
            420                 425                 430

Asp Thr Ser Tyr Val Ile Glu Ser Asp Glu Asp Leu Glu Met Glu Me
            435                 440                 445

Leu Lys His Leu Ser Pro Asn Asp Asn Glu Asn Asp Thr Ser Tyr Va
        450                 455                 460

Ile Glu Ser Asp Glu Asp Leu Glu Met Glu Met Leu Lys Ser Leu Gl
465                 470                 475                 480

Asn Leu Asn Ser Gly Thr Val Glu Pro Thr His Ser Lys Cys Leu Ly
                485                 490                 495

Met Glu Arg Asn Leu Gly Leu Pro Thr Lys Glu Glu Glu Glu Asp As
            500                 505                 510

Glu Asn Glu Ala Asn Glu Gly Glu Glu Asp Asp Lys Asp Phe Le
        515                 520                 525

Trp Pro Ala Pro Asn Glu Glu Gln Val Thr Cys Leu Lys Met Tyr Ph
        530                 535                 540

Gly His Ser Ser Phe Lys Pro Val Gln Trp Lys Val Ile His Ser Va
545                 550                 555                 560

Leu Glu Glu Arg Arg Asp Asn Val Ala Val Met Ala Thr Gly Tyr Gl
                565                 570                 575

Lys Ser Leu Cys Phe Gln Tyr Pro Pro Val Tyr Val Gly Lys Ile Gl
            580                 585                 590

Leu Val Ile Ser Pro Leu Ile Ser Leu Met Glu Asp Gln Val Leu Gl
        595                 600                 605

Leu Lys Met Ser Asn Ile Pro Ala Cys Phe Leu Gly Ser Ala Gln Se
    610                 615                 620

Glu Asn Val Leu Thr Asp Ile Lys Leu Gly Lys Tyr Arg Ile Val Ty
625                 630                 635                 640

Val Thr Pro Glu Tyr Cys Ser Gly Asn Met Gly Leu Leu Gln Gln Le
                645                 650                 655

Glu Ala Asp Ile Gly Ile Thr Leu Ile Ala Val Asp Glu Ala His Cy
            660                 665                 670

Ile Ser Glu Trp Gly His Asp Phe Arg Asp Ser Phe Arg Lys Leu Gl
        675                 680                 685

Ser Leu Lys Thr Ala Leu Pro Met Val Pro Ile Val Ala Leu Thr Al
    690                 695                 700

Thr Ala Ser Ser Ser Ile Arg Glu Asp Ile Val Arg Cys Leu Asn Le
705                 710                 715                 720

Arg Asn Pro Gln Ile Thr Cys Thr Gly Phe Asp Arg Pro Asn Leu Ty
                725                 730                 735

Leu Glu Val Arg Arg Lys Thr Gly Asn Ile Leu Gln Asp Leu Gln Pr
            740                 745                 750

Phe Leu Val Lys Thr Ser Ser His Trp Glu Phe Glu Gly Pro Thr Il
        755                 760                 765
```

-continued

```
Ile Tyr Cys Pro Ser Arg Lys Met Thr Gln Val Thr Gly Glu Le
    770                 775                 780

Arg Lys Leu Asn Leu Ser Cys Gly Thr Tyr His Ala Gly Met Ser Ph
785                 790                 795                 800

Ser Thr Arg Lys Asp Ile His His Arg Phe Val Arg Asp Glu Ile Gl
                805                 810                 815

Cys Val Ile Ala Thr Ile Ala Phe Gly Met Gly Ile Asn Lys Ala As
                820                 825                 830

Ile Arg Gln Val Ile His Tyr Gly Ala Pro Lys Asp Met Glu Ser Ty
            835                 840                 845

Tyr Gln Glu Ile Gly Arg Ala Gly Arg Asp Gly Leu Gln Ser Ser Cy
        850                 855                 860

His Val Leu Trp Ala Pro Ala Asp Ile Asn Leu Asn Arg His Leu Le
865                 870                 875                 880

Thr Glu Ile Arg Asn Glu Lys Phe Arg Leu Tyr Lys Leu Lys Met Me
                885                 890                 895

Ala Lys Met Glu Lys Tyr Leu His Ser Ser Arg Cys Arg Arg Gln Il
                900                 905                 910

Ile Leu Ser His Phe Glu Asp Lys Gln Val Gln Lys Ala Ser Leu Gl
            915                 920                 925

Ile Met Gly Thr Glu Lys Cys Cys Asp Asn Cys Arg Ser Arg Leu As
        930                 935                 940

His Cys Tyr Ser Met Asp Asp Ser Glu Asp Thr Ser Trp Asp Phe Gl
945                 950                 955                 960

Pro Gln Ala Phe Lys Leu Leu Ser Ala Val Asp Ile Leu Gly Glu Ly
                965                 970                 975

Phe Gly Ile Gly Leu Pro Ile Leu Phe Leu Arg Gly Ser Asn Ser Gl
                980                 985                 990

Arg Leu Ala Asp Gln Tyr Arg Arg His Ser Leu Phe Gly Thr Gly Ly
            995                 1000                1005

Asp Gln Thr Glu Ser Trp Trp Lys Ala Phe Ser Arg Gln Leu Ile Th
        1010                1015                1020

Glu Gly Phe Leu Val Glu Val Ser Arg Tyr Asn Lys Phe Met Lys Il
1025                1030                1035                1040

Cys Ala Leu Thr Lys Lys Gly Arg Asn Trp Leu His Lys Ala Asn Th
                1045                1050                1055

Glu Ser Gln Ser Leu Ile Leu Gln Ala Asn Glu Glu Leu Cys Pro Ly
                1060                1065                1070

Lys Phe Leu Leu Pro Ser Ser Lys Thr Val Ser Ser Gly Thr Lys Gl
            1075                1080                1085

His Cys Tyr Asn Gln Val Pro Val Glu Leu Ser Thr Glu Lys Lys Se
    1090                1095                1100

Asn Leu Glu Lys Leu Tyr Ser Tyr Lys Pro Cys Asp Lys Ile Ser Se
1105                1110                1115                1120

Gly Ser Asn Ile Ser Lys Lys Ser Ile Met Val Gln Ser Pro Glu Ly
                1125                1130                1135

Ala Tyr Ser Ser Ser Gln Pro Val Ile Ser Ala Gln Glu Gln Glu Th
                1140                1145                1150

Gln Ile Val Leu Tyr Gly Lys Leu Val Glu Ala Arg Gln Lys His Al
            1155                1160                1165

Asn Lys Met Asp Val Pro Pro Ala Ile Leu Ala Thr Asn Lys Ile Le
        1170                1175                1180
```

Val Asp Met Ala Lys Met Arg Pro Thr Thr Val Glu Asn Val Lys Ar
1185             1190            1195            1200

Ile Asp Gly Val Ser Glu Gly Lys Ala Ala Met Leu Ala Pro Leu Le
        1205            1210            1215

Glu Val Ile Lys His Phe Cys Gln Thr Asn Ser Val Gln Thr Asp Le
        1220            1225            1230

Phe Ser Ser Thr Lys Pro Gln Glu Glu Gln Lys Thr Ser Leu Val Al
        1235            1240            1245

Lys Asn Lys Ile Cys Thr Leu Ser Gln Ser Met Ala Ile Thr Tyr Se
        1250            1255            1260

Leu Phe Gln Glu Lys Lys Met Pro Leu Lys Ser Ile Ala Glu Ser Ar
1265            1270            1275            1280

Ile Leu Pro Leu Met Thr Ile Gly Met His Leu Ser Gln Ala Val Ly
        1285            1290            1295

Ala Gly Cys Pro Leu Asp Leu Glu Arg Ala Gly Leu Thr Pro Glu Va
        1300            1305            1310

Gln Lys Ile Ile Ala Asp Val Ile Arg Asn Pro Pro Val Asn Ser As
        1315            1320            1325

Met Ser Lys Ile Ser Leu Ile Arg Met Leu Val Pro Glu Asn Ile As
        1330            1335            1340

Thr Tyr Leu Ile His Met Ala Ile Glu Ile Leu Lys His Gly Pro As
1345            1350            1355            1360

Ser Gly Leu Gln Pro Ser Cys Asp Val Asn Lys Arg Arg Cys Phe Pr
        1365            1370            1375

Gly Ser Glu Glu Ile Cys Ser Ser Ser Lys Arg Ser Lys Glu Glu Va
        1380            1385            1390

Gly Ile Asn Thr Glu Thr Ser Ser Ala Glu Arg Lys Arg Arg Leu Pr
        1395            1400            1405

Val Trp Phe Ala Lys Gly Ser Asp Thr Ser Lys Lys Leu Met Asp Ly
        1410            1415            1420

Thr Lys Arg Gly Gly Leu Phe Ser
1425            1430

(2) INFORMATION FOR SEQ ID NO: 72:

(i) SEQUENCE CHARACTERISTICS:
        (A) LENGTH: 2178 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 313..1497

(xi) SEQUENCE DESCRIPTION: SEQ ID NO: 72:

TTTGGAATTG GGCTTCCAAT TTTATTTCTC CGAGGATCTG GTCTCACTCT GTTGCTCAGT      60

CTGTAGTGCA GTGGTGTCAT CATAGCTCAC TGCAGTCTTG ATCTCCTGAG CTCAAACGAT     120

TCTCCTGCCT CAGCTCCTGC TTCAGCCTCC TGAGTAGCGG AACAACAGAA TTCTCAGCGT     180

CTTGCCGATC AATATCGCAG GCACAGTTTA TTTGGCACTG GCAAGGATCA AACAGAGAGT     240

TGGTGGAAGG CTTTTTCCCG TCAGCTGATC ACTGAGGGAT TCTTGGTAGA AGTTTCTCGG     300

TATAACAAAT TT ATG AAG ATT TGC GCC CTT ACG AAA AAG GGT AGA AAT          348
            Met Lys Ile Cys Ala Leu Thr Lys Lys Gly Arg Asn
            1065                    1070

-continued

```
TGG CTT CAT AAA GCT AAT ACA GAA TCT CAG AGC CTC ATC CTT CAA GCT      396
Trp Leu His Lys Ala Asn Thr Glu Ser Gln Ser Leu Ile Leu Gln Ala
1075                1080                1085                1090

AAT GAA GAA TTG TGT CCA AAG AAG TTT CTT CTG CCT AGT TCG AAA ACT      444
Asn Glu Glu Leu Cys Pro Lys Lys Phe Leu Leu Pro Ser Ser Lys Thr
                1095                1100                1105

GTA TCT TCG GGC ACC AAA GAG CAT TGT TAT AAT CAA GTA CCA GTT GAA      492
Val Ser Ser Gly Thr Lys Glu His Cys Tyr Asn Gln Val Pro Val Glu
        1110                1115                1120

TTA AGT ACA GAG AAG AAG TCT AAC TTG GAG AAG TTA TAT TCT TAT AAA      540
Leu Ser Thr Glu Lys Lys Ser Asn Leu Glu Lys Leu Tyr Ser Tyr Lys
            1125                1130                1135

CCA TGT GAT AAG ATT TCT TCT GGG AGT AAC ATT TCT AAA AAA AGT ATC      588
Pro Cys Asp Lys Ile Ser Ser Gly Ser Asn Ile Ser Lys Lys Ser Ile
    1140                1145                1150

ATG GTA CAG TCA CCA GAA AAA GCT TAC AGT TCC TCA CAG CCT GTT ATT      636
Met Val Gln Ser Pro Glu Lys Ala Tyr Ser Ser Ser Gln Pro Val Ile
1155                1160                1165                1170

TCG GCA CAA GAG CAG GAG ACT CAG ATT GTG TTA TAT GGC AAA TTG GTA      684
Ser Ala Gln Glu Gln Glu Thr Gln Ile Val Leu Tyr Gly Lys Leu Val
                1175                1180                1185

GAA GCT AGG CAG AAA CAT GCC AAT AAA ATG GAT GTT CCC CCA GCT ATT      732
Glu Ala Arg Gln Lys His Ala Asn Lys Met Asp Val Pro Pro Ala Ile
        1190                1195                1200

CTG GCA ACA AAC AAG ATA CTG GTG GAT ATG GCC AAA ATG AGA CCA ACT      780
Leu Ala Thr Asn Lys Ile Leu Val Asp Met Ala Lys Met Arg Pro Thr
            1205                1210                1215

ACG GTT GAA AAC GTA AAA AGG ATT GAT GGT GTT TCT GAA GGC AAA GCT      828
Thr Val Glu Asn Val Lys Arg Ile Asp Gly Val Ser Glu Gly Lys Ala
    1220                1225                1230

GCC ATG TTG GCC CCT CTG TTG GAA GTC ATC AAA CAT TTC TGC CAA ACA      876
Ala Met Leu Ala Pro Leu Leu Glu Val Ile Lys His Phe Cys Gln Thr
1235                1240                1245                1250

AAT AGT GTT CAG ACA GAC CTC TTT TCA AGT ACA AAA CCT CAA GAA GAA      924
Asn Ser Val Gln Thr Asp Leu Phe Ser Ser Thr Lys Pro Gln Glu Glu
                1255                1260                1265

CAG AAG ACG AGT CTG GTA GCA AAA AAT AAA ATA TGC ACA CTT TCA CAG      972
Gln Lys Thr Ser Leu Val Ala Lys Asn Lys Ile Cys Thr Leu Ser Gln
        1270                1275                1280

TCT ATG GCC ATC ACA TAC TCT TTA TTC CAA GAA AAG AAG ATG CCT TTG     1020
Ser Met Ala Ile Thr Tyr Ser Leu Phe Gln Glu Lys Lys Met Pro Leu
            1285                1290                1295

AAG AGC ATA GCT GAG AGC AGG ATT CTG CCT CTC ATG ACA ATT GGC ATG     1068
Lys Ser Ile Ala Glu Ser Arg Ile Leu Pro Leu Met Thr Ile Gly Met
    1300                1305                1310

CAC TTA TCC CAA GCG GTG AAA GCT GGC TGC CCC CTT GAT TTG GAG CGA     1116
His Leu Ser Gln Ala Val Lys Ala Gly Cys Pro Leu Asp Leu Glu Arg
1315                1320                1325                1330

GCA GGC CTG ACT CCA GAG GTT CAG AAG ATT ATT GCT GAT GTT ATC CGA     1164
Ala Gly Leu Thr Pro Glu Val Gln Lys Ile Ile Ala Asp Val Ile Arg
                1335                1340                1345

AAC CCT CCC GTC AAC TCA GAT ATG AGT AAA ATT AGC CTA ATC AGA ATG     1212
Asn Pro Pro Val Asn Ser Asp Met Ser Lys Ile Ser Leu Ile Arg Met
        1350                1355                1360

TTA GTT CCT GAA AAC ATT GAC ACG TAC CTT ATC CAC ATG GCA ATT GAG     1260
Leu Val Pro Glu Asn Ile Asp Thr Tyr Leu Ile His Met Ala Ile Glu
            1365                1370                1375

ATC CTT AAA CAT GGT CCT GAC AGC GGA CTT CAA CCT TCA TGT GAT GTC     1308
Ile Leu Lys His Gly Pro Asp Ser Gly Leu Gln Pro Ser Cys Asp Val
    1380                1385                1390
```

```
AAC AAA AGG AGA TGT TTT CCC GGT TCT GAA GAG ATC TGT TCA AGT TCT        1356
Asn Lys Arg Arg Cys Phe Pro Gly Ser Glu Glu Ile Cys Ser Ser Ser
1395                1400                1405                1410

AAG AGA AGC AAG GAA GAA GTA GGC ATC AAT ACT GAG ACT TCA TCT GCA        1404
Lys Arg Ser Lys Glu Glu Val Gly Ile Asn Thr Glu Thr Ser Ser Ala
            1415                1420                1425

GAG AGA AAG AGA CGA TTA CCT GTG TGG TTT GCC AAA GGA AGT GAT ACC        1452
Glu Arg Lys Arg Arg Leu Pro Val Trp Phe Ala Lys Gly Ser Asp Thr
        1430                1435                1440

AGC AAG AAA TTA ATG GAC AAA ACG AAA AGG GGA GGT CTT TTT AGT            1497
Ser Lys Lys Leu Met Asp Lys Thr Lys Arg Gly Gly Leu Phe Ser
        1445                1450                1455

TAAGCTGGCA ATTACCAGAA CAATTATGTT TCTTGCTGTA TTATAAGAGG ATAGCTATAT      1557

TTTATTTCTG AAGAGTAAGG AGTAGTATTT TGGCTTAAAA ATCATTCTAA TTACAAAGTT      1617

CACTGTTTAT TGAAGAACTG GCATCTTAAA TCAGCCTTCC GCAATTCATG TAGTTTCTGG      1677

GTCTTCTGGG AGCCTACGTG AGTACATCAC CTAACAGAAT ATTAAATTAG ACTTCCTGTA      1737

AGATTGCTTT AAGAAACTGT TACTGTCCTG TTTTCTAATC TCTTTATTAA AACAGTGTAT      1797

TTGGAAAATG TTATGTGCTC TGATTTGATA TAGATAACAG ATTAGTAGTT ACATGGTAAT      1857

TATGTGATAT AAAATATTCA TATATTATCA AAATTCTGTT TTGTAAATGT AAGAAAGCAT      1917

AGTTATTTTA CAAATTGTTT TTACTGTCTT TTGAAGAAGT TCTTAAATAC GTTGTTAAAT      1977

GGTATTAGTT GACCAGGGCA GTGAAAATGA ACCGCATTT TGGGTGCCAT TAAATAGGGA       2037

AAAAACATGT AAAAAATGTA AAATGGAGAC CAATTGCACT AGGCAAGTGT ATATTTTGTA      2097

TTTTATATAC AATTTCTATT ATTTTTCAAG TAATAAAACA ATGTTTTTCA TACTGAATAT      2157

TAAAAAAAAA AAAAAAAAA A                                                 2178
```

(2) INFORMATION FOR SEQ ID NO: 73:

(i) SEQUENCE CHARACTERISTICS:
        (A) LENGTH: 395 amino acids
        (B) TYPE: amino acid
        (D) TOPOLOGY: linear (ii) MOLECULE TYPE: protein (xi) SEQUENCE DESCRIPTION: SEQ ID NO: 73:

```
Met Lys Ile Cys Ala Leu Thr Lys Lys Gly Arg Asn Trp Leu His Lys
 1               5                  10                  15

Ala Asn Thr Glu Ser Gln Ser Leu Ile Leu Gln Ala Asn Glu Glu Leu
            20                  25                  30

Cys Pro Lys Lys Phe Leu Leu Pro Ser Ser Lys Thr Val Ser Ser Gly
        35                  40                  45

Thr Lys Glu His Cys Tyr Asn Gln Val Pro Val Glu Leu Ser Thr Glu
    50                  55                  60

Lys Lys Ser Asn Leu Glu Lys Leu Tyr Ser Tyr Lys Pro Cys Asp Lys
65                  70                  75                  80

Ile Ser Ser Gly Ser Asn Ile Ser Lys Lys Ser Ile Met Val Gln Ser
                85                  90                  95

Pro Glu Lys Ala Tyr Ser Ser Ser Gln Pro Val Ile Ser Ala Gln Glu
            100                 105                 110

Gln Glu Thr Gln Ile Val Leu Tyr Gly Lys Leu Val Glu Ala Arg Gln
        115                 120                 125

Lys His Ala Asn Lys Met Asp Val Pro Pro Ala Ile Leu Ala Thr Asn
    130                 135                 140
```

```
Lys Ile Leu Val Asp Met Ala Lys Met Arg Pro Thr Thr Val Glu Asn
145                 150                 155                 160

Val Lys Arg Ile Asp Gly Val Ser Glu Gly Lys Ala Ala Met Leu Ala
                165                 170                 175

Pro Leu Leu Glu Val Ile Lys His Phe Cys Gln Thr Asn Ser Val Gln
                180                 185                 190

Thr Asp Leu Phe Ser Ser Thr Lys Pro Gln Glu Gln Lys Thr Ser
                195                 200                 205

Leu Val Ala Lys Asn Lys Ile Cys Thr Leu Ser Gln Ser Met Ala Ile
                210                 215                 220

Thr Tyr Ser Leu Phe Gln Glu Lys Lys Met Pro Leu Lys Ser Ile Ala
225                 230                 235                 240

Glu Ser Arg Ile Leu Pro Leu Met Thr Ile Gly Met His Leu Ser Gln
                245                 250                 255

Ala Val Lys Ala Gly Cys Pro Leu Asp Leu Glu Arg Ala Gly Leu Thr
                260                 265                 270

Pro Glu Val Gln Lys Ile Ile Ala Asp Val Ile Arg Asn Pro Pro Val
                275                 280                 285

Asn Ser Asp Met Ser Lys Ile Ser Leu Ile Arg Met Leu Val Pro Glu
290                 295                 300

Asn Ile Asp Thr Tyr Leu Ile His Met Ala Ile Glu Ile Leu Lys His
305                 310                 315                 320

Gly Pro Asp Ser Gly Leu Gln Pro Ser Cys Asp Val Asn Lys Arg Arg
                325                 330                 335

Cys Phe Pro Gly Ser Glu Glu Ile Cys Ser Ser Lys Arg Ser Lys
                340                 345                 350

Glu Glu Val Gly Ile Asn Thr Glu Thr Ser Ser Ala Glu Arg Lys Arg
                355                 360                 365

Arg Leu Pro Val Trp Phe Ala Lys Gly Ser Asp Thr Ser Lys Lys Leu
                370                 375                 380

Met Asp Lys Thr Lys Arg Gly Gly Leu Phe Ser
385                 390                 395

(2) INFORMATION FOR SEQ ID NO: 74:

(i) SEQUENCE CHARACTERISTICS:
        (A) LENGTH: 1269 amino acids
        (B) TYPE: amino acid
        (C) STRANDEDNESS: single
        (D) TOPOLOGY: linear (xi) SEQUENCE DESCRIPTION: SEQ ID NO: 74:

Glu Asp Gly Phe Glu Asp Gly Val Glu Asp Asn Lys Leu Lys Glu As
1               5                   10                  15

Met Glu Arg Ala Cys Leu Met Ser Leu Asp Ile Thr Glu His Glu Le
                20                  25                  30

Gln Ile Leu Glu Gln Gln Ser Gln Glu Glu Tyr Leu Ser Asp Ile Al
                35                  40                  45

Tyr Lys Ser Thr Glu His Leu Ser Pro Asn Asp Glu Asn Asp Th
    50                  55                  60

Ser Tyr Val Ile Glu Ser Asp Glu Asp Leu Glu Met Glu Met Leu Ly
65                  70                  75                  80

His Leu Ser Pro Asn Asp Asn Glu Asn Asp Thr Ser Tyr Val Ile Gl
                85                  90                  95

Ser Asp Glu Asp Leu Glu Met Glu Met Leu Lys Ser Leu Glu Asn Le
                100                 105                 110
```

```
Asn Ser Gly Thr Val Glu Pro Thr His Ser Lys Cys Leu Lys Met Gl
        115                 120                 125
Arg Asn Leu Gly Leu Pro Thr Lys Glu Glu Glu Asp Asp Glu As
130                 135                 140
Glu Ala Asn Glu Gly Glu Glu Asp Asp Asp Lys Asp Phe Leu Trp Pr
145                 150                 155                 160
Ala Pro Asn Glu Glu Gln Val Thr Cys Leu Lys Met Tyr Phe Gly Hi
                165                 170                 175
Ser Ser Phe Lys Pro Val Gln Trp Lys Val Ile His Ser Val Leu Gl
            180                 185                 190
Glu Arg Arg Asp Asn Val Ala Val Met Ala Thr Gly Tyr Gly Lys Se
        195                 200                 205
Leu Cys Phe Gln Tyr Pro Pro Val Tyr Val Gly Lys Ile Gly Leu Va
    210                 215                 220
Ile Ser Pro Leu Ile Ser Leu Met Glu Asp Gln Val Leu Gln Leu Ly
225                 230                 235                 240
Met Ser Asn Ile Pro Ala Cys Phe Leu Gly Ser Ala Gln Ser Glu As
                245                 250                 255
Val Leu Thr Asp Ile Lys Leu Gly Lys Tyr Arg Ile Val Tyr Val Th
            260                 265                 270
Pro Glu Tyr Cys Ser Gly Asn Met Gly Leu Leu Gln Gln Leu Glu Al
        275                 280                 285
Asp Ile Gly Ile Thr Leu Ile Ala Val Asp Glu Ala His Cys Ile Se
    290                 295                 300
Glu Trp Gly His Asp Phe Arg Asp Ser Phe Arg Lys Leu Gly Ser Le
305                 310                 315                 320
Lys Thr Ala Leu Pro Met Val Pro Ile Val Ala Leu Thr Ala Thr Al
                325                 330                 335
Ser Ser Ser Ile Arg Glu Asp Ile Val Arg Cys Leu Asn Leu Arg As
            340                 345                 350
Pro Gln Ile Thr Cys Thr Gly Phe Asp Arg Pro Asn Leu Tyr Leu Gl
        355                 360                 365
Val Arg Arg Lys Thr Gly Asn Ile Leu Gln Asp Leu Gln Pro Phe Le
    370                 375                 380
Val Lys Thr Ser Ser His Trp Glu Phe Glu Gly Pro Thr Ile Ile Ty
385                 390                 395                 400
Cys Pro Ser Arg Lys Met Thr Gln Gln Val Thr Gly Glu Leu Arg Ly
                405                 410                 415
Leu Asn Leu Ser Cys Gly Thr Tyr His Ala Gly Met Ser Phe Ser Th
            420                 425                 430
Arg Lys Asp Ile His His Arg Phe Val Arg Asp Glu Ile Gln Cys Va
        435                 440                 445
Ile Ala Thr Ile Ala Phe Gly Met Gly Ile Asn Lys Ala Asp Ile Ar
    450                 455                 460
Gln Val Ile His Tyr Gly Ala Pro Lys Asp Met Glu Ser Tyr Tyr Gl
465                 470                 475                 480
Glu Ile Gly Arg Ala Gly Arg Asp Gly Leu Gln Ser Ser Cys His Va
                485                 490                 495
Leu Trp Ala Pro Ala Asp Ile Asn Leu Asn Arg His Leu Leu Thr Gl
            500                 505                 510
Ile Arg Asn Glu Lys Phe Arg Leu Tyr Lys Leu Lys Met Met Ala Ly
        515                 520                 525
```

```
Met Glu Lys Tyr Leu His Ser Ser Arg Cys Arg Gln Ile Ile Le
    530                 535                 540
Ser His Phe Glu Asp Lys Gln Val Gln Lys Ala Ser Leu Gly Ile Me
545                 550                 555                 560
Gly Thr Glu Lys Cys Cys Asp Asn Cys Arg Ser Arg Leu Asp His Cy
                565                 570                 575
Tyr Ser Met Asp Asp Ser Glu Asp Thr Ser Trp Asp Phe Gly Pro Gl
            580                 585                 590
Ala Phe Lys Leu Leu Ser Ala Val Asp Ile Leu Gly Glu Lys Phe Gl
        595                 600                 605
Ile Gly Leu Pro Ile Leu Phe Leu Arg Gly Ser Asn Ser Gln Arg Le
    610                 615                 620
Ala Asp Gln Tyr Arg Arg His Ser Leu Phe Gly Thr Gly Lys Asp Gl
625                 630                 635                 640
Thr Glu Ser Trp Trp Lys Ala Phe Ser Arg Gln Leu Ile Thr Glu Gl
                645                 650                 655
Phe Leu Val Glu Val Ser Arg Tyr Asn Lys Phe Met Lys Ile Cys Al
            660                 665                 670
Leu Thr Lys Lys Gly Arg Asn Trp Leu His Lys Ala Asn Thr Glu Se
        675                 680                 685
Gln Ser Leu Ile Leu Gln Ala Asn Glu Glu Leu Cys Pro Lys Lys Ph
    690                 695                 700
Leu Leu Pro Ser Ser Lys Thr Val Ser Ser Gly Thr Lys Glu His Cy
705                 710                 715                 720
Tyr Asn Gln Val Pro Val Glu Leu Ser Thr Glu Lys Lys Ser Asn Le
                725                 730                 735
Glu Lys Leu Tyr Ser Tyr Lys Pro Cys Asp Lys Ile Ser Ser Gly Se
            740                 745                 750
Asn Ile Ser Lys Lys Ser Ile Met Val Gln Ser Pro Glu Lys Ala Ty
        755                 760                 765
Ser Ser Ser Gln Pro Val Ile Ser Ala Gln Glu Gln Glu Thr Gln Il
    770                 775                 780
Val Leu Tyr Gly Lys Leu Val Glu Ala Arg Gln Lys His Ala Asn Ly
785                 790                 795                 800
Met Asp Val Pro Pro Ala Ile Leu Ala Thr Asn Lys Ile Leu Val As
                805                 810                 815
Met Ala Lys Met Arg Pro Thr Thr Val Glu Asn Val Lys Arg Ile As
            820                 825                 830
Gly Val Ser Glu Gly Lys Ala Ala Met Leu Ala Pro Leu Leu Glu Va
        835                 840                 845
Ile Lys His Phe Cys Gln Thr Asn Ser Val Gln Thr Asp Leu Phe Se
    850                 855                 860
Ser Thr Lys Pro Gln Glu Glu Gln Lys Thr Ser Leu Val Ala Lys As
865                 870                 875                 880
Lys Ile Cys Thr Leu Ser Gln Ser Met Ala Ile Thr Tyr Ser Leu Ph
                885                 890                 895
Gln Glu Lys Lys Met Pro Leu Lys Ser Ile Ala Glu Ser Arg Ile Le
            900                 905                 910
Pro Leu Met Thr Ile Gly Met His Leu Ser Gln Ala Val Lys Ala Gl
        915                 920                 925
Cys Pro Leu Asp Leu Glu Arg Ala Gly Leu Thr Pro Glu Val Gln Ly
930                 935                 940
```

-continued

```
Ile Ile Ala Asp Val Ile Arg Asn Pro Pro Val Asn Ser Asp Met Se
945                 950                 955                 960

Lys Ile Ser Leu Ile Arg Met Leu Val Pro Glu Asn Ile Asp Thr Ty
            965                 970                 975

Leu Ile His Met Ala Ile Glu Ile Leu Lys His Gly Pro Asp Ser Gl
                980                 985                 990

Leu Gln Pro Ser Cys Asp Val Asn Lys Arg Arg Cys Phe Pro Gly Se
        995                 1000                1005

Glu Glu Ile Cys Ser Ser Lys Arg Ser Lys Glu Glu Val Gly Il
    1010                1015                1020

Asn Thr Glu Thr Ser Ser Ala Glu Arg Lys Arg Arg Leu Pro Val Tr
1025                1030                1035                1040

Phe Ala Lys Gly Ser Asp Thr Ser Lys Lys Leu Met Asp Lys Thr Ly
            1045                1050                1055

Arg Gly Gly Leu Phe Ser Ala Gly Asn Tyr Gln Asn Asn Tyr Val Se
            1060                1065                1070

Cys Cys Ile Ile Arg Gly Leu Tyr Phe Ile Ser Glu Glu Gly Val Va
            1075                1080                1085

Phe Trp Leu Lys Asn His Ser Asn Tyr Lys Val His Cys Leu Leu Ly
    1090                1095                1100

Asn Trp His Leu Lys Ser Ala Phe Arg Asn Ser Cys Ser Phe Trp Va
1105                1110                1115                1120

Phe Trp Glu Pro Thr Val His His Leu Thr Glu Tyr Ile Arg Leu Pr
            1125                1130                1135

Val Arg Leu Leu Glu Thr Val Thr Val Leu Phe Ser Asn Leu Phe Il
            1140                1145                1150

Lys Thr Val Tyr Leu Glu Asn Val Met Cys Ser Asp Leu Ile Ile Th
        1155                1160                1165

Asp Leu His Gly Asn Tyr Val Ile Asn Ile His Ile Leu Ser Lys Ph
        1170                1175                1180

Cys Phe Val Asn Val Arg Lys His Ser Tyr Phe Thr Asn Cys Phe Ty
1185                1190                1195                1200

Cys Leu Leu Lys Lys Phe Leu Asn Thr Leu Leu Asn Gly Ile Ser Pr
            1205                1210                1215

Gly Gln Lys Asn Arg Ile Leu Gly Ala Ile Lys Gly Lys Asn Met Ly
        1220                1225                1230

Met Asn Gly Asp Gln Leu His Ala Ser Val Tyr Phe Val Phe Tyr Il
        1235                1240                1245

Gln Phe Leu Leu Phe Phe Lys Asn Asn Val Phe His Thr Glu Tyr Ly
    1250                1255                1260

Lys Lys Lys Lys Lys
1265
```

(2) INFORMATION FOR SEQ ID NO: 75:

(i) SEQUENCE CHARACTERISTICS:
        (A) LENGTH: 607 amino acids
        (B) TYPE: amino acid
        (C) STRANDEDNESS: single
        (D) TOPOLOGY: linear (xi) SEQUENCE DESCRIPTION: SEQ ID NO: 75:

```
Ala Gln Ala Glu Val Leu Asn Leu Glu Ser Gly Ala Lys Gln Val Le
1               5                   10                  15

Gln Glu Thr Phe Gly Tyr Gln Gln Phe Arg Pro Gly Gln Glu Glu Il
            20                  25                  30
```

-continued

```
Ile Asp Thr Val Leu Ser Gly Arg Asp Cys Leu Val Val Met Pro Th
         35                  40                  45

Gly Gly Gly Lys Ser Leu Cys Tyr Gln Ile Pro Ala Leu Leu Leu As
     50                  55                  60

Gly Leu Thr Val Val Ser Pro Leu Ile Ser Leu Met Lys Asp Gl
65                  70                  75                  80

Val Asp Gln Leu Gln Ala Asn Gly Val Ala Ala Cys Leu Asn Se
                 85                  90                  95

Thr Gln Thr Arg Glu Gln Gln Leu Glu Val Met Thr Gly Cys Arg Th
             100                 105                 110

Gly Gln Ile Arg Leu Leu Tyr Ile Ala Pro Glu Arg Leu Met Leu As
         115                 120                 125

Asn Phe Leu Glu His Leu Ala His Trp Asn Pro Val Leu Leu Ala Va
     130                 135                 140

Asp Glu Ala His Cys Ile Ser Gln Trp Gly His Asp Phe Arg Pro Gl
145                 150                 155                 160

Tyr Ala Ala Leu Gly Gln Leu Arg Gln Arg Phe Pro Thr Leu Pro Ph
                 165                 170                 175

Met Ala Leu Thr Ala Thr Ala Asp Asp Thr Thr Arg Gln Asp Ile Va
             180                 185                 190

Arg Leu Leu Gly Leu Asn Asp Pro Leu Ile Gln Ile Ser Ser Phe As
         195                 200                 205

Arg Pro Asn Ile Arg Tyr Met Leu Met Glu Lys Phe Lys Pro Leu As
     210                 215                 220

Gln Leu Met Arg Tyr Val Gln Glu Gln Arg Gly Lys Ser Gly Ile Il
225                 230                 235                 240

Tyr Cys Asn Ser Arg Ala Lys Val Glu Asp Thr Ala Ala Ala Leu Gl
                 245                 250                 255

Ser Lys Gly Ile Ser Ala Ala Tyr His Ala Gly Leu Glu Asn As
             260                 265                 270

Val Arg Ala Asp Val Gln Glu Lys Phe Gln Arg Asp Leu Gln Il
         275                 280                 285

Val Val Ala Thr Val Ala Phe Gly Met Gly Ile Asn Lys Pro Asn Va
     290                 295                 300

Arg Phe Val Val His Phe Asp Ile Pro Arg Asn Ile Glu Ser Tyr Ty
305                 310                 315                 320

Gln Glu Thr Gly Arg Ala Gly Arg Asp Gly Leu Pro Ala Glu Ala Me
                 325                 330                 335

Leu Phe Tyr Asp Pro Ala Asp Met Ala Trp Leu Arg Arg Cys Leu Gl
             340                 345                 350

Glu Lys Pro Gln Gly Gln Leu Gln Asp Ile Glu Arg His Lys Leu As
         355                 360                 365

Ala Met Gly Ala Phe Ala Glu Ala Gln Thr Cys Arg Arg Leu Val Le
     370                 375                 380

Leu Asn Tyr Phe Gly Glu Gly Arg Gln Glu Pro Cys Gly Asn Cys As
385                 390                 395                 400

Ile Cys Leu Asp Pro Pro Lys Gln Tyr Asp Gly Ser Thr Asp Ala Gl
                 405                 410                 415

Ile Ala Leu Ser Thr Ile Gly Arg Val Asn Gln Arg Phe Gly Met Gl
             420                 425                 430

Tyr Val Val Glu Val Ile Arg Gly Ala Asn Asn Gln Arg Ile Arg As
         435                 440                 445
```

```
Tyr Gly His Asp Lys Leu Lys Val Tyr Gly Met Gly Arg Asp Lys Se
    450                 455                 460
His Glu His Trp Val Ser Val Ile Arg Gln Leu Ile His Leu Gly Le
465                 470                 475                 480
Val Thr Gln Asn Ile Ala Gln His Ser Ala Leu Gln Leu Thr Glu Al
                    485                 490                 495
Ala Arg Pro Val Leu Ala Glu Ser Ser Leu Gln Leu Ala Val Pro Ar
                500                 505                 510
Ile Val Ala Leu Lys Pro Lys Ala Met Gln Lys Ser Phe Gly Gly As
                515                 520                 525
Tyr Asp Arg Lys Leu Phe Ala Lys Leu Arg Lys Leu Arg Lys Ser Il
                530                 535                 540
Ala Asp Glu Ser Asn Val Pro Pro Tyr Val Val Phe Asn Asp Ala Th
545                 550                 555                 560
Leu Ile Glu Met Ala Glu Gln Met Pro Ile Thr Ala Ser Glu Met Le
                565                 570                 575
Ser Val Asn Gly Val Gly Met Arg Lys Leu Glu Arg Phe Gly Lys Pr
                580                 585                 590
Phe Met Ala Leu Ile Arg Ala His Val Asp Gly Asp Glu Glu
                595                 600                 605

(2) INFORMATION FOR SEQ ID NO: 76:

(i) SEQUENCE CHARACTERISTICS:
        (A) LENGTH: 1328 amino acids
        (B) TYPE: amino acid
        (C) STRANDEDNESS: single
        (D) TOPOLOGY: linear (xi) SEQUENCE DESCRIPTION: SEQ ID NO: 76:

Met Thr Val Thr Lys Thr Asn Leu Asn Arg His Leu Asp Trp Phe Ph
1               5                   10                  15
Arg Glu Ser Pro Gln Lys Ile Glu Asn Val Thr Ser Pro Ile Lys Th
                20                  25                  30
Leu Asp Phe Val Lys Val Lys Val Ser Ser Ser Asp Ile Val Val Ly
                35                  40                  45
Asp Ser Ile Pro His Lys Ser Lys Asn Val Phe Asp Asp Phe Asp As
    50                  55                  60
Gly Tyr Ala Ile Asp Leu Thr Glu Glu His Gln Ser Ser Ser Leu As
65                  70                  75                  80
Asn Leu Lys Trp Lys Asp Val Glu Gly Pro Asn Ile Leu Lys Pro Il
                85                  90                  95
Lys Lys Ile Ala Val Pro Ala Ser Glu Ser Glu Asp Phe Asp As
                100                 105                 110
Val Asp Glu Glu Met Leu Arg Ala Ala Glu Met Glu Val Phe Gln Se
                115                 120                 125
Cys Gln Pro Leu Ala Val Asn Thr Ala Asp Thr Thr Val Ser His Se
    130                 135                 140
Thr Ser Ser Ser Asn Val Pro Arg Ser Leu Asn Lys Ile His Asp Pr
145                 150                 155                 160
Ser Arg Phe Ile Lys Asp Asn Asp Val Glu Asn Arg Ile His Val Se
                165                 170                 175
Ser Ala Ser Lys Val Ala Ser Ile Ser Asn Thr Ser Lys Pro Asn Pr
                180                 185                 190
Ile Val Ser Glu Asn Pro Ile Ser Ala Thr Ser Val Ser Ile Glu Il
                195                 200                 205
```

```
Pro Ile Lys Pro Lys Glu Leu Ser Asn Asn Leu Pro Phe Pro Arg Le
    210                 215                 220
Asn Asn Asn Asn Thr Asn Asn Asn Asp Asn Asn Ala Ile Glu Ly
225                 230                 235                 240
Arg Asp Ser Ala Ser Pro Thr Pro Ser Ser Val Ser Ser Gln Ile Se
                245                 250                 255
Ile Asp Phe Ser Thr Trp Pro His Gln Asn Leu Leu Gln Tyr Leu As
            260                 265                 270
Ile Leu Arg Asp Glu Lys Ser Glu Ile Ser Asp Arg Ile Ile Glu Va
        275                 280                 285
Met Glu Arg Tyr Pro Phe Ser Ser Arg Phe Lys Glu Trp Ile Pro Ly
    290                 295                 300
Arg Asp Ile Leu Ser Gln Lys Ile Ser Ser Val Leu Glu Val Leu Se
305                 310                 315                 320
Asn Asn Asn Asn Ser Asn Asn Asn Asn Gly Asn Asn Gly Thr Val Pr
                325                 330                 335
Asn Ala Lys Thr Phe Phe Thr Pro Pro Ser Ser Ile Thr Gln Gln Va
            340                 345                 350
Pro Phe Pro Ser Thr Ile Ile Pro Glu Ser Thr Val Lys Glu Asn Se
        355                 360                 365
Thr Arg Pro Tyr Val Asn Ser His Leu Val Ala Asn Asp Lys Ile Th
    370                 375                 380
Ala Thr Pro Phe His Ser Glu Ala Val Val Ser Pro Leu Gln Ser As
385                 390                 395                 400
Ile Arg Asn Ser Asp Ile Ala Glu Phe Asp Glu Phe Asp Ile Asp As
                405                 410                 415
Ala Asp Phe Thr Phe Asn Thr Thr Asp Pro Ile Asn Asp Glu Ser Gl
            420                 425                 430
Ala Ser Ser Asp Val Val Ile Asp Asp Glu Glu Asp Asp Ile Gl
        435                 440                 445
Asn Arg Pro Leu Asn Gln Ala Leu Lys Ala Ser Lys Ala Ala Val Se
    450                 455                 460
Asn Ala Ser Leu Leu Gln Ser Ser Ser Leu Asp Arg Pro Leu Leu Gl
465                 470                 475                 480
Glu Met Lys Asp Lys Asn His Lys Val Leu Met Pro Ser Leu Asp As
                485                 490                 495
Pro Met Leu Ser Tyr Pro Trp Ser Lys Glu Val Leu Gly Cys Leu Ly
            500                 505                 510
His Lys Phe His Leu Lys Gly Phe Arg Lys Asn Gln Leu Glu Ala Il
        515                 520                 525
Asn Gly Thr Leu Ser Gly Lys Asp Val Phe Ile Leu Met Pro Thr Gl
    530                 535                 540
Gly Gly Lys Ser Leu Cys Tyr Gln Leu Pro Ala Val Ile Glu Gly Gl
545                 550                 555                 560
Ala Ser Arg Gly Val Thr Leu Val Ile Ser Pro Leu Leu Ser Leu Me
                565                 570                 575
Gln Asp Gln Leu Asp His Leu Arg Lys Leu Asn Ile Pro Ser Leu Pr
            580                 585                 590
Leu Ser Gly Glu Gln Pro Ala Asp Glu Arg Arg Gln Val Ile Ser Ph
        595                 600                 605
Leu Met Ala Lys Asn Val Leu Val Lys Leu Leu Tyr Val Thr Pro Gl
    610                 615                 620
```

```
-continued

Gly Leu Ala Ser Asn Gly Ala Ile Thr Arg Val Leu Lys Ser Leu Ty
625                 630                 635                 640

Glu Arg Lys Leu Leu Ala Arg Ile Val Ile Asp Glu Ala His Cys Va
                645                 650                 655

Ser His Trp Gly His Asp Phe Arg Pro Asp Tyr Lys Gln Leu Gly Le
            660                 665                 670

Leu Arg Asp Arg Tyr Gln Gly Ile Pro Phe Met Ala Leu Thr Ala Th
        675                 680                 685

Ala Asn Glu Ile Val Lys Lys Asp Ile Ile Asn Thr Leu Arg Met Gl
690                 695                 700

Asn Cys Leu Glu Leu Lys Ser Ser Phe Asn Arg Pro Asn Leu Phe Ty
705                 710                 715                 720

Glu Ile Lys Pro Lys Lys Asp Leu Tyr Thr Glu Leu Tyr Arg Phe Il
                725                 730                 735

Ser Asn Gly His Leu His Glu Ser Gly Ile Ile Tyr Cys Leu Ser Ar
            740                 745                 750

Thr Ser Cys Glu Gln Val Ala Ala Lys Leu Arg Asn Asp Tyr Gly Le
        755                 760                 765

Lys Ala Trp His Tyr His Ala Gly Leu Glu Lys Val Glu Arg Gln Ar
770                 775                 780

Ile Gln Asn Glu Trp Gln Ser Gly Ser Tyr Lys Ile Ile Val Ala Th
785                 790                 795                 800

Ile Ala Phe Gly Met Gly Val Asp Lys Gly Asp Val Arg Phe Val Il
                805                 810                 815

His His Ser Phe Pro Lys Ser Leu Glu Gly Tyr Tyr Gln Glu Thr Gl
            820                 825                 830

Arg Ala Gly Arg Asp Gly Lys Pro Ala His Cys Ile Met Phe Tyr Se
        835                 840                 845

Tyr Lys Asp His Val Thr Phe Gln Lys Leu Ile Met Ser Gly Asp Gl
850                 855                 860

Asp Ala Glu Thr Lys Glu Arg Gln Arg Gln Met Leu Arg Gln Val Il
865                 870                 875                 880

Gln Phe Cys Glu Asn Lys Thr Asp Cys Arg Arg Lys Gln Val Leu Al
                885                 890                 895

Tyr Phe Gly Glu Asn Phe Asp Lys Val His Cys Arg Lys Gly Cys As
            900                 905                 910

Ile Cys Cys Glu Glu Ala Thr Tyr Ile Lys Gln Asp Met Thr Glu Ph
        915                 920                 925

Ser Leu Gln Ala Ile Lys Leu Leu Lys Ser Ile Ser Gly Lys Ala Th
930                 935                 940

Leu Leu Gln Leu Met Asp Ile Phe Arg Gly Ser Lys Ser Ala Lys Il
945                 950                 955                 960

Val Glu Asn Gly Trp Asp Arg Leu Glu Gly Ala Gly Val Gly Lys Le
                965                 970                 975

Leu Asn Arg Gly Asp Ser Glu Arg Leu Phe His His Leu Val Ser Gl
            980                 985                 990

Gly Val Phe Val Glu Lys Val Glu Ala Asn Arg Arg Gly Phe Val Se
        995                 1000                1005

Ala Tyr Val Val Pro Gly Arg Gln Thr Ile Ile Asn Ser Val Leu Al
            1010                1015                1020

Gly Lys Arg Arg Ile Ile Leu Asp Val Lys Glu Ser Ser Ser Lys Pr
1025                1030                1035                1040
```

```
Asp Thr Ser Ser Arg Ser Leu Ser Arg Ser Lys Thr Leu Pro Ala Le
                1045                1050                1055

Arg Glu Tyr Gln Leu Lys Ser Thr Thr Ala Ser Val Asp Cys Ser Il
                1060                1065                1070

Gly Thr Arg Glu Val Asp Glu Ile Tyr Asp Ser Gln Met Pro Pro Va
                1075                1080                1085

Lys Pro Ser Leu Ile His Ser Arg Asn Lys Ile Asp Leu Glu Glu Le
                1090                1095                1100

Ser Gly Gln Lys Phe Met Ser Glu Tyr Glu Ile Asp Val Met Thr Ar
1105                1110                1115                1120

Cys Leu Lys Asp Leu Lys Leu Leu Arg Ser Asn Leu Met Ala Ile As
                1125                1130                1135

Asp Ser Arg Val Ser Ser Tyr Phe Thr Asp Ser Val Leu Leu Ser Me
                1140                1145                1150

Ala Lys Lys Leu Pro Arg Asn Val Lys Glu Leu Lys Glu Ile His Gl
                1155                1160                1165

Val Ser Asn Glu Lys Ala Val Asn Leu Gly Pro Lys Phe Leu Gln Va
                1170                1175                1180

Ile Gln Lys Phe Ile Asp Glu Lys Glu Gln Asn Leu Glu Gly Thr Gl
1185                1190                1195                1200

Leu Asp Pro Ser Leu Gln Ser Leu Asp Thr Asp Tyr Pro Ile Asp Th
                1205                1210                1215

Asn Ala Leu Ser Leu Asp His Glu Gln Gly Phe Ser Asp Asp Ser As
                1220                1225                1230

Ser Val Tyr Glu Pro Ser Ser Pro Ile Glu Glu Gly Asp Glu Glu Va
                1235                1240                1245

Asp Gly Gln Arg Lys Asp Ile Leu Asn Phe Met Asn Ser Gln Ser Le
                1250                1255                1260

Thr Gln Thr Gly Ser Val Pro Lys Arg Lys Ser Thr Ser Tyr Thr Ar
1265                1270                1275                1280

Pro Ser Lys Ser Tyr Arg His Lys Arg Gly Ser Thr Ser Tyr Ser Ar
                1285                1290                1295

Lys Arg Lys Tyr Ser Thr Ser Gln Lys Asp Ser Arg Lys Thr Ser Ly
                1300                1305                1310

Ser Ala Asn Thr Ser Phe Ile His Pro Met Val Lys Gln Asn Tyr Ar
                1315                1320                1325

(2) INFORMATION FOR SEQ ID NO: 77:

(i) SEQUENCE CHARACTERISTICS:
        (A) LENGTH: 659 amino acids
        (B) TYPE: amino acid
        (C) STRANDEDNESS: single
        (D) TOPOLOGY: linear (xi) SEQUENCE DESCRIPTION: SEQ ID NO: 77:

Met Ala Ser Val Ser Ala Leu Thr Glu Glu Leu Asp Ser Ile Thr Se
1               5                   10                  15

Glu Leu His Ala Val Glu Ile Gln Ile Gln Glu Leu Thr Glu Arg Gl
                20                  25                  30

Gln Glu Leu Ile Gln Lys Lys Val Leu Thr Lys Lys Ile Lys Gl
                35                  40                  45

Cys Leu Glu Asp Ser Asp Ala Gly Ala Ser Asn Glu Tyr Asp Ser Se
                50                  55                  60

Pro Ala Ala Trp Asn Lys Glu Asp Phe Pro Trp Ser Gly Lys Val Ly
65                  70                  75                  80
```

-continued

```
Asp Ile Leu Gln Asn Val Phe Lys Leu Glu Lys Phe Arg Pro Leu Gl
                85                  90                  95

Leu Glu Thr Ile Asn Val Thr Met Ala Gly Lys Glu Val Phe Leu Va
                100                 105                 110

Met Pro Thr Gly Gly Lys Ser Leu Cys Tyr Gln Leu Pro Ala Le
            115                 120                 125

Cys Ser Asp Gly Phe Thr Leu Val Ile Cys Pro Leu Ile Ser Leu Me
    130                 135                 140

Glu Asp Gln Leu Met Val Leu Lys Gln Leu Gly Ile Ser Ala Thr Me
145                 150                 155                 160

Leu Asn Ala Ser Ser Lys Glu His Val Lys Trp Val His Asp Gl
                165                 170                 175

Met Val Asn Lys Asn Ser Glu Leu Lys Leu Ile Tyr Val Thr Pro Gl
                180                 185                 190

Lys Ile Ala Lys Ser Lys Met Phe Met Ser Arg Leu Glu Lys Ala Ty
                195                 200                 205

Glu Ala Arg Arg Phe Thr Arg Ile Ala Val Asp Glu Val His Cys Cy
    210                 215                 220

Ser Gln Trp Gly His Asp Phe Arg Pro Asp Tyr Lys Ala Leu Gly Il
225                 230                 235                 240

Leu Lys Arg Gln Phe Pro Asn Ala Ser Leu Ile Gly Leu Thr Ala Th
                245                 250                 255

Ala Thr Asn His Val Leu Thr Asp Ala Gln Lys Ile Leu Cys Ile Gl
                260                 265                 270

Lys Cys Phe Thr Phe Thr Ala Ser Phe Asn Arg Pro Asn Leu Tyr Ty
                275                 280                 285

Glu Val Arg Gln Lys Pro Ser Asn Thr Glu Asp Phe Ile Glu Asp Il
                290                 295                 300

Val Lys Leu Ile Asn Gly Arg Tyr Lys Gly Gln Ser Gly Ile Ile Ty
305                 310                 315                 320

Cys Phe Ser Gln Lys Asp Ser Glu Gln Val Thr Val Ser Leu Gln As
                325                 330                 335

Leu Gly Ile His Ala Gly Ala Tyr His Ala Asn Leu Glu Pro Glu As
                340                 345                 350

Lys Thr Thr Val His Arg Lys Trp Ser Ala Asn Glu Ile Gln Val Va
                355                 360                 365

Val Ala Thr Val Ala Phe Gly Met Gly Ile Asp Lys Pro Asp Val Ar
    370                 375                 380

Phe Val Ile His His Ser Met Ser Lys Ser Met Glu Asn Tyr Tyr Gl
385                 390                 395                 400

Glu Ser Gly Arg Ala Gly Arg Asp Asp Met Lys Ala Asp Cys Ile Le
                405                 410                 415

Tyr Tyr Gly Phe Gly Asp Ile Phe Arg Ile Ser Ser Met Val Val Me
                420                 425                 430

Glu Asn Val Gly Gln Gln Lys Leu Tyr Glu Met Val Ser Tyr Cys Gl
                435                 440                 445

Asn Ile Ser Lys Ser Arg Arg Val Leu Met Ala Gln His Phe Asp Gl
                450                 455                 460

Val Trp Asn Ser Glu Ala Cys Asn Lys Met Cys Asp Asn Cys Cys Ly
465                 470                 475                 480

Asp Ser Ala Phe Glu Arg Thr Asn Ile Thr Glu Tyr Cys Arg Asp Le
                485                 490                 495
```

```
Ile Lys Ile Leu Lys Gln Ala Glu Glu Leu Asn Glu Lys Leu Thr Pr
                500                 505                 510
Leu Lys Leu Ile Asp Ser Trp Met Gly Lys Gly Ala Ala Lys Leu Ar
            515                 520                 525
Val Ala Gly Val Val Ala Pro Thr Leu Pro Arg Glu Asp Leu Glu Ly
        530                 535                 540
Ile Ile Ala His Phe Leu Ile Gln Gln Tyr Leu Lys Glu Asp Tyr Se
545                 550                 555                 560
Phe Thr Ala Tyr Ala Ala Ile Ser Tyr Leu Lys Ile Gly Pro Lys Al
                565                 570                 575
Asn Leu Leu Asn Asn Glu Ala His Ala Ile Thr Met Gln Val Thr Ly
                580                 585                 590
Ser Thr Gln Asn Ser Phe Arg Ala Glu Ser Ser Gln Thr Cys His Se
                595                 600                 605
Glu Gln Gly Asp Lys Lys Asn Gly Gly Lys Lys Ile Gln Ala Thr Se
                610                 615                 620
Arg Arg Arg Leu Gln Thr Cys Phe Ser Asn Leu Val Leu Arg Ile Gl
625                 630                 635                 640
Glu Leu Arg Lys Glu Lys Ser Met Met Pro Asp Met Asn Val Thr Ly
                645                 650                 655
Phe Ser Asn
```

(2) INFORMATION FOR SEQ ID NO: 78:

(i) SEQUENCE CHARACTERISTICS:
        (A) LENGTH: 1417 amino acids
        (B) TYPE: amino acid
        (C) STRANDEDNESS: single
        (D) TOPOLOGY: linear (xi) SEQUENCE DESCRIPTION: SEQ ID NO: 78:

```
Met Ala Ala Val Pro Gln Asn Asn Leu Gln Glu Gln Leu Glu Arg Hi
1               5                   10                  15
Ser Ala Arg Thr Leu Asn Asn Lys Leu Ser Leu Ser Lys Pro Lys Ph
                20                  25                  30
Ser Gly Phe Thr Phe Lys Lys Lys Thr Ser Ser Asp Asn Asn Val Se
            35                  40                  45
Val Thr Asn Val Ser Val Ala Lys Thr Pro Val Leu Arg Asn Lys As
        50                  55                  60
Val Asn Val Thr Glu Asp Phe Ser Phe Ser Glu Pro Leu Pro Asn Th
65                  70                  75                  80
Thr Asn Gln Gln Arg Val Lys Asp Phe Phe Lys Asn Ala Pro Ala Gl
                85                  90                  95
Gln Glu Thr Gln Arg Gly Gly Ser Lys Ser Leu Leu Pro Asp Phe Le
                100                 105                 110
Gln Thr Pro Lys Glu Val Val Cys Thr Thr Gln Asn Thr Pro Thr Va
            115                 120                 125
Lys Lys Ser Arg Asp Thr Ala Leu Lys Lys Leu Glu Phe Ser Ser Se
        130                 135                 140
Pro Asp Ser Leu Ser Thr Ile Asn Asp Trp Asp Asp Met Asp Asp Ph
145                 150                 155                 160
Asp Thr Ser Glu Thr Ser Lys Ser Phe Val Thr Pro Pro Gln Ser Hi
                165                 170                 175
Phe Val Arg Val Ser Thr Ala Gln Lys Ser Lys Lys Gly Lys Arg As
                180                 185                 190
```

-continued

```
Phe Phe Lys Ala Gln Leu Tyr Thr Thr Asn Thr Val Lys Thr Asp Le
        195                 200                 205

Pro Pro Pro Ser Ser Glu Ser Glu Gln Ile Asp Leu Thr Glu Glu Gl
210                 215                 220

Lys Asp Asp Ser Glu Trp Leu Ser Ser Asp Val Ile Cys Ile Asp As
225                 230                 235                 240

Gly Pro Ile Ala Glu Val His Ile Asn Glu Asp Ala Gln Glu Ser As
                245                 250                 255

Ser Leu Lys Thr His Leu Glu Asp Glu Arg Asp Asn Ser Glu Lys Ly
                260                 265                 270

Lys Asn Leu Glu Glu Ala Glu Leu His Ser Thr Glu Lys Val Pro Cy
            275                 280                 285

Ile Glu Phe Asp Asp Asp Tyr Asp Thr Asp Phe Val Pro Pro Se
    290                 295                 300

Pro Glu Glu Ile Ile Ser Ala Ser Ser Ser Ser Lys Cys Leu Se
305                 310                 315                 320

Thr Leu Lys Asp Leu Asp Thr Ser Asp Arg Lys Glu Asp Val Leu Se
                325                 330                 335

Thr Ser Lys Asp Leu Leu Ser Lys Pro Glu Lys Met Ser Met Gln Gl
                340                 345                 350

Leu Asn Pro Glu Thr Ser Thr Asp Cys Asp Ala Arg Gln Ile Ser Le
            355                 360                 365

Gln Gln Gln Leu Ile His Val Met Glu His Ile Cys Lys Leu Ile As
    370                 375                 380

Thr Ile Pro Asp Asp Lys Leu Lys Leu Leu Asp Cys Gly Asn Glu Le
385                 390                 395                 400

Leu Gln Gln Arg Asn Ile Arg Arg Lys Leu Leu Thr Glu Val Asp Ph
                405                 410                 415

Asn Lys Ser Asp Ala Ser Leu Leu Gly Ser Leu Trp Arg Tyr Arg Pr
                420                 425                 430

Asp Ser Leu Asp Gly Pro Met Glu Gly Asp Ser Cys Pro Thr Gly As
            435                 440                 445

Ser Met Lys Glu Leu Asn Phe Ser His Leu Pro Ser Asn Ser Val Se
    450                 455                 460

Pro Gly Asp Cys Leu Leu Thr Thr Leu Gly Lys Thr Gly Phe Se
465                 470                 475                 480

Ala Thr Arg Lys Asn Leu Phe Glu Arg Pro Leu Phe Asn Thr His Le
                485                 490                 495

Gln Lys Ser Phe Val Ser Ser Asn Trp Ala Glu Thr Pro Arg Leu Gl
            500                 505                 510

Lys Lys Asn Glu Ser Ser Tyr Phe Pro Gly Asn Val Leu Thr Ser Th
            515                 520                 525

Ala Val Lys Asp Gln Asn Lys His Thr Ala Ser Ile Asn Asp Leu Gl
        530                 535                 540

Arg Glu Thr Gln Pro Ser Tyr Asp Ile Asp Asn Phe Asp Ile Asp As
545                 550                 555                 560

Phe Asp Asp Asp Asp Trp Glu Asp Ile Met His Asn Leu Ala Al
                565                 570                 575

Ser Lys Ser Ser Thr Ala Ala Tyr Gln Pro Ile Lys Glu Gly Arg Pr
            580                 585                 590

Ile Lys Ser Val Ser Glu Arg Leu Ser Ser Ala Lys Thr Asp Cys Le
            595                 600                 605
```

-continued

```
Pro Val Ser Ser Thr Ala Gln Asn Ile Asn Phe Ser Glu Ser Ile Gl
    610                 615                 620
Asn Tyr Thr Asp Lys Ser Ala Gln Asn Leu Ala Ser Arg Asn Leu Ly
625                 630                 635                 640
His Glu Arg Phe Gln Ser Leu Ser Phe Pro His Thr Lys Glu Met Me
                645                 650                 655
Lys Ile Phe His Lys Lys Phe Gly Leu His Asn Phe Arg Thr Asn Gl
                660                 665                 670
Leu Glu Ala Ile Asn Ala Ala Leu Leu Gly Glu Asp Cys Phe Ile Le
                675                 680                 685
Met Pro Thr Gly Gly Gly Lys Ser Leu Cys Tyr Gln Leu Pro Ala Cy
    690                 695                 700
Val Ser Pro Gly Val Thr Val Val Ile Ser Pro Leu Arg Ser Leu Il
705                 710                 715                 720
Val Asp Gln Val Gln Lys Leu Thr Ser Leu Asp Ile Pro Ala Thr Ty
                725                 730                 735
Leu Thr Gly Asp Lys Thr Asp Ser Glu Ala Thr Asn Ile Tyr Leu Gl
                740                 745                 750
Leu Ser Lys Lys Asp Pro Ile Ile Lys Leu Leu Tyr Val Thr Pro Gl
                755                 760                 765
Lys Ile Cys Ala Ser Asn Arg Leu Ile Ser Thr Leu Glu Asn Leu Ty
770                 775                 780
Glu Arg Lys Leu Leu Ala Arg Phe Val Ile Asp Glu Ala His Cys Va
785                 790                 795                 800
Ser Gln Trp Gly His Asp Phe Arg Gln Asp Tyr Lys Arg Met Asn Me
                805                 810                 815
Leu Arg Gln Lys Phe Pro Ser Val Pro Val Met Ala Leu Thr Ala Th
                820                 825                 830
Ala Asn Pro Arg Val Gln Lys Asp Ile Leu Thr Gln Leu Lys Ile Le
                835                 840                 845
Arg Pro Gln Val Phe Ser Met Ser Phe Asn Arg His Asn Leu Lys Ty
    850                 855                 860
Tyr Val Leu Pro Lys Lys Pro Lys Lys Val Ala Phe Asp Cys Leu Gl
865                 870                 875                 880
Trp Ile Arg Lys His His Pro Tyr Asp Ser Gly Ile Ile Tyr Cys Le
                885                 890                 895
Ser Arg Arg Glu Cys Asp Thr Met Ala Asp Thr Leu Gln Arg Asp Gl
                900                 905                 910
Leu Ala Ala Leu Ala Tyr His Ala Gly Leu Ser Asp Ser Ala Arg As
                915                 920                 925
Glu Val Gln Gln Lys Trp Ile Asn Gln Asp Gly Cys Gln Val Ile Cy
    930                 935                 940
Ala Thr Ile Ala Phe Gly Met Gly Ile Asp Lys Pro Asp Val Arg Ph
945                 950                 955                 960
Val Ile His Ala Ser Leu Pro Lys Ser Val Glu Gly Tyr Tyr Gln Gl
                965                 970                 975
Ser Gly Arg Ala Gly Arg Asp Gly Glu Ile Ser His Cys Leu Leu Ph
                980                 985                 990
Tyr Thr Tyr His Asp Val Thr Arg Leu Lys Arg Leu Ile Met Met Gl
                995                 1000                1005
Lys Asp Gly Asn His His Thr Arg Glu Thr His Phe Asn Asn Leu Ty
    1010                1015                1020
```

-continued

Ser Met Val His Tyr Cys Glu Asn Ile Thr Glu Cys Arg Arg Ile Gl
1025                    1030                    1035                    1040

Leu Leu Ala Tyr Phe Gly Glu Asn Gly Phe Asn Pro Asp Phe Cys Ly
            1045                    1050                    1055

Lys His Pro Asp Val Ser Cys Asn Cys Cys Lys Thr Lys Asp Ty
        1060                    1065                    1070

Lys Thr Arg Asp Val Thr Asp Asp Val Lys Ser Ile Val Arg Phe Va
            1075                    1080                    1085

Gln Glu His Ser Ser Gln Gly Met Arg Asn Ile Lys His Val Gl
        1090                    1095                    1100

Pro Ser Gly Arg Phe Thr Met Asn Met Leu Val Asp Ile Phe Leu Gl
1105                    1110                    1115                    1120

Ser Lys Ser Ala Lys Ile Gln Ser Gly Ile Phe Gly Lys Gly Ser Al
            1125                    1130                    1135

Tyr Ser Arg His Asn Ala Glu Arg Leu Phe Lys Lys Leu Ile Leu As
            1140                    1145                    1150

Lys Ile Leu Asp Glu Asp Leu Tyr Ile Asn Ala Asn Asp Gln Ala Il
        1155                    1160                    1165

Ala Tyr Val Met Leu Gly Asn Lys Ala Gln Thr Val Leu Asn Gly As
        1170                    1175                    1180

Leu Lys Val Asp Phe Met Glu Thr Glu Asn Ser Ser Val Lys Ly
1185                    1190                    1195                    1200

Gln Lys Ala Leu Val Ala Lys Val Ser Gln Arg Glu Glu Met Val Ly
            1205                    1210                    1215

Lys Cys Leu Gly Glu Leu Thr Glu Val Cys Lys Ser Leu Gly Lys Va
            1220                    1225                    1230

Phe Gly Val His Tyr Phe Asn Ile Phe Asn Thr Val Thr Leu Lys Ly
            1235                    1240                    1245

Leu Ala Glu Ser Leu Ser Ser Asp Pro Glu Val Leu Leu Gln Ile As
            1250                    1255                    1260

Gly Val Thr Glu Asp Lys Leu Glu Lys Tyr Gly Ala Glu Val Ile Se
1265                    1270                    1275                    1280

Val Leu Gln Lys Tyr Ser Glu Trp Thr Ser Pro Ala Glu Asp Ser Se
            1285                    1290                    1295

Pro Gly Ile Ser Leu Ser Ser Arg Gly Pro Gly Arg Ser Ala Al
            1300                    1305                    1310

Glu Glu Leu Asp Glu Glu Ile Pro Val Ser Ser His Tyr Phe Ala Se
            1315                    1320                    1325

Lys Thr Arg Asn Glu Arg Lys Arg Lys Lys Met Pro Ala Ser Gln Ar
        1330                    1335                    1340

Ser Lys Arg Arg Lys Thr Ala Ser Ser Gly Ser Lys Ala Lys Gly Gl
1345                    1350                    1355                    1360

Ser Ala Thr Cys Arg Lys Ile Ser Ser Lys Thr Lys Ser Ser Ser Il
            1365                    1370                    1375

Ile Gly Ser Ser Ser Ala Ser His Thr Ser Gln Ala Thr Ser Gly Al
            1380                    1385                    1390

Asn Ser Lys Leu Gly Ile Met Ala Pro Pro Lys Pro Ile Asn Arg Pr
            1395                    1400                    1405

Phe Leu Lys Pro Ser Tyr Ala Phe Ser
        1410                    1415

(2) INFORMATION FOR SEQ ID NO: 79:

(i) SEQUENCE CHARACTERISTICS:
        (A) LENGTH: 87350 base pairs
        (B) TYPE: nucleic acid
        (C) STRANDEDNESS: single
        (D) TOPOLOGY: linear (xi) SEQUENCE DESCRIPTION: SEQ ID NO: 79:

```
TATATTATGG CTATTTTTCT TTCTTATCTA TTTGTATTTT TATTGTTATT ACCTAAAAAA      60

AAATTTTCTA TGTCTTATCA CTAATTCTTC CCTAAAATTT CCCACAATTG TGTAAACTTA     120

CCTCAGTATA TTCATAGATA TGAGACATTC TATCAATTTT ACCCTCTTAA AGATGCAGAA     180

ATAATGCATT ATGTTTCATC CCACCATCTT TAATGAGAAG CTTCCATCTT AGATTAATAT     240

TAGAGAATGT TAAAATACTC TGCAATCAGG TAAGGACGCT TGAAACTTCA TCATAATGCA     300

AAAGTTTTCT TTAACACAAT AAATATTTTG AACCCCTTTT GTGTCTTGTA TTCATAGGAG     360

TTCAGATAGA CCACTTTATT TACTATTTTT TATAGAGAGT GAACAGAAAT CCCATTTCTA     420

GTCACCAGTC CTTAATCTGT AAATCAGGCA GATAATCTGT AAATGATTGG TTGAAATCAC     480

ATTGAATTCC ACTTTGTGCC AGGGACTTAA GTTAACGAAC AAATTATTCT TACAAAAAGG     540

TATAAATGTA AGGTTTTCAT TCCGCTAAAT ATGTTTGTCA AACTGTGTTG TGATTTGTTC     600

TCAGTGTGTC ATAGCTACCA TAGCTTTTGG AATGGGCATT AATAAAGCTG ACATTCGCCA     660

AGTCATTCAT TACGGTGCTC CTAAGGACAT GGAATCATAT TATCAGGAGA TTGGTAGAGC     720

TGGTCGTGAT GGACTTCAAA GTTCTTGTCA CGTCCTCTGG GCTCCTGCAG ACATTAACTT     780

AAATAGGTAA AAAAAATTTA TTGTTTTTAC TCTTGCAGAT TTCTTTCTTT CTTTCCATAT     840

AAACCTCAAA AGTGTTTGAG GCTATTTCCA GTATCCCAAG TAATTTGTGA GTGCATTTAA     900

AGTAAAAAAA AAAAAAAAAG AAAAATAAAA CCTCCCCAAA TCCAGAGGAC ATGTAAGAAG     960

AACATTTGTG GTAAGAGTTG CCACTTGGAG ATGAGCTAAT TTCAGCATGC CTTAGTTAGT    1020

GTGAGGAATT AACTAAATCA GGACAATACT TGGGCCTGTC ACAGAGATCC TATGGAATAC    1080

TTTCCTACCA TTGTGCATTA ATGAACAGGT TCTTTTCCTC TCCTCAGATC CTGTCAAGTT    1140

GCGATGTCTT CAGCCATAGT TACTTCAACT ACCACTGATT TTGTTACTGA TTCTTTCTTC    1200

CCATGCTACA GTGGTGATTA TTCCAGAGGA TTTCTCTCAG TCCCTATTTG ACTCTTGTTA    1260

CTATTTGTTT TCTTGGTTAG TTCCATGAGA CCATGCCAGT TCTCCTTGAC TGTGTATGAA    1320

TCATTGTGTT GCACTGTACT GACAGACTGC CGTAAGTCAA TATTAAGTGT TCAGTATCTA    1380

AGTGCAGGAG AACCTTTCTA CTTAAGTACT CAACAAGTAG TTTGTTGGCA CTTAAGTTCT    1440

ATGAGATTTT TTGTTGTAAA GGAAAACATT ATCTTGCAAA GATTTGGGG CAGCATTTAC     1500

CAATACTTTG TTCCTTCATC CGTAGGAAAA AGAATCTCAG GAGAAAAACC TATACATGGT    1560

AACCAATGGG GCTGCCAAGC TGATGAAGTA TTTTCAGAGT ACACCTTTGT GTAGCTGAAT    1620

AAATTGAGAT CTTGAATGGA CATATTAGCT CATTTTAGTA AAATGATAAG AGAGTGCCTC    1680

CCACTACAGT TTTTGTTTTT ATGCATCATT AAACAATGTG TTTTTGATTG TCCACTGTGT    1740

TCCATGAACT ATGCTATGTG TGGGAGATAT AGTAGTAAAG AAAAGCAAAG TACCTGCTTC    1800

CATAGAATTC AGTATAATGG GAATGGTAAT TCTTTAGAGA ATCACATAAC TATGGATACA    1860

TAGGCTTCAT TTTACTGTTC TCCTTTTGTG TTTGAAAATG TCAACAATCA AAATTTTGTA    1920

AAAAAGGAAT CATGCAACAT ATTTAAAATT ATAACTGTGT TAAGTGTAAT GAAGGGAAAT    1980

TGCACTGAGT AGTAAGAATA TATAATGGTG TGTGGTATTT CCCAAGTTAA AAAGGTCAGA    2040

TAAGGCTTCC TTGTGGAAGT GATAGTTCAA ATCTGAAAGA AGAATAGGAA TTAATTAGGT    2100
```

```
AAAAATGTTT GATGCAAATT TTAAGATTTT CCTTCTGAGT AGTCAGTAGC TTTTCCTTCT    2160

TAACATAGAA GATGACAAAA CCATCCTTTT TTTGTACATA ACAATTCTTG TTTTCCTTTA    2220

GACAGTTGTA TCTGTCAAGC TTCTTATGAT CTAATTTAAA TAATTGGGAT AGAACACAGC    2280

TGTACATGTT ACTATTAAAT ATGGAATATA TCAAACATAA GTTGATTCCT ACCAGTTCTG    2340

ATTTTATTTG TGTATTTTGT TAAAGGTACT GAGGACATTA ATATCCAGTT TTATATTGTG    2400

CATTTGAAGG TTCATCAATA AATACAATTC TTGTTTCTCT GGGTCTTAAA AGATATTTTA    2460

AATGGTTATC TCATTAAGAT TTAACAGGAA ATAACAGTGA TTCAAATCAA ATAGTGGTGC    2520

CAGAAACCCA TACTTGAATT TTGGGTATAG ACAGGTTACC CTTTGCATCA ATCCTGAGGA    2580

AACTAAAACT ATAGGATTAA TCAGGATAAA AAAGAATTGA GCAAGGATTC AGGAGGGATC    2640

TGTATCATCC TGGTGACAAC CCTCTTCTAG AAAAAACTAG AAAGTCTAAG AATAAATGAA    2700

GTTGCTGGTT CTCACCTGGA AAGGTCAGTT ACTCACAAAA TTTTTAGAGT CTATCTTATG    2760

CCATAATTCT ATCACTGAGA GAAGAAACTT GTCCAGTCAT CATGTAATCT TCATGTAAAT    2820

TTATGTTTTT AATTGCAGAA TTCATACCAC AGGCAAAGTC CCAATGTCTG CATTTGCTGT    2880

TACCTTAAAT AGTCAAACCC CAAAGTTATT GTAATCTTTT TTTAACAGAG AATAATTTGC    2940

AGAGTAATCT CGGTCCGGTA GATCTTTCAG TGGATCCCAA ATGATTGCCA TGAATGGTTT    3000

AGAATTTTTT TAATTTTCAA GTTGTTTTTA TTCTGTGGAA TACTGGCTTA TTTTTGTAGT    3060

CCCAAAAGAA AAATAAATAT TTATTTATTT GCCGTTAAGA GTTGTAGTTT TGTTTTCTCA    3120

AATTTGTCCT GACACTGACG AGATTAGTTA AATGTAGGTC ATCTGAACCA AATACAAGGA    3180

AGGAAGGACC CAGTTCTGAA GAGTGTGGGC ATTTCTTTTC TTGTTTTTTT TTTTTTTTTT    3240

TTTTTTTTTT CTATAGGAGG GGAACGAGGT GAACTAAACA AACAAAATAA AGCAAAAAAG    3300

AACTGATTTT TATCCCTTGA GGTAGAAAGA ATGAGATTAC AGTGGACCCC CTTGTCTGCA    3360

TTTTCACTTT CTATGTTTTA GTTACTCACA ACCACGTCCA AAATGTTAAA TAGAAAATTC    3420

CAGAAATAAA CAATTTATAA ATTTTAAATC AGTGGTGGCT TTGAGTACTG TAATGAAATG    3480

TTGTGCCATC CCACTCAGTC GGCCTCGACT TCCCTTAGAA TCATCCCTTT GTCCGGTGCA    3540

TTCACGTTGT ATTTACTCCC TGTCTGTTAG TCACTTGTTG CAGTATCACA GTGCTTGTGT    3600

TCAAGTAACG CTTATTTTAC TTAAGAATGA CCCCAAAGCA CAAGAGTACT GTGCCTAATT    3660

TATAAATTAA ACTTTTTCAT AGGTATATAC ATATAGGAAA AAACATAATA CATACAGGAT    3720

TTGGTTGGTA CTATTCTGCG GCTTCAGGCA TCCACTGGAC GTCTTGGAAT GTATCCCTTG    3780

TGGATAAGGA GGAACTGTAT ATGGTTAACC TAGGAGCTAG AGTCAACAGT TGGAAGAGAC    3840

TTTGGGGATA ATTACATGGA AGGGCATGGT GGGTGGTCGT TTCAGATGAC AAGAATGTTT    3900

TTGAATAACG GATCATTTGT GTCTTCAGAC TTTCCAGAAC TCCTTGAGAA TTATGCAGAG    3960

GTATTTAATC AGTCAGAAGG TTGAATAGTC AAATTATTAG TGAGTGAAGT CTATTTTGAT    4020

GAGGATTTTA CTAATGCTGT CCCTTAGATG TTATAAGTAA ATCGTTGTTT TCTTTTGAAA    4080

TATCTGAAAC CTAGTTAACA TGGACTTTCA TTTGTTCTTG TAAAGATATG CAAAGCTATT    4140

TGGGAGATTG TCATCATCTG ATATTTGATA TTCATGGGCT TTCTTCACAG AAGACTAGAA    4200

ATTAACAGAG TCATGATGAA TTATGGCTGC ATTGACTTTA AAAACAAAC ACCTCCTTAA    4260

TGTTATTTAA CAATTTTGAA TAAATTTGAT ATGGCAAACA AATCAGTTAT AATCGATTGA    4320

GAAAGGAACT TAATTCTAAT ACTTGACTGG TGTCCCATAA TAACCCATAA TACTAAGAGA    4380

CAGTTTTGGA GGGCGAGAAG TCCTGAAGAG CTGATAGAGA TAAAGGTTCA AATTTGAGCT    4440

TCTTTCAGTG TTCCTTACGT CAATGCTTTT AGTTCTCAT ACAAAATAAA ATAAAGAATA    4500
```

```
ACCTTTTTAC TGGGAAAAGG TAAAAATTAA TAAATTGTAG AAGCATTGTT TGAAGCCAAA    4560

AAGTGTGTGA CATGTAAATT GAAATGAAAA ACCTTAGAGT TTTTGATACT TTTTCAAAGC    4620

AGCTAAAGAA TTGATACTTG GACACAGGAA GAATTTTTTT TCAAAAGCAA TTTTTATAAA    4680

ATCAGAAAAA TGTTTACCTC TTGTTGGGGG CATTGACTGG AAAGGAATAC AACAGAACTT    4740

TCTGAGATGC TAGAAATGTT TTTTTATCTT GATGGGGTGT GGGTTTTGTA GATAATGAAA    4800

AATAAACAGT AAAAAATAAG TAAAAAAAAA AGTAAGAAAG TTGCCAATAC AGTTTTACAT    4860

ATTCCTGTGA TGTTTTTAAT CGACAGGCAC CTTCTTACTG AGATACGTAA TGAGAAGTTT    4920

CGATTATACA AATTAAAGAT GATGGCAAAG ATGGAAAAAT ATCTTCATTC TAGCAGATGT    4980

AGGAGACAGT ATGTATTATT TATTTTATGC CAATAGTATG GATTTATGGA TGATGCTCTT    5040

TTAAGACAAC AATTTGGCTA AATAATTATC AGTATTTTGA AAAAATATTT TGTTGCTGTT    5100

ACATGTGTGC TGAATTTTTA AGGCTAACTT CTTTGTGTCT GAGTAAACTG AAGTCAAATA    5160

ATGAAGTCCC AAGTGAATCA ATTAATGGTG ATTTTACCTC ATTATTTTCA GGAATGAACT    5220

TAACATATAC GTTTCTGTTC TTTTATTTAA TTTAAAATTT TGTCTTGGGT AGAATCATCT    5280

TGTCTCATTT TGAGGACAAA CAAGTACAAA AAGCCTCCTT GGGAATTATG GGAACTGAAA    5340

AATGCTGTGA TAATTGCAGG TCCAGGTAAA GATTTCTTAT TATAGATGGA CATTCTAAAA    5400

GTCTTTCTTT CTCTTCCTTT TCATGTTTAA CTGAATTTTT GTTGAATGAT AAGTATTTCA    5460

GTTTTTTAAA CAAACAATG AATGTGTTTA GATATGAGAA AGCAAACAAT ATTAAAGTAT     5520

TTTGCTTAAA AATAGATAA AGCAATAAAA TGGTAGCCCT AAATCTAAAC ATATCAATAG     5580

TTATGTTAAA TGTAAATGAT CTAAAATATT ATTTAAAGGC GTAAATTGTA AGAATTGGTT    5640

TAAAAACATG ACCCTGTTCT GTACGTTGTC CACAAGAAAT CCACTGTAAT TATATAGATA    5700

GGTTTAAAAA AGAATGAAAC ATTACATTCC ATGAAAACAT TAATCAAAAG GAAGTTGGAG    5760

TTACTTTAAT ATCAGACAAT GGACACTTTG GAGCAAAGAA TATTATCAGG ATAAAGAAGG    5820

ATATTATATG ATGTAAAAGA ATCATTTCAC CAATGTATCA GTCAGGGTTC ACCAGAGAAA    5880

TAGGACGATT GATATTATGG AGATATATAT ATATATATAT ATATATATAT ATATATATAT    5940

ATATATATAT ATATATATAT ATGGGGAGGG AAAGGAAGAA CAAATATGGG GAGAGAGGGA    6000

TGAGGCGACT GATTTGAAG AATTAGCTCA CGAAATTGTG GGGGTTGGCA AGTCTGAAAT     6060

TTGTAGAGCA GGTCAATAGG CTGGAAACTC AGGCAAGAGG TGATGTTGCA GTCTTGAGGC    6120

AGAATTTCTT CTCTAGCAAA CCTAGTTTTT GCCCTTTAGT CCTGCCACTG AGTGGATGAG    6180

GCCCACCCAC ATTATTGACA ATAATCTCCT TTACTTAAAG TCAACTGATT ATAAATGTTA    6240

ATCACGTCTA CAAAATATTT TACAGCAACA TCTAGATTAG TGTTTGACCA AACAACTGAG    6300

CATCATAGGC TAGCCAAGTT GATGCATAAT ATTAATCATC ACAACCAAGA AGACATCATC    6360

CTAAATATAT ATATATATCT ACTTAACAAA AAGACTGACA GAACTGAAAG GAGAAATAGA    6420

GAAATCTACA GTTACATTTG GTGACTTCCA GCATCTCTCA ATAATCAATA AAACTGACAG    6480

ACCAAAAAAT CAGTAAGAAG ACAGAAGAAA TGAACAGGAT TATCAGCATG CTGGATCTCA    6540

TTGACCTTTT TAGAACATTC TACCCAACAA CAGTAGAGTA CACATTCAAG TGCAGATGCA    6600

GTATTCATGA ACATGGATTA TATTCAGAGT CATAAAACAA ACCTTAACAA ATTTAAGAAT    6660

CTTGTATTTG TATATTTTTT GACTAGAATG GAATTAAACT AGAAAACAAT AACAGAAAGA    6720

TAACAGAAAA GTCTCTAAAC CTTAGAAATT AAATAACACA CTTATAAATA AATCCATGAG    6780

TCAAAGAGGA AGTCTCAAGG CAAATCAGAA AATGTTTTGA ACTGAATGAA ATGAAAATAC    6840

AAAATGTGTG AGATGCAGCT AATGCAATAC TGAGAAGGAA ATTTATAGCA TTAAATACCT    6900
```

| | |
|---|---|
| ATGTAATAAA AGAAGAAAGG TCTCAAATCA GTACCTAAGC TTACATCTTA AGCAACAAGC | 6960 |
| AAATAAGAGC AAAATAAATC AAAATGAAGT AAACATAAGG AAATAACAAA GAACATAAGT | 7020 |
| CAATGAATAG AAAAGCTATG GTCATACCAC TGCTGTCCAG CCTGGGTGAC AGAGTGAGAC | 7080 |
| CCTATGTCAA AAAAATTTAA AAACAAAGCA GCATGCAGCA TTCATTGTCA GTGAATAGAA | 7140 |
| AATGGGAAAA CAATAGAGAA AATCAACTCA AAAGCTCATT CTGTATAAAG ATCAACAAAA | 7200 |
| TTGATATAAA CTTCTAACAA GACTGACGGN AAAGANGAAA AGACACAGAA GACCAATACC | 7260 |
| AGGAATGAAA GAGGGAATTT CACTACAGAC CTCCCAGGTA TTACTAGGGA TGATAAGGGA | 7320 |
| ACACTATGAA CAACTCAGAA CATAACTTTA ATAATTTAGA TGAAATGGAT CAATTTCTTG | 7380 |
| ATAATCTCAA GCTAATTAAA CTTACAGTGA ATTAGATAAC CTGCATAGTG TTACAACCAT | 7440 |
| TAGAGGGATT GAATTCTATG TTAAAAATCT CTGAAAATAA AATCCCCTAG CCCAAAGAAT | 7500 |
| TTCAATGACA AATTCTACCA AACATTTAGA AGACAAAATA ATACCAATTC TATAGCATGA | 7560 |
| TTCCATTTAT ATAATAGTCT TTGAAACATA AAACTATACT AGAGGGATGA AGAAAAGATC | 7620 |
| AGTGGTTATT AGAGATTGGG GGAGGGAGAA GGTATGATTC CAAAGGATAG TACAAGGCAG | 7680 |
| TATTTTGGAG TGATAGATTT ATCGTGCCCT GATTGTGATG GGAGTTAGAT GAATCTATGG | 7740 |
| ATATCTTAAA ATGTGTAGAA CTTTACACAT ACATACAACC AATTTGCCTA TGTTAATTGA | 7800 |
| AAAAATAAAA TAAAAACAAA TTATTTACCT GGTGGGTTAG CTACGTACCT AAGTTCAATA | 7860 |
| GCTGCGTTAC TGTAAGACAA AAGAAGCATT ATTAGGGATG GAGTTGTTNC TCTGTGTAAT | 7920 |
| GACAAATACT TCCTTCACTA AGAAGACAGA ATTGTTTTAT GCACCTTTAA AAAAAAACAA | 7980 |
| AAACAAAAAA AATACAACCA ACAAACAGTA ACTTGCTGGT GCGGTGGCTC ACACTTGTAG | 8040 |
| TATTAGCACT TTGGGAGGCT GAGGTGGGAG GATCACTTGA GACCAGGATT TTTAAGACCA | 8100 |
| GTCTGGGCAA AAAACCGAGA CTGTGTCTCT ACAAAAATAA AAAATAAATA AAAAAAATTA | 8160 |
| GCTAGGCATA GCATTATGTG CCTCTAGTCC CAGCTACTCT GGAGGCTAAG GTGGAAAGAT | 8220 |
| CGCTTGAGCC TGGAAGGTTG AGACTGCAGT TGCAGTGAGC CATGATGGCA CCACTACACT | 8280 |
| CCAGGCTGGG CATCAGAGTA AGACTCTGTC TCACATAAAA AAAATAATAA TAATGATAAA | 8340 |
| AACTAGTCTG GCATGGTGG CTCACACCTG TAGTCCCAGT CCTTTGGAAG GCCGAGGCAA | 8400 |
| GAGAATTGCT TGAACCCAAG ACTTTGAGAA CAGCCTGGGC AACATAGCAA GACCCCATCT | 8460 |
| CTATTTAAAA AAAAAAACAA ACTTAAAAAT CCAGCAAATA CATAAAGCAC AAAGCCGACA | 8520 |
| GAAGAGGTGG AGAAATCAAC AAATCCACCA TCAAAGTGGG AGAATTTGAT ATAATTTTAA | 8580 |
| GTTATTGGTA GGGTAAACAA TCCAAAAATT AGTACACTGT AGAAAATTTG GTCAACATAG | 8640 |
| TAATAAGTTT GCTTATTACT ATTTATCAGT ATACATAGTA TACTGATTTA TCAGATACAT | 8700 |
| AGTATATGGA GCCCTAGAGC AAGCAACTAT AGCAGTGTAT CTCAAGTATT TTTACTTCAT | 8760 |
| GACCCACATA GCAAATGATA TGTGTATATA ACACACTGGG CTAATTGTCA GAGTTCAGTT | 8820 |
| TCTGTCCAAA ACCCTAAGAT CTGGAGTGAT TAACCTTTCA GCACTCTTAG AACTCACTTG | 8880 |
| TTTGTAGCAC ACTGATTGAG AAGCACTGAA AGACTTCACT CCTCAAACAT ACATGGAATA | 8940 |
| TTTCTAAAAA CTATGTATTG GGCCGGGTGC AGTGGCTCAT GCCTGTAATC CCAGCACTTT | 9000 |
| GGGAGGCCGA GGCGGGTGGA TCCCGAGGTC AGGAGATCGA GACCATCCTG GCTAACATGA | 9060 |
| TGAAACGCCG TCTCTACTAA AAATACAAAA AATTAGCCGG ATGTGGTGGC GAGTGCCTGT | 9120 |
| AGTCCCAGCT ACTCGGGAGG CTGAGGCAGG AGAATGGTGT GAACCCAGGA GGCGGAGTTG | 9180 |
| CAGTGAGCCG AGATCGTGCC ACTGCACTCC AGCCTGGGCA ACAGAGCGAG ACTCTGTCTC | 9240 |
| AAAAAAAACC AACCAACTGA ACAAACAAAA AAACTAAAAA ACAAAACAA AAAACTATG | 9300 |

```
TATTAGAGCA TGGGTTGGCA AACTATGGCC TGTAGGCAAA TCTGCATGCT GTTTTATTTT      9360

TTTTATTTTT TTGACATAGG GTCACTACAG GCTGTCACAC AGGCTGGAGA GCAGTGGTAT      9420

GATCATAGCT CACTGTAACC TCAAATTCCT GGGCTCAAGC AATTCTCTTG CCTCACCTCA      9480

GCTTCCCAAG TAGCTACAGG CATGCACTAC CAGACCCAGT TAATTAAAAC AAATTTTTTT      9540

TTGGTAGAGA CAGTCTCAGT ATGTTGCCCA GGCTGGTTTT CAAACTCCTT GCCTCAATCA      9600

GTCCTCCTAC TTCAGCCTCC TAAAGTGCTG GGATTATAGG CCTGAGCCAT CACGCTTGAC      9660

TAATGTTTTT GTAAATAAAG TTTTCTCAGA ACACAGCCAT GCCTTTTGTT TATGTGTTAT      9720

GTAGGGCTGC CTGAGTTAAG TAGTTGGCTA CAAAGCCTAT CATGGCCTAT AAAGCCTGAA      9780

ATACTTACTA TCTGGTCCTT TATAGAAAGT GTTTTCTGAC CCTGTACTAG ACTAGCTTGT      9840

CTCAAAATTC TTCAATGAAT TTGGAAGTTT TCTCACCACA TTTTCTGACC ATAATGCACT      9900

TGAGTTAGAA GTAAATAAGC AGATAAACAA CAAAATCCTC ATGCATTTGG AAATTAAAAA      9960

TAACACTTAA ATAATTCATA TTCAAAGAAA AAATCAAACT GGAAATTAAA AAAAATTTTA     10020

AACCTACAGA TAACTACATT AATATGCATT AACATTTTTA GAACTTAGGG ATAGTTACAA     10080

TGATATACAT TAAAACTGGT AAGAGGCTGG GTGCGTTGGC TCACGCCTGT AATCCCAGCA     10140

CTTTGGGAGG CCGAGGCTGG GGGATCACGA GGTCAAGAGA TTGAAACCAT CCTGGCCAAC     10200

ATGGTGAAAT CCCGTCTCTA CTAAAAATAC AAAAATCAGC TGGGCGTGGT GGCACGCGCC     10260

TGTAGTCCCA GCTACTTGGG AGGCTGAGGC AGGAGAATCG CTTGAACCTG GGAGGCGGAG     10320

GTTGCCGTGA GCCGAGATTG GGCCACTGCA CTCCAGCCTG GCGACAGAGC GACACTCTTG     10380

TCTCAAAAAA AAAACAAAAA AAAAACAAA AAAAAAACT AGTAAGAGGT CCCAGTGGCT     10440

CACACCTGTC ATTCTAGCTC TTTGGGAGAC TGAGGAGAGA GGATCAGTTG AGGCCAGGAT     10500

TCAAGACCAG TCTGGGCAAC ATAACGAGAC CGCATCTCTA CAAAATTTTA ATAACAACAA     10560

CAAAAAAACT GGTAAGAGGC AACATTGAAT AGTACTTTGT GGGAGTTTAT TAGCTTGAAA     10620

TACTCATAAT AGAAAAGAAA ATTAATCAGC TAAGCATCTC ACTAAAGAGA TTAGGAGAAT     10680

AAACCTAAGC ATAGTTTTTT TCCCCCAAAC ATTATTATAT CTGGAATATT GAATGCATTC     10740

TTATTGCTAT TTCAAAGATA CTTACTCTAA GGAAAGCAAT TGAATTAGGT AGTTGAACTC     10800

TATAGTAGAT TTTCTTTAAT GAGTCCTTTT GTTCTCAACC TACTTAAATA ATTCTCATTT     10860

GAATTTATGA TAGTTTCAGA TCTACCCAAA GGGTGACTTA GGAATTTAAC TTCTAAATCT     10920

ATTTAAATGA AAGGTTTATA ATCTTTGTGT CATATTTTAC AGTCGTTAGC GTTTAACAAT     10980

TTATAGCATA GGATTTGGGT TTTTTTTTTT TTCATTTTAA AGAAGAAGTT TATTTAAGCA     11040

AGACACTTGA CTAAGGGAAG ACTATCTTGG AGTTATTATT ACTAGAGTAA TTTATTTCTA     11100

CTTAAAGACA GATTGCCCCA CAAGTAACAG CTACATAAAA AACAGTTGTA AAATTGTCCT     11160

TGGTTTTACA ATGATAAATG AAAAACATTA AAATTCTCTA ATTGAACAAG GTATGCAAGG     11220

ATTTTTATAT TGTTTTTTGC TAAAACTATG ACAGCAAAAT AACATCCTGG AGTATAAAGA     11280

TAAGAGCTGA ATGAGCAGGC CACTAGGGGA CAAAGGGAGT CTTTTCACAG AACCAATGCT     11340

TCTTTTGCCC ACCCCATCTC CATCGAAGTC AATCTAAACA TATTATTGGC CATTTAGTTA     11400

AAAAAAGAAA GAAAAGNAAA AGCAATATGC TTGTGGACAT ACACCAGTTA CTTTATGTGC     11460

AATAAAAGAG TAGGAAGGGG AAGGTGAAAG AATAGAGAAA ACTATGTAGT CAGGATGTGG     11520

TGGAACCAAA TTGCAACTTT CTTTTTTTTT TTTTTTTTTT TTTTTGAGAC AGAGTTTTGC     11580

TCTTGTCACC CAGGCTGGAG TGTAGTGGTG GCCCAATCTT GGCTCACTGC AACCTCCGCC     11640

TCTCAGATTC AAGCCATTCT CCTGCCTCAG CCTTCTGAGT AGCTGGGATT ACAGGTGCAT     11700
```

```
GCCACCATGC CTGGCTAATT TTTGTATTTT TAGTAGAGAT GGGTTTTCAC CATGTTGGCC   11760

AGGCTGGTCT TGAATGCCTG ACTTCAAGTG ATCCACCCGC CTCAGCCTCC CAAAGTGCTG   11820

GGATTACAGG CGTGAGCACT GCGCCTGGCC AAATTGTAGC TTTCTAATTG AGACTGTCTT   11880

CTTGGTCTGG AAGAGCAGAG TTCTGCAGTA AAATAACAGG TCCCCCTTTT AGTAGACATC   11940

TCCATGTCTG CTGCTGGAAC ACATCAGTTT TGTCTTAAGC CTCACTTCCA AATGTGCAGA   12000

TGTGTCTGGT TCATTGATTG GCTGCCTGTC AAATTGAAAC CTGATCTGCC TCATTGGCAA   12060

ACCGTGCCCC TTACAATAGG CTTTCATTGG TTTACTAAGC GGTGTGGTGC GTGGCTGTTC   12120

ATCTTAAACT GCACCACAGT TTAAGATGAA CCTTCAAATG AACATTATCC TTGTTCTCAG   12180

TCTTGACTTT CCTTGGGCTT TTTGTGGACC CTGGTGAGTG TGGCAGTCTC CTCAGCTGCT   12240

GCTTCACAAA AGAGGTACCA GGTCTGCCCC GAATGAGTGA GCCCTAAAC AGGACCAGGA   12300

GTGGCAGAAG AAAGAGGCAG CAACTGAGAT GTGTTTTTC TAAGCTGAAA GGCTTTTTTT   12360

TTTTTTTTTT GCAACACACC TTTAACACTA AAGTCCAATA TTTATATAAT TNGGTCAAGT   12420

AAGTGGAGCT GTTCTAGCTA TAAATATGGC AACTCTGCTT GCTCGTCCTA TTATTGATTG   12480

TATTCCTTTC TGTGGTCTGA GGTGCCTCCC ATGAAACTTG CTTCTAGGAC ACTAGGATTG   12540

AGAACCATNC AGCGTAACAT ATCTGTTACG CTACAATAGT TTATTTTCAT ATTTTAGCTA   12600

CTTTACATAC TCGGGTATAA TGAACTTTAT TCATAGCTTC TGAAGCAGTT GGCACATTTG   12660

AGATATTTTT TACTTGGCTA ATTGTTATGC TAAATCTTTT GATTTCTAAA GATACATGCC   12720

TTTGCTAAGC TTTCTTCAAA TGTTATTATT TTTATTTAGA TTGGATCATT GCTATTCCAT   12780

GGATGACTCA GAGGATACAT CCTGGGACTT TGGTCCACAA GCATTTAAGC TTTTGTCTGC   12840

TGTGGACATC TTAGGCGAAA AATTTGGAAT TGGGCTTCCA ATTTTATTTC TCCGAGGATC   12900

TGTAAGTATA TATCTGTGAA TTCCCTTCAT AGATCTTCTT TTACTTCTAT TACACTTTTC   12960

TTCAGAGGTT TGCAGTATTA TGATTGTAAC TTTGACTTCA GATGGGTGAC TAGGAACTCA   13020

TAGAGTCTTA CTAAGTTCCA GTTAAACACT ACATTCATTA CTTTGGATAA AACCCGTGTG   13080

TATGGCATCT TCTGCTGTTT TCATGTTCAA GCCGATGTTC AGCTCTGCAG CTCAGTCTGG   13140

AAGCATTGTG TTAATTTATC ACATTGCATT TGGGTGAATC CCTAGACTAG TCTTGCTTAG   13200

GATAATTAGG AAAAGTTAAC TTTCATTGTA TCAAGGGACA GGTAGAACAA AATTGTCCTT   13260

TTGTCCAGGA AACTATTAAA TTCTTCAAGG AAAACTTTAG TTATAGGGAT TATTTTTTAA   13320

ATGTCTAATT TCAGTAACAA TATTTGGGAC ATATTTATTT TTCCTTCTGT TTCCTATCAG   13380

AAGTATTTAA AGTTATAAGA AAATTGTGGT TTTTGCCTTT ACTAATGAAT AAATAATCAA   13440

TTAAATTCAG TTACTTTTTT TTGGAGTGAT TGATGTTCCA GTATTCTTCT AAACAACCAC   13500

GGGTACAAAT GTGAATAAGA TAGGACCGTT GCAGTCCAAG AGCTTGTTCT GTAGTCCTTT   13560

CCTTTATATG ATTTTTTCCC CTGATTTAGA AGTCTATAAA GCAAAGCTAA GTATTACACA   13620

CTGATAATGG CTGAATAAAT CAAGAGCAAG AGATAGGATA CTTTGCAAAT ATGCATATTT   13680

ATTAAAAATG TACTTTAAAA TAGAGATTAA AATTCTCGTA TTGAATGTAG AATAGGTAAG   13740

CATTTATTTG TGAAATACTC GAATGCTTCA TGTAAATACT TTCTGAGTTT GTATTTTAG    13800

AAAGGAACAT TTTGGAGGCT GAGGCAGGAG AATGGCGTGA ACGTGGGAGG CGGAGCTTGC   13860

AGTGAGCTGA GATTGTGCCA CTGCACTCCA GCCTGCGCGA CAGAGCAAGA TTCTGTCTCA   13920

ATAAAAAAAA AAAAGAAAC ATATTTATTA AATTAGTTGT GAAATATTTT TAATGAAATA    13980

TATTGAAAAC TTCTGTTGAT TTTTCATGTA CTGATGTTTT TAGATTCTAA ATGGAGTTTA   14040

AAATTTTGTT TGTAAATCAC AAGTTGGATT AGAAATTTAA TAGTAGAAGT GTTGCCTAAG   14100
```

-continued

```
GACTATTTTA GGTGCTGTGA GTGAAACTGT ATTTTTTATA ACAAGAATTT TAGTTGTAAG   14160

GGACAGCTTA AATATAATTG AGATCTGTGA AAATGTATTC TGTCTCTATC ACCTTCAGAA   14220

CCTGTGTATC TCAGTTGAAT GTATAATTTA TAAAAATTAT TCTTGTTTTA ATTTGGTGTA   14280

ATCCAGCCAT ATCCAGTATC AACAAATAAG TCTAAGTAGG CTCCTTGACA AACTTGAACT   14340

GGCCACAAGA GAGATCAGAT TTCACCTATT AAAAAACCAA ATCAGACCAC TTACACTGAC   14400

AGTCTCTTCT GGGAGTCCTC AAATTAAGAA GTCTATCCTT TGTGAAATAT TACACTACCC   14460

TTGCTAGATA AAACTTTTCT AAAAGTACCA CTTAATGAAA ATCTGTAGAC ACTAAATGCA   14520

ATGAAAATAA GGCATTGTTT TTTTTTCTCC CCATTTCAGT GATCTTGGTA TCCTGGGATA   14580

TTGTTTTTAA AATTATCGTT ATAATTCCTT TGAGAATTTA GTGAAACGTT CCCTTTAACC   14640

AACTTAGGAA AAATTAATAT CTTTGTACAT GATTTTGAGC TGTAAAATAA ACATTTAAA    14700

CTGGGAATAA TTGGAGTTTA GTTAAAGAGA TAATGTATAT AAATATATAA CATAGTAGCA   14760

GCATATAATT CTGTCTTACA CAAGATTTTT CTGAATAGTA TAAACAGTTA TGTAGCCTAT   14820

CTAGGAGTTT GTGAATAGAG TTTAAAATTT TGTTTTGAAG CTGCAAATTT GATTAGAAAT   14880

TAAACAGTAA AGTTATTACT TAAGGAACTT CGTTTTAGCT GTCTGAACAA CTTACTGTAT   14940

AAAAATCTTT AAACATTCTG TATAAATATG TGATAAGATA TGCAATGACC TTAATTTTAT   15000

AGATTAGAAA ATAAAAACAC ACTCATTAAT TTACATAACT GACAGATTAA GTGAAACTTC   15060

TCTTCTGATC ACGTTAGCAG AATGCCAAAT CTTGTCGTGG CACTAGAATT AGACGGTAGT   15120

TTTGATAATA CATGATTTGA CTATAGACAT TTGTTGAAAC TATTGGTAGT TTTAATCACT   15180

CTTGTAATTT TCAAACTATC TAACGGGAGA GGATTATCCA TCCTGTTTTC TAGACAAACT   15240

GTTTCATCTG AATGAAATAT ATTCCTAGAG ATAATTATCA CTACTTCATC TTTTGGTTTT   15300

ATTTTGCACA TAGAATTATA GTTCACAATG ACTTTCTGAA GCTCTAAAGT TGCAGCTGTG   15360

AGCTTCTTTG GCCTGTAGGG ACTGGGAAAA AGCACCCCCG TCCTCCCCCA AGCCCCCCCA   15420

CCAAAAAAAG TTAAAGTGTT TTTAACAATA GCTGTGGGCT TTTTGTAGTT TCAGAACTTA   15480

GGAGTTGCCC AGGCTGGAAT GCAGTGGTGT GATCATAGCT TGATGCAGCC TTGAACTCCT   15540

GGGTTCAAGC AATCCTCCCA CCTCAGCCTC CAGAGTAGCT GGGACCACAG GTGCCACCCC   15600

ACCCAGCTAT TTTTTTTATT TTTTAATTTT TTTGTAGGTA TGGGGTCTCC CCATGTTGCC   15660

CTGCCTGTCT CAAACTCCAG GGCTCTCAGG TGATACCCAC CACCCTTGGC CTCCCAAAGC   15720

ACCGAGAGTC ACTGTGCCAG GCTGAGTTTA AAATTTCTTG AGTTGGAGTT TATGGCTATT   15780

TTTTCCACTA GTTATTAAAC ATGTATTTTT GTATAAGGCA CTGTATTACA TTTTGTGGGG   15840

GGATTCAAAG CTAAATTAGA TGAGACGCAT CATCTATTAT GGAAGATGTT ACTTAAGAAG   15900

AAATGAGTGT AATGTAGCAG AGAATTAGAT AAGGGACGTA TGAATACATA TAAATGCTGT   15960

TGAAGTTCTG AAGAGAGAGA GTGTTTAGAG AAATTAGAGG AGTCTTTGTG AAGTTATCAC   16020

TAGAACTTCC TATTTTGTG GAATATATAG TAGATTTTGG TGTGATACTG TGGATTTGGA    16080

CATTCACTCA GAGAAGGAAT GAGGGAAGAA TGGTGGAGAA GAATGGCATT CACAGTACTC   16140

AAAGCAACTG TGACTTTTAA AGAAGTTAAT ATGGAGAAGT GGCAAGTCTT TCTTCTCTG    16200

TTCTCTTCTC TTCTCTTCTC TCTTCTTTTT CTTTTTTCTT TTTTTCTCTG TCAGATATCA   16260

TTGTAAAGAC TTTGCTTTTA CCGGAAACTG ATACGTTGGG TCATGTACCC TGGCCAGCAG   16320

GTTCTCTTTA TTCTAACACT TAGCCGATCA ATTAGATTTC CACATTCCAT GATATGTCCC   16380

TTTTGGTGAC CCTTATTTTT CCACCTGGTT TATAAAGGGA AAGAATGTGA TATGTCACAA   16440

AGGCTCTGGA GTACAGTGGC ATGATCATAG GTCACAGCAG CCTCAAAGTT TCCAGTTCCC   16500
```

```
GCGATCCTAC CTCCTTGGCT TCCTGAGTAT GTGGCACTAC AGGTGCATGC CACCATGCCT    16560

AGCTAACTTT TTTGTAGAGA CAGGGTCTCC CTATGTTTCC CAGGCTGGTC TTGAACCCCA    16620

GACCTCAAGT GATCCGCCCA CCTTGGCTTC CAAGATATT GGCATTACAG GCATGAGTAG     16680

CTGTGCCGGC CTGAAAATTT CTCTTTTGAG ATGGCATCCC ACAGAAGTAT ACCTGCTATT    16740

AGCTAACACT GGTAAAAAGA CTATTTAACC CTATTGCCTT ATTTTACTGT AGTTGAGGTC    16800

GAGTTAAACT GAAAGCTGAA TGACCTGTCC TAGGTCATAC TGTTACTTTG TGCCAGATGT    16860

AGGATGAGCA AATGGATTTC CTGCCTGCTA GTCTAGTGTC TTTTCTATTT ATTGTGCTAA    16920

AACATACAGT TTTAAATTTG TATTTTTATG CCCAATGGAC ATGGTAGCTC ACACCTGTGA    16980

TTTCAGCACT TTTGGGAAGC CGAGGTGGGG GGATTGCTCG AGACCAGGAG TTCAAGATGA    17040

GCCTGGGCAA CATAGCGAGA CTCCGTCTCT ATAAAAAAAA ATTTAAAAAT TAGCTGAGTG    17100

GTGATGTGTG TGCGTGTAGT CCTCCTTGTG GGAGGTTGAG GTGGGAGGAT CGATTGAATC    17160

TAGGAATTCA GGACTGCAGT GAGCCATGAT TACACCACTG CACTCCAGCC TGGGTGACAG    17220

AGCAATACCC TGTCTCGAAT GAATGAATGA ATGAATGAAT GAATGAATGA ATGCCCAAAT    17280

CCGTAAGCTA TGTTCTGTAT AGCAGCTTTT TCATCATAGG CAGTTTTTAC TCTTATCAGT    17340

GGACAACCTA CAAAATTAAC TAAACACTTA AGCAATTAAC AGAGGAGGCC TTGTTCAGAG    17400

TGAGAAATCA TTAAGCATTT GTTGTTGAAA TTTCTTACTG TACTCTGTTT TAATTCTGTT    17460

TTTTTTTTTT TTTAATGTTA CTTGTTTTAG TTTGGATTCC TAGTTGAAAA GGGAATATGA    17520

TTCCTTTAAA ACAAAGATAC TCTGCTTTAA AGCAAAGGTA TATCATCCTC TTCATGGTGA    17580

TTGCCATGGA AACAAGACAA TGTAAATTTA TTCAAATAGT ACACAGTTTT TATAGTTATT    17640

GATCATGAGG GGAAGGGACA GTTAATCCCT ACTGATCAGA TAAAACCTCA TTGTTTCATA    17700

CTAATAAATG GTTTTTTTAT GCTTATGAAA GGAAAAGCCA GAAGGGTAAT TTTTAGTGTT    17760

TAGAGAGCTA GTGATTCTAG TTAGGGAACT TAATACCTTT GAAGTTATTA GTTTGCAAGC    17820

AATAGAATCT ACTACTACCA AGGTGACCCC TAGCAGATGT AGAGTACCAT TAACAAGTGT    17880

TCCAGGGAAG GAAAGCCAAC TAGATACCAA GTCATGCTTT TTACTCTTAG ATTAAGAAAT    17940

TCAGGTTGAG TTAAAGGATC AGCTGTTAAC TAATAAAAAG CAGATTAATA TTACAGAGCC    18000

AGGCTCTGTC CTGGTTATGG ACTTAATCTT CACAGCATCC TCAAGAGATA AAATGAATA    18060

TACCTGCATA TTAGATGAGG AAATAGAAGA TAAGTAACTT GCCAGAGCTA TGACGTGAAC    18120

TCAGGTAATG TAGCTTAAGA GCCCCCACAT GTATGTATAT TGGGTGTGTG TGTGGAGGGG    18180

GTGCGTGTGA GTGCTTGTGC ATGCGTGTGG TATAATAAGA AAAAATTAGC ATTTATGCCT    18240

GTAATCCCAG CACTTTGGGA GACCGAGGCA CGAGGATCTC TCAACCCCAG GAGTTCAAGA    18300

CCAGTCTAGG CAACATAGCG AGACCCTACC TCTACAAAAA AAGTTTTAAA AATATTAGCG    18360

GGCATGGTGG AATACACCTG TAGTCTCAGC TGCTTGGGAC GCTGAGGTGG GAGGATCCTT    18420

GAGTCCAGGA GATTGAGGCT ACAGTGAGCT ATGATGACAC CTCTGCACTC CAGCTTGGGT    18480

GACAAAGAGA GACCCTGTCT CCAAAAAAAA AAATTAGAAC TAGTTATCTG GAGGCCTGTG    18540

TTCTAGTCCT AGCTTTAGTA CGGCTACACA GTGACACATT AGGCTACCAT TTAACATCTT    18600

TGAACCTCTG ATAATTTGTT AACAATATGG GTAAAAATGA CTAAGATAAA TCAAAGAGCT    18660

CCAGCATTCC CTCCAGCTCT GAAATTCTAT GATGTTTTAT CTTATTTTAC TTACAAAAAT    18720

AAATTATATT ATGTATATTT AAAGTATACA ATTTGATGTT ATGGGTTACC TATAGTAAAA    18780

TGATTACTAT AATGAAACTA ATTAACATAT CCATCATCTT ATATTGTTAA CCATTTTTTT    18840

GTTTTTGTGG CAAAAGCAGC TGAAATCCAC TCATTTAGCA GGAATCCCAA ATACAGTTCA    18900
```

```
GTTGTATTAA TTGTAATTCT CATGTTGTAC ATTCGATCTC TAGACTTGTT TATGCTACAT    18960
ATGTTTGACT TTTAAACATT CTACTCAAAT CAACCCTAAG TCAGGGTTAG CACAGACAGG    19020
ACTTGTTAAC AAGGTAGAAG GTGCCACATT GTACCTGGGT GTTTATATTT CTCTAAATCT    19080
TGTTCTGATC ATATTTTAAT AAATATAATC ATCAGGACAC CAAAATTCAT TCCTTAGCTA    19140
TTAAAAAATT CTATTCTATT TTATTGTTAA GATTTAGGAG AGCATGGTAC AGATTCTCTT    19200
AACTATACCT ATCAGAAGCC TATGTTTTAA GTCCAATGTA TAGGCACTGC TCTGTTTGTC    19260
TCTGGTGGGA ACTTACCCTG CTTTACCTAA TTTCATCCTA GCTTCCTTTT TGTGAAAGAT    19320
CACCCTTGCT TAGCCTATTT TTTGGCAAAT CTACACCTTG GAAATAGTAG TAAATGACAT    19380
AAGCATATTA ATATTTATGA TGTGATTTAT TTTTGTTTTC AAGTCATATA CTGGGGAAGA    19440
TTCTCAAATA TTAAAACAAT GTATCTTTAC ATTTATGTAT GTCGTTCTTG TTCTGTTTTA    19500
GAAGGCTTGT ATTTGCATTT TTAACATTCC AAAAGGTAAA CCTGTAATCA TAATGTTTTC    19560
ATCAATTCAA TAAAACCATT ACGTTTGTAA TAGAGAGCCC TATAGTTGCC TTAGTTAAGT    19620
TTGCTGCAAC TCATTTTATA TATTCTTTTA ATTTTGATCC CTGGATTTTT AATTGATTAT    19680
TAAACCTTCA TTAGGATATA TATGAAATGT AAAAATATTG AGTTATAATC TACCGTTTTC    19740
TAAAATTTTA TACTGCATTT TTATATAGAA ATTCAAATTG CTCATAATCA TTCTAGTGAA    19800
TTTAAGTAGA AAGGTATTTA TTACTAGGTA TTAAATGGCT TATAATATTG TTGACAAGGT    19860
TCCACTGCAA AATAGTTCAC CAAGGGAGCT GTGGCCTCTT CTGTGATCAA GAAGCCATCT    19920
GTCAACTTGG GAAGCTTCCA CTATAGCACC TAACCCCAGA CTACATTGAG TAGGAAGCTG    19980
TAATAATCAG GAAGCTTCTA CCTTTGCATG CTCTGCAAAC CAACGTGAAC CTGCTGTAAT    20040
TTGTAACCAC AAAATGGATG CCTGTTGATA CTTACGAAGC TCATCATTGT ATGCTGGGTT    20100
CTTTGCTAAT ACTTTCTTAT AAAAATTAAA TACCTCCACA ATCATGCATG CTAGCAGAAA    20160
CAGCAGAGGA GTAGCCTTAG CCTCACTTCC TGCTTATACC TGTCATGCAG ATATACAGAA    20220
CCCAGAACCC TAGCTGAAAG GGAGTTTGAG AACTAGTATT TGTATTGTCC CAGATTCTGC    20280
AGTGGAAGAA TTCATAGTGG ATGGAAGTTA GAATGACCCT TGAATTACAA TCGGCCACAT    20340
TCATCACAAA TACATTAAAT AAGAGTAATT TGCCATAAAG CTCTATGTTT GTATACTTCT    20400
TTGTTTTTTT TTTTTTTTTT TTTTTTTTTT GAGACAGGGT CTCACTCTGT TGCTCAGTCT    20460
GTAGTGCAGT GGTGTCATCA TAGCTCACTG CAGTCTTGAT CTCCTGAGCT CAAACGATTC    20520
TCCTGCCTCA GCTCCTGCTT CAGCCTCCTG AGTAGCGGAA CAACAGGTAC ACACCACCAC    20580
ACTTTGCTAA TTTTTTATTT TTTATTTTTT GTAGAGATGT GGGTCTCACT GTGTTGCCCA    20640
GGATGGTCTC GAACTCCTGG GCTTAAGTGA TCCTCCCAAA GTGTTGGGAT TACAGGCATG    20700
AACCACTGTG CCTGGCCCAT ATACTACATA TATTTAAAAG TAGTATTTAA ATGTGTAGAA    20760
TGAATGAAAG AGGCAGTAAG AGAACAAAGT GAATGAAAAA GTATTCTAT ATGAAGTGAA    20820
AGCAGGAGAG TCCTCTCTGT TAGAGAACAA CAGAATTGCA TATGACAGAC TAGCTTTCTT    20880
AATATTTCTA GAACTTGATG GCTGTGAAGA GCGTCCCGTA GGAATTCTCC CTTCACTTAG    20940
GAAAACATAC CTCAAAACCA TCAGCTGTTT AGCATGCACC TGCTTTTCCT GGTATATCTC    21000
AGTGAAGCAG CTAAATTGTA AATGATTAAG TAAACTTTGC AGTGTATCAT GTGCAAAAGC    21060
ACAGTAAAAA CAAAAATGCA TTGGAAGCTG TGAGTTGTTG CACTGCACTC ATGGATGAAT    21120
AGCTGTTGGT TCGCATTGCG TTTTTTTGTT TTGTTTTGTT TTGTTTTTTT GAGATGGAGT    21180
CTTGCTCTGT TGCCCAGGCT GGAGTGCAGT GGCGTGATCT CGGCTCACTG CAAGCTCTGC    21240
CTCCCAGATT CACGCCATCC TCCTGCCTCA GCCTCCCGAG CAGCTGGGAC CACAGGTGCC    21300
```

```
CGCCACAACA CCTGGCTAAT TTTTTGTATT TTTAGTAGAG ACGGGGTTTC ACCATGTTAG    21360

CCATGATGGT CTCAATCTCC TGACCTCGTG ATCTGCCTGC CTTGGCCTCC CAAAGTGCTA    21420

GGATTACAGG CATGCCGCAT TGCGTTTTAT ATAATTCTCA TGGTTCTAGT CTCGAGCTGT    21480

AGGATTTTGA TCACTGTTTC AAACAATAAT GTGAGTTTGC TAAGAGGTCT AAATAACAAA    21540

AGCTAAGTGT CCAAACACAT ATCCAAACCT ATACACTGGG CAATGCATCT GAATTATATG    21600

TGAAATTTCC TGCCATTATT TAAGACACAA AAGGAACATT ATTTTGATAA TGTATTTATT    21660

TGTGAGTGGA GTGTTCAGAA TGAGCACGAT GGGTATAACA TTTTTGTAGG TTTTTAAAGT    21720

TGAAATTTAG TGTAAATCCA AAGAATCAAT AGACAAGTCT GTGTTTACT  TAACCTATAT    21780

GTTTAAATTA GCATTTTTAG ATACTGATTT TATTCCTAAT TTCAGAATTC TCAGCGTCTT    21840

GCCGATCAAT ATCGCAGGCA CAGTTTATTT GGCACTGGCA AGGATCAAAC AGAGAGTTGG    21900

TGGAAGGCTT TTTCCCGTCA GCTGATCACT GAGGGATTCT TGGTAGAAGT TTCTCGGTAT    21960

AACAAATTTA TGAAGATTTG CGCCCTTACG AAAAAGGTAA ACAGTGTAGG AGTCTGCCTG    22020

TTTGACTTAA TTTTGTTTCC CACTCCACAT TAAAAGATCC TTTTTGCTTT TAATAGGGTA    22080

GAAATTGGCT TCATAAAGCT AATACAGAAT CTCAGAGCCT CATCCTTCAA GCTAATGAAG    22140

AATTGTGTCC AAAGAAGTTT CTTCTGCCTA GGTTCATTTT TCAGTTTTTT TCTTGTAACT    22200

TCTGCATTTT TTGTTGCTAT TTATGTGATT CAAATTATAC CAGTTTATAG GCCTCTCACA    22260

AGTAAAATGA ATTGCCTGTT TGTTTTTGTA TGCCTATTTT AGTCAGTTTG GGGAAGGGA     22320

TCTGTGAGGA AAGGATAAGT CATAGAGCAC TTTTCTTTTT TAAGAGACAG AGTCTCTCTG    22380

TGTTGCTCAA GCTGGAGTGC AGTGGTGCGA TCATAGCTTA CTGCAGCCTC GATCTCGTGG    22440

GCCCAAGTAA TCCTCAGCCA CCTGAGTAGA TGGGACTACA GACATGCACT ACTATGCCCA    22500

GCTAATATAT TTTAATTTTT TGTATAGAGA CAGGGTCTTC TAGTGCTTCC TAGGCTGGTC    22560

TTGAACTCCT GAGCTCAAGT GATCCTCCTG CCTCAGCCTC CCAAACTACT GGGATTACAG    22620

GCATGATCCA CCGCTCCCAG CCAGAACATT TTCTTGGTTG ATGGGAAGTA GCTGACCATG    22680

GTATTTAGAA AACTTCTTTC TCATCGATTA AAGAAGCAGT ACTGAAATCA ATGCGGAGGA    22740

ATCCATATAT CATATTTACT TCTGGTGTGT AGAAGTGGAA AGGGAATACA TTTGTTGCTT    22800

ACTTTTTTGT ACCTTTACAT GTGATTGATC ACTTGTGAGT TTTTTCTTTC AAACATCTTA    22860

AAGCTTCCAG AGCTTTTTCT AGAAAAAAAA ACCAGTTTTA AGAATCACCA GTTCTAAAAG    22920

GGTAATATCT TATTCATCTT TCTGAGAATG GAGTATCATG ATTCATGAAT TAGATACTTG    22980

CATCTTAACA TTTGAAATAA TTTAATTTTA TTATTTTTTA GTTCGAAAAC TGTATCTTCG    23040

GGCACCAAAG AGCATTGTTA TAATCAAGTA CCAGTTGAAT TAAGTACAGA GAAGAAGGTT    23100

TGTTTTAAAG AAATTGTTCT GACTTATTTC ATTCTTTATT GATTCAAATT CTGTTTAAAA    23160

TTTTATATTT TAATTCCTTT CCAATTAAAG AGAAAATGGC ATATATAACA AAGCATAAAA    23220

TTCGGCCAGG GAAGTGATGT GAACAGACTA AAATTTATTG TATATAATTT CTGGGGCTAA    23280

TAAAGAATTG GAGGTATTTG AGAAAGGAAT TAATTTGGGT TCTTTTAAAC CTATCTGCTA    23340

ACTCATTTGG CTTAGAGTAG TCACATGTTA TAATACTTAT AGTTGATCAA AAAATTGATT    23400

CCTAAGTGTT CTTATTAAAG ACACACACAC ACACACACAC ACACACACAC ATTCTTTCTC    23460

TCTCTCTCTC TCACACACAC ACACATGCAC ACACACTTAT GTACTTTCTT GCTTTTTTTG    23520

ACCTAAGATC TTAGATAACT ATTACAGATT AAATACTAAT CCACTGGCAG ACTTCAGCTA    23580

ATTAGAACAC TGGAATAATA GGCAAGCATA GTGAATTACA TTTTCTGGTG AACTTTTTCT    23640

GCTTTATTGA AGTATGCAGA ATGTAAATGA ATTGTTTTTA TAACTTTGGC ACTTGCTGTA    23700
```

```
TCTTAGAACA TTCTTTTGAT GATTTATTTT CTGTAGTTTT GGGAGAGATA AGACATTGGA    23760

ATGCGTTTCT AACTACCTTT AGAACTTTAG AAACTGATAA TTTAGGAGGT TATTTTCAGG    23820

TGATTAATTT GACAGCTTGA TTAGGCAAAG AAAAAATTGT GATTTGAGA TTTTTGTTTC     23880

TTATTTTCTT CACATTTAAA AGTTTTTTGA AACTTTTTTT AATGGACCTT TATATGTTTA    23940

AATGCAGTCT AACTTGGAGA AGTTATATTC TTATAAACCA TGTGATAAGA TTTCTTCTGG    24000

GAGTAACATT TCTAAAAAAA GGTACAGAGT TCCATATTTC TATGTTCTAT ACTTGCTTTA    24060

TGAGTACTTT TTTTTCTAAA GAGAAAGAAC TGTCAGATGT TGGGCTATTT CATTGGCAAA    24120

AGGAAGTTAA ATTTAAAACA TAAGCTTTTC AGTATTAGAA TGATCAAAGT GAGCTATAAA    24180

AGAATAATGT TAATTAATA GCTAACACTT CTTGGATATT ACTGTTTGTC AGGCATTATG     24240

TTAAATGCTA AGAACTTTAT ATGTGATATC TCATTTAATT CTTACAAGAG CTAACAGCT    24300

GTTACTATTT ATCGCCATTT TATAGTTGAA GATACCAAGG GTTAAGAAGT TGACAAACTT    24360

GTTCAAGAGC ATACAGCTAA TGGCCGAGCT GGCTTTCAAG TCTATATTTG TCTACCTCTA    24420

GCATCAAGAC ACTATTTATT TTTCTTTGTA TGAAATATAT ACAGGCATAC TTTGTTTTAT    24480

TGTGCCTGGC TTTATTGTGA CTTGCAGATA TTGCATTTCT TATAAATTGA AGGTTTGTGG    24540

CAACCCTGCG TCAAACAGGT CATATTAGCC CCATTTTCCA ATAGCATGTT CTGTTGTCAT    24600

GTCTTTGTGT TATATTTTGG TAGTTCTTGA CTGGCCATTC ACCATTTCTC TCCCTCTCCT    24660

CGGGTCTCCC TGTTCCCTGA GATACAACAA AATTGAAATT AGGCCAATTA ATAACTCTAT    24720

AATAGTCTCT AAGTGTGTTT TTTTTTTTTT TCGAGACTGA GTCTCACTCT GTTGTTCAGG    24780

CTGGAGTGCA GTAGCACAAT CTCGGCTCAC TGCAATCTTC GCCTCCCGGG TTCAAGCGAT    24840

TCTCCTGTCT TAGCCTCCTG AGTAGCTGGG ACTACAGGCG CCCCCCGATC ATGTCTGGCT    24900

AATTTTTGTA TTTTTAGTAG AGATGGGTTT TTGCCGTGTT GGTCAGGTGG ATCTTGAACT    24960

CCTGAACTCA GGTGATCCGC CTGCCTTGGC CTCCCAAAGT GCTGGGATTA CAGGTGTGAG    25020

CCGCTGTGCC TGGCCCATCT CTAAGTGTTT AAGAGAAAGG AAGATTCACA TGTCTCTCAA    25080

TTTAAATCAA AAGCTAAAAG TGATTAGGCT TAGTGAGGAA GCCATGTCGA AAGCTGAGAT    25140

AGGCCAAAAG CTAGGCCCCT TGCACCAAAC AGTTAGTTTG CAAAGGCAAA AGTTCCTGAA    25200

GGAAATTAAA AATGCTACCC CAGTGAATAA AACAATGATA AGAAAGCAAA GCAGGCTTTT    25260

TGCTGATATG GAGAAAGTTT TAGTGGTCTT TATAGGAGAT TAAACCAGCC ACAACATTCC    25320

CTTGAGCCAA AGCCTAATCC AGAGCAAAGC CCTAACTCTC TTCAATTCTC TGAAAGCTGA    25380

GAGAGGTGAG GAAGCTGCAG AATAAAAGTT TGAGGCCAGC AGAGGTTGGT TCATGAGGTT    25440

TAAGGAAAGA AGCCATCTCC ATAACATAAA AGTGCAAAGT GAAACAGCAA GTGCTGGTAT    25500

AGAAGCTGTA GCAAGTTATC CAGAAGATCT AGCTAAGATC ATCGATGAAG GTGCCTGCAC    25560

TAACAGACTT TGAATGTAGA CCAAATGCTT TCTACCAGAA GAAGAAGCTG TCTAGTACTT    25620

TCATAGCTAG AGAGAAGTCA ATGCCTGGCT TCAAAGCTTC AAAGGACAAG CTGACTCTCT    25680

TGTTAGAAGC TGATGCAGCT GGTGACTTTA AGTTGAAGCC AGTGCTCAAT TAGCATTCTG    25740

AAAATCCTAG GGCCCTTAAG AATTATGCTA TATCTACTCT GCCTTTGCTA CATACATGTA    25800

ACAACAAAGT CTTGATGATA CCTGTTTACA GCATGGTTTC CTGAATACTT TAAGCCCATT    25860

GTTGAAACCT GCTTAGACAA AAGATTCCTT TCAAAATGTT ATTGCTCATT GACAACACTT    25920

AGTCACCAAG AGCCGTAATG GAGACATACA AGGAGACTAA CGTTGTTTTC ATGCCTGCTC    25980

GCTTAACATC CATTCTGTAG CTCATGGATC AAGAAGTAAA TTAACCTTTT AAGTATTATT    26040

ATTTAAGAAA TACAGTTTGT AATGCTTTAG CTTCTGTAGA TAGTGATTAT CAGAGATGGG    26100
```

```
TTTTTAAGAG GTTTTCCAGA AAACCTTCTG GAAAATATTC ACTATTCTAG AAGTCATGAA    26160

GAATATTTGT GATTCAGGAG AGTAGGTCAG AATATCAATA TTAATAGGAA TTTGGAAGAA    26220

GTCGATTCTT ATTAAAATCA AGAGTTTAGT GATAGACATA CTGAGTTTGG GATACCTGTG    26280

GAGTAGTCCA GAAGTTAATT TAAATATATG GGCTTAGTGT ACAGAAGTGA GCAGGGTGCT    26340

TATATATGAA TAAATATTAT TTTAAGATAT ATTTAAATTT TCCTTAAAAT AATACCTATA    26400

CTTGATATAA AAAGTTAATT GGAAATTAGT GGCTTATGAC AAGCATACCA GCCCACACTC    26460

TTCCCAAACC CACTTTGCTC TTATTCATAG AAGCTGTCAT CTTCAAATCT TCCAGCTGAT    26520

TTCCCTGGCG TGTGCCTTCT TATTTCTGAA TGACACGCTT AGAGTACTAT TTTTTTGACT    26580

TAGCAATTTT AGAAATTTTC TACTCATCTC CTATTATGGT AGATTTCCCC TCCTTCATTC    26640

CTCCTCCAAT ATAATTATAT TTCGTCATAT TAATAATTTG TTTATATATA TTTTTAATAT    26700

AATATGATAA TATTGTATTT ATATTATTAA AACTACACAA ATATTATATA CACACTACTA    26760

ACCCAACCGT GTTATTATGG CCACCACTAC CTTTATTTTT TTCCTTGTGT TAGTGATTGT    26820

CTTTGTTTTA TTTTCTTGGT TTTGAGTATT CCTTTTACTA ATTTTCTTTT TTCCTATTTC    26880

AATCTCTCAT TATTTGTTTA CTCATTTGGA GTGTTCCTTG ACTTTTATCC CCTCTTACCT    26940

AGTGACATTT TAATTTTAGT TATCAAATTT TTAATTTCTA AGAATGCTTC TTGTTCTCTT    27000

CTTGTTTCTT CTTCCCCACC AGCCAAAAAT CTATGATGTT ATAGCAAGGA TCATACATTG    27060

TTTCCCAGTA GGTTAAGAAA CCTTGGTTAA AACCTGTTGT ATCCCAGTAA GTTAAAAGAC    27120

GTTAACGTGT CATCTTCAGT ATGGATGAAA GAATATTTTC TTTCAAAAGC AGTTGGTTGA    27180

GGAAGAGAAT GGGACAAATG CTCTTTTTAA AACACCAATT TTGTGATGAA CTCAAATTGC    27240

AATTTTAACT TTACCATTAT AATGAATGTA TTTGATCCAA AATGTTTAAA ATCTAGGCTG    27300

TTGTCATTTA AATAACAAAT TACCTTACTG GTATCATGAA GAATAAATGT TTGTACTGAT    27360

TTGGAAAGAC ATTCTCATTT AGGGGATGAA ATAGAAAGTC AATGAGGAGA AAGAAAAGCT    27420

TTTATTATTT ATTTTCTTTT AAATATTTTA GTATCATGGT ACAGTCACCA GAAAAAGCTT    27480

ACAGTTCCTC ACAGCCTGTT ATTTCGGCAC AAGAGCAGGA GACTCAGGTA AGGCTTTTGT    27540

AAAAAGGTAA TTAGTTTATG ATAGGATAGT TATGATTCTA TGTATGCTTA AAATTCTGTA    27600

TTTTGCCAGC ATTTTAAAAA TTGTTCTTAA GCTAAGAGTC TGAGTTTATA TTTCAGTTTA    27660

TATTCATTCT AAGGAAAAAT GTGGTATCTG AAGCTCTAAA AATAAAGGAC TAGATCTTTT    27720

AAGTACACTT TAAAAAGTGT TGTTTCTTTG TTTTTTGTTC AGATTGTGTT ATATGGCAAA    27780

TTGGTAGAAG CTAGGCAGAA ACATGCCAAT AAAATGGATG TTCCCCCAGC TATTCTGGCA    27840

ACAAACAAGA TACTGGTGGA TATGGCCAAA ATGAGGTAAA CTATCTTTTG CATGTGTTCT    27900

CATTTATTTC CTTCTAACAA AATAGATTTG GAAAATATAT CTAAGTTGAT AATATGACCA    27960

TAGCTTCCAC TGTCACATCT GGGAGGTGAC TCAGATTCCC CCTGCTGCGA TGCTTATCTC    28020

TTTGCCAAGC TTTAGTACCG TGTTTCTGTA TGAATAAAAA CCAGTTACGT TTTCAGCAAT    28080

CATATTCAAT ATTTATAAAA TCTAACTCAT TATTTACCCA CCCTGCATTT TATCCAAATG    28140

CCGAAACTCC TCTTTTTGGA TTCTTTATTT TTGATTATCT TACCATCACA TTTGTAGTCA    28200

GAGGTTCCTA ATGCTTAAAA CCTCTGATCT GAATTTTCTC TCCTCCAATA TAAAACCCCT    28260

TCGTCTTCCT CTTCTTCTTC TTCATTTTTT TTTTTTTTT TGTCTGAAGA CTTGTCTCAC    28320

TGTGTTGCCC AGGCTGGAGT GTAGTGGTGC GATCACTGCT CACTGCAGCC TTGACCCCCT    28380

GGACTCAAGC TATCCTCGCA CCTCAGCCTC CCGAGTAGCT GGGACTACAG AACATGCCAC    28440

CATGCTCAGC TAATTTTTGT ATTTTTTGTA GAGACAGGGT TTTGCCATAT TGCCTAGGCT    28500
```

```
GGTCTTGAAC TCCTAAGCTC AAGCAATCTT CCCGCCTCAG TCTCCAAAGT TCTGGCACTA   28560

CAGGTGTGAG CCACTGTGCC TGGCCTCTTT TTCTCATTTA AATACTTTTC ATACCTTTTG   28620

TAAAACGGGT TCCTTGTTGC CTGTCTATGC CTTCCTCCTC CTTCTTAATG ACACCACGTT   28680

AATTCTGACT GTTTTCCCTT GGCCTGTTGC AGAAGCCTCT TAACTATTAA CCCTTCATTC   28740

TCTCTCTCTG TTTCATCTGA TATATGAGTA CCAAACTAAA TCTTCCTTTA TCATATCTTA   28800

CTTCTGCTTA AATGTTTTTT TTCTAGCTTA GAATTCAAGG CCCTCTATTT ATGAACTTAA   28860

ACTTACTTTT CCCTCTAAGT TACAGAATTT GAAATGGTTT ATCTTACCTG GATTGTTTAT   28920

CACTTGTTGA AGATCCATTT TCAACTTCCA TATATTTATT TACAGTGTTG CTTCTCCTTG   28980

TAGTTTCCTT GATTCCTCAA AACTCCTTTT AAGAATTCTT GAAGATCTCG CTTTATTACT   29040

ATTTCTCGCT TTATTACTGT AAAGACTATG AGAAGGTCTT TCATGATCTT ATCAGCAAAG   29100

TAATTCCTCT CTCTTGAATT CATAGAGGAC TTTCAGATGA ATTCTAAAGA TGCTTCTGTA   29160

GCACTTACCA CACAATNGCT ATATTTATT TTTTTGTAAT TAGTGGTAAA CAAGTATTAT   29220

TATATCTTNC TAGATTTTAA ACTCCAAATA AAGATACTAG CTCCTTACCT TTTTGTGTGT   29280

CTCCTGTAGC ACCTAGCACA ATGCCTCATA AACAGGAGGT GATCATTAAA TATTTAGAAG   29340

AAATTATTTC CCAAGAATAG TTGCTTGGTA ATTGTATTTG TCTTTTACTT CCTTTTAAAA   29400

AATTGTTTCT GTCACTAAAT TGCATCCAAT AGATGTTACT TGAGTGCAGA ATTTTCTAAT   29460

GACATTACAC AGTGCTACAT CTGACACTAA TTCTTTTGTT AAAAAATAAA TATTCTGGCC   29520

GGGCGCTGTG GCTCACGCTT GTAAATCCCA GGACTTTGGG AGGCCGAGGC GGGCGGATCA   29580

CGAGGTTAGG AGATCGAGGC CATCCTGGCT AACACGGTGA AACCCCGTTT CTACTAAAAA   29640

TACAAAAAAT TAGCCGGGCG TGGTGGCGGG TGCCTGTAGT CCCAGTTACT CTGGCGGCTG   29700

AGGCAGGAGA ATGGCGTGAA CCCGGGAGGC GGAGCTTGCA GTGAGCGGAG ATCGCGCCAC   29760

TGCACTCCAG CCTGGGTGAC AGAGCNNNAC TCCGTCTCAA AAAAAAATAA AAAATAAAAA   29820

TAAATAAATA TTCTAAGACC ATACTTTAAT GGAGGTGTTT TTTGTTTTTT TTTGTTTTTT   29880

TTTTTTTTTT TTGGTGATAG AGTTCTCACT CTGTCACCTA GGCTAGAGTG CAGTGGCGCG   29940

ATNCTCNGGC TCACTGCAAC CTCCGCCTCC TGGGTTCAAG CCATTCTCCT GCCTCAGCCT   30000

CCGGAATAGC TGGGACTACA GGTGCGCGCT GCCACCCCG GCTAATTTTT TGTATTTTAG   30060

TAGAGATGAG GTTTCACTGT GTTGTCCAGG CTGGTGTTGA ACTCCTGAGC TCAGGCAATC   30120

CACCCGCCCC GGCCTCCCAA ATTGTTGGGA TTACAGGCGT GAGCCACAGT GCCTGGCCCA   30180

GAGGAGATAT TTAATGAAAA ATAATAATCA TTAGATAGGC AGATTTTTAG AAGGAGGGCA   30240

TCGAATGGGT TCTTGGATAT TGGACACAAT AAGAAATATT GAGCTAAAAG TCTGAAGGAA   30300

TTGGCAGATA TACTGTTACA GGTAAACACT TTGTAGAAGA AAATAATGAA TGAGACTTTC   30360

TTTTGAGATT TTCTTAGCCT CTTAGTTGTT CCCAGTTAAA GCCTCATATT TTTCCTTTTC   30420

ATGACAATAA AAATAATAAT AAAATCAGTA ATAAAGTGAA TATATGAGAT GTTAACCTGT   30480

TCCTTTATGA CAATGTCCTG TTTACCAATT AACAGTGTGT TTTTGTGGTG ATGGGGCAA    30540

GACAAATCTT TAAATGGTGG AAAGCAAAGA AAGAAATTAT AAAACATGAT TAGTTGTATT   30600

ATACGTTGTT TTTGGTTGTT GGAAAAACTA TACATTTATT GAGAGAATCA TTAGGAAGCT   30660

GAACATCAGC TATATTGCTG GAGTGATACT GTTTCAGTGG TTTCTTGACC TTTTTGTTGT   30720

TGTTGTTGTT GTTGTTAAAC ACAGACCAAC TACGGTTGAA AACGTAAAAA GGATTGATGG   30780

TGTTTCTGAA GGCAAAGCTG CCATGTTGGC CCCTCTGTTG GAAGTCATCA AACATTTCTG   30840

CCAAACAAAT AGTGTTCAGG TAAAATACTG TGGTTTGCAG GAGCTCTTAG AGAATAAGCA   30900
```

```
TTTTTTGTAA CCATTTCAAA AGTACCCTCC AGAAGCAACA TTTGCTCACT TTATTTGCAT   30960

TTCCATACTG GACACTTAGA AAATGAATTA AAATTGTTTT TACAGTCAAT CNNTGTTGTA   31020

AAAACATGTC AGTTATCTAC TTTTAAAGAT GATACTAAAA AGTAGTTGTC CAGGCTGCTG   31080

ATGTCTTTCT ATTTCATTGG GAGGTTTTGT TTTTAAATTG GAAACATTAT TTTAGGTTGA   31140

TAAATTATAA TTTTACATTC AAATGTGGTA GTTGGAATTT AAAGCTGGAA AGTTATCCTT   31200

GCTATGAGTT GGTCAGGAGC TCAGCCACTT TCTTTTGGTT TAGCATCTTC TCTAATCTCC   31260

CTCCCCTTCC AGTAATGCTG TCTTTTGATA GTAAGTGGAT TTCATATTAT TCTCTTCAGT   31320

TTTAATAGTG TTTCCTTCAT ATCCTTTTAT TATTGCTTGT TCTGCCCTAA GTGACCATTT   31380

CCAGAAATGT CATTTAGGNA TTTTCTCTAA ACTCCACGTA GCAGACTCTA TAATGCATAC   31440

TCTGCAGAAG GTGAGGCAGT GGGAGGTAGA GGGGAGACTA CTAGACTAGG AGTCACGGAA   31500

TCAGGACTTT AGTTCTTCCT TACAGTTGTT CACCTGGTGA ACCTGCACAT GTCCTTTAAT   31560

TTCCTTGGGT CTCCATTTCC TCAGCTATAC AATGGAAATG ACACTTCCTC CCCCACATCC   31620

AGGAAACAAC AGATGACATT AGAAAATAGA AGACATGGGA TAAGTATAAA ATGTTGAAAG   31680

AGTTAAACAC ATTCAAGGCA ATATTAAGGG ATTATTTTTT ACTTCCAAGA AGCTCCTGGA   31740

AGCTTTGGGC AGGCACAGTT GGATCCTACT TTAGAAAAAT CTTTCTCTAA CTATAAGTAG   31800

AAAACCCTTC TGCTTTTTGA ATGTAGCATT TCCCTCTTTT GATATAGAGT ATCTTTGGCA   31860

ACTTTGAATT TTCTTTTTCA TACTCTTATA TAAGACATCA TGTGAAAATT CTTATTTCTT   31920

ACTGAGTTTT TGGAAATGAA ATTATAATGT CTTAATAGTT TGAGAAAGAA TATCATACCT   31980

ACCAGCGGTA ATTGAGTAAG TTCCCTCTCT TTGGACACTT GAAAGTAGTA TCTTCTTTCA   32040

TGAATTAGTG ATATTATTTA ATAATGAATG AGTGATCTCT CCTAACTCCC CTTCAGAAGA   32100

GGAAAATGAA GTAGGGGAAA AGGTAAATTC CCCAAGGGAT AGGTATGAAA CCTTTATGAA   32160

CCTTCTGGAT AGAGAAGATG ACTGCTGATT TCTGTGATTA GAAATTATAC TTGGGTTATT   32220

CTGCAAATTG AAATGAATTA TTTAAAAAAA AACAACTTTA ATGTTATTA AGCAAGTTTT    32280

GTTATTCATG AGTTTCATTA GCCTTTTATT TTTTTTTTAA ATTTTGAAGT AAAATTTCTT   32340

GCTGTCACAA TACACATTAA AAATTACAAA TATGACACAT ATTAAACACA TTAAGATGGC   32400

CGAATAGGAA AAATATGCTA AAATATTTTT ATATAAATAC ATTTTTTGAG AATTTTGAGA   32460

ATTTCTGGAA CAAAGTAATG ATATAATCCA TAAATGTACA ATTAAAGAGT TTAAGGATAT   32520

CCAAAATACT TGGCAAAGTA ATCTGAAATA ATACTCTTAG GAAGGTAGGG CAAGAATGTG   32580

ATTCTAGTAA GCAAAAATGT AATCAAATCG TATTCTAGTC CCAGCTACTC GGGAGGCTGA   32640

GGCAGGAGAA TGGCGTGAAC CTGGGAGGCG GAGCTTGGAG TAAGCCGAGA TCGTGCCACT   32700

GCACTCCAGC CTGGGCGACA GAGCGAGACT CCATCTCAAA AAAAAAAAA GACTATATGA    32760

ACTTGTATGG CATAAATATG TACAAATATT ATTTATTTTA AAAAAATTCA GGGGTAGGGA   32820

CAGGGTAGTT AGAAAATATC TAAGGATGTT CATGAAATAA TACTGGCTAT GAATGACAGT   32880

TGATGAAACC GGGTGGTGCC CNATCTTATT CCCTCGACTC GTGTATATGT TTGATATATC   32940

CCACAATAAA CCTTAAAAAA AAAAAGNATG AGTGGTCAAT TATAGGAAGA TATAAATAGA   33000

AAAGGCAATA AGGACAAAAG TTGGCAAAGC TTACCTAAGC ACTCTTCAGA TAAAAAGACA   33060

TTTTTGCTAA CTAGATTTGA ATATTATAGT TTAATTGTCA AGGAAAATGC CTCAACTTAA   33120

TCTTTGTTAA GAGACTACTT AAGGCACTAT CAGAAGTTCC CTCATGGCAA GGTGCAATCC   33180

CTCATGCCTG TAATCCCAGC ACTTTGGGAG GCCAAGGCAG GCAGGTTACC TGAGGCCAGG   33240

AGTTAGAAAA CAACCTGGGA AACATAGTGA GACCCGACCT CTACAAAAAC AATTTCTTAA   33300
```

```
AATTAGCCAG GCATGGTGGT GCTAGCCTGT AATCCCAGCT ATTTAGGATG CTTAGGCAGG    33360

AGGATTGCTT GAGCCCGGGG ATTTGAGGCT GCAGTGAGCC ATCATTGTGC CACAATACTC    33420

CAGCCTGAGT GATAGAAAAA AAAAAAAAAA GTGTCTTTGT TATATTCCAA ACTTGTTCTC    33480

AACTTTCAGG TGAGCTGGCT TCCTGTATAA CTCTTGTATA GGACAGAACA TACTGGTTGG    33540

GGCAAGTGAA ACTGTCTAGT TGTATGCCTC ATAAATTAAT GAATTTCCTT TCTAATATAT    33600

ACACTGATAT TTATACACAC ATACACATAA AACCAAGCTC AATAGATGGG TAGTGCAGCT    33660

CTATTCCCCA AAACCCAACT ACCCTGTAAC AAGCACATT AGACTTTGA GATTGCAAGG    33720

ATGAGGACTG AAATGCTGGC CTAGACCATG GTGTTGCCAT AGTGGGGTGA CCAGTCTGAA    33780

TAGCCAACAA TGCTTCCTCA GTAAATACCC ATTTTGTCTT GGTGGGATTT CTACAAATTG    33840

CAAAATGCAG CTATTATGAA GCTGTAAAAG AGNAAACANG AAACATGTAA CACCTGGGAC    33900

TGTTTTATTA GGCCCACCGT ATGCTCAGAA CATGAAATCT CCACTGCTAG GGTTATTTGA    33960

TTGAAATTAT CTTTTGTGTT GATGTGAGAG TTTAGCTCTG AGATTCTTCC ACATGTAAAA    34020

TGTAATCCCC CAAAGTATTT GGCAAGCACA TTTTATTGCC TTGGGTCAGA TAATTGAAAC    34080

ATTAGGCATC ATATATATAG CATGTAAAAA GTAAACAGA AACATTTATG TTTCTCACCA    34140

AGCAGTAAAT TAGTACTCAA CTAATAAATT TCTTAAACTC CCTAATAACA GAATATGGAA    34200

ACAAAAAATA AATCTTTCCA AAAGAAGAGC TCATGGACAC ATTTCCTCAT ATATGTATAC    34260

ATAATATAGT AGAACACATG ATAAAATAACC TATAAAAATG ATACCAATAT CATTCATCAA    34320

GAGACGAGGC TCTTCTTTAA ATTATTAATT TCATCTGTTA CAGGTTTTAT TATGACTGTA    34380

GTATGCTGTT TTCATCTACC TTTTATGTGT AGTTAAAAAA ATAGTTTTCT ATCTCTTTAC    34440

CTTTATTTCA GCCTTTAAAA AGATTCCATT ATTTTTTCAT TAATCTTGTT TTTCAGTTTT    34500

TCCCATTTTT TCTTTTAAAC ATTTCTTAAG GAACCATATT TAAGATTTTA TAGAATACTT    34560

AGATTTCTAG TTGGGATGTA TCATTTAAAA TTAGATATGT AGAGAGAGTG TTATGATATA    34620

TTTCCTTACG ATATATTAGT GGTTATAGTA CCTAAATTTG AATAGTGATT CTGTTCATTC    34680

ATTCATTCAT TCATTCAATA TTCACTTCCA GGAGATTGGG GACTTATTTA AAGACAGAGT    34740

AGTTCACATT ATAGTTCCTT TTTTTAGTCC TTCTTATTCG TTAAAGAAAA GACTAGGAAA    34800

TGTTTGTTAT TACAAATATT TTATTAAAAT TTTGTGTGCT CTAGCATTAT TTTACCTTTT    34860

AAAATCAATA TGTTAAAAAT CCAACTTCTT TTTGAGCTCC CCATAAAAAG GGAATTATTT    34920

GTTGCTTATG GGTTTAACTT GTGTTATTTT TTTCTTAATG GCTAATTATC ATACATATAT    34980

TCTATTATTG TATTGATATT ACTGATCATT TGTGCTACAT TAAAAATTCT GTAGACAGAC    35040

CTCTTTTCAA GTACAAAACC TCAAGAAGAA CAGAAGACGA GTCTGGTAGC AAAAAATAAA    35100

ATATGCACAC TTTCACAGTC TATGGCCATC ACATACTCTT TATTCCAAGA AAAGAAGATG    35160

CCTTTGGTAA GTGTGACTTT CATGTTACAG GGAATTTTTT TAGTTTACTT AAACTTGTGT    35220

TTTATCAGCT TTTTAGTATT AAAGTTCTGA CTTGGGATCA ATTTCCTCCA ACCCTACAAT    35280

AAATCTCAGT TTATCTTTAA TTTTAAAAGA GAATGTTGTT TTCTTTTTCT GTTAAGCCTG    35340

CCTGTTAAGT AATAGCAGCA AGTTTAGTTT GGCCATGAAT ATCTTCTAGA GATTGTATCG    35400

GGGTACTGAT AAACACATTT ATAGCTCAGG GATACTGCAT CAGCCATATT TTAAAATGGG    35460

ACTAACAGTT TAAAAACTAT AAATATTCAC AGTGTTAAGA AACAATCTCA AGATGCATTA    35520

AGAAAAAGGA AGGTGCAAAA CAGAAAAACA AACGTAAACG TGTGTGCATA TGCATGCTTA    35580

TATAGTCACA TATTCTTGTA TGTGTACAAA AAATACACAC TGGATCTCTG CAAGCATAGC    35640

CAAGCAACTG GAAATATGTT TTTAAAAACT TGCTTTTCAT TCTATCTCTT CTAGTACTGT    35700
```

```
TTTGATGCTC TTTGAAAACA ATCTAATTGC TGTAACAAAT GACCATACGT AGGCCGGGTG    35760

TGGTGGCTCA TGCCTGTAAT CCCAGCACTT CGGGAGGCTG AGGCAGGCAG ATCATTTGAG    35820

GCCAGGGATT TGAGACCAGT TGGACAACAT AGGGAGACCC TGTCTTTACT AAAAATACAA    35880

AAATTAGCTG GGCGTAGTGA CGCATGCCTG TAATCCCAGA TACTTGGGAG GCGGAGACAT    35940

GGGACTTGCA TGAACCCAGG AGGCAGAGGT TGCAGTGAGC TGAGATTGCG ACACTGCATT    36000

CCAACCTGGG CGACCGAGCA AGACGCGGTC TCCAAAAAAA AAAAAAAAAA AGACCATATG    36060

TAATGTTTCT TCATTGTTCT AAGATAAATC TTTAAGGCTG TTGAGGTTTT TTGTATACAA    36120

AATGGAGAGT AAGTTTTAAT GGGATGGGAC AAAATGAGGC TTACAGTTGA GTTTAATTTG    36180

AGTTCACATC CTGTTGACAT TAAGTTGATT TGGAACAAGT GATATGGTCC AATGCCTGCT    36240

TTTCTATTGT CTGTGGTTCC ATCCACTAGT GCCTGTGTTA CACACCTCTT GTTCAGGTTT    36300

TATCATTTAA AATAAATAAG AATAAACAGT CCATAGCTTA TCTTACTTAC TGAATAAATG    36360

CTCTGATTTG ACAGTCATGT TTCTTAAAGT TCCTTACAAA GGCCATTGCC CAAGAAACCA    36420

AATAATTCCA TTATACTATT TTTGAAATAG AACACATAAT AAATGGGAAT TTTAAGTTCA    36480

GTTTCTTATG TAAACAATAA CTTCTATGTA CATGTTAAAT ATGCCTGTAT ATACCTAATT    36540

TGACCATGTA TGTATAGTAG AAATGAAAAC AGTTACTAAG AAAATTTGTT ATTGGCTCCA    36600

AATTTTCTGA ATTAAGTGTA TTNCTAATGC TCAGCCATAA TATGGGGTTT CATGTGTTAG    36660

TTTATGTATT CATGGTTAAA AATGTGAAGA CTGTTATATC TTCATTTGTG TCTTTTGGTA    36720

TTATTTGGTT GTATTTTATT GTGTGATATG GTGGTATAAT TATCCTTACC TCCCAGGAGT    36780

TTGAGAGGGT CTTGCCAGTT AACCGCAGAA TTAAACATGC CTAGGACTAA TTAATCAGGA    36840

GCAATACTAC AATTAATTGG AGGTAATTTG AAACCTGGTT TCAAATAACC CTGATATTAT    36900

GCACACATGG TGCACACTTT TCTAGTAGAC ATTTAATGAA AGTAATTTAA AACCTACCTT    36960

TGAAGGATGA AAAACATTGC CTTAAATGCT CTATTCTGTG AAAGTATCAA CATTTATGCA    37020

AATACAGTCT AAATTCAGAC TTTGAAAATG TATTGAAAGA GAGGATCATG AAATAAGTTA    37080

GAGCTGAGTG ACAAAGCTTT CTGAGTGTTT AAAAGAATGT TTTACCTAAT AAATATCTGA    37140

AATGTATTTG GAGCCACATT TGTTTAAAGA ACTGTATAAA TATGTAGCAC TGTTCATGTG    37200

AAGTTCAATA GTAGGAAAAT GCTGACAGCC CTTGTGGAAC TGTGGTTATT ATTATTTTAT    37260

GAATAGAGCC AATTTCAAAC ACCTATTAGA GTCTTCTCAG GAACATTTTA TAGAATGCAT    37320

CTGGAGCCTT ATGTTATCTC TAAGCATTTT AGGATTTGTC TTCTTGGAAA TTCATGTAAC    37380

CAAACCACCA TGTGTTATTT CAAGTGTATA TAGTATTGGG TTACAGTTTA CTATGTTTTC    37440

AGAAGGTTGT GACAACTATT AGACTTACAG AGAATGACTT CTCTGCCACT AACGGCTTTC    37500

TAAAGTGAAT AGAGAGGGGC GAGGATTGAA TTCTTCGGTA AAGCTGGGTG ATTTTGTTTT    37560

ATTCAATACA GTATAATAAG TATAAAAAGT AGAACCTATA GAGAGCTATA ATGGGGGTAG    37620

TTTTAAAGAA ATTCTGAAAA TGAAAAACTT AAGTAAAGGT TTAGTTCATT GTTTATTTCA    37680

CACTGAGCAT TTACTACCTG AATGTTTTGG ACATTTATTT TCCATGACTG GAGTGGACAC    37740

TTTTACAACT CACTGGGTTC TTTGCTGATC TTTCTCTAGA AGAGCATAGC TGAGAGCAGG    37800

ATTCTGCCTC TCATGACAAT TGGCATGCAC TTATCCCAAG CGGTGAAAGC TGGCTGCCCC    37860

CTTGATTTGG AGCGAGCAGG CCTGACTCCA GAGGTTCAGA AGATTATTGC TGATGTTATC    37920

CGAAACCCTC CCGTCAACTC AGGTGAGAGG CATGGCCTAG CTCTGCACCC TTAATGACTT    37980

GATGAAGTAA ACAAGCAATC CACTATATTT TTCACTGTTA ACAGCATTAA TCCTTTATGC    38040

TATTATGAAA ACCTTACTTT TGTGATTCTT TTTCTTGTTT TAGGAAAACA ATCTTTCTTC    38100
```

```
CCATTATCAC TCAGAGGAAA GTATACTGAG AAATTTTTTT GTTTTGTTTT GTTTTTTGAG   38160

ACAGAGTCTT GCTCTCTTGT CTAGGCTGGA GTGCAGTGGC GTGATCTTGG CTCGCTGCAA   38220

CCTCTATCTC CCAGGTTCAA GTGATTCTCT TGCCTCAGCT TCCTGAGTAG CTGGGACTAC   38280

AGGCGTGTGC CACCATGCCC AGCTACTTTT TGTATTTTTT GATAGAGACA GGGTTTTCCA   38340

TGTTGGCTAG GCAGGTCTCG AACTCCTGAC CTCTGATGAT CCGCCCACCT CAGCCTCCCA   38400

AAGTGCTGCG ATTACAGGTG TGAGCCATGG CACCTGGCCA ATACACTGAG AAATTTTTAT   38460

TTTCCTTTTC AGCTTAAGGT TACAACTTCC CCACCATCCA AAACGTGCAC TTTCATTTTT   38520

TTTCTAATTT CTATCTCATC ACTTGCAAAA ACCATATTTT TCTCCACATT CATTCCCAGT   38580

AGCTTCCTGA CTCCTAGTTC TTCCCTAAAT CCTTCTGAGT CCTTGTCATT GGTTTCGCTT   38640

GAGTAGCCTT TCTAATCAAC ACAGTCATTG GTATCAGTTA CTGTGACATG AAGGGACAG    38700

ACCAAGTTCT GTGGGCCGCT ACGTAGAAGG ATTTCCTGTC ACTTTGCTGC AGAACCTCAG   38760

CTCGCGGAGA GCAAGCCCCT TTGCTTGCCC TGTAGAAATA TTTTAAATTA TTATCCTTTT   38820

TTTTTTNAAC AGAAGTAAAT AGGAGATACG TTAGAGGATT TTCTCTCCTA GATGTGTAAA   38880

TACAAACTTG GGGTCTTATA ACTCAATAAA TCTGATAAAT TTCTTTTGAC TGTTAGGATA   38940

GAGCAGTGGC CATACCAATA GCCTCATCTC CAAAGCTGCA GTGAAGATAC TTTTTACTAC   39000

CTTAAAGTCT TTCCCATTTG TGAACAACTT GTGAACAATT CCCCCCAAGA ATTTGGAAGA   39060

TCACTCTCTG AAAGCACAGT CAATACTGTA CTTAAATGGA TCTGAGCAAA ATAAGTCAC    39120

TTAGAAGACA GGATTATTTC TAGACTTGAG TGTGACTTGA CTGAAGGTCT AAAGAACAAA   39180

CAGCTCCTTC ACTTCCATTG ATCACGGTGG AAGCACAGGG AAAGGACAGA CACGGAGGCA   39240

AGTTGGAGTA GTGCTCATCT AAGTTCCAGG GATGCGGGGG AGTGGCCAGG GGACTTCAGG   39300

TATAGTAAAT AAATAACCTA TTTATAAGTT ATGTCAATGT CATGTTTGAA ATAGAAAACC   39360

AAATACTGCA TGTTCTTACT TACAAGCAGG AGCTAAAGTT GGTGCATATG GATATAAAAA   39420

TGAGAACAGG CCGGGCGTGG TGGCTTGTGT CTGTAATCCC AGCACTTTGG GAGACCTAGA   39480

TGGAAGGATT GCTTGAGCTC AGGAGTTCAA GACCAGCCTG AGCAACATAG TGTGACCCCC   39540

ATCTCTACAA AAAATAAGAA AATTAGCCAG ACGTGGTGGC ATATACCTAT AGTCTCAGCT   39600

ACTTGGGAGT CTGAGTCAGG AGGAGTGCTT GAGCTCAGGA GTTTGGGGTT ATAATAAGCT   39660

GTGATCATGC CACTGTGCTC CAGCCTGAGT GACACCCAGA GTGAGAACCT GTCTCAAAAG   39720

GAGAAAAAAA AAAAGTAAC AGTAGACGCT GGGAACTACT GAGGGGAGGG AAGGAACAAT    39780

GGTTGAAAAG GTGGGAAGGG ACAGTGGTTG AAAAACTACG TGTTGGGTAC TATGCTCACT   39840

ATCTGGGTGA TGGGATCAAT TGTACCTCAA ACCTCAGCAT CCTGCAATAT ACTAATGTTA   39900

CAAACCTGCC CATGTACTAC CTGAATCTAA AGTAAAAGTT ATAATTTAAA AAATTATAA    39960

TAAAATCAGA AAATAAAGGT CTGAGATGGA AAATTAAAAG ACCAAAGCCA CCCATAAGCA   40020

CAATAAATCC CTCCCCCCAA AAAATTATAT CTATTAAAAA AAGGTGTTGC GCCAGGCACT   40080

GTGGCTCATG CCTATTGCCT ATAATCCTAG CACTTTGGGA GGCCAAGACG GGCAGATGAC   40140

TTGACTTGAG GTCAGGAGTT CAAGACCAGC CTGGCCAACA TGGTGAAACC CTGTCTCTAC   40200

TGAAAATACA AAAATTAGCC AGCAGTGGTG GCATGCGCCT GTAATCCCAG CTACTCAGGA   40260

GACTGAGGCA GGAGAATCGC TTGAACTGGG GAGGCGGAGG TTGCAGTGAG CCGAGATCAT   40320

GCCACTGCAC TTCAGCCTGG GTGACAGAGT GAGACTCTGT CTCAAAAAAA AAAAAAAAA    40380

AAGACCTTGT ACCCTGACAA GTTTTAGTTT GTGCAGGAAT GACACAATCT AGAATGACTC   40440
```

-continued

```
AAGATTGGAA AAATCTTTAA ATGTTAATTA CACAATAAGG GTAAAAGGAG AAAAATTACC    40500

TAATGTCATC TGAGCAACAA GAAGAAGAAA TGAAAGGCAT TAAAAATTGG GAAAAATTTA    40560

TATTTGACAG TATCTTAACA ACGAATTCTG CTTCTATATC ACTTCCTAGC TTTCTGATGA    40620

TAACTTCCCG TGCAGATCTG TATGTAAGGA ATGGACGTAG TAGTCATGCT AATCTGAGTA    40680

TTTATCTGTG TGATACTTAC GAATTAACGA TGTAAGTTAA TAAGTTAGCA TTTCGTGAAC    40740

CTGGTTAATA CCATTTGCTA AGGTTAAATT AGCCAAATCC TGAAGTAAGC TGTAAAACAT    40800

CCAAGGTAGG GTAGAGAGGC ATCTTATGAG AAAGCTGGCC AACTCTCCTG GTCACCTTCT    40860

AATCTTCCTA ACTTCAGAAA TCAAGGCAGA GAGAGGAAAA TAGTAATTAC TTTGTAGGAT    40920

TAGATTTATG GTTGTCGAAA CCTTTGTTTC TCCAGTGCAG AATGAGATAG CGTTTTAAGG    40980

AAAGCCAAAG ACTCAGATGT CTTCTTCATG CTCATCGTGT GGAATTTTTC TTCCTTTAGA    41040

AATGTATTGT CTCTCAGGGC TTAAAGCAAT TTGCATCTTT CGATGAGACA TTGAGTAATA    41100

GGCAATATTC TCTGAAATAA TTTGTGCAGG CTGGGCACAG TGGCTCACAC CTGTAATCCC    41160

AGCACTTTGG GAGGCCGAGG CGGGCAGGTC ACTGAGGTCA GGTGTTGGAG ACGAGCCTGA    41220

CCAACATGGT GAAACCCCGT CTCTACTAAA AATACCAAAA TTAGCTGGGC TTGGTGGCAC    41280

ACACCTGTAA TCCCAGCTAC TTGGGAGGCT GAGGCAGGAG AATTGCTTGA ACCCCCATGG    41340

AAGGTGGAGG TTGTGGTGAG CCAAGATTGT GTCATTGTAC TACAGTCTGG ACAACAGAGT    41400

GAGACTCTGT CTCAAAAAAA AAAAAATAGA ATTTGTGCAG TTCCCCCCAC CCCCTTTTTT    41460

TTTTCTGTTG GCATTTTTGC TATCATTTAG CTGCCTTCTT TATATCCTGA AACTTACAGG    41520

TGGTGTTGGT CTAGTCAGTA AGAGCAAAGG CTTTGGGAAT AGATAGATCT GTATTTAGAC    41580

CTTGGCTCTA GCATCTCATT GTTATGTGAC CTCCATCAAG TGACCTAATT TCCCTAATAT    41640

TCAATTTCCT CATCTCTAAG ACAGGGAGTT AATATTGCCT CTCTTATAGA ATTGTGAGAA    41700

ATATAGTCAT GTGTCGCTTG ATGATGGGGA TGAATTCTGA GAAATGTGTT GTTGGGCGAT    41760

TTCATTTTGT GGGAACCTCA CAGGGTGGAC TTAAACAAAC CTAGATGGTA TGGCCTACTA    41820

CACACCTAGG CTGTACGGTA TAGCTCCTGT CTTCAAACCT GTACAGCATG TGACTTTACT    41880

GAACACTGTA GGCAATTATA ACACAGTGGT ATTTGTATAT ATAAACATAG TGAAACATAG    41940

AAAAGGCCCA GTAGAAATAC AGTGTAAAAG NATTTTTTAA AAAAGCTGGG CATGGTGGCT    42000

CACGCCTGTA ATCCCAGCAC TTTGGGAGGC CGAGGCAGGC AGATCACTTG AGGTCAGGAG    42060

TTCAAGACCA GCCTGGCCAA CATGATGAAA CTCCGTTTCT ACTAAAAGTA CAAAAATTAG    42120

CTGGGCGTGG TGTTGGGTGC CTGTAATCCC AGCTATTCAG GAGGCTGAGG CAGGAGAATT    42180

GCTTGAACCC AGGAGGTGGA GGTTGCAGTG AGTCAAGATT GTGCCACTGC ACTTCAGCCT    42240

GGGAGACAGA GCGAGACTCT GTCTCNAAAA AAAAAAAAA AAAAAAGAGA TAAAAGGTA     42300

CATCTGTACA GGGCACTTAC CACGAATGGA GCTTGCACCC TGGGAGTTGC TCTGGGTAAG    42360

TCAGTGAGTG AGCGGTGAGT GAATGTGAAG ACCTAGGACT GTGCACTGCT GTAGACTTTA    42420

TAAACCCTGT GCACTTAGGC CACACTCACC CCTGTGATAC GAGTCTACCT ACTGTATAAC    42480

GTACCTGCAT ATGTACCCTT GAAACTAAAA CAAAAGTTAA AAAATTTATC TTCTTTTGCC    42540

AATAATAAAT TAACCTTAGC TTACTGTAAT GATTTTTCTT TATGAATTAA AATCTTTTTA    42600

CTCTTTTGTA ATAACACTTG GCTTAAAACA CAAACATATT GTACAGCTAT ACAAATATAT    42660

TTTCTTTATA TCCTTCTTCT CTAAGATTTT TTCTGTTTTT GATTTTGTTA AATTTGTTTT    42720

TACTTTTTAC ATTTTTTTTG TTAAAAACCA AGACAAAAAC CCACACATCA GCCTAGGCCT    42780

ACATGGGCTC AGGATCATCA GTCTCACTAT CTTCCACCTC CACATCTTGT CCCACCAGGT    42840
```

```
CTTCAGGGGC AGTCATATGC ATGGGGCTGT CATCTCCTGT GATAACAATG CCTTCTTCTG    42900

GACACCTCCA GAAGGGCCTG CGTGTTTTAC AGTGAACTTC TAAAAAATAA TAAAATGTAT    42960

AGTATAGCAA ACACATAAAC ATAGTAACAT AGTCATTTAT TATCATTTTC AAGTATTATA    43020

TACTGTACAT AATTGTACAT GCTAGACTTT TACACAGCTG GCAGCAAGGT GAGTTTGTTT    43080

ACACCATTAC CACCACAAAC ACATGGGTGA TGCTTTGCAT TGTGATGTTA CGATGGCATG    43140

ATGTCACTAG GTGGTAGGAA CTTTTCAGCT CCATGATAAT CTAATGGATA CTTGTTCCTG    43200

TTGGCTGCCC GTCGTTGACT GCAACATCAT TATGTGGTGC ATGACTGTAA ATTAGATACT    43260

GTTCAGAAAG CTTTGGCACA CTGGTAATAG CAAATGGTGG TGGCAAATAT GATGATGATG    43320

ATGATGATGA TTGAAGACAT AGATGGTAAA ATTTTATGGT GTCTTAAAAG TACCCTCTAA    43380

ATATGATTAT TTTTATAGTC TGTCCTTTTG AATAGGCACT TAAGAATGTA TGAACTTAAT    43440

AAGTATATAA GAAAGAATGT TCCCCAAAAT ATATCTTACA GAGGCATACA ATTTAAGAAT    43500

TCAAACAGGT TGTAATGGGG TGTGTGTGTG TGTGCACACG CGCACGCATG CGTGCTCAAT    43560

CACACTAAAG AATTCTTGGG CATATGTTCC TGAATGTCCT AAATGGACAT TCAACATCA    43620

CTTCATTATG GGCAGAGGGA AATGGTAAAG AAAAATTTCA TATTATATTA TTCAGCCACA    43680

TATTGACAGC ATCTGTTTTA TTTGCCTATG GTAAAGAATT GAAGCACTGT TAATTTGCTT    43740

TTTAAATCAT GTAGGCACAA AGTTATCGAA CTTTAGATTT AGAAATGAAA CTGGAAATCA    43800

TTACACTTTC CCTTTCCTAT CCCCACCCTG TTTTGGAGAG AAAGAGTGTG AGGCTTAGAG    43860

AGTTATAAAA CTGTTTTAAT ACCATGTCTA AGATTAATAA CTGAACAAGT TTCTCTTTTT    43920

ACTCGTGTTA AAGTTGTACT GCCAATTAAC TTAAAAGAAA GAAATATGCA ATTTCTAATC    43980

CTGATATAGG ATATGGGTAT ATAAACTCTA ACTTGATGAG TGAAACAAAT TAACTTATTT    44040

ATAATCAGTT TCATATCTTT ATTTATTGAG TGTCTTTAAA TACCCCTTAC CTTTAAAGTA    44100

AGAAATATTA AAATCAAGCA GAATATAATA ATGAAAAATT CTTAAGATAT ACTTACTAAA    44160

AACTTATCGT TCGGTTAATA CACTGTATGT AGGTTGTACA TACAATATGA AAAGTATAT    44220

TTTTGTAGCC TACTTTTAAA TCCAGAATAG AGGAGGTTAA GAAGGTTGTG ATAACCATGA    44280

GCTCTTTTTT TTTTTTTTTT GAGACAAGGT CTTACTCTGT TTCCCAGGCT GGAGTGCCGT    44340

GGCACAATCA TAGCTTACTG CAGCCTTGAA CTCTTGGGCT CAAGCAAGCC TTCCACTTCA    44400

GCCTTCCAAG TAGCTGGGAC CACACCTGGC TAATTTTTAA GTATTTTTGT AGAGATGAGT    44460

TCTCACTACA TTGCCCAGGC TAGTCTTGAA CCCCTAGCCT TAAGCGATCC TCCCACCTCA    44520

GCCTGCCTAA GTGCTGGGAT TACAGGTGTG AGCCACTGAG CCCAGCCCTC TTTTATTTCT    44580

TTTGATAGTA CACTCATAAT CATTAAACTA TCATTTCTGG ATGTGAGATT GTGCTTTTGG    44640

ATTCTTATTT TTTCTTTATA AAATACTTTT TGTTCTCTTA CTGGAGAAAA CATTGTTGGA    44700

TTATAAATGA TATAACAAGG AATGAGGATA TACATACTAT AATAACGATT CAGATATGTT    44760

ATTTTCATAT TTTATTTAAC TGTAGCCATG CCACAATAAT TTAGAGTTTT AAAGAACAAG    44820

TTTGATTGAA ATCTAAACTT TGTACAATCC TGAATTGAGA AGTTTCCTGT ATTTTATTAT    44880

GACACAATAT TTACCTAAAA ATAGGGTAAT TATGAATTGA GAAAACATAG CTATTAATTT    44940

CATACTCTTA TTTGTTAAGT AGATTTTGTC TGGAAAACTG TTCATATTTA AAGGAGCTTT    45000

GTACCTTTGT ATTCTTTTTG TTTTTCCTTG TTTATATAAT TTTAAACTCT GTTTATGGAT    45060

TTGGGATTCT AACTATGCTA AATAATAAAT TAAGGCATTG AATGAAGTAC CTAGACAGTA    45120

TTTTGATTAA TTTTATTCCC CCATTCTTAA TGTGCATGTA ACTGGAAAAT TAAGAGTGGC    45180

TTCCAAGGGA TCTACTACAA AAGTAAGGTT AATATGATCT CTTTTAAAAC ACTGAAGGCG    45240
```

```
TGTAGCCAGT GTTGTCATTA ATTCTGCAGT AGATATTTTC AGCACTTATT TACATGGGAA   45300

GTTAGAGCAG AGTAAGATGC ACCTGTAAAG CTAAATGCCA CTTATTTGCA TATATATAAA   45360

ACGCAGGATG AATTTACCAT AGAAATATAA AGGGTACTTA TAGAAATGTA TTAGAAAAAT   45420

ATATGAATTT TTAACTTATA TCTAGAAGTT AACTTTATAC ATTTAACTTT AAATCATTAA   45480

TAGTGGTTTA ACACCATAAG CGGATGTTTA TGCATCATCA TTTTATGAAC AAAAGACATT   45540

CTAATTTTAG AAATAAAGTG ATTCAAAGA GAATAAAATA TCTTACTTTT TCTTTTAAAA    45600

TTAATTTGTT TAGCGCATTA CATGATAATA GCTCAAGCTT GTGTGATTTT TCCCTAAAAA   45660

ATTGGTTTAT AAATATTACA TTTATAGTAT GAAGAAATTA ATCATACATA GTTTATTTAT   45720

CTAATTTCTA AATACCCATG GAAGAAAATG AATTTAATGG AATGTAGTTG TGTATTACTT   45780

GGTTTCGAGT GTGGGAAAAT TTATATGGTC TTTCTAAAAC AGCACTGTCA GTAGAAATAC   45840

AATGTGAGCT ACATATGCAA TTTTAAATTT TCTAGTAGCC ACATTTTAAA AAGTAAATGG   45900

ATGCAATTTA TTTTGATAAT ATAATTTAAT TAGTCTACTA TATTTAAAAT TTTATCATTT   45960

CAACATGTAA TCAATATGAA AATTATTAAT GAGATATTTT ACATACTTTT TTCTGTAATA   46020

AGCCTTTGTA ATCAGGTATG TACTTTATAT ATACAACAAA TCTTCTGATG CTAAATTTTA   46080

ACTGGAAATA CTTGATCTGT GTTTAGCTTT TGTAAAATTT ACTGTTGAAC AACGTGGACT   46140

AATGTGCCTA AGTGGTTCCA AACATATTTT AAAATTTGAA GACAAATAAA AGGGAACTCA   46200

AAGTAAATTG GGATACATAC ATACAACAGA ATACTGAGCC ATTAAAAAAT GATGAAAATAG  46260

TAAAATTGGG GGAATTTTGA TGATACTAGG ATGATATAAT GACCAAGAGA CAAATACAAT   46320

TTTAGTTTGG TTGAGAGATG TGATCATCAC GTTGCTGATT TTACTATGTA TAGAGGTTAT   46380

CTTTTCCTTT CTAAGATTTT GAAACTTTAA TTAGTTAACC CACTTACCTA GTTTCTATTA   46440

GCTGTGTAAC TTTCTCTTCC TGTTTTTTGT TTTGTTTTGT TTTGTTTTTT GCTTTTTAAC   46500

TGCAGTATTT TGAGGAGTCT TGGAGTAGCA AGCTAATCTT TGGAAGAAAG GAAAATATAA   46560

ACCTGAAAAC TAATAATTTA AGAACGTCT TTTCAGGTTG TCATTTGAAA AATANCTTGA    46620

TTTCTGATCN ACNTGATTTG AATTGAGTGT CAAATATTTG ATATGTTTTG TAAATTAGGT   46680

GAAGATGAGT GAGTAGGTTC TAAACTGCTT GGGTTTACCG CACTCTGGAG CATTGCAGGA   46740

GAATGTGATG TTGGAAGGAA GTGCTGAAAC ATAATTATTG GCTTGCCTAT AGGAGGGTGC   46800

TACATAATTT TAGAAGGTGT CAAGAAATTG ACACAGTCTG AATTAGTTCT GTTGAGTTGC   46860

AAAAAATGTA AAGTTTCTTG ATTCTGAAAA TAAGAAATAT GTTCCCAGAA ATCTCATCTA   46920

GTTAATGTGC TTTTAAAATC ATTGATGTCT CTTGTTATTA CAATAATAGC CATTGAAAGA   46980

ATCTTTTTTA TTGAATGTT ATTTACAGGT ACGATTAGCT TCTATTTAAA TAAATTATTT    47040

TTATACTTGA TCTTAGGCAA AAGGCCAACA AGTGATCAGA ATAAATTATT TTAAGAGNAA   47100

AACTAATTAT AATTGATATT TGGAATTGGA AGCACAATTT CCTTTAGAAC AATTCCACGA   47160

ATGGTTGTTT TGATTCTCAA GGCAGCCCAC AAAAGACAGT TTGAAACACA ATTTATGCAG   47220

TGTCAATAGT ACTGACCTGA CTTTGGATCT TGGAGGCAGG GGCTTCAGGT GATACCCGAG   47280

TGGAGTTTTT ACTCCATTTC CATTCCGTAA GGCTATAGGC ATTTGAAAGA GGAAACTTTT   47340

CTTTGGCAAC CTTCCACCTT CCTTTCTACA GAATATTTCA GTATTTCTAG CTCATAGGTT   47400

TTCTAAAATA TTCTCTGTAA TTTATTTTGA AATGGAGTTT TTTTATCGTT TACAGATATG   47460

AGTAAAATTA GCCTAATCAG AATGTTAGTT CCTGAAAACA TTGACACGTA CCTTATCCAC   47520

ATGGCAATTG AGATCCTTAA ACATGGTCCT GACAGCGGAC TTCAACCTTC ATGTGATGTC   47580

AACAAAAGGA GATGTTTTCC CGGTTCTGAA GAGATCTGTT CAAGTTCTAA GAGAAGCAAG   47640
```

```
GAAGAAGTAG GCATCAATAC TGAGGTATTA ATTATATATA GAATTTTCAT AAAGTGTCAG   47700

TTTGTTCAAT TTGCATATCC TAGTACTAGA ATGCTGTATT TTTTTGAACT GTTATGAATT   47760

CTGATATGAT TACTTTCTCT ATGTGCTACA TTTCCTTTGC TTTTCATAAA TATGATCTGA   47820

GAAAAGTGAT TAAAAAAAAG ACAGTAAAAG GGAGGTTTAG TCCATCTGTT TAGCTTATTA   47880

TGTAGAATGT CAGCTTAAAT TTTACCTGTA CCTCATATTG ACCGTATAGC CTGGAAAATC   47940

TTTCGGAGGT ATAGTTAATG GATTAAGCA TATGGCAGTT TATGTAGTTA ATGAAAGTGA    48000

AAACAAATTG TATTATAAAT ACCTCCCAAA CTGGTTTATT ATCATTCTAT CATTCTTCAT   48060

GCTCTGTTAG TATGATATTG AATATCTGAG GTACCAGGAT TATTGTTGCT TGTGGCTCTG   48120

AGCATTTCGT AGTGCTTTTG CATGATGAGA GAAAGATTAC AAATTTAGTA TTATGTTAGA   48180

TGGTACGTTT TATTAAAATC AAATGCTTCA AAAATAATTG CTCTGTGTAT GGCATGAGAT   48240

AAATAGCAAT CAGATATATT GTTAATAAT ATGACTCTAT TAAATGATGG CATAAATTTG    48300

AAAATTTGAC CTTCGGTATC TTCCGGGTCT AAAATTATAT GACTCCATTA TAAATATTTT   48360

GGAAATGATT AACTAAAAAA TTGTTTCAAT TCTTAGTTGG TAAATTCAAT GTGGTAGTAG   48420

GTGGTGGTGA TTATTTTGTA TTAGAGAATT AGGAATTACA CTTAGTTCTA AGGTAATCTT   48480

TATAGGATGT CCAGCAATTA AACCCCTACT TTTTTGAATT GCTTAAAAAT AAGGGAACTG   48540

ATCTTTTTAA ATTCTGTACT TGAGTTACGT CTGTATATAT AGTCATGTCC TAGATAATCT   48600

AATGGAACTT AATTAGTTGG AAATCTTTAT ATTGTTTATA ACTGAACTAG CTATAAGAGG   48660

AACATTAAAG AAAACATATT TTGAGTGGAG GTAATGAAAT TTAGCTTCTA ATGCTCAGCC   48720

TTTTATTTCT GTAATCTATA CCAGATACCT AAGACCCTCT TATTGTTTCC CAGCTTCAAC   48780

CTGTCAGTAT AGAAAACGGT GTAACTTACT ATTTTTTCTC AATATTGAAG CACATTTGTA   48840

GTGAAATATT ATTTTAACTA TATATTGCCA TTTTTGCTTT TTCCCTATTT CAGTAACATT   48900

TTTCGCTATT TCAGTAACAT TACATGTCAA CAAGAGAATG GTGGGTATTT TGGGGGGGGT   48960

TGGGTGGGAA GAAATTTTAC TAAGCTTGCT AGATTCTAAA AGGTATACCT TATTTGGCCC   49020

CTTTTCCCCA TTTAGGGGAA CAAGGGTGTT GGGGCTGGGA AGTAGATAAG AGGTGAAGTA   49080

AGTCATCCAA AGCATATGTC TTCATTAGCC TCCCTGTATG AAAAGCTGAT TTCTGTAGAG   49140

TGTTGGAGGC CTACTTTCAG AATCTGTCAT ATGTTAACAT TCATCTTCTC TACTGACCTG   49200

ATTTATATCC CTTAGTCTAT TTCATTTTAT AATTATGACA AAGGATAAAG TCATTAGAAC   49260

AAATTCTTTT TATTAGTTGA CGTATTGTTG TGTTTATATC TCTTGTGTTT GTTATTAAGA   49320

TGGAAGCTCA ATCATGTCCT TGTTAACAG AAAGGTGATG TCTTGGCATT GATAATTCTG    49380

ATTCAATATC CATAGGTACA TGGTGGATTC TTTAAATATT TAGTATTCTT TTATTTCTGG   49440

AAAGTTTTCT TAAATGATAG TTTTTTTAAA ATTTCATTTC TATAAAGTTT TCTTAAATCA   49500

TACTTTTTAG TGTTTTATTC CATTACTTCA TATTTCTTCT TCAGGAACTC CTGCTATACA   49560

TGTATGTTGG ATCTTCATTA CCCAGCTTCA ATATTTTTCA CTTTTCATGC ATTCTTTTA    49620

TTTCTTCATT TCTCTTTAAA TTTTTTTCTT CCTTTTCACC TTCTATTTCT CTTTTAACAT   49680

AATTGTATTT ATTTCTGTAT TCCACATAGC TTAGTATTCA CTTATTTTAA AATTATTTTA   49740

AAACGTTTTT TAGATTTAAA AATTCTTTTT TTATTTATAT ATACATATTT TATTTTTACC   49800

AAAGGAGCAA CACTATAAC TGAAGACTTC TATAATTTTT TTCTTTTATT TCTGATTCTT    49860

TCTTCGGTTT TCCCCCTCAG TTTTGAACTT TTCTAATTTT GATTGTGAT GTCCTTTTGT    49920

ATTTTAGATA ATTTTCCTAA TGTTTTCCAG CTCATTTGGA AAGGCTACAG TTTTATTCTG   49980
```

```
TACCTAAGCA AGTCTTTCTG GTGTCAAAGA TTTGACCTTG ATACTTTTCT TTTGCTCATT    50040

TTCGTATGAG ATTAGTTTTC CTGTACTTTC AAAAGAAGGC GTGGTTCAAG ATGGCTTTCC    50100

CAATTTCACA TCTGTCTCTA ATGTTTTTGT GTAATGTCTA AAATATGGAA ACTTGGTTTA    50160

TGAGATCTAC TCTGCCATTT TTATCTGGGC TTTCTCTTCC TTTTGTCTCT GTTGTACCTG    50220

TCCTGCTTGG TTCTGATTTA ACCCCAGTGG TTTCTCCTGA ATGTGGAGCC TTCTCCTAGA    50280

AGGCAGCCTC GGCTAGTCCC AGGGTTCAGA GTAGCCAGCT GCTCTCTTCA CCTAAGAGAC    50340

CACTGTGGAT TCCTTGTACT CACTTGCTAT TGGCTTGGAC AAAAGCCCTC CCATTTTCAG    50400

ATGCTATTAT CAGATTAATC TCTCATTAAT CTGTCTTTCC AGTGTATGCC TGTGGGCTAT    50460

CTTGGGGTTC TCTTGTTATC AGACACCTCC CTGCTGGCCT CTGCTTTCTC CCGTACAGAT    50520

GTCAGTACTG TGCAGGTCTT AATTGCTGTT GGTGGTTTGC CCCTACATTC TTACAGTTTT    50580

AGTTTCCCAA GGATACCTTT AAACTTGGTT TTATTGTAAA TGTCGACAAT GGATTTGGG     50640

TTTTACTATC TAGTTCTGTC TTAATTCTGG AATTCAGAAA GATTAAAAGC TCTGTTGTTG    50700

CAGCTGCTGC CACCTCTTCC CAGTACCCTC TCCTCCTATG TCATTTTTTT CTTCTTATTT    50760

TTCTTGACTG TATAAGAGAG AATGTATGAC ATTTCCTGCT TGACCGCTGA GTTTGATTAT    50820

AAATTAAAAT ACACAATATT TTATACAAAT TGTTTTGTAG AAGATTTATT TACAGATGCT    50880

CATTCACAGG TAAAATTGAC TTATGAAAAT AGTTTTCATG ACAAATGTAT CAGGCTCGGT    50940

AACTAAATAT ATGGATTGAT CTTGTTTATA AATGAAATTA AATGTGAATG TAACTTACAT    51000

ATTTCTGTAT TTGCTTACAT CCGTATGTAC ACATATAATC AGCAAATGAG TTGATGTTTC    51060

CTATTCGTAA CTTAATGGTA ATAGCTTGGT AACAGAGTTG GGAGTATTAA AAAGATGTAA    51120

AGAGCCCCTT AAAATTTTGT TGCTGGGAAT TTTAGTGTTC TACTGATGAA GGAAATAGAC    51180

ACTGGAAGGT GTTGTTTCTA TTAGGTAACT TAGATATCAT ACTGAAGACT TCAAATACTT    51240

ATTGTTGACA CTCAAAAGAC ACACTTAGTG TAAGTAAGCA TTTCCCCGCT TTTCCCAATG    51300

AAATAAGATC ATTATTATAA TTCCATTATA AATGCTGATG ATCATATTTA TAGAAATATA    51360

GAAGATAAGA CTTGAAATGA TATTCGCTAC CAATTAATGA GTTGAAGAA  GAAATCAGGA    51420

TGTGTTTTGC TATTTTACAT TTATTCTTAT TTAACTCCAA AGAATTCAGT GATGTTATGT    51480

ACTATTATTT CCATTTCTCT GTGAAGACGT TGAAGCTTAA GTAACACGCA TAATAAGGTC    51540

ATACATTTAG CAAGTGGCTC AATTAAAGTT CAAACCTGGT TCTGCCTGGT TTCAAAGTCT    51600

GTGCTACTCC ATGGTATTAG GCTACAACAT GACTTAGGGT TTCTTCCTCT GCTCTATTGC    51660

TGTTCAGATG TACTCCTCTT TTGGCAGAGT GGGAGAAAAT TTTTGCAATC TATGCATCTG    51720

ACAAAGGCCC AATATCCAGA ATCTACAAGG AACCTAAACA AATTTACAAG AAAAAAAAAA    51780

AAACATTAAA AAGTGGGCAA AGGACTTGAT CAGACACATC TCAAAAGAAG ACATTTATGT    51840

AGCCAACAAA CATATGAAGA AAAGCTCAAC ATCACTGATC ATTAGAAAGA TGCAAAATGC    51900

CTTTTCTGTA TGCCACCTTA TATCCCCAGT ATTTATTATT TCTAAGTCAT AGTATCTTAC    51960

AGTGTATATA AGTCTCATCC GTTCTTTTGA TTTTCTCTTC CCTGCTTGCA ATTGGGTACC    52020

TAGGAACAAA GTTGCAATCT TAGCCAGTTT TTTCTTTAGC CTTTGCTGAT GTGTGAAAAG    52080

CCCTTTTTTC TACCCTGGAT TTCTGTACTT AAGCTGGAAC AGCTAAGTTT TTACCTTTTT    52140

TAAATATAAA GTTTCAGAGT CTTCTGCCAA GGATCTTTTG CTGTTTTCCT ACTGTTAAAT    52200

ATTTCAAAGC CTTTTTTAAA CATAGGGAAT ATAATCAAAC ATAGCAAGCA GCTGATGAAC    52260

AATATCTAGA TAGTCTTCAT TATTGAAATG GAATAAATGG TATTTTGTA  TTTTAGGCTA    52320

ACAGACACCT TGTACCTTAG ATAAGGCCAA CCTTCTCATA AAATCCCTCA GTTACTTTTA    52380
```

```
TTAATAATAA CCAAATTAAC TCTGGATTCC AGGGTGTACT CATGATGGAA TGATTTCTCT   52440

GTCATGTTAT CCTGAGGATC TAGTACTCTG AGATAACATA AGTGTATGAC ACTTTAGGCT   52500

TATGAAACAC TTAGCTACTT AAATTATTTA ATTTTTTTTC ATGTGCAGAT GGTATTGTAC   52560

CCAAACACTA CCTTTGTGTG TGTGTGTGTG TGNNCGCCTG TGTGTGTGTT TTTGAGACAG   52620

GGTCTTACTC TGCTCAGGCT GGAGTGCAGT GGCGTGATTA TAGCTCACTA CAGCCTTGAC   52680

CTCCTGGGCT CCAGTGATCC TGCCAAAGTG TTGGGATTGC AGGCGTGAGC CACCTCACCC   52740

AGCCTTAAAT TATTTTTTTT TCAAGGATGT TTAACCTGAG GGTTAGAGGC TCTTTGGCAC   52800

GTGAGCTGCT GAAATGTGTG TGAAAGTGTT GTGCACGTGT ATGTTTCTCT TTTTTTCTGG   52860

GAAGTGGATC TGTAGTGATT CTTAGATGAG TCTATGAGAC AAGAAACTTT TATTTTTTTC   52920

ATTTATTTAG CGAATGTTTG TTAAGCGTAC TATGCCTTGG CCACTCTACA GGGTGCTGAT   52980

TGGACCAGTC TGTCTACCTA CCGTTGTAGA TGTTAGAAGC TATATTCTTT TCACATGCCT   53040

AATATAACTC TTTGTGTATG TATACATGCC CAGGCATGTT CCTTCCTCAG AACATTAAAT   53100

TCACCATTTT GGTCAACTCA AAGCAAGTAC ACCATGGGAC ACAGATCTGA AATAATGTCC   53160

AGATTTTTAC TTACTGAATG AGGTGTGTTG NAGTGTATAA GACTACATGA TGAGATGGCA   53220

AGTAATTGCC TGAAGAAATG ATGTAGTGAT TTTGTGTGTC TTATATTTAT TTACTTTTTG   53280

ATCCAGAAAT AAATTATATA GATACCACTA TTTTGTTTGG ATGGGGAGA AAGGATGGGT    53340

GTGTATTCAG GAACTTATGT TACTTTTTTG CAACTAATAC CCCTTCTCAG TAGTACAAAG   53400

ATTTGATTTC TTTTTCTTTC TATTTCCTAC AGACTTCATC TGCAGAGAGA AAGAGACGAT   53460

TACCTGTGTG GTTTGCCAAA GGAAGTGATA CCAGCAAGAA ATTAATGGAC AAAACGAAAA   53520

GGGGAGGTCT TTTTAGTTAA GCTGGCAATT ACCAGAACAA TTATGTTTCT TGCTGTATTA   53580

TAAGAGGATA GCTATATTTT ATTTCTGAAG AGTAAGGAGT AGTATTTTGG CTTAAAAATC   53640

ATTCTAATTA CAAAGTTCAC TGTTTATTGA AGAACTGGCA TCTTAAATCA GCCTTCCGCA   53700

ATTCATGTAG TTTCTGGGTC TTCTGGGAGC CTACGTGAGT ACATCACCTA ACAGAATATT   53760

AAATTAGACT TCCTGTAAGA TTGCTTTAAG AAACTGTTAC TGTCCTGTTT TCTAATCTCT   53820

TTATTAAAAC AGTGTATTTG GAAAATGTTA TGTGCTCTGA TTTGATATAG ATAACAGATT   53880

AGTAGTTACA TGGTAATTAT GTGATATAAA ATATTCATAT ATTATCAAAA TTCTGTTTTG   53940

TAAATGTAAG AAAGCATAGT TATTTTACAA ATTGTTTTTA CTGTCTTTTG AAGAAGTTCT   54000

TAAATACGTT GTTAAATGGT ATTAGTTGAC CAGGGCAGTG AAAATGAAAC CGCATTTTGG   54060

GTGCCATTAA ATAGGGAAAA AACATGTAAA AAATGTAAAA TGGAGACCAA TTGCACTAGG   54120

CAAGTGTATA TTTTGTATTT TATATACAAT TTCTATTATT TTTCAAGTAA TAAAACAATG   54180

TTTTTCATAC TGAATATTAT ATATATATTT TTTAGCTTTC ATTTACTTAA TTATTTTAAG   54240

TACCTTTATT TTTCCAGGAT GTCAGAATTT GATTCTAATC TCTCTTATGT AGCACATGTG   54300

ACTTAATTTA AAACCTATAC TGTGACACAG AGTTGGGTAA ACGATGATTA TTTAACTTTA   54360

AGCAGTTCAC CATCCATTTC AAAGCCTTTG ATTGGCTTTT TTGTAAATAA AAATAACTTG   54420

TTAAGAAACA AATATATCTG TCATAGAAGA ACTAGAAAAT CCAGGGAAGT GAGAAAAATG   54480

AAAATAAAAA NTCATTCATA GTTTTACTAG TAGCTAATCA CAGTCAACCT CTTTTGTTGA   54540

TCCCACCAGA CTTTTTTATA TTCATTTGTT TTTAGGTAAA ATATAAAAGT CTCGTATATT   54600

CCCATTTTTC TGCATTGCAT TACCAGAAGG TAGTGGCGCC TATTAAATAT GTGATATGTT   54660

GTTGTCCAGC CATGGCTTCT GCATTTGCAT GCTTTTGTGT GTGCATCTGC AATACCCTGT   54720
```

```
GAATATCCTG TGTGATGGAG TGGCAAGTAC GCACAGACAC GTCTGCTGCA TGCCTAGGTA    54780

CGAGGCTGTC TCCAGGAGAA GCACTTGTTT GATTATTTGA GTTGCCAATT GAATTTGCTG    54840

CTTTTTTTCA TGGCTTGCCA TTTTCACTGA AAAGAATGAC TAATGAAAAA CGATGATTGG    54900

TTATTAGATT TGGATGTTTG GCAGACATTT TCTCAAAATT GAACTAAGTT GGCCTCTTCA    54960

CGGAAAACAA CTGGTATTTG TTGTGCCAAT GATAAAATTG GAGATTTCTA GCAAAATGTA    55020

TAATTTTGGA AAAGTTGTGT TCCTCCACTG GAAGCTTGAC AGCTTTCCTT AACATAAAGA    55080

CTTCTCTTTC TCTTCGCTTT CACTACTACT ACTACTAATT CTTCTTCTGA TTCTTCTTCT    55140

TCTCCTTCTT CCTTCTTCCT TCCTTCCTCC TCCTCCTCCT TCTTCTTCCT CTTCCTCTTC    55200

TTCTTTCTCT CTTTCCTTCC TTCCCTTCCC TTTCCCTTCC TTCCTTCCTT CCTTCCTGCC    55260

CGTCCGACCG CCCTGCCTTC CTTCCTTCCT TCCTCCCTCC CTCCCTCCCT CCCTCCTTTC    55320

TTTTTCTTTC TCTTTCTTTC TTTCTTTCTC TCTCTCTCTC TCTTTCTTTC TTTTTCTTTC    55380

TCTTTTTCTT TCTTTCAAGC AGTCCTCCCG CCTCAGTCCC CCAAAATAGT GGGATTATAG    55440

GTGTGAGCCA CCATGCACAG CCTTACATAA AGCCTTTTCT AATGAGATGG ATAGTAATTA    55500

ACAAATGTGA GTTTTTGATA TTATATAAAG ATTTTTTCTG TGTTTCGAAG ATCCGTATAA    55560

CTCAGTGAAT CAGTATGTTC TGGATGACTA ATATGTGATG TTAAGAAATC ATGACTGAGG    55620

CCGGGCGCGG TGGCTCACGC CTGTAATCCC AGCACTTTGG GAGGCCGAGG CGGGCGGATC    55680

ACGAGATCAG GAGATCGAGA CCACCCTGGC CAACATGGTG AAACCCCGTC TCTACTAAAA    55740

ATACAAAAAT TAGCTGGGTG TGTTGGTGCG TGCCTATAAT CCCAGCTACT CGGGAGGCTG    55800

AGGCAGGAGA ATCGCTTGAA CTCAGGAGGC GGAGATTGCA GTGAGCTGAG ACTGCGCCAC    55860

TGCACCCCAG CCTGGCGACA GAGCAAGACT CCGTCTCAAA AATAAAAAAA GAAATCATGA    55920

CTGGGTAAAA GATCTGTTCA GAGTACAAGA TGGACCAATG GATTTGATAT ATTTGAATAT    55980

AACAGAGTAT GAAAAAGTTT ATTGATATAG TTTCAGATTA CACACTGCAA CTAATCTTTA    56040

AGAAACTATT ACTTGTCCAC TTTTTGGTAA AATTTCAGAG AACAATGTCC ACCATTATCT    56100

GAACAGGCTA TTAAAATACT CTTCTCTTTT CCAACTACGT GCCTGTGCAA AGTCAGATTT    56160

TTTTCATATA CTTCAGCCAA AACAGCATAT CAAAATGGAT TGAATGCAGA AGTAGATCTG    56220

AGAATACAGC CACTTTTGTT AAGCCAGACA ATGAGATTTG CAAAATGTAA ACAATGCTGC    56280

TGTTCTCAGT TTTTAAAAAT ATGTTTTTTA AAAGTATTTA TGTTAATGTG TACTTGGTTT    56340

ACTACTGCTA TTTTTAAATA AAACAAGAAA CATTTTTAAA TGTCTGTTTT AATTTCTAAA    56400

GTGGTAGTGA TAGATATAAC CCATATTAAT AAAAGCTCTT TGGGGTCCTC AGTGATTTTT    56460

TTTTAAGAGT ATGGAAGGGT TCTCAGACCT AAGAGATTGA GAAATGCTGA TGTAATGTTT    56520

TATTATAAAG GTGTACCATG AATTATGTAC CTTACTTCAT ATTGTTGGAC ATTAAAGTTG    56580

CTTTCAGTTT TTTTGTTTTA AACAGCACTG CTTTGACCTT TTTTAAAAAA TGAGTCAGGG    56640

TCTTGCTGTG TTGCCCAGGT TGGAGTGCAG TGGCTATTCA CAGACATGAT CATAGCATGC    56700

TATAGCCTTG AATTCCTGGG CTCATGTGAT ACTTCTGCTT CAGCCTCCTG AGTAGCTGGG    56760

ACTATAGGCG TGCACCACTA TGCCCAGCTG CTTTGAATAT TCTTGAAATG AAATATGGTA    56820

TAGTCTCATA CCATATCATA GCCAGAGGGG GAGAGAGAGA ATTTTGTTGT TGTTGTTATG    56880

TTATCTGTAG TGGACTTTAT GCCTTCCCAG CATAAATTCT CTCTTTCCCC ATTTTTCGTG    56940

ACCCTTGATT TTTGTTGGGG TTCGTTCCAA GGAGAATAAT TTCCATCTGG ATATTGGATT    57000

GGCACCTGTG ACCTCTTCTG AGCTAGACCC TAGTAACAGC GTTTGGATCT GGGGTAGGTG    57060

TGTGGCCAAC TGAGCTGCTG GTTCATGCCT TTCCTGAAAT GAGCCCTACC TCTGAATATT    57120
```

```
TCAGAAACAT GGGACATTAA CTTCCCTTTA CTTACGTTAA ACCCCTTTGA ATGAGGAGTT   57180

GTTTTTCACT TCCAGTTGTG TTCAGTTGTC ACAGAAGCAC AGCGATGTGA TTGGTGGAAG   57240

GACCCGTCAA CAGACCCAGA AGATGTAAAG TGTTTTTAAT CTCAAAGGAT GTGGAATCTC   57300

AGAGATAGTT ACACCGAGTA GAGGATGAAG CGGCTCCTGG ATGGAGGCAG AGGCTTCCTG   57360

GATCTTCAAG TTCTGTATGG GTTGTTGTAT GAGGTTGGTG CAAAAGTGAG GCAGGAGAAT   57420

AGGGTCTGGA GGCAAGGAAA CTAAGGCCGA TTCACACTGA CTTCCTAGAA CTAAATCAAA   57480

AGGAAAACCC CAATTTTCCA GACCTAAATA ACAAAAGTAC CAGATGGCTC CTCCCTTTCA   57540

ACTGCCCCTC CCCCACACCT TTCTGCGTGA CACATGGAAA ATTGAAAGTA TCTCTGGTTG   57600

CTTCTGCGTA GGAATGTAAC TTTGTAACCA ATCAGACGGA TCGCAGGCCA AGTCGCCTGC   57660

ATAGAAATGT AACTTTGTAA CTTCACTTTA GCCTCTGATT GGTTGCTTTC CACAACCAAT   57720

CAGATGCTTG CATAGGGTGT ACCTGTTGTG ACTTCACAAA GTGGTGGAAG TGGTGGAAGT   57780

GGTGGAAGGG TGGAAGGGCT ATTTAAATTT TTATTCATCC TCTGATTGGT TGTTTCACTT   57840

AAGCCTCTAA TTGGTTCTTG AGTCCTGGAG CCTGTGAAGG GTACTTTATT TTCAGTAAAT   57900

GCATGCTTTT TTTGCTTCAT TCTTTCCTTG CTTTGTGCAT TTTGTTCAGT TCTTAGTTCA   57960

AGACACCAAG AGCCTGGACA CCCTCCACTG GTAACAAAAG TAACTGGTGT TTTTGCCATT   58020

AGAAGTAATG GCACAGAACA AGTACATGAG AGCGATTTCT TATGGAAAAT TAAATGGCGA   58080

ATAAGTCGTG TGCTCAGGTA AGGGAGCTGG GAACCGGTAG AGGAAGGTCT CCAACCCACA   58140

CCCGTGGGAT CTCTGAGTCT TTGAAAGTCC GTCCTCACCC TTTGTGAAGA ATGGGAGCAC   58200

GGCTGGACTC GTCACCGGGG GTTTTGGGGG GCTGAACTTG TCATTTGAGG GTGTAGGGAG   58260

GTTGGATGAA TCGCAGGGGT GCAGGGAGGG GGCCCACTGG AGCTCCACCA GGACCCCAGC   58320

ACCCTAGATC CAAACCTGGT CATGCTTCCC ATGCTCAGAG GCAAATCTCC CTCCCCTTGG   58380

GGGGCGGAGT CAGACGAGAC CCCCTCTCCA TCCTTTTCCA GGTCCGGTGG GGGCGGGACT   58440

TTAAAGGTAA AAACAGCAAT TACTTTTGCA CCAACTTATC TTCTAAGTTT CGCTCCCTAC   58500

CACCTGAGTG TGTTTGGAGG CTCTGGCTCA TTGTACCTGC CTGATCACCA GGTGCAAGTA   58560

GCTGGGCCAG AAGGACCTCG GCACGTTACG GAATATTTAC TACAGGAACA GGTGAGCTGA   58620

AGGCGAATTC CCCAGGTGTA GCCTGTGACC ATAGATTCAG ACAAAGCCCT GACTGTTGCC   58680

TGGAATTCAA AAAAGCTGTA GCCCTACCAG ATAGAATAAG AAAAGAATAT AGGATTCTTC   58740

CTATTCAAAT AGGTTGCATA TAATTAAGAG CATGAACGAT CCAATGGAAT GAACTCAAAG   58800

TAGTTTTTGA GTGTAATAGA CTTGAAGTGT CTTATGGAAA AGAATTGCAA AACCACAGAA   58860

ACAGTGAAGA AGGTTAGTTA TAGCCTTGAT GGGGTAGCTG ACTTCAGCAG TCTCAGCTAT   58920

CTGAAAAGTT ATTTACCAGA TTTTGGTTGG GAACATAATC CCTAAATCAT TTGAGATAAT   58980

GTACTTGTTT CCTTACTGGG TAAATGTGTT TAAACCTTGA GNAAAATGTA GACATAAGTA   59040

GNAATATANG AATAAATTAA ACCTTTGGTA GTTATGTTTT AGGATTAAGG ACTAATAAGT   59100

ACATATTTGA TATTTAAGCA TTTGTAATGC TTGAGATAAT TTATCCTACT CAAGTAACAG   59160

ATTACTCTTG TGACTCCAAT GTAAAATATA TCATTGAAAA ATTAGTATCT GCTTGTGATT   59220

TTTAAGTAGA AACCCTGCCA TTTGAAAGGT ATTTGCCTTT ATTATTGGAG ATATTTCATA   59280

TGAATGTTTA ACTTTGTTAT TGCATAGAAG TATTTAAACA GATTTCACTT GCAAGAGAAA   59340

GATATCTAAT AGGTTACTCT TAATCAGTAC TAAATTACTA CAATTACTAT ATTCTATTAA   59400

TATCGATTCA TTAAAACCCA GAGCTTTAAT TATGTCTCAG AAAATTAATT AAACTTTAGC   59460
```

```
CTCATAATCA GCTTTATTTT CTAACTCAAT GTTTAAAAAT TGACAAGTAT GTATTATACT      59520

TATTTATGTC TTCATTCAGT AAACATTTGC ATTTGTAGCA TGCAAGACAA CATGCTAGAC      59580

ACACGAAAGA TGGAATAAAT GGAAGAAAAT GCAACACAGA TCTCATGCTT AAGAGGGACA      59640

GATTTACTCT GAAGATTCAA TGAAAAAACA TCCACAAACA ACTTTTCTAC AAGAAACAAA      59700

ACATTTTAAA GAAAACATTT ACTTCAGCCG GGCGCGGTGG CTTACGCCTG TAATCCCAGC      59760

ACTTTGGGAG GGCGAGGTGG GTGCATCACG AGGTCAGAAG TTCGAAACCA GACTGGCCAG      59820

TATGGTGAAA CTGTGTCTCT ACTAAAAATA CAAAAATTAG CCTGGCGTGG TGGTGTGTGC      59880

CTGTGATCCC AGCTACTCAG GAGGCTGAGG CAGGAGAATC GCTTGAACCT GGGAGGCAGA      59940

GGTTGCAGTG AGCTGAGATC AGGCCATTGT GCTCCAGCCT GGGCAACAGA GCGAGACTCC      60000

GACTCAAAAA AAAAAAAAAG AAAAAAAAAA AGAAAACATT TACTTCACAT AATAAGATAT      60060

GAGAAAAAAT GGACTCTCTG AATGAAAAAA AGAGGAGATA ATGTGAAAGA TTTGCGCTTT      60120

TTTTTTTTTT AAAGTTATGG ACTGAAACAC TCCTAATCAT TAACATTTGT TATTTTAGGG      60180

GAGTGGAATT GGAAAGGTGG AAAGGGCTAT TTACATTTTT ATAATCTCCA TGTCTTTTAA      60240

ATCAATATAT ATTGCATTTA TTCTTTTAGT TAAAATTTTA AGAACTCTAT AAAAAATAGA      60300

GACAGGGACT CCCTTTGTTA CCCAGGCTGG TCTCAAACTC CTGGGATTAA GTGATCCTCC      60360

CACCTCAATT AGAAGGGTGG AAGGGCCAGC TGTTTAAGTT TCTATAATCT CTGTTAAATC      60420

AAATGTATAT TGCATTTATT ATTTTAAATT TTAAAAACTT TTTTAAAAAT AGAGATGGGA      60480

TCTTCCTATG TTGTCCAGGC TGGTTGTGAG CTCCTAGGAT CAAGTGATTC TCCCGCCTTG      60540

ACCTTTCAAA GAGCTGGGAT TACAGGCATG AGCCACCATG CCCAGCCTAT TTATTTGTTT      60600

ATTTATTTTT AGAGGCAGGG TCTCACTCTC ACTAGACTGA AGTGCAGTGG TGTGATCATA      60660

GCTCACTGCA GTCTCAAACT CCTGGACTCA AGCAATCAAC TAGCCTCAGC CTCTGAGTAC      60720

TGAGATGACA GGCATGTGCC TTCATACCCA GCTAATATTT TTGTAGAGAT GGGGTCTTCC      60780

TGTGTTGCCC GGAAGAGTCT CAAACTCTTG GCCTCAGCCT CCCAAAGCAC TGGGATTGCA      60840

GGCATGAGCC ACAACACATG GCCCTGCTTT TAAAAAATAT ATAGTGGGCC AGGCTTTCTG      60900

GGATGATGGG CAACCATTAC ATTTGCTTTC TCTCCATTCT GAATGTCAGC CTCCATACAC      60960

CTCTCTTGAG CCATCTCTTG ATGCCCAGGA CTGGCAGGCA AGCAGGATGT TAGGGTGCTG      61020

GCTGGAGGGC TGGAAAGCCC CAGGGCAAGG ATATGAACGT GAAGGATTTT AAGGAGATTC      61080

TTGGACCTCA AGGGAACTTT TGGTCCTGGT TTCCTAGAGT ATGTTAGATC TTCTTGGCCC      61140

CCAAAGAATC AAGGAAAAGC TGAATAGGTG GACCGAATCC TTTCCAGCAC TGAGGCTGGG      61200

AGAACTCTAT GACACCAGTG GGTGCTCATC CTGGTGCTGC CATGGACCTG ACTACCTACT      61260

TCCGCTAAAC TCTCCAGCAG CTGAGCCTTC AAGAGAAGAC GTCCTCCACC TTTTCCATGA      61320

GATGAAGAAT CCTTGGGGCC AGGGGATGTG CTCACTAGCT CACACCTGTC TCCATCCTCT      61380

AGACCATGCT TGCAGTACAC AGGACCCCAG AATGCCTGGC CCAAACACTC GTGAGCCTCC      61440

AGGGGCTGCA GGGGCTTCTG GCCTTGTTTC CCCATCTGAT GAGTTCGTTT CTTGGTCTGA      61500

AAGATTGTGA CAGTTACTAC GAGACTGAAT GAAGGGGAT GAATGCAGAA ATGAAAACTT      61560

AAGACAAAAG TAACTTTTAA TGAGAGGGGC CGAGGGAAGA AGAAGAGGGC TCCCTGCTTC      61620

TAATGAGCAA AGGCAGCCAC CCTGAGCTTC TACAGCCCTT CGTATTTATT GAGTAGAAAG      61680

AGCAGGGAGG AGGAGGTAAT GATTGGTCAG CTGCTGGATT GATCACAGGT TCATATTATT      61740

GCTAACAGGC TTCAGATGTG CCTGATCACA AGAAACACTT GCGCCTGGGC ATGACTGCCC      61800

TCAGCATTCC TTCTGGGCGG CAGATGCAGT TTGTCAGTTT GCTAACAACC TGCTTTCATG      61860
```

```
AGAACAGTTT GCTGCTTACT TACACAGCCA CCAGTGATTT ACTGAGTTGA TCACGACCCT  61920
CACTCTTTCG GCCTCCAACA AAAGACGATC AAAGAATGGT TGTTTGCAGA GGTTATGGAC  61980
AAGACTTGAT GTCCAGGCCG AGTGTCCGTA TGCACAGGAG CCTCTTGGTG GTGCAGAGTG  62040
AAGCCAGAGG AGGAGGAGTG GGTTGTGTCC ATGGGCTGAT TCTCCCTGCA CCAACAGGAC  62100
AGAATCCTAA GGAATCCGAG CATTTGAAAT TCAAATCTGG TCTTACAGGT TGTTATGTAT  62160
TTGTCTAGGT AGGAGGCTAG AATGTATTGA ATGGGGTTA GCCTGACATA TTTATATATT  62220
TCATATTTAG GCTTCCATTT GTTCCTTTGT CTTGGGTCCC AAAAATATAT TAGAGGTGGG  62280
CCTGTCTGTT CTCTTGGACA CGAGGACCTC AACGAGTTTC CACTGTTCTC TGAATGTTTC  62340
CTTCCTGGTT TTCTGTGTAT ACAATAATTC CTAGTTTTCT GTTATTTACA ATTTTACTTC  62400
CACTTTTTAA AGACAAAAAT GTATGTTTTT TTAGTCAATA TTGATATAGT GGACCAATAT  62460
ATTTTACCGT TATTTTTGCT TACTGTTTTT GTTTTTTTGC CTTCCTCATC TTCTCACTAA  62520
GTTTGTCTGA CTACAGCCAC ACACCATTCA TTCAATACCA ACTCTTTTTT ATTTTTATTT  62580
TTTGGAGAGA GGGTCTCACT CTGTCACCCA GGCTGGAGTG CAGTGGCATG ATCTTGGTTC  62640
ACTGCAGTCT CAAACTCTTG GACTCAAATG TTCTTCCTGC CTCAGCCTCC TGAGTAGCTG  62700
GGACCACAGG TGCACACGAC CATGCCTGGC TAATTAAAAA CAAAACAATT TTTTTTTTTT  62760
TAGAGACGGG GTCTCACTAT GTTGCCTAGG CTGGTTTCAA ACTCCTGGGG TCAAGTGATC  62820
CAATACCAAC TCAACACGTG GTGAGACCCA GTGGTCTAGA CAAACAGCCA CATAGCAATA  62880
TGTTTTTCTC CATGATTCAT ATCCATGTTC GTTTGTTACA AAATAACAGG CATGAACATT  62940
TTCTTCAGAG AGGGAGATCC CCACTTATCC ATTAATGACT CATTTGGTGT CCATTCCAAA  63000
CTATTAAACT GCAAAAGCAG ACATGAGAAA AGAAACTTAA GTCAATGTTT TTATCACATG  63060
TTGGTGCCAG CCTCCCATAG TGGTGCTAAA TTTATGNAAA TTGCAACAAA ACAAAAACCC  63120
AAACAACCCA ACAACGAAAA GCTATTTAGT GAACACCGTG ACTAACAAGC TTATTAGAAC  63180
TGCTTATCAG AGCTATGTGT GGATTTTGTA GGGGGAAAGA TTTTCTTCCC TCGTAGACAT  63240
TTTGCAAAAT AAAGTAAAA TATTACCTTT ATGTACGTGG TAGATAGAAT TCCACAAGCT  63300
TCAAATTCAA CGACTCAAAA ATGTTGCTTT TACTTTCCAT ATCTCAGAAG TCACTTTTCT  63360
TTTATTTATT TTTTAGAGAT AGGGTCTCGC TCTGTTGCCC AAGCTGGAGT TGCAGTGGCA  63420
CAATCATAGC TCACTGCAGC CTTGAACTCC TGGGCTCAAG CAGTCCTCTT ATCTCAGCAT  63480
CCTGAGTAGC TGGGACTACA GGCGCATACC ACCACTCCTA GCTGATTTTT AAATTCTGTG  63540
TAGACATAGG ATCTTGCTGT ACTGCCCAGG CTAGTCTTGA ACTCTTGGCC TCAAGTGATC  63600
CTCCCACCTT GGCCTCCTAA AGTGCCGGGA TTGCAGGTGT GAGCCACCAT ACCTGCCCAG  63660
AAATCTCTTA TTTTAAACCC CAATTCCTCC TGATAGTAAA AAAAAAAAA AAAAAAAAT   63720
GTCATCTTGG TGTATTTTGG GTAGGCTGGA TCACTTCAAG TTTCCCCCTC CTCCTGAAGC  63780
TCCGACAGAG GCCTGCAAGC CCTGCTGGGA TCTGTCCTCA GTCCCTCTCG GGCTCATCTT  63840
CTACCATCTT GCTGTCACTC CATCTCCCTG TCCTTCCCTT TGCTTCACCC ATACCAGACC  63900
CTGTACTGTT TCTGGAAGAC ACCAGGCATG CTGTGTCTTA GGGGAGAATG TGATTTCACC  63960
AACTAGTGCC GCCCAAGTAA CATGCATTTG CCCTGACTGC TCTTTTCACC TGCTGTGCTG  64020
CTCCCCCAGA TAACCACAGG CAAACCCCGC CAACTCCTAG TTTATTGAAC TATACCATGA  64080
GTAACTTACT TAAAATCTCC ATACCTTGTC CCATTCTCTC TTACCTGTTC CAATACTTAT  64140
TTATGATGTT GATAGATGAT CTCCCTCTAC TAGACTGGAA GCTCCTTGAC AGCGGGGATT  64200
```

```
CTTGTCTGTT TTGTTCACTG CTGTGTCTTT AGCACCTGGA GAAATGCCTG GCACACAGCA    64260

GGAACTCAGT AAATAACTGC TGAATAAATA AACATGAATA AATCAATGAA TGGGGATGCC    64320

TAAGTGCTTC GGGATTCTGG TCAAAGCTTT GGCAACTAGG GACGCACAGG GACCCTCATC    64380

ATCTCTGCCT CCTAGGCAGG TATCCACTGA GATCCGCAAT CCCATCTGGT CCTTGGACCA    64440

GTTACCCTTC ATGTTGGCCT CTGTTAAGAT GTCCAGGTTG TATCTGGTCT CCCACACAGC    64500

ATCCCTTTAT TACTACCCCT GGACCTCAGC AGTCAGCCAC ACATTCAGTA AAGGCCACAG    64560

CTCTGCCATC TCCTAGCTAG GGACTTTGG ACAAATTACT TAGACACTCT GAGCCTCGTT    64620

TGTAACATGC AGAGACGTTG CTGGGATTAG ACACAATGCC TGTAGACCAT TTAACAATTG    64680

CTGTCACACA TGGTTGGTAT TCACTCAGCT GTCGCTATGG AATTAGCAGA CAGAAAAGGC    64740

ACAGCGTCAG TGGCTGGGTG TCCAGAGAGA AGCAGCCTGT CTCTCTAGAT AATACTTGGC    64800

AAAATCACAG CAGTCCGGTG TGTGGCCCTT TACTGACCTT GATTAAAAAT CGGGTGTCAG    64860

CACCCCAAGT GGATCCTTCT TACAGGTGCA GATTCAGACT CATTATCCAA GTTGACAGAG    64920

ACAGAAGTAA ATATTCAACA AATATTTATT GAGCACTTAC TATGTGCCAG GCACTGTTGT    64980

TGTAGGTGCT GGAATACAGC AATGAACAAA AAAAGTGAAA CATTCTTCCT TAGATGGTGG    65040

TAAAGCGATA GGAGGACACA GCAGGGAAGG GGTTTGGACT ATTTCAATTT GGGACAGGAA    65100

ACGCCTTGCT GAGAGAGTGA GGGTTGAGCT CTGGAATTAG CCTGAGTTTG ACCACATGTA    65160

ACTGCAACTT TGAGCAAGTC GATCCACTGT AAGTCTCTTT TATTAACACC ATTGTGTGTA    65220

AGAGGAAATA GAAACTCAGC TAAAGTCGTT GGAGAATTGA ATGTGGTGCA GCATTTAGCA    65280

CAGCGCAGGA ATAATAAAAG CCAGCTGTTC TCATCCTTTG CCCATAGAAA AGCTATCCGG    65340

GAAGCCACAT TATAGTCTGA AGGCTGCCTA CTGGTTTGGT CAAAGAAAGG GCAGTTAGAT    65400

AATTTTCATG TTTAATTAAG GGCACGGGGC TAGATTTCTT GAGGTGCCAG AGTAATGCTT    65460

GCTTTTCATG AACAACGGAT ACAAGATATG GGCATTGCAG AACCTTTAAA GAACATAACT    65520

GGAATAATCA AATAACCGAA AGTTCATGAA ATATTCTGGC TCATGAATTA GTTATCTGGT    65580

AAATCACAGT CTGAAAGTCA CAGAATACAA ATTACTTTAA ATTTCCTCCA AAGCTTACTG    65640

AGTAAGGGGA GGGACATTTA AGATGCGGAG GAAGCGCTGA ACTTGCAAGA GGAACAAGGA    65700

GGACGGTGGC TGCTGGAACT CTGTAACCCT TAGAGAAGAT GTGGGTGGGA TTTGGCAAGC    65760

CCCCTAGACT CTCTTTGTTT TGGGTCTTAA TAGGGACAGT TTATTATTTT TAATGACTCG    65820

CGTGAATTGT ATACTGTTTT AAGCATCCAC CAAAAGCCTT TCGGCTTTTT CCCTAATTAG    65880

ACTCATTCTC ACACAGAGAG GAACTGAACT TTTTACCTCT TTGGTTCAAG AGCACCATCT    65940

ACTGGTCAGA TTTGGTAATT TCGGGTTTAT GGCACTGGAA AATCAAAGAG CATTTTGATT    66000

TGGTTGTGTT TGGTTTTGGT CCATTTATCA ATACAGGTTT TTTGGCGGAC AAAATAATGT    66060

GAAAATCAGG GGAATCAGGT GAGGGCATTG GATGTCTCTG TCACAGACGA TGGGGAGCTC    66120

AGCCGATTTT AAGCTTCTAA CCTCAGCTGG TCTGGAGAAG AGCAAACCTG ACAACCAGCA    66180

CGAAGAAAGT AGCTCTGCCT CTGTGGTGTG CTGGACATTC TGGTTACATA GATGGGAAGA    66240

CGAGGCCCTT TCCGACAAAT ATGCAAATCC CCCACATCTC CAAATTTGGT AGCTCTGGGG    66300

CTTAGGGCAG CTTCTGGAAA CAGAACTCAG ACCTAGCCTG CTGGAGCAGG AAGGGCTTCT    66360

GAGAAGATGA TATCTGGACC ATCTAAGGAG TGTAAATAAG AAATAGCCGC CAGGCATGGT    66420

NGCTCACGCC TGTAATCCCA GCACTTTGGG AGGCTGAGGC GGGCAAGTCG CTTGACAAAG    66480

TCAGGAGTTT GAGTCCAGTC GGGGCAACAT GATGAAACCC CATCTCTACA AAAAATACAA    66540

AAATTAGCTG GGTATGGTGG TGCATGCCTG TAGTCCCAGC TACTCTGGAG GCTGAGGTGG    66600
```

```
GAGGATCACT TGAGCCTGAG AGGTTGAGGC TGCAGTGAGT CGTGATGGCT GCACTCCAGC    66660

CCGGGCAACA GAGTGAGACC CTATCTTAAA AAAGAAAGAA AAAAGGAAGA GGTCAGGAGT    66720

TTGAGACCAG CATGGCCAAC ATGATGAAAC CCCATCTCTA CTAAAAATAA AAAAAAAATC    66780

AGCTGGGCGT GGTGCATGCG CCTGTAATCC CAGCTACTGG GGAGGTTGAA ACTGGAGGAT    66840

TCCTTGAACC CGGGAGGCGG ACGTTGCAGT GAGCCGAGAC CACACCACTG CACTCCAGCC    66900

TGGGCGATAG AGCGAGACTC CACCTCAAAA AAAAGAAAAA AGAAAAAGAA AAGAAAAGAA    66960

ATAGCCAGAT GGAGAACAGG GGAAAGGCCA GAAGAGCAGG GGCGTAAAAG GCGTGGAATG    67020

GCATGCGGGG GAGTAACAAG GTTTTTTTTT TTTAAACGGA GTCTCACTCT GTTGCCCAGT    67080

TTGGAGTACA GTGGCGCGAT CTTGGCTCGC TGCAACCTCT ACCTCCCGGG TTCTAGCGAT    67140

TCTCCTGCCT CAGCCTCCTG AGTAGCTGGG ACTACAGGCG TGTGCCACCA CACCTGGCTA    67200

ATTTCTGTAT TTTTAGTAGA GATGGGGTTT CATCATGTTG GCCAGGCTGG TCTCGAACTC    67260

CTGACCTCAA GTGATCTGCC CGCCTCAGCC TCCGAAAGTG CTAGGATTAC AGGCGTGAGC    67320

ACCGTGCCCA GCTAGTAACA AGGTATTGAC TGAACCAGAG TGGGGTGTGT CAAGATCGGG    67380

AATCAGCAAG CAGCACAGGG GGTGTCCTGG GTGGGGATCT GGGGCTCAGG TCTTCCTGCT    67440

ATCCTGCTAC CCACCTGCAC ACTTGTTCGT TTTCTTTCCA CTCATTTTTC TCCCTTGCCC    67500

AGACTTCAGG TCTACCAGCT ACACTTCTTG ATTTCTTTGG CCTTCAAAAT TCGGTTCAAT    67560

AAGGAAAGTT TTAGCATTAT TTTCATATAG GTCCTTGACA TTTCTTGCTA AGGTTATCAT    67620

TAGATTTTTT TTTAATGGTG TAATAGTTCA GGCCTTCACT CAAATGTCAT CTCTCTAGAG    67680

AAGCCTTCCT TAACTACCAT ACCAAAAACG GTTCCAGCGC CGCTACCGTC TATCCCAGCC    67740

TATCCTCTCA CGTCCTGTGG TCCTGAGGTT CTGTGATAAT GTTCTATAAT TCTGTGCTGT    67800

CCAATATGGT AGCCACGAGC CACATGTATT CATATCGTCG TTATTGAGCA CTATATAATG    67860

TGGCTAGTGC AATTGACACA CTACAATTTT AGTTGAATGC AATTTAAATT AATTTACATT    67920

GAAATAGCCA CATGTTTGGC TCACACCTGT AATCCCAGCA CTTTGGGAGG CTGAGGCGGG    67980

TGGATCACCT GAGGTCAAGA GTTCGGGACC AGCCTGGCCA ACATGGTGAA ACCCCATCTC    68040

TACTAAAAAT ACAAAAATTA GCCGGGTGTG GTGGCACGCG CCTGCAATCC CAGCTACTCG    68100

GGAGGCTGAG GCAGGAGAAT CACTTGAACC TGGAGGGTGG AGGTTGCAGT GAGCCAAGAT    68160

TGCACCACTT CACTCCAACC TGGGCAAAAG AGTGACACTC TGTCCAAAAA AAAGAGAAAT    68220

AGCCATATGT GGCTGGTGGC TATTGTATTG GACAGCACAG CTCTGTTTCT CCCACTAGAA    68280

TGTAATTTGA TGAGGGTGGG GACTTGGACT TATTCACAGC TGAATACCTA GAATGGAACA    68340

TAACTGCTAT GTTTTGAATG TTTGTGTCCC TTCCAAAATG TATGTTGAAA CTTAATCCCC    68400

TATATAAGAG TTGAAGAACC TTTTAGAAGG TAATTAGGCC ATGAGGGCAG AGTCCTCATG    68460

GATGGGNATT AGGGTCTTAT AACAGGACTT GAGTCCTCTA TAANGGAACG GAGAGTTCAC    68520

CTTTNCCTTC CCTTCTGCCN ATGTGNAGGA CACAGCGTGT GTCCCCTCTG AAGGACACAG    68580

CGACAAGCCT CCATTTTGGA AGCAGAGAGC AGCCCTCACC AGACACTGAA CCTACTGGCG    68640

CCTTGATCTT GGACCTCCAG CCTCCAGAAC TATGAGAAAT AAACTACTGT TGTTTGTAAA    68700

TTGCCCAGTC TGTGGCATTT TGTTATGAAA ACAGCAAAAA CAGACTAAGA CAAATCAGTT    68760

CTGGCACATA CTAGTAACTC AGTGATTCTT TGTAGAGTGA GCAAACGTGT GAATGAATGA    68820

ATGAATACAT TGTCATGCGC AGCTTTCGTG GGTCGTGAGT ACAAATGAGA AAATACGATC    68880

ATGGTGCCAT TGCAATGGCT TGAAACCCCA GCACTTACTG GCAGGAAGTC TGTCATTTTT    68940
```

```
TGCAATTCTC CTTCCCAAGT GTTTCCAGAC TCCCGAGAAG TGCACATGTA TATTTAGGAA    69000
TCAGTTCTCA TCTGCTAGAA CATGGGAAGG GAGTTAGTTG ATAGCAGTTC AGCTGCTTCA    69060
AATGCAGTCC TAGCTGACCC TGGAGGATCC AGGTACCTAT GGGTGCCATC ACGGCCACCT    69120
TTGCACTATC CTGTGAGAAA CTCTCTCCCA TCCTTGGTGA TGTCCTCCTG TGGTAACCTC    69180
AGTGAGAGAA CTCCATTGAT TCCCTAAACC AGAGGTCCCC AACCTTTTTG GCACCAGGGA    69240
CTGGTTTTGT GGGAGACAAT TTTTCCATGG ACCATGGGTG GGGAGGGGGG GATGGTTTTG    69300
GAATAATTCA AGTGCATTAT AATACGTTTA TTGTGTACCT TGTTATTATT ATTACATTGT    69360
AGTATAGAAT AATTATACAA CACACGATAA TGTCTAATCA GTGGGAGCCC TGAGCTTGTT    69420
TTCCTGCAAC TAGACAGTCC CATCTGGGGG TGATGGGACA CAGTGGCAGA TCATCAGGCA    69480
TTAGATTCTC TTAAGGAACA TGCAACCTAG ATCCCTCGCA TACACAGTTC ACAATAGGGC    69540
TCATGCTCCT GTAAGAATCT AACGCTGCTG CTGATCTGAC AGGGGCGGA GNTCAAGTGG     69600
TAATGTGATG GATGGGAAC TGCTGTAAAT ACAGTTGAAG CCGCTCACCT CTTGCTTTGT     69660
GGCTGGGGCC TGGGTACCCC TGCCCTAGAC AGTAGACTTC TCAAGGGGAG GGGAAAGATT    69720
GGGCCAAGGA ACTGTGTCAG TCAAGAGGGC CCCCACTCAA CGGAAACAGA CCAGCCACTG    69780
GTCTCACAGT GCAAGTCAAG GAAGCTGGTC TCAGAGCTGT CCTCAGAGGG GACGCGTGAT    69840
AAGCAGATCA CACCCGGGAA GACTCGGCAT CAAGATGGAG AGGAGGGAAT GCGATGCGCC    69900
TGGTGGCAGC CGTAGGATCT CCTTCCAAGG CCGCACTGGA GGAGAGCTGC CTCCTAAGAA    69960
CAGGAAAGTG AATCAGAGTG AGGCTGTCAT TATAGTAAGA TAAAGAAAGA TGAGTGCTTG    70020
TTTGGGAATC TGGACAGAAT TAGCATCTGC TTGCTTTAGG ATAGTGGCTT CTTTTCTCTC    70080
TTGAACAAAA TACTCTCCTT AATAACTGCA GACCCAGGAT AACATGGAGT CATTGTTCAA    70140
ATTCACCCCG TTGCAGAATT CTCCAGTTAT CAGCATTTGT GTGTGTGTGC GTGTGTACCT    70200
ACATGTGCAC AGATGTATAC ACACACAGAT AAACACACTC CAGGCTTTGG GGAAATCGTA    70260
TTCGTAGATG CCTGTCTCTA CCTTTATTAT GTTAAAGAGA ATTCTGACTC TCAGGTCGTG    70320
GACTTCATTC ATTGTGTTGC TCACATGCAG GAAAAAAAAA AACCAGAATG CAATAAGGAT    70380
AATTCATTGA TTTGTGGGA AGAGAAAAT TCATTGTTTT GGGGGAAAG AGAGAATGTA       70440
TTGATTTGTG GGGAAAGAGT CAATAAGTGA ATGTTTCCTG TTCTAGGACT GGCTTTGCCT    70500
TGTCAATAAT TGATTTTGTT GTTGAGAATA CATTTCAAAG CCTTTAAAGC AGTGTGCAGT    70560
TAAGGATGAT ATTTTTGCTT GAAATGACTA CTTTGCATCA TGTAGAAGGA ATAGTGTCTT    70620
TTAAAGGCAA CAGATGCAAG TCTAGGACCC CAGAGCTTTA GAAGGCTCTG GCTTCGGGT     70680
ATGTGTCTGA TGTGTTGAGA GTTGCAGGGG ACGGGAGGGA TGTCCACTGT GGGCCAGTTT    70740
CTACCAGCCA CCGAGAAGCT GGAATTTGTT TATTCATTTA TAGAGCAACA GGAACTGGAA    70800
TCGAAATCTG TCAGTCCCTA TGTGCAGGGT GTAATTGAAT TGACTTCTCT GCTCTCAATT    70860
GGAACTTCCT TTGACCTGTA GTGAGAACAT TTTATGGCTC CCTCTAATCT AAAAAGGGTT    70920
TTTTTTTTTT TTTAACTTT CCTTCCTATT CCCTTGTCTG CTAACCAACA GAGAACTCAG     70980
CCCACAGCCT CACAGACAGA ATGAGAGCAA TGCTTAATCC TTGTTCAGTG AATCTCATGG    71040
CCTCCTCTAG TCTTCAAACT TGGATTCCAA GTGCCTTGAA GAGCCAGACA CAGTGGCTCA    71100
TGCCTGTAAT CCCAACACTA TCGGAGGCTG AGGCAAGGGT GGATCACTTG AGATCAGGAG    71160
TTTAAGACCA GCCTGGCCCA CATGGCGAAA CCCTGATTCT ACAAAACATA CAAAAATTAG    71220
CCAGTCCTAG TGGTGCATGC CTGAAATCCC AGATACTCCA GAGGCTGAGG GAGGAGAATC    71280
ACTTGAACCT GGGAGGTGGA GGTTGCAGTG AGTGGAGATC GCACTACTGC ACTCTACTCT    71340
```

```
GTCTCAAATA ATAATAATAT ATATTTTTAA GTGCCTAGAA GAAAGAACTG CACTTCTGCA   71400

GAGAGCGCCT CCAAAGCTCA GGGTAAGTGA CATGCTGCTT ACCATCCTAG AATGGAACCA   71460

GGCCACCCAT CCCCAGGTGG GACAACTGCA CTCCCAGGAT AACCCCTGAG TTATGGGCAG   71520

ACTTGTGTCT CTCCCCAGTT CAGATCTTGA AGTCCTAGAC CCAGTGCCTC AGGATGTAAC   71580

TGTAGATTCT TTAAAGAGTG AATTAAGATG AGGCCATTAC TAAAAGCCTA GACCTGACCA   71640

CTATGCAATC TATGCATGTA ACAAAATTGC ACATGTATCC CATCTCTACA AATTAAAATA   71700

AATAAATAAA ACTACGTCAT TACAGTGGGT CCTAATCCAG TATGACTAGT GTTTTTGTGT   71760

TTGTTTTTGT TTTGAGATGG AGTCTCTGTC ACCTAGGCTG GAGTGCAGTG ACACGACCTC   71820

GGCTCACTGC AACCTCCACT TCCCAGGTTC AAGCAATTCT CCTGCCTCAG CCTCCCGAGC   71880

AGCTGGGATT ACAGGCACGT GCCACCACAT TCAGCTAATT GTTTTGTAAT TTTTTTTTGA   71940

AGTTTTATT TTTTATTTAT TTATTTTTAA TCTTTTTTTA TTTTATTTTA TTTTTTTACT   72000

TTAAGTTTTA GGGTACATGT GCACAACGTG CAGGTTAGTT ACATATGTAT ACGTGTGCCA   72060

TGCTGGTGCG CTGCACCCAC TAACTCGTCA TCTAGCATTA GGTATATCTC CCAATGCTAT   72120

CCCTCCCCCC TCCCCCAAC CCACAACAGT CCCCAGAGTG TGATGTTCCC CTTCCTGTGT   72180

CCATGTGTTC TCATTGTTCA ATTCCCACCT ATGAGTGAGA ATATGCGGTG TTTGGTTTTT   72240

TGTTCTTGCG ATAGTTTACT GAGAATGATG ATTTCCAAAT AGAGACAGGG TTTCATCGTG   72300

TTGCCCAGGC TGGTCTCGAA CTCCTGACCT CAAGTGAGTT GCCTGCCTTG GCCTCCCAAA   72360

GTGCTGGGAT TACAGGCGTG AGCCACCACT CCCCGCCTGG TGTTATTAGA AGAAGAGATT   72420

AGGACAGAGA CACAGACACA GAGGAAAGGC TGAGTGAGGA CACAGGGAGA AGACAGCCAT   72480

CTGCAAGCCA AGGAGAGAGG CCTCAGAAGA AACCAACCCT ACTGACATCC TGAGCTTGGG   72540

CTTCCAGCAT CTAGAAACTG TGAAAAAATA AATGTCTGCT GTCTAAGCCA CCCAGCCAGT   72600

GGTATTTCGT TGTGGTAGCC CTAACAGACT AATACATGCT GAGTCTCTCA TTGTTCAAAT   72660

CATCCTGTAA AACTGACTCA ACAGGCTTTT TTTGAGCAGG GTTTTCTATT CATGTACTCA   72720

TTAATTTTCC TTAAATTAAA AGTTGCAAAT ACAATATACA AAATTAAAAG TTCAATTAGA   72780

AAAATGAGTT TCTATAATCA GCCTACTCAG AATTAACCAT GGTTTCAAAT AGGGGTTTTG   72840

CTGGTGTTTT TTGTTTTGTT TTGTTTTGAG AGAAAGTTTT GCTCTTGTCT CTCAGGCTGG   72900

AGTGCAATGA CGTGATCTCA TCTCACTGCA ACCTCCACCT CCGGGTTCAA GTGATTCTCC   72960

CGCCTCAGCC TCCCAAGCAG CTGGGATTAC AGGCAAGCGC CACCATGCCC AGCTAATTTT   73020

GTATTTTTAG TAGAGACGGG GTGATCTGCC CTCCTTGGCC TCCCAAAGTG CTGGGATTAC   73080

AGGCGTGAGC CACTGCGCCC GTTAGCTGTT TTGTTTTGAA ATCAACTTTG AAAAATGTTT   73140

TGATATCTCA TCATGTCCCC AATGCCATTT GTAATGGTCA CACAGCATTC TGTTGTATGA   73200

TGTACCATGC TTTATCTAAC CTGTGTCCTA TTTTTGGATA GTTCGAATTT TCCTATTTCT   73260

TTTCACTATT AGAAGCAAGG CTGCAATGGA CATCCTTTTA AATACTTTTT AAAAACAAAA   73320

ACCTTGGTAC AAGTACCTGT ATATAGACTT GCAGGGTCAA AACTTCCCAT TTGATGGCTA   73380

TTGATATGTA CTAACAAATT GTCCTCCAGA AAGTGGTCTT TTCCTCACCC TCATCAGTTC   73440

TTGGTGTTAC CACCTTTTTG CATTTTGCCA AGCTGATAGG TAAAAAGTG TCTCTTACTA    73500

TTGTATGTAT TGAATTAAAT TTATTTATTT ATTTATTTAG ACAGGGTCTG GTTCTGTCCC   73560

CCAGGTAGGA GTGCAGTGGT GCAATCATAG CTCACTGCAG GCTTCAACTC CTGGGCTCCA   73620

GCAATCCTCC TGCCTCAGCT TCCTAAGTAG CTGGGACTAT AGGTGGGCCC AGCTAATTAA   73680
```

```
ATTTTTTTTT TTTTTTTTTT TTTAAGATAC AAGGTCTCAC TACTTCGCCC AAGCTGGTCT   73740
TGAACTCCTG AGCTCAAGAC ATCCTCCCAC CTCAGCCTCC TGAGTTGCTG GGATTACAGG   73800
CAGGAGCCAC TGTGCCTGCT TATTATATAT TTCAAAATAA CGAAAAGAGT GGAATTGCAA   73860
GTTCCTCACA CAAAGAAATG ACAAATGCTT GAGATAATGA TTATCATAAT TATCCTGATT   73920
TGATCACTAC AACTTGTATG CTTATATCAA AATATCACAT ATTTATATTT TTAAAAATTA   73980
TATTTATATT TATGTGATAT TTTGATATAT TTTGTAATGA TCATTTTACA TATGAACATA   74040
TTTATACATA TATACAAACC AAATAAACCA TACATATTTA TACATATGCA CCTATGTACA   74100
AACCAAAGAA ATTGGGATAT AGCTATCCCA GTTCTATTAA AAAATTGAGA TTTTTTTCTT   74160
CTCTATTGAT ATTTCCTACT TTTTTTTTGT TTTGAAAAAT AATTTATCCT TGAGTCAGTT   74220
GTGATGATTT ATACCTGTAT AGAGATTACT AGTTTGATCA AAATCATTTC ATTTATTGTT   74280
AAAAATTGTA TAATGATATT ATCTCCTAAC TGAAAATTTT CCTTTATCTC TGTGATTATA   74340
TTCCATTTCT CATTCATCAT ATTTTCATTT CATTCCAGTT TTCCTTGGTT AGACTTTCCT   74400
ATGATTTGTG TCTTTTACTG TTCTTTTCAA AGAACAGCCT TGGTATTTAT TTATCAATTC   74460
TATTTCTTTT TAATTTCACA ATTAATTGTT TTCTGTTTTT ACCATGACTA ATTCCCACCA   74520
CTGCTTTCAT AGATTAATTT TGTGTTCTTT TTCTAATTTC TTCAATTAAT TTATTTTCAT   74580
TTTTTAAAAA CTTAATAATA AAAGTTCTTA AAGTCCTAAA TCTTTTCCTG AGTACTGTGG   74640
GATTCTTTCC ATGTGCTTCT GCATGTAGTA TGACTATTGC AATTGGTATA GATGGTATTA   74700
CAGTTCTTAC TCCTTCTTAC ATCCAGGGAT TACTAAGGAG ACTGATTTTA AATTTGCAAG   74760
AAGTTTGACT TCTAAAAGTG CCAGGCTCCT TTTTGATGTC AAGTCTCACC TATTTCTTCT   74820
GTTTTCTCT AGTAACTGAG CTCAGGTTTT GTTGAAGGCA GCAAACTACT GGCTAAAACT    74880
GCTCAATGTT TTCCAGCTAA AATTGCTCAA GTATTTCCTG CAGCTAGTTA GGGCAAGTTA   74940
CCTGGCTCTG TCTAGAGAGA TGGAGGTGCA GGTCCTTGGA GACAGAGTAC CCTCTGAACA   75000
AAAAGGCAAA GACTTACCAG CAGAAAACCC ATTTGCCTTT TCCCTTTCCT CCTCACTGAC   75060
ATGCAAGGGT TATGTCTGGA GGTACGAGAA AAGGAAAGCA TAAGGATAAA ATCTAACAGG   75120
CTAAGAATGA CAGGGCAGAA AGATAGAAAG GATCTGTGTC CCCGATGGCA TCGTTGTACC   75180
AGCAAGACTG ATGATCATGA TGTAAGTCAA ATGAATGCCC AGCTGCTGCT GGCTGTGTTT   75240
TTTGTTATTT GCGGCTGAAT GCATTGCTAA TGTAAACATT ACCTTGCAGC CAGAGAATAC   75300
GGCTTGCCAA AAGTCTAGTT TTGTATGTTA ATCATGATAC ACCAGCCAGA CAGAGTGGCC   75360
CTCAGCTGTA ATCCCAGCAC TTGGGGAGGC CAAGGCAGGC GGATCACTTG AGGTTAGGAG   75420
TTCGAGACCA GCCTGACCAA CATGACAAAC CCCCGTCTCT ACTAAAAATG CAAAAATTAG   75480
CTGGGCATGG TGGCTCCTGC CTGTAGTTCC AGCTACACGG GAGGCTGAGG CAGGAGAATC   75540
GCCTGAATGC AGGAGGAGGA GGTTGCAGTG AGCCAAGATG GTGCCATTGC ACTCCAGCCT   75600
GGGCGACAGA GTGAGACTCT GTCTCAAAAA ATAAAAATAA TAATAATAAT GATATGCCCA   75660
CTGCTATAGC ACCTAGACTG CAAAATGTAC ATCACAACAG TCCGATTCTC TGTTCTCTTT   75720
GTTCAGGGGT AAGCATGGAG CTTAATTTTG ATCTATGAGT CAACGTGGGA AGTCCGTTAG   75780
GTTAGAAGTG CTTCTGGTCA AGGTTTCTTT GCTTCTAAAA GAGGAATGTG AGGAAAAAGT   75840
CCCTGTCTTG GTGTGGATTT TGGTGTGGGG GGATGTATAT AAAGCCTGTA GCTATTGAAG   75900
CCATCTGGCA AACTTGAAGG GAGCAGCTGA CTCTGAGCTG GTAGAATATA GAAATGGAAA   75960
GGATTTAGAT CTTGATGTGG TTGAGAGGCT GCCCTCCCTT GGGACTTCTT TTTTGTGTGT   76020
GAGTTAACAA GTTTTCCTTA TTGTTAAGTT GCTTTAGTGG GTTTGCTATT ACTTGTAGTC   76080
```

```
AAAACATTTA TTATGGCATC ATCTACTTTA TTCTATCCTT CTGCTTTCCT TATTACAAGT    76140

ATATTTACAA GCTCATTGTC ATTCATGTCA TCATTTTAAT CAGCACCAAC AACAGCATCA    76200

CCAGTAACAT TTATTGAGTG TTTTTAAGTG CCAGGCCCTG TTGTTGTCAT TTAAATCTTA    76260

CACCAATCCC TACTGCTCAG ATACTATTCT TTTTAAAAAT TATTTTTTTT TTAGGCACAG    76320

GATCTTGCTC TGTTGCCCAG GCTGGAGTGC AGTGGCATAA TCATAGCTCA CTGCAGCCTC    76380

AAACTCCTGG GCTCCAGTGA TCTTCCTGCT TCAGTTTCCC AAAGTGCTGG GATTACAGGT    76440

GTGACCACTA CCCCCTGTCC TATTATTATT GATTCAGATT TACAGATGAG GAAAATAAGG    76500

CTTAGGAAGG CTACATAATT TCCTAGATTG CTTATTTAGT AAGCGGCAGA GCCAGGATTC    76560

AAACCCAGAC CTGAGGGACT CCTAGACTAG TCCATGCCAC TGTGTATATGG CCTTTCACAT    76620

CTCTTCTTTC ATCCGTCATC ATGATATCTT TCTCCTCTGA GTTCTGGGGA AGTTTCTCAA    76680

GTTGGACTGC CAATTTTCTG CAGGATTTTC CTGTGATATA TAACTCCTTC ATTTACTGCT    76740

TCCATTTTAT TTCATATCAC CTACAATTTC CCTTATGTCT AAAACCAATT GCTCCTATAT    76800

CTAAGATGCA ACGTCCTTCT GAATTATAGT GTTAATGCAA TAGGGTATTT TGAAGGTTTC    76860

TGTATGTTTT CTGTAGAAAA GTTATCTCAA AGGGGATAT ATACTTCCAT TTCCCAGTGG      76920

TCTACTTCTT TTAAGCCACA AATAGGGCAC TTTCTCTTGT TAGTTAATC CTACGGGTAT      76980

ATAATTTTCA GTATTTCTAG TGTTAGAATT TGAGATTCAG AGAACTATGA GTCTCTGTTT    77040

TAATCTTTCA GTCCTAGGAA AAGGAGAAAT AGGGCTGCCT ATCTTTTCTG TGGTTTTATT    77100

TTGCCATTTA ATTTCTAATT GACTGTGAGA TGTATCAAGA GATCTGTAGC TCAAGGCAGT    77160

TGAATGTCCC AGAGCTTCAC AGCTGAGCCA AGTGACTTCT TTTCCATGTT TATTGTGGCA    77220

GCCAAGGTCA GCAGATGCCA TGCCTCTTGC TCTGAGTGCC TGGACCACCC CCATTAAGAG    77280

CCTCCCACAG CAACAACTCC ACTTGACCCA CGATAAGTGA GGTTGGCACT GTGTCTCTCT    77340

CTTTGTACAT TTTGTTTTCT AAGTTGCTTG TAGGGCCAAG CTTTGAGTCC TTGTTACCAT    77400

CAGCTTAAGC TCCGGCCTCT CTGAATTGGA GGATTTTGTT TGTGTTTGAT TAGAGCCTGT    77460

TGGCAGAAGC AAGTGCCAAA GTCAGACATA AAACAGAAAA CTCTAATGTG GTGTCAAGTC    77520

TTTTCCAGAT GTTACTGATC CTCTTTCTTT TCCTTCTTTT TTTTTCTTT TTTGTTATTT      77580

TTGATCCCCT TCCTTTTTGC TTCCCTTAGG TTGACCTTTG CTGTCCTACG GGCAGTACAA    77640

AGATTGGGTC TTTCTGTCTC TGCCTCTCCT GCCCTCGGAC TCCTACCATG GGTCTTTTCT    77700

TTTTTTATAG AGATAGGGGT CTCACTTTGT TTATCGTGTT TTTTTTTTTG TTTGTTTTTT    77760

GAGGTGGAGT CTTACTCTGT CACCAGGCTG CAGTGCAGTG GCGTGATCTT GGCTCACTGC    77820

AACCTCCGCC TCCTGGGTTC AAGCGATTCT CCTGCCTCGG CCTCCTGAGT AGCTGGGACT    77880

ACAGGTGTGT GCCACTATGC CCAGTTAATT GTTGTATTTT TACTAGAGAC AAGGTTTCAC    77940

CATGTTGGCC AGGATGGTCT CAATCTCTTG ACCTTGTGAT CCACCCGCCT CAGCTTCCCA    78000

AAGTTCTGGG ATTACAGGTG TGAGCCACAG CGCTCAGCCT GAACTTTTAC TTTTAAGACA    78060

ATTGTAGATT CAAATCCTGT GTCCTCTCTT ACACAGTTTC CTCCAATGGG GGCATTTTAC    78120

AAATATAATA ACCAGGATAT TGACATTGAT ACATTTGATA CAGTCAAGTT ACATTTTCAT    78180

CACCACAAAG ATCCTGGTGT TACTCTTTTA TAGCCATACC TGCCTCCTTC TCCCCTCCCC    78240

CATCCCTCAC GCCGGCAACC ACTAATCTGT TCTCCATTTC TACAATTTTG TCGTTTCAAA    78300

AATGTTATGT AAACAGAATC ATACAGTTTC TCATCTTTAA GATTCGTTCT TTCCTGTTTT    78360

TTTTTTCTTT TTTTTCTTTT CTTTGTTTTT TTGAGATGGA GTCTCACTGT GCCACCCAGG    78420
```

```
CTGGAGTGCA CTGGTGTGAT CTCGGCTCAC TGCAACCTCC GCCTCAAGT  TGTGGGTTGA    78480
AGCGATTCTC CTGCCTCAGC CTCCCAAGTA GCTGGGATTA CAGGTGCCTG CCACCACGCT    78540
CGGCTAATTT TTTTTTTGTA TTTTTAGTAC AGACAAGGTT TCACCATGTT GGCCAAGCTG    78600
GTCTCGAGCT CCTGACCTCA GGTGATCTGC CTCGGCCTCC CAACTTGCTG GGATTACAGG    78660
CATGAGCCAC CGCACCCGGC TGAGATTGGC TCTTTCACTC AGCATAATTC CTGGAGACT     78720
TCATCCAAGT TGTTGCATGT ATCAATAGCT TGTTTCTTTT CATTGCCACC TAGTTTTCAA    78780
TGGTATGAAT GCCGCATTGC TTGTTTCATC AGTCACCTGG TGGAAAACAT CAGGGTTGTT    78840
CCCAGTTTTT AACTATTATG AATAAAGCTG CTATGAACAT TTGTGTACAG GTTTTTGTGT    78900
GAACATATTA TCATTTCTCT GAGATGAATC AATGCCAAAG NAATGCAATG GTATGTTTAG    78960
TTTTATAAGA AACTGCCAAA CTGTTTTCCA GAGTGGCTAT ATGANTTTTG TATTCCTACT    79020
AGCAGTGTAT GAATAATCTA GTTTCTTTAC ATCCTCACCA GCATTTCATG TTCTCAGTAT    79080
TTTTTTTATT TTAGTTAATC CGATATGTAT GTAGTGCAAT ATCACTGTGG TCTTAATTTT    79140
TAGTTCACCA GTGCTAATGA TGTTGAATAT CTTTCATGTA CTTATTTGCC ATCTGTATAT    79200
CCACTTGGTG AAATACTTCA TGTCTTTAAA GAAGACCCAG GATTTCTAAA AAACTGTTGA    79260
GTTTTGAGAA TTTAAGAAAT ATATTCTAGA TACTGGTACT TGTTGGATA  CATGGTTTGT    79320
AAATATGTTC TCCTAGTTTG TAGCTTGTCT TTTCATATGT GTTAAAGCTT ATCTCCCATT    79380
TTATTATTTG TTTTCTGTTT ACTTTGTTTC TTATTCCTCT ATTCTCACTT TGGGTGGATT    79440
ATTTAAATAT TTTTTAAGGT TTCATCTTGA TTTATTTGTA GCATTTTGGG TACATCTCTT    79500
TGTACACTTT TCTTAGTGGT TGCCCTGGGT GTTACCATAT ACATATGTCA AGAGTCACAT    79560
TCTGCTGGTG TCAGTGTTTT TCCAGTTGAA GGCAAGTGTG GAAAACTTAC CTCCATTTAG    79620
ATTCCTTTAC TCTTCCCATT TTTAAAACAT GTGTCTCAAG TATTCCCTCT ACATTCATTG    79680
ATCAGCACAC TAGAGAGTGT TATTTTGGCT TTAACCTTCA AATATAATTT AAGACACTCA    79740
GGAGAATAGG ATCATCTATT ATGTTTACCC CTGTCTTTGC CTGTTTTGAT GTTCTTCATT    79800
CTTTTCTAAA GTTTCAAGCA TTCTTCTGTT ATCATTTCCT TTCTGTTTAA AGAACTTCCT    79860
TTAGTCGTTC TTTAAGGACA GATTACTAG  CAACAGATTC TCAGTTTTCC TTCATCTGAG    79920
AATGTCTTTA TTTCCCCTGC ATTCCTGAAG GATATTTTCA CCTGATATGG AATTTGTGAG    79980
TGATAGTTCT TTTTCCTCTA AGCACTTGAA AAATGTTATG CCACTTTCTG CTGTCTTTTA    80040
TGGTTTCCGA AGAGAAATCC ACTTTCATTC AAACTGTCAT TTCCCTGTAA GTAATGGATG    80100
TTTTCTGTCT AGTTGCCTTC AAGACTTTGT CTTTAGTTTT TACAAGTTTA ATTATGATAT    80160
GTCTTGGTGT GAATTTCTTT GAGTTTATCC TGCTTATGAT AGTTCACACA GCTTTTTGAA    80220
ACTGTAGGTT TATGTCTTCC ACCAAATTTT ACTGAATTTC TTCAGTTCTA TGGTCTTGCT    80280
CCTCTTCCTG AAGTATTCCA ATGATACCGT GTTCTCTTTT GTTACGGTCC CACTGGTCTT    80340
TGAGACTCTC TGTTCATTTT ATTTCGGTCT TTCTTTTCTC TGTTGTTCAG ATTGGGTAAA    80400
TTCCATTGAT CTACCTTCAA GCCCACTGAT TCTGTCCTCT ATCATCTCTA TTATTGAGCC    80460
CAACCACACA GTTTAATTT  TGATTATTGT ATTTCTCAGT TCTATAATTT CCATTTGGTT    80520
ATTTTTCAAT GACTTCCATT TTTGCTGAAA TTTTCACTTG TTTCAAGAGA ATTTGTAATT    80580
ACTTGTTGAA GCACTTTTAT AATATCTGTT TAAATACTT  GTCATATAAT TCCAGTAACT    80640
AATTCATCTT GGTGTTGACA TCTGTTTATT GCTCACTTAA AAATAAAAAA TAAAAACAC    80700
CTAGACTTTA TTTTTTATAG CAGTTTAAGG TTCACAGCAA AATTGAGAAG AAAGTAAAGA    80760
GTGTGCCCAG AAAAATAGTA CCCCTATGCA GAACCTCCCT GATATTGTTT GGCTGTGTCC    80820
```

-continued

```
CCCACCAAAT CTCATCTTGA ATGGTAGCTC CCACAATTCC CACGTGTTGT GGGAGGGATC  80880
CAGTGGGAGG TAATTGGATA ATGGGGGCGA ATCTTTCCCA TGCTGTTCTC ATGATAGTGA  80940
ATAAGTCTCA TGAGATCTGA TGGTTTTATA AAGAGGGGTT CCCCTGCACA AGTCCTCTCT  81000
TGCCTGGCGC CAGGTAAGAA GTCCCTTTGC TCTTCCTTCA TCTTCCATTA TGATTGCGAG  81060
GTCTCCCCAG CCATGTGGAA CTGTAAGTCC ATTAAACCTC CTTTTCTGTA TAAAGTAACC  81120
AGTCTCAGGT ATGTCTTTAT TAGCAGTGTG AGAATGGACT AATACACTCC CTATCAACAT  81180
CCCCTACCAG ATTGGTATGT TTGTTGTAAT CGATGAACCT ATGTCAACAC AGCGTTATTT  81240
CCCAAGCTCC ATAGCTTATA TGAGGATTCG CTCTTGGTGT TTACATTCTG TGAGTATTGA  81300
CAAATGTATG ATGAAATGTA TTGACCATTA TAGTGTCATA CAGAATACAG GATAGTTTCA  81360
CTGTCTTAAA AAATCTTCTG TGCTCCCCTT ATTCATCCCT TCCTTCTGTG TAAGCCCTGG  81420
CAACCACCGA GCTTTTCACT GCCTCCATTG TTTTGCTTTT TCCAGGATGT CATAGAGATG  81480
GACTCATACA GTAGGTAGCC TTTTGAAATT GACTTCTTTC ACTTAGTAAT ATGATTCCTC  81540
CATGTCTTTT CATGGCTTGA TAGCTAATTT CTTTATAGTG CTGAGTAGTA TTCCATTCAC  81600
TTATAATTCC TTGAATTCAT TGTTTGGAAT ATTTTGCAGA TGATATGCTA TTCCCTAACT  81660
TTATGCATCT TCACTCACAG GATTGTTTTT TTCTCACCAA TGCTTATTTA TATAAAAGCC  81720
ATATCAACAA AATTTTACAC ATCAAAAATT TTCAGACTTC TGGTTGCTCC AAAGAAGGAA  81780
TGACCCCATT CTTCTCAGGT CCTCTTCCTC ATGACTAAAA AACTCTGAAC AAAGCACAGA  81840
AAGTTGCGGA AGGCTCTGAA AGGTGAAAGG AGGTGGACTG CCTAGGGACC TCAGGACTTG  81900
GAAAACAACT CAGTGGGAA TTCCGTGGAT TTCCTTATCA CCTCCCTTAT ATCCTGGACA  81960
CGGAGCTGCA GAAGACTCCA ACCTACAGTC ACCAATGCGC ATAGAAGAAA AAAGCTCCAA  82020
GAAAAGCCTT TTCCTCCTGG CCAGATGACT GGACAAGGGT GGCCTGACAA CAGAAAACCC  82080
ACAACAAGGA ATTACAGGTA ACTCCAGAGA GGATCAGCTT GAGTGGTTAA AACAAGTACA  82140
TGGAAAACAA AAAGAAGCAT TTTTCTTTTT TTGTAAAAGA GCTTGTACTG TAATAACTTT  82200
GATTTTGTTT TTTGTTTTTT GTTTTTTGTT TTTTTTTGA GACTGAGTCT CACTCTATTG  82260
CCCAGGCTAG AGTGCTGTGG CGCAATCTTG GCTTACTGCA ACTTTTGCCT CCTGGGTTCA  82320
AGTGATTCTC ATGTCTCAGC TTCCTGAGTA GTTGGGATTA CAGGCATGCA CCACCACACC  82380
AACTAATTTT TGTATTTTTA GTAGAGATGG GGTTTGACCA TGTTGGCCAG ACTGGTCTTG  82440
AACTCCTGAC CTCAAATGAT CTGCCCACCT TGGCCTCCCA AAGTGCTGAG ATTACAAGCC  82500
TGAGCCACCG CACCTGGCCA ACTTGGACTT ATTTTTATAA TAAGTAGATA TTGTTCACTG  82560
TAGATATTGA ATCAATTTTT ATTTAATCTT GATTTTTTTT CTTGAGCTGC ATTAGAAATT  82620
CATTACAATA TTTCAATTTA TAAATCTTAT TAAAAATTAC TACTACCTAG ATCTCATTGT  82680
TTTCTTTTTT CTTTTTTGAG ACATGGTCTT GCTCTGTCAA GCAGGAGTGC AGTGGGACAA  82740
TCATAACTCA CTGTAGCCTC CAACTCCTGG GCTCAAACGA TCCTGCTACC TCAGCCTCCT  82800
GAGTAGGTGG GACTATAGGT GCACGCCACC CATGTGTGGC TAATTTTCTT TATTTTTTTT  82860
TGTAGAGACA AGGTCTCACT GTGTTGCCCA AGCTGGTCTT GAATTCCTGG CTTCAATCAA  82920
TCCTCCCGCC TCAGCCTCCC AAGGTGTTGG GATTTCAGAC GTGAGCCACT GCACACCTGG  82980
CCCCATTTTT TTTCCTTGAA TAAAGTGTAC TGGTAAATTT TAGGCTCATG AGGGTATATA  83040
TGCATTATTT TCTTCAAATC AAGCCTGAAT CAAAGAAACT TCTGCTTTAG TTTTAGTGAT  83100
ATTTGTCCCA AATGTTTAAA GACTGTATCA TTCTGATGAA TTGGATATTC CCATTGAGAG  83160
```

```
ATATTCAATA GGCCTTGATT GAAATGTTCT TCATTTTCTT TTTAAATTCT ATTTACAGTA    83220
GTCTGCATGT GTTAGAACTT TCAGAAAGGG AGAGATTTCT GTCTGGGCTG TCCCCACCAG    83280
CCAGAAGGGT CTGAGAGGCA CTGACTTGCC CTGGGGTGAT ATTTCTGCAG GACTTTGCTC    83340
CTCTGTAGGA AGACAGCCTA AACAGAGGT GAAGGATGCC TCGGGCCTGC CTAGACCAAC     83400
AGCCATTCCC TGGTGATGCT GTAGTGTGAA GACCCTTGTC TTTCCCAACA CCTGTGATAG    83460
CTTTCAAATT ATTCTTTTCA GACAAACTTT ATGCCTGTTT CTTTATCTCT ATTTTGCATC    83520
CTAACAGAAA AAGCCAATCA CCTAGAAGGG AAAGTCAGAC TGGTCCCTGC TGCTTTCCCC    83580
ACATCTCCAC TGCCCCCAAT ATTGAATGCC GTGACAATGG AATGAAATTC CAATGTCCAT    83640
GAAATTCTGA GGGGAGACAT TTGACTCAA GATTATATAC TCAGTGAAGA TGTCCTTTAT     83700
TTATTTATTA AATTAATTTT TTTTGAGATG GAGTCTCTCT CTGTCTCCCA GTTTGGAGTG    83760
CAGTGGTGCG ATCTCGGCTC ACTGCAACCT CTGCCTCCTG GGTTAAAGTG ATTCTCCTGC    83820
TGCAGCCTCC TGAATAGCTG GGACTATAGG TACTCACCAC CACACCTAGC TAATTTTTTT    83880
TTTTTTTTTT TTTTTTTTGG TAAAGATGGG GTTTCACCAT GTTGGCCCGT CTGGTCTTGA    83940
ACTCCAGACC TCAGGTGATC TGCCCGCTTT GGCCTCCCAA AGTGCTGGGA TTACAGGCGT    84000
GAGCCACCTT GTCTGGCCAA AGACGTCCTT TAACTAAAGA CTTCTGGTGT ATGTTACCTT    84060
AAAAATATAA ATATAAAAGC ATGAAGAAAA TACAACCTCC ATGGAATTTT TTTGCCAATG    84120
AATCTAGAAA AATAAGAATT GATTCAAAAT AATGAATAGG GAAGCTGTAA TAAAATGACT    84180
TGAGGGTTCA TTGAGTCCAT TTAAATATAT ATCTCTTACT AAAATCACTA AGGGTCATAA    84240
TTAGACAATG AAGTAAGTGC CATAAATCTA AACAATGTAA ATAACAATAT ATCTAAAAAA    84300
AAAAAACTAA GGAGTTTGGA GAGAGGATAC GGGAGGATGT GTTCTTTCAT AGTAGGGAAT    84360
TAGTTAATAT TCTTTAAAAT GGAAACATGT AAGAAAAAAG ACCCTAATGA CTGAAAACTA    84420
AGTTTTCCTC AATCTTTTTT TCATATCCTT TGAAGGCTAT TTTAAGAAAT AATATCTAAA    84480
GAACATCGAT TTGATGTTCA CAATTCCAGT TGATTTTCCT TCTGTGAAAT TCAAATGAAA    84540
TTAAATAAAT ATGTTTTGTT AAAAATGGTG TCATCCCATT TAAGTAAATG TCCTTTCTTT    84600
TACCTATTTA TCCATCTATA ATCTGTATCT ATTCATCCAT CAATGGATAC ATGTGCACAG    84660
ATAAATGGCC CCTTTGGTGA AGGGCTGAGA GGGTATTGTT TTCTAACCCC AACCTGTGAC    84720
GGCTTCCATG AGGCCAATGG AATCATTTTG AAATGTGTTT ACCACAGCAG GGAGACACAG    84780
AAGACTGGGG TCTCACACCT GTGTGGGAAC TCCAGAGGGT GAGAAAAGGG CCAATGAACT    84840
GCTCCGGTGA CACAGCAGGG AGGGTGGCTG CCGTGCTGGG TGCGGCCTGC CTTCCTAGAG    84900
AATGTCAGGG AAAGGGATGT GGGGTCATTT CCTGTGGACA CATTTAAGCC AAGTAGGGGA    84960
GAGGTCTGGT ATGGGTCCT CTTGGGGCCT GTTGGACAGG GTTGACCAGC AGAGAGAGGA     85020
TGCCCAAGGA TTGAAGGAGG AGTGGGTAAG AGGTTCTCTA GGTCATGGGA ACTTCTGAAT    85080
TTCCCATGGA AAGCACCACC ATAATCTGTG TGCAATGAAC AGCCAGACCC ACGTGGGAAT    85140
TCTAGGCCAG CAAGAATCCC TTACTTGCTC ACTGGCTGCC ACGTGGCTCT GACCATGGAG    85200
AGGTCTGGAA CTGTAGCTTC CCAGTGGGGG AGAAGTAGGC TGGGAGAGAG AAGGGGACAG    85260
AGGAACCACA CCCTCCTTCC CCACCTCCAA ACAGAAGCCA GTAAAAATTG AGGGATGGAG    85320
AAAAATATAA GGCTAAATTA AGTTTTGGAA CTTTGGCATG ATCAAGGCTC ACTGCAGCCT    85380
CAACCTCCTG GGCTCAAACA ATCCTCCCTT CTCAGCCTCC TGAGTAGCTG GGACTACAGG    85440
CACATACAAC CATGCTCACC TTTTTTTTTT TTTTTTTTT GTAGAGATGG GGTATTGCTA     85500
TGTTGCTCAG GGCTGGTCTC AAACTCCTGG GCTCAAGCAA TTCTCCTGCC TCAGCCTCCA    85560
```

```
AAAGTGCTGG GATTACAGGT GTAAGCCATT GGCCCTGCCA AGTTTAAGAA CTTTTACAGT      85620

TATAAGAGAC TAGATATTTT AATTATTATT ATTATTTTTT AGACAGAGTC TTACTCCGTA      85680

TCCAGGCTGG AGTGCGGTGG CACAATCTTG GCTCACTGTA ACCTCCACCT TCTAGGTTTA      85740

AGCGATTCTC CTGTCTCGGC CTCCTGAGTA GCCAGAATTA GTAGAGACGG GGATTCGCCA      85800

TGTTGATCAG GCTGGTCTCG AACTCCTGAC CTCAAGTAAT CCACCTGCCT TAGCCTCCCA      85860

AAGTGCTGGG ATTACAGTAG ATATTTTAAT TTTTTTGCAT GGAGGCTATT TTTACTACTA      85920

AAAGTGAATG AAGTATATTT TGTATCTTCC AGGAGTTTGG AAAGTCAAGT CTATTTGCAC      85980

CCAGCCACGT GCCTGCCATG GTGCCCGCGG CCTCTCAATT TTTGACCTTT GTTTATGCTG      86040

CTCTGTCTAC CCAGAATGCT CTCCATCGAG GGAAACCTAC TCTCTCTTCA AGGCCAAATT      86100

CCAGCATCAC CTCCGCCATG AAGCCTTCAT AGATCTACTC AANGTAGAAA CTTCTTAACC      86160

CCTCTAAACT GTCTTAGCAT CTTGGTTGTA GTATTGGTTT AGAATAGCAC AAATTCTACC      86220

CAAAATCTCA CTAAGTCTAT TCTAAGCAAA TCTTGGATAA TTTGCTAACA CTAAAATTAA      86280

ACCTGTTCTC TTTTGGTTTT TTGCTAACAA TGAAACAAAC TTGGTCTTAC TCTTTTGCTC      86340

AAGCTGGAGT ACAGTGGTGT AATCATGTCT CACTGCAGCC AGGAATTCCC GGACTCAAGG      86400

GATCGTCCTA CCTCAGCCTC CTGAGTAGCC GGGACTACAG GTGTGCATAA CCGTGCCTGG      86460

CCAGTTTTAA AATTTTTATT TAGGGACAGA GTTTTGCTAT GTTGTCCAGG CTGGTCTTGA      86520

ACTATTGACC TCAAGTGATC CTCCCACCTT GGCCTTTCAA AGTGCTGGGA TTAGAGGTGT      86580

GAGCTGCCAC ACCCAGCCCC GTTCTCTCTT TTGCATCTAT ATTAGTCTCT GTGCTCTTGG      86640

GAAAAGTGGA CCAATATCAT TTCAAAACTT GATGAAAAAG AAAATTAAAA TCTCATCCTC      86700

GGGAACTGAA ATCACAAACC ACCCAGCAAG GTCCACACCT CTAGGAGACT GGCATTTAGA      86760

AGACAGGACC ACAGTTGAAG CAACGGTTCT TTCTTTACCC TCCCTGCCTG TGACAGACTG      86820

CATGTGCTGA TTATCCCTGC GTTTTCTGCA GAGCTTGCCT TCCTGGTGAT ACAGTACTTT      86880

ATTTTATTCT GAGGGCCCCT TCCTGCCAGG GGATATCTGT CAGGGGATAC ATAAAACTGC      86940

ACAAAATGGA ACAAGTTATA GGTCATATAA AATTTCAGGA CATTGTTGAG AAGGAGAAGT      87000

TGCTAAATTG GAGACACCAT GATGTGAAAT CCCAGGGTCC CAGAATATTG ATGGAACTAG      87060

TATGTTTTTC TTATGTAATA TTTTATGGTG TCTGGGAAAT GGAGTTGCCT AAGTGAACTC      87120

ATTTTTTATG TCTAGGGAA TAGCAACATA ACTATCATCT AACACTAAAT AAAGAGGAGC       87180

AAAATGTGCT ACATTTAGAA AGTGATGGTA TTATCCCCAG CTGAGGCAGA CTTAGTGATG      87240

GTGTTAGAAA TAAAGTATGG TAGGAGGCTG AGGCAGGTGG ATTGCATGAG CTCAGGAGTT      87300

TGAGACCAGA CTGGGCAACA TGGCGGAAAC CCCATCTCTA CAAAAATCCA                87350
```

(2) INFORMATION FOR SEQ ID NO: 80:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO: 80:

CATTGGGAGA TAAATGCTCA GTAGA                                              25

(2) INFORMATION FOR SEQ ID NO: 81:

(i) SEQUENCE CHARACTERISTICS:
        (A) LENGTH: 22 base pairs
        (B) TYPE: nucleic acid

```
        (C) STRANDEDNESS: single
        (D) TOPOLOGY: linear (xi) SEQUENCE DESCRIPTION: SEQ ID NO: 81:

AGATGTACTT TGGCCATTCC AG                                         22

(2) INFORMATION FOR SEQ ID NO: 82:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO: 82:

GCCATGACAG CAACATTATC TC                                         22

(2) INFORMATION FOR SEQ ID NO: 83:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO: 83:

CTTACTGCTA CTGCAAGTTC TTC                                        23

(2) INFORMATION FOR SEQ ID NO: 84:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO: 84:

TCGATCAAAA CCAGTACAGG TG                                         22

(2) INFORMATION FOR SEQ ID NO: 85:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO: 85:

GCAGATGTAG GAGACAAATC ATC                                        23

(2) INFORMATION FOR SEQ ID NO: 86:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 86:

TCATCCAAAA TCTCTAAATT TCGG                                       24

(2) INFORMATION FOR SEQ ID NO: 87:

(i) SEQUENCE CHARACTERISTICS:
        (A) LENGTH: 22 base pairs
        (B) TYPE: nucleic acid
```

```
        (C) STRANDEDNESS: single
        (D) TOPOLOGY: linear (xi) SEQUENCE DESCRIPTION: SEQ ID NO: 87:

CTGAGGACCA GAAACTGTAT GC                                            22

(2) INFORMATION FOR SEQ ID NO: 88:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO: 88:

GCTGATTTGG TGTCTAGCCT GG                                            22

(2) INFORMATION FOR SEQ ID NO: 89:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 89:

TGCCTGGGTT GCAGGCCTGC                                               20

(2) INFORMATION FOR SEQ ID NO: 90:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO: 90:

TTGGAAACAA CTGCACAGCA GC                                            22

(2) INFORMATION FOR SEQ ID NO: 91:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO: 91:

GATCCAGTGA ATTCTAAGAA GGG                                           23

(2) INFORMATION FOR SEQ ID NO: 92:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 92:

AGGGCCTCCA CGCATGACGC                                               20

(2) INFORMATION FOR SEQ ID NO: 93:

(i) SEQUENCE CHARACTERISTICS:
        (A) LENGTH: 23 base pairs
        (B) TYPE: nucleic acid
```

(C) STRANDEDNESS: single
            (D) TOPOLOGY: linear (xi) SEQUENCE DESCRIPTION: SEQ ID NO: 93:

AGTCTGTTTT TCCAGAATCT CCC                                          23

(2) INFORMATION FOR SEQ ID NO: 94:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (xi) SEQUENCE DESCRIPTION: SEQ ID NO: 94:

CCTATGCTTG GACCTAGGTG TC                                           22

(2) INFORMATION FOR SEQ ID NO: 95:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (xi) SEQUENCE DESCRIPTION: SEQ ID NO: 95:

GAAGTTTACA AGTAACAACT GACTC                                        25

(2) INFORMATION FOR SEQ ID NO: 96:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (xi) SEQUENCE DESCRIPTION: SEQ ID NO: 96:

ACTATAAATT GAATGCTTCA GTGAAC                                       26

(2) INFORMATION FOR SEQ ID NO: 97:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (xi) SEQUENCE DESCRIPTION: SEQ ID NO: 97:

GAACACACCT CACCTGTAAA ACTC                                         24

(2) INFORMATION FOR SEQ ID NO: 98:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (xi) SEQUENCE DESCRIPTION: SEQ ID NO: 98:

GGTAAACCAC CATACCTGGC C                                            21

(2) INFORMATION FOR SEQ ID NO: 99:

(i) SEQUENCE CHARACTERISTICS:
            (A) LENGTH: 23 base pairs
            (B) TYPE: nucleic acid (C) STRANDEDNESS: single
        (D) TOPOLOGY: linear (xi) SEQUENCE DESCRIPTION: SEQ ID NO: 99:

GTACATATCC TGGTCATTTA GCC                                              23

(2) INFORMATION FOR SEQ ID NO: 100:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO: 100:

ATTCAGATAG AAAGTACATT CTGTG                                            25

(2) INFORMATION FOR SEQ ID NO: 101:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO: 101:

GTTAAGAAAT ACTCAAGGTC AATGTG                                           26

(2) INFORMATION FOR SEQ ID NO: 102:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO: 102:

GGTTGTATTT TGGTATAACA TTTCC                                            25

(2) INFORMATION FOR SEQ ID NO: 103:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 103:

ATATTTTGGT AGAGTTTCTG CCAC                                             24

(2) INFORMATION FOR SEQ ID NO: 104:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 104:

CTCTTCGATT TTTCTGAAGA TGGG                                             24

(2) INFORMATION FOR SEQ ID NO: 105:

(i) SEQUENCE CHARACTERISTICS:
        (A) LENGTH: 23 base pairs
        (B) TYPE: nucleic acid

```
        (C) STRANDEDNESS: single
        (D) TOPOLOGY: linear (xi) SEQUENCE DESCRIPTION: SEQ ID NO: 105:

CCCTAATAGT CAGGAGTGTT CAG                                              23

(2) INFORMATION FOR SEQ ID NO: 106:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO: 106:

GGAAAGAAAA TGAAAATTTG ATCCC                                            25

(2) INFORMATION FOR SEQ ID NO: 107:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO: 107:

CAGCCTTAAT GAATAGTATT CTTCAC                                           26

(2) INFORMATION FOR SEQ ID NO: 108:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO: 108:

ATTGATCTTT TAAGTGAAGG TCAGC                                            25

(2) INFORMATION FOR SEQ ID NO: 109:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO: 109:

CTGCAACAGA GACTGTATGT CCC                                              23

(2) INFORMATION FOR SEQ ID NO: 110:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO: 110:

GCTTTCGACA AAATTGTAGG CCC                                              23

(2) INFORMATION FOR SEQ ID NO: 111:

(i) SEQUENCE CHARACTERISTICS:
        (A) LENGTH: 23 base pairs
        (B) TYPE: nucleic acid
```

(C) STRANDEDNESS: single
            (D) TOPOLOGY: linear (xi) SEQUENCE DESCRIPTION: SEQ ID NO: 111:

CCAAACCATC CAAAACTGGA TCC                                        23

(2) INFORMATION FOR SEQ ID NO: 112:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (xi) SEQUENCE DESCRIPTION: SEQ ID NO: 112:

TAACCCATGG TAGCTGTCAC TG                                         22

(2) INFORMATION FOR SEQ ID NO: 113:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (xi) SEQUENCE DESCRIPTION: SEQ ID NO: 113:

CTGTTGCTGT TAAGCAGACA GG                                         22

(2) INFORMATION FOR SEQ ID NO: 114:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (xi) SEQUENCE DESCRIPTION: SEQ ID NO: 114:

TTGAATGGGA CATTGGTCAA ATGG                                       24

(2) INFORMATION FOR SEQ ID NO: 115:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (xi) SEQUENCE DESCRIPTION: SEQ ID NO: 115:

GTAGTTGCAT TTGTATTTTG AGAGT                                      25

(2) INFORMATION FOR SEQ ID NO: 116:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (xi) SEQUENCE DESCRIPTION: SEQ ID NO: 116:

GTAAAAAGAA ATGAAAGCAT CAAAGG                                     26

(2) INFORMATION FOR SEQ ID NO: 117:

(i) SEQUENCE CHARACTERISTICS:
            (A) LENGTH: 24 base pairs
            (B) TYPE: nucleic acid

```
            (C) STRANDEDNESS: single
            (D) TOPOLOGY: linear (xi) SEQUENCE DESCRIPTION: SEQ ID NO: 117:

TCACCCACAG AAGAAAAAAA GAGG                                              24

(2) INFORMATION FOR SEQ ID NO: 118:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (xi) SEQUENCE DESCRIPTION: SEQ ID NO: 118:

CAAAAAAGAA AATTGCAAAG AACAGG                                            26

(2) INFORMATION FOR SEQ ID NO: 119:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (xi) SEQUENCE DESCRIPTION: SEQ ID NO: 119:

CAGCAACATG TAATTCACCC ACG                                               23

(2) INFORMATION FOR SEQ ID NO: 120:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (xi) SEQUENCE DESCRIPTION: SEQ ID NO: 120:

GAAGAGACTG GAATTGGGTT TGG                                               23

(2) INFORMATION FOR SEQ ID NO: 121:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (xi) SEQUENCE DESCRIPTION: SEQ ID NO: 121:

ATAGAGTATC ATGGGATAAG ATAGG                                             25

(2) INFORMATION FOR SEQ ID NO: 122:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (xi) SEQUENCE DESCRIPTION: SEQ ID NO: 122:

TTCTCCTTTG GAGATGTAGA TGAG                                              24

(2) INFORMATION FOR SEQ ID NO: 123:

(i) SEQUENCE CHARACTERISTICS:
            (A) LENGTH: 25 base pairs
            (B) TYPE: nucleic acid
```

```
            (C) STRANDEDNESS: single
            (D) TOPOLOGY: linear (xi) SEQUENCE DESCRIPTION: SEQ ID NO: 123:

TCTTCAGCTT CTTTACCACT CCCCA                                          25

(2) INFORMATION FOR SEQ ID NO: 124:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (xi) SEQUENCE DESCRIPTION: SEQ ID NO: 124:

CATGGTGTTT GACAACAGGA TGG                                            23

(2) INFORMATION FOR SEQ ID NO: 125:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (xi) SEQUENCE DESCRIPTION: SEQ ID NO: 125:

GTTAAATATG CATTAGAAGG AAATCG                                         26

(2) INFORMATION FOR SEQ ID NO: 126:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (xi) SEQUENCE DESCRIPTION: SEQ ID NO: 126:

ATAAAACCAA ACGGGTCTGA AGC                                            23

(2) INFORMATION FOR SEQ ID NO: 127:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (xi) SEQUENCE DESCRIPTION: SEQ ID NO: 127:

AAAAGAAGTA TTCAATAAAG ATCTGG                                         26

(2) INFORMATION FOR SEQ ID NO: 128:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (xi) SEQUENCE DESCRIPTION: SEQ ID NO: 128:

AATTCCACTT TGTGCCAGGG ACT                                            23

(2) INFORMATION FOR SEQ ID NO: 129:

(i) SEQUENCE CHARACTERISTICS:
            (A) LENGTH: 23 base pairs
            (B) TYPE: nucleic acid
```

```
            (C) STRANDEDNESS: single
            (D) TOPOLOGY: linear (xi) SEQUENCE DESCRIPTION: SEQ ID NO: 129:

ACTTGGGATA CTGGAAATAG CCT                                              23

(2) INFORMATION FOR SEQ ID NO: 130:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (xi) SEQUENCE DESCRIPTION: SEQ ID NO: 130:

TTTTTATCTT GATGGGGTGT GGG                                              23

(2) INFORMATION FOR SEQ ID NO: 131:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (xi) SEQUENCE DESCRIPTION: SEQ ID NO: 131:

AAATTCAGCA CACATGTAAC AGCA                                             24

(2) INFORMATION FOR SEQ ID NO: 132:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (xi) SEQUENCE DESCRIPTION: SEQ ID NO: 132:

CTGAAGTCAA ATAATGAAGT CCCA                                             24

(2) INFORMATION FOR SEQ ID NO: 133:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (xi) SEQUENCE DESCRIPTION: SEQ ID NO: 133:

GTTTGCTTTC TCATATCTAA ACACA                                            25

(2) INFORMATION FOR SEQ ID NO: 134:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (xi) SEQUENCE DESCRIPTION: SEQ ID NO: 134:

CTTGTGAGAG GCCTATAAAC TGG                                              23

(2) INFORMATION FOR SEQ ID NO: 135:

(i) SEQUENCE CHARACTERISTICS:
            (A) LENGTH: 22 base pairs
            (B) TYPE: nucleic acid
```

```
        (C) STRANDEDNESS: single
        (D) TOPOLOGY: linear (xi) SEQUENCE DESCRIPTION: SEQ ID NO: 135:

GGTAAACAGT GTAGGAGTCT GC                                              22

(2) INFORMATION FOR SEQ ID NO: 136:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO: 136:

GCTTGAAGGA TGAGGCTCTG AG                                              22

(2) INFORMATION FOR SEQ ID NO: 137:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO: 137:

TGTTCAGAAT GAGCACGATG GG                                              22

(2) INFORMATION FOR SEQ ID NO: 138:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO: 138:

CTTGTGAGAG GCCTATAAAC TGG                                             23

(2) INFORMATION FOR SEQ ID NO: 139:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO: 139:

GGTAAACAGT GTAGGAGTCT GC                                              22

(2) INFORMATION FOR SEQ ID NO: 140:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO: 140:

GCCATTTTCT CTTTAATTGG AAAGG                                           25

(2) INFORMATION FOR SEQ ID NO: 141:

(i) SEQUENCE CHARACTERISTICS:
        (A) LENGTH: 25 base pairs
        (B) TYPE: nucleic acid
```

(C) STRANDEDNESS: single
        (D) TOPOLOGY: linear (xi) SEQUENCE DESCRIPTION: SEQ ID NO: 141:

ATCTTATTCA TCTTTCTGAG AATGG                                              25

(2) INFORMATION FOR SEQ ID NO: 142:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO: 142:

TGAAATAGCC CAACATCTGA CAG                                                23

(2) INFORMATION FOR SEQ ID NO: 143:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO: 143:

GATTAATTTG ACAGCTTGAT TAGGC                                              25

(2) INFORMATION FOR SEQ ID NO: 144:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO: 144:

TGAAATATAA ACTCAGACTC TTAGC                                              25

(2) INFORMATION FOR SEQ ID NO: 145:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 145:

GTACTGATTT GGAAAGACAT TCTC                                               24

(2) INFORMATION FOR SEQ ID NO: 146:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO: 146:

GATGTGACAG TGGAAGCTAT GG                                                 22

(2) INFORMATION FOR SEQ ID NO: 147:

(i) SEQUENCE CHARACTERISTICS:
        (A) LENGTH: 24 base pairs
        (B) TYPE: nucleic acid

```
        (C) STRANDEDNESS: single
        (D) TOPOLOGY: linear (xi) SEQUENCE DESCRIPTION: SEQ ID NO: 147:

GGAAAAATGT GGTATCTGAA GCTC                                          24

(2) INFORMATION FOR SEQ ID NO: 148:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO: 148:

AAGTGAGCAA ATGTTGCTTC TGG                                           23

(2) INFORMATION FOR SEQ ID NO: 149:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO: 149:

TCATTAGGAA GCTGAACATC AGC                                           23

(2) INFORMATION FOR SEQ ID NO: 150:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 150:

GTTGGAGGAA ATTGATCCCA AGTC                                          24

(2) INFORMATION FOR SEQ ID NO: 151:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 151:

TGTTGCTTAT GGGTTTAACT TGTG                                          24

(2) INFORMATION FOR SEQ ID NO: 152:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO: 152:

TAAAGGATTA ATGCTGTTAA CAGTG                                         25

(2) INFORMATION FOR SEQ ID NO: 153:

(i) SEQUENCE CHARACTERISTICS:
        (A) LENGTH: 23 base pairs
        (B) TYPE: nucleic acid
```

(C) STRANDEDNESS: single
        (D) TOPOLOGY: linear (xi) SEQUENCE DESCRIPTION: SEQ ID NO: 153:

TCACACTGAG CATTTACTAC CTG                                               23

(2) INFORMATION FOR SEQ ID NO: 154:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 154:

GCAAAGGAAA TGTAGCACAT AGAG                                              24

(2) INFORMATION FOR SEQ ID NO: 155:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO: 155:

AGGCTATAGG CATTTGAAAG AGG                                               23

(2) INFORMATION FOR SEQ ID NO: 156:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 156:

GTAGGCTCCC AGAAGACCCA G                                                 21

(2) INFORMATION FOR SEQ ID NO: 157:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO: 157:

GAAAGGATGG GTGTGTATTC AGG                                               23

(2) INFORMATION FOR SEQ ID NO: 158:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO: 158:

ACAGGCCATA GTTTGCCAAC CC                                                22

(2) INFORMATION FOR SEQ ID NO: 159:

(i) SEQUENCE CHARACTERISTICS:
        (A) LENGTH: 25 base pairs
        (B) TYPE: nucleic acid (C) STRANDEDNESS: single
        (D) TOPOLOGY: linear (xi) SEQUENCE DESCRIPTION: SEQ ID NO: 159:

TGGTATTAGA ATTTCCCTTT CTTCC                                         25

(2) INFORMATION FOR SEQ ID NO: 160:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO: 160:

TGAAAGAGAA TATGGAAAGA GGCTTG                                        26

(2) INFORMATION FOR SEQ ID NO: 161:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO: 161:

CTTTATGAAG CCAATTTCTA CCC                                           23

(2) INFORMATION FOR SEQ ID NO: 162:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO: 162:

TCAAAATCAG TCGCCTCATC CC                                            22

(2) INFORMATION FOR SEQ ID NO: 163:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO: 163:

CAATGTATCA GTCAGGGTTC ACC                                           23

(2) INFORMATION FOR SEQ ID NO: 164:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO: 164:

GATATTGTTT TGTATTTACC CATGAAGAC                                     29

(2) INFORMATION FOR SEQ ID NO: 165:

(i) SEQUENCE CHARACTERISTICS:
        (A) LENGTH: 23 base pairs
        (B) TYPE: nucleic acid (C) STRANDEDNESS: single
        (D) TOPOLOGY: linear (xi) SEQUENCE DESCRIPTION: SEQ ID NO: 165:

TCCGCTGCTG TGCAGTTGTT TCC                                              23

(2) INFORMATION FOR SEQ ID NO: 166:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO: 166:

TCAGTAGATT TATAAGCAAT ATCAC                                            25

(2) INFORMATION FOR SEQ ID NO: 167:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO: 167:

CTGGCAAGGA TCAAACAGAG AG                                               22

(2) INFORMATION FOR SEQ ID NO: 168:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO: 168:

CTTTATGAAG CCAATTTCTA CCC                                              23

(2) INFORMATION FOR SEQ ID NO: 169:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 169:

TTCTCGGGGT AAAGTGTC                                                    18

(2) INFORMATION FOR SEQ ID NO: 170:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 170:

TACCTCTCAG TTTTCTTTAA AGAAAGGTAT GTTGTT                                36

(2) INFORMATION FOR SEQ ID NO: 171:

(i) SEQUENCE CHARACTERISTICS:
        (A) LENGTH: 36 base pairs
        (B) TYPE: nucleic acid (C) STRANDEDNESS: single
        (D) TOPOLOGY: linear (xi) SEQUENCE DESCRIPTION: SEQ ID NO: 171:

TAAACTCAAG GCATGTGTGA TATTAGGTAA GTGATT                              36

(2) INFORMATION FOR SEQ ID NO: 172:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 172:

CTCACTTTAG CATGAGTCCA TGTCAGGTTG GTATCT                              36

(2) INFORMATION FOR SEQ ID NO: 173:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 173:

AATGTTACAG TTTTTCCCAT AAAAAGGTAA AAGCAA                              36

(2) INFORMATION FOR SEQ ID NO: 174:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 174:

TCATTTCTAG CTGAAATGAT GCTTATGTAC GTGCTT                              36

(2) INFORMATION FOR SEQ ID NO: 175:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 175:

TTTTTTATAG GCTGGTTTAA ATAAAGGTAT GTTAAG                              36

(2) INFORMATION FOR SEQ ID NO: 176:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 176:

TTCCCCCTAG AGGAAGAACC ACGGAGGTTA AATATT                              36

(2) INFORMATION FOR SEQ ID NO: 177:

(i) SEQUENCE CHARACTERISTICS:
        (A) LENGTH: 36 base pairs
        (B) TYPE: nucleic acid (C) STRANDEDNESS: single
            (D) TOPOLOGY: linear (xi) SEQUENCE DESCRIPTION: SEQ ID NO: 177:

TTTTTTTTAG GGTTTCTACT ACTGAGGTAC TAAAAT                                36

(2) INFORMATION FOR SEQ ID NO: 178:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (xi) SEQUENCE DESCRIPTION: SEQ ID NO: 178:

TTTTTTAAAG CATTTATCTG CTTAAGGGTA TGTTTA                                36

(2) INFORMATION FOR SEQ ID NO: 179:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (xi) SEQUENCE DESCRIPTION: SEQ ID NO: 179:

TTTTTTAAAG CATTTATCTG CTTAAGGGTA TGTTTA                                36

(2) INFORMATION FOR SEQ ID NO: 180:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (xi) SEQUENCE DESCRIPTION: SEQ ID NO: 180:

AAACTTTCAG TCTTTAGATG ATAAGGGTAA GCACTG                                36

(2) INFORMATION FOR SEQ ID NO: 181:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (xi) SEQUENCE DESCRIPTION: SEQ ID NO: 181:

TTATTTCCAG ACTTTTTGTT TAAACCGTGA GTATAA                                36

(2) INFORMATION FOR SEQ ID NO: 182:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (xi) SEQUENCE DESCRIPTION: SEQ ID NO: 182:

CACCTTCAAG AGTTCAGTGG CAACTGGTAA GTTGTA                                36

(2) INFORMATION FOR SEQ ID NO: 183:

(i) SEQUENCE CHARACTERISTICS:
            (A) LENGTH: 36 base pairs
            (B) TYPE: nucleic acid (C) STRANDEDNESS: single
        (D) TOPOLOGY: linear (xi) SEQUENCE DESCRIPTION: SEQ ID NO: 183:

TCATTTCAAG GATATGGACA GCTTAAGTAA GTCATG    36

(2) INFORMATION FOR SEQ ID NO: 184:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 184:

CTTCTTATAG AATGTCCAAT TAAATTGTGA GTAATT    36

(2) INFORMATION FOR SEQ ID NO: 185:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 185:

GTTTTTACAG AGGTAAATTG ATATTGGTAA GTGATA    36

(2) INFORMATION FOR SEQ ID NO: 186:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 186:

TTTTTTACAG GTATCACGTG CCAATGGTAA GCTTTG    36

(2) INFORMATION FOR SEQ ID NO: 187:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 187:

CATCATTCAG GTTCCAATAA AACAAGGTAA GGATTT    36

(2) INFORMATION FOR SEQ ID NO: 188:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 188:

TTTTCTTTAG TTCCCACTAA ATTCAGGTAT GAGGAT    36

(2) INFORMATION FOR SEQ ID NO: 189:

(i) SEQUENCE CHARACTERISTICS:
        (A) LENGTH: 36 base pairs
        (B) TYPE: nucleic acid

```
            (C) STRANDEDNESS: single
            (D) TOPOLOGY: linear (xi) SEQUENCE DESCRIPTION: SEQ ID NO: 189:

TTGTTCTCAG TGTGTCATTT AAATAGGTAA AAAAAA                              36

(2) INFORMATION FOR SEQ ID NO: 190:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (xi) SEQUENCE DESCRIPTION: SEQ ID NO: 190:

TAATCGACAG GCACCTTCAG GAGACAGTAT GTATTA                              36

(2) INFORMATION FOR SEQ ID NO: 191:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (xi) SEQUENCE DESCRIPTION: SEQ ID NO: 191:

TCTTGGGTAG AATCATCTAG GTCCAGGTAA AGATTT                              36

(2) INFORMATION FOR SEQ ID NO: 192:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (xi) SEQUENCE DESCRIPTION: SEQ ID NO: 192:

TTTTATTTAG ATTGGATCGA GGATCTGTAA GTATAT                              36

(2) INFORMATION FOR SEQ ID NO: 193:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (xi) SEQUENCE DESCRIPTION: SEQ ID NO: 193:

CTAATTTCAG AATTCTCACG AAAAAGGTAA ACAGTG                              36

(2) INFORMATION FOR SEQ ID NO: 194:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (xi) SEQUENCE DESCRIPTION: SEQ ID NO: 194:

CTTTTAATAG GGTAGAAACT GCCTAGGTTC ATTTTT                              36

(2) INFORMATION FOR SEQ ID NO: 195:

(i) SEQUENCE CHARACTERISTICS:
            (A) LENGTH: 36 base pairs
            (B) TYPE: nucleic acid
```

(C) STRANDEDNESS: single
        (D) TOPOLOGY: linear (xi) SEQUENCE DESCRIPTION: SEQ ID NO: 195:

TATTTTTTAG TTCGAAAAAG AAGAAGGTTT GTTTTA                                      36

(2) INFORMATION FOR SEQ ID NO: 196:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 196:

TTAAATGCAG TCTAACTTAA AAAAGGTAC AGAGTT                                       36

(2) INFORMATION FOR SEQ ID NO: 197:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 197:

AATATTTTAG TATCATGGAG ACTCAGGTAA GGCTTT                                      36

(2) INFORMATION FOR SEQ ID NO: 198:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 198:

TTTTGTTCAG ATTGTGTTAA AATGAGGTAA ACTATC                                      36

(2) INFORMATION FOR SEQ ID NO: 199:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 199:

TTAAACACAG ACCAACTAGT GTTCAGGTAA AATACT                                      36

(2) INFORMATION FOR SEQ ID NO: 200:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 200:

AATTCTGTAG ACAGACCTTG CCTTTGGTAA GTGTGA                                      36

(2) INFORMATION FOR SEQ ID NO: 201:

(i) SEQUENCE CHARACTERISTICS:
        (A) LENGTH: 36 base pairs
        (B) TYPE: nucleic acid (C) STRANDEDNESS: single
            (D) TOPOLOGY: linear (xi) SEQUENCE DESCRIPTION: SEQ ID NO: 201:

CTTTCTCTAG AAGAGCATCA ACTCAGGTGA GAGGCA                                36

(2) INFORMATION FOR SEQ ID NO: 202:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (xi) SEQUENCE DESCRIPTION: SEQ ID NO: 202:

TCGTTTACAG ATATGAGTAT ACTGAGGTAT TAATTA                                36

(2) INFORMATION FOR SEQ ID NO: 203:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (xi) SEQUENCE DESCRIPTION: SEQ ID NO: 203:

TTTCCTACAG ACTTCATC                                                   18

(2) INFORMATION FOR SEQ ID NO: 204:

(i) SEQUENCE CHARACTERISTICS:
            (A) LENGTH: 13 amino acids
            (B) TYPE: amino acid
            (C) STRANDEDNESS: single
            (D) TOPOLOGY: linear (xi) SEQUENCE DESCRIPTION: SEQ ID NO: 204:

Phe Pro Gly Ser Glu Glu Ile Cys Ser Ser Ser Lys Arg
 1               5                  10

(2) INFORMATION FOR SEQ ID NO: 205:

(i) SEQUENCE CHARACTERISTICS:
            (A) LENGTH: 4792 base pairs
            (B) TYPE: nucleic acid
            (C) STRANDEDNESS: single
            (D) TOPOLOGY: linear (ix) FEATURE:
            (A) NAME/KEY: CDS
            (B) LOCATION: 145..4347

(xi) SEQUENCE DESCRIPTION: SEQ ID NO: 205:

GTATAAAGTT AGTAAATGTG AGGCCTCTCT CGATGCCTGG GTCCTGGGCT TTGGTTCTCA      60

GTCCTCCATA AATCATCCTG CTGGAGGAGA AGACCCTTAG ATCTGGCTCT TCTCAGGGG      120

ATTTTAAAGA CAAATGAAAA TAAA ATG GAA ACC ACT TCA CTA CAG CGG AAA       171
                          Met Glu Thr Thr Ser Leu Gln Arg Lys
                            1               5

TTT CCA GAA TGG ATG TCT ATG CAG AGT CAA AGA TGT GCT ACA GAA GAA       219
Phe Pro Glu Trp Met Ser Met Gln Ser Gln Arg Cys Ala Thr Glu Glu
 10               15                  20                  25

AAG GCC TGC GTT CAG AAG AGT GTT CTT GAA GAT AAC CTC CCA TTC TTA       267
Lys Ala Cys Val Gln Lys Ser Val Leu Glu Asp Asn Leu Pro Phe Leu
              30                  35                  40

```
GAA TTC CCT GGA TCC ATT GTT TAC AGT TAT GAA GCT AGT GAT TGC TCC      315
Glu Phe Pro Gly Ser Ile Val Tyr Ser Tyr Glu Ala Ser Asp Cys Ser
            45                  50                  55

TTC CTG TCT GAA GAC ATT AGC ATG CGT CTG TCT GAT GGC GAT GTG GTG      363
Phe Leu Ser Glu Asp Ile Ser Met Arg Leu Ser Asp Gly Asp Val Val
        60                  65                  70

GGA TTT GAC ATG GAA TGG CCG CCC ATA TAC AAG CCA GGG AAA AGA AGC      411
Gly Phe Asp Met Glu Trp Pro Pro Ile Tyr Lys Pro Gly Lys Arg Ser
    75                  80                  85

AGA GTC GCA GTG ATC CAG TTG TGT GTG TCT GAG AGC AAA TGT TAC TTG      459
Arg Val Ala Val Ile Gln Leu Cys Val Ser Glu Ser Lys Cys Tyr Leu
90                  95                  100                 105

TTT CAC ATT TCT TCC ATG TCA GTT TTC CCC CAG GGA TTA AAA ATG TTA      507
Phe His Ile Ser Ser Met Ser Val Phe Pro Gln Gly Leu Lys Met Leu
                110                 115                 120

CTA GAA AAC AAA TCA ATT AAG AAG GCA GGG GTT GGG ATT GAA GGG GAC      555
Leu Glu Asn Lys Ser Ile Lys Lys Ala Gly Val Gly Ile Glu Gly Asp
            125                 130                 135

CAG TGG AAA CTT CTG CGT GAT TTT GAC GTC AAG TTG GAG AGT TTT GTG      603
Gln Trp Lys Leu Leu Arg Asp Phe Asp Val Lys Leu Glu Ser Phe Val
        140                 145                 150

GAG CTG ACG GAT GTT GCC AAT GAA AAG TTG AAG TGC GCA GAG ACC TGG      651
Glu Leu Thr Asp Val Ala Asn Glu Lys Leu Lys Cys Ala Glu Thr Trp
    155                 160                 165

AGC CTC AAT GGT CTG GTT AAA CAC GTC TTA GGG AAA CAA CTT TTG AAA      699
Ser Leu Asn Gly Leu Val Lys His Val Leu Gly Lys Gln Leu Leu Lys
170                 175                 180                 185

GAC AAG TCC ATC CGC TGC AGC AAT TGG AGT AAT TTC CCC CTC ACT GAG      747
Asp Lys Ser Ile Arg Cys Ser Asn Trp Ser Asn Phe Pro Leu Thr Glu
                190                 195                 200

GAC CAG AAA CTG TAT GCA GCC ACT GAT GCT TAT GCT GGT CTT ATC ATC      795
Asp Gln Lys Leu Tyr Ala Ala Thr Asp Ala Tyr Ala Gly Leu Ile Ile
            205                 210                 215

TAT CAA AAA TTA GGA AAT TTG GGT GAT ACT GCG CAA GTG TTT GCT CTA      843
Tyr Gln Lys Leu Gly Asn Leu Gly Asp Thr Ala Gln Val Phe Ala Leu
        220                 225                 230

AAT AAA GCA GAG GAA AAC CTA CCT CTG GAG ATG AAG AAA CAG TTG AAT      891
Asn Lys Ala Glu Glu Asn Leu Pro Leu Glu Met Lys Lys Gln Leu Asn
    235                 240                 245

TCA ATC TCC GAA GAA ATG AGG GAC CTA GCC AAT CGT TTT CCT GTC ACT      939
Ser Ile Ser Glu Glu Met Arg Asp Leu Ala Asn Arg Phe Pro Val Thr
250                 255                 260                 265

TGC AGA AAT TTG GAA ACT CTC CAG AGG GTT CCT GTA ATA TTG AAG AGT      987
Cys Arg Asn Leu Glu Thr Leu Gln Arg Val Pro Val Ile Leu Lys Ser
                270                 275                 280

ATT TCA GAA AAT CTC TGT TCA TTG AGA AAA GTG ATC TGT GGT CCT ACA     1035
Ile Ser Glu Asn Leu Cys Ser Leu Arg Lys Val Ile Cys Gly Pro Thr
            285                 290                 295

AAC ACT GAG ACT AGA CTG AAG CCG GGC AGT AGT TTT AAT TTA CTG TCA     1083
Asn Thr Glu Thr Arg Leu Lys Pro Gly Ser Ser Phe Asn Leu Leu Ser
        300                 305                 310

TCA GAG GAT TCA GCT GCT GCT GGA GAA AAA GAG AAA CAG ATT GGA AAA     1131
Ser Glu Asp Ser Ala Ala Ala Gly Glu Lys Glu Lys Gln Ile Gly Lys
    315                 320                 325

CAT AGT ACT TTT GCT AAA ATT AAA GAA GAA CCA TGG GAC CCA GAA CTT     1179
His Ser Thr Phe Ala Lys Ile Lys Glu Glu Pro Trp Asp Pro Glu Leu
330                 335                 340                 345

GAC AGT TTA GTG AAG CAA GAG GAG GTT GAT GTA TTT AGA AAT CAA GTG     1227
Asp Ser Leu Val Lys Gln Glu Glu Val Asp Val Phe Arg Asn Gln Val
                350                 355                 360
```

```
AAG CAA GAA AAA GGT GAA TCT GAA AAT GAA ATA GAA GAC AAT CTG TTG    1275
Lys Gln Glu Lys Gly Glu Ser Glu Asn Glu Ile Glu Asp Asn Leu Leu
        365                 370                 375

AGA GAA GAT ATG GAA AGA ACT TGT GTG ATT CCT AGT ATT TCA GAA AAT    1323
Arg Glu Asp Met Glu Arg Thr Cys Val Ile Pro Ser Ile Ser Glu Asn
        380                 385                 390

GAA CTC CAA GAT TTG GAA CAG CAA GCT AAA GAA GAA AAA TAT AAT GAT    1371
Glu Leu Gln Asp Leu Glu Gln Gln Ala Lys Glu Glu Lys Tyr Asn Asp
395                 400                 405

GTT TCT CAC CAA CTT TCT GAG CAT TTA TCT CCC AAT GAT GAT GAG AAT    1419
Val Ser His Gln Leu Ser Glu His Leu Ser Pro Asn Asp Asp Glu Asn
410                 415                 420                 425

GAC TCC TCC TAT ATA ATT GAA AGT GAT GAA GAT TTG GAA ATG GAG ATG    1467
Asp Ser Ser Tyr Ile Ile Glu Ser Asp Glu Asp Leu Glu Met Glu Met
            430                 435                 440

CTG AAG TCT TTA GAA AAC CTA AAT AGT GAC GTG GTG GAA CCC ACT CAC    1515
Leu Lys Ser Leu Glu Asn Leu Asn Ser Asp Val Val Glu Pro Thr His
            445                 450                 455

TCT ACA TGG TTG GAA ATG GGA ACC AAT GGG CGT CTT CCT CCT GAG GAG    1563
Ser Thr Trp Leu Glu Met Gly Thr Asn Gly Arg Leu Pro Pro Glu Glu
        460                 465                 470

GAA GAT GGA CAC GGA AAT GAA GCC ATC AAA GAG GAG CAG GAA GAA GAG    1611
Glu Asp Gly His Gly Asn Glu Ala Ile Lys Glu Glu Gln Glu Glu Glu
475                 480                 485

GAC CAT TTA TTG CCG GAA CCC AAC GCA AAG CAA ATT AAT TGC CTC AAG    1659
Asp His Leu Leu Pro Glu Pro Asn Ala Lys Gln Ile Asn Cys Leu Lys
490                 495                 500                 505

ACC TAT TTC GGA CAC AGC AGT TTT AAA CCG GTT CAG TGG AAA GTC ATC    1707
Thr Tyr Phe Gly His Ser Ser Phe Lys Pro Val Gln Trp Lys Val Ile
            510                 515                 520

CAT TCT GTA TTA GAA GAG AGA AGA GAT AAT GTT GTT GTC ATG GCA ACT    1755
His Ser Val Leu Glu Glu Arg Arg Asp Asn Val Val Val Met Ala Thr
            525                 530                 535

GGA TAT GGG AAG AGT CTG TGC TTC CAG TAT CCG CCT GTT TAT ACA GGC    1803
Gly Tyr Gly Lys Ser Leu Cys Phe Gln Tyr Pro Pro Val Tyr Thr Gly
        540                 545                 550

AAG ATT GGC ATT GTC ATT TCA CCT CTC ATT TCC TTA ATG GAA GAC CAA    1851
Lys Ile Gly Ile Val Ile Ser Pro Leu Ile Ser Leu Met Glu Asp Gln
555                 560                 565

GTC CTC CAG CTT GAG CTG TCC AAT GTT CCA GCC TGT TTA CTT GGA TCT    1899
Val Leu Gln Leu Glu Leu Ser Asn Val Pro Ala Cys Leu Leu Gly Ser
570                 575                 580                 585

GCA CAG TCA AAA AAT ATT CTA GGA GAT GTT AAA TTA GGC AAA TAT AGG    1947
Ala Gln Ser Lys Asn Ile Leu Gly Asp Val Lys Leu Gly Lys Tyr Arg
            590                 595                 600

GTC ATC TAC ATA ACT CCA GAG TTC TGT TCT GGT AAC TTG GAT CTA CTC    1995
Val Ile Tyr Ile Thr Pro Glu Phe Cys Ser Gly Asn Leu Asp Leu Leu
            605                 610                 615

CAG CAA CTT GAC TCT AGT ATT GGC ATC ACT CTC ATT GCT GTG GAT GAG    2043
Gln Gln Leu Asp Ser Ser Ile Gly Ile Thr Leu Ile Ala Val Asp Glu
        620                 625                 630

GCT CAC TGC ATT TCA GAG TGG GGC CAT GAT TTC AGA AGT TCA TTC AGG    2091
Ala His Cys Ile Ser Glu Trp Gly His Asp Phe Arg Ser Ser Phe Arg
635                 640                 645

ATG CTG GGC TCT CTT AAA ACA GCG CTC CCA TTG GTT CCA GTC ATT GCA    2139
Met Leu Gly Ser Leu Lys Thr Ala Leu Pro Leu Val Pro Val Ile Ala
650                 655                 660                 665

CTC TCC GCT ACT GCA AGC TCT TCC ATC CGG GAA GAC ATT ATA AGC TGC    2187
Leu Ser Ala Thr Ala Ser Ser Ser Ile Arg Glu Asp Ile Ile Ser Cys
            670                 675                 680
```

```
TTA AAC CTG AAA GAC CCT CAG ATC ACC TGC ACT GGA TTT GAT CGG CCA      2235
Leu Asn Leu Lys Asp Pro Gln Ile Thr Cys Thr Gly Phe Asp Arg Pro
        685                 690                 695

AAT CTG TAC TTA GAA GTT GGA CGG AAA ACA GGG AAC ATC CTT CAG GAT      2283
Asn Leu Tyr Leu Glu Val Gly Arg Lys Thr Gly Asn Ile Leu Gln Asp
            700                 705                 710

CTA AAG CCG TTT CTC GTC CGA AAG GCA AGT TCT GCC TGG GAA TTT GAA      2331
Leu Lys Pro Phe Leu Val Arg Lys Ala Ser Ser Ala Trp Glu Phe Glu
        715                 720                 725

GGT CCA ACC ATC ATC TAT TGT CCT TCG AGA AAA ATG ACA GAA CAA GTT      2379
Gly Pro Thr Ile Ile Tyr Cys Pro Ser Arg Lys Met Thr Glu Gln Val
730                 735                 740                 745

ACT GCT GAA CTT GGG AAA CTG AAC TTA GCC TGC AGA ACA TAC CAC GCT      2427
Thr Ala Glu Leu Gly Lys Leu Asn Leu Ala Cys Arg Thr Tyr His Ala
                750                 755                 760

GGC ATG AAA ATT AGC GAA AGG AAG GAC GTT CAT CAT AGG TTC CTG AGA      2475
Gly Met Lys Ile Ser Glu Arg Lys Asp Val His His Arg Phe Leu Arg
            765                 770                 775

GAT GAA ATT CAG TGT GTT GTA GCT ACT GTA GCT TTT GGA ATG GGC ATT      2523
Asp Glu Ile Gln Cys Val Val Ala Thr Val Ala Phe Gly Met Gly Ile
        780                 785                 790

AAT AAA GCT GAC ATT CGC AAA GTT ATT CAT TAT GGT GCG CCT AAG GAA      2571
Asn Lys Ala Asp Ile Arg Lys Val Ile His Tyr Gly Ala Pro Lys Glu
795                 800                 805

ATG GAA TCC TAT TAC CAG GAA ATT GGT AGA GCT GGC CGG GAT GGA CTT      2619
Met Glu Ser Tyr Tyr Gln Glu Ile Gly Arg Ala Gly Arg Asp Gly Leu
810                 815                 820                 825

CAG AGT TCC TGT CAC TTG CTC TGG GCT CCA GCA GAC TTT AAC ACA TCC      2667
Gln Ser Ser Cys His Leu Leu Trp Ala Pro Ala Asp Phe Asn Thr Ser
                830                 835                 840

AGG AAT CTC CTT ATT GAG ATT CAC GAT GAA AAG TTC CGG TTA TAT AAA      2715
Arg Asn Leu Leu Ile Glu Ile His Asp Glu Lys Phe Arg Leu Tyr Lys
            845                 850                 855

TTA AAG ATG ATG GTA AAG ATG GAA AAA TAC CTT CAC TCC AGT CAG TGT      2763
Leu Lys Met Met Val Lys Met Glu Lys Tyr Leu His Ser Ser Gln Cys
        860                 865                 870

AGG CGA CGA ATC ATC TTG TCC CAT TTT GAG GAC AAA TGT CTG CAG AAG      2811
Arg Arg Arg Ile Ile Leu Ser His Phe Glu Asp Lys Cys Leu Gln Lys
875                 880                 885

GCC TCC TTG GAC ATT ATG GGA ACT GAA AAA TGC TGT GAT AAT TGC AGG      2859
Ala Ser Leu Asp Ile Met Gly Thr Glu Lys Cys Cys Asp Asn Cys Arg
890                 895                 900                 905

CCC AGG CTG AAT CAT TGC ATT ACT GCT AAC AAC TCA GAG GAC GCA TCC      2907
Pro Arg Leu Asn His Cys Ile Thr Ala Asn Asn Ser Glu Asp Ala Ser
                910                 915                 920

CAA GAC TTT GGG CCA CAA GCA TTC CAG CTA CTG TCT GCT GTG GAC ATC      2955
Gln Asp Phe Gly Pro Gln Ala Phe Gln Leu Leu Ser Ala Val Asp Ile
            925                 930                 935

CTG CAG GAG AAA TTT GGA ATT GGG ATT CCG ATC TTA TTT CTC CGA GGA      3003
Leu Gln Glu Lys Phe Gly Ile Gly Ile Pro Ile Leu Phe Leu Arg Gly
        940                 945                 950

TCT AAT TCT CAG CGT CTT CCT GAT AAA TAT CGG GGT CAC AGG CTC TTT      3051
Ser Asn Ser Gln Arg Leu Pro Asp Lys Tyr Arg Gly His Arg Leu Phe
955                 960                 965

GGT GCT GGA AAG GAG CAA GCA GAA AGT TGG TGG AAG ACC CTT TCT CAC      3099
Gly Ala Gly Lys Glu Gln Ala Glu Ser Trp Trp Lys Thr Leu Ser His
970                 975                 980                 985

CAT CTC ATA GCT GAA GGA TTC TTG GTA GAA GTT CCC AAG GAA AAC AAA      3147
His Leu Ile Ala Glu Gly Phe Leu Val Glu Val Pro Lys Glu Asn Lys
                990                 995                 1000
```

```
TAT ATA AAG ACA TGT TCC CTC ACA AAA AAG GGT AGA AAG TGG CTT GGA        3195
Tyr Ile Lys Thr Cys Ser Leu Thr Lys Lys Gly Arg Lys Trp Leu Gly
        1005                1010                1015

GAA GCC AGT TCG CAG TCT CCT CCG AGC CTT CTC CTT CAA GCT AAT GAA        3243
Glu Ala Ser Ser Gln Ser Pro Pro Ser Leu Leu Leu Gln Ala Asn Glu
        1020                1025                1030

GAG ATG TTT CCA AGG AAA GTT CTG CTA CCA AGT TCT AAT CCT GTA TCT        3291
Glu Met Phe Pro Arg Lys Val Leu Leu Pro Ser Ser Asn Pro Val Ser
        1035                1040                1045

CCA GAA ACG ACG CAA CAT TCC TCT AAT CAA AAC CCA GCT GGA TTA ACT        3339
Pro Glu Thr Thr Gln His Ser Ser Asn Gln Asn Pro Ala Gly Leu Thr
1050                1055                1060                1065

ACC AAG CAG TCT AAT TTG GAG AGA ACG CAT TCT TAC AAA GTG CCT GAG        3387
Thr Lys Gln Ser Asn Leu Glu Arg Thr His Ser Tyr Lys Val Pro Glu
                1070                1075                1080

AAA GTT TCT TCT GGG ACT AAC ATT CCT AAA AAA AGT GCC GTG ATG CCG        3435
Lys Val Ser Ser Gly Thr Asn Ile Pro Lys Lys Ser Ala Val Met Pro
                1085                1090                1095

TCA CCA GGA ACA TCT TCC AGC CCC TTA GAA CCT GCC ATC TCA GCC CAA        3483
Ser Pro Gly Thr Ser Ser Ser Pro Leu Glu Pro Ala Ile Ser Ala Gln
                1100                1105                1110

GAG CTG GAC GCT CGG ACT GGG CTA TAT GCC AGG CTG GTG GAA GCA AGG        3531
Glu Leu Asp Ala Arg Thr Gly Leu Tyr Ala Arg Leu Val Glu Ala Arg
        1115                1120                1125

CAG AAA CAC GCT AAT AAG ATG GAT GTA CCT CCA GCT ATT TTA GCA ACA        3579
Gln Lys His Ala Asn Lys Met Asp Val Pro Pro Ala Ile Leu Ala Thr
1130                1135                1140                1145

AAC AAG GTT CTG CTG GAC ATG GCT AAA ATG AGA CCG ACT ACT GTT GAA        3627
Asn Lys Val Leu Leu Asp Met Ala Lys Met Arg Pro Thr Thr Val Glu
                1150                1155                1160

AAC ATG AAA CAG ATC GAC GGT GTC TCT GAA GGC AAA GCT GCT CTG TTG        3675
Asn Met Lys Gln Ile Asp Gly Val Ser Glu Gly Lys Ala Ala Leu Leu
                1165                1170                1175

GCC CCT CTG TTG GAA GTC ATC AAA CAT TTC TGT CAA GTA ACT AGT GTT        3723
Ala Pro Leu Leu Glu Val Ile Lys His Phe Cys Gln Val Thr Ser Val
                1180                1185                1190

CAG ACA GAC CTC CTT TCC AGT GCC AAA CCT CAC AAG GAA CAG GAG AAA        3771
Gln Thr Asp Leu Leu Ser Ser Ala Lys Pro His Lys Glu Gln Glu Lys
        1195                1200                1205

AGT CAG GAG ATG GAA AAG AAA GAC TGC TCA CTC CCC CAG TCT GTG GCC        3819
Ser Gln Glu Met Glu Lys Lys Asp Cys Ser Leu Pro Gln Ser Val Ala
1210                1215                1220                1225

GTC ACA TAC ACT CTA TTC CAG GAA AAG AAA ATG CCC TTA CAC AGC ATA        3867
Val Thr Tyr Thr Leu Phe Gln Glu Lys Lys Met Pro Leu His Ser Ile
                1230                1235                1240

GCT GAG AAC AGG CTC CTG CCT CTC ACA GCA GCC GGC ATG CAC TTA GCC        3915
Ala Glu Asn Arg Leu Leu Pro Leu Thr Ala Ala Gly Met His Leu Ala
                1245                1250                1255

CAG GCG GTG AAA GCC GGC TAC CCC CTG GAT ATG GAG CGA GCT GGC CTG        3963
Gln Ala Val Lys Ala Gly Tyr Pro Leu Asp Met Glu Arg Ala Gly Leu
        1260                1265                1270

ACC CCA GAG ACT TGG AAG ATT ATT ATG GAT GTC ATC CGA AAC CCT CCC        4011
Thr Pro Glu Thr Trp Lys Ile Ile Met Asp Val Ile Arg Asn Pro Pro
        1275                1280                1285

ATC AAC TCA GAT ATG TAT AAA GTT AAA CTC ATC AGA ATG TTA GTT CCT        4059
Ile Asn Ser Asp Met Tyr Lys Val Lys Leu Ile Arg Met Leu Val Pro
1290                1295                1300                1305

GAA AAC TTA GAC ACG TAC CTC ATC CAC ATG GCG ATT GAG ATT CTT CAG        4107
Glu Asn Leu Asp Thr Tyr Leu Ile His Met Ala Ile Glu Ile Leu Gln
        1310                1315                1320
```

```
AGT GGT TCC GAC AGC AGA ACC CAG CCT CCT TGT GAT TCC AGC AGG AAG                4155
Ser Gly Ser Asp Ser Arg Thr Gln Pro Pro Cys Asp Ser Ser Arg Lys
            1325                1330                1335

AGG CGT TTC CCC AGC TCT GCA GAG AGT TGT GAG AGC TGT AAG GAG AGC                4203
Arg Arg Phe Pro Ser Ser Ala Glu Ser Cys Glu Ser Cys Lys Glu Ser
        1340                1345                1350

AAA GAG GCG GTC ACC GAG ACC AAG GCA TCA TCT TCA GAG TCA AAG AGA                4251
Lys Glu Ala Val Thr Glu Thr Lys Ala Ser Ser Ser Glu Ser Lys Arg
        1355                1360                1365

AAA TTA CCC GAG TGG TTT GCC AAA GGA AAT GTG CCC TCA GCT GAT ACC                4299
Lys Leu Pro Glu Trp Phe Ala Lys Gly Asn Val Pro Ser Ala Asp Thr
1370                1375                1380                1385

GGC AGC TCA TCA TCA ATG GCC AAG ACC AAA AAG AAA GGT CTC TTT AGT                4347
Gly Ser Ser Ser Ser Met Ala Lys Thr Lys Lys Lys Gly Leu Phe Ser
                1390                1395                1400

TAANATGACN ACGATGGAAC AGTTTGTGTG TCCTACATCT TCATTCCTAT AAAGAATGAA              4407

NAGAAATATT TTAACCTCAA AATTATTTAA AGTCCAAAGT GAAGCTCACC TAAACGTCGA              4467

GCCATAGAGT CTTTAATTGN CCGTTGGCAG TTGAGCTACA GTATCTGAAC CTTCTGAGAC              4527

CCGGAGTGCA GCATAGACTG TGAAGTCGGC TTCCTTTCCG ATTGCCTTCC GAACCCGTTGT             4587

CACTGTCAGG TTGCAGTCTT TCTCTTCTTG CAGCAGTGTG TGTTGGAAAT GGAGGCTGTG              4647

TCGCTTTGAC ATATAGAACA GATCAGTANT TGCATAGGGA CAGATATGAA GATNCAGCCG              4707

GTCTTTGCTT TCTTATGCAG ATGCCTGTAT GACAGTATCA GTGCACCAGC CCAGCCAGGG              4767

AGACATCAGC TTCCATTTAA AAAGG                                                    4792
```

(2) INFORMATION FOR SEQ ID NO: 206:

(i) SEQUENCE CHARACTERISTICS:
        (A) LENGTH: 1401 amino acids
        (B) TYPE: amino acid
        (D) TOPOLOGY: linear (ii) MOLECULE TYPE: protein (xi) SEQUENCE DESCRIPTION: SEQ ID NO: 206:

```
Met Glu Thr Thr Ser Leu Gln Arg Lys Phe Pro Glu Trp Met Ser Met
 1               5                  10                  15

Gln Ser Gln Arg Cys Ala Thr Glu Glu Lys Ala Cys Val Gln Lys Ser
            20                  25                  30

Val Leu Glu Asp Asn Leu Pro Phe Leu Glu Phe Pro Gly Ser Ile Val
        35                  40                  45

Tyr Ser Tyr Glu Ala Ser Asp Cys Ser Phe Leu Ser Glu Asp Ile Ser
    50                  55                  60

Met Arg Leu Ser Asp Gly Asp Val Val Gly Phe Asp Met Glu Trp Pro
65                  70                  75                  80

Pro Ile Tyr Lys Pro Gly Lys Arg Ser Arg Val Ala Val Ile Gln Leu
                85                  90                  95

Cys Val Ser Glu Ser Lys Cys Tyr Leu Phe His Ile Ser Ser Met Ser
            100                 105                 110

Val Phe Pro Gln Gly Leu Lys Met Leu Leu Glu Asn Lys Ser Ile Lys
        115                 120                 125

Lys Ala Gly Val Gly Ile Glu Gly Asp Gln Trp Lys Leu Leu Arg Asp
    130                 135                 140

Phe Asp Val Lys Leu Glu Ser Phe Val Glu Leu Thr Asp Val Ala Asn
145                 150                 155                 160
```

-continued

```
Glu Lys Leu Lys Cys Ala Glu Thr Trp Ser Leu Asn Gly Leu Val Lys
                165                 170                 175
His Val Leu Gly Lys Gln Leu Leu Lys Asp Lys Ser Ile Arg Cys Ser
            180                 185                 190
Asn Trp Ser Asn Phe Pro Leu Thr Glu Asp Gln Lys Leu Tyr Ala Ala
        195                 200                 205
Thr Asp Ala Tyr Ala Gly Leu Ile Ile Tyr Gln Lys Leu Gly Asn Leu
    210                 215                 220
Gly Asp Thr Ala Gln Val Phe Ala Leu Asn Lys Ala Glu Glu Asn Leu
225                 230                 235                 240
Pro Leu Glu Met Lys Lys Gln Leu Asn Ser Ile Ser Glu Glu Met Arg
                245                 250                 255
Asp Leu Ala Asn Arg Phe Pro Val Thr Cys Arg Asn Leu Glu Thr Leu
            260                 265                 270
Gln Arg Val Pro Val Ile Leu Lys Ser Ile Ser Glu Asn Leu Cys Ser
        275                 280                 285
Leu Arg Lys Val Ile Cys Gly Pro Thr Asn Thr Glu Thr Arg Leu Lys
    290                 295                 300
Pro Gly Ser Ser Phe Asn Leu Leu Ser Ser Glu Asp Ser Ala Ala Ala
305                 310                 315                 320
Gly Glu Lys Glu Lys Gln Ile Gly Lys His Ser Thr Phe Ala Lys Ile
                325                 330                 335
Lys Glu Glu Pro Trp Asp Pro Glu Leu Asp Ser Leu Val Lys Gln Glu
            340                 345                 350
Glu Val Asp Val Phe Arg Asn Gln Val Lys Gln Glu Lys Gly Glu Ser
        355                 360                 365
Glu Asn Glu Ile Glu Asp Asn Leu Leu Arg Glu Asp Met Glu Arg Thr
    370                 375                 380
Cys Val Ile Pro Ser Ile Ser Glu Asn Glu Leu Gln Asp Leu Glu Gln
385                 390                 395                 400
Gln Ala Lys Glu Glu Lys Tyr Asn Asp Val Ser His Gln Leu Ser Glu
                405                 410                 415
His Leu Ser Pro Asn Asp Asp Glu Asn Asp Ser Ser Tyr Ile Ile Glu
            420                 425                 430
Ser Asp Glu Asp Leu Glu Met Glu Met Leu Lys Ser Leu Glu Asn Leu
        435                 440                 445
Asn Ser Asp Val Val Glu Pro Thr His Ser Thr Trp Leu Glu Met Gly
    450                 455                 460
Thr Asn Gly Arg Leu Pro Pro Glu Glu Glu Asp Gly His Gly Asn Glu
465                 470                 475                 480
Ala Ile Lys Glu Glu Gln Glu Glu Asp His Leu Leu Pro Glu Pro
                485                 490                 495
Asn Ala Lys Gln Ile Asn Cys Leu Lys Thr Tyr Phe Gly His Ser Ser
            500                 505                 510
Phe Lys Pro Val Gln Trp Lys Val Ile His Ser Val Leu Glu Glu Arg
        515                 520                 525
Arg Asp Asn Val Val Val Met Ala Thr Gly Tyr Gly Lys Ser Leu Cys
    530                 535                 540
Phe Gln Tyr Pro Pro Val Tyr Thr Gly Lys Ile Gly Ile Val Ile Ser
545                 550                 555                 560
Pro Leu Ile Ser Leu Met Glu Asp Gln Val Leu Gln Leu Glu Leu Ser
                565                 570                 575
```

-continued

```
Asn Val Pro Ala Cys Leu Leu Gly Ser Ala Gln Ser Lys Asn Ile Leu
            580                 585                 590
Gly Asp Val Lys Leu Gly Lys Tyr Arg Val Ile Tyr Ile Thr Pro Glu
        595                 600                 605
Phe Cys Ser Gly Asn Leu Asp Leu Leu Gln Gln Leu Asp Ser Ser Ile
        610                 615                 620
Gly Ile Thr Leu Ile Ala Val Asp Glu Ala His Cys Ile Ser Glu Trp
625                 630                 635                 640
Gly His Asp Phe Arg Ser Ser Phe Arg Met Leu Gly Ser Leu Lys Thr
                645                 650                 655
Ala Leu Pro Leu Val Pro Val Ile Ala Leu Ser Ala Thr Ala Ser Ser
            660                 665                 670
Ser Ile Arg Glu Asp Ile Ile Ser Cys Leu Asn Leu Lys Asp Pro Gln
        675                 680                 685
Ile Thr Cys Thr Gly Phe Asp Arg Pro Asn Leu Tyr Leu Glu Val Gly
        690                 695                 700
Arg Lys Thr Gly Asn Ile Leu Gln Asp Leu Lys Pro Phe Leu Val Arg
705                 710                 715                 720
Lys Ala Ser Ser Ala Trp Glu Phe Glu Gly Pro Thr Ile Ile Tyr Cys
                725                 730                 735
Pro Ser Arg Lys Met Thr Glu Gln Val Thr Ala Glu Leu Gly Lys Leu
            740                 745                 750
Asn Leu Ala Cys Arg Thr Tyr His Ala Gly Met Lys Ile Ser Glu Arg
        755                 760                 765
Lys Asp Val His His Arg Phe Leu Arg Asp Glu Ile Gln Cys Val Val
        770                 775                 780
Ala Thr Val Ala Phe Gly Met Gly Ile Asn Lys Ala Asp Ile Arg Lys
785                 790                 795                 800
Val Ile His Tyr Gly Ala Pro Lys Glu Met Glu Ser Tyr Tyr Gln Glu
                805                 810                 815
Ile Gly Arg Ala Gly Arg Asp Gly Leu Gln Ser Ser Cys His Leu Leu
            820                 825                 830
Trp Ala Pro Ala Asp Phe Asn Thr Ser Arg Asn Leu Leu Ile Glu Ile
        835                 840                 845
His Asp Glu Lys Phe Arg Leu Tyr Lys Leu Lys Met Met Val Lys Met
        850                 855                 860
Glu Lys Tyr Leu His Ser Ser Gln Cys Arg Arg Arg Ile Ile Leu Ser
865                 870                 875                 880
His Phe Glu Asp Lys Cys Leu Gln Lys Ala Ser Leu Asp Ile Met Gly
                885                 890                 895
Thr Glu Lys Cys Cys Asp Asn Cys Arg Pro Arg Leu Asn His Cys Ile
            900                 905                 910
Thr Ala Asn Asn Ser Glu Asp Ala Ser Gln Asp Phe Gly Pro Gln Ala
        915                 920                 925
Phe Gln Leu Leu Ser Ala Val Asp Ile Leu Gln Glu Lys Phe Gly Ile
        930                 935                 940
Gly Ile Pro Ile Leu Phe Leu Arg Gly Ser Asn Ser Gln Arg Leu Pro
945                 950                 955                 960
Asp Lys Tyr Arg Gly His Arg Leu Phe Gly Ala Gly Lys Glu Gln Ala
                965                 970                 975
Glu Ser Trp Trp Lys Thr Leu Ser His His Leu Ile Ala Glu Gly Phe
            980                 985                 990
```

```
Leu Val Glu Val Pro Lys Glu Asn Lys Tyr Ile Lys Thr Cys Ser Leu
        995                 1000                1005

Thr Lys Lys Gly Arg Lys Trp Leu Gly Glu Ala Ser Ser Gln Ser Pro
    1010                1015                1020

Pro Ser Leu Leu Gln Ala Asn Glu Glu Met Phe Pro Arg Lys Val
1025                1030                1035                1040

Leu Leu Pro Ser Ser Asn Pro Val Ser Pro Glu Thr Thr Gln His Ser
                1045                1050                1055

Ser Asn Gln Asn Pro Ala Gly Leu Thr Thr Lys Gln Ser Asn Leu Glu
            1060                1065                1070

Arg Thr His Ser Tyr Lys Val Pro Glu Lys Val Ser Ser Gly Thr Asn
            1075                1080                1085

Ile Pro Lys Lys Ser Ala Val Met Pro Ser Pro Gly Thr Ser Ser Ser
        1090                1095                1100

Pro Leu Glu Pro Ala Ile Ser Ala Gln Glu Leu Asp Ala Arg Thr Gly
1105                1110                1115                1120

Leu Tyr Ala Arg Leu Val Glu Ala Arg Gln Lys His Ala Asn Lys Met
                1125                1130                1135

Asp Val Pro Pro Ala Ile Leu Ala Thr Asn Lys Val Leu Leu Asp Met
                1140                1145                1150

Ala Lys Met Arg Pro Thr Thr Val Glu Asn Met Lys Gln Ile Asp Gly
            1155                1160                1165

Val Ser Glu Gly Lys Ala Ala Leu Leu Ala Pro Leu Leu Glu Val Ile
    1170                1175                1180

Lys His Phe Cys Gln Val Thr Ser Val Gln Thr Asp Leu Leu Ser Ser
1185                1190                1195                1200

Ala Lys Pro His Lys Glu Gln Glu Lys Ser Gln Glu Met Glu Lys Lys
                1205                1210                1215

Asp Cys Ser Leu Pro Gln Ser Val Ala Val Thr Tyr Thr Leu Phe Gln
                1220                1225                1230

Glu Lys Lys Met Pro Leu His Ser Ile Ala Glu Asn Arg Leu Leu Pro
            1235                1240                1245

Leu Thr Ala Ala Gly Met His Leu Ala Gln Ala Val Lys Ala Gly Tyr
    1250                1255                1260

Pro Leu Asp Met Glu Arg Ala Gly Leu Thr Pro Glu Thr Trp Lys Ile
1265                1270                1275                1280

Ile Met Asp Val Ile Arg Asn Pro Pro Ile Asn Ser Asp Met Tyr Lys
                1285                1290                1295

Val Lys Leu Ile Arg Met Leu Val Pro Glu Asn Leu Asp Thr Tyr Leu
            1300                1305                1310

Ile His Met Ala Ile Glu Ile Leu Gln Ser Gly Ser Asp Ser Arg Thr
    1315                1320                1325

Gln Pro Pro Cys Asp Ser Ser Arg Lys Arg Phe Pro Ser Ser Ala
1330                1335                1340

Glu Ser Cys Glu Ser Cys Lys Glu Ser Lys Glu Ala Val Thr Glu Thr
1345                1350                1355                1360

Lys Ala Ser Ser Ser Glu Ser Lys Arg Lys Leu Pro Glu Trp Phe Ala
                1365                1370                1375

Lys Gly Asn Val Pro Ser Ala Asp Thr Gly Ser Ser Ser Met Ala
            1380                1385                1390

Lys Thr Lys Lys Lys Gly Leu Phe Ser
            1395                1400
```

(2) INFORMATION FOR SEQ ID NO: 207:

(i) SEQUENCE CHARACTERISTICS:
        (A) LENGTH: 29604 base pairs
        (B) TYPE: nucleic acid
        (C) STRANDEDNESS: single
        (D) TOPOLOGY: linear (xi) SEQUENCE DESCRIPTION: SEQ ID NO: 207:

```
TGAGGTTATT CTTTGAAGGG ACAGAATCC  CATTTCACTT TTACTAGATA AGAATTTAGA    60
ACCTAACATC TGCCACCGTA GACTCTGAGT TATTAAATTG AGAGGAAATG GCCAAAGTGT   120
ATCCTGTAAT GAAATAATCC TCATATGAAA TTGTTCTTAT ATGACATTGG AAGACCTGTC   180
TTGCTCTGTC TTTTCAGTTT TGGATACATT TTCTTGACAC AAACCGGTAT CAGAGCCAGA   240
CTCTTTTCTG CTCTAACATC TTGCTTCTGT ACGTTATAAT CCTCAGTCCT CAAGCGGTCT   300
CTAACATCTT GCTTCTGTAC GTTATAATCC TCAGTCCTCA AGCGGTCTTC GGCGACGTCA   360
GCTACTCTTT TTTTGTACAG AGTGATGGTT ATAAAGTCTT CTTGTTGAAA ATCACTGTGA   420
ACTTAGTAGC TATAGTAAAA TTTTCATAAA GATCCGTAGA AATTAAAATT ATAGCATAAA   480
TATACAACTA GCTTTTTCTA ACATTTTGTT ATCAGATTTC AGAATAATCA TACATTTTTT   540
ACATTTTTAC TAAAAAATGA GTATTTACAT ATTTGACCAA AATAAAATTG AACCATTTTA   600
GATAATTATT GAAACAATTT CCACATTAAG CAGTATAACT GCCAATTAGT TAATTGCTGA   660
ATGATTACAT ATTAGTTATT AATATTGTCT AGCAACAACT TTATCTTATA CTCAAAATGA   720
TTATATTGGC CATTTAACTT AATTAAGTTT CTCGCTTTTT TAATGCTTTT AGAAAAGATT   780
GGGATGCCTT ATTTAGTTTA GCCCTCAAGC AATTAGGTGA GGCAATTACC ATGGTAACAG   840
AAGGTATTCA TTTCCTTACC TTAGCTAAAG GTTTTGGGAA CAAAGAAACC TCTCAGCTCA   900
TCCATTGAAA CCCAACTTTC TCCTGAGCCT GGCATTAAGT GTTTGTTCTC TAAAAGAGGA   960
CTTAATTTTA AGTGGGGAAA ACATGCCCCT GAGCTGAGTC TCTTTGTCAT AGGGCGATTA  1020
AAAAGCTACC TCTTCTTAAT AGGAAGTGTG GTCTTAACTT TTATATTTCA CATTTTATAT  1080
TGAGAATTTC TACACTCATA TAATGTTTTG ATCAAACTTT CCCTTTAAAT CCTTGCCTTC  1140
CCTATCCTCT TTCTTCCTTT GTTTCCTTCT TTGTTTGTTT CTCTCTCTCT CTCTCTCTAC  1200
CTCTCTCTCT CTCTCTCTCT CTCTTTCTTT CTTTCCTTCA AATGCCCTGA ACGTCCTTCC  1260
GCTGCTTCTC GCTGCATGAG TACAGGATCA CCTGAGATAC CTACCTAGCT GTCAGGAATG  1320
ACATCCTGAA GAAGACAGAC CCTTGCTTCC CCAGTGGCTG GCTATCTGTT GCCAATACTG  1380
TAGGCTTCAT GAGCTTCCCC TCAGTGCACG CTGAGATTTG GCTGGCTTGA TTTTTTTGCA  1440
TGCAGACATA GCCTCTGAGA TGGACAATAA TCCTGCCAAC AGTCTTCCTG CCCCTCTTCT  1500
GCAATGATTC CCAAGCCTTG TGACATGGGA GTCACATTTA GAGCTGGTCA GTTTTTGTTC  1560
TTTTTTCTTT TGTTTTGAAT TAAACTCGAA ATCTCATTGG TATGCTCTCT TTTGACAAAA  1620
GGATACCAGA CCACCTCTCC TAACGGTCTA ATTGCTGTCA AATAAAATCA CTTAAGGTGT  1680
ATTTTTCAAC ACATAATTTA TAGTTTTTGA CAGGTAATTT ATTAATATTT ATTTGGCTAG  1740
TTCTACCATT CCCAAGCAGA AAGTCTACTT ACTAAATTAG CTATCATGAG GCAAATTTTG  1800
TAACTAATTT ATCAAAAATT CTGGTCATGG TGGTGCATAT CTATAATCCT ATCACCCAGG  1860
ATTGTGGTTC AAGGCCAATC TCAAAGGAAA CTTTGTCTCA AACAAACAA  ACAAACAAAC  1920
AAACAAATTA ACATGAAACA GAACACATTA AAAAAACCCA GGGTTTTTAC CAGAAATTTA  1980
ATTATTAAAT ATATCTTGGA AATTAAAACC AGACAACAAC AACAACAACA TCAACCCACC  2040
CTGAGTATGC TGTTAAAAAT ACCAGTACTA GAGGCCTGGA GACATTGCTC ATGCTTGAGA  2100
```

```
CTATTAAGCA TTCTTACAGA AGAATGGGTT CTGTTTCTTG CAACCTCATG GTGGCTCACA    2160

GCTCCCAGTA TATGGACATC TGAGACTGGA AATGATAGGA AGAATTAAGG CTTTACACAA    2220

ATATCTGTCT AAAAACACGC ATGCGCCAGG CTGTCTATAT ACAGCGACTC CTGAATATTC    2280

ACACTTGCAT TTAATTTGAA TTCTGCATTG TGATGCCATA TAAACTGTTA AGTGCAGTGG    2340

AATTCAGGAA CTTGTGGTAC TTTCTGTTTA GTTAAGATT AAAAGTGCAG TTACTATGTA     2400

GTGGGTAAAG GTGCTTGCTT TGCAAGCCTG ACAGCCTGGC TCAGGGTTCA GCCTCTGTGT    2460

GATGTAGGAG AGAAGCACAC CAGAGCATCA GTAACACTGT CAGGCATTGG TGCCTCTCAT    2520

GAGCTGGATC CCAAGTTGGG CCTGTCATTC CTGTTCCCCA GGCTCTTCTC CATATTTTTC    2580

CCTGCAGTTC CTTTAGACAG GAACAATTCT GAGTCAGAGT TTTTGACTGT GGGATGACAA    2640

CCCCATCCCT CCACTTGGTG CCCTGTCTTT CTATTGGAGG TGGACTCTAC AAGTTCCCTC    2700

TCCCCACTTT TGAGCATTTC GTCTAAGGTC CCTTGCTTTG AGTCCTGAGA GTCTCTCACC    2760

TCCGAGGTCT CTGGTACTTT CTAGAGGGTC CCCCCATTTG AGGGCAACTG ACAGTGCATT    2820

GAGCTTACCA AATATTTTGT AAACTTCTTG TTGTTCAGAT TTAATTACAT CTTTAAAGAG    2880

TTTTGTCCCT AGCTATCGTT CTCGCCGGCA AGAACACACG CGGACAACCG GATTCTTCTG    2940

CGGCAAGCTT TATTGCTTCT TAAGGAGGGA AGACCCAGAC CCTGGAAAAT GGTGCTGCTT    3000

ATATAGCCCT CAGCGTGGCG TTTCAGCACC TGATGTGGCA TGTCACCTCC TGATTTGTTG    3060

CTCGCCCATC ACTTCATTAC TATGCCCCGA GATGGGCAGT GACTAGGCGT GAGTTCACTC    3120

TTGCACTTGC GCACAAGGCT TGTTTATTAG GCACAGCGGA AGCCAGCGCC ATCTTATAAT    3180

GGTGATTACT CGCGGCACGG CTCTCCACAG AGTTTACCAG AAAATGTATT CATAAAATGA    3240

GTGTTATATT ACTTTCCTGT TATATTTATT CCCAATAATA TTGTTTATTT TATTGTATAG    3300

CTTTTTGCTA TTGTAAATAT AATTTTGACT CTGCCCTAAT TTCTGAGGAT GCATTGTCAT    3360

ATCAGAAAAA GTTTTATTAT AGTTTCTATT GTGTTTCTAT AGTTTTTATT ATAGTTTCTA    3420

GTTCAAACCA TATTACTGTT TTCTTTATCA ATTGAAAAAG AGCTACTTTT TAAATTATAG    3480

GCTCCTTGGT TCTCTGGTTA TAAACAATGG TATGCAAAAT AAAACCATTT ACCACTGTGT    3540

CTCTTAAAAA GAAAGTAGGA GATAACTGAC TTCACAAAGT TGCTCTGTGA TCCCCCACGC    3600

ATGTGTCATG GTGGGAGCTT GCTGGCATTC AAACATAAAC ATATCACAAA CGCACACACA    3660

TGCACACATA CTCTCTCTCT CTCACACATG CACACACACA CAATTTGTTA TTTCACTATT    3720

GAAGTCTTGA GAGACCAAAA GAAGGTTTTA CACTAAAAGG AACATTTTTA ATTATCCCCT    3780

CTGTTTCCTT TTTGAAGACT TGTAATATAA TTACATTATA GTTAAAACTG TAGCAATCAC    3840

AGATCACAGG GAAGATGCCC TGATAGCCCA GAAGTAGTAG CATGAAACAA TGTTTAATTA    3900

ATGCTGTCTG ACTCTCAAAT AATAACTAAT AGTACTAACA GAGCAGATGA GAGCTTTTAA    3960

TAGTATTTTG AAAATATTTT ATATAAAATT TAGTCATATT CAAAGCTGTC TATATGATTG    4020

GAAGGAATTA ACATGTCTCC TCTTTAAGGA AACAGAGACT CTCTTAGCTT TAAGGGCTTT    4080

GTGCCCTTGG TAATCCATGT AAGGGGCCTG AACTGCTGCA CAGCAGTTGG TTGTAAAGAA    4140

GTTTTTAGAC TGCCAAGCGA GACACTCCTC CTGCTGTTTG CTACCACTTG ATTAGAAAAT    4200

AGTTGTGTG GTGGTTGTTA AATAAAATTC AAGTCATGAT CAAAAGTAAG CATAAAGTCC     4260

AATATATAGT AACCTTAATA ATGGGGGAG GAGAGTGAGT ACTTGTCGAG TGTTCAAGAA      4320

GTCTCAGGTT CCGTCCACAG TCCCACATAC ACCAGGCACA GGGCACAGA CCTGTCATCT     4380

CATCTCAGTA CGCGGGCAAG AAAATCAGGA GTTCAAAGCC ATCCTTGGCT ACATAGCA      4440

TTTGAGGCCA GCGTAGACGT CATGACATTC TGTCTCAATA AACAAGCAA CAACAAGA       4500
```

```
ACTCCCCAAA CAACAACCTT CCCTCAAGTC CAAAGAAGAC TGAGACATGC GAGATGCA      4560

GTAAACTAAG GTCATCAGGA GTGTGAGGGG CTTAGAGAGG ATGGGTGGGG GGGACTAC      4620

TGTATGAAGC TGTCACAAAG ATGCACACTA GACAAGGGAA AATGTCTTTA AAATGCAG      4680

ATATAATCTT ATTTATTATT GTGTGTGAGT GTGGGTAGAC ACATGCCATG GCATGCAT      4740

CAACTTTGTG GAGTTGCTTC TCTTTTTCTA CCTTTCCATG GATTCTGAGT CTCCAATT      4800

GGTCACCACA CCTGTGGAGT TAATACCCTT ATCTGCTGGG CTGTCTCATC AGCGCCAA      4860

AACTTGTTTT TAATACTGCC TGTGAATGAG ATGAATGGCA CTACTGAAAA ACTGTAAA      4920

AATATAAATT ATGCTGATCC CTGCTTAGCC TCAAATGAAT GAGACCCAAA CTATAATT      4980

TTTATTGGGC TCTGCTCAAT TACCTCGGGA TGACCCAAA TCTATTCTCT AATGCTAG       5040

TGGCTACTTC CCCAACTGTG CTCCCCAAAT ACTTGCCGTC TGAATCTTCC TGGGTGAT      5100

CTGCTCTAGC AGCCTGGTGT CCCAGGAAGG CATTTCACTC AGGCAGTGCT GCTGGTCC      5160

CAGGACTAAT GGAGATCTCC TCTTTTCTAT GTCTTCTTCC CCATTCCCAC CCCACCCT      5220

TAATTGGTTG TTGCCAGTTT TACTAACTA ATAGTTTTAA ATTGGATAAG TTTGCACA       5280

AAAGGTGGGT TGTAACTAGG GATTTGCTTG TCTTGGCGCA ACCAGATCAT GGAGTACA      5340

ATTTAACATA TGGATACAAG TAGCACCAGA CCAACCCACA ATAAAAAACA GACAAAAA      5400

AAAAAAAAAA AAAAACCAG CAAAAAAAAC CCCCATAGAC AGTCTTTAAA TGATAAGA      5460

GGAAAAGTTG TAGGTGGTAA TAGATGGTTA GACAGGATAA TTTCAGGGAA GATTTAAG      5520

ATTTAAAAAA AATCTATTTA TATATGCATG CAATTGTGTG TGAGTGTGTG TGTGCGCA      5580

TGATTGTATG AGTATGTGAT GGCCAGTGCT CTTGGAGGTC AGGGTGTCAG ATCTGGTA      5640

TGGAGTCTCA ACTTGGGTAG AAACTTTTAA CCTCTGAGCC ATCTTTCTAG CCCCAAGA      5700

CTGGTTTTGT AAATAAATTT ACCTTTAAAT TCTCTTCCTG GGGGTATCT AGATCCAA       5760

TTGTACGTAA GCAGATATTT CAAATTAAAA TGATGCTGGT GTCACACAGC TGCCGATT      5820

TTACTGAGAT TTACGTTTGC TTCAACATTG TGCTGAACTA CATGCATAGC TTTTGTAA      5880

GGTTATTTGC TGAAACTAGC TTTCTGGTAT TTCACCAGTA ATATACTCTG GCACAGA       5940

AAACTTGTTT TCTGACTCAA TATAAATATA TTGCGTGTGT GTGTGTGTGT GTGTGTGT      6000

GTGTGTGTGT GTGTGTGTGC ATGTTATAAA ATCCTGTCTT CTGCTCATGA CATAGCTG      6060

TCATTAACTC ACAGCAGTTT GTATTTGCCT GCATGAGACC TATATAAGAT CAAGCCAG      6120

TGAATCCCAG CATGCAAAGG GGAGATGCTA TCTGGGACCC ACCCTTCATG GGAGATAC      6180

GAATTGGTGG CTCCTGGGGG AGGGAAGAGT AATTTTTCTT TGGGAGTGTG GCCATTGT      6240

TCTTGTCCAT GTTCCAGTGG ATAGCCCTAC ACTCATACAC AGAAGCAACA GTAACTGG      6300

TTAGTGGGTT ATAAAAAATA TTAGAAATGG AATTTGTATA CAACCGAGCC GTATCACT      6360

TGATCATATA CCCAAAGGAC TTTACCATAC AATAGAAGTA TTTGCTTAGC CATGTTTA      6420

GCTAATCTTT TCATAATAGT GAGTATGTGA ATAAGTGGAT GAGTGGATAG AGAGTCTG      6480

ACTAGGTAGG AGACCATGAA CGGGAACAGT AGGTGTTGAG AAGGGGCAGG AGCAGAAA      6540

AAAAGGTCAC ATTGGGCATT GTCTTAGTTA GGCTTACTAT CGTTGTGACA AAACACAA      6600

TAAAATCTCC AAAAGCAACT TGGGGAGGAA AAGATTAGAA TTTACGACTC TTGAGTTC      6660

ACTCCATCAC TGTGGGAAGT CAGAGCAGGA ACTCTAGGCA GGAACTGAAG GAGAGGCC      6720

GGAGGAACAC TGCTTACTGG CTTTCTCTTC ATGGCTTGCT CAGCCTGTTT TCTTAGAC      6780

CAAGAACAAC CTGCCCTGGG GTGACATCAC TTACTGTAGA CCAGGCCCTC CCACATTA      6840

CATGTGTCAA GAAAATGTCC CACATGCTTT CTTTAAGGCC AATCTTATAG AGCTGTGG      6900
```

```
AGCCACATGT GCCGTTGCAG AGTGGCACCG GCTACTGCTG GCTACCACGC ATAAGTTT      6960

ACAAACAACC AATGTGTACA TATGCAGTAA AGCTTTTTGC CAAGTCACTG CCTGGCCC      7020

GCATGTTAAT GAGGTACTGA GAATATAACC AATCAGATGT GAGACATGCA AATGAGGT      7080

GATAATGAGG TTCTGTGAGG TACTGAGAGA GAGTAGCCAA TCAGATGAGG AACATGCA      7140

TGAGGCATAG TGCATAACCA ATCCGTGTGT GAGACACGCC TCTCCTAGGC CTATATAA      7200

AGCACCAGTT CTGGGCTCAG GGTCTCTTTG CCTCTGCAAT CAAGCTCTCC CAGAAGGA      7260

CTGTTGCAGC GTCGTTCTTG CTGGTCAAGT CGGGCGAGCA CAAAATAGAG CCTTTTTT      7320

TTTTTAAATT GAGAGTCCCT CCTCCCAAAT GACTCCCGCT TGTGTCAGGT GGACAGTA      7380

CTAGCCAGGA CAGATGACCC CCTTGTCAAC TTGGCACACC AGTACTTATT ATGAAAAC      7440

AACCTTTCCC TTTTTGTTCA TTTTTAAGGT CTCATATTAA TATTATAATA TAAGCTAT      7500

ATAACTTTAA AAGTTTCATA TTCTTTAAAA ATTCAAAAAA TTTACAAGTT AAGTCTCT      7560

AAAATATCCA AAATTTCTCT AAAATTACCA AGTTTCTTTG AAATATCCAA GGCCTCAT      7620

ATGGATGTTT CTGTAAAATT AAAATAAATT ACTTTCTTAT TCCAAGAGAG AAGAAGCA      7680

GCACAGCCAC AGAAAATTCT GAGTGCACAT TAATAACTAA GTAAGATAAT GCCCCATA      7740

GTTGTCTTCT GTCGGCCTGT CTTACAGAGG CAATTTCTCA ATTATGCTTC CCTTTTCT      7800

GACAACACAT ACTTGTGTCA CATTGGCAAA AATCTAGCCA ACAAAGGCTT GAAAGCAG      7860

GGCTACTGGG GATGGCAGGG CTCAAGGACT GGGGACTTGG TGATTAGGGA GAAATAGG      7920

ATAGGAAGAG AAACCGCAAA AACAAAAATT TCTTGTAAAA ATGCTACAAT GAAACCTA      7980

CATCTGTATA TAATAAAAAG TGAATAGAAC AGATTGTACA TCTGTAATTT GCTATCAT      8040

TTTGACTTCT GTTAGTGGTT TTGAAATCTT GGCAAAAAGC AACTTAACCA TTAACAGT      8100

TAAATTGCTT TAGGGTTTAT AAAACCTGCA TTTTCACATG AGATTGTCTT ATTACATT      8160

AGTTGGGTGG ATCTGGGAAG AGTTACACTA TGTATGCAAT TCTCAAAGAA CCGAGGAA      8220

GAAGATAAAA TTTCTTTATA TTATTTAATA GTGCTGAGTG TAGTAGGCTG TTCCTCCA      8280

TTAAATGCGT GCTCTGATTT CTTCATGGTA ACAGAGGTTT CATCAGGAGA CTCTTCCA      8340

ACATATTTAA AACTTTACTC CCCACAAGAC ATTTGGGTAA CAGGAACTTT CCGGANGT      8400

GAGGAGTTTA TTACTTGGCT TTAGTATAAA TCATGTAGGA GCATGGATGC ATTTCATT      8460

TGAAAAAATA ATATATTTGG AGTCTCATAC TTGAAGTCTG GGTTATATTC CAGAGAGC      8520

TCAAAACTAG TAACAGCTTA AGAGAAAGAT CATCCAAGAA ACCCTTTCTT TTTAGGGA      8580

TGTCTCTTAC TCAGCCAAGA GCACAGTGAA AGGGCTTAGT ATTGGACAGC TATTATAT      8640

TCAAAACTAG GTCTTTATTT TATTTTACGA ATAAATCCAG TAGTTGCTCT GAGTCAGC      8700

ATACCTTATG AGAGATGATA ATTATACAGA AAATCAAAGA TGCTGAAAAT GTAATACC      8760

ACATACTGAG GGATCCTGTT CATTAAGGAG ATAAAAATTA TTCTTTTGAA GGAGCAAA      8820

TATACACATA ACATATTAGA ATTTGAAAC AGCCACAATC ATAGAACTTA ATTTGTTA      8880

AAAGGAAGAA GTAATGTATA GTTAATAAGT GGTTTAAGCC TTGTCCTTGA GGCTAGAT      8940

TATAACTCAT ACTAAATATG TATGTTTGTT TCAGGCTAGG TATCATATCC TACACGAA      9000

ATGTATGTAT GTTTCAGGTT AGATGCTATA TCCTACACTA ATTATATATG TTTGTTTC      9060

TTTCAGTCCT ATCTATGGAG CTGTCTCTGA GCTTTCTATC AAATATTTGT CATATTTA      9120

CATAGATATT GTTTATTGGA ATTTGCAAAC AGGGCATTTT AAAGACAAAT GAAAATAA      9180

TGGAAACCAC TTCACTACAG CGGAAATTTC CAGAATGGAT GTCTATGCAG AGTCAAAG      9240

GTGCTACAGA AGAAAAGGTA ATTGTTCATT GATTATTTGT CTAAATGGGC AATCTTGT      9300
```

```
GAGTTTGACT ATGCAGTGAG TCACATCATT GCTTGTGAGC TTTGGGTCAT TGTTGAGG      9360

AAACTTTCTG TTGTGTGAAT GAACCAGAAC TAAGTTGTTC AAAGGTAAAT GAGACTCA      9420

TTTATACATG TTTTATAAAA TGAGATTCCC TAGAGTATAT TCTTTCTTTT TATAGTTA      9480

ATTCTTAGTT GAAGTTATTG GTTTGTTCAA ATTCAAGTAA TAATTTATAC AATATTAA      9540

TTGGCATTTT TTGGTTAAAA TAGTTTGAGT CCTTAGAGGC TTAAGATCTG ATAATTAG      9600

ACCAACATTT TTTTGTTTTC TTTTTCAATA TTTTATTAGA TATTTTCTTC ATTTACGT      9660

CAAATGCTAT CCCGAAAGTC CCTTATACTC CCTCACTCCA CCCACTCCCC TACCCACC      9720

CTCCCACTTC TTGGCCCTGG CGTTTCCCTG TACTGGGCA TATAAAGTTT GCAAGACC       9780

GGGGCCTCTC TTCCCAATGA TGGCTGACTA GGACATCTTC TGCTACATAT GCATCTAG      9840

ACATGAGCTC TGGGGGGTAC TGGTTAGTTC ATATTGTTGT TCTACCTATA GGGTTGCA     9900

TCCCCCCAGC TCCTTGGGTA CTTTCTCTAG CTCCTCCATT GGGGGCCCTG TGATCCAT     9960

TATAGATGAC TGTGAGCATC CACGTCTGTG TTTGCCAGGC ACTGGCATAG CCTCACA     10020

GACAGCTATA TCAGGGTCCT TTCAGCAAAA TCTTGCTGGC ATGTGCAATA GTGTCTG     10080

TTGGTAGCCA CCAACATTTT AAGGTTACAT TATTGCATCT AGCATGCTAA TATAATT     10140

AGGAAAAAAC AAGTAAATTA AGTGACTTCA CAAAAGAAAG ATTGGATGTT TGAAAAT     10200

ATTGTGTGGA AAAATAACTT TATGTTTACC CTTGTTAATC TGACCTTATG AATTCTT     10260

CTATAATATA AAATGTAGTG CTATAAATTT CTTCAGTGAA CTTTATTATT TCAGTTA     10320

CTACAACTTA CTGTGATATT TATTTGTGCC TGTTTTGAAT TTTGCTCAAC TCAAGGC     10380

CGTTCAGAAG AGTGTTCTTG AAGATAATCT CCCATTCTTA GAATTCCCTG GATCCAT     10440

TTACAGTTAT GAAGCTAGTG ATTGCTCCTT CCTGTCTGAA GACATTAGGT AAGGGAT     10500

AAGTTCTTAC CATTAAGTTT GTACCCGTAA GAAATAGCGA TATTTATGAG TGCCTAG     10560

TACAATGGAA GTATATCTCA GAAGTATATT TACATACATC ATATCACAGT TGTATTC     10620

TTTTTAAAAT ATAAAATAAA CTCACTAAAT TAAATTAGTA AGGTTCCTAT TTGTTAA      10680

GTAACCTTTT CTACTTTATT AGATACTTTT TTTTTCTTTT AGTGCTTTAG ATGTAAA     10740

AGGTAAAACT ATTGAAGACA ACTGTTTACC AATTTAGGAA AAAATGGAAA ATGTTAT     10800

ATGTCGAACT ATTTTCATAT CTTAAAACAT CAATGTATTA AGTAATGTTT ATGATTC     10860

GTTTTATTTT TTTTAATTTA TTTTTTAGCTT TTAAAATTGT GTTAGGATGC CTCCTCT     10920

TGTATGTTTG TATACCACAT GGTTACGGTG TCCACAGAGG CCAGGAGAGG GCTTTGG     10980

CCCTTGAACT GGAGTTGTGA GCGATCTTAT GGGTGCCGGG AATCAAGCCT AGGTTCT     11040

GAAGAGCAGC CAGTGCATTC AGCTGCTGAA CCATTTTAAA AGATAGTGAT AGTTCCT     11100

AATGGTCCAT GAAAAGAGCT TTAGCAATGA CTGTTGGTAC TTTAAGAGTT GCCTGTC     11160

GTTTTTCTAA GGCTATAACA AAATCCATGG CCTGAGTAAA TTATAAAAAA ATACATA     11220

GTAAATTCAT AAATAAATTT ATTCCTTACA GTTTTGGAGG CTATAGAGCC CCCAGAG     11280

GGGATTGGCA TTTGTAAGGG GACCATTTTT TTTTTTAAAT TGGATATTTT CTTTATT     11340

ATTTCAAATG TTATCATCTT TTCTGGTTTC CTTCCCTCCT GGAAACCCCC TATCACA     11400

TCCGTCTCTC TGCTTCTGTA AGAGTGTTCC TCTACCCACC CACCCACCCA CCCACCC     11460

CCCACCTTCC TGCCCTTGAT TCACCTACAC TGATGCATCT ATTGAGCCTT CATAGGA     11520

CGGACATCTC CTCCCACTGA TGAATGACAA GGCCATCCTC TGCAACATAT GCAGCTG     11580

CTATGTGTAC TCCTTGGTTG ATGGCTTAGT CCCTAGTTTT CTGGGGGTGG GGGAGGT     11640

ATCTGGTTGG TTTATGTTGT TGTTCTTCCT ATGGGATTTC AAACCCTTTC AACTCTT     11700
```

| | |
|---|---|
| GTCCCTTCTC TAACTCCTCT ATTAAGGACC CTGCGCTCAG TCCAATGGTT GGCTGTT | 11760 |
| ATCCACCTCT GTATTTGTAA GGCTCTGGCA GGGCCTCTCA GGAGCAGGCT CCTTTCA | 11820 |
| TGCACTTCTT GGCATCCACA ATAGTGTCTG GGTTTGGTAA CTGTATATGG AATGAAT | 11880 |
| CAGGTGAGAC AGTTTCTGGG TGGTCTTTCC TTCAGTCTCT GCTCTTCACT TTATCTC | 11940 |
| ATTTGCTCCT GTGAGTATTT TGTTCTCCTT CTAAGAAGGA CCGAAGCACC CCCACTT | 12000 |
| TCTTCTTTCT TATTGACCTT CATGTAGTCT GTGAATTGTA TCCTGGTCAT TTGGAGC | 12060 |
| TGGGCTAATA TCCACTTATC AATGAGTGTA TAATATTTGT GTTCTTCTGC GATTGGG | 12120 |
| CCTCACTCAG GATGATATTT TCTGTCCATT TGCCTAAGAA TTTCATGAAT TCATCAT | 12180 |
| TAATAGCTGA GTAGTAAGTA CTCCATTGTG TAAATGTACC ACATTTCTG TATCTAT | 12240 |
| TCTTTTGAAG GACATCTGGC TTCCTTCCAG CTCCTGGCTA TTATAAATAA ATATATA | 12300 |
| ATAGTGGAGC ATGTGTTCTT ATTACATATT GGAACAGAAA GAGCAATTTG CAAATTC | 12360 |
| TGGAATAACA AAAAAAAAAA AAAAAAAAAC CCAGGATAGC GAAAACTATT CTCAACA | 12420 |
| GAAGAACTTC TGGGGGAATC ACCATCCTGA CCTCAAGTTG TATTACAGAG CAATAGT | 12480 |
| AAAGACTGCT TGGTAATGGT TCAGAGACAG GCAGGAAGAT CAATGGAATA GAATTGA | 12540 |
| CCCAGAAATG AACCCACACT CATATGGTCA CTTAATCTTT GACAAAGGAG CTAAAAC | 12600 |
| CCAGTGGAAA AATGACAGCA TTTTTAACAA ATGGTGTTAG TTTAACTGGT AGTCAGC | 12660 |
| TAGAAGAATG CAAATCGACC CATTTTTTTC TTTTCTTTTC TTTATTTACA TTTCAAA | 12720 |
| TATTCCCTTT CCTGGTTTCC CCTCTAACCC CCCCCCCCCC CCACACACAC ACACACA | 12780 |
| ACCAACCCAC TGGCTTCCTC TTCCTGGCCC TGGCATTCCT CTATACTGGG GCATAGA | 12840 |
| TTCAAAAGAC CAAGGGCCTC TCCTCCCATT GATGACCAAC TAGGCCATCC TCAGCTA | 12900 |
| ATGTAGCTGA AGCCATGAGT GTGCTCTTTG GTTAGTGGTT TAGTCTCTGA GAGCTCT | 12960 |
| GGTACTGGTT AGTTCATATT GTTGTTCCTC CAATGGGGCT GCAAACCTCT GCTACTC | 13020 |
| GGTTACTTTC TCTAACTCCT TCACTGGGGA TCCTGTGCTC AGTCCAATGG ATGGCTG | 13080 |
| GCATCCATTT CTGTATTTGA AGTTGACCCA TTCTTACCTC CTTGTACAAA GCTCAAG | 13140 |
| AAGTGGATCA AGGACCTTCA CATAAAACCA GATACACTGA AACTTATAGA GAAGAAA | 13200 |
| GGGAAGAGCC CCAAACATAT GGGCACAGGG GAAAAATTCC TGAACAGAAC ACCAATG | 13260 |
| TATGCTGTAA GATAAAGAAT CAACAAATGG GACCTCATAA AATTGCAAAG CTTCTGT | 13320 |
| GCAAAGCACA TTGTCAATAA GAAAAAAAGG CCACCAACAG ATTGGGAAAA GATCTTT | 13380 |
| AATCCTACAT CTGATAGAGG GCTAATATCC AATATATTCA AAGAACTCAA GAAGTTA | 13440 |
| TTCAGAGAAC CAAATAACCC TATTAAAAAT GGGGTTCAGA GCTGTCTTAG TCAGGGT | 13500 |
| TATTCCTGCA CAAACATCAT GACCAAGAAG CAAGTTGGGG AGGAAAGGGT TTATTCG | 13560 |
| TACATTTCCA TATTGCTGTT GATCACCAAA GGATGCAGGA CTGGAACTCA AGCAGGT | 13620 |
| AAAGCAGGAG CTGATGCAGA GACCATGGAG GGATGTTCTT TACTGGCTTG CTTCCCC | 13680 |
| CTTGCTCAGC CTGCTCTCTT ATAGAACCCA AGACTACCAG CCCAGAGATG GTTCCAC | 13740 |
| CAAGGGGCCT TTCCCCCTTT ATCACTAATT GAGAAAATGC CTTAGAGTTG GATCTCA | 13800 |
| AGGCATTTCC TCAACTGAAG CTCCTTTCTC TGTGATAACC CCAGCTGTGT CAAGTTG | 13860 |
| CAAAACCAGC CAGTACAAGA GCTAAACAAA GAATTTTCAA CTGAGGAATA CTGAATG | 13920 |
| GAGAAGCACC TAAAGAAATG TTCAACATCC TTAATGATCA GGGAAATGCA AATCAAA | 13980 |
| ACCATGAGAT TCCACCTCAC ACCAGTCAGA ATGGCTAAGA TCAAAACTC AGGTGAC | 14040 |
| AGATGCTGGC AAGGATGTGG AGAAAGAGGA ACACTCCTCC ATTGCTGGTG GGATTGC | 14100 |

| | |
|---|---|
| CTTGTACAAC CACTCTGGAA ATCAGTCTGG CGGTTCCTCA GAAAACTGAA CATAGTA | 14160 |
| ACTACCTGAG GACCCAGCTA TACCACTCCT GGGCATATAT CCAGAAGATG CTGCAAC | 14220 |
| TAAGGGAACT TTGTACTGCG TCTGTATCAG GGTAGAGGCT AAGATGGGTT GGGATTA | 14280 |
| CAGTTCTCTG GATACCTGTT CTGGGAGTGG AGCCCTGATG AGCCAAACAC TTGTGTT | 14340 |
| GCCCCACCTC CACGCCCTGC TCCATTAAGG ATTCCATTTT AACAGGGACT ATGAATA | 14400 |
| TATTCATGAC CCAGCACCTT GTGTAATTCG GGTTCTGGAG TAATGCAATC TAAGCCT | 14460 |
| GATGCAACTT ACACTGAGAA GTAGTAAATC AATTCAGATC ATTGAAATGA CTGCGTG | 14520 |
| CCTTTTGGTT TTTAACTATT TTCATGAAAA GCAGAAGTGA ATAAAGTTGT TCATCAG | 14580 |
| CCTCCTGGTG GTTGGTAAAT GTGATCTAGA AGTGGCATTT AGGTATCTTT ACTTCCA | 14640 |
| CATTTACTGG TTATGTGTGG GCTTCATTTT GCTGAACTAA AATTAGACTT ACAGAAT | 14700 |
| TAAATCTATT ACACACGGTT ATATATTGTC CTCACCATGT TACCTTTGTC TTCCTAC | 14760 |
| ATGACATGTG TTTTATTAGT CAGAGGGTTT TTTTTTTTTG GTTTGTTTGT TTATCTT | 14820 |
| TTTTTAAAGG AATAGAACTG GCAGAATGAA CGTATATATA TATCAAACAG GGATTTA | 14880 |
| GTGTGGCTTT GCAGACTGAG GTCTCTTGTC CAACAATGGC TGTGCCTCAT CAAAGCC | 14940 |
| AATCCTTTTT TCTCGTAGTT GTTCATTCGA GGAGCCTGGG TGTCTAAGTC AGTCTTC | 15000 |
| CTGCATGGGC TTCCTGAAGA AGGAATTTCT AACACCAGCT AAGTAGTGCC TTAGTAG | 15060 |
| GACAGACGAA CTTGCCAGCC AGACTGAGGA CAGGCTGACA AAAAGCCAAA GCTTCCC | 15120 |
| TCCGTGCCCC TTCAGAAGTG GGCCGCCATC AGAAAGCGTA ACCTAGATTT AGGATGC | 15180 |
| TCTCCTGTCA CATAATCTAA TCAAGAAAAG CCCTCATAGG TGAGCCCAGG GCTTATA | 15240 |
| TAGATGATTC CAAATGGAGT CAGGTTGCCA GCCAAGATCA GCTCAGCACA GTAAGTT | 15300 |
| GTGGTCTGAA TGAAGCTCTG TGTTCATTTT GAAGTGCAAG ACGGGCTTGG TTTGCTT | 15360 |
| ATTACTTTTC ATATGGCCAC TTTGGAGATC CTCGCATCAG GGGCTGGAAA CATGGCC | 15420 |
| CATTAAGAGC AGGAAGCGCT ATTGCAGAGG ACCCCAGTCT GGTTCCCAGT ACCCATA | 15480 |
| GTGGCTCACA GACCTCTGTT TTCTATGACT CCAGCTCCAG GGTGCTGAGT CCCTCTT | 15540 |
| CCCTCTACAG GCACCTGTGC TTATGTGCAC ATATGTACCC CTCTTCCCAT ACACACC | 15600 |
| TTAGAAAAAT AAAAATCTTA AGAATATTT TTACACCAGG GCCAGTGACA TGGCTCA | 15660 |
| GGTAACAGGG CCTGCCACCA AGACTGGAGA TCTGAGTTCT AATCCCATTT CAACCTC | 15720 |
| GGCTCATGGT GGAAGCCAAG AGCTGATCCT GAATTCAACA TGCATGGGGC CACCAAA | 15780 |
| GAAAGAAAGA AAGAAAGCAA TTTAAAAAGA TGTTTACCCC ATGGGGTTTC AACAGTT | 15840 |
| TATGACATAC CTTTGTGTGC TGAAGTTTGT GCTGATCCTG CTTGGGGACC ATCGACC | 15900 |
| TTTTTTTTTT TTTTTAAATT TGTGGGTTTA ATAGTTTTTG TCCAATTTGA AAATCAT | 15960 |
| CAGTTTTAT TTTTTTCAGT ACTGTGCTTT TCTGGGACTC TGATATACAT ACACTAG | 16020 |
| GCTGGATACT ATGTCTTAAC TTCTTTTCTC TTTTTGTTTA TGCTTTGGTT TGAATGT | 16080 |
| TTCTGCTGTG TCTTTAAGTT AATCACCTAT ATTTCTTCTG TAGTGGCTGA TCTACTG | 16140 |
| ATCCTCCCTG TGTATTTTTA ATTTTCATTG TGTTTTTCTC TTTTTTGTTA TTGAAAA | 16200 |
| TTTTTTTAAA AATACAACAC ATTTGGACTG TGGTTTCCCT TTCCACAACT CACCCCA | 16260 |
| CCTCTCCACC TCAACAGAAA AAGAAAGGGC CAGAGAAGAA GCACAGGAAA CACATAC | 16320 |
| TGCAGGCCAC ACACGTGTAC ACACAGGAAT CTCATAAGTA CACAAAATCA GAAACCA | 16380 |
| ATATAAAAAT TATATAAGCA AAAGACTTGC TAGATTAACA AAATAAAGGT TCATTCT | 16440 |
| TTGGCCATTT ACTGCTGGGC CTAGGGCCTG CTGGTGAGTG TGGTTTGTAT ACCCAGT | 16500 |

```
TCTGGTGGAG AAACTAGTTT TTCCTTTGTG AGTGGTTATA AATAGGAGAT AATTTCT      16560

TGAGGGATAG GATCGGCGCT GGGACTTTAT CTGGTTAGAC CTGGGTAGAC CCTGTGT      16620

CTCCCACATG AAAGCTCTTC TGTGCTTTAT CAGCCCTGCT GTGTCTTGAA GGGCTTC      16680

CCTTGGTGTC TTCCATCCCA CTGGGTCTTA CAACCTCTCT GCCCCCTCTT TTGCAAA      16740

CCCTGAGCCA TGCGGGGAGG GGTCTGTCAT TGTTCCCATC TCCTGCAGGA GGCAGTG      16800

CTGACATTGG CTGGGCAAGA CACTGAGCCA TGAGCATAAA AAACCCTGC CAATTTG       16860

TTCATTGTGT GCATGCTTTC CTTTAAATTC CTGAACATAT TTACAATTTA TAATAGT      16920

CGTTTGTCTT GTTTTGAGCA GGGGCTTATG TAGCCTAGGC TGGCCTTGAA TGTACTC      16980

CGCCAAGGCT GATCTTAGTT CCTGATCCTA TTGCCTATGC CACCAAGTGC TGGGATC      17040

GACTTGTGCC AGCAGGCCCT GCTGTGACCA TAATGCAAAT TTCAGTGATA TTTTAGC      17100

ATTTTTGCCT CTATTGAGTG ATCACCCCGC CAACTGATTA TGTTTATGTT TGATATG      17160

CAGGGCTGTT GAGGTTTTTT TTCTTTTTCT TTTTTTTTT TTTTTTTTGG TCTGCTG       17220

TGATTTTACC TTGCTCAATA TATATATATA TATATATATA TATATATATT TTTTTTT     17280

TAGTTTGCTT TCTAAGAAAA GAGGTTTTGC CAGAGGGCTC ACCCAGAGAT GGGTTTT      17340

TTCGGAGGCT TGCTTTTAGA CCTCATTAGG CCGGCAATTG CTTTTCCTCC AAAGGTA      17400

TAGTTCTCTC AGGTGCGATC ATAAGGGAGG CTGCTGCATG TTCCTAGAGT TCAGCAA      17460

TGTCTGCTGG GACTTGGGAA CTTACGCTCT TACCTCTGTC TGTGTCCCCA CCTCAGG      17520

GTCCTTTCTC TGTTGTCTGT AAGGCATTCT AGGAGAACCA GGGACAACGA CAGAGAC      17580

CCTCTTGTTC AGAGAACAGT AAATTTAGAC GTGTTTGTAC AATTTATTGT TTCTTTT      17640

TGGAAAAAGA AGTACTTGTA AATTTATCT TAGCCTGAGG TATTAGTTGA TATTCTT       17700

TGTTTGTAAT AAATTTTTAA TCAAAACTTG TGAACTAGGC ATAGAAACAA TAGTAAA      17760

AACCGTATCT TCTTATTTAA TTATATCAAA TCTTTATTAT TTAGTGTGTA TGTGTGT      17820

CTCATGTATG TAGATATATA CTTGGTCAGA GGACAACTTT CAGGAGTAGT TTTCTTC      17880

TATTTATGTC TAAAATTAAA TAGAAAATAA AAGCTCATGT ATACCCTTTT TAATTTA      17940

TCTTCCAACC CCCGTGCTAC TTTAAATAAC ATGTCATGAA TTTAGTATTT ATCATTT      18000

TATATTGTGT TATTTGCCAA CTTAGAAACT ATATGGTTTT CCTGAAGCTT GTCTTTT      18060

CTCAAGTTTT GAGAATTTTT CATTTTGATA TATGTAGTTC CATTATTTTA TATGCTA      18120

TATGTTTTGG CATGCCACAA TTTCTTTATT TTTTTGTTTT ATGGAAACAT AGTTTTT      18180

ATTCCCCCGT CTGCAAAAGG ATCAGGGTTG TAGTGAACAT TCTTTCTTTG CTGTGTT      18240

TAGTGTTTCT TGTCCATTTG GCACAGCCTA GAGTCGTCTG AGGCTAAGGA ACCCAAC      18300

GAGAATGCCC CATCAGATTG GTGTATAGGC AAGCGTGGGA ATAGGGTTTT CTTGACT      18360

GATTGATGTG GGAGGGACCA GCTCACCTTG GGCAATGTCA TCCCTTGGGA GTTGGTC      18420

CCTTGTATAA GAAAGCAAAC CTAGCAAGCC AGTTAGCAGT GTTTCTCCAT GGCCTCT      18480

TCCGCTCCTG CTTCTAGGGA CCTGCCTTGA GTTCCTGCCC TGACTTCCTT TTCTTCC      18540

ATTGCTTTTG GACATGGTGA TGATCACAGC AATAGATGGC AAACTAAGAC ATTAATC      18600

TGAGCTGTCT CACCTTTTAG AGTGGTTTGA ATAAGCATGG CCCTCAAAGG CTCATAT      18660

GAATGGCTAA TCACCGAGGA GTGGAACTCT TTGATAGGAT TGGAACAGTG GTTCTCA      18720

TGAGAGTCTT GATGTCTTTG GACATTAAGC GACCCTTTCA CAGATATCCT GAATATC      18780

TATTTACATC GTGATTCATA GCAGTAACAA AATTACAGTT ATGAAGTACC AATGAAA      18840

TTTTATGGTT GGCGTCATTA GGAAGGTTGA CAACCACTGG ATTAGAAGAA TTAGGAC      18900
```

```
TGACCTTGTT GGGGGAAGTG TGTCACTTGG GGTGGGCTTT GAGGCTTCAA AAGCCTA      18960

TTTGAACAGA CCTTTTGCAC AAGAACAGGC CTCTTGTTCT CTCTACTGCT GCTCAGG      19020

TAGCTCTCAG CTGCTGCCGC AGTGCCGTGC TTTACACCAT GATAATGGAC TAAGCCT      19080

AGCTGTAAGC CAGCCACCAA TTACATGCTT TCTTTTATGA GAGTTGCCAT GGTCATG      19140

TCTCTGCAGC AGTACAACAG TGACTAAGAC AGAAGGAAAC ATAGAAACAT TCACGCA      19200

AATCCACACA ATTTTTCCTT TGATAGCATG CGTCTGTCTG ATGGCGATGT GGTGGGA      19260

GACATGGAAT GGCCGCCCAT ATACAAGCCA GGGAAACGAA GCAGAGTCGC AGTGATC      19320

TTGTGTGTGT CTGAGAACAA ATGTTACTTG TTTCACATTT CTTCCATGTC AGGTTGG      19380

CTCTGCTTCA TTGTCATATG GCCATCAATA ATACCATATC AACTTTCTTC CTGCAAA      19440

AAGTTCTTTC ATTAGCAGGC CTTCTTTCAT GATCTTGTAT TTGTTTAAGT ATTTATA      19500

TTACTTGATT TTTATACCTT TTCCCTTGGT TAGAGAATAG AGAACTGAAG TTTAGAG      19560

TAAATGACTA GGAATAATAC CCTATTACTG TTACTACAGG TGGCGTTCGA ACTCATT      19620

TCTAGTCAAA TTTCAGTCTG GACTCTGCAT TAGCTAAGAA AAGAGATAGT TAAGGTG      19680

GTGATTCTAA ATTTAAGCTT AATATAAACA GTTTACCACA CATTCCGTGT GCATTAA      19740

AGTAAATCCA TTATATTAAA GAGTTTTATG GAAATAATAA TGAAATGTTT TAGTTTT      19800

CCAGGGATTA AAAATGTTAC TAGAAAACAA ATCAATTAAG AAGGCAGGGG TTGGGAT      19860

AGGGGACCAG TGGAAACTTC TGCGTGATTT TGACGTCAAG TTGGAGAGTT TTGTGGA      19920

GACGGATGTT GCCAATGAAA AGGTAGGCGT AATAAATGCA GTATTTAAT AAACATG      19980

ACCTGAGTTT CATAGAATGT GCATTTTCAT CTAAATGTTA AGTTTCTTTT TTTTTCC      20040

TTTTATTAGG TATTTAGCTC ATTTACATTT CCAATGCTAT ACCAAAAGTC CCCCATA      20100

ACCCACCCCC ACTCCCCTGC CCACCCACTC CCCCTTTTTG GCCCTGGCGT TACCCTG      20160

TGGGGCATAT AAAGTTTGCA AGTCCAATGG GCCTCTCTTT CCAGTGATGG CCGACTA      20220

CATCTTTTGA TATATATGCA GCTAGAGTCA AGAGCTCCGG GGTACTGGTT AGTTCAT      20280

GTTGTTCCAC CTATAGGGTT GCAGATCCCT TTAGCTCCTT GGCTACTTTC TCTAGCT      20340

CCATTGGGAG CCCTATGATC CATCCATTAG CTGACTGTGA GCATCCACTT CTGTGTT      20400

TAGGCCCCGG CATAGTCTCA CAAGAGACAG CTACATCTGG GTCCTTTCAA TAAAATC      20460

CTAGTGTATG CAATGGTGTC AGCGTTTGGA TGCTGATTAT GGGGTGGATC CCTGGAT      20520

GCAGTCTCTA CATGGTCCAT CCTTTCATCT CAGCTCCAAA CTTTGTCTCT GTAACTC      20580

CCATGGGTGT TTTGTTCCCA AATCTAAGGA AGGGCATAGT GTTCACACTT CAGTCTT      20640

TCTTCTTGAG TTTCATGTGT TTAGCAAATT ATATCTTATA TCTGGGTAT CCTAGGT      20700

GGGCTAATAT CCACTTATCA GTGAGTACAT ATTGTGTGAG TTTCTTTGTG AATGTGT      20760

CTCACTCAGG ATGATGCCCT CCAGGTCCAT CCATTTGGCT AGGAATTTCA TAAATTC      20820

CTTTTTAATA GCTGAGTAGT ACTCCATTGT GTAGATGTAC CACATTTTCT GTATCCA      20880

CTCTGTTGAG GGGCATCTAG GTTCTTTCCA GCTTCTGGCT ATTATAAATA AGGCTGC      20940

GAACATAGTG GAGCATGTGT CCTTCTTACC AGTTGGGGCA TCTTCTGGAT ATATGCC      21000

GAGAGGTATT GCTGGATCCT CCGGTAGTAA ATATGTCCAA TTTTCTGAGG AACCGCC      21060

CTGATTTCCA GAGTGGTTGT ACAAGCCTGC AATCCCACCA ACAATGGAGG AGTGTTC      21120

TTTCTCCACA TCCACGCCAG CATCTGCTGT CACCTGAATT TTTGATCTTA GCCATTC      21180

CTGGTGTGAG GTGGAATCTC AGGGTTGTTT TGATTTGCAT TTCCCTGATG ATTAAGG      21240

TTGAACATTT TTTCAGGTGT TTCTCTGCCA TTCGGTATTC CTCAGGTGAG AATTCTT      21300
```

```
TCAGTTCTGA GCCCCATTTT TTAATGGGGT TATTTGATTT TCTGAAGTCC ACCTTCT      21360

GTTCTTTATA TATGTTGGAT ATTAGTCCCC TATCTGATTT AGGATAGGTA AAGATCC      21420

CCCAATCTGT TGGTGGTCTT TTTGTCTTAT TGACGGTGTC TTTTGCCTTG CAGAAAC      21480

GGAGTTTCAT TAGGTCCCAT TTGTCAATTC TCGATCTTAC AGCACAAGCC ATTGCTG      21540

TGTTCAGGAA TTTTTCCCCT GTGCCCATAT CTTCAAGGCT TTTCCCCACT TTCTCCT      21600

TAAGTTTCAG TGTCTCTGGT TTTATGTGAA GATCCTTGAT CCACTTAGAT TTGACCT      21660

TACAAGGAGA TAAGTATGGA TCGATTCGCA TTCTTCTACA CGATAACAAC CAGTTGT      21720

AGCACCAATT GTTGAAAATG CTGTCTTTCT TCCACTGGAT GGTTTTAGCT CCCTTGT      21780

AGATCAAGTG ACCATAGGTG TGTGGGTTCA TTTCTGGGTC TTCAATTCTA TTCCATT      21840

CTACTTGTCT GTCTCTATAC CAGTACCATG CAGTTTTTAT CACAATTGCT CTGTAGT      21900

GCTTTAGGTC TGGCATGGTG ATTCCGCCAG AAGTTCTTTT ATCCTTGAGA AGACTTT      21960

CTATCCTAGG TTTTTTGTTA TTCCAGACAA ATTTGCAAAT TGCTCCTTCC AATTCGT      22020

AGAATTGAGT TGGAATTTTG ATGGGGATTG CATTGAATCT GTAGATTGCT TTTGGCA      22080

TAGCCATTTT TACAATGTTA ATCCTGCCAA TCCATGAGCA TGGGAGATCT TTCCATC      22140

TGAGATCTTC CTTAATTTCT TTCTTCAGAG ATTTGAAGTT TTTATCATAC AGATCTT      22200

CTTCCTTAGT TAGAGTCACG CCAAGATATT TTATATTATT TGTGACTATT GAGAAGG      22260

TTGTTTCCCT AATTTCTTTC TCAGCCTGTT TATTCTTTGT ATAGAGAAAG GCCATTG      22320

TGTTTGAGTT TATTTTATAT CCAGCTACTT CACCGAAGCT GTTTATCAGG TTTAGGA      22380

CTCTGGTAGA ATTTTTAGGG TCACTTATAT ATACTATCAT ATCATCTGCA AAAAGTG      22440

TTTTGACTTC CTCTTTTCCA ATTTGTATCC CCTTGATCTC CTTTTCTTGT CGAATTG      22500

TGGCTAATAC TTCAAGTACT ATGTTGAAAA GGTAGGGAGA AAGTGGGCAG CCTTGTC      22560

TCCCTGATTT TAGTGGGATT GCTTCCAGCT TCTCTCCATT TACTTTGATG TTGGCTA      22620

GTTTGCTGTA GATTGCTTTT ATCATGTTTA GGTATGGGCC TTGAATTCCT GATCTTT      22680

ACACTTTTAT CATGAATGGG TGTTGGATCT TGTCAAATGC TTTTTCTGCA TCTAACG      22740

TGATCATGTG GTTTTTGTCT TTGAGTTTGT TTATATAATG GATTACATTG ATGGATT      22800

GTATATTAAA CCATCCCTGC ATCCCTGGAA TAAAACCTAC TTGGTCAGGA TGGATGA      22860

CTTTAATGTG TTCTTGGATT CGGTTAGCGA GAATTTTATT GAGGATTTTT GCATCGA      22920

TCATAAGAGA AATTGGTCTG AAGTTCTCTA TCTTTGTTGG GTCTTTCTGT GGTTTAG      22980

TCAGAGTAAT AGTGGCTTCA TAAAATGAGT TGGGTAGAGT ACCTTCTACT TCTATTT      23040

GAAATAGTTT GTGCAGAAGT GGAATTAGAT CTTCTTTGAA GGTCTGATAG AACTCTG      23100

TAAACCCATC TGGTCCTGGG CTTTTTTTGG TTGGGAGACT ATTAATAACT GCTTCTA      23160

CTTTAGGTGA TATGGGACTG TTTAGATAGT CAACTTGATC CTGATTCAAC TTTGGTA      23220

GGTATCTTTC CAGAAATTTG TCCATTTCGT CCAGGTTTAC CAGTTTTGTT GAGTATA      23280

TTTTGTAGAA GGATCTGATG GTGTTTTGGA TTTCTTCAGG ATCTGTTGTT ATGTCTC      23340

TTTCATTTCT GATTTGTTA ATTAGGATTT TGTCCCTGTG CCCTCTAGTG AGTCTAG      23400

AGGGTTTATC TATCTTGTTG ATTTTCTCAA AGAACCAGCT CCTCGTTTGG TTAATTC      23460

GAATAGTTCT TCTTGTTTCC ACTTGGTTGA TTTCACCCCT GAGTTTGATT ATTTCCT      23520

GTCTACTCCT CTTGGGTGAA TTTGCTTCCT TTTTTTCTAG AGCTTTTAGA TGTGTTG      23580

AGCTGCTAGT ATGTGCTCTC TCCCGTTTCT TCTTGGAGGC ACTCAGAGAT ATGAGTT      23640

CTCTTAGAAA TGCTTTCATT GTGTCCCATA GATTTGGGTA CGTTGTGGCT TCATTTT      23700
```

```
TAAACTCTAA AAAGTCTTTA ATTTCTTTCT TTATTCCTTC CTTGACCAAG GTATCAT        23760

GAAGAGTGTT ATTCAGTTTC CACGTGAATG TTGGCTTTCC ATTATTTATG TTGTTAT        23820

AGATCAGCCT TAGGCCATGG TGGTCTGATA GGATACATGG GACAATTTCA ATATTTT        23880

ATCTATTGAG GCCTGTTTTG TGACCAATTA TATGGTCAAT TTTGGAGAAG GTCCCGT        23940

GTGCTGAGAA GAAGGTATAT CCTTTTGTTT TAGGATAAAA TGTTCTGTAG ATATCTG        24000

GGTCCATTTG TTTCATAACT TCTGTTAGTT TCACTGTGTC CCTGTTTAGT TTCTGTT        24060

ACGATCTGTC CTTTGAAGAA AGTGGTGTGT TGAAGTCTCC CACTATTATT GTGTGAG        24120

CAATGTATGC TTTGAGCTTT ACTAAAGTGT CTCTAATGAA TGTGGCTGCC CTTGCAT        24180

GTGCGTAGAT ATTCAGAATT GAGTGTTCCT CTTGGAGGAT TTTACCTTTG ATGAGTA        24240

AGTGTCCCTC CTTGTCTTTT TTGATAACTT TGGGTTGGAA GTCGATTTTA TCCGATA        24300

AAATGGCTAC TCCAGCTTGT TTCTTCAGTC CATTTGCTTG GAAAATTGTT TTCCAGC        24360

TTACTCTGAG GTAGTGTCTG TCTTTTTCCC TGAGATGGGT TTCCTGTAAG CAGCAGA        24420

TTGGGTCCTG TTTGTGTAGC CAGTCTGTTA GTCTATGTCT TTTTATTGGG GAATTGA        24480

CATTGATATT AAGAGATATT AAGGAAAAGT AATTGTTGCT TCCTTTTATT TTTGTTG        24540

GAGTTGGCAT TCTGTTCTTG TGGCTTTCTT CTTTTTGGTT TGTTGAATGA TTACTTT        24600

GGTTGTTCTA GGGCGTGATT TCCGTTCTTG TATTGCTTCT TTTCTGTTAT TATCCTT        24660

AGGGCTGGAT TCGTGGAAAG ATATTGTGTG AATTTGTTTT TGTCGTGGAA TACTTTG        24720

TCTCCATCTA TGGTAATTGA GAGTTTGGCC TGGTATAGTA GCCTGGGCTG GCATTTG        24780

TCTCTTAGTT TCTGTATAAC ATCTGTCCAG GCTCTTCTGG CTTTCATAGT CTCTGGT        24840

AAGTCTGGTG TAATTCTGAT AGGCCTTCCT TTATATGTTA CTTGACCTTT CTCCCTT        24900

GCTTTTAATA TTCTATCTTT ATTTAGTGCA TTTGTTGTTC TGATTATTAT GTGTCGG        24960

GAATTTCTTT TCTGGTCCAG TCTATTTGGA GTTCTGTAGG CTTCTTGTAT GATCATG        25020

ATCTCTTTTT TTATGTTTGG GAAGTTTTCT TCTATTATTT TGTTGAAGAT ATTAGCT        25080

CCTTTAAGTT GAAAATCTTC ATTCTCATCA ATTCCTATTA TCCGTAGGTT TGGTCTT        25140

ATTGTGTCCT GGATTACCTG GATGTTTTGA GTTAGGATCC TTTTGCATTT TGTATTT        25200

TTGACTGTTG TGTCGATGTT CTCTATGGAA TCTTCTGCAC CTGAGATTCT CTCTTCC        25260

TCTTGTATTC TGTTGCTGAT GCTCGCATCT ATGGTTCCAG ATCTCTTTCC TAGGATT        25320

ATCTCCAGCG TTGCCTCGCT TTGGGTTTTC TTTATTGTGT CTACTTCCCC TTTTAGT        25380

AGTATGGTTT TGTTCATTTC CATCACCTGT TTGGATGTGT TTTCCTGTTT TTCTTTA        25440

ATTTCTACCT GTTTGGCTGT GTTTTCCTGC TTTTCTTTAA GGGCCTGTAA CTCTTTA        25500

GTGCTCTCCT GTAATTCTTT AAGTGACTTA TGAAAGTCCT TCTTGATGTC CTCTATC        25560

ATCATGAGAA ATGTTTTTAA ATCTGGGTCT AGATTTTCGG TTGTGTTGGG GTGCCCA        25620

CTAGGTGGGG TGGGAGTGCT GCGTTCTGAT GATGGTGAGT GGTCTTGATT TCTGTTA        25680

GGATTCTTAC GTTTGCCTTT CGCCATCTGG TAATCTCTGA AGCTAGCTGT TTTAGTT        25740

ACTGTTAAGA GCTTGTTCTT CAGGTGACTC TGTTAGCCTC TATAAGCAGA CCTGGAG        25800

AGCACTCTCC TTAGTTTCAG TGAGCAGAGT ATTCTCTGCA GGCAAGCTCT CTTCTTG        25860

GGCAGGTACC CAGATATCTG GTGTTCGAAC CAGACTCCTG GCAGAAGTTG TGTTCCA        25920

ACTAGAGGTC TTAGGATCTT GTGTGGAATC CTGTGTGGGC CCTTGCAGGT GTCAGGC        25980

TCTGCTGGCA AGGTAGCCCG GGGCTCGAGT CGAGTGGAAG GGACTTGTGC CCCAGAT        26040

GCCCGGGTAG CCTGCTTCCC TATGTACTGC AGTCTCAGGT TCCGCGCGAT TGGATTG        26100
```

-continued

| | |
|---|---|
| CAGGCACTGT GTTCCACTCA TCAGAGGTCT TAGGATCCTG TGGGGGGTCC CGTGTGG | 26160 |
| CTTGCGGGTG TTGGGCAAAC TCTGCTGGCA AGGTAGCCCT GGGCTCGAGT CGAGCGG | 26220 |
| GGACTTGTGC CCCAGATCAG GCCAGGGTAG CCTGCTTCCC TATGTACTGC AGTCTCA | 26280 |
| TCCGCGCGAT TGGATTGGGG CAGGCGCTGT GTTCCACTCA CCAGAGGTCT TAGGATC | 26340 |
| TGGGGGGTCC CGTGTGGGCC CTTTCGGGTG TTGGGCAAGA CTCTGCTGGC AAGGTAG | 26400 |
| GGGGCTCGAG CTCTTTTTTT TTCTTTAAAA AAAAATTTTT TTTATTAGGT ATTTTCC | 26460 |
| TTTACATTTC CAATGCTATC CCAAAAGTCC CCCATACCCT CCCCCTGACT CCCCTAC | 26520 |
| CCCACTGCCA CTTCTTGGCC CTGGCGTTCC CCTGTACTGA GGCAGATAAA GTTTGCA | 26580 |
| CCAATGGGCC TCTCTTTCCA CTGATGGCCT GCTAGGCCAT CTTCTGCTAC ATATGCA | 26640 |
| AGAGACAAGA GCTCCAGGGG GTACTGGTTA GTTCATATTG TTGTTCCACT TATAGGG | 26700 |
| CAGATCCCTT TAGCTCCTTG GATACTTTCT CTAGCTCCTC CATTGGTGCC CTGTGAT | 26760 |
| TCCAATAGCT GACTGTGATC ATCCACTTCT GTGTTTGCTA GGCCCCGGCA TAGTCTC | 26820 |
| AGAGACAGCT ATATCAGGGT CCTTTCAGCA AAATCTTGCT AGTGTATGCA ATGGTAT | 26880 |
| TGTTTGGCGG CTGATTATGG GATGGATCCC CGGATATGGT AGTCTCTAGA TGGTCCA | 26940 |
| TATTGTCTCA GCTCCAAACT TTGTCTCTGT AACTTCTTCC ATGGGTGTTT TGTTCCC | 27000 |
| TCTAAGAAGG GGCAAACTGT CCACACTTTG GTCTTCATTC TTCTTGAGTT TCATGTG | 27060 |
| TGTATCTTGT ATCTTGGGTA TTCTAAGTTT CTGGGCTAAT ATCCACTTAT CAGTGAG | 27120 |
| ATATCATGTG AGTTCTTTTG TGATTGGGTT ACCTCACTCA GGATGATGCC CTCCAGG | 27180 |
| ATCCATTTGC CTAGGAATTT CATAAATTCA TTCTTTTTAA TAGGTGAGTA GTACTCT | 27240 |
| GTGTAAATGT ACCACATTTT CTGTATCCAT TCCTCTGTTG AGGGGCATCT GGGTTCT | 27300 |
| CATCTTCTGG CTATTATAAA TAAGGCTGCT ATGAACATGG TGGGCATGT GTCTTTC | 27360 |
| CCAGTTGGAA CATCTTCTGG ATATATGCCC AGGAGAGGTA TGTCGGGATC CTCTGGT | 27420 |
| ACTATGTCCA TTTTTCTGAG GAACCGCCAG ACTGATTTCC AGAGTGGTTG TACAGCT | 27480 |
| AATCTGACCA GCAATGGAGG AGTGTTCCTC TTTCTCCACA TCCTCACCAG CATCTGC | 27540 |
| CACCTGAATT TTTGATCTTA GCCATTCTGA CTGGTGTGAG ATGGAATCTC AGGGTTG | 27600 |
| TGATTTGCAT TTCCCTGATG ATTAAGGATG CTGAACATTT TTTCAGGTGC TTCTCGG | 27660 |
| TTCGGTATTC CTCAGGTGAG AATTCTTTGT TTAGCTCTGA GCCCCATTTT TAATGGG | 27720 |
| ATCTGATTTT CTGGAGTCCA CCTTCTTCAG TTCTTTATAT ATATTAGATA TTAGTTC | 27780 |
| ATCTGATTTA GGATAGGTAA AGATCCTTTC CCAGTCTGTT GGTGGCCTTT TTGTCTT | 27840 |
| GACGGTGTCC TTTGCTTTAC AGAAGCTTTG CAATTTTATG AGGTTCCATT GGTCAAT | 27900 |
| AGATCTTACA GCACAAGCCA TTGCTCTTCT ATTCAGGAAT TTTTCCCCTG TGCCCAT | 27960 |
| TTCAAGGCTT TTCCCCACTT TCTCCTCTAT AAGTTTAAGT GTCTCTGGTT TTATGTG | 28020 |
| TTCCTTGATC CTATTAGATT TAACCTTAGA ACAAGGAGAT AGGAATGGAT TAATTCG | 28080 |
| TCTTCTATAT GTTAACCACC AGTTGTGCCA GCACCATTTG TTGAAAATGC TGTCATT | 28140 |
| CCACTGGATG GTTTTAGCTC CCTTGTCAAA GATCAAGTGA CCATAGGTGT GTGGGCT | 28200 |
| TTTTGGGTCT TCAATTCTAT TCTACTGGTC TACTTGTCTG TCACTATACC AGTACCA | 28260 |
| AGTTTTTATC ACAATTTAGG TCAGGCATGG TGATTCCACC AGAGGTTCTT TTATCCT | 28320 |
| GAAGAGTTTT TGCTAACCTA GGGTTTTTGT TATTCCAGAT GAATTTGCAG ATTGCTC | 28380 |
| TTCATTGAAG AATTGAGTTG AAATTTTGAT AGGGATTGCA TTGAATCTAT AGATTGC | 28440 |
| TGGGAAGATA GCCATTTTTA CTATATTGAT CCTGCCAATC CATGAGCATG GGAGATC | 28500 |

```
CCATCTTCTG AGATCTTCTT TAATTTCTTT CTTCAGAGAC TTGAAGTTTT TTTTCAT      28560

GATCTTTCAC TTAGTTAGAG TCACACCAAG GTATTTTATA TTATTTGTGA CTATTGA      28620

GGGTGTTGTA TCCCTAATTT CTTTCTCAGC CTTTTTATTC TTTGTGTAGA GAAAGGC      28680

TGACTTGTTT GAGTTAATAT CCAGCCACTT CACCGAAGCT GTTTATCAGG TTTAGGA      28740

CTCTGGTGGA ATTTTTAGGG TCACTTATAT ATACTATCAT ATTATCATCT GCAAAAA      28800

ATATTTTGAC TTCTTCTTTC CAATTTGTAT CCCCTTGATC TCCTTTTCTT GTCGAAT      28860

TCTGGCTAGG ACTTCAAGTA CAATGTTGAA TAGGTAGGGA GAAAGTGGGC AGCCTTG      28920

AGTCCCTAAT TTTAGTGGGA TTGCTTCCAG CTTCTCACCA TTTACTTTGA TGTTGGC      28980

TGGTTTGCTG TAGATTGCTT TTATCATGTT TACGTATGGG TCTTGAATTC CTGATCT      29040

CAAGACTTTT ATCATGAATG GGTGTTGGAT TTTGTCAAAT GCTTTCTCCT CTTCTAA      29100

GATGATCATG TGGTTTTTGT CTTTGAGTTT GTTTATATAA TGGATTACGT TGCTGGA      29160

CCATATATTA AACCATCCCT GCATCCCTGA AATAAAATCT ACTTGGTAAG GATGGAT      29220

TGTTTTAATG TGTTCTTGGG TTCGGGTAGC GAGAATTTTA TTGCTTATTT TTGCATC      29280

ATTCATAAGG GAAATTGGTC TGAAGTTCTC TATCTTTGTT GGATCTTTCT TTGTTTT      29340

TATCAGAGTA TTGTGTCTTC ATAGAATGAA TTGGGTAGAG TACCTTCTGC TTCTATT      29400

TGGAATAGTT TGTGCAGAAC TGGAATTAGA TATTCTTTGA AGGTCTGATA GAACTCT      29460

TTAAACCCAT CTGTCCCTGG GCTTTTTTTG GTTGGCAGAC TATTAACGAC TGCTTCT      29520

TCTTTAGGGG ATATAGGATT GTTTAGATCA TTAACCTGAT CTTGATTTAA TTTTGGT      29580

TGGTATCTGT CTAGAAACTT GTCC                                          29604

(2) INFORMATION FOR SEQ ID NO: 208:

(i) SEQUENCE CHARACTERISTICS:
        (A) LENGTH: 16442 base pairs
        (B) TYPE: nucleic acid
        (C) STRANDEDNESS: single
        (D) TOPOLOGY: linear (xi) SEQUENCE DESCRIPTION: SEQ ID NO: 208:

TGTTCTTGTG GCTGTCTTTT TGGTTTGTTG AAGGATTACT TTCTTATTTT TTCTAGGGCG     60

TGGTTTCTAT CCTTGTATTG GGTTTTTTTT TTTTTTCTGT TATTATCCTT TGAAGGGCT    120

GATTCGTGGA GAGATAATGT GTGAATTTGG TATTGTCATG GAATACTTTG TTTTCTCCA    180

CTATGGCAAT TGAGAGTTTG GTTGGGTATA GTAGCCTGGG CTGGCGTTTG TGTTCTCTT    240

GGGTCTTTAT AACATCTGTC TAGGATCTTC TGGCTTTCAT AGTCTCTGGT GCAAAGGTC    300

GGTATAATTC TGATAGGCCT GCCTTTATAT GTTACTTGAC TTTTTTCCCT TACTGCTTT    360

AATATTCTAT CTTTATTTAG TGCACTTGTT GTTCTGATTA TTATGTGTGG GGAGGAATT    420

CTTTTCTGGT CCTGTCTATT TGGAGTTCTG TAGGCTTCTT GTATGTTCAT GTGCATCTC    480

TTAAGTTTGG GAAGGTTTCT TCTATTATTT TGTTGAAGAT ATTTGTTGGC CCTTTAAGT    540

GAAAATCTTC ATTTTCATCT ACTCCTATTA TCCGTANGTT TGGACTTCTC ATTGTGTCC    600

GAATTTCCTG GATGTTTTAA GTTAGGATCT TTTTGCATTT TGCATTTTCT TTGATTGTT    660

TGCCTATGTT CTCTATGGAA TCTTCTGCAC CTGAGATTCT CTCTTCCATG TCTTGTATT    720

TGCTGCTGAT GCTTGCATCT ATGGTTCCAG ATTTCTTTCC TAGGGTTTCT ATCTCTAGC    780

TTGCCTCATT TTGGGTTTTC TTTATTGTGT CTACTTCGCT TTTTAGGTCT ACTATGGTT    840

TGTTCATTTC CATCACCTAT TTGGATGTGT TTTCCTGTTT TTCTTTAAGG ACTTCTACC    900
```

-continued

```
GTTTGGTTAT TTTTTCGTGT TTTTCTTTAA GGACTTGTAA CTCTTTAGCA GTGTTCTCC      960
GTATTTCTTT GAGTTATTAA AGTCCTTCTT GATGTCCTCT ACTATCATCA TGAGATAT      1020
TTTTAAATCC GGGTCTAGCT TTTCGGGTGT GTTTGGGTGC CCAGGACTGG GTGAGGTG      1080
AATGCTGCAT TCTGATGATG GTGAGTGGTC TTGGCTTCTG TTACTAAGAT TCTTACGT      1140
GCCTCTCACC ATCCAGTAAT CTCTGGAGTC AGTTGTTATA GTTGTCTCTG GTTAGAGC      1200
GTTCCTCTTG TGATTCTGTT AGTGTCTATC AGCAGACCTG GGAGACTAGC CTTCTCCT      1260
GTTTCAGTAG TCAGAGCACT CTCTGCAGAT AAGCTCTCCT CTTGTAGGGA CGGTGCCC      1320
ATATCTGGCA TTTGAACCTG CCTCCTGGCA GATTTTGTGT TCCACTCACC AGAGGTCC      1380
AGATCTCGTG GAGAGTGTTC TGGGTACCTT GGGGGTGTCC GACAACTCCG TGTCCGAC      1440
TTCTAGTGCT GGGGCCGACT GGAAGGGACC TCTTTTTCTT TTATAAAGTA ATGAAAGC      1500
TGTGTTGATT TTGGTGGCAA AAGAGAAGTT CAAAGTGCAA TAATGAAACC CTCCATTT      1560
GAAACTCCAT CTCAGCGTCC AGTTGCCTGA ACTAACGCCC GTTCATCTTT CCTGCCAA      1620
TTAGTATTTT GTATATTGCA CACTTGAATG TTTATTGTAT CTAACGGATT TATTCCAA      1680
GCACGTCTTT GGAAAAGATG ACTACAGGGC AACTCTCAAT ATAGAATGTT GAGTGTCT      1740
TTGACCTTTA ACATCATCAC CTATGTTTCC ATCATTTTAT TGATGAGATG ATTACATC      1800
TATATTCAGC CACGTATTCA TTTGGTTTTG AGATCAAAAC CATTCTTGCC TATTCCGC      1860
CCTTCTAGGA ACAGCATCTT TAACGTTTCA GCCCTTTGAT ACCCACATTA TGGAACCT      1920
GAGTTAAATT CCTACTGTCC ACTATGAATG AGGTCTCAGA TGGGAGGCTT GTTTTTTT      1980
TGGTCCCTGG GGACAGCTGA CTATGACTGT GAATGTTTGC TCTGTCCCCC TTTCACTC      2040
TCCAGTTGAA GTGCGCAGAG ACCTGGAGCC TCAATGGTCT GGTTAAACAC GTCTTAGG      2100
AACAACTTTT GAAAGACAAG TCCATCCGCT GCAGCAATTG GAGTAATTTC CCCCTCAC      2160
AGGACCAGAA ACTGTATGCA GCCACTGATG CTTATGTATG TATTTAAAGA CCTTTAAT      2220
GACATCATTC TCATTTCTCG GACCAAATCA CTTTAGTAAA AATGTATTGG GGTTATGT      2280
TTAGCTGAAA TATTTTATTA TAGTTTGGCA TTAAAATTTG CTTAGGAATA CATCAAGT      2340
AATTCTTCAT GTTAATTAGA AAATACCAAT TAATAGGTTG TTTAGCAGTA GTTATTTC      2400
CTATTACGAT GTAAAGTGAT GTCCAATTCC TGTGTAAAAA AATGTGAACT TACTGAAA      2460
ATGAAAGGCT TTGAGCTTAG CAGGCACAAA TAGTTTGATG ATGTATTTTG TATATAAG      2520
ACTCAGAATC AGAAAAATCA CAGGCTTTCC ATATTTAAAC TAGCCTTATT CCCTACAT      2580
ATATTTAAAA TGTGGAAATT TAGATAAATT GCCTCCAAAT TTAGTTGCTG CTGTTCTT      2640
ATGTATTTTC ATATGTGTAA TCTGTACATA CTGGCATCTA GGCTTGTCTT TATATATA      2700
ACTGTGGTCT GTGTGTGCTT TACCTTAAGA AATGTTTCTT TTGTAAATTT CTTTGCCC      2760
GATCATACTT ATTGCTCATA TTTAAATAGT ATTTATTGAT AAATATCTTG TTAATTTT      2820
ACCTTACATT TATTTTTAAG ACATCGATAC TCTAACTTTT AGCCAGAAAA ACAAAGGA      2880
ACCAACTGTC TTAGTCAGGG TTTCTATTCC TGCACAAACA TCATGACCAA GAAGCAAG      2940
GGGGAGGAAA GGGTTTATTC AGCTTACACT TCCATACTGC TGTTCATCAC CAAGGAAG      3000
AGGGCTGGAA CTCAAGCAGG TCAGAAAGCA GGAGCTGATG CAGAAGCCAT GGAGGGAT      3060
TCTTTACTGG CTTGCTTCCC CTGGCTTGCT CAGCCTTCTC TCTTATAGAA CCCAAGAC      3120
CCAGCCCAGA GATGGTCCCA CCCACAAGGT GTCTTTCCCC CTTGATCACT AATTGAGA      3180
ATACCCCACA GCTGGATCGC ATGTAGGCAC TTCCTCAACT GAAGCTCCTT TCTCTGTG      3240
AACTCCAGCC TGTGTCAAGT TGACACAAAA CTAGCCAGTA CAGCAACAGA TGCTTTTT      3300
```

```
CAGGAGAACA GCTGGATGAG TTGGGATGTG CTGTTGTTCC TTTGGCTTCC TTTGCTTC     3360

TGCTTACTTG CTTTAAAAAA AATAACAGAC TCTCTTGCAG CTTATTCCAC TCTTGAAC     3420

TTCATGCAGC CGAGGCTGCC CTTAATGTCC AGATCCTCTT GCCCCTGTTT CCTTGCTA     3480

GAGATTACAG GCTGTAGTGT CTATATTCTT GACAGTTTGT ATGACTTGAT CAAGTCTG     3540

AAAAATACCC AGCATGCATT GTTGTTCATA CACTGACCAG CATTCTCAGT TGGTTTAA     3600

AAATCTCAAG AATTGGATAG GATCTGTCAC CAAAACAGAT GTTTCTTACT AGATGGTA     3660

TATTAGATTT TGTTTACAGA TCATTTCATT TGGATACCTA TTTACAATAC TGAAAATT     3720

TAAGTGAAAA TTTAAAGCTG TATTTTATAG CCTAGGCAGC TTTTGTTTCC CCATTGGG     3780

GTGCTTACAT GAAGACCCGA GTCTTTGCAT ACTGAAATAG TTTTACTTCA TTTTTGGA     3840

GTATTTTGGA AATCATTCTT GTAGATGTTG CTTGAGATAT CACATATATA TATTTATT     3900

GGTAATCTTT AACTTGCACT TTGTTTTTCT TTTGTCTTTT TATAGGCTGG TCTTATCA     3960

TATCAAAAAT TAGGAAATTT GGGTGATACT GTGCAAGTGT TTGCTCTAAA TAAAGGTA     4020

TTGTGGCCTA AAATAAAAGA TAAAAATATG AATTTGCTAT TTTGTGAGAT TCATTTAA     4080

AAGTCAAAGT ATTATGTATC TTTGCAAAGT ATTATGGTAC TTCTTAAATG TCTGAGCA     4140

GTTGCTGTAA AGGTGACATC CATCAGGATC AGAAATTAGA GTTGTAGATC TTCCCTTG     4200

AAAAGCAGGG ATTCCATTGC TAGTTTGATA GTGTTGCTGC TCTTCTTGTC CATGGAGT     4260

CCATGTTATT GTCCTTGATA ACATCAGTTA GCCAGCCAGC TGCCTCTTGG CTGGTAAC     4320

CCACATTCTT TCTACACTTG TTTAAAACGG ATTTGCCTCG ACTATTCCTG TGTATATG     4380

GCACTGTAGT GTTCTGCCTT TCTGTGTTCG GTTGCTGTTT TCTTCACTCA GCTTCATT     4440

CCTTGTCAGA TGCTTTGATC TGTTAGTGAT TACAGGCAGA GTCAGCCAGT AGGTGGAT     4500

GCACCAGCTT TTGTGCTGCA GAACCTCTGT GGTGGAGCCT TAGCCATCTG ACCTGTAA     4560

TGTCCCTTTC CCCATGCTTG TAATGTGGAC AATAGATAAG TGTCTATCTC ATGGATTG     4620

TGTGACCACT AAAGGGACAG ATGTTCAAAG TAAGATGGTC AGAGAAAATT GTTAAATA     4680

TTGAACAGTC CTATAATACA TGATCTGAAA TGCTTTGAAA TCGGAAACTT TTTGGTGA     4740

ACATGATTTA CGTATTCATT AGTATATTTC ATTGAAAATA TTTCCTGGAA GAAGCAAT     4800

TTGAGAAGCC TGAAATAGGA ACAGAAATTT GCCAGCCAAA GCCAGAGGGA AAGTGATA     4860

CAGGTACAAA GCCTCAGAGG GCAGCTCTCT GGAACTTATG CAGTGTAAGG AAACTGTT     4920

CTGTGACAGT GTAATGTAGG AGAAGCAGAA AAATGAGACA GGCCTCACTA AAGAGGTT     4980

ATGTAGCCTT CCAAAGAGCA AATTGAAGCT GTTATTGACG GTTCTAAATG TGGAAGTG     5040

ATGCGCTGGA TTGAAAACAA GCTAACAAAA CAAGCTGTAG AATAAAACAC ACTAACTA     5100

CGAGCCACAG AGAAAGAAAG TGGATCTTAG GATTACAAAA GAATGGTGGG AAAGGCTT     5160

TGGAGGCTAT GATGGTAAGC CAAGAAAGAG GAATTGGTAC CTTGAATTGG TTATTTGT     5220

CAAGGGTCGG CACAGTGGGT AGCGTCANCC TACATTTAAT GGAGGCAACA GAATCTGC     5280

TAATGACAGG CACACGCCAA GGATCCTCCT GGCTTTTGGC TGCACGACAG ATTAAAAT     5340

AGGGTAAAGA CTCACTTTAT ATAGACCAGG CTGGCCTAGA ACTCAGAGAC CTACCTGC     5400

CTGCCTCCTG AGTGCTGGGA TTAAAGGTGT GCACCACCAC CACTCAGCTG GAAGTAAA     5460

TTTATAGTTG TTTTTTTAGA CATGTTCAAG GAGAGTAACA TCTCAGGTAG CAAGAGGG     5520

GTAGCCTGTG GACACCTAGA TATGTAGGTT GTATCTCAGA AGACAGTTTG TCTGAGAT     5580

AATGTAAGCA CTAAGTGTCC TAAGAAACTG CTGGCGTCTA ATCTTTGTGT GGGGGAGG     5640

ACCCTATAGG AGTTGCCCTG GGTGTGGAAG GAGATGAGAA AGTGCTGGAC AATTCAAG     5700
```

| | |
|---|---|
| CCAGTGTGCT GAAAGTCAAG GGAGGGCTAG GTTTGAGGGA GGAGGATGTT ATCAACTG | 5760 |
| TTGAATTCTG CTGAGATTTT GGCAAAGTGA AGGCTTGTAG GCAATCATCA GATTTGGC | 5820 |
| AATGGCCACT ATCATTTGTA ACCTTCTACA CCAGTGGTTC TCAACCTTCC TGTACTGT | 5880 |
| CCCTTTAATA CAGTTCCTCG TGCTGTGATG GCACCAACCA TGACATTATT TCCTTTGC | 5940 |
| CTTCTTGACT GTAATTTTGC CACCGTTATG AATTGTGATG TAACTATCTG ATATACAG | 6000 |
| TGTTTGATTT GTAAACCCTG TGAAAGAGCC ATTTGATCAA TCATTGTTCT GTGCTCTA | 6060 |
| TCTGGTGTCC TGGGTGTTGA CAAAAGAGTA TTGCAATCAG AGGGTGAACT TCTAGAGC | 6120 |
| ACAGGGTCCA GAGGCTTTGG TAGTATAAAA ATATTATAGG CATAGCAAGA ATAAAGTA | 6180 |
| TTAATGAGGT AGGTAGAAAC CAGTACTAAA ATTATATCAA TCATATTACT GCAAATAG | 6240 |
| GAGAAAGATG TAAGGAATTG ATTTTAAGTG TATATAAATA ATATTTTTTA AAGACTTA | 6300 |
| TTAGAAAGGG AACGTTCATA AAACACAGGT TTGTCTAGTG TTTGCTATAT TTTAGTGT | 6360 |
| ATTATGTATT GATTTTATTT GACAAGCAAG GTAACATGCT ATTTGGCTCT CTGAAGGA | 6420 |
| AGAGCCAAAT GCTTAGAGCT GAGAAAGTAC AAAGCCACTG AGGGCAACTG CTTCCCTA | 6480 |
| GTAAGGAACA GAAATATAAC CAAAGAGAAA CGAGTGTGAG GGAGACTTGT AGGAAACA | 6540 |
| GCTGGAAAAG AGGCTTGGGG CCAGTCAGTT AGGGCATCAG ATTGTGTGAA TTGGACTT | 6600 |
| TGTTTTAATA CTCAAAACCA TCAACAACCA CGGTACAACG ATGCCAATA GGAAACCC | 6660 |
| AGTTTGGGTG TGTGGAGCAG CAGAGTAAAA TGATCCAGAT TTTGTCTTAA AGTGTTTT | 6720 |
| TTTTCTCACT GCTGTAAGAA GGTCAGGAAG TTAGATAGGA GGCTTTTTCA ATTGTCCA | 6780 |
| AATAGAAGAT AGTTGTACTG GGCCAGTGGA GGTAGCAAGA AATGTAAATG CAGTAGGT | 6840 |
| TCTGAAGGCA TACACTGAAG AATTCTAGGT GAATTCCTTA TAAAGGGTGA GGAAAAGA | 6900 |
| GCTAGGATGG CCAAGGTATT TTTCTTTTCT TTTCTTTTTC AGTTTTTCGA GACAGGGT | 6960 |
| CTCTGTGTAG CCCTGGCTGT CCTGGAGCTC ACTCTGTAGA CCAGGCTGGC CTTGAACT | 7020 |
| GAAATCTGCC TATCTGCGCC TCTCAAGTGT TGGGATTAAA GGCGCCCGGC TTAAGGTA | 7080 |
| TTTCTTGAAT GACCTGATGA CTGGCAGTGC AGGATGATAT GAAGAGTATG TTTTGGTT | 7140 |
| AAAAAATCCA CCAAAGTTGC AACGTGGACA TGAAAAAAAA CTAGAGGTGG ATTTTGAT | 7200 |
| CCACGAACGG CTCCATACTA GTTATTTTCT GTTACTGTGA TAAAACACCG TGACCAGA | 7260 |
| GGTCTTTAAG GAAAGGAGTT CTTTTTGCT CACAGTCCCA GAGGGAAGTC TTCAGTGG | 7320 |
| CTGCGGGAGC ATGGCAGAAA GCAGCCGGCT TGGCAGTGGG GCAGGAAACT GTTAGGTC | 7380 |
| ATCTTGAACA GCAGTCTTGA AGCAGAGAGA GCAAACAGGA AGTAGGGTGA AGCTGTGC | 7440 |
| TCTCAAAGCC ACCCCCAGTG TCAAACTTAC TCCCGGAAGG TTGCACCACC TAAACCTC | 7500 |
| CAAATGGAGT CACCAACTGA GCATCCAGTG TTCCACTGCC CGCGAGCCTG TGGGAAAT | 7560 |
| TTCCCACCTA ACCACCACTG CACTGTGAGA AATGGAATTC CAGAGTACAC GGCGGAAG | 7620 |
| GGGGTTAGAA ATATAGATTG TCCAGTGGTG AAACTGGAGA TAAAACTGGG AGTGAATA | 7680 |
| CTGAAGAATA TAGGTGGTGT CAGCTTCAAG GTCACACTGA CATTTAGAAA ATGAGAGT | 7740 |
| CTTGAGGGCG GAGACGGGGC ATCAGTGAAT GAGGAGGGGG GCGAAGGACA TGCTTTAA | 7800 |
| AGGAAGGAGA CATCAGCCCC TTAAACCTCG GAGGAGTTGA ACGATGCACA GATCGTGG | 7860 |
| TAACTATTAG GGTTGATAAT GTGGTAGCCT TCCCAGAGGA AGCTGTGCTG CTGAGGGC | 7920 |
| AACTCTTGAG TTGGAGTTAG TTTAGGAGAA AATAAGAGCA GAACATTCGA GGATGAGC | 7980 |
| CAGGCGTTGG AAACGTAAAA GAGAAAGAAG AGGTGTAAAA TTGTCATCTT AAGATAAG | 8040 |
| GGGTCTGCGT CATGAGTTTA AAACTAAACC GGCCATTATC ATTTTGTTTT AATTTCAA | 8100 |

| | |
|---|---|
| ATGTCCAGCT ACTTAGGCAC CGATTAGCTA AAGAAGTTGA GTATGATTAG AGTAGATT | 8160 |
| GCCCCGTGAG TTCCACGGAG TTGGGTAAAG AAGGCAGAAG TGGAGAGTCT GTATCAAA | 8220 |
| AATGGCTAAG AAAGGAAAGG AGACCAGGTA GGGAGAGTGA GAGTGGGTGC TGGAGGGG | 8280 |
| GGATTCAACA GGTTTCATTC TGAAGTGTTA ACTCACTGAG CTGGGGTAAG CAAGCCAG | 8340 |
| AGAGCGGTGG GATGGCTCTA TTTATGGTGG AAAGTGTTTG TAATAGAAGG TTTGGGTG | 8400 |
| GTGGAGGTTT TATTGGGCAG TTTTAAGGTC GAGAGTCTGA TTGTGGGAAT GAGTAGCT | 8460 |
| GATTAGATGA GGAAGATTGT TGGAATGAAG GGTGACCCTT GGGCAAGGGT TCCAAACG | 8520 |
| GTTAAGTTTG AACGTGCCTG GATTGGGGCT TACTGACTTC CAAGTCAGAA ACAGTGTC | 8580 |
| GTGAGTTTAG AGTCCCAGGC TTGTCCTCTG GCCCAGGTCA GTAACATTTA GATTGGAT | 8640 |
| TGTATACATT TGGAATTCAC TCTAAATTTC AAATAGCAAA AATTTGAAAG GAACATTA | 8700 |
| ACAAGGGAGT AAAGAGGAAA GTGATTTAGA GATCCGAGAG GGAAGTGTTC TGTTAGAA | 8760 |
| CATTGTGCGA ATAGATGAAA ATCTGGATAC TAATACTATG CTGTGATGTG GTTAAATA | 8820 |
| ATCTCTGCTT TCTAATTTTA ATATTAATCT TTTCTCTCTC TCTCTCTCTC TCTCTCTT | 8880 |
| TCTCTCTCTC TCTCTCTTCT TTTATTTAGC AGAGGAAAAC CTACCTCTGG AGATGAAG | 8940 |
| ACAGTTGAAT TTAATCTCCG AAGAAATGAG GGATCTAGCC AATCGTTTTC CTGTCACT | 9000 |
| CAGAAATTTG GAAACTCTCC AGAGGTTAAA TATTGTGCTT TTTAAAATAT TTATTTTA | 9060 |
| TTTAATTGTA TGTGTATGCG CGTTCAGTCA CCTTTTATGC TATTTTCTTA AACATGGA | 9120 |
| TCTGATTTTT ACAGAATGCC TGCTTGTTAT AAATTACATA TACCTACAGC TTGGCTTT | 9180 |
| AACAGCAAGT TAAGTAGGAT TTATTAGCAT CAAGAACTCA CAACAGAGTG GTTTGAAG | 9240 |
| TATTGTAGGA AGGAACAGTT GTTTTTGTCT CAGAGGACCC TAATAGAATC GATGTGAT | 9300 |
| AGTATTGTTT AGTCATTTAT TTACATTCAG TGTGCTGCGG TGTTGCTGCA GTGTGATT | 9360 |
| CACTCTACTG GCTGTTGAGC TTGTCTGCTG CTAACTAATG AGCAGGATAG AAATCTTA | 9420 |
| GAAGGAAATG TGCATGCCAC CATGTATGCC TTCCTAGTCC AGCCTTTAAC GTTAGAGT | 9480 |
| GTGGTTATGT CTTACTCTGA TGTGAGTGCT TGGTAAATAA GATATTATAA TAGTATCA | 9540 |
| GTTGCTATAG CAACACATTT ATTTCACAAT TAAATTGAAT CATAACTTCT CATACCAT | 9600 |
| TATTTATACA CAGTTGTTAT ATATAAGCAG TATATGTATA TACATATAAT TATATACT | 9660 |
| GTATGTAGTA AAATTTACAA AATTGCCAGG CACCACGGTA CATACCTGTA ATCTGTGC | 9720 |
| TCAGGAGGCA GAGGCAGGAG AATTCCAAGC TCAAGGCCAG CCTGACTAAT AAAAAGCT | 9780 |
| ATAAATTTTT ATTATTTTAA AATAACTTGT TATTAGATTT TGAATTTAGT TAATAGTT | 9840 |
| AAAAGTTTTT TTTTTGTATC ATTTTATGTG TATGGCTGTC TTTGCCTGCA TGTATGTC | 9900 |
| TGTACAACTT ATGTGATGTA TTCCTGAGAG GTGCAGAGGA GGGTATTGGA TCTTCTGG | 9960 |
| CTGGTGTTAC ACACAGTTGA AAGCTGCCAT GTGGGTGCTG GGAATCAAAC CTGGGTC | 10020 |
| TAGAAGAGCA GCCAATGCTC TTAACTGCTG AGCTATCTTT CCAGCCCTGA ATTTAAT | 10080 |
| GATCTTGATT TTTGCTTATG TTAATATAGA CTTTGACAGT TTAAGGTTGA GCTAAAG | 10140 |
| GGAGAGTTGA TAATTGTGTA GTTTTGTTTT TTTGAGTATT TTTGTACATT TTATTAT | 10200 |
| CATAATTACT TTCCATTACA CTCTCTTATC CCCCTGATTC CTGCTGACTC CCTCTTA | 10260 |
| AAGTAGCTCC TTTCCTTCTT TCACGTCTCA TGTGTGTTTG TGTATTTGTG TGTGCAT | 10320 |
| TGTGCATGTG TGTGTGTGTG TGTGTGAGTG TGTGTGAGTG GCACTGTGTT TATTTAG | 10380 |
| TATTTGTATG AGCATGGTTA AGAGGCTGCT GACTAAGCAC TGGCAACTTT ACCAGTG | 10440 |
| ACTGAAGAGA ATGATGACTG TTTGCCTAGA AGCCAAGCAA AAGCTCCCTA GGGAAGG | 10500 |

| | |
|---|---|
| GGGTGGGTCA CTTTTGAGCT TCACCATCCA CGTGGGAGCG GCAGAAGGCC CTGTGTT | 10560 |
| TGGGTTTTAT GCAGATATCC ATAGCTGCTG CGTGTTTATG ATTTCAGTAG CCATGCA | 10620 |
| TCTACATGGC AATGTTTCAC AGCACTCCCC CACATCGTCT GACTCTTACG GTTTGTC | 10680 |
| CCATCCTGTT ATGTCCACTG GGCCATTGAA GGAGTTTTAT GTACAGGCTG GTCCCAA | 10740 |
| AGGCAGAGCA CCCAGTATTC ATTTATGCTC AACACTTTGA TCATTGTGAG TCTTCTT | 10800 |
| CCAAAAGCTT CTTTGACCAA GACTGAGAGT AGCACTCTGG ATAAGAACAA GAGTTCG | 10860 |
| GCAATATGAT ATGTGTCTAT CTAGCAATGT GTCAGCAGTT GGTACCCCTC TGCTATG | 10920 |
| TGTGATCTCC CCAGCCAAAG GCTTCTGACC AGATTTATAC TTCCAGTCAC GTATTCC | 10980 |
| CTGAAGGTCC AGGCTTCAAA TGCCTCGATT GCTGATTGAT GTGACCCACC CCCAGTC | 11040 |
| TCATTGGTTC TCCAGCAGAC ATACCTTGCC TGGCAGGTTG GTACTGTAGC ATGCAGG | 11100 |
| CAGAGTTGGG TAAGACCCTT GATGACCATC GCCACCCCTC CCCCCTGGCA GGTGGCA | 11160 |
| TACCTTTTCC AAGTATGAAT GCTGACTGGC AGGATGAAAC TGAAGCATCC GGTCAGT | 11220 |
| AGTTTGATTT TTCTGTGTCT TGTAAGAATG AGCTCCCAGT GTAGGACCAA CCCCTGG | 11280 |
| AACTCAGACT TTGATGGTTT ATTCTCATAG AAGAGCAGAG TTTCATCTGA ACCATTA | 11340 |
| TAAAAATTAG CTGGAACTAC CTGAACATTT CTGGTTTTAT AAATCATTGA GTTAAAT | 11400 |
| GGAAAATTAG AATACATAGT CCAAAGCACT TATTACATAA CAACATACGT CTCTTTG | 11460 |
| ATTACCATCT TTTGTCTTTC TCTAATTTCC TCACTTATTT AGGTAATTTT TCTTTCT | 11520 |
| GTGCTGAGGA TTGAGCTTGA AGCCTTGTGC ACTCCAGGCA AGCATCACAG AGTTGTC | 11580 |
| AAAGTAGTCC TGTTGTTTGG TGTTCTGCAC AGTGTTTCTT ATTTACACTA CGTTCAG | 11640 |
| GTATTACCTA CAATTTCTAC TTTTAGTTTC TTTAAAGTGG AATGATAATT CAATATA | 11700 |
| GAAGTCATGT GACTACAAAG TCCTAAGAAT TTTTAAGTTT TTTTCTTATG AGCTTTT | 11760 |
| GTTATTTTGA CTATGGGCA TAATTTTTTG ATTATAATTT TATGTAATA GATAATT | 11820 |
| TTTTTCCTAT CCCCCAACCC TTTCCAGATC CTAACCACCT CCCTATCCAC CCAAGGT | 11880 |
| AGCCCCTTTC TATCAACAAT GAACAATCTA ACAAAGAAAA ATCAGAACAA AAAACCA | 11940 |
| AGGAAAAACA GATACCTCAA CAAAATGAAA TTAAAAGCCT ACAAAAAAAA AAAAAAA | 12000 |
| AAAAACCAAA ACAAAACAAG GCGTTCATTT TGTGTTGGTT ATCTTCTCCT GGGCATG | 12060 |
| CCTGCCCTGG ACTGTTGCCA ATACATCCAG TGACACGTAA TTAGAGAAAG CAGATTT | 12120 |
| TTCTTTCCCA GCTTTTGCAA AGAAGTTTTT AGTTAGGAGT GCTGGGATTT TGTCTAG | 12180 |
| GAACCTTTGC TATTCATGTG CAAGCTACCA CAGTCTCTGG GAGTTCATAT GTGCATC | 12240 |
| CTTGTGTCTG GAAGACAGTG TTTCTGTGTC ATTTTATTGT AAAATTTACT ACTTAAC | 12300 |
| GAGTTATCAA TAATTTTTTT TTCTTTTTTA GTTTTGTTTT TTGACTTTGT TATTTTG | 12360 |
| TTAAAGTGTG GCTTGCTTCC TCCTCTTCTG ATTTACTGGT CTGGGATTGT TCCTTCT | 12420 |
| TTCTTGGATG TGATTAACTG CTTCAGACTA AAGTTTTCCT TCTAATGCCT TCAGTAG | 12480 |
| TGGTTTAGTA GACTGATATG CTTAAAATTG GTTAATCAC AGAATGTCCC CCTCGCC | 12540 |
| AAGCTACTGT GATTGATAGT TTTGCTGGGT ATAGTAGTCT GGGCAGGGAT TTGTGAT | 12600 |
| TCAGAGCTTG TAGACTATTT GCCCAGGTCC TTTATGGGTT TTTAAAATCT CCATTTA | 12660 |
| GCCAGAAGAT ATTTTAATAG CTCTGCCTTT ATATGTTATA TGGTCTTTAA ACCTTGT | 12720 |
| CTTTAATATT CTTTCTTTCC TCTGTATGTT TAGTATTTTG ATTATGTGGC GAGGGAT | 12780 |
| TATTCCTATC TATTTTGTTT TCTGTATACT TCTTGTACCT TAAAACGCAT TTCCTGC | 12840 |
| AGATTGGGAG AAATTTCTTG TATGGTTTTG TTAATAATAT TTTCTGTGAC TTTACAT | 12900 |

| | |
|---|---|
| TTTCTTCTCC TTCCTTTATA TCTACTTTTT ATAAGTTTGA TCCTTTCATT GTATTAC | 12960 |
| ATTTCCAAAT GGCTTGTGCC TGCGTCTTTT TAGATTTAAC ATTTTTTGAC TGAACTG | 13020 |
| ATTTTTTTCT ACCTTGTTTT TAAGACTTGA ACTTCATTCT TCCATGTTGT GTGATAT | 13080 |
| GATGACACTT ACCTCTCAAG TTTTTCTTTA ACACCCTGAG TTTTTCATTT TAGAAAA | 13140 |
| ATTAACAAAT AACAAATTTA CGAACAGAAC TTTATTGGCT TTTCCCATGT GTTTAGT | 13200 |
| GAATAGAATG AAATAGTTTT TGCTTTGTTT TTTGTCATAT CTTATTGCTG CAGTTTA | 13260 |
| TTCATTAAAT TAATTATCAA AAAGGGCCAT CTGGCATAAA GGGGATGGGG ACTCAGA | 13320 |
| AGTAAACTCT GAGTGAGTAT GCAAGGCTAC TTCTACAATG AGAAGCACCT GATCACA | 13380 |
| GCAAGTTGGC TGTTACTCAT ATTCACGTGT GGCCACATGG AAATAAGGAA CAGTTTT | 13440 |
| CCCAATGGGT CTCCTCAGTA AGCCTTCGTT CAGTAAGAAC TTTTAAAGCT CATCTTT | 13500 |
| ATGAATAAAA TTAGAGCTGA ATAATGCTTA TTGAATTTTT TTTAGGGTTC CTGTAAT | 13560 |
| GAAGAGTATT TCAGAAAATC TCTGTTCATT GAGAAAAGTG ATCTGTGGTC CTACAAA | 13620 |
| TGAGACTAGA CTGAAGCCGG GCAGTAGTTT TAATTTACTG TCATCAGAGG ATTCAGC | 13680 |
| TGCTGGAGAA AAAGAGAAAC AGATTGGAAA ACATAGTACT TTTGCTAAAA TTAAAGA | 13740 |
| ACCATGGGAC CCAGAACTTG ACAGTTTAGT GAAGCAAGAG GAGGTTGATG TATTTAG | 13800 |
| TCAAGTGAAG CAAGAAAAAG GTGAATCTGA AAATGAAATA GAAGATAATC TGTTGAG | 13860 |
| AGATATGGAA AGAACTTGTG TGATTCCTAG TATTTCAGAA AATGAACTCC AAGATTT | 13920 |
| ACAGCAAGCT AAAGAAGAAA AATATAATGA TGTTTCTCAC CAACTTTCTG AGGTACT | 13980 |
| TCAAGAGGGA ATAATATATT CATCAGTGGT TGGTTTACTT TGTTGTATAA ATGCACA | 14040 |
| AACAAATATT TTAGTTTTTG TGGGATGCAT GGTCTCTGTT GTACCTATCC AGTTCAT | 14100 |
| TTGTAAAGCT GCCATAGACA CATGCAAGCA GTGGTACCTG TGTGCTTCAG TAAAACT | 14160 |
| TTTAAAAATA CAAACAGAGG GCCATGTTAA CTTGTGAGAT CCACTTAATA CAATAAG | 14220 |
| AATTGTATAA GTGAAAAATT TTGCTGCTTT ACTATTTATG TTTTTTATAT GATAGGT | 14280 |
| AGTTTTTTGG TGGATTCTTC CTAAGTATTT ACTCATTCAA ACTTGATTTG GGGGGTG | 14340 |
| GGGTTTTATT CCTTCAAATA GAAATTATTT GTTAGGGTGA AAGGGTCCTT TGATTTA | 14400 |
| GCATCCATAC TGTGACCTGG AGAGCCAGGA AGCTCTTGTC TCCTTCCTAA TTCTTAT | 14460 |
| CTTGCAAATT ACTGAAGACA TTTATCATTT CTGGGAGGTT TTTCTTTTTC TTTTCTT | 14520 |
| TTTTCTTTTC TTTTTTTTC TTTTCTCTTC TCTCTTTTTT TTTGCAATAA CAAATTT | 14580 |
| TTTAGATTTT GAAAAGATTG TATAGGTTTA AACCTCTCAA TTTCATTACA GAAGTGG | 14640 |
| CCCAGTCTTA TATACAATTC TTTGATTTTT TTTTTACAGG AGTTTTTCAA TTGTTTC | 14700 |
| TGAGTATATA AATGTAAATT GTTTTAAAAA TTTCAAAATA TTCTCATTCT AATTTTT | 14760 |
| GAACCAGATT CCCTCTCTAG AAAATGCTGT CTTTCACTTA CATGTGCATC ATTCTAA | 14820 |
| TGTAGAAATT TCTAATTAGA TCTGCACTTT CATATTTTTA TATATTAGAG AATTATG | 14880 |
| ATGAGTTTGA TTTGACTGAT ATCTTTTATA TCAATTATTG CCATTTTATT ATGTAAT | 14940 |
| TAGCATCATT TTTATTATTT AAGACTGCGT TTAGAAGTCA AGAAAACCTT ACTCAGT | 15000 |
| AAGTGTACTT TAATACATTT TAATAGCTTT AAATTAGCAT GTTAATTAAG GCTATTT | 15060 |
| TTTTCCCATT AACAAATTAA ATATGAAGCA TTTGGGGAGA TATTCCTTCA AGTTTCT | 15120 |
| TGATTTGTGT GTGTGTGTGT GTGTGTGTGT GTGTGTGTGT GTGTGAAGGG TAGATTT | 15180 |
| GCTTGTTAGG CACCCGGTTC CTTGGGATTG CCAAATTATT GTAAAGATTC TTCATAT | 15240 |
| AACATCAACA ACAGATCAAG AAAATAATAT ATTTAGTATT TTTTCAAATA GATGGTC | 15300 |

-continued

| | |
|---|---|
| GTAAAACACT AATTTATTGA AAGATTATTA TGTATTAGTC TTTGGTATTT TTAAGTC | 15360 |
| GTATGTAAGA AAACCATTGA TTTTCTTGGT TTGTACAGAC TTTTTTCAAC ATTGATT | 15420 |
| ATGCCATCTA TTGGAAAGTT GGGGAGACCC AGGTTGACCT GGTTGACCTT CAACTTG | 15480 |
| TTTCTCTTCT TTTGCATGTA GATTCTACTT GACGTCTGTT TATCTAACTT GCCTGTC | 15540 |
| TTAATTACGC TCTCTCTCTC TCTCTCATTA TTTGAAGATT AAAACACTCA TTCTCCT | 15600 |
| TCTCCCGTCC TCTCTGTGCT CATGCTGTGA ACATATAAAT ATGCTTTAAA CATCTGC | 15660 |
| TTAAAGAAGA GGAAGATGTC TAAATACTTC AGTGAAAGCA GCTGAGAGCA TAGTGTC | 15720 |
| CTCGCAGAAC GTTAATCTTT GAAATCCTTT TCTTTAAAGC ATTTATCTCC CAATGAT | 15780 |
| GAGAATGACT CCTCCTATAT AATTGAAAGT GATGAAGATT TGGAAATGGA GATGCTG | 15840 |
| GTATGTTTGA ACACAAGAGA AAGTTACTTC AAGTTTTTAA AAGAACACTT TAATAAT | 15900 |
| AATATTATCC ACTTCCAAAT CAGATGCCAC CACAATGATA TTCATACCCA TTATTTA | 15960 |
| TTAGACTTTA AGTTTTCAAT TTACATGTCC TCATCTGTAA GTAGTCTTAG GTGTAAC | 16020 |
| GGGAGTTCTC ACGGGAGTTC TGTGTCCTCA TACGTCTCTC TCTCTGGAAA CTGGGCA | 16080 |
| ACTAAGCACT TGAGCAGGAA ACTCATTATT TCTTCTTCTT CTTCTTCTTC TTCTTCT | 16140 |
| TCTTCTTCTT CTTCTTCTTC TTCTTCTTCT TCTTCTTCTT CTTCTTCTTC TTCTCCT | 16200 |
| ACTCCTCCTC CTCCTCCTCC TCCTCCTGCT CCTGCTCCTC CTCCTCCTGC TCCTCCT | 16260 |
| CCTCCTCCTC CTGCTCCTGC TCCTCCTCCT GCTCCTCCTC CTCCTCCTGC TCCTCCT | 16320 |
| CCTCCTCCTC CTCCTGCTCC TCCTGCTCCT GCTCCTCCTC CTGCTCCTGC TCCTGCT | 16380 |
| CCTCCTCCTC CTGCTCCTGC TCCTCCTCCT CCTCCTCCTG CTCCTGCTCC TCCTCCT | 16440 |
| CC | 16442 |

(2) INFORMATION FOR SEQ ID NO: 209:

(i) SEQUENCE CHARACTERISTICS:
        (A) LENGTH: 51259 base pairs
        (B) TYPE: nucleic acid
        (C) STRANDEDNESS: single
        (D) TOPOLOGY: linear (xi) SEQUENCE DESCRIPTION: SEQ ID NO: 209:

| | |
|---|---|
| GCTCCTCCTC CTCCTGCTCC TCCTGCTCCT GCTCCTGCTC CTCCTCCTCC TCCTGCTCCT | 60 |
| GTTCCTGCTC CTGCTCCTCC TCCTCCTCCT CCTCCTCCTC CTGCCCCTCC TTCTCCTCC | 120 |
| TCTCCTTCTC CTCCTTCTCC TCCTCCTCCT GCTCCTCCTC CTCCTCCTGC TCCTCCTTC | 180 |
| TCTCCTCCTC CTCCTCTTCC TCCTCCTCCT CCTGCTCCTC CTCCTCCTCC TCCTCCTCC | 240 |
| CCTCCTCCTC CTCCTCCTCC TTCTTCATGT ATTTGTTGTG TTTTAGACAT TCTGTGTTT | 300 |
| ACTCATTCAA TCATTTACAG GGTCTGGATT TTCTTATTGT GTGTTTTTTT TTTTTTAAA | 360 |
| ACTGATTATA TATAATGGCT GTTTACTCTG TTATCAAAGC TGAAGTATGG ATCTGTGCA | 420 |
| TTCTATCCTG TCACTCATCC TCCAGCTTAT CAAGTGTCGT AAGCCATGTG CAGACAGAA | 480 |
| AATCCAGACT GAGAGAGTAA GGGAAAGCAC AGTTTAGTTA AATCAAATGA AAAATAAAA | 540 |
| GAAATAGAAG TATGCTTTTG TGTCTGCCTT TTAAGCTGCC ACCTGTAGGT TAGTGTGCT | 600 |
| TTTCTTTTCA TTAAATGAGA GTAATTTTCT AGTTCTTTAG TTTTGAGTTT TAGATAAAT | 660 |
| AGGATAAATA AAGATGTGGA TTCCTAATTG AATGTAGACC TGAGTCCTCC CTTCCCCAT | 720 |
| GGTGTCCATT GCTAACATCA CAGTTTACCA GGGAGCCTGT CTCCTATTTA AGAAATATG | 780 |
| GCTAAATCAC AATCTATTCA CTAGGTATCC ATTTTTCTAG TGCATTCAGT TCAAGTGGT | 840 |

```
CCAAGTGTAG GATGCTTGTA GACATCTGTA CCATATATTA TACACTGGAC ATCTCTGTT      900

TCTGGATATG TTGGTAGAGT TAAAGAAATA TCATCACCTC TTTTTTCCCC TCATTTTTC      960

TTTATAGGAC GGAAATATTA TACTTTAAAG GACATTCTTA AAACCAAACT AAAAAATA      1020

ACGCCTCATA AAAAGTGAAG ATAACTTGTG TTAAATGAAT AGTCTATGTA ACTCCTTA      1080

AAAAAGTTTT ATAGATACAG CGATTTGAAA TATACTAATA TTTTTGAAAT AGTGGAGA      1140

ATACATATCA AAACACCTTT TTTTCACATC AGTAATATTT CTTTCCTAAA ATTATTTG      1200

TCCTTTTTTA CAATTCCAAA ACACATTTAT TGCTTGCTCA TAATTTAAGC ATCATCTT      1260

CTCAAGAAAA ATGCAATTGA CATGTAACAT AGAGAAATCT ATGATAAAAA TAGCATTA      1320

ATGTTTCATT TTACCACTTA GAATTCTAAA ACGTTAAGT CCAATAAGAA AAACTGGT       1380

AATTATGCAA ATTTTAAATT TACGATACGT TTCCCAGAGG CCGTTCATTA TGTGCTAT     1440

CTGAACCTTG TTTATGCTGG CCATGCTCCA TCCTGGCCTC GTGCCTTGGA GCATCTTC     1500

CACGTATTTA TAGAGGAGCA CACATGTTCT TTTGTGCTGT TGTTTGCACA TCTGCCGG     1560

TTCAACCAAA TTGTAGGCTT TGTTAATAAC CCTCCTTTTG TACTCAGTAA AAAGATAC     1620

TATTGTCAGT GTTCTGCCTC AAATTTCTTT TAAACTTCCA GTCTTTAGAA AACCTAAA     1680

GTGACATGGT GGAACCCACT CACTCTAAAT GGTTGGAAAT GGGAACCAAT GGGTGTCT     1740

CTCCTGAGGA GGAAGATGGA CACGGAAATG AAGCCATCAA AGAGGAGCAG GAAGAAGA    1800

GTAAGAATCA GGGTGGAAAC AAACTCACCT TTCATGGATT TCGTGTCAGT TTTCCCGT    1860

TTGGAAGTTT AACAAGTTGG TGGCACGTAG TTACTTATCC AGTCTATAAA CCAACCAC    1920

AAGTCCTTAG TGCTCCTGTC TCTCGGGAAC TGTGGATGAT GAAACCTTTA ATCCTGAA    1980

GAAAGATTTG GTTTGGGTCC CAATGACAGT GGTGAAATAG TTTACTAATT GTTCATAT    2040

AATGCCCTTG TTGGTGATAC AAATACATGC AGTCTGCTAC CCACCAGGAG CTTATGGT    2100

AAACAAGTGC CACACCATAT GTTCAATTAA ATGTATAGAA TAGTAAATGA GTGTGCAA    2160

GATAGAACTG TCATCTACGT GTAACCAATC ATGGTCATTC GGTCAACTTT GTAGTACT    2220

CACTATACTT ACAATATATT GTGGTGGGAA AATGTGGGCA TTTCAAAATC ATTTTGTA    2280

TAGAAGGTAC TTATAAATGT ATTGATGAGT TATTCTCCTT TGTTTCCTTT TATTAAGT    2340

AGCCATCTGT TTGTTAAGAT GTGCCATAGC ACTTATTTTT CATGTTTAAT GATAGCTT    2400

CTAGAATCTG TGTTTTATCC TTTCTTGGCT GCTTGTGAAT CTTTGCATCA ATGGACAG    2460

AGTGGTGGGA CTTAGGGAGA GCTAACATAG TCCACCATGT GGTACCATTA AAATTTTT    2520

CTAAAGATTT AAGTAGCTAT ATTAACCTAA CTAAATAGGA TAGGTAGCTA AATTAGAT    2580

AGGTAACTTA ATTTATATAA CTAGATTTAG TTTTAAACAG CTAAATGAAA ATTTTATT    2640

TTTTCTGTAC ACTTAATTTG GGATACTAAT ATAATTCATG TTTATCATTA ATTGAAAA    2700

ACTTCTAATA TAAAATTTTT ATCGGCATTT CTATTGTTTG CTTGGTTCGC TTCATTCT    2760

ATTGTAGATC CTGCAAGTTT CCCAATTACA GGATGTTGGG CCTCTTCTTA CCACTATT    2820

TAAAGCGGGC CACAAGGATA GGTCTAGTTT GTAAGTAGTG ATCAGAGGAT TTGCCTGG    2880

TCATGCTAGA TATCTGTAGA GTCAAGTGTG ACTGGGATGG AAACAGTGGA TGTCACCC    2940

CACTCTGTTC TTTATCACAG CAATGGAATG AACATTTTCC TCTTCTTGCA TAGCATAT    3000

GCTTTTGAAC ATAAATGTCA ATTTTATTAT TTTATTTATT TTAAGACCA TTTATTGC     3060

GAACCCAACG CAAAGCAAAT TAATTGCCTC AAGACCTATT TCGGACACAG CAGTTTTA    3120

CCGTGAGTAT GATCTCAATT AACTATATTA TGTACATATT TTTTTTCAC AAAGAGAA     3180

AGTAAATAAT CCATCCCCAT ATCCTAACAG CAGCAGCCTA ATTTTATTGT AGGCATAT    3240
```

```
GTCAGGTATA GATTATATAC AACTGTAAAA TTATTGGAAA TATTAATTAC ATAAGTTT    3300

TTGTCCTTTT AATAGGAAAG GAAGCGGTTC TATTTTTCTT TAACTGAGTG CTTCTATG    3360

AAAACTATAT AATAATAAAA AAAGAATTTT TCTCACTGCT GAGTTATCTT TTATTGAG    3420

TGAATTCAGA GGAAAGGCAC ATTGCTTACT GCTTTCTGCA GGTGTTGCAA GGCACACT    3480

TGTGAGTCTC TGAGAGAACA GTTTGAGAAG CTGAAGGTTT ATTGTTTTAA CATTTCAA    3540

TATATTTCCA TCTAAAGGGC TGTCTTAGTC CATGTCCCAT TGTCGTGAAG GACACCA     3600

ACTACAGCAA CTCCGATAAA GGAAAACATT TGATCAGGGC TGGCTTACCA GTTCAGAG    3660

TTAGTCCATT ATCATGGAAG GCATGGCAGT GTACAGGCAG ACATGGTGCT GGAGAAGG    3720

CTGAGAGTTC TACATCCCAA TTGGCGGGCA GGAGGAAGAG AGAGTGAGAC ACTGGTTG    3780

GCTTGAGCTT TTGACACCTC AAAGCTCACA TCTGGTGACA TACTTCCTCC AACAAGGC    3840

CACCTGGTCC AACAAGGCCA CACCTCCTAA TCTGTTCAGA TACTGCCAAT CCCTGTGA    3900

CTTAGGGGAG TGTTTTCATT CCAACCATCA CAAGGGCACA CTAATAACTA GAAACAAT    3960

GATGAACACA AACGAGATTA GGAACAAGTG CATTTGAATA AGACCAGTAA GTAACTAA    4020

ATCTAGACAG GGTTTTTTCA ATTTTTTTTA TAACTTTTTT TTGGGGGGGG GTGCGTGT    4080

CGAGACAGGG TTTCTCTGTG TAGCCCTGGC TGTCCTGGAA CTCACTCTGT AGACCAGG    4140

GACTTTGAAC TCAGAAATCT GCCTGCCTCT GCCTCCCAAG TCCTGGGATT AAAGGCGT    4200

ATCACCACTG CCCGTTTTTT GTTTTTTTTT TTAAATAACT TTAAAAGAA TTCATCGG     4260

CATTTTTCCT TCTTTTAATA AACTATCACC TCCAGTTGAT TTCACCTTAG TCCATCAC    4320

TACACAGGTC TCATTTCAAA CCTATAGCAG TCCTCTTATT TATTCTAAAA TATTAACT    4380

TCGGTCTATA GTACAAAGCT GGGTATTTGT TTTATACTTT AGATATATGT AATAAAAT    4440

CATATACATA CTATATGGCA ACTCATGGTT ATTCAGTCAG TCTGAATGAA AAGTTAAT    4500

AATGATCAAA TTTTTTCTCT CAAATTTCTA GGATTTGAAT ATATTTTTAT AGGTAGCT    4560

AAAAAAAAAT CTGAGTTTAT TGGAGAGAAG TTAAATAGAT TTGAACTTGT GCTTTGGA    4620

CTATTGATAA AACATTTTAC TTTGTACCTT CAAGGGTTCA GTGGAAAGTC ATCCATTC    4680

TATTAGAAGA GAGAAGAGAT AATGTTGTTG TCATGGCAAC TGGTAAGCTA TACTTAAA    4740

AAATAATTTA ATCATCTAAA AGTCATAAAG GGTCTAAAGT GCTTAATCTT TCAGAAAC    4800

ATAAAATATA GGAAGGAATG ATTGGGGAA AAGCCTTCAA ACTTATGCAT GAATTACC     4860

GTCAGTCCAC TTATTCTGCT ATATAAGCAC ACTGTAAGAA GAAAGTAAAG CATCAAGA    4920

TTCTTTTTAT TTTTTTGTGT TATTTTTTTT TTATTCAAGG ATATGGGAAG AGTCTGTG    4980

TCCAGTATCC GCCTGTTTAT ACAGGCAAGA TTGGCATTGT CATTTCACCT CTCATTTC    5040

TAATGGAAGA CCAAGTCCTC CAGCTTGAGT AAGTAATGCT TGCACTGCTG CAGCGTCG    5100

TTGGATAAGC AAGTGGAAAG AACATGGCAA GGCAGGATCT TACTACACAG GCTTAGCT    5160

GCTCTTCTCT CAGTGCAGTG GCCCTTTGCC CAGTTGTCCC TCTCTGTTCT ATCGATGA    5220

TATCAGAAGA TGAACGTGAA TCTAGGTCAC AGGATTACGT TTTGGGAAGT AACTTGAT    5280

TCTTTATTTC TATTTTTAAT TTTTGAGATA GGGTCTTGAT ATATATATAG TCCAGGGT    5340

TGTCGCTCTG GCCTCTTGCC TTGCCCTTCA TGCCTTGGGC TCACAGAGCA TGCACTAG    5400

CCCCTGGCTG CATTCATTAG TAGCAAACGA AGTGTTAGTG GAAGAGTTTA CATTCATT    5460

TGAGGTCTCC AATGCAAGGC TACCTGTTTT CTCTGATCAG GGTTTAAAAG GACTGATT    5520

TTTATGCTAG TTAGCTGTCT CAAATTCTTT TTTTTTGTT CTGCTCTCTG GGCTCCCA     5580

CTTGCAATGA GATATATATA AAAGTTTACT TTTTAAGATA TGTTTTTATT AGTTCTTT    5640
```

```
AAATCTCCTA CATGTTTTGA TTATAGTCAC CCCTCTTCTA ACCCTAAGTT CACCTTTC      5700

TTCCTTCTTG AAAGATCCAC ATTAAAGACT TGCCTCCTCA TCAGGCTTTT GAAGGAAT      5760

ATCAAGTTAT ATAGACACAA AAAGGAAGAA CATTAGAAAG ATGAGGAACA TAGGAGGT      5820

ATGTTTATGT GTGTATTCAT CAGAGCGTTT GTCTCTTGTA GGCTATCCAA TGTTCCAG      5880

TGTTTACTTG GATCTGCACA ATCAAAAAAT ATTCTAGGAG ATGTTAAATT GTGAGTAA      5940

TATATCATGT CACATAATAT TGTAAGATGT ATATAGAGTA AGAGAATTTT GTATATAT      6000

TTACTTATAT GAGTAAATTG CCCATATTTG AAAACATACT TTAAAAAGCC TTATTTCT      6060

AATAATAACA TAGTTCCATT TCTTCCTTTC CTTTCTTCCT TCCAAACTCT GCCAAACA      6120

CTTCCTTGTT CTCTTTCAGA TTGATGGATT TTTTTCCCAT TAGTTGTCAT TACATGGA      6180

CATGTTTATA CATATGTATT ACCAAATGCC CCGTTTTTTC TCAGCAGAAG TCATGTAA      6240

CTCCTTTATC CTTAAGATAA ATATTCACTT TTGGGGGGCT GGTAAGATGG CTCAGTGG      6300

GAGAGCATAC TGAGTGCTTT TCTGGAGGTT ATGAGTTCAA ATCCCAGCAA CCACATGG      6360

GCTCACAACC ATCTGTAATG AGAAACAAAT AAAAAAAATC CCTATGGGCC AGAACGAG      6420

GGGCCCCGGA GTGAGTGGGG TCAGAGCAAG AGGGAGAGAA AGGGAAGTGG ATTTTTAT      6480

ACTTTTTGTT TAAATTATTA TTGTATTTGT ATTATTAACT TGTCTTCCAT TATCTTAT      6540

TATCATATCT AGTATTATAT GTTATACATA TATATCGTAT ATATGTATTT ATATGTAT      6600

TACTTTATAT TATATGGTTA ATTTGCTATT ATGATAATTT TTATAAAAGA AGGCTAGA      6660

TTACTTATGG CATGTCTCTA CCATATAAAA GCAGATAAAA TTAAATTAAA AATTTTAA      6720

TAAAAGTTCT TTAAGTTTTT AATTTATCTA TTCCACTAGT ATTTTAGTGT CTATTACA      6780

CTAAACATTA TGTTTTCACT AGTAATTTAT TAGGCATGTA ATAAATTTTA TCGTATCT      6840

AGGAAATTGA TGCAGTTTTC TAATTACTGT AAGAAACAAT AAAAATAATG AAGGCTAA      6900

TCACTGTACC CAGGTTTGGA ATCAGTTCTC CGTCCGACTA GGAAACTGAT CTGAGATG      6960

CCAGTCAACT CCAGTGTATC CCAGTTTCTT GAAAATTAGC TGTTTACTTA CAGAGACA      7020

CTTAGGACAT CTCAGTTAAG AAACGGACAC TGGAACCTTC ATGGAACCAA AGAGCAGC      7080

GGAAAACTAA CACACCCCTG AAAACAAAGA GCATAACTGG GGGCTTGTCA TCGAGACT      7140

CAGGCTTTTA CTGTAGCTAC AGCAGCCAAC ACAGGCAGAC GGAGCCACAG AAGCAGAT      7200

CAGCAAGGAA TCTGCACATG CCTACAAAGC TCATCATCTG AGAAAGGCTC AAAGGTGA      7260

CAGTGGAAAA GAGACAATCC AGAATAATGG CTTATATGAA AACAATGGCC TTATAAGA      7320

AACAAACCAA ACAAACCAAA CCAAAACAAA CAAAACCCCC CAAACTAATA CACCACAC      7380

TATAAACATT TTTTGCTAAA AGCGAATTAT GCGTCCAAGC ATAAAATTGT GAAATGTT      7440

AGGAAAAGCA TGCCATCTTT ATAACCTTCA GTTAGGGAGA CTTCTTAAAT ACCCAAAG      7500

AAATCTATAG GAACAAACTA GCAGCTGGAC TTTTACAAAC TGAAACCTA CTTCTCTT       7560

AAAGAATTAT TGAAAAGGA AGAAAGGCCA TAAACTAGCA AAGTATATGC AAAGTACA       7620

TCCATACAAG ATTTCTACCT ATAATATAGA AATTACCACC AAAAGAGAAT TAAAAAAA      7680

TAAAGTGTCA AAAGATTGGA ACAGACACTA GCACAAAGAT ATACAAACAG CAATAAGT      7740

AAGATGCTTA TAATTGGT CACCAGGCAA AAACAAATTC AAGGTACAGT GAGATTCT       7800

CCAAGTGGCT AAAGCCAATG ACTGGCTAAG AAATGTCAGG GGTAGTGAGC AACAAGAC      7860

TTCACACACC ACTTCTAGGG ATGAGAGATG GTAGAATGTT TGTTTGGGGA GTAGACTG      7920

AGAAACCATA ATTTGGCTTA TAATTCCAGC TTAGTGGTGA ATCCTACACA TCAAGAAT      7980

TTATATTTTA TTTTGGTGAA TTGAAGATAA ATGAAAGGAC TAACATCTGA ATTATGTA      8040
```

```
TATATAAAAT ATTCCTTTGG ATTTTAATAA TCAGCATGAT GCATTACTTA AAAACCTA      8100

GAATGCTTCT TTCCAGTCTA GGGCAGGGAC CTTAGCTGAC CTTGGGTGCT AACTCTGC      8160

CCAGCCCCAC AATACCCAAA GGAAGCTCCA CTTCTAGGCG CTCTAACACG CCAAGTCC      8220

AGGATTCCAG GATCCCAGGA ACTTGGTCAC ACCAGGATCT CAGGGTTTTA GAGGAACC      8280

GGCTCCCAGG AGCTCTGACA CACCCAGGAT CTCAGGATCA CAGGATCACA GAGACAGC      8340

AACTCTGAGA AGGTCTGACA CGACCAGGAT CACAGGAAGG ACAGGCTCCA GTCAGATA      8400

GTGAAGGCAG GTAGCACTAT AGATAACCAG ATGGTGGGAG GCAAGGGGAA GAACATAA      8460

AACAGAAACC AAGGTTACTT GGCATCATCA GAACCCAGTT CTCTCACCAT AGCAAGTC      8520

GGATACCCCA ACACACTGGA AAAGCAAGAT TCAGATCTAA AAATCACTTC TCAGGATG      8580

GATAGAGGAC ATTAAGAAGG ACATCAACAA CTCCCTTAAA GAATACAGGA GAACACAA      8640

AAACAACTAG AAGCCCTTAA AGAGGAAACA CAAAAATCTT TTAAAGAACT ACAGGAGA      8700

AAAATCAAAC AGGTGAAGGA AATGAACAAA ACCATCCAGG ATCTAAAAAT GGAACTAG      8760

ACAATAAAGA AATCACAAAG GGAGACAACG CTGGAGACAG AAAACCTAGG AAAGAGAT      8820

GCAGTCATAT ATACAAGCAT CACCAACAGA ATACAAGAGA TAGAAGAGAG AATCTCAG      8880

GCAGAAGATA CCATAGAAAA CATTGACACA ACAGTCAAAG AAAATACAAA ATGCAAAA      8940

CTCCTAACCC AAAACATCCA GGAAATATAG GACACAATGA GAAAATGAAA CCTAAGGA      9000

ATAGGTATAG AAGAAAGTGA AGATTCCCAA CTCAAAGGGC CAGTAAATAT CTTCAACA      9060

ATTATAGAAG AAAACTTCCA TAACCTAAAG AAAGCGATGT CCATGAACAT ACAAGAAA      9120

TCCAGAACTC CAAATAGACT GGACAAGAAA AGAATTCCTC CTGTCACATA ATAATTGA      9180

CATCAAATGC ATTAAACAAA GAAAGAATAA TGAAAGCAGT AAGGGAAAGA AGTCAAGT      9240

CATATAAAGG CAGACCTATC AGATATAGGA CTAGACTTCT CACCAGAGAC TATGAAAG      9300

AGAAGATCCT AGGCAGATGT CATACAGACC CAAAGAGAAC ACAAATGCCA GCCCAGGC      9360

CTATACCCAG CAAAACTCTG AATTATCATA GATGGAGAAA CCAAGATATT CCATGACA      9420

ACCAAATTTA CACAATATCA TTCCACAAAT CCAGCTCTAA AAAGGATAAT AGATGGAA      9480

CACCAACACA AGGAGGGAAA CTACACCCTA GAAGAAGCAA GAAAGTAATC TTTCAACA      9540

CCCAAAAGAA GATAGCCACA CAAACATAAT TCCACCTCTA ACAACAACAA AAATAACA      9600

AAGTAACAAT CACTTTTCCT TAATATCTCT TAACATCAAT GGACTCAATT CCTCAAAA      9660

GGACATAGAC TAACAGACTG GATGTGTAAG CAGGACCCAG CATTTTGCTG CATACAGG      9720

ATGCACCTCA GTGACAAAGG CAGACACTAC CTCAGAGTTC AAGGTTGGAA ACAATTT      9780

CAAGCAAATG GTTGTTTCCC AAGAAACAAG CTGGAGTAGC CATTCTAATA TGGAATAA      9840

TCAACTCTCA ACCAAGTTAT CAAAAAAAAA AAAAGATAAG GAAGGACACT TCATACTG      9900

CAAAGGAAAC ATCTGCCAAG ATGAACTCTC AATTCTGAAC ATGTATGCTA CAAATGCA      9960

GGCACCCACA TTCATAAAAG AAACTTTACT AAATCTCAAA GCACACATCA CACCCGA     10020

AATAATAGTG GGAGATTTCA GCACCCCACT CTCAGCAATG GACAGGATCA CGGAAAC     10080

AACTAATCAG AGACACAGTG AAACTAACAG ATGTTATGAA CCAAATGGAT CTAACAG     10140

TTTATAGAAC ATGTCATCCA AAAGCAATAA ATATACCTTC TTCTCAGCAC CTCATGG     10200

CTTCTCCAAA ACTGACCATA TAGCTGGTCA CAAAACAGAC TTCTACAGAT TCAAGAT     10260

GGAAATCATC CCATGCACCC TATCATCAGA CCACCACGGC CTAAGATTGG TCTTAAA     10320

CAACACAAAC AACGGAAAGC ACACATACAT ATGGAAGCTG AACAGCGCTC TACTCAA     10380

TACCTTGGTC AAGGCAGAAA TGAAAATGAA GACACATCAT ACCAAAACTT CCGGGAC     10440
```

-continued

| | |
|---|---|
| GTGAAAGCAG TGGTAGGAGG AAAACTCATA GCTCTAAGTG CTTCCAAAAA GAAACTG | 10500 |
| AGAGCTTACA CTAGCAGCTT GACAGCTCAC CTGAAAACTC TAGAACTAAA AGAAGCA | 10560 |
| ACACTCAAGA GGAGTAGACT GCAGGAAATG ATCAAACTCA GGGCTGAAAT CAACCAA | 10620 |
| GAAGCAAAAA GAACTATACA AAGAATCAAC AAAACCAGGA GCTCGTTCTT TCAAGAA | 10680 |
| AACAAGATAG ATAAATCCTT AGCCAGAGTA ACCAGAGGGT ACAGAAACAG TATCCAA | 10740 |
| AATAAAATCA GAAAGGAAAA AGGAAACATA ACAACAAAGT ATATCTTAAA ATAACTA | 10800 |
| TGTTTGTTGA ATATCAATAG TTGAAAATAT TAAAATCATG TTCTACAAAC ATCATGG | 10860 |
| TATTATTGAT AATTTTTCTC ACTGTGCTTG AAATTAGCAT TTTCTTAATG TTTATGT | 10920 |
| AGTGTTTTTG CTATTTTGAA ATGTTTAAAA TATACTTACT GATAAAATAA TTTCTCT | 10980 |
| AGAAACACTG ATAATCTTTT TTCTGTAAAC TGATTTTTGG ACAATGTACA CAGATAT | 11040 |
| ATGTGTTTTA AATACTCTCT CACTATGTCA GGTGTTATTA TATAAAGGCT TTCAAAT | 11100 |
| TTTCTTAGTG ATTCTTTTTA AATATTTTAT GCTCTTTTAC TATGCCTAGC TCCCAAA | 11160 |
| TATTCTGTAT GTTTTGAAAC AATTTAGTAT TCAATATTAG GTACAGGATC CTCAGTT | 11220 |
| GATAGTATTA AATATTAATT AATGATATTT TTAGGATATG AAAGGATATG AATATAA | 11280 |
| TTGGACAAAA TTTTAAAGTA TTATCTGATA TCAAAATACT CAATATTATT GATATGT | 11340 |
| ATGTATAAAA TACATTTAAA TAATAAGTTT TAAAAAATGT CTATTGAACA TTTTGAT | 11400 |
| GTTATCATTC ATTGACTGCC TTTTTTTCCT ATTAGAGTGT TTCAATTTAT GTTTCTA | 11460 |
| TTGTTTGTCT TTACAGAGGC AAATATAGGG TCATCTACAT AACTCCAGAG TTCTGTT | 11520 |
| GTAACTTGGA TCTACTCCAG AAACTTGACT CTAGTATTGG TAAGTAATGA AGTAGGA | 11580 |
| CGGTGAATAC AAAGTAACCC ATTTATGGTT GAAGACCAGA TTCCAGTTTT GTTAAAG | 11640 |
| TATTTCAAAC ATTTGCTCCT CTAGGAAATT TCTAATCAGT TTTACATTTG TCCCATT | 11700 |
| CAATGCTGTA TAATTCCTCA TTCCATAGAG GTGGTACTCC TGGGTGGGTG TCATATT | 11760 |
| ATATAAGCAT GTATGTATCC CTGTCACACT CAACCCTTTT GAGGCTTCTC TGCTCTT | 11820 |
| GGCCTCCCAA CTCCTTCATG CAGGATGTGG CACACAGTTG TCTATCCTGT GCATTGC | 11880 |
| ATGAACGCTG AGTCTTGTTT CATATTCTGA GTCTAAATGA AATCAGTGTG TGGTTCC | 11940 |
| TTCTTGCTCG TCAGAATCGC CCTTCAAGCT CTAGAACAAT GCTGTTAAAT GGCGTAT | 12000 |
| TTAGAAAATA TAAATATAAA ATAGGTTAAA TGCTGTGATA TTGTTTATGC TGAAACT | 12060 |
| GTTTTTTGGT GGTGGAAGTG TGGTCAGGTT TAGCTAAGAG CTCCAAAGGA AACAAAC | 12120 |
| ATCCATATTC AAAACTTTCA TTTAAATTTT ATCCAACTTA TCAGATAAAA TTGTTTT | 12180 |
| AATTTGTGGG ATTTTCGTTT TTGAAGAATT AGGTATTAAG TAATTTCATA TAGGTTA | 12240 |
| TTTCAGTATT GTACTGGACT AGCTAGTGGA GTGTCAACTT GATTTAAGCT ATGGTCT | 12300 |
| AAGAGGAGGA AACTCAGTTA AGAAAATGTC TCCTTAAGTC AAGATGAAGG CAATCCT | 12360 |
| GAACATTTTC TCAATTACGG ATTGATGGTA GAGGGCCATT GTGGATGGTA CTATCTC | 12420 |
| CCTGGTGGTC TTGGGTGCTA TAAGAAAACA GGCTGAACAT GCCATGGAGA GCAAGCC | 12480 |
| AAGCAGCATC CCTCCGTGGG CTCTGCATCA GCTTGTATTG ATTGGTGTTG CTTGTTG | 12540 |
| CCACAGTAGA GAGAGGAGCT CACCAAGTTC CTAAGCCATC CTTTTTGGAA GGAGCAG | 12600 |
| GGTTCAGCCT TCCTGGGAAG GCTCACTCCA GTTACTTTAT TCAAGCATTG TTCAAGG | 12660 |
| ATTGGGGCTG GGAAAGGTTT CAACCACCAC AGTTGTTATC TTGTGTTTGC TGCTCAA | 12720 |
| ACAACATGAC CCACACAGAT CTTAGTCCCT TTTGACCATG GCTAGGCATA ATCAAAG | 12780 |
| AGAACTCCAG GTTTGCCAGG AGTGTCTTAG GACCAAGGTT GATGCAGCTG CAGGCCT | 12840 |

-continued

```
GGTAGTACTG AGTGCAGACT TTGCAGGGAG ACAACATTTC TTCAAATAAT CTCAAAA      12900

TTTCTCAGCC TCTACTCATT AACCCAAACA CAGCAGAGGC TTCGCTGAAA CATTTCA      12960

AAAGCTAGGC ACAAAGGCTT CACTGAACAT TTCACTTCAG GCTCCTGCCT CCAGGTC      13020

TCCCTGCTTG AGTTCCCACA TTGGCTTCCA TCAATAATGA GGATGATGTG GAAGTGT      13080

CCAAATAAAC CCTTCCTCCA CAAATCGCTT TGGTCATGGT AACAAAGACA TGTACCC      13140

CACTTAATAG TATTTCTCTT ATCAGGCATC CATGGGAGGA GGGGCCCTTG GTCCTGT      13200

GGCTCCATGC CCCAGTGTAG GGAATTCGA GGCTAGGGAG GCAGGAGTCG GGGGTGG      13260

GAACACCCTT ATGGAGGCAG GGGGATGGAG AATGGGACAG GGGATAACAT TTGAAAT      13320

AATAATGAAA ATATCCAATA AAAATAAATA AATAAATAAA TAAATAAATA AGGAAAT      13380

AAAAAAAAAC AAAACAAAAA GAGAGTAGAC TTTTATATTT CAGTATGTGT TGAAAGC      13440

AAAGAATGAG GACCTACATT AATATTTATG GAAATATATT ATCACAGTGT ACCTATG      13500

TCTCTCTGTT AGCTCTCATT GCCATGTTTT TGCCTGTAAT GGAAACAAG TTTGATG       13560

AGTCTGTAAT AGCTGGAAGG TGTTCCTTCA AGCATCTCTC TATGGGTTTA GCCTTAT      13620

TTTACCTTAT AGATCTATAG CCTTATAGAT CTACCTTATA GGTCAATTTC ATGGTTG      13680

CTAAAAACCT GGTTATCAGT AACTCTGTAT TCTGAGTATA TTTTTTTCCA CTTTCAG      13740

TTATTTGTTT TAATTTATAA TGATGTTAAA TTAATAACTC CTGTAAGTAA ATAAACA      13800

AGAGCCTTTG ACAAGTAGTT ATAACTTTTT ATGAGGTAAA TGGTCATTGC TGCCGAG      13860

AGGACACTGT TCAATGATTC TGTTTGCCTA GCATGTTCCA GGCCTGGCTT CAAACCT      13920

TCAGTTTCAC TTATTTTTGT TTTTACTCCA TGTGTTGGTG TTTGTGGTCA CAGGGTA      13980

TGAAGGAGAA GGGGAGATGG TCCTCTCCGT CAACCATGTG GGTTCTGGGC ATTTGCT      14040

ATGCCAAAGG GAAGTGGTTT TACCCACTCC CTCTTGCTCA CCTTAGACAC TGTATGT      14100

GTTTATTGTG CTTTTCTCCC CCCCCCCCG TGAATCAGTT TAGGAGAATG ATACAGG       14160

ATCAGATAGT CTGACCTCCC TTCTGTTTTA AAAACATACA CACAAGTGAG CAAACAA      14220

CAGATAACAC GTGTAAGTTT TTCATCACTA GAGCAGAATT GTTTGCTTTT AATAGAT      14280

AATATTTCCC TGGGTGATTT AGAAAAAGGG ATAAGGAAAA TGAAAATTAT TTTTTTT      14340

TATTTCCACT GGCTTTTGTT TGCAGGAAAC AGTAAAAAGT CTACAAAAAT GAATATA      14400

GGGATGTTAT TTGTACAGTA GTCTGACATT TAACTAATCA GATTTGTCAT TTTTAGG      14460

ATGTTACATT TTTTTTTAAA GTAGTCCGGG TCTATAACAG AAATAGCAAG CATACTT      14520

GGGGTGCCTT CCCAGGCGTA CTTGTGATTG TCTTTTAACT TTGGGAATGA GACTTGA      14580

GCAGATGCCT AAATGAAATC TCTACAGGAC CTTGGAAGAC CCTTGAACTT TTGCATT      14640

AGTGAATTTT GCCAAAGCTT GTCTGAACTA ACTGTGTAGG TGAAAGTTCA ACTCTAT      14700

CTGCTTGTCA GATCTCTTTT AACTTAAAGT CTAGCCATGT TAATTTCTAC ATTCAGA      14760

AGTGTATGAG TGACACTGGA ATTTCCGCAG TCACTCAGTG GTATAAAGTC AGCGTTT      14820

TCTTCGCTTC CTTCCTTCTC GCAGTCTGAG GACATTGGTG TAATCTCAAT GAGTTGC      14880

TGTTTCTTTT GTTTCCTCTC TGGATTGTGA GACCCTTGAG GTCAAGTATA CTTTGGT      14940

CAAGAAAAGG GTTAATTCAG TTTTCTTATT TAGATAGAGC CTCCAGCAGC TCAGGCC      15000

CTTGAACTTT CTATGTGGCT GAAGAGAGCC TTGAATTCCT GATCCTGAAT TACATGC      15060

TGGCTCTTAA AAGGGCTTTA AATCATAATG ACCATGTAGT AATAACCGCT GAAGTAT      15120

TTTATTAAGC TCTTTTTGGG CCCATCCTTA TCTGAGTGTT TTATGTGAAT GTTCTAA      15180

AACCTTAGAG GAGTAAGAAG TATTAGGTGC TGTTACTACC TACCGTGTTT TATTTTT      15240
```

```
TACGATGCTG TTTGTGCTGC TGGTGCTGCT GGGGGTGATG GTGGTGATGG TGATGGT      15300

GGTGGTAGTG GTGGTGATGA GTGTTTGTGGT GGTAGTGGTC AGTGTGTGTG TGTGTGT     15360

TGTGAAATAC CACAGTGTGT TTGTAGAGGT CAGAGAACAC CTGTGTAAGT GGGAGAC      15420

TCTCTCTGTG GTTTCTGAGG GTTGAACTCA AGTTCTCAGA CTTTTACCCA CTGAGCC      15480

TCAGCAGGTC CACGATGTAG TTTTGAGGAA ACTGAGAACT GAAAAGATTT GTAGCTT      15540

CAAGGCTTTG TGTACAGCTA ATCTAATTCT AAAGCACATG TTTTAAATCA TCTCACT      15600

AGGGTATATC AGCAAATAAC AGAAGGTTAT TTTTCTCTTA AAAGTACTAA TTTGATA      15660

GTAAAGGCAT TACTAGTCAG TTCTTTGAAA TGTCTGAAGA TGTCATGATG ATTACAT      15720

GAAGCCCTTT CAGATGCATT AAGACACCAT TGATCTTGTA TTAGTGTGTG GTGTGGG      15780

CCGTGGAGGG TTATGTTCTT TTTCACTACT TACTTTGCAC ACGGTGGGAA TTAGTTC      15840

CCAAGCCGTT TTATGTTAGC CAATGTGGAT GTCATCTCGT CTTCAGTTAT TGGCATT      15900

GAGGAACTTC CTGTAATATG ATATGTGCCG GATTGCAGAT AACGATGTAC TTAATCT      15960

TAGAAATGTG CTGACTATTT GTCTCCGTTG ATAGCTAATC TATGAGATAA GATTAAC      16020

ATTGCCAAAA AGAAATGGAA CAATTCTTTT GAAAGGATAT TGTTGTAGAT GTTATAA      16080

ATAATTTTGG GACACAGTAA TAATAAGCAA TTTATGTCTT TGAGGAATAG TAATGAA      16140

TGAAAGATAG TGTGTTGTTT CAATTACGAC GTAAATATTT CCTGTATGCG AACCTCT      16200

ATTCATTTCT CCTCTTACCT CCTATTCTGC CTTCGGAAGT TTGATGTTAT CTGGTAT      16260

TTATGCTTCT TATATGTGTG TGTGTTTGAG CCCAATACTT TGATTTGACT TATACTT      16320

GTGAGGTATA TGTTCTAATA GGAACAGACA ATATTGACTT AGCTAGCATT TTCCTTC      16380

GCCTTATTTC TCCTGTATAT TTTCTTCTGT GTAGGCATCA CTCTCATTGC TGTGGAT      16440

GCTCACTGCA TTTCAGAGTG GGGCCATGAT TTCAGAAGTT CATTCAGGAT GCTGGGC      16500

CTTAAAACAG CGCTCCCATT GGTAAGCCTT GCCAGATCTC ATGCCCCCAC CCCACCC      16560

TCAGCTGAGG ACTGACCCCA GGGCTCCTAC CACCAGGCTA GACCCTCAAT CCCGAAT      16620

CTGAAGTGAC ATTTTCATCA AGGCCTTTCC AGGACTGGGT AATGTCCACC CATCTCA      16680

CTTCTCTATA AAAGGGATCA GATGTGAGCA ATGGGGCATA TTTAGTTTTA AAATTTT      16740

AATTCTCACG CTGGCTTCCT TTTGAGGTTG ACGTGTAGCT TACTAAGGAA TACTCTT      16800

AGGAGTGTCC AGGCTGTGAC ATTGAGCTAC TCCAGTGTCA TCTTCAAGGT TCTCCCT      16860

GAACCACAAA ATTGTGTTAT TCAAAGACAT CACAAAGATG CCTCTGTTTT AGTTCAC      16920

TGACTTTGTG TTGTGCCACA TTCCTACTGT CAGGGCACGG GCTGGATGCT CTTCACT      16980

ACAAGAGCTG GAAAACAAGT TTTGAACATG GCAGATAAAA ATGGCAGTTA CTATTCC      17040

GTGAAAGGGG ATACAGTTTC AAGAATCCGT GGATGCCTGG AAACACCCCC TCAGTGT      17100

TTATGCACAG TAGAAGAATT TTTAAAATGA CTATCTGTGA CAATATACTA TAGCAAA      17160

GACCACAGTC ATTATTCTTG ACCGCGTGGC TCATGATTAA GTAGAGTAGG TAGCACC      17220

CCACAAGCAC TTCCTAGTCT CCTAACTGAG ATGGTTAGTC AGTAGGTAAT GGGGGAG      17280

GTGGATTGTG TGGAAACTTT GGACCAAGGG GAGAATGGGG TGATATCTTT GAGAGTA      17340

TGCAGAATTT CATCATGTTA CTCAGCACGC CTTTAATCCC AGCACTCGGG AGACAGA      17400

AGGTGGATCT CTGAGTTTGA GGCAGCCTAC TTTAGTCCTG TCTTAGGAGA AAGATAA      17460

AAAATGTAAG TTGGGTTTTA GGTTTTTTTG GTTTTTTTT TTTTCTATTT GTTTGTT       17520

GTTTTGTTTT TTGTTTTTTG GTATAACTTT TCATTTAGTA TATTCAGATT TGGTTGT      17580

CAAGAATCTG AAATCAGAAA ACGCCATTGT GGATAGAGAA GGTGGGTGTG AAGTGGA      17640
```

```
GAGGGCGGGT GTGTGGTGGA TAGAGATGGG AGTGTAGTAG ATGGAGGGGG CGGGTGT       17700

GTAAATGGAA AGGGCGGTGC GTAGTATAGT ATGGCTTTCA CATACAGTTC TCTTTTC       17760

AATAGTCCAT AAAAAATGTA GTTACCTGGT GTTCCTCACT AATGGCCTCT GTAAAAT       17820

CTGGGGACTG CGATAGTTCT ACTTATCACA GTTTGTAGAA ACTTTTAGGT TGTTTGT       17880

AGTTAGGATA TTATGAATGG GGATACTGTA AACATTGTC TATAGTCCCA GGGTCCA        17940

CAGCGGTTAC AAAGTTTGTG AACATAAGTT TTAGTTTTCT GGGATAAATG ATGTTCT       18000

TTCTATGGGA AGTGCTGGTT TCACTTTTAG GAAGACCCCA GTGCTACTCT CTAGACT       18060

TGCTCTGTTT TGTATCGTCC CCTCCCCAGC AGCTTAGGAA CAATAGCTTC TTCTCTT       18120

TGCCACTGTT TAGTCTTATT ACTATGTAGT ATTTTAGCAA TTATGATACG AGTGGAG       18180

TAGCTTGTGT TTTCAATTTG CATTTCTCTA ATAGCTAGTG GTGTTGAACA TCTTTTG       18240

GCTTCTTATT TGGTTAAATG CCTAGTTTAA TTGGGTTGTA TTTTTTCTGT TAAGCAC       18300

GGGGAGGTGG AGGGAGAGAA AGGGAGGGAG AGGGATAAGG AAGGAGAGGA GAGAGAA       18360

AGGAGAGAGG GAGGGGGAGG GTTGTGCTTA TGCACATATA CCTCTGCGGT GTGCTCT       18420

GTGCAGCCCC TGCAGGCGCC AGATGTTGAC GCTGCTGTCC TCCTCTGTTA CTCTCTA       18480

CATTTTATTT GAAACACAGT CTCAGTAGCC AGGGAGCTCC TCATTGTGC TAGACTA        18540

GGCCACCAAG CCCCTGGGCT CTTCCTACTT TGGAACATTG GCTCCTAGG TGTGCAC        18600

GTGCCTGGCT TTTCTGTTGG TTCTGGGAAT CCTTGCTCAT GTCCTGATAC TCACTGA       18660

ATCTCTTCAG TCCCTCTGTT AACTGCTAAG AATTAAATGT TTATAAGTGT GAGTTAT       18720

TTGGATATTG AGCTTGTAAA TATTTCTTTG TAAATTTTAT TTTTTTCTCC TATTTTC       18780

ATCTTTTATA AAAAATATTA TAAGTTGGGT AAAATTCAGA ATATTTTTTT TCCTTTA       18840

GCTTTCTTTC TCAGTCTCAG ATCTTGAAAG TTTGTCCCTG TAGTTTTTCC TAAAATG       18900

ATGATGTAAA TTTAGGTCCG ACAGGGTACA GAGATGTCAT GGCAGGTAAA GAGCTTG       18960

TGCAAGTGTG AAGACATGAG CTTGAGTCTG TGAAGTACAG TGACATGTGC CCCATCC       19020

ACTATATGGC AGAGGAGACC CAAGGGCCCA CTCCTCCCCT AACTGGGTAA AAAGAGG       19080

TTTTATCTAC TTAATTGCTT TTGCCTCTTT GTTGAGAATC TTTTGAGTGT GTTTTGT       19140

CCTGTTTCTC TGGGCTGTAG TCATTTGGAT TGAATTAACG AAGCGGCCTA TATTTAG       19200

CTGGTGCTAG AGAGACGGTG TGCACAAGCC TCACAGTTAA ATGGGTCAAA CCAAGAG       19260

CATTCAAAGT TCTTATCCTT TTGGCGAGAT TGTCTGACTT AGTTCCCTTA ATCATCA       19320

TTACACATTA ATAGCAAATT GCTATGTTTA AAATGACTTC TTTCTGTTCG GGTTTTC       19380

TCAAGATTTG ATTGAGCAGT GATTAAGTAA GTCAAAAACA GTAGGAGACA GGTAATG       19440

CAGCTAGCAG ATACTACATC AAAGGAAAAG AAACTAATGT ATTTGGGGTC TAAGTAT       19500

TCTGGCCTTG GGTCAGACAC TCTTGTCTCA GTCTTCAGGA CTGTTAATTA AGTTAGC       19560

AATGCCATCA TATTTCATCA TTTGTCAAAG GACAGCTCAT TCCCCTTGCT TTCTTTC       19620

GCATAACCTT CTCCTCAAGT CTCTTCTGTT CCTTTGTACC TTCTTGTTTT ATTAGGG       19680

GTGTCCTGGT CCCTGTTTTA GACTTACTCT CTCTCTCTTC TGTGCTCTCT TTTCTGT       19740

TAATTGGATA CCATCCATCC CATTATGGAG AACCCTCAAA TCTACAACTT GGATTAG       19800

CAGATGTGAC TGAGTTCCTC CGCCTACTTA CCGGCACTTG CTGTTGTACT ACATTTT       19860

TTAGCAATTT TATTGCATAT AAATCACACA TATTATAGGG GATTTATAGG ATATGTA       19920

ATACACAATT GTCAACTTGA GGGTTTGCTC TTTGGGTTCC TAATAGGTAT CTCAAAC       19980

ACCCCTCCAA AACTGGCTCC TGATGTTCTT CGCACTCTGA GTGCTTTTCC CGCAGAC       20040
```

```
ATCACCTTGT TTAATAGCAG CACCAGAGTG TTTTGCTATG CAGCCCGGAC TAAACAA    20100
ATCCTCCTGC CTCAGTGTAC CCAGTTGCCT GGAATGCAAG TGTGTACTAC TCTGCCT    20160
AGCTTGATTA TTGTTACCAC TCTGCAGCAT ACATTTCACC AGTAAGGAAA GCCTGTG    20220
GATCTTCCGA GCCTATACAG CTGCTAATCG CTTCCCTCTT GATCCCTGCC GTAGCCC    20280
TGCTGGCTTA CATCTTCCTT CATGTAGGCT GTTACAATAA TCGCCTGGTT TCCACCT    20340
GTCTATTTCT ATACAGCGTT CAAAGTGATA CTTCTGAATC TGTCCCCTAG TTCTGTG    20400
TCTGTGCAGG ATGTGATGGC ATCGCCCCTC ACTGAGGTTA TGCTATGTCG TCTTTCA    20460
TCATGCCCGA ATGGTGATGT TAGCTTCTTA ATGCAATCCA TCAGTGAATT AAGTCTT    20520
GTCAGGTTAC AGCCATCGTT ATCTAATCAC CTCTCCGTGG TTGGGTCTGT GACTTGG    20580
TTTTCACCCT TCTACACACA GAGAGGGCAG TTTGTATCTA AACCATAACA AGAGGGA    20640
TTTCTTTTTC TTTTTGTTTA TATAAGCAGG GGTACTATCT GACTCATAGC AGTTGCT    20700
TAATTACACG AATCAATTAA TTCTGGTCAG AAAGCTGGGA ATTAGCGAAG TAACTTT    20760
ATATAGGTAG TTATAAAAGA GTTGGGTAAT AAATAGCTAT ACCATAATAT ACTGTGC    20820
TTTCAACACA AATGATTTGA AGAGACAAG CTATATTTTC TACCCTTAGG TAGTTCA    20880
CCCCGAGAGG GAGTTGAGAT CCACATCCAG GAAAGTAGAG GCAATAGAAA CAAACTG    20940
ACCATGCATG GAAAGATGAG TAGTGCCCAT AGCACAGTCG CACATGGGAG GGCAAGT    21000
GGTGTCCCAC AGTGCAGTCA CTGAGCGCTG CTCTGAAGGA CTGGTTCCCA CTGACTT    21060
AAGATTTAAT GAGACAGAGC GAGCTGTGGA ATTGAAAAGC AAGAGGATGC TTGTGTA    21120
CTTTCTTAGG CCTTTGATTC TAGGATTGCG TTAAAGGAGT TTTAAATAAT TTAAGTG    21180
CTCAAATATT CTTCAGGTGG AAAAAAAAAG AATTAAATCT TTTATTATAT CTAACTC    21240
ACATAATGAG ATCGCTTTCA GTTCTTGCAG TGATGAAACA GCGTATTCCT TCAGCTG    21300
GTCTTGGCAG GTTGTTCCTC CTGCAGAGGC CGAGGATCCT TAGCCCCTGT GCTTTTA    21360
ATGGACTCTG TTGGGGGTGG TAAGAAACGC CACCTGGTGG ATATTCCTTT TCTTATT    21420
CTTGATCTTA CTGTTTTAAC CCTGTTATGC TGGGATTACT GTTGGGTTCA TTACACC    21480
TTAGTATAGC AAATCTAAAA GTGCTGGAAA CCACCAAACA ATTAACACAG AGGACCC    21540
TGGAAGGAAT CACAAAAGTG AGCCCAGAGA GGTGAAAGCC AGGTGAAAGT TCTGCAT    21600
CGTCAAAGTT TATATCTAAC CAGGAGGACG GACTTTTGAA GACTATGAGG TATATTG    21660
CTTCCCACTA ATTTGTCGTA AGGACCCATT AAAAAGATCA GAATAGTAGA CACTAAA    21720
CTGGAAGAAG AGATTAACTA AAATCTGTGT GCAGAGTGTG AAGTAGTTAT GTCATCC    21780
TTAGAAAAAA GATTGTTATG TTTTCTTTCA ACCGTTGTTT CATGGAGCAT GTAGTTA    21840
TTCATCTCAA TGTACAGTGT CATAAGATTA ATCTGCATTA TATATTCATT GGGTTTT    21900
GCTTACTTTG TCAACAACTG GTGTCTCTTA CCAAGGAAAT CAAGGCAGGC AAACTTA    21960
AACAAATTCC TGGTGCTAAG TGCTTGATAT ATGTAGACAC CAGTATAATT CAGCACA    22020
CCAGCTTTCT TCTCAAACAG GTTACACTAT TTATAATTGT GCTGTAGCCA CAAAAAC    22080
CTGGAAATAG CCCATCCAAC AAGGGCATAT GGTCCCATTT CTCAGTACTG ACCCATG    22140
TATTTGTAAG CATTGTCCTT GACTAAAATT TTCACATTAT AAAATGCTGC AGACTTC    22200
GGGATCCGTT CTAGTCACAT TCATTTTCAT GAAGACTGTT ATTTTTATT CTACTTT    22260
GTTGGAAGAG CAGTATTCCT CTCTGTGTCT TTGGAATGTT GTAGTGAGTT TACAATA    22320
TCCCTGCTAG CAGTCTGCTT GACTTTTTGA GGACCTTATA AGAAAATGA AAATTTT    22380
TAAAAGATCT ATCAATCTTG TAGCTCTGTG TCTCTCACTT CACTTTTCCT TAAGTTG    22440
```

```
CCTTGCTGGA GTCAGTGGGG AATGCGCTAG CATTTGAAAT TCTCCACCAT TGACATT    22500
ATGCAGAAAG AAATGTCTTC TGTTGTTTTG TGACTGCACT AGTTATAAGG AACATTT    22560
GTGCTGGCTC TAATACCCTG AATAGAATTA AGCACTTAGC ATGCTTTTGT AGATATG    22620
ATGTGTTTTG TGTGGAGTCC AGGTGTGTAT AAAGACTACA GGTCATTCTT GGGTGTT    22680
CCTCAGGTAC AATCCACATT GTCTTTGAGA ACAGGATCT TTCACTGGCC TGGAGCT     22740
CAAGTAGGAT GGAGTGACTG GCCCTAGAGT CCTGGGAACC TCCATATTTC TTTTATA    22800
GGCATAAGAC CGCTGTCCTT TTTCTTTGAT TCTTAAAATA TTGTTCAGCC TCTTTGC    22860
TGCAAAGGCG ATCTATCAAT CAGTAAAGTT CTGGCCTGAG AAGTCTGTTC AGGAAGA    22920
GCCATTGGCT GAGATCATCT ACCCAGTGCC GGTATTACAA ACTGGAATTT CAAGTGT    22980
TCACAACATC TAGGTGTGTG TGTGTGTGTG TGTGTACACA TATATATGTA TATATGG    23040
TGCCCAGCGT CCTGAAGGCG CTGTTTGACA AAGTTCCAGT TCTTGGACCA AGCCTTC    23100
GCCCTTGGTG GATATTCGCT GCACACCTCT TGCTAGTCTT ATGTTTCTCA CTGTTAA    23160
CCTCTCTCTG AAAGCTAGAG GTGGGATAAC AAGAAGCTAG TGTAAACAAG AATCAAG    23220
ATTAAAGTTC CCTGGGGGGG GGGAAGTTAT GCAGAAAATT GAGTCTCTTC TAAGAAG    23280
TTTCTTAAAT AAACATTTAG ATCATTAATG AATGTTGTTA GTAAGCATGA GATAGAA    23340
TTGAGAAGAA TTATTAAAGA AGTAAAACTT AGGGAGAACT TAGAAGTTGA GAAGTTG    23400
TTGGATTGCT AGGTTTTTAA GGTTCAACTT GAGAAACGAG CAGTTTGTAT GTATAGG    23460
GGATTTGGAT CATGCAGGTT TATGACAAGC CTCGGTGCCT TCCTGAAGGC AAAAGTA    23520
AGGTTTAGGA ACCCTGATGT TCTTCTGTTC TTCACAGAAT TGTTGTAAAG ATAGGGA    23580
TATTGAAACA AGGGTTCAAG ACAGAGACAC AGAAGAAGGC ACTCTGGCTC AGTGAAC    23640
CTGCCTTCCT GAACATGTAA GGTTAAAAAT GTAAATTCCT AGGAAACTGT TATATTT    23700
TTTAAAATGT TAGGTTTTGT TTGTTTGTTT GTTTGTTTTG TTTTTTAGTT TTAGTTT    23760
TTTTTTTTAG ACAGGGTCTC ACTGTGTAGC TGGGGACAAG CTCCACCCCT GTTCCCC    23820
TCCTCACCCT CCTGAGTGCT GGGATCACAG GCGTGTGCCA CCACCCCTGT CAGGGTC    23880
TACACACCCA GGAGTCCTTA CTGTCAGGCT GTGTCTGTTA TCGTATCTTA TATCAAC    23940
TAATCAACCA TTGTAATGCT TGATTAGAGA ATCTGATTTC TTCAAAACAA ACAAGGC    24000
GCATGACTTA ATCACTACAT ATACATTCCT AACGCAGAGA GCAGTCGGAT TATTGGC    24060
AAGATTAATG TGGGGTTACA TTTTAAAGTG GTTTCACAAA TTTAAAAATA GACAATA    24120
AAAATTATCC TAATTACTTG GTTTCATTGA GTTTATTTTT GTATGACTTT GGATAGG    24180
TAATCTAATT AAGTTATTTT AATCGTAAGA GTAGCTGTTT CTTAATTAAT TTACTGC    24240
AGACCAAACC CAAGGCCTTG ACAGGCTCGT ACATTCCCAA TGAGCCATGC CTTCAGC    24300
TTAACTATTC CTTTCTGTGT GTGACTGAAA ATAAGCTTTA TTTTTCTAAG CCAACAA    24360
TGAAATAATG CTTGAAGCTT TGTCCAAGTC TATATTATTT TATGGGTAAT ATTTATT    24420
TATTGAACAC TTTTATTTTT TAACTATGAA GGTCTTTTAT TTTCATAGAT ATCTATT    24480
GTAAAAATTT AAAGGTAATA AACTATGATA AATTGAGCTA AAGATGTGGC TCAGTGG    24540
GATGTTCATA TTGCTCTTAC ATGAGAGGAG AGTTCAATTC CGATCACCCA CATTAGG    24600
CTCACACCTA ACCATAACCC CAGCTCCAGG GGTGTCTGAA AGCTCTGGCC TTTGAGG    24660
ACTTCACACA CACACACACA CACACACACA CACACACACA CACACACAAA GTAATAA    24720
AAAATGATCC CTAAGTACAT AAATCATAAT TGAAGTAACA TTCAATGTTG TTATGGA    24780
TCAGCTTATT GGGAGGTTAT GTAACTATAA TATTTACATT TTTAAAGAAT AGAAAAA    24840
```

| | |
|---|---|
| TATTTCTATA ACAAAGCTAA CTGAAACAGT AGAATATAAA AGGCAAAAAC ATTGATA | 24900 |
| ATATTTTGTG AAATTTAAAT AAAAACCAGC AATCAACTGA AACTGAAAAT ACCATAA | 24960 |
| ACAATGCTCT TTCTTAGGTA TTTCTTAGTA GTTTTGTTTC GCATTCTTAA TTTACAT | 25020 |
| TGTATAAAGA AGAATAAACC GAGTTACTGA ACAGAGCAGC AAAGCTTGTA ATCTAAA | 25080 |
| TAAAGATGTT TATGTTTTAG TTTTCGAATT AACAATTTAT AATTCTGAAG ATAATTT | 25140 |
| CTTAATTTGT TTATTATCTA AATGCATTTT ATACATCAAC CATATTAATA ATATTGA | 25200 |
| TTTTGAGACT CAAATAATAC ATAAAAAATT TGTTCAACTT TTATTTTCAT ATCCTGA | 25260 |
| TATCATTAAT GAATATTTAA TACTATCCAT AACTGAGGAT CCTATATCTA ATGTTAA | 25320 |
| CTAAATTGTT TCAAAACATA CAGAATATGC TTAGGGAGTT AAGCATAGTA AAAGAGC | 25380 |
| GAATATTAAA AATGAATCAT TAAAAAATAC ATTAAAAAGC CCTTATATGA TACCACA | 25440 |
| CATAGTGAGA GAGTATTTAA AACGCATTAT ATATCTGTGT GCATTGTCTA ACAATCA | 25500 |
| TACTTAAAAA AGATTATCAG TGTTTCTAGG AGAGAAATTA TTTTATCAGT AAGTATA | 25560 |
| TAAAAATTAC AAAATAGCAA AAACTCTTTG AAGTTAACAG TAAGAAAATG CTAATTT | 25620 |
| GCACAGTGAG AAAAATTATC AATAATATTT CCATGATGTT TGTAGAACAT GATTTTA | 25680 |
| TTTTCAAATG TTGATATTCA ATAAACAGAA AAGTTATTTG AAGATATATT TCATTGT | 25740 |
| GTCTCCCTTT TAATTTTTGA TTTTATTAAT TTGGATACTG TCTCTATGCC CTCTGGT | 25800 |
| TCTGGCTTAG GGTTTATCTA TCTTGTTGAT TTTTTTTTCA AAGAACCAGC TCCTAGT | 25860 |
| GTTGATTCTT TGTATAGTTC TTTTTGCTTC TATTTGGTTG ATTTCAGCCC TGAGTTT | 25920 |
| TATTTCCTGC AGTCTACTCC TCTTGAGTGT TTTTGCTTCT TTTAGTTCTA GAGTTTT | 25980 |
| GTGAGCTGTC AAGCTGCTAG TGTAAGCTCT CTTCAGTTTC TTTTTGGAAG CACTTAG | 26040 |
| TATGAGTTTT CCTCCTACCA CTGCTTTCAC TGTGTCCCGG AAGTTTTGGT ATGATGT | 26100 |
| TTCATTTTCA TTTCTGCCTT GACCAAGTTA TCATTGAGTA GAGCGCTGTT CAGCTTC | 26160 |
| ATGTATGTGT GCTTTCCGTT GTTTGTGTTG GTATTTAAGA CCAACCTTAG TCCGTGG | 26220 |
| TCTGATGATA GGGTGCATGG GATGATTTCC ATCATCTTGA ATCTGTAGAA GTCTGTT | 26280 |
| TGACCAGCTA TATGGTCAGT TTTGGAGAAG GTTCCATGAG GTGCTGAGAA GAAGGTA | 26340 |
| TTTTTGCTTT TGGATGACAT GTTCTATAAA TATCTGTTAG ATCCATTTGG TTCATAA | 26400 |
| CTGTTAGTTT CACTGTGTCT CTGCTTAGTT TCTGTTTCCG TGATCCTGTC CATTGCT | 26460 |
| AGTGGGGTGC TGAAATCTCC CACTATTATT GTATCAGGTA TGATGTGTGC TTTGAGA | 26520 |
| AGTAAAGTTT TTTTATGAAT GTGGGTGCCC TTGCATTTGG AGCATACATG TTCAGAA | 26580 |
| AGAGTTCATC TTGGCAGATG TTTCCTTTGA CCAATATGAA GTGTCCTTCC TTATCTT | 26640 |
| TTTGATAACT TGGTTGAGAG TTGAATTTAT TCCATATTAG AATGGCTACT CCAGCTT | 26700 |
| TCTTGGGAAA CAACCATTTG CTTGGAAAAT TGTTTTCCAA CCTTGAACTC TGAGGTA | 26760 |
| TCTGCCTTTG TCACTGAGGT GCATTCCTG TATGCAGCAA AATGCTGGGT CCTGTTT | 26820 |
| CACCCAGTCT GTTAGTCTAT GTCTTTTTTT GAGGAATTGA GTCCATTGAT GTTAAGA | 26880 |
| ATTAAGGAAA AGTGATTGTT ACTTCCTGTT ATTTTTGTTG TTGTTAGAGG TGGAATT | 26940 |
| TTTGTGTGGC TATCTTCTTT TGGGTTTGTT GAAAGATTGC TTTCTTGCTT TTTCTAG | 27000 |
| GTAGTTTCCC TCCTTGTGTT GGTGTTTTCC ATCTATTATC CTTTTTAGAG CTGGAAA | 27060 |
| ATTGTGTAAA TTTGGTTTTG TCATGAAATA CCTAGCAGCT TGACAGCACA CCTGAAC | 27120 |
| CTAGAACTAA AAGAAGCAAA TACACCCAAG AGGAGTAGAC TGAGATTGGG AGTTTTG | 27180 |
| GGGCTGGCAT TTGTGTTCTC TTAGGGTCTG TATGACATCT GCCTAGGATC TTTTAGC | 27240 |

```
CATAGTTTCT GGTGAGAAGT CTGGTGTAAT TCTGATAGGC CTGCCTTTAT ATGTTAC      27300

ACCTTTTCCA TTGCTGCTTT TAATATTCTT TCTTTGTTTA GTGCATTTGG TGTTTTG      27360

ATTATGTGAC AGGAGGAATT TCTTTTCTGG TCCAGTCTAT TTGGAGTTCT GGAGGCT      27420

TGCATGTTCA TGGGCATCGC TTTTTTTAGG TTAGGGAAGT TTTCTTCTAT AATTTTG      27480

AAGATATTTA CTGGCCCTTT GAGTTGGGAA TCTTCACTCT CTTCTATACA TATTATC      27540

AGGTTTGGTC TTCTCATTGT GTCCTGGATT TCCTGGATGT TTTGGGTTAG GAGCTTT      27600

CATTTTGTAT TTTCTTTGAC TGTTGTGTCA ATATTTTCTA TGGTATCTTC TGCACCT      27660

ATTCTCTCTT CTATCTCTTG TATTCTGTTT GGTGATGCTT GCATCTCTGA CTCCTGA      27720

CTTTCCTAGA TTTTCTAACT CCAGGGTTGT CTCCCTTTGT GATTTCTTTA TTGTTTC      27780

TTCCATTTTT AGACTCTGGA TGGTTTTGTT CATTTCCTTT GCCTGTTTTA AAGTGTT      27840

TGGTAATTCT GTAAGGAATT TTTGTGTTTC CTCTTTAAGG GCTTCTAGCT GTTTACC      27900

GTTCTCCTGT ATTTCTTTAA GGGAATTATT TGTGTCCTTC CTAACGTCCT CTATCAT      27960

CATGAGAAGT GATTTTCGAT CTGAATCTTG CTTTTCCAGT GTGTTGGGGT ATCCAGG      28020

TGCTATGGTG GGAGAATTGG GTTCTGATGA TGCCAAGTAA CTTTTGTTTC TATTGTT      28080

GTTCTTCAGC TTGCCTCCCG CTATCTGATT ATCTCTAGTG CTACTTGCCC TCGCTCT      28140

TGACTGGAGC CTGTCCTTCC CGTGATCCTG GTTGTGTCAG AACTCCTCAG AGTTCAG      28200

TCTCTGGGAT CCTGTGATTC TGGAATCCTG TGATCCTGAG ATCCTGGGTG TGTCAGA      28260

CCTGGGACTC AAGCTGCCTC TAGGAACCTG AGATCCTGGT GTGACCAAGC TCCTGGG      28320

CTGGGATCCT GGGATCCTGT GGACCTGGGT GTGTTAGAGC TCCTGGGAGT AGAGCTT      28380

TTGGGTGTTG TGCTACTGGC TGTGGAGTTT GCTCTCAAGA TCTGCTCTGG GCAACGG      28440

AGAGTGGATG GGACCTGTGC CGCTGGTCAG GTGGAGTTCC TGGGTGCCTG GGTTCCA      28500

CTCCCAGTTA CTCCCGGTGT TGGGGCAGAT GTTGTGCCCT CCTCACCTCT GATCCTA      28560

TCCTGGGAAT GTTTAGGGCA CTTGGGAGTG AGCTTCCTCT GGGTGTTGTG GGACTGG      28620

CGGAGTTAAT GCCCAAGGTC TCTGCTCAGG GCACTGGCCC TGACTGGAAG GAACCTG      28680

CAGTGGTGGG GCGGATTTCC TGGGCACCAG CCCAGACTGG AACAGAACAC TTTTATT      28740

ATTCATTTAT ATTGTTCAAA ATAATGAGTT TCGTTTCATT TCCATAACAT ATTTAAT      28800

CTTTGGTCAT ACTTATTCCC TAAGAGATCG TATTTTGTTT AATTTTAAG TCAAATT       28860

TACATATTTC TTTGTAAATT AGCAAACTGC ATACACATTT ATACTTAGAT ACAAGAT      28920

TGCTTAAATT ATTTTATGAG GTATTTACCG TTATGTTTGA ATAATTTAT TAGGATG       28980

TTTCCTCTAT CTGTAACAGG TAATAAAATA AAAAATTGAA TTCTTAGCAA TAGAATA      29040

AATGATTTAG AAATAAATTT TAAGACAGCC TTTTTCTTTT CTGATAATGA AATGGTT      29100

TACCCTGGTT GAGTGTGTCC CCATTGTAAT AGTTATAAAA CATGAGCCAT CTACATG      29160

GATACCTTGC TCACCTACAT GTGAATTTCT GAACGAAATA TTCATGGTCT TCCTGCC      29220

TATTGTGCCT CTTGATTTTG ATGCTCACCC TATGGAGAAA TGCTAGAAAA TAGCCTA      29280

GTCAGTTGCT TAAAGAATCG GGTAGTCATA CATGTCTCAC TTTCTACATA TTGATTA      29340

CCAGAATGGC ACTGAGAACT CAGTAAGACA GGAGAGAGG TGTAATGGCT GTTGGGA       29400

TTGCTTCCAC AGCTGGAAAG CCACATGCCA ATATAATTTT GAAGAACGCT TCTCACA      29460

TAAAAGATAA ATTGTTTTAT GTAGCTAGGC TATTAATTTA TAACCCTGCC AGGGCTT      29520

TATTGCAAGT TACAGATTAT TAAAAAGAA CGAGATGTAT TAATCCCCAC TTCTATT       29580

ACTAAAGTAT AAATGGCTAA TAAGTAGTTT TAATTTAGTG GGACAAGATA AATTGCA      29640
```

| | |
|---|---|
| AAATCTCATG ATTTAGTGTT TGATTTATTA AGTAGGAGAT AACTTTTCTC GTTTAAA | 29700 |
| ATTTTTTTTT CTCTTTACGT AGGGCTCGTA GCTTGGTGGT AGAGCACCCA CTAAGCA | 29760 |
| CCAAGGTCCT GGGTACCATC CCCAACATGA CAAAAGAAA TAAATATTCT AATAAAC | 29820 |
| AACGTTAGCA TGTGTGTCTT GGCCATGGTT CCTGTATGGT TGTGACTGTG GATGTGT | 29880 |
| AAGACAGTGA GAAGTCAATG CGCCTTTTAA ACGTCCGTTT GTATTGGATT TCCCCCC | 29940 |
| TTCCAGTCAT TGCACTCTCC GCTACTGCAA GCTCTTCCAT CCGGGAAGAC ATTATAA | 30000 |
| GCTTAAACCT GAAAGACCCT CAGATCACCT GCACTGGATT TGATCGGCCA AATCTGT | 30060 |
| TAGAAGTTGG ACGGAAAACA GGGAACATCC TTCAGGATCT AAAGCCGTTT CTCGTCC | 30120 |
| AGGCAAGGTA AAGATAGGAC GCTAGACGAA AGGATCTTTT AAAGAAGTTA TTTTATT | 30180 |
| TTCTATTTCT TTTTTTGATA TATATTTAAT GTCTCAAATT TTATGTAGCC TTGGCTC | 30240 |
| TGAGTGTAAT ACTACATAAT CAATTCAGTG ACCAATATGA AACCACTAAA AGAAATA | 30300 |
| CCATTCATTC TTTTAGAATT TCATATAGTA TACTTTGATC ATATCCACCC CTTATTA | 30360 |
| TCCCAACTTC TCAACGGAAA CTAGCTCTCC CTCTCCCAGA AGCTATCAGC TGTCTAC | 30420 |
| CTACTGCTTG GTTAGGGGTA GGGGCTTGGT CTAGTGTAGA CAAGGGTTCA TGAGCGC | 30480 |
| GGTCCTGCCA TGACCAGGAC ACATGGCTTT GCTTCAGTTT TCTCTGACCA TTGGCCT | 30540 |
| TGTTCTATTT GTCCACTCTC CCATGGTGTT CAAAGCATTT GTATTTGCA AGGGCAG | 30600 |
| AGATGTGGCC AGGAACTAAT TTGTCTAATA TTATTTTTCT TTTATATTGT TATTCAA | 30660 |
| AGAGATATTC TTTTAATAAT TTACAACTAA ATGAACAAAT ATGACATGAG CATTTCT | 30720 |
| GAGTTCTGTC TGCTTTCATA TTTAGATGAT CTACCTCTGC TGGAGGGGCT TTTTAAT | 30780 |
| CAGTATAGAG TCTGTCCATG TTCCAAGGAC TGTCCTAGAT GCTTTATACA AGTGATC | 30840 |
| TTAAATCCTC TAGCATAAGG AAGTTCCTGT GTACATCTAT ATTTTACTGA TGAAACT | 30900 |
| CATTACACTT CTAAGATTTG TATTTTAAAA TATACTTTAT GCTTTATTTT GTATGCG | 30960 |
| AACCTTTGTA ATGCCATTAT TCTCTGTCCT GCCTGCTGAG TTAAAAGTTG ATATTTT | 31020 |
| TATATTAAGT ATTCTGAATA ATGAAAAATA ATTTTCTCCT ACCAATACCA ATGCAAA | 31080 |
| AGTCCAAGCA AGAAAGAGCT GAGAGCATTG TTAGTGTTTT CCTCGTCCAG AAAGGAT | 31140 |
| AATGGGAAGA GAGATCCTAG GTTAAGGAAG TGATAGTGTT TGTTGTAGAT ACTAGGA | 31200 |
| AGTTTAAGTA CCACCTGAGA AGTGCTCGCT ATTCCGAGTA GAATAGGAAG ATGGGGA | 31260 |
| TATTGATAGG GTTTTGCTGC TCAAGCTGCC TCCTTGAACC TGCTGTTCCA TGGTCCT | 31320 |
| CAGTAAAGGA AAAGTTCTCT TGTCAAAGGC TTCTTCTAAA CTGGATGTTT CTACACT | 31380 |
| GTCATTACTA ACCCCTGATC TTTTAGTTCT TGTCAATGCA CATTATTTTT AATATCT | 31440 |
| GCTAATTTTT ATAGTGACCC TCTTCTTTCA TATGTATATG TGTGTGTGTG TGTGAGT | 31500 |
| TGTGTGTGTA TGTATATATG TGTGAGTGTG TGTGTATGTA TGTATATGTG TGTGTGT | 31560 |
| TGAGTGTGTG TGTGAGTGTG TATCTGTGTG TGTGTGTGTG TATGTGTGTA CACACAC | 31620 |
| AAAGTGCCTT CCCCCATCTT TTCTTGTGAT GTTTTGTTTT CCCATTTTTG GCATCAT | 31680 |
| CCTTACAATA TCTTATGCAA ATGCCTTCTT CCCAATTTAT ATTGATATTC TGGTAAC | 31740 |
| GATTAATTTA ATTTTTAGCC CAGATTTTTC TGATCACTCA TAACACATCT ATATCCT | 31800 |
| TGCTACTTGA TATATTCCAC AGATAACTTT CAGGTTTATC ATCTGCAGAC ACGTCCT | 31860 |
| ACCTTGGAGT AAAATTTTAT TTTTAAACCT TGTATAATAT TTTATGCAAC AGTGAAA | 31920 |
| TTCTCTCACC TCTTAAATAA GAATAGATTA ATCTATTGTG CTGCCTTTCT AGACTCA | 31980 |
| TTATCCATAC CTTGTAAGTT TTAGAATCAT TTTTTTCCTA AAACAAAGTG ATTCCTG | 32040 |

```
TTAACTTTAA TTTGGGCCAA TGTTGAGTGC CAGAGTTTTG CTTTCACACA ATACGTT      32100

ACGTTTGTCT TTCCAGAATG TTCTGGAGTT TCAGGGAGTT GAAGTGTTTT TCAGTCT      32160

GACTTCTTTA AGACTTTTGC TTAGTGAAAG CAAAGATTAT GAAAGATGAA TCCCAAA      32220

CGATGAAACA TACATGTAAC AGGCGTGTTT GCTTTCTCTG TCTCCCTACC TCTTCCC      32280

CCTTCCACAG TTCTGCCTGG GAATTTGAAG GTCCAACCAT CATCTATTGT CCTTCGA      32340

AAATGACAGA ACAAGTTACT GCTGAACTTG GGAAACTGAA CTTAGCCTGC AGAACAT      32400

ACGCTGGCAT GAAAATTAGC GAAAGGAAGG ACGTTCATCA TAGGTTCCTG AGAGATG      32460

TTCAGGTGTG CAGAGCAACC ATCTTTCTCT GAATTCTTCA CAGGAAGTAT ACGTATC      32520

CAAACATTTA TGTCACCAAT TTTTTTTTTA AAATTGTTGT ATTAAGCACA GTTTCAC      32580

TCTGATAAAG GTAATGACTG TATAGTGAAA TTGGATTAAA TAAACCCTAC AGCTTAG      32640

AAATAGCAAA GACTGTCATC TGTTACTGGG CTACACAGAG AATCAACACC AGTTCTG      32700

GAGTAGGTTA TGTAATGAGA GTGGTCATCA GGAAGCTGAA ATCTGAGAAG AGTCTTA      32760

ATGTCAAGTT TACCAGGTCA GTAGGTAACG AGGGCTGTAG AGTCCCAGGA AGCAGCA      32820

GGTGCAGAGA CACACGTTGA GTGCATCCTG GGCTCAGAGA GGAAGAGCCT GAGGTGA      32880

GAGGAGAAGA TGAGCGGTAG GAATGGCACA GTCAGGGGAC ACAATGAGAA GGTTAGA      32940

TCTCAGGAAG GCTGCGTTGG ATGGTTGGCC AGCTTAAAGA TGAGAAGGAT CCCTGGT      33000

TGGTGCTCGC CCCCTACCAG AAAGCATCTA TTGTCACTCT TCCTGTAGGA ACGGCAC      33060

TGCTTATGAG AGGTTGTTGT GCACACTTAT TAATACTTTT ATTACTTTAG CGACTGG      33120

CTTTGGATGC ATCTGGCATA CTGCCTGTCT TAGGTACTTT TCTGTTCTAC TACTGAC      33180

GGCAACTTAC AGAAGAAATA GTTTATTGGG GCCTACAGTT TCAGAGAGGG GGTCTGT      33240

CACTGTGGAG AGTGTGCAGC AAGCAGATAG GCATGGTGCT GGCGCAGCGG GTAGGCA      33300

TGCTGGAGCA GCGGGTAGGC AAGGTGCTGG AGCAGCGGGT AGGCAAGGTG CTGGAGC      33360

GGGTAGGCGT GGTGCTGGAG CAGCGGGTAG GCGTGGTGCT GGAGCAGCGG GTAGGCG      33420

TGCTGGAGCA GGAGCTGGCA GCTTGAGCAC CAAGAGAGAG AGCTAGCTGG AATGGCA      33480

ACCTTTGAAA TTTCAAGGCC AGCCTTTAAA GCCTGCTCTT CCCCACAAGG ACACACG      33540

TAACTCTTCC CAAACAGTTC TCTCACCTAT GGATCAGCGT CCAAACATAT GAACCTA      33600

GGGCCATTCT TGTTCAAACC ACCACACTGC CAATGTATAA CTTGATTGAA GCATTAA      33660

TATATATATT AGTTTTTTGA GACAGGGTTT CTCTGTATAG CCCTAGCTGT TCTGTGG      33720

TATTAATATT TTAAAAGAAG GCTTAAAAAT CTTTAGTGAT CTTTCATTAC AGTTAAT      33780

GAAGGTTATC TATCTACCTA CCTACCTACC TACCTACCTA CCTACCTACC TACCTAC      33840

TCTACCTACC TACCTACCTA CCTACTTACC TACCTATCTA TATTTTGCAT GCCCTGC      33900

ATTTTCTCTT TCTAGTACAG GAAGTCATCA ATTCGAATCC ATATTATAAA AATTAAA      33960

TAGATGAATA GTTGCATTCT AGGTAGCCCG AGGTAGTGTT TTGTCTAACA GCTGAAC      34020

TAGACTCCTT CCTGGTCACA ATTCAGAAGC CTGGCATATG CTTCGAACCT TCCCCTT      34080

TAGCACAGTG AAAGGCATGT TGTCATCAGT GTAGACTTAT CTGGACTCTT AGAGCTG      34140

ACTTTTTGTT GGGTGTTCGT TGAGTGCCGA CTGAATTCAT AAATGTAATG ACTTCTA      34200

AGCTACTTCC TGACCATTTT ACAGTGGATT TTTACTGTAT GGCAGGCACA GAGGCTG      34260

TCTGTAGCTC TTCATATGTT AGACTGATGC ATAAAGCCAT TTTCTGTTTT ACAATTT      34320

AAACAAAGGG AATTTCCTTT ATGTCATATA TACTCAAATC CCATGCACAT TAGCTTT      34380

TGATTTGTTT ATAACTGTCT GTTCTCAAAT TTTATCCCAA CCCTTAGTTT CGTCCTT      34440
```

-continued

| | |
|---|---|
| ACATTTGCCA TTTTAAGGTG GCTTTTTAAA AAATGAAATG ATGAATAACT TATTTGG | 34500 |
| AATAGTTTTC ATTTATATCT AAAAGTTTAT AGGGACAGTG TGAAAATCTG GTTAATA | 34560 |
| TAGTTAACAT CAAATGAAAG AATAATCCGG TGAAGCTTAG AATTCCATTG GTTATTG | 34620 |
| GCTAGCTGGA CTGAGCTGTT AGAATTCCAT TGGTTATTGA CTGCTCGCTG GACTGAG | 34680 |
| TTAGAATTCC ATTGGTTATT GATTGCTCGC TGGACTGAGC TGTTAGAATT CCATTGG | 34740 |
| TTGACTGCTA GCTGGACTGA GCTGTTAGAA TTCCATTGGT TATTGACTGC TAGCTGG | 34800 |
| GAGCTGTTAG AATTCCATTG GTTATTGACT GCTCGCTGGA CTGAGCTGGC TTCTTGC | 34860 |
| AAAGCTTTTG CTTCCCACGT CTGTGCCGTT ATCCCCGCTC CCTCACCCCT CACCCAT | 34920 |
| TTGCGTGTTT CCTATGCTCT TCCTTTCTCC TTTCTGTCAA TCTCCTGGGC CATCCTA | 34980 |
| CATACCCTAT GAGCTTATTT TACTGTTGTC TCTTCAATGA GGCGTCTTCT CCCCTCC | 35040 |
| CTCCTAAGCC TTCGATCTGA CTTTGGAGGT GTTTATTGCT CTACCCTGAC ACAATTT | 35100 |
| TATACTGCTA TCTTAATTTA TTGTCAGTTT TTATGATTCT CTATTGATTC CCCACTA | 35160 |
| ATGCCGGAAA TTCACCAGCC TTTCCTCTGT GTTCCTGCAG CCCTGGACCC CTTTCCC | 35220 |
| GCCTGTTGGT TTATATCTTA ATTCTGCTTA AATGTCATAT GGTTATCAAC TTAAGCA | 35280 |
| TACCTTTAAT TTTTATAATA TATGGTTATA GTTCTCACAT ATATTTTGT ATTCTTG | 35340 |
| TTAAAGGATT TTTTTTCTGA GTATTTGTCC CTAATTCTCC TGTGAGTTTT TTCCAAC | 35400 |
| ATGAACTTTA TTTTGTTAGG TTCATTCACA TTAGGTCATT TGACAGTTTT ATCCTCT | 35460 |
| TATTATACCC GTCTTTTTTG TTTTTGTTTC TGTTTTTGTT TTGTTTTGTT TTGTTGT | 35520 |
| CTATTGTACC CATCTTAATG ATGCTTCATT AGCTGTATTT CTCTTTGCAG TAGTGAA | 35580 |
| TATTATACTT AGATTCTGTC ATCAGGAGAG GACATTCGAA ACTTGATAAT AATACAA | 35640 |
| TTTTATTCAC TACAGTAACT GTTTCTCATA GCTTCGGGTC TCCAGAGAAA CTCCTTT | 35700 |
| TGCTCCTTTT TATAGAGATG AAGAGAAGTC ACATTTTTTT TTTTAAAGAC AGGGTTT | 35760 |
| TGTATAGCCT TAGCTGTCCT GGAACTCACT CTGTAGATCA GGCTGGCCTC AAACTCA | 35820 |
| ATCCGCCTGT CTCTGCCTCC CAAGTGCTGT GATTAAAGGC GTGCACCACC ACTGCCC | 35880 |
| CAGAAATCAC ATTTTTATAG CCACTATTTA TCCAAATCTG TATTTGGATA GATTATC | 35940 |
| TAGTCTGTAA GTAAAGTTAT ATTTAATTTA GTTTTACACT GGCGGGCAAG CTGCTGT | 36000 |
| ATTTTGTAAG TTTTAGTTAA GTTGAAATGT GATTCTTACT CTGCGTTGTT GTTCATT | 36060 |
| AGTGTGTTGT AGCTACTGTA GCTTTTGGAA TGGGCATTAA TAAAGCTGAC ATTCGCA | 36120 |
| TTATTCATTA TGGTGCGCCT AAGGAAATGG AATCCTATTA CCAGGAAATT GGTAGAG | 36180 |
| GCCGGGATGG ACTTCAGAGT TCCTGTCACT TGCTCTGGGC TCCAGCAGAC TTTAACA | 36240 |
| CCAGGTATAA ATGCTTATTG TTTTCACCTT ACAAATTCCT TTTTCCTTTC CAAGAAA | 36300 |
| TTTGAGGGAG TATCCAAAAT ATCAAGTGAC CCCTGAGTAT ATTTAAAGGG GTCGCCA | 36360 |
| GAAAGTGAGC AAAATGAACA GAATATCCCT GAAGAGTGTT TTTGGTAAGT CTTCCCA | 36420 |
| AGCAGGTGAT CCAGTTGGAG TTAACAAGAT CGGGACTGCA CTTGGACGTA TAACATA | 36480 |
| CTTATGGCAT CCTGTCCTAT TGTGCAGCAG TAAGCAGTTC CCACATTTTA AATCCTC | 36540 |
| TCATATGGCT CTAGGTTTAA GTAAGTACCA TGTGTCCAGT GCTATAATGG TGGTTAT | 36600 |
| AAAAGATGTA TCCAATTCTT GTTAACTCT CTTTACTATT GTTTCTGTGA TTAGTTC | 36660 |
| AAGTGCATGC CACTGCTCAT AGACTGAAAA CTCACCTGGT TGATAGTGCC TAAATAA | 36720 |
| AACAGCGTAG TGTTAGAGTG CTGTCATAAA ATAGTATATG TTCGTGGTTT AAATTCA | 36780 |
| AAAGGGAAAC TGCCTACTTA AATGCTAACT AAATTGTAAC TTACATCCTG CCAGATT | 36840 |

-continued

| | |
|---|---|
| TTAGAAGCAA CAGCTTCAAT TTCCAAAATC ATAGGGACAT TATTTACCAG TTATCTA | 36900 |
| ATAGGGAACC AGGAAAAGAA GCCAGTGCAG CCCAGCCAGT GAACGTGCCA ACATAAA | 36960 |
| CCTTTCAGTG CTCCTCCAGG CTGATGAGTA AGCTAGACAC TGGTAGCTAA AAGAGTA | 37020 |
| TTAGATAAGT AAAAAGGGTT GTTACAAAAT CTAAGATCTT GCTAGGAATA GTCAGTA | 37080 |
| TTTACTTTGT AATAAGTAGA GCTGAACTCT GATCCCCTGA AAGCAAGCAT TCTTAGC | 37140 |
| TGAGCCATCT CTCCAGACCA GGCGCCAGAG TCTTTACCCA GCCTTTTAAA AACCAAT | 37200 |
| AAGTAAGTTG GATAGAACAC ATCTCTGCAA GCTACTATTA AATTTGGAAT ATATCAA | 37260 |
| TCACTTGGTT AAGACCAGAT CTTATTTTAT TTGTGTATTA TGCTAACATG CTGGAAA | 37320 |
| TATAGGCCTG AGTTGTATAA TGCAATCTCA CCCGTGGATA TAGTGTTGAT TTATGTG | 37380 |
| TTTGAAAGAT ATGCTGAGTG GTTTATCTCA TTAAGATTGA TCAGGAAATA ATAGTTG | 37440 |
| CAGAATACCC GTGCAATTGT TACTTAGTAT CCATGGTGAC TGGTTCTGAG TTCCTTA | 37500 |
| TAGAAATAAA TAAATAATCT CCCTATACAT GAGGCTCTTA TACAACATAG TATTTGT | 37560 |
| CAGGCTGTGT ACTCTTCTAC ATACTATCTT CCTAGCTCAC ATATAACATC TATTATA | 37620 |
| TAATTGATGT GTAAGCATTT AGTTTTACAC TGTAATCTTT AGAGAATAAC AATAAGA | 37680 |
| ATGTCTCAAT GTGTTTAGTA CAGATGCAAC TACTGTAAGC CTAATTGGGG TTTAACT | 37740 |
| GGTTGACCGA CTCTCAAGTG CTGAACTAGT GGGTGCAGAG CTGAACCACT CGCTCTT | 37800 |
| GTACAGATAG GCTACTCTGT GTATCAGAGA CAAAGGAGAA AAACTGTAAA AGGATAA | 37860 |
| GGAGAGAGCC AAGGATTAAG GGTGAGTTTG TACCATCGAG ATCTTGAAGC AGAAGAA | 37920 |
| AGTGAGATTC TGGGTCTCAG CTCTAAGGGT CATTGTAACT TATAAAGTTG TAGTCTC | 37980 |
| TATGCTAAAA TTCTGTGACA AGGGAAGAGT CTTGTTTGAG GGATCATGCC GTGATTT | 38040 |
| CTAACTAATG TTTATTTGTT AGTTTTGTGA TGCTGGGTAT CAAATCTGGG CCACCCT | 38100 |
| GCTAGACAGC CTATGTAAGC CACATCCTCA GAGACGATTA TGTAGTTTTA TGTTCCC | 38160 |
| TTGTGTGATT TTTGTGTTTC TTACTGCCGA GCCGTAACAA GGCAGTGTCC CAGTGAT | 38220 |
| GTTTATTATA TTTGTAGTCA TACCCAGTAG TTACTGCCAT CTTTTGTTTC AAAGTGA | 38280 |
| ACTTAGAGAA TAATCTCTAA TAAATCTTTG AATTCTCTTA AAGTTAATGA ATTGTTA | 38340 |
| TTTATGGTTT TTTTGGTGAA ATAAGTTGTA TTGCGCATTT AATAGTAGCA AAAGAAG | 38400 |
| AAACTAATAA ATATTTAATT GAGTTTCTTT TTCTCAAATG AACATGTAAA TGAGCAT | 38460 |
| TGAAATCAAA TAAATATATT TCATCTCAAT CCAATATACT AAGATATAGT TCTGAGT | 38520 |
| GTTGACTTTA TCTCTGAAGG ACAAGGGAAC TAAATGAAAC TGATTTTTTT ACAAATC | 38580 |
| GATCCATTAA GTATGGGCTT GGATAATAGC TCAGGTTAGT ATTTTAGTT CAGGGTA | 38640 |
| GGAGGAGAAA ATTCATGTGA AGGGTGTTAT CCATTGAGAA CATATCTTTG AATAATG | 38700 |
| CATTTGTACA TTCAAATTTT CTAGAATAGA GATTGTATAC AGATATTTTG ATTAATC | 38760 |
| AGGCTGGATG TTACAAACAT TAGTGAGCAA AGTCCCTAAT GATGAAGTTC AGTATTA | 38820 |
| TTTAGTTCTT GTATATTAAA TCAGAATGTT ATATTGCAAT ATCTAAAATT CATTTCA | 38880 |
| AGGTTTTTTT TTATTATTAT TCTTGGAAAG ATGTGGAACA CTGCCTGGAA GATTTCA | 38940 |
| CCTAATGCAA TAGCACTGAT GTTTAAAGAT AAAAACAAAC ATACTGGTAC TGTTATT | 39000 |
| CAATTATAAA CAACTTCATT ATTGTGACCA AAAAAATTCA TTACAACTCA CCAAGGA | 39060 |
| CACTCAATTC TAATACTTTA CTCCTGTCCT CAAGGGCTTC GCAATACAGA GGGACAG | 39120 |
| TGGAGCTGAG CTGTCCTCTG AAAAGCCAGT AGGAGTAGAT GAAGGTTCAG ACTGGAG | 39180 |
| CGGGGATGGA GACTAGAGCG ATGGGGATGA AGGGTCATAC AGACTAATGA GCCTCTT | 39240 |

```
GTTTTCCTTA CATAGATATT TTAACTTTCT CAGAGAACAT TTATTAAAAT AAAAGAT      39300

TTTCCAGTGA AAGGTCCAGG ATCCATGTGC TAGAAGGCTT ACTAGAAACT GTGATGA      39360

AGGTCTGTAA ATCAAAAGGA AACCTTGAAA GTTATCAGTG GAACTCTCTT GTCCAGG      39420

TGATTAGGAA GAATGCAGGC ATTTGGGGGA GCAAAATAAT AAAATTAACA GTATAAT      39480

AGATATTCTT GTGATTTTTC CATTGGCAGG AATCACCTTA TTGAGATTCA TGATGAA      39540

TTCCGGTTAT ATAAATTAAA GATGATGGTA AGATGGAAA AATACCTTCA CTCCAGT       39600

TGTAGGCGAC GGTATGTATT ACCTGCTTTT TCCAATTGGA AGCATAGGTC TTTAGCT      39660

ACTTTTTTTG TTGTTTGTTT TTTTGAGACA GGGTTTCTCT GTGTAGCCCT GGCTGTC      39720

GAACTCACTC TGTAGACCAG GCTGGCCTCG AACTCAGAAA TCTGCCTACC TCTGCCT      39780

GAGTGCTGGG ATTAAAGGCG TGTGCCACCA CTGCCCGGCT AGATGGTACT TTTTTTT      39840

TAAAGTTAAT TAAAAGTGTT TTTAAAGAAT GTTTGCTGTA TACATGCTGA ACTTTAG      39900

AGGCTTATTT CTGTTTAAAT AAATTAATAT GAAATAATGC TGAGACAAGT AAATACA      39960

GTGGTACTAT CGTGTCATTT TGGGTGGTGG GTGTAGTATG TCTATATTTG TTCTTTA      40020

TAAGATTTTC CCTTCATCAG AATCATCTTG TCCCATTTTG AGGACAAATG TCTGCAG      40080

GCCTCCTTGG ACATTATGGG AACTGAAAAA TGCTGTGATA ATTGCAGGCC CAGGTAA      40140

TATCTTCCTG ACGAACCTTC TAGAAACTGT CGATTCTCTT TCTGTTCAAC TCCTGCT      40200

TTAAATTTTT GTTAATATA AGTATTTTAG GTTTTGTTTT GTTTTGTTTT GTTTGT        40260

TTTCGAGACA GGGTTTCTCT GTATAGCCCT GGCTGTCCTG GAACTCATTT TGTAGAC      40320

GCTGGCCTCG AACTCAGAAA TCCACCTGCC TCTGCCTCCC GAGTGCTGGG ATTAAAG      40380

TGCTATTTTA GTTTTTTTAA ATGACATAGT TACTTTATTT AAAATAAAAC AAAGTGA      40440

GGTTTACTTT TATACAATAA AGTCTTAAAA CGGTAGGCCT AGTTAGTCAA TAGTTGC      40500

TCAATATGAT TAGCCTAAAA ATACTCATTA AAGGCATAAT TTATCAAAAT TGATTTG      40560

GGCATTCTAC TTGATGTTTA CCATAAGGGC AAGTACAATT ATGTAGATAG TTTTAAA      40620

TGAAATAGAA AACACTGCAA AAACACTAGC CAAAAGAAAC CGTACGTTAC TGTTTTA      40680

TTTAGTGGTA TGGACTTTGG AGCAAAGCAT GCTATCAGGG ATGAATCAAG ACACCGA      40740

GTGTGAAGTA TCAGCGTTCT GCAGAGAAGT GGCACCAAGG AGAGAGCAAG AGGGGCA      40800

GAGGTGTGGG ATGAAAGAA CAGGACAGAG GTGACAGGCA TCAGTGAGGT GGCAAAT       40860

AAACTTGTA GCCAAGTTTT GGTCTGAACC CTGCGTCAGG CACACGCTAA TGTTAGT       40920

GAAACAAAGT TTATTGCCCA GCAAGCTTGT TTGTATTAAG GCTTTCAACC CAAAGAG      40980

AGTTATTGGG CATGATTTCC ATTGTTGAAG TCGTCTCATC ATAAGTAATA TTCACAT      41040

CAAAATACAT TTGCTGTGGC ATCTAAATTA TTTTCTGATC AAACAACAGC CCCACTT      41100

CATGCAAGCT ATACAGCCCA GAAGACATAA TCCCAAGTGG GCACATAAGA ACCTGCA      41160

AAGAACCTGC ACATAAGTAC CACAGAAGCA GAAGGCGGGG GGATCAGAAA CCCACGT      41220

TTAGGTGACG TCGGCGTCTG CTTACAAGGC AGTGGAATTA ATGGACAAGA ATGAGTA      41280

CTGCGGGGAG CGATGGGCGT GTCTGCAATG GCAAATTCAG AGGTTCAGAC GGGAGAT      41340

GAGACTGAGA CCAGCCTGTG ATGCAAGTGA TCTCAAAAAG AACCCAGGTC CCATAGT      41400

ACTGTGTCTC AAGATCCCGA GAACAAAAGC AAGCGTAAGA CTCAACAGCA AGCATGA      41460

ACCCAAAGC CCCAAACAG CCCCCTACCC CCACCCCACT GACTCTATGA GGAGATG        41520

GAATGAAGAG GGTGTCAGCA AACCAGTTCT AATTAATTTC TTGAAAGCAT TTCAGCC      41580

TGTTCCAATG GCGGCTTATA CACACATGTT TACATAAAGC TAACCTTGAC AAATGAG      41640
```

| | |
|---|---|
| CTATTCGATT TGGATCAAGT ATGCTTTTTG CTTTAATGGC ATCAATCTAG AAAGCAG | 41700 |
| TGGGAAGAAA AGAGAAATCT CCAAACCCTT AGAAACCGTA CCTCCAAATA ATCTTAC | 41760 |
| CACTCAGAAA ATGATCTGAA CCGACGAAGA AGAATATGAA GTACCTGGGA TACAGCT | 41820 |
| ATGACTCTGC AAAGATAATT TATAGTGTTA ATACAACATG GAAGAGCACA GGCTTCA | 41880 |
| ACATAACTAG CATTCACTTT AAGAAACGGG CAGAGCCGGG CGTGGTGGCA CAAAACA | 41940 |
| AAACAAACAA ACAAACAAAA AACAAAAAAC AAAAACAAAA AAGAAATGGG CAAATAT | 42000 |
| GAAGATGAAC AGGAAGGGAG TTAAAAAGAG AAGTGCGTAG ATCAATGCCG TAGACGA | 42060 |
| AGCCAATAGA GGGGAGTCGG CGAGCTCACA GGCTTCATAT TTTCCAAGAC TGGTGGG | 42120 |
| AGGGGAGGAC AGTACCAATA TCAAAATGAA GGAATTTCAC TGCAGACCCC ATGAATG | 42180 |
| TGAACAAGCC AGGTTACTGG AAATGCAGTA AAACTGATCT AATAGACCAG TTTCTTA | 42240 |
| GGCTCTAATT GACAGTGCTC AGGCATGGTG AAACTTAGGA AGAATACTCC TCTAACT | 42300 |
| ATAAGGATTG AGTTCTTCCT TAAAAAACCT CTGAAAAGAG AACTCTCTAG CCCACCT | 42360 |
| TTTAGTGACA AATTCCAGCA CCAGAAGAGG ACATCAAACT CATTACAGAT GGTTGTG | 42420 |
| CACCATGTGG TTGCTGGGAT TTGAACTCAG GACCTTCAGA AGAGCTGTCA GTGCTGA | 42480 |
| ACTGAGCCAT CTCGCCAGCC CTCCAGCAAA CATTTAAATG AGGAGATATC CCTGCTT | 42540 |
| TAGTGTGGCT GCACATGCAC ACTCTCTGAA AGGCAGAGCT GTAGGGAAGA TCAGCCG | 42600 |
| GCAGAGGTTA AAGGCAGGCA GAATAGATCT GAGAGCAGGG CATTCAGTGG GTCTTGA | 42660 |
| TGACGAAGGT TCGATGGGTC TGCTTATAGG GATATGTACG CTTTATTATA CTGTAAA | 42720 |
| AATAAGTATA AGTGGTGCCT CTTTGAGTTA ATCGTGTCTC TAGGTACAGT AGCTGTA | 42780 |
| CAGAAGCAGC GCTGTTAGAG ATAGAAATCT AAAGATGTTT GGAAATTAGT GATAACC | 42840 |
| ATAACATATA TTTAAGGTGG TAAGATAATA TGTATAGGTC ATACTTCATG GGAACTT | 42900 |
| AACTTTAAAT TCTCTGAAGA AAGTCACCTG AGCATCCTAC TAAAGAGGTA AATGGGA | 42960 |
| TAAACCTAAG GCAGGGGATT TCTTCTTTAA ATCAAAACAT AATGGCTTTA ACTGGAA | 43020 |
| TGACTGCATT CTTATTGCTA CTTTAAAGAT ATATGTGATG TGGAAAGTAG TTGAATT | 43080 |
| TAATTGAATA TATTAGTTGA TAGTCTCTAA GGACTTCTTT TGTTCTCAAG CTAAAAA | 43140 |
| AATCCTCATT TACACCAATG ATAATTTTAC ATCTACTTGG AGGATGACTA AGGAATT | 43200 |
| CTGCTGAATG TACCAGCAGG ACAAGCTTAT AGGCTCGGTG CTCTGTTGTA AAATTAT | 43260 |
| GGTTCAAGCT AACATGTTAC TGCATAGCAG CTTTTTACTT AAAACCAATT TTACCCT | 43320 |
| TGGTGTAACG TAGCACAAGC TTCCGTATTT ATATAACTGA TCGTGTGGAG CTGCCCT | 43380 |
| CGGGATGCTT TCCTTGAGCC TGGCATCTTC CCAGCGCCTC CATAACATTT AGCTTCT | 43440 |
| TGCCACAAGA AAGCGCTGTC TGTAGTGCCG TATTTGTTAT TTGTGTCTCA TACGCAT | 43500 |
| TCACACACAT GCCCTTGATT GTAATAAGCT TTATGTGTAG AGTTGGAAGT GTCAGAC | 43560 |
| TTTGAGAATT TTTTTTTTTA CGTGGTCTAT GTTTGTATCT TTCTATTTCT AAGGGAG | 43620 |
| GCTTTTGTCA GTGTTTTCTT AGGCTGTTCT TACTTTCCTT CAGGCTGAAT CATTGCC | 43680 |
| CTGCTAACAA CTCAGAGGAC GCATCCCAAG ACTTTGGGCC ACAAGCATTC CAGCTAC | 43740 |
| CTGCTGTGGA CATCCTGCAG GAGAAATTTG GAATTGGGAT TCCGATCTTA TTTCTCC | 43800 |
| GATCTGTGAG TGTATCTGTG ATAGCTCCTG GGACTGTTTC TGACAGTGCT TTCCACT | 43860 |
| TGGCTATGGC TTTGGCTTTC TTTAGATGGC TAACTAGCAA CCCGTGTTAG CAACACC | 43920 |
| AGTTCCATCC TAACCCTGCA TTCATTGTCT TGGACAAATC TTGTCTCACG TCAGACG | 43980 |
| TTTTGCTATG TTGGATGCTG GCGGTCAGCT GTGTGCTGCA GTCTGAAAAT AGCCTAT | 44040 |

```
TTTACCACAC TGCAATTGCA TTAATCCCTA GACTGGTTTT TCTTAGGATA ATTAGGG     44100

GTTAACTCCC AGTGTGTCAA GGGACTGGTA GAACAAAGTT GCAGCTTCTG GTGCCCA     44160

ACGATTATGT TCTTTGCGCA AAACTTGAAT TTCAGGGATT ATGTTGTCAG AGGCTGG     44220

CAGCAACAGT GTACAGCAAC ATAGTCTCCC TCCGATGGTG TTTTATGTCA GAAGTAC     44280

ACATGCTAAG AAAGGGCTTT TGCTTGTTTT AGTGGTTTAC CAGTGAATAC CTGATTT     44340

TGGACTCCTT TCTGTTTTGA GTGATTCATG TGGCCTCATT ATGCTGCCAA ATGTCAC     44400

CAAAGTGACA ATAATAAGGT ACAAATACAC ATACAGAGCT GGTTTTCTGT AGTCCTT     44460

CTTTTATGAT AATTTTATTT CTGAATTAAG AGTCTGTAAA TTTAAGAATT GTATATT     44520

ATCACTTAAA TAAACCAAGA GTAGAAGAAG GCAGAGTACT TTGTAGATGG ATCTATC     44580

TTATTTAAAA CATGCTTTAG AGTAGAGGCT AAATGTTCAT TTTGTATATA GAATTTT     44640

ATAATTTAGG TAAGCTTTTG CTGCTTAAAT ACTCAAGAGC TTCATGTAAA TGCATTT     44700

TGTGCTTGCT TGTGCTTAGA AAGTAATCTA TGGAGTTAGT TATGAAATAT TTTTAAT     44760

ACACATTGAA AACTTGTACT ATCCTTTCAA GTGTCAGTGC TTTCAAGATA ATAGAGT     44820

AATTTTTGGT TTTAAATGGC AAAAAAGCAT ATAAATGTAA CAATAGAAGT GTTACTT     44880

CAGTTTTTAT TTCTATCAGC TCTGCAAGAA ATCTCAAATG CCACTGAAAT CCGTACA     44940

GTTTTCTATC TTTGTCACCT TTAAAATCCC TGTAGCCAGT GTGAGTATTT AATTTAT     45000

AAGTGTCCTT GTTTTGGTTT GGTGCGATCT AGCTGTATCC AATATCAATA AATAAGT     45060

TTTCTCGTCA AACTTTCAGT GGTCACAGGA GGGATCAGGT TCACTTATT ATTTGAA      45120

CAAGTCAGAC GTCCTCTACC GGCAGTGTCT TCTGGGAGTC CTCAAATTAA GCAGTTC     45180

CTTAGTGAAA CTTTATACTA CCCTTGCTAG CGCAACGTGT AAAGCTTTTA AAAAGTA     45240

CTTAATGAAA ATGTGTAGAT GCTAACAATA GTGAAAATAA GACAGGCTTC CTTTCTC     45300

TTTCAGTGAC TTTGATATCT ATTGGGATAT CGGTGAAAAA GTATGACTGT AATTCTC     45360

AGAACTGAGC AAGTTGTTCC CCTTAACCAA TTTAGGACAA GCTAATACCT TTGTAAT     45420

AATTTGTAAG ATGATATATC AAACTGTCTT GGAGTTATTT TGAAGAGATA ATTTTTA     45480

GCATAAATTC GGTTTTGGTA GTGCTTGATT CTCTCCTACA TGTTTTTTTA ATATTAT     45540

CACTTAATTT ATCCATAAAT TTGTTAAATT TAGTTTAAAA ATTTGTTTTA ATGTGTC     45600

TTAGAAAGTA ACCAAGATTG TCTAGAGAAC TTTGTTTTAA CTGACTAAAC AGTTCAC     45660

GTTCAGCAAT CTTTGACATT GCTCAAACGT GTCATAACAT AATCAATAGC CATAATT     45720

GGGAAAAAAA CCACATTGAT CATTTGCATA CCAAGATTAG CATCTTCCCA AATGCCT     45780

CCAAGTGCTA ATCTTTATCA TGGCCTCAGG AGTAGGTACC ACTTAATATT TTAGGAT     45840

TGTATATGCA CGTGTTCAGG TGCTCTCACA TCTGTGTGTG CATATGAACA CCAGAGG     45900

ACATTGGATG TCTCCCTCTG GTACCCTCCA TTTCATTCGT ACTCTTTTGA CCCAGTT     45960

CACCGAACCA GGAGCTCAGT GTCTTGGTTA GACTGGCTTG CCATTAGTCC CTGACAT     46020

CCTGCCTCCG TTTCCTGCCA GCCAGCTGAC ACTGTAGTAA CAGCACCCAG CTTGTCT     46080

TAAATTATAG TTTACTGGCG TTTCAAGAAC ATCATAACGG ATGCAGTGTA TTTTGGT     46140

AATCAACCTC AGTATTCTCC CAGCTCTTCC CAGACTGATC CCACTGCCTC TTCACCA     46200

CCAACTTTAT GACCTCCCCC GCCCAACTTC CCCAGCCATG GGTATGGGCA TCTGTTA     46260

TGTGGTCAAC CTATCAGGAG CTATGCCCGT AAAGAATGAC GATCTCCCTG AAGAGCC     46320

AGCTGTGAAT AGTTGTTCCC CAGGAGCTCC TGAACCCTTT TCTCCATCCC TTGATGA     46380

TTTTGCTAAC TTGGTTCTGT GCAGGCAGCC ACAGATGCTG TGGGTTAACG GGTGCAG     46440
```

```
TCTGTCATGC CCAAAAGACA CTGTTTGGTT CTGGTTCTAC ATGACCTCTG GCTCTAA      46500

TCTCCTTTTG GGACGAACCC TGAGCCTTGA GGGAAAGGAG TGTGACCCAG ATCTCCC      46560

TGTAGATGAA CACTCTATAT AGACAATATC CTCTGTGCTG TGCTTTGACC AGATGTG      46620

TTCTGCGTTA ACCGCCATCC ACTGCACAAA GAACCTTCTC TGATGAGGCT TGAGAGT      46680

ACCAATCTAT GGCTATAGGA ACAGGAACTT AGAGACAAGT ATAATTCTAT GTCAGTT      46740

CAAAATAATA GTAAGAAATA TACTGCTGGG GCCGTGAGCT CCTTGACCAA ATGTTCT      46800

CAGATTTACA GCATCCTGTA TGGAATGGGT GTGGGAACGG TAGGGAGAGG ATGGTAC      46860

TTAAATCCTG TCAGAAAGTG CTATGATATT GAGGCCACTT TTGCACCCAT GGGCATA      46920

GCCATGCTGG TTGTCATTTT AGTGTACAGG GTTAATAACT GGAGGAGAAA TTGACTT      46980

CTTCCCCAGT AGCCTGCATA GCACCTTCTG GTATTGTGAA AGCTAGCCAG CAGAAAG      47040

ACTTCTGGGC CAGGACCAGC GTGATTTCTC CATGTTCTAT GGCCAAAGCA GGTGGTG      47100

TCAGCAATAC AGCCTTACCA CTAAGTTCTG ATGAGAAACC AAGAACAGTA GCGGTGA      47160

GTATTATTTG AGGTGGGGCA TCTGTAGGAA AAACTGAGCA ACAGTTTGAG AGGAGGT      47220

TCACACTGGA CTATTTGTTT GGTGACCTGT GGCTTCCTTG AGTAACATTA GCTTTTA      47280

AGCCTGATTC CAATTAAACT CTTATATAAG TGTGTGTGAG TTTAGGAAGC TTATAAA      47340

TAAGTTTCCA TATGGGTTTT AATTTTTTTT TAATTTTATT TTGTGATTTT ACTAATT      47400

TTTACATCCC GCTCACTGCC CTACTCCTGG TCACTCCCTC CCACAATCCT TTCCTTA      47460

CTCCTCCCCC CTTCTCCTCT GAGAAGTTGG GCCCCCCTGG GTATCCCTCC ACCCTGG      47520

TTCAAGTCTA TGCGAGGATA GGGTCTTCCT CTCCAATTGA GGCCAGACAA GGTAGCC      47580

CTAGTAGAAC ATATCCCACG TACGGGCAAC AGCTTTGGGA TAGCCCCCAC TCCAGTT      47640

TGGGACCCAC ATGAAGACCA AGCTGGACAC CTGCTACATA TGTGTAAGGA AACCTAG      47700

CATATGTTCT TTGGTTCGTG GTACAGTTTC TGAGAGCTCC AAGGGTCAGG TTAGTTG      47760

CTGTTGGTTT TCCTGTGGAG TTCTATCCCT TTCTGGGCTG CAATCCGTCT TCCTAGT      47820

CCAAGAGTCC CCAAGCTCCA TTCACTGTTT GGCTGTGGGT GTCTGCATCT GTCTAAG      47880

GCTGCTGTGT GGAGCCTCTC AAAAGACAAC ATGCTCCTGT CTGCAAGCAT AACAGAA      47940

CATTAATAGT GTCAAGGATT GGTGCTTGCC CATGGGATGG GTCTCAAGTT GGACCGG      48000

TTGGTTGGCC ATTCCCTCAG TCTCTGCTCC CTCCCCTGTG CCTATATTAC TTGTAGA      48060

GATAAATTTT GGGTTGATAA TTTTGTGGGT GGGTCAGTGT CTTTATTGCT CTACTTG      48120

TGCTGCCTGG CTACAGGAGG TGGCCTCTTC AAGTTCCATA TCCCCAGTGT AGTAAGT      48180

AGCTAAGGTC ACACCTATTA ATCCTTGGAT GCCTCCCTTA TCCAGGTTT CTGTCTC      48240

CTGTAAATGC CACCCACTTC CCCACTTTTC CTCTGCAGAT TTCCATTCAT TCTCATT      48300

TCTAGCTCTC TCCCTGCCCT TCCCTACACC CAATCCTGAA CTCCCATCTC CCTCCGC      48360

CCCCGTCCTA GTTCCCTCTT TCCATGTGCC TCTTATAACT ATTTTATTCC CACTTCT      48420

TGAGATTCAA GCATCCTTCT GCCTTCCTTC TTGTTTAGCT TCTTTGGGTC TATGGAG      48480

ACCATGGTAC TTGTATGTTT TGGCTAATGT CCGCTTATAA GTAAGTACAT ATCATGC      48540

TCCTTTTGGG GTTGGGTCAC CTCACTCAGG ATGATATTCT CAAGTTCCAG CCATTGG      48600

GCAAAATTCA TGATGTCTTT CTTTTTAATA GCGGAATGGT ATTCCATTCT GTAGATG      48660

CACATTTTAT CCATTCTTCA GTTGAGGGAC AGCTAGGTTG TTTCCAGCTT CTGGCTA      48720

TGAATAAAGC TTTAGGAACA TAGTTGGGTA TGTGTCTTTA TGGGATGTTG GAGCATC      48780

TGGGTATGTG CCCAGGAATG GTATAGCTGG GTCTTGAGGT AGGACTATTC CCAGTTT      48840
```

-continued

```
GAGAAACTGC CAAAGTTTCA AGTGGTTGTA TAAGTTCCCC TCACTCCACA CCCTTGC     48900

CCTGTGTTAT CTTTTGAGTT TTTGATCTTA GCTATTCTGA TGGGTATAAG ATGGAAC     48960

AATGTTGTTT TGATTTGCAT TTCCCTCATG ACTAAGGACT TGAACATTT CTCTAAG      49020

CTTTCAGCCA TTTGAGAGTC CTCTTTTGAG AATTCTCTGT TTAGCTCTGT TTCCCAT     49080

TAAATTGGGT TATTTGGGTC ATTGTTGTCC AACTTCTTGA ATTCTTCGTA AATTTTA     49140

ATTTGCCTTC TGTCCGATGT AGGATTGGTG AAGATTCTTT TCCAATCTGA AGATTGC     49200

CTTGTCCTAT TGACAGTGTC CTTTGCCTTA CAGAAGCTTT GCAATTTCTT GGGGTCC     49260

TTATCAGTTG TTGATCTTAG AGCCTGAGCC ATTGGTGTTC TGTTCAGGAA CTTGTCT     49320

GTACCAATGC ATTCAAGGTA TTTCCCTCTT TCTCTTCTAT GATATTTAGT GTATATA     49380

TTAAGTCGAG GTCTTTCATC CACTTGGACT TGACTCTTTT AATAAATGTG TGTGTGT     49440

TATGTGTGTG TTTAGGAAGC TTATAAATAG TAAATTTCCA TGTGTTTTTT TTAAACT     49500

TTTTTTACCT CTCTCTCTCT CCCTACCTCT CCACTCTGCC CTCGCATCCC ACTCTAC     49560

TTAAACCTCT TCCCCCTTTA TATCACATAT TGTTCCAGTA TCCCCGTCAT AATGTTT     49620

TCTTTCACCT ACCTCTACCA ATAAATGGTC CCTTTCTAGT TTCTTGGATT CTTCAGG     49680

TCCAAGTTAA ACACACTATG TGAAACATTC AATGGTAGGA TCACATGTGC GAACATG     49740

TGATGTTTGT CCTTCTGGGT CTGGGTTCCC TGAATCACTA TTGTTCCCCA GCTCCAT     49800

TTTCCCTGCA AATTGTTATG ATTGTAGTTT TCTTTATAGC CAAATAAAAC GGCATTG     49860

ATAGGTGGTC CCACACTTTC GTGATCTATT TTGTAATTTA ATGGCTGTTT TCATGTC     49920

GCAGTCATGA ACATAGCAGC TAGACCATGG CTGAGCATGC ATCTCTCTGG TAGGAAA     49980

AGGCCTTTGG TTATATACCC AGGGGTGATT TATGTGGGCC ATCGGATTCA TCATTTT     50040

TGTTTGAGGA TTCTCTTTAC TGATTTCGAA GGAGCTGCAC CAGCTTTCTG TCTCACC     50100

GGTGCACAGG GGTTCCCCAG ATCATCACCT GCATTTCTTG TCTTTTATGT TTTTTAA     50160

TATCCTCGAA GTAGTTTCAA CTTGAGTTAA GGATGGTAAA CTCTCCTGAA AGCATTT     50220

TTCCTAGGCA CCTGCATTTC TTCTTCTGCA ACTTCTGTTT CATTCTATAA CTCACTT     50280

GTTTTTAGTT TTTTCAACTC TTTTTTGTAT TCTGTAGACT AACCCTCTGT CAGATGT     50340

GCTGGAATTA TACTCTAGGC TGCTCCTTTG GTCATGTAAT GGTTTCTTTC TTAGTAG     50400

CTTTTCATTT ATAAAATTCT ATTTGTTGAT TAGTGGTCAT ATTTTGTAGA TGACAGG     50460

CCTTTTCAGA GTCCTTACCT GAGCTGGTAT ACTGAGGCAT ACTTCACATT CTTCTGG     50520

TTTCAGATCT AGCATTGAAA CCTTTGATTT CATTTGGAAT TTATTTGCCA TATCTTA     50580

GTCCTGGGGA TCCAATCTCA GGTGCTTATA TTTAGACATA GAGCCCTTTG TCTCATG     50640

TATCTCCCCA ACCCAGATAA TGCTTTTAAG AAAAGATTGG ACCTATTCAG CTGTTAG     50700

TGTTGATAGA TTTGTGTGTG TATGTGTGTG TGTGTGTGTG TGTGTGTGTG TGTACAT     50760

TGTACCTATA TGCACACATC TGTATGTATC TATTTTAAAG ACAAGATCAT GCCTAGG     50820

ACTCTCACTC AACTGGAAAT TCTCCTGTCT AAGCCTCCTG ATTACAGCAG TAGGATT     50880

GGCATGTACT ACTATAGTCA ACGGCAATTG CTGTAGTTCT AATCACTCTC CAAAGTT     50940

AGAACATGTA GCTGGGGTGG GCTATTTCGT TTAATTTTCT AGACAAATAT TGAGTCT     51000

AGAAATATAT TACTATGGGT TAGGTCTGCT TTTCAGGACT AAAGAACTTG GCTAAAT     51060

CAAGGCACTT GGTTCATGAA GAATTACCTA TTGAACCCCT GAAATGGCAG CTGGGAC     51120

CTCTGGACTA TAGGAGCTGG AAAGGGGCAG GGCTGGTGGG AGGAGAAGGT GGAGAGG     51180
```

```
GCTAGGAACT TAAATGTCTT TGAGCTATTG AGCATCTGTT TTTATGTAAG GCATGAC        51240

GATTTTGTAG AGGATACAC                                                 51259
```

GENE PRODUCTS RELATED TO WERNER'S SYNDROME

This application is a continuation of U.S. patent application Ser. No. 08/781,891, filed Dec. 27, 1996, now U.S. Pat. No. 6,090,620, which application is a continuation-in-part of U.S. application Ser. No. 08/632,175, filed Apr. 12, 1996, now abandoned; which is a continuation-in-part of U.S. patent application Ser. No. 08/594,242, filed Jan. 30, 1996, now abandoned; which is a continuation-in-part of U.S. patent application Ser. No. 08/580,539, filed Dec. 29, 1995, now abandoned. This application also claims priority to U.S. patent application Ser. No. 60/009,409 filed Dec. 29, 1995, and U.S. patent application Ser. No. 60/010,835 filed Jan. 30, 1996.

TECHNICAL FIELD

The present invention relates generally to Werner's Syndrome and more specifically to methods and compositions suitable for use in diagnosis and treatment of Werner's Syndrome.

BACKGROUND OF THE INVENTION

Werner Syndrome (WS) is an autosomal recessive disorder with a complex phenotype. The disorder manifests itself in premature occurrence of age-related diseases and premature appearance of some of the physical features of normal aging. The onset of symptoms usually occurs after adolescence. The disorder progresses throughout life and typically patients have a shortened life expectancy with a modal age of death at 47. The prevalence of Werner Syndrome is estimated for heterozygotes to be 1–5 per 1,000 individuals, and for homozygotes to be 1–22 per 1,000,000 individuals.

Clinical symptoms of Werner Syndrome include both a prevalence of age-related diseases and physical features of aging. Such diseases include arteriosclerosis and heart disease, both benign and malignant neoplasms (usually sarcomas), diabetes mellitus, osteoporosis, and ocular cataracts. The physical appearance of WS patients is often manifest as a short stature, premature graying or loss sarcomas), diabetes mellitus, osteoporosis, and ocular cataracts. The physical appearance of WS patients is often manifest as a short stature, premature graying or loss of hair, hypogonadism, altered skin pigmentation, hyperkeratosis, tight skin, bird-like facies, cutaneous atrophy, cutaneous leg ulcers, and telangiectasia. Most of these diseases and features are present in from 40–90% of WS patients. Diagnosis of WS relies mainly upon the appearance of a certain number of these diseases and features. One biochemical test, excessive excretion of hyaluronic acid in urine, may also be used to assist diagnosis.

In addition to the noted signs and symptoms of aging, Werner Syndrome mimics normal aging as evidenced by the replicative potential of fibroblasts isolated from WS subjects. Replication potential of fibroblasts is reduced in these patients compared to fibroblasts isolated from age-matched controls, and is comparable to the replicative potential of fibroblasts taken from elderly subjects. Moreover, an increased mutation rate has been described in WS patients. Such abnormality is manifest as chromosomal instability, such as inversions, reciprocal translocations, deletions, and pseudodiploidy, and as increased mutation rate at the hypoxanthine phosphoribosyl transferase (HPRT) gene.

Werner Syndrome has been recognized as an autosomal recessive disorder. Goto et al. (Goto et al., *Nature* 355:735–738, 1992) mapped the WS gene onto the short arm of chromosome 8, using 21 affected Japanese families. The gene is located between marker D8S87 and ankyrin (ANK1). More recently, more refined mapping has pinpointed the WS gene to a region between marker D8S131 and D8S87, an 8.3 cM interval. Identification of the gene and gene product should add considerably to understanding the basis of Werner Syndrome and enable biochemical and genetic approaches to diagnosis and treatment.

The present invention provides a novel, previously unidentified gene for Werner Syndrome and compositions for diagnosis and treatment of WS, and further provides other related advantages.

SUMMARY OF THE INVENTION

Briefly stated, the present invention provides isolated nucleic acid molecules encoding the WRN gene, as well as portions thereof, representative of which are provided in the Figures. The protein which is encoded by the WRN gene is referred to hereinafter as the "WRN protein". Within other embodiments, nucleic acid molecules are provided which encode a mutant WRN gene product that increases the probability of Werner's Syndrome (in a statistically significant manner). Representative illustrations of such mutants are provided in Example 3.

Within other aspects of the present invention, isolated nucleic acid molecules are provided, selected from the group consisting of (a) an isolated nucleic acid molecule as set forth in the Figures, or complementary sequence thereof, (b) an isolated nucleic acid molecule that specifically hybridizes to the nucleic acid molecule of (a) under conditions of high stringency, and (c) an isolated nucleic acid that encodes a WRN gene product (WRN protein). As utilized herein, it should be understood that a nucleic acid molecule hybridizes "specifically" to an WRN gene (or related sequence) if it hybridizes detectably to such a sequence, but does not significantly or detectably hybridize to the Bloom's Syndrome gene (Ellis et al., *Cell* 83:655–666, 1995).

Within other aspects, expression vectors are provided comprising a promoter operably linked to one of the nucleic acid molecule described above. Representative examples of suitable promoters include tissue-specific promoters, as well as promoters such as the CMV I-E promoter, SV40 early promoter and MuLV LTR. Within related aspects, viral vectors are provided that are capable of directing the expression of a nucleic acid molecule as described above. Representative examples of such viral vectors include herpes simplex viral vectors, adenoviral vectors, adenovirus-associated viral vectors and retroviral vectors. Also provided are host cells (e.g., human, dog, monkey, rat or mouse cells) which carry the above-described vectors.

Within other aspects of the present invention, isolated proteins or polypeptides are provided comprising a WRN gene product, as well as peptides of greater than 12, 13 or 20 amino acids. Within another embodiment, the protein is a mutant WRN gene product that increases the probability of Werner's Syndrome.

Within yet another aspect of the present invention, methods of treating or preventing Werner's Syndrome are provided (as well as for related diseases which are discussed in more detail below), comprising the step of administering to a patient a vector containing or expressing a nucleic acid molecule as described above, thereby reducing the likelihood or delaying the onset of Werner's Syndrome (or the related disease) in the patient. Within a related aspect, methods of treating or preventing Werner's Syndrome (and related diseases) are provided, comprising the step of administering to a patient a protein as described above, thereby reducing the likelihood or delaying the onset of Werner's Syndrome (or a related disease) in the patient. Within certain embodiments, the above methods may be accomplished by in vivo administration.

Also provided by the present invention are pharmaceutical compositions comprising a nucleic acid molecule, vector, host cell, protein, or antibody as described above, along with a pharmaceutically acceptable carrier or diluent.

Within other aspects of the present invention, antibodies are provided which specifically bind to an WRN protein or to unique peptides derived therefrom. As utilized herein, it should be understood that an antibody is specific for an WRN protein (or peptide) if it binds detectably, and with a $K_d$ of $10^{-7}M$ or less (e.g., $10^{-8}M$, $10^{-9}M$, etc.), but does not bind detectably (or with an affinity of greater than $10^{-7}M$, (e.g., $10^{-6}M$, $10^{-5}M$, etc.) to an unrelated helicase (e.g., the Bloom's Syndrome gene, supra). Also provided are hybridomas which are capable of producing such antibodies.

Within other aspects of the present invention, nucleic acid probes are provided which are capable of specifically hybridizing (as defined below) to an WRN gene under conditions of high stringency. Within one related aspect, such probes comprise at least a portion of the nucleotide sequence shown in the Figures, or its complementary sequence, the probe being capable of specifically hybridizing to a mutant WRN gene under conditions of high stringency. Representative probes of the present invention are generally at least 12 nucleotide bases in length, although they may be 14, 16, 18 bases or longer. Also provided are primer pairs capable of specifically amplifying all or a portion of any of the nucleic acid molecules disclosed herein.

Within other aspects of the invention, methods are provided for diagnosing a patient having an increased likelihood of contracting Werner's Syndrome (or a related disease), comprising the steps of (a) obtaining from a patient a biological sample containing nucleic acid, (b) incubating the nucleic acid with a probe which is capable of specifically hybridizing to a mutant WRN gene under conditions and for time sufficient to allow hybridization to occur, and (c) detecting the presence of hybridized probe, and thereby determining that said patient has an increased likelihood of contracting Werner's Syndrome (or a related disease). Within another aspect, methods are provided comprising the steps of (a) obtaining from a patient a biological sample containing nucleic acid, (b) amplifying a selected nucleic acid sequence associated with a mutant WRN gene, and (c) detecting the presence of an amplified nucleic acid sequence, and thereby determining that the patient has an increased likelihood of contracting Werner's Syndrome (or a related disease). Suitable biological samples include nucleated cells obtained from the peripheral blood, from buccal swabs, or brain tissue.

Within another aspect, peptide vaccines are provided which comprise a portion of a mutant WRN gene product containing a mutation, in combination with a pharmaceutically acceptable carrier or diluent.

Within yet another aspect, transgenic animals are provided whose germ cells and somatic cells contain a WRN gene (or lack thereof, i.e., a "knockout") which is operably linked to a promoter effective for the expression of the gene, the gene being introduced into the animal, or an ancestor of the animal, at an embryonic stage. Within one embodiment, the animal is a mouse, rat or dog. Within other embodiments, the WRN gene is expressed from a vector as described above. Within yet another embodiment, the WRN gene encodes a mutant WRN gene product.

These and other aspects of the present invention will become evident upon reference to the following detailed description and attached drawings. In addition, various references are set forth herein which describe in more detail certain procedures or compositions (e.g., plasmids, etc.), and are therefore incorporated by reference in their entirety.

BRIEF DESCRIPTION OF THE DRAWINGS AND SEQUENCE LISTING

FIG. 1 is a genetic and physical map of the WRN region. The genetic map (A) of the region is sex-equal with distances given in cM. The polymorphic loci used (B) are di-nucleotide and tri-nucleotide repeat STRP loci. The physical map presented (C) has approximate distances determined from sizes of over-lapping non-chimeric YACs, and from genomic DNA sequence from overlapping P1 clones 2233, 2253, 3833, 2236, and 3101. Marker order was determined from the sequence-tagged site (STS) content of YACs, P1 clones, and cosmid clones and from genomic DNA sequence from P1 clones. The YACs presented (D) represent the minimal tiling and are the YACs used for cDNA selection experiments. The P1 and cosmid clones needed for the minimum tiling path are shown (E). Clones shown are P1 clones except for 8C11, which is a cosmid clone. Clone order was established by STS content.

FIGS. 2A and 2B are the DNA (SEQ ID No. 70) and predicted amino acid (SEQ ID No. 71) sequences of the WRN gene transcript. The one-letter amino acid code is used in FIG. 2B.

FIGS. 3A–3C are the DNA and predicted amino acid sequence of an alternate WRN gene transcript (SEQ ID Nos. 72 and 73).

FIGS. 4A–4G are an alignment of the WRN gene product (SEQ ID No. 74) with known helicases from S. pombe (SEQ ID No. 76), E. coli (SEQ ID No. 75), human (SEQ ID No. 77) and the Bloom's Syndrome gene "BLM" (SEQ ID No. 78).

FIGS. 5A–5U are the genomic DNA sequence of the region containing a WRN gene (SEQ ID No. 79).

FIG. 6 presents a cDNA sequence of the mouse WRN gene (SEQ ID Nos. 205 and 206).

FIG. 7 is a genomic DNA sequence of the mouse WRN gene (SEQ ID Nos. 207–209).

FIGS. 8A–8D depicts a diagram of the WRN gene product with location of mutations. A, WRN cDNA. Numbering across the top refers to the cDNA sequence as numbered in GenBank L76937. B, Predicted WRN gene product. The helicase domain is designated as "HD", motifs from I to VI are indicated. C, Location of mutations. Numbering across the bottom refer to the mutations. *: nonsense mutation. ^: frame shift mutation caused by a single base deletion. Gray lines: frame shift mutations causing deletion of exon(s). D, Predicted proteins. Lines represent the different predicted truncated proteins produced from mutations in the WRN gene.

Figure 9A:
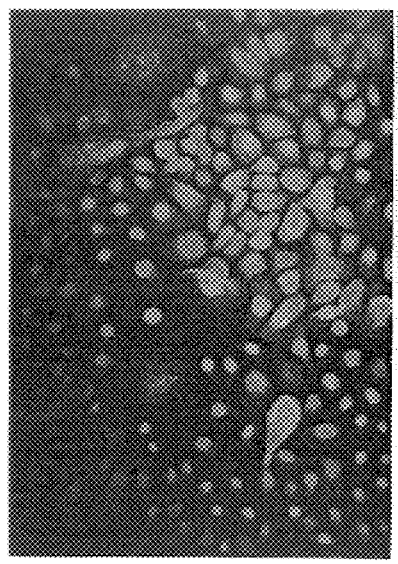
Figure 9B:
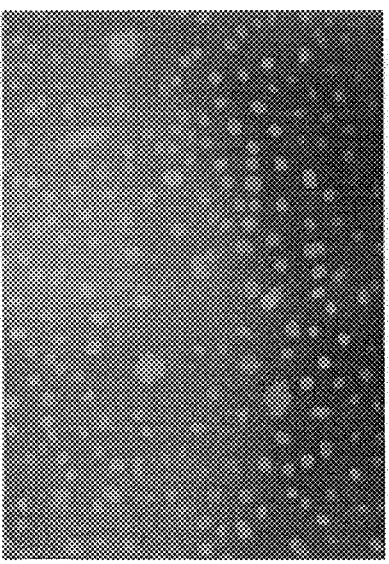
Figure 9C:
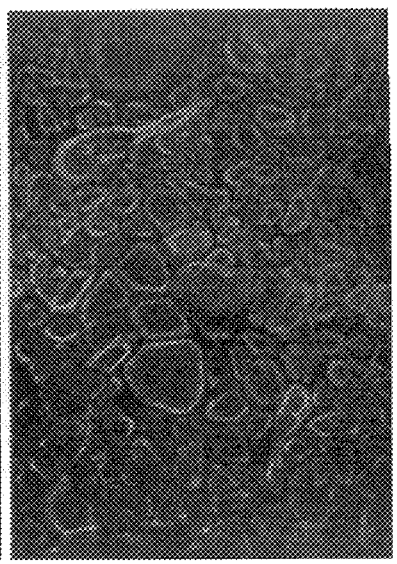

FIGS. 9A, 9B, and 9C are photomeceographs showing localization of the WRN gene product by fluorescent antibody staining (panel A), nuclei (panel B), and the size of cells (panel C) expressing the WRN gene.

FIG. 10 shows the alignment of the mouse and human WRN gene products.

DETAILED DESCRIPTION OF THE INVENTION

Definitions

Prior to setting forth the invention in detail, it may be helpful to an understanding thereof to set forth definitions of certain terms and to list and to define the abbreviations that will be used hereinafter.

"Genetic marker" is any segment of a chromosome that is distinguishably unique in the genome, and polymorphic in the population so as to provide information about the inheritance of linked DNA sequences, genes and/or other markers.

"Vector" refers to an assembly which is capable of directing the expression of a WRN gene, as well as any additional sequence(s) or gene(s) of interest. The vector must include transcriptional promoter elements which are operably linked to the genes of interest. The vector may be composed of either deoxyribonucleic acids ("DNA"), ribonucleic acids ("RNA"), or a combination of the two (e.g., a DNA-RNA chimeric). Optionally, the vector may include a polyadenylation sequence, one or more restriction sites, as well as one or more selectable markers such as neomycin phosphotransferase or hygromycin phosphotransferase. Additionally, .depending on the host cell chosen and the vector employed, other genetic elements such as an origin of replication, additional nucleic acid restriction sites, enhancers, sequences conferring inducibility of transcription, and selectable markers, may also be incorporated into the vectors described herein.

Abbreviations: YAC, yeast artificial chromosome; EST, expressed sequence tag; PCR, polymerase chain reaction; RT-PCR, PCR process in which RNA is first transcribed into DNA at the first step using reverse transcriptase (RT); cDNA, any DNA made by copying an RNA sequence into DNA form.

As noted above, the present invention provides methods and compositions for the detection and treatment of Werner's Syndrome, as well as related diseases. These methods and compositions include a family of Werner's Syndrome-related genes, and the proteins encoded thereby, that have been implicated in the onset of Werner's Syndrome. These genes and proteins, including genetic markers, nucleic acid sequences and clones, are also useful in the creation of in vitro and animal models and screening tests useful for the study of Werner's Syndrome, including the possible identification of other genes implicated in Werner's Syndrome. The present invention also provides vector constructs, genetic markers, nucleic acid sequences, clones, diagnostic tests and compositions and methods for the identification of individuals likely to suffer from Werner's Syndrome.

Genes and Gene Products Related to Werner's Syndrome

The present invention provides isolated nucleic acid molecules comprising a portion of the gene which is implicated in the onset of WS. Briefly, as can be seen from FIG. 4, this gene encodes a protein that is similar in amino acid sequence to several known ATP-dependent DNA helicases (enzymes that unwind the DNA duplex). It is less similar to known RNA-DNA helicases. Helicases are involved in the replication of DNA, often binding the replication origin, and/or the replication complex. In addition, the single stranded DNA that is involved in recombination can be generated by DNA helicases.

Although various aspects of the WRN gene (or portions thereof) are shown in the Figures, it should be understood that within the context of the present invention, reference to one or more of these genes includes derivatives of the genes that are substantially similar to the genes (and, where appropriate, the proteins (including peptides and polypeptides) that are encoded by the genes and their derivatives). As used herein, a nucleotide sequence is deemed to be "substantially similar" if: (a) the nucleotide sequence is derived from the coding region of the described genes and includes, for example, portions of the sequence or allelic variations of the sequences discussed above, or alternatively, encodes a helicase-like activity (Bjornson et al., *Biochem.* 3307:14306–14316, 1994); (b) the nucleotide sequence is capable of hybridization to nucleotide sequences of the present invention under high or very high stringency (see Sambrook et al., *Molecular Cloning: A Laboratory Manual*, 2nd ed., Cold Spring Harbor Laboratory Press, NY, 1989); or (c) the DNA sequences are degenerate as a result of the genetic code to the DNA sequences defined in (a) or (b). Further, the nucleic acid molecule disclosed herein includes both complementary and non-complementary sequences, provided the sequences otherwise meet the criteria set forth herein. Within the context of the present invention, high stringency means standard hybridization conditions (e.g., 5×SSPE, 0.5% SDS at 65° C., or the equivalent) while very high stringency means conditions of hybridization such that the nucleotide sequence is able to selectively hybridize to a single allele of the WS-related gene.

The WRN gene may be isolated from genomic DNA or cDNA. Genomic DNA libraries constructed in chromosomal vectors, such as YACs (yeast artificial chromosomes), bacteriophage vectors, such as λEMBL3, λgt10, cosmids, or plasmids are suitable for use. cDNA libraries constructed in bacteriophage vectors, plasmids, or others, are suitable for screening. Such libraries may be constructed using methods and techniques known in the art (see Sambrook et al., *Molecular Cloning: A Laboratory Manual*, Cold Spring Harbor Press, 1989) or purchased from commercial sources (e.g., Clontech, Palo Alto, Calif.). Within one embodiment, the WRN gene is isolated by PCR performed on genomic DNA, cDNA or DNA from libraries, or is isolated by probe hybridization of genomic DNA or cDNA libraries. Primers for PCR and probes for hybridization screening may be designed based on the DNA sequence of WRN presented herein. The DNA sequence of a portion of the WRN gene and the entire coding sequence is presented in the Figures. Primers for PCR should be derived from sequences in the 5' and 3' untranslated region in order to isolate a full-length cDNA. The primers should not have self-complementary sequences nor have complementary sequences at their 3' end (to prevent primer-dimer formation). Preferably, the primers have a GC content of about 50% and contain restriction sites. The primers are annealed to cDNA and sufficient cycles of PCR are performed to yield a product readily visualized by gel electrophoresis and staining. The amplified fragment is purified and inserted into a vector, such as λgt10 or pBS(M13+), and propagated. An oligonucleotide hybridization probe suitable for screening genomic or cDNA libraries may be designed based on the sequence provided herein. Preferably, the oligonucleotide is 20–30 bases long. Such an oligonucleotide may be synthesized by automated synthesis. The oligonucleotide may be conveniently labeled at the 5' end with a reporter molecule, such as a radionuclide, (e.g., $^{32}P$) or biotin. The library is plated as colonies or phage, depending upon the vector, and the recombinant DNA is transferred to nylon or nitrocellulose membranes. Following denaturation, neutralization, and fixation of the DNA to the membrane, the membranes are hybridized with the labeled probe. The membranes are washed and the reporter molecule detected. The hybridizing colonies or phage are isolated and propagated. Candidate clones or PCR amplified fragments may be verified as containing WRN DNA by any of various means. For example, the candidate clones may be hybridized with a second, nonoverlapping probe or subjected to DNA sequence analysis. In these ways, clones containing WRN gene, which are suitable for use in the present invention are isolated.

The structure of the proteins encoded by the nucleic acid molecules described herein may be predicted from the primary translation products using the hydrophobicity plot function of, for example, P/C Gene, Lasergen System, DNA STAR, Madison, Wisconsin, or according to the methods described by Kyte and Doolittle (*J. Mol. Biol.* 157:105–132, 1982).

WRN proteins of the present invention may be prepared in the form of acidic or basic salts, or in neutral form. In addition, individual amino acid residues may be modified by oxidation or reduction. Furthermore, various substitutions, deletions, or additions may be made to the amino acid or nucleic acid sequences, the net effect of which is to retain or further enhance or decrease the biological activity of the mutant or wild-type protein. Moreover, due to degeneracy in the genetic code, for example, there may be considerable variation in nucleotide sequences encoding the same amino acid sequence.

Other derivatives of the WRN proteins disclosed herein include conjugates of the proteins along with other proteins or polypeptides. This may be accomplished, for example, by the synthesis of N-terminal or C-terminal fusion proteins which may be added to facilitate purification or identification of WRN proteins (see U.S. Pat. No. 4,851,341; see also, Hopp et al., Bio/Technology 6:1204, 1988.) Alternatively, fusion proteins such as WRN protein-β-galactosidase or WRN protein-luciferase may be constructed in order to assist in the identification, expression, and analysis of WRN proteins.

WRN proteins of the present invention may be constructed using a wide variety of techniques described herein. Further, mutations may be introduced at particular loci by synthesizing oligonucleotides containing a mutant sequence, flanked by restriction sites enabling ligation to fragments of the native sequence. Following ligation, the resulting reconstructed sequence encodes a derivative having the desired amino acid insertion, substitution, or deletion.

Alternatively, oligonucleotide-directed site-specific (or segment specific) mutagenesis procedures may be employed to provide an altered gene having particular codons altered according to the substitution, deletion, or insertion required. Exemplary methods of making the alterations set forth above are disclosed by Walder et al. (*Gene* 42:133, 1986); Bauer et al. (*Gene* 37:73, 1985); Craik (*BioTechniques*, January 1985, 12–19); Smith et al. (*Genetic Engineering: Principles and Methods*, Plenum Press, 1981); and Sambrook et al. (supra). Deletion or truncation derivatives of WRN proteins (e.g., a soluble extracellular portion) may also be constructed by utilizing convenient restriction endonuclease sites adjacent to the desired deletion. Subsequent to restriction, overhangs may be filled in, and the DNA religated. Exemplary methods of making the alterations set forth above are disclosed by Sambrook et al. (*Molecular Cloning: A Laboratory Manual*, 2d Ed., Cold Spring Harbor Laboratory Press, 1989).

Mutations of the present invention preferably preserve the reading frame of the coding sequences. Furthermore, the mutations will preferably not create complementary regions that could hybridize to produce secondary mRNA structures, such as loops or hairpins, that would adversely affect translation of the mRNA. Although a mutation site may be predetermined, it is not necessary that the nature of the mutation per se be predetermined. For example, in order to select for optimum characteristics of mutants at a given site, random mutagenesis may be conducted at the target codon and the expressed mutants screened for indicative biological activity. Alternatively, mutations may be introduced at particular loci by synthesizing oligonucleotides containing a mutant sequence, flanked by restriction sites enabling ligation to fragments of the native sequence. Following ligation, the resulting reconstructed sequence encodes a derivative having the desired amino acid insertion, substitution, or deletion.

WRN proteins may also be constructed utilizing techniques of PCR mutagenesis, chemical mutagenesis (Drinlkwater and Klinedinst, *PNAS* 83:3402–3406, 1986), by forced nucleotide misincorporation (e.g, Liao and Wise *Gene* 88:107–111, 1990), or by use of randomly mutagenized oligonucleotides (Horwitz et al., *Genome* 3:112–117, 1989).

Proteins can be isolated by, among other methods, culturing suitable host and vector systems to produce the recombinant translation products of the present invention. Supernates from such cell lines, or protein inclusions or whole cells where the protein is not excreted into the supemate, can then be treated by a variety of purification procedures in order to isolate the desired proteins. For example, the supernate may be first concentrated using commercially available protein concentration filters, such as an Amicon or Millipore Pellicon ultrafiltration unit. Following concentration, the concentrate may be applied to a suitable purification matrix such as, for example, an anti-protein antibody bound to a suitable support. Alternatively, anion or cation exchange resins may be employed in order to purify the protein. As a further alternative, one or more reverse-phase high performance liquid chromatography (RP- HPLC) steps may be employed to further purify the protein. Other methods of isolating the proteins of the present invention are well known in the skill of the art.

A protein is deemed to be "isolated" within the context of the present invention if no other (undesired) protein is detected pursuant to sodium dodecyl sulfate-polyacrylamide gel electrophoresis (SDS-PAGE) analysis followed by Coomassie blue staining. Within other embodiments, the desired protein can be isolated such that no other (undesired) protein is detected pursuant to SDS-PAGE analysis followed by silver staining.

Expression of a WRN Gene

The present invention also provides for the manipulation and expression of the above described genes by culturing host cells containing a vector capable of expressing the above-described genes. Such vectors or vector constructs include either synthetic or cDNA-derived nucleic acid molecules encoding WRN proteins, which are operably linked to suitable transcriptional or translational regulatory elements. Suitable regulatory elements may be derived from a variety of sources, including bacterial, fungal, viral, mammalian, insect, or plant genes. Selection of appropriate regulatory elements is dependent on the host cell chosen, and may be readily accomplished by one of ordinary skill in the art. Examples of regulatory elements include: a transcriptional promoter and enhancer or RNA polymerase binding sequence, a transcriptional termninator, and a ribosomal binding sequence, including a translation initiation signal.

Nucleic acid molecules that encode any of the WRN proteins described above may be readily expressed by a wide variety of prokaryotic and eukaryotic host cells, including bacterial, mammalian, yeast or other fungi, viral, insect, or plant cells. Methods for transforming or transfecting such cells to express foreign DNA are well known in the art (see, e.g., Itakura et al., U.S. Pat. No. 4,704,362; Hinnen et al., *Proc. Natl. Acad Sci. USA* 75:1929–1933, 1978; Murray et al., U.S. Pat. No. 4,801,542; Upshall et al., U.S. Pat. No. 4,935,349; Hagen et al., U.S. Pat. No. 4,784,950; Axel et al. U.S. Pat. No. 4,399,216; Goeddel et al., U.S. Pat. No. 4,766,075; and Sambrook et al. *Molecular Cloning: A*

*Laboratory Manual* 2nd edition, Cold Spring Harbor Laboratory Press, 1989; for plant cells see Czako and Marton, *Plant Physiol.* 104:1067–1071, 1994; and Paszkowski et al., *Biotech.* 24:387–392, 1992).

Bacterial host cells suitable for carrying out the present invention include *E. coli, B. subtilis, Salmonella typhimurium*, and various species within the genera Pseudomonas, Streptomyces, and Staphylococcus, as well as many other bacterial species well known to one of ordinary skill in the art. Representative examples of bacterial host cells include DH5α (Stratagene, LaJolla, Calif.).

Bacterial expression vectors preferably comprise a promoter which functions in the host cell, one or more selectable phenotypic markers, and a bacterial origin of replication. Representative promoters include the β-lactamase (penicillinase) and lactose promoter system (see Chang et al., *Nature* 275:615, 1978), the T7 RNA polymerase promoter (Studier et al., *Meth. Enzymol.* 185:60–89, 1990), the lambda promoter (Elvin et al., *Gene* 87:123–126, 1990), the trp promoter (Nichols and Yanofsky, *Meth. in Enzymology* 101:155, 1983) and the tac promoter (Russell et al., *Gene* 20: 231, 1982). Representative selectable markers include various antibiotic resistance markers such as the kanamycin or ampicillin resistance genes. Many plasmids suitable for transforming host cells are well known in the art. including among others, pBR322 (see Bolivar et al., *Gene* 2:95, 1977), the pUC plasmids pUC18, pUC19, pUC118, pUC119 (see Messing, *Meth. in Enzymology* 101:20–77, 1983 and Vieira and Messing, *Gene* 19:259–268, 1982), and pNH8A, pNH16a, pNH18a, and Bluescript M13 (Stratagene, La Jolla, Calif.).

Yeast and fungi host cells suitable for carrying out the present invention include, among others, *Saccharomyces pombe, Saccharomyces cerevisiae*, the genera Pichia or Kluyveromyces and various species of the genus Aspergillus (McKnight et al., U.S. Pat. No. 4,935,349). Suitable expression vectors for yeast and fungi include, among others, YCp50 (ATCC No. 37419) for yeast, and the amdS cloning vector pV3 (Turnbull, *Bio/Technology* 7:169, 1989), YRp7 (Struhl et al., *Proc. Natl. Acad. Sci. USA* 76:1035–1039, 1978), YEp13 (Broach et al., *Gene* 8:121–133, 1979), pJDB249 and pJDB219 (Beggs, *Nature* 275:104–108, 1978) and derivatives thereof.

Preferred promoters for use in yeast include promoters from yeast glycolytic genes (Hitzeman et al., *J. Biol. Chem.* 255:12073–12080, 1980; Alber and Kawasaki, *J. Mol. Appl. Genet.* 1:419–434, 1982) or alcohol dehydrogenase genes (Young et al., in *Genetic Engineering of Microorganisms for Chemicals*, Hollaender et al. (eds.), p. 355, Plenum, New York, 1982; Ammerer, *Meth. Enzymol.* 101:192–201, 1983). Examples of useful promoters for fungi vectors include those derived from *Aspergillus nidulans* glycolytic genes, such as the adh3 promoter (McKnight et al., *EMBO J.* 4:2093–2099, 1985). The expression units may also include a transcriptional terminator. An example of a suitable terminator is the adh3 terminator (McKnight et al., ibid., 1985).

As with bacterial vectors, the yeast vectors will generally include a selectable marker, which may be one of any number of genes that exhibit a dominant phenotype for which a phenotypic assay exists to enable transformants to be selected. Preferred selectable markers are those that complement host cell auxotrophy, provide antibiotic resistance or enable a cell to utilize specific carbon sources, and include leu2 (Broach et al., ibid.), ura3 (Botstein et al., *Gene* 8:17, 1979), or his3 (Struhl et al., ibid.). Another suitable selectable marker is the cat gene, which confers chloramphenicol resistance on yeast cells.

Techniques for transforming fungi are well known in the literature, and have been described, for instance, by Beggs (ibid.), Hinnen et al. (*Proc. Natl. Acad. Sci. USA* 75:1929–1933, 1978), Yelton et al. (*Proc. Natl. Acad. Sci. USA* 81:1740–1747, 1984), and Russell (*Nature* 301:167–169, 1983). The genotype of the host cell may contain a genetic defect that is complemented by the selectable marker present on the expression vector. Choice of a particular host and selectable marker is well within the level of ordinary skill in the art.

Protocols for the transformation of yeast are also well known to those of ordinary skill in the art. For example, transformation may be readily accomplished either by preparation of spheroplasts of yeast with DNA (see Hinnen et al., *PNAS USA* 75:1929, 1978) or by treatment with alkaline salts such as LiCl (see Itoh et al., *J. Bacteriology* 153:163, 1983). Transformation of fungi may also be carried out using polyethylene glycol as described by Cullen et al. (*Bio/Technology* 5:369, 1987).

Viral vectors include those which comprise a promoter that directs the expression of an isolated nucleic acid molecule that encodes an WRN protein as described above. A wide variety of promoters may be utilized within the context of the present invention; including for example, promoters such as MoMLV LTR, RSV LTR, Friend MuLV LTR, adenoviral promoter (Ohno et al., *Science* 265: 781–784, 1994), neomycin phosphotransferase promoter/enhancer, late parvovirus promoter (Koering et al., *Hum. Gene Therap.* 5:457–463, 1994), Herpes TK promoter, SV40 promoter, metallothionein IIa gene enhancer/promoter, cytomegalovirus immediate early promoter, and the cytomegalovirus immediate late promoter. Within particularly preferred embodiments of the invention, the promoter is a tissue-specific promoter (see e.g., WO 91/02805; EP 0,415,731; and WO 90/07936). Representative examples of suitable tissue specific promoters include neural specific enolase promoter, platelet derived growth factor beta promoter, bone morpho-genetic protein promoter, human alphal-chimaerin promoter, synapsin I promoter and synapsin II promoter. In addition to the above-noted promoters, other viral-specific promoters (e.g., retroviral promoters (including those noted above, as well as others such as HIV promoters), hepatitis, herpes (e.g., EBV), and bacterial, fungal or parasitic (e.g., malarial) -specific promoters may be utilized in order to target a specific cell or tissue which is infected with a virus, bacteria, fungus or parasite.

Thus, WRN proteins of the present invention may be expressed from a variety of viral vectors, including for example, herpes viral vectors (e.g., U.S. Pat. No. 5,288,641), adenoviral vectors (e.g., WO 94/26914, WO 93/9191; Kolls et al., *PNAS* 91(1):215–219, 1994; Kass-Eisler et al., *PNAS* 90(24):11498–502, 1993; Guzman et al., *Circulation* 88(6): 2838–48, 1993; Guzman et al., *Cir. Res.* 73(6):1202–1207, 1993; Zabner et al., *Cell* 75(2):207–216, 1993; Li et al., *Hum Gene Ther.* 4(4):403–409, 1993; Caillaud et al., *Eur. J. Neurosci.* 5(10:1287–1291, 1993; Vincent et al., *Nat. Genet.* 5(2):130–134, 1993; Jaffe et al., *Nat. Genet.* 1(5):372–378, 1992; and Levrero et al, *Gene* 101(2):195–202, 1991), adeno-associated viral vectors (WO 95/13365; Flotte et al., *PNAS* 90(22):10613–10617, 1993), baculovirus vectors, parvovirus vectors (Koering et al., *Hum. Gene Therap.* 5:457–463, 1994), pox virus vectors (Panicali and Paoletti, *PNAS* 79:4927–4931, 1982; and Ozaki et al., *Biochem. Biophys. Res. Comm.* 193(2):653–660, 1993), and retroviruses (e.g., EP 0,415,731; WO 90/07936; WO 91/0285, WO 94/03622; WO 93/25698; WO 93/25234; U.S. Pat. No. 5,219,740; WO 93/11230; WO 93/10218. Viral vectors may likewise be constructed which contain a mixture of different elements (e.g., promoters, envelope sequences and the like) from different viruses, or non-viral sources. Within various embodiments, either the viral vector itself, or a viral particle which contains the viral vector may be utilized in the methods and compositions described below.

Mammalian cells suitable for carrying out the present invention include, among others: PC12 (ATCC No. CRL1721), N1E-115 neuroblastoma, SK-N-BE(2)C neuroblastoma, SHSY5 adrenergic neuroblastoma, NS20Y and NG108-15 murine cholinergic cell lines, or rat F2 dorsal root ganglion line, COS (e.g., ATCC No. CRL 1650 or 1651), BHK (e.g., ATCC No. CRL 6281; BHK 570 cell line (deposited with the American Type Culture Collection under accession number CRL 10314), CHO (ATCC No. CCL 61), HeLa (e.g., ATCC No. CCL 2), 293 (ATCC No. 1573; Graham et al., *J. Gen. Virol.* 36:59–72, 1977) and NS-1 cells. Other mammalian cell lines may be used within the present invention, including Rat Hep I (ATCC No. CRL 1600), Rat Hep II (ATCC No. CRL 1548), TCMK (ATCC No. CCL 139), Human lung (ATCC No. CCL 75.1), Human hepatoma (ATCC No. HTB-52), Hep G2 (ATCC No. HB 8065), Mouse liver (ATCC No. CCL 29.1), NCTC 1469 (ATCC No. CCL 9.1), SP2/0-Ag14 (ATCC No. 1581), HIT-T15 (ATCC No. CRL 1777), and RINm 5AHT$_2$B (Orskov and Nielson, *FEBS* 229(1):175–178, 1988).

Mammalian expression vectors for use in carrying out the present invention will include a promoter capable of directing the transcription of a cloned gene or cDNA. Preferred promoters include viral promoters and cellular promoters. Viral promoters include the cytomegalovirus immediate early promoter (Boshart et al., *Cell* 41:521–530, 1985), cytomegalovirus immediate late promoter, SV40 promoter (Subramani et al., *Mol. Cell. Biol.* 1:854–864, 1981), MMTV LTR, RSV LTR, metallothionein-1, adenovirus E1a. Cellular promoters include the mouse metallothionein-1 promoter (Palmiter et al., U.S. Pat. No. 4,579,821), a mouse V$_\kappa$ promoter (Bergman et al., *Proc. Natl. Acad. Sci. USA* 81:7041–7045, 1983; Grant et al., *Nucl. Acids Res.* 15:5496, 1987) and a mouse V$_H$ promoter (Loh et al., *Cell* 33:85–93, 1983). The choice of promoter will depend, at least in part, upon the level of expression desired or the recipient cell line to be transfected.

Such expression vectors may also contain a set of RNA splice sites located downstream from the promoter and upstream from the DNA sequence encoding the peptide or protein of interest. Preferred RNA splice sites may be obtained from adenovirus and/or immunoglobulin genes. Also contained in the expression vectors is a polyadenylation signal located downstream of the coding sequence of interest. Suitable polyadenylation signals include the early or late polyadenylation signals from SV40 (Kaufman and Sharp, ibid), the polyadenylation signal from the Adenovirus 5 E1B region and the human growth hormone gene terminator (DeNoto et al., *Nuc. Acids Res.* 9:3719–3730, 1981). The expression vectors may include a noncoding viral leader sequence, such as the Adenovirus 2 tripartite leader, located between the promoter and the RNA splice sites. Preferred vectors may also include enhancer sequences, such as the SV40 enhancer. Expression vectors may also include sequences encoding the adenovirus VA RNAs. Suitable expression vectors can be obtained from commercial sources (e.g., Stratagene, La Jolla, Calif.).

Vector constructs comprising cloned DNA sequences can be introduced into cultured mammalian cells by, for example, calcium phosphate-mediated transfection (Wigler et al., *Cell* 14:725, 1978; Corsaro and Pearson, *Somatic Cell Genetics* 7:603, 1981; Graham and Van der Eb, *Virology* 52:456, 1973), electroporation (Neumann et al., *EMBO J.* 1:841–845, 1982), or DEAE-dextran mediated transfection (Ausubel et al. (eds.), *Current Protocols in Molecular Biology*, John Wiley and Sons, Inc., NY, 1987). To identify cells that have stably integrated the cloned DNA, a selectable marker is generally introduced into the cells along with the gene or cDNA of interest. Preferred selectable markers for use in cultured mammalian cells include genes that confer resistance to drugs. such as neomycin, hygromycin, and methotrexate. The selectable marker may be an amplifiable selectable marker. Preferred amplifiable selectable markers are the DHFR gene and the neomycin resistance gene. Selectable markers are reviewed by Thilly (*Mammalian Cell Technology*, Butterworth Publishers, Stoneham, Mass., which is incorporated herein by reference).

Mammalian cells containing a suitable vector are allowed to grow for a period of time, typically 1–2 days, to begin expressing the DNA sequence(s) of interest. Drug selection is then applied to select for growth of cells that are expressing the selectable marker in a stable fashion. For cells that have been transfected with an amplifiable, selectable marker the drug concentration may be increased in a stepwise manner to select for increased copy number of the cloned sequences, thereby increasing expression levels. Cells expressing the introduced sequences are selected and screened for production of the protein of interest in the desired form or at the desired level. Cells that satisfy these criteria can then be cloned and scaled up for production.

Protocols for the transfection of mammalian cells are well known to those of ordinary skill in the art. Representative methods include calcium phosphate mediated transfection, electroporation, lipofection, retroviral, adenoviral and protoplast fusion-mediated transfection (see Sambrook et al., supra). Naked vector constructs can also be taken up by muscular cells or other suitable cells subsequent to injection into the muscle of a mammal (or other animals).

Numerous insect host cells known in the art can also be useful within the present invention, in light of the subject specification. For example, the use of baculoviruses as vectors for expressing heterologous DNA sequences in insect cells has been reviewed by Atkinson et al. (*Pestic. Sci.* 28:215–224,1990).

Numerous plant host cells known in the art can also be useful within the present invention, in light of the subject specification. For example, the use of *Agrobacterium rhizogenes* as vectors for expressing genes in plant cells has been reviewed by Sinkar et al., (*J. Biosci.* (*Bangalore*) 11:47–58, 1987).

WRN proteins may be prepared by growing (typically by culturing) the host/vector systems described above, in order to express the recombinant WRN proteins. Recombinantly produced WRN proteins may be further purified as described in more detail below.

Within related aspects of the present invention, WRN proteins may be expressed in a transgenic animal whose germ cells and somatic cells contain a WRN gene which is operably linked to a promoter effective for the expression of the gene. Alternatively, in a similar manner transgenic animals may be prepared that lack the WRN gene (e.g., "knockout" mice). Such transgenics may be prepared in a variety non-human animals, including mice, rats, rabbits, sheep, dogs, goats and pigs (see Hammer et al. *Nature* 315:680–683, 1985, Palmiter et al. *Science* 222:809–814, 1983, Brinster et al. *Proc. Natl. Acad. Sci. USA* 82:4438–4442, 1985, Palmiter and Brinster *Cell*

41:343–345, 1985 and U.S. Pat. Nos. 5,175,383, 5,087,571, 4,736,866, 5,387,742, 5,347,075, 5,221,778, and 5,175, 384).

Briefly, an expression vector, including a nucleic acid molecule to be expressed together with appropriately positioned expression control sequences, is introduced into pronuclei of fertilized eggs, for example, by microinjection. Integration of the injected DNA is detected by blot analysis of DNA from tissue samples. It is preferred that the introduced DNA be incorporated into the germ line of the animal so that it is passed on to the animal's progeny. Tissue-specific expression may be achieved through the use of a tissue-specific promoter, or through the use of an inducible promoter, such as the metallothionein gene promoter (Palmiter et al., 1983, ibid), which allows regulated expression of the transgene.

Vectors of the present invention may contain or express a wide variety of additional nucleic acid molecules in place of or in addition to an WRN protein as described above, either from one or several separate promoters. For example, the viral vector may express a lymphokine or lymphokine receptor, antisense or ribozyme sequence or toxins. Representative examples of lymphokines include IL-1, IL-2, IL-3, IL-4, IL-5, IL-6, IL-7, IL-8, IL-9, IL-10, IL-11, IL-12, IL-13, IL-14, IL-15, G-CSF, M-CSF, alpha-interferon, beta-interferon, gamma-interferon, and tumor necrosis factors, as well as their respective receptors. Representative examples of antisense sequences include antisense sequences which block the expression of WRN protein mutants. Representative examples of toxins include: ricin, abrin, diphtheria toxin, cholera toxin, saporin, gelonin, pokeweed antiviral protein, tritin, Shigella toxin, and Pseudomonas exotoxin A.

Within other aspects of the invention, antisense oligonucleotide molecules are provided which specifically inhibit expression of mutant WRN nucleic acid sequences (see generally, Hirashima et al. in *Molecular Biology of RNA: New Perspectives* (M. Inouye and B. S. Dudock, eds., 1987 Academic Press, San Diego, p. 401); *Oligonucleotides: Antisense Inhibitors of Gene Expression* (J. S. Cohen, ed., 1989 MacMillan Press, London); Stein and Cheng, *Science* 261:1004–1012 (1993); WO 95/10607; U.S. Pat. No. 5,359, 051; WO 92/06693; and EP-A2-612844). Briefly, such molecules are constructed such that they are complementary to, and able to form Watson-Crick base pairs with, a region of transcribed WRN mutant mRNA sequence containing an WRN mutation. The resultant double-stranded nucleic acid interferes with subsequent processing of the mRNA, thereby preventing protein synthesis.

Within other related aspects of the invention, ribozyme molecules are provided wherein an antisense oligonucleotide sequence is incorporated into a ribozyme which can specifically cleave mRNA molecules transcribed from a mutant WRN gene (see generally, Kim et al. *Proc. Nat. Acad Sci. USA* 84:8788 (1987); Haseloff, et al. *Nature* 234:585 (1988), Cech, *JAMA* 260:3030 (1988); Jeffries, et al. *Nucleic Acids Res.* 17:1371 (1989); U.S. Pat. No. 5,093,246; U.S. Pat. No. 5,354,855; U.S. Pat. No. 5,144,019; U.S. Pat. No. 5,272,262; U.S. Pat. No. 5,254,678; and U.S. Pat. No. 4,987,071). According to this aspect of the invention, the antisense sequence which is incorporated into a ribozyme includes a sequence complementary to, and able to form Watson-Crick base pairs with, a region of the transcribed mutant WRN mRNA containing an WRN mutation. The antisense sequence thus becomes a targeting agent for delivery of catalytic ribozyme activity specifically to mutant WRN mRNA, where such catalytic activity cleaves the mRNA to render it incapable of being subsequently processed for WRN protein translation.

Host Cells

As discussed above, nucleic acid molecules which encode the WRN proteins of the present invention (or the vectors which contain and/or express related mutants) may readily be introduced into a wide variety of host cells. Representative examples of such host cells include plant cells, eukaryotic cells, and prokaryotic cells. Within preferred embodiments, the nucleic acid molecules are introduced into cells from a vertebrate or warrn-blooded animal, such as a human, macaque, dog, cow, horse, pig, sheep, rat, hamster, mouse or fish cell, or any hybrid thereof.

Preferred prokaryotic host cells for use within the present invention include *E. coli*, Salmonella, Bacillus, Shigella, Pseudomonas, Streptomyces and other genera. Techniques for transforming these hosts and expressing foreign DNA sequences cloned therein are well known in the art (see, e.g., Maniatis et al., *Molecular Cloning: A Laboratory Manual*, Cold Spring Harbor Laboratory, 1982, which is incorporated herein by reference; or Sambrook et al., supra). Vectors used for expressing cloned DNA sequences in bacterial hosts will generally contain a selectable marker, such as a gene for antibiotic resistance, and a promoter that functions in the host cell. Appropriate promoters include the trp (Nichols and Yanofsky, *Meth. Enzymol.* 101:155–164, 1983), lac (Casadaban et al., *J. Bacteriol.* 143:971–980, 1980), and phage λ (Queen, *J. Mol. Appl. Genet.* 2:1–10, 1983) promoter systems. Plasmids useful for transforming bacteria include the pUC plasmids (Messing, *Meth. Enzymol.* 101:20–78, 1983; Vieira and Messing, *Gene* 19:259–268, 1982), pBR322 (Bolivar et al., *Gene* 2:95–113, 1977), pCQV2 (Queen, ibid.), and derivatives thereof. Plasmids may contain both viral and bacterial elements.

Preferred eukaryotic cells include cultured mammalian cell lines (e.g., rodent or human cell lines) and fungal cells, including species of yeast (e.g., Saccharomyces spp., particularly *S. cerevisiae*, Schizosaccharomyces spp., or Kluyveromyces spp.) or filamentous fungi (e.g., Aspergillus spp., Neurospora spp.). Strains of the yeast *Saccharomyces cerevisiae* are particularly preferred. Methods for producing recombinant proteins in a variety of prokaryotic and eukaryotic host cells are generally known in the art (see, "Gene Expression Technology," *Methods in Enzymology*, Vol. 185, Goeddel (ed.), Academic Press, San Diego, Calif., 1990; see also, "Guide to Yeast Genetics and Molecular Biology," *Methods in Enzymology*, Guthrie and Fink (eds.), Academic Press, San Diego, Calif., 1991). In general, a host cell will be selected on the basis of its ability to produce the protein of interest at a high level or its ability to carry out at least some of the processing steps necessary for the biological activity of the protein. In this way, the number of cloned DNA sequences that must be introduced into the host cell can be minimized and overall yield of biologically active protein can be maximized.

The nucleic acid molecules (or vectors) may be introduced into host cells by a wide variety of mechanisms, including for example calcium phosphate-mediated transfection (Wigler et al., *Cell* 14:725, 1978), lipofection; gene gun (Corsaro and Pearson, *Somatic Cell Gen.* 7:603, 1981; Graham and Van der Eb, *Virology* 52:456, 1973), electroporation (Neumann et al., *EMBO J.* 1:841–845, 1982), retroviral, adenoviral, protoplast fusion-mediated transfection or DEAE-dextran mediated transfection (Ausubel et al., (eds.), *Current Protocols in Molecular Biology*, John Wiley and Sons, Inc., New York, N.Y., 1987).

Host cells containing vector constructs of the present invention are then cultured to express a DNA molecule as described above. The cells are cultured according to standard methods in a culture medium containing nutrients required for growth of the chosen host cells. A variety of suitable media are known in the art and generally include a carbon source, a nitrogen source, essential amino acids, vitamins and minerals, as well as other components, e.g., growth factors or serum, that may be required by the particular host cells. The growth medium will generally select for cells containing the DNA construct(s) by, for example, drug selection or deficiency in an essential nutrient which is complemented by the selectable marker on the DNA construct or co-transfected with the DNA construct.

Suitable growth conditions for yeast cells, for example, include culturing in a chemically defined medium, comprising a nitrogen source, which may be a non-amino acid nitrogen source or a yeast extract, inorganic salts, vitamins and essential amino acid supplements at a temperature between 4° C. and 37° C., with 30° C. being particularly preferred. The pH of the medium is preferably maintained at a pH greater than 2 and less than 8, more preferably pH 5–6. Methods for maintaining a stable pH include buffering and constant pH control. Preferred agents for pH control include sodium hydroxide. Preferred buffering agents include succinic acid and Bis-Tris (Sigma Chemical Co., St. Louis, Mo.). Due to the tendency of yeast host cells to hyperglycosylate heterologous proteins, it may be preferable to express the nucleic acid molecules of the present invention in yeast cells having a defect in a gene required for asparagine-linked glycosylation. Such cells are preferably grown in a medium containing an osmotic stabilizer. A preferred osmotic stabilizer is sorbitol supplemented into the medium at a concentration between 0.1 M and 1.5 M, preferably at 0.5 M or 1.0 M.

Cultured mammalian cells are generally cultured in commercially available serum-containing or serum-free media. Selection of a medium and growth conditions appropriate for the particular cell line used is well within the level of ordinary skill in the art.

Antibodies

Antibodies to the WRN proteins discussed above may readily be prepared given the disclosure provided herein. Such antibodies may, within certain embodiments, specifically recognize wild type WRN protein rather than a mutant WRN protein, mutant WRN protein rather than wild type WRN protein, or equally recognize both the mutant and wild-type forms of WRN protein. Antibodies may be used for isolation of the protein, establishing intracellular localization of the WRN protein, inhibiting activity of the protein (antagonist), or enhancing activity of the protein (agonist). Knowledge of the intracellular location of the WRN gene product may be abnormal in patients with WRN mutations, thus allowing the development of a rapid screening assay. As well, assays for small molecules that interact with the WRN gene product will be facilitated by the development of antibodies and localization studies.

Within the context of the present invention, antibodies are understood to include monoclonal antibodies, polyclonal antibodies, anti-idiotypic antibodies, antibody fragments (e.g., Fab, and $F(ab')_2$, $F_v$ variable regions, or complementarity determining regions). As discussed above, antibodies are understood to be specific against an WRN protein if it binds with a $K_d$ of greater than or equal to $10^{-7}$M, preferably greater than of equal to $10^{-8}$M. The affinity of a monoclonal antibody or binding partner can be readily determined by one of ordinary skill in the art (see Scatchard, *Ann. N.Y. Acad. Sci.* 51:660–672, 1949).

Briefly, polyclonal antibodies may be readily generated by one of ordinary skill in the art from a variety of warm-blooded animals such as horses, cows, various fowl, rabbits, mice, or rats. Typically, an WRN protein or unique peptide thereof of 13–20 amino acids (preferably conjugated to keyhole limpet hemocyanin by cross-linking with glutaraldehyde) is utilized to immunize the animal through intraperitoneal, intramuscular, intraocular, or subcutaneous injections, an adjuvant such as Freund's complete or incomplete adjuvant. Merely as an example, a peptide corresponding to residues 1375 through 1387 of the WRN polypeptide sequence is used to raise a rabbit polyclonal antiserum. Following several booster immunizations. samples of serum are collected and tested for reactivity to the WRN protein or peptide. Particularly preferred polyclonal antisera will give a signal on one of these assays that is at least three times greater than background. Once the titer of the animal has reached a plateau in terms of its reactivity to the protein, larger quantities of antisera may be readily obtained either by weekly bleedings, or by exsanguinating the animal.

Monoclonal antibodies may also be readily generated using conventional techniques (see U.S. Pat. Nos. RE 32,011, 4,902,614, 4,543,439, and 4,411,993 which are incorporated herein by reference; see also *Monoclonal Antibodies, Hybridomas: A New Dimension in Biological Analyses*, Plenum Press, Kennett. McKearn. and Bechtol (eds.), 1980, and *Antibodies: A Laboratory Manual*, Harlow and Lane (eds.), Cold Spring Harbor Laboratory Press, 1988, which are also incorporated herein by reference).

Briefly, within one embodiment a subject animal such as a rat or mouse is injected with an WRN protein or portion thereof as described above. The protein may be admixed with an adjuvant such as Freund's complete or incomplete adjuvant in order to increase the resultant immune response. Between one and three weeks after the initial immunization the animal may be reimmunized with another booster immunization, and tested for reactivity to the protein utilizing assays described above. Once the animal has reached a plateau in its reactivity to the injected protein, it is sacrificed, and organs which contain large numbers of B cells such as the spleen and lymph nodes are harvested.

Cells which are obtained from the immunized animal may be immortalized by transfection with a virus such as the Epstein-Barr virus (EBV) (see Glasky and Reading, *Hybridoma* 8(4):377–389, 1989). Alternatively, within a preferred embodiment, the harvested spleen and/or lymph node cell suspensions are fused with a suitable myeloma cell in order to create a "hybridoma" which secretes monoclonal antibody. Suitable myeloma lines include, for example, NS-1 (ATCC No. TIB 18), and P3X63- Ag8.653 (ATCC No. CRL 1580).

Following the fusion, the cells may be placed into culture plates containing a suitable medium, such as RPMI 1640, or DMEM (Dulbecco's Modified Eagles Medium) (JRH Biosciences, Lenexa, Kans.), as well as additional ingredients, such as fetal bovine serum (FBS, i.e., from Hyclone, Logan, Utah, or JRH Biosciences). Additionally, the medium should contain a reagent which selectively allows for the growth of fused spleen and myeloma cells such as HAT (hypoxanthine, aminopterin, and thymidine) (Sigma Chemical Co., St. Louis, Mo.). After about seven days, the resulting fused cells or hybridomas may be screened in order to determine the presence of antibodies which are reactive against an WRN protein. A wide variety of assays may be utilized to determine the presence of antibodies which are reactive against the proteins of the present invention, including for example countercurrent immuno-electrophoresis, radioimmunoassays, radioimmunoprecipitations, enzyme-linked immunosorbent assays (ELISA), dot blot assays, western blots, immunoprecipitation, Inhibition or Competition Assays, and sandwich assays (see U.S. Pat. Nos. 4,376,110 and 4,486,530; see also *Antibodies: A Laboratory Manual*, Harlow and Lane (eds.), Cold Spring Harbor Laboratory Press, 1988). Following several clonal dilutions and reassays, a hybridoma producing antibodies reactive against the WRN protein may be isolated.

Other techniques may also be utilized to construct monoclonal antibodies (see William D. Huse et al., "Generation of a Large Combinational Library of the Immunoglobulin Repertoire in Phage Lambda," *Science* 246:1275–1281, December 1989; see also L. Sastry et al., "Cloning of the Immunological Repertoire in *Escherichia coli* for Generation of Monoclonal Catalytic Antibodies: Construction of a Heavy Chain Variable Region-Specific cDNA Library," *Proc. Natl. Acad. Sci. USA* 86:5728–5732, August 1989; see also Michelle Alting-Mees et al., "Monoclonal Antibody Expression Libraries: A Rapid Alternative to Hybridomas," *Strategies in Molecular Biology* 3:1–9, January 1990; these references describe a commercial system available from Stratacyte, La Jolla, Calif., which enables the production of antibodies through recombinant techniques). Briefly, mRNA is isolated from a B cell population, and utilized to create heavy and light chain immunoglobulin cDNA expression libraries in the λImmunoZap(H) and λImmunoZap(L) vectors. These vectors may be screened individually or co-expressed to form Fab fragments or antibodies (see Huse et al., supra; see also Sastry et al., supra). Positive plaques may subsequently be converted to a non-lytic plasmid which allows high level expression of monoclonal antibody fragments from *E. coli*.

Similarly, portions or fragments, such as Fab and Fv fragments, of antibodies may also be constructed utilizing conventional enzymatic digestion or recombinant DNA techniques to incorporate the variable regions of a gene which encodes a specifically binding antibody. Within one embodiment, the genes which encode the variable region from a hybridoma producing a monoclonal antibody of interest are amplified using nucleotide primers for the variable region. These primers may be synthesized by one of ordinary skill in the art, or may be purchased from commercially available sources. Stratacyte (La Jolla, Calif.) sells primers for mouse and human variable regions including, among others, primers for $V_{Ha}$, $V_{Hb}$, $V_{Hc}$, $V_{Hd}$, $C_{H1}$, $V_L$ and $C_L$ regions. These primers may be utilized to amplify heavy or light chain variable regions, which may then be inserted into vectors such as ImmunoZAP™ H or ImmunoZAP™ L (Stratacyte), respectively. These vectors may then be introduced into *E. coli*, yeast, or mammalian-based systems for expression. Utilizing these techniques, large amounts of a single-chain protein containing a fusion of the $V_H$ and $V_L$ domains may be produced (see Bird et al., *Science* 242:423–426, 1988). In addition, such techniques may be utilized to change a "murine" antibody to a "human" antibody, without altering the binding specificity of the antibody.

Once suitable antibodies have been obtained, they may be isolated or purified by many techniques well known to those of ordinary skill in the art (see *Antibodies. A Laboratory Manual*, Harlow and Lane (eds.), Cold Spring Harbor Laboratory Press, 1988). Suitable techniques include peptide or protein affinity columns, HPLC or RP-HPLC, purification on protein A or protein G columns, or any combination of these techniques.

Assays

Assays useful within the context of the present invention include those assays for detecting agonists or antagonists of WRN protein activity. Other assays are useful for the screening of peptide or organic molecule libraries. Still other assays are useful for the identification and/or isolation of nucleic acid molecules and/or peptides within the present invention, the identification of proteins that interact or bind the WRN protein, for diagnosis of a patient with an increased likelihood of contracting Werner's Syndrome, or for diagnosis of a patient with susceptibility to or manifestation of a WRN-related disease.

Nucleic Acid Based Diagnostic Tests

Briefly, another aspect of the present invention provides probes and primers for detecting the WRN genes and/or mutants thereof. In one embodiment of this aspect, probes are provided that are capable of specifically hybridizing to DNA or RNA of the WRN genes. For purposes of the present invention, probes are "capable of hybridizing" to DNA or RNA of the WRN gene if they hybridize to an WRN gene under conditions of either high or moderate stringency (see Sambrook et al., supra) but not significantly or detectably to the an unrelated helicase gene such as the Bloom's Syndrome gene (Ellis et al., *Cell* 83:655–666, 1995). Preferably, the probe hybridizes to suitable nucleotide sequences under high stringency conditions, such as hybridization in 5×SSPE, 1×Denhardt's solution, 0.1% SDS at 65° C., and at least one wash to remove unhybridized probe in the presence of 0.2×SSC, 1×Denhardt's solution, 0.1% SDS at 65° C. Except as otherwise provided herein, probe sequences are designed to allow hybridization to WRN genes, but not to DNA or RNA sequences from other genes. The probes are used, for example, to hybridize to nucleic acid that is present in a biological sample isolated from a patient. The hybridized probe is then detected, thereby indicating the presence of the desired cellular nucleic acid. Preferably, the cellular nucleic acid is subjected to an amplification procedure, such as PCR, prior to hybridization. Alternatively, the WRN gene may be amplified and the amplified product subjected to DNA sequencing. Mutants of WRN may be detected by DNA sequence analysis or hybridization with allele-specific oligonucleotide probes under conditions and for time sufficient to allow hybridization to the specific allele. Typically, the hybridization buffer and wash will contain tetramethyl ammonium chloride or the like (see Sambrook et al., supra).

Nucleic acid probes of the present invention may be composed of either deoxyribonucleic acids (DNA), ribonucleic acids (RNA), nucleic acid analogues (e.g., peptide nucleic acids), or any combination thereof, and may be as few as about 12 nucleotides in length, usually about 14 to 18 nucleotides in length, and possibly as large as the entire sequence of a WRN gene. Selection of probe size is somewhat dependent upon the use of the probe, and is within the skill of the art.

Suitable probes can be constructed and labeled using techniques that are well known in the art. Shorter probes of, for example, 12 bases can be generated synthetically and labeled with $^{32}P$ using $T_4$ polynucleotide kinase. Longer probes of about 75 bases to less than 1.5 kb are preferably generated by, for example, PCR amplification in the presence of labeled precursors such as [$\alpha$-$^{32}P$]dCTP, digoxigenin-dUTP, or biotin-dATP. Probes of more than 1.5 kb are generally most easily amplified by transfecting a cell with a plasmid containing the relevant probe, growing the transfected cell into large quantities, and purifying the relevant sequence from the transfected cells. (See Sambrook et al., supra.) Probes can be labeled by a variety of markers, including for example, radioactive markers, fluorescent markers, enzymatic markers, and chromogenic markers. The use of $^{32}P$ is particularly preferred for marking or labeling a particular probe.

It is a feature of this aspect of the invention that the probes can be utilized to detect the presence of WRN mRNA or DNA within a sample. However, if the relevant sample is present in only a limited number, then it may be beneficial to amplify the relevant sequence so that it may be more readily detected or obtained.

A variety of methods may be utilized in order to amplify a selected sequence, including, for example, RNA amplification (see Lizardi et al., *Bio/Technology* 6:1197–1202, 1988; Kramer et al., *Nature* 339:401–402, 1989; Lomeli et al., *Clinical Chem.* 35(9):1826–1831, 1989; U.S. Pat. No. 4,786,600), and DNA amplification utilizing LCR or polymerase chain reaction ("PCR") (see, U.S. Pat. Nos. 4,683, 195, 4,683,202, and 4,800,159) (see also U.S. Pat. Nos. 4,876.187 and 5,011,769, which describe an alternative detection/amplification system comprising the use of scissile linkages), or other nucleic acid amplification procedures that are well within the level of ordinary skill in the art. With respect to PCR, for example, the method may be modified as known in the art. Transcriptional enhancement of PCR may be accomplished by incorporation of bacteriophage T7 RNA polymerase promoter sequences in one of the primary oligonucleotides, and immunoenzymatic detection of the products from the enhanced emitter may be effected using anti-RNA:DNA antibodies (Blais, *Appl. Environ. Microbiol.* 60:348–352, 1994). PCR may also be used in combination with reverse dot-blot hybridization (Iida et al., *FEMS Microbiol. Lett.* 114:167–172, 1993). PCR products may be quantitatively analyzed by incorporation of dUTP (Duplaà et al., *Anal. Biochem.* 212:229–236, 1993), and samples may be filter sampled for PCR-gene probe detection (Bej et al., *Appl. Environ. Microbiol.* 57:3529–3534, 1991).

Within a particularly preferred embodiment, PCR amplification is utilized to detect the WRN DNA. Briefly, as described in greater detail below, a DNA sample is denatured at 95° C. in order to generate single-stranded DNA. The DNA sample may be a cDNA generated from RNA. Specific primers are then annealed to the single-stranded DNA at 37° C. to 70° C., depending on the proportion of AT/GC in the primers. The primers are extended at 72° C. with Taq DNA polymerase or other thermostable DNA polymerase in order to generate the opposite strand to the template. These steps constitute one cycle, which may be repeated in order to amplify the selected sequence. For greater specificity, nested PCR may be performed. In nested PCR, a second amplification is performed using a second set of primers derived from sequences within the first amplified product. The entire coding region of WRN may be amplified from cDNA using three sets of primers to generate fragment lengths that are a convenient size for determining their sequence. In a preferred embodiment, nested PCR is performed.

Within an alternative preferred embodiment, LCR amplification is utilized for amplification. LCR primers are synthesized such that the 5' base of the upstream primer is capable of hybridizing to a unique base pair in a desired gene to specifically detect an WRN gene.

Within another preferred embodiment, the probes are used in an automated, non-isotopic strategy wherein target nucleic acid sequences are amplified by PCR, and then desired products are determined by a colorimetric oligonucleotide ligation assay (OLA) (Nickerson et al., *Proc. Natl. Acad. Sci. USA* 81:8923–8927, 1990).

Primers for the amplification of a selected sequence should be selected from sequences that are highly specific to WRN (and not, e.g., the Bloom's Syndrome gene. supra) and form stable duplexes with the target sequence. The primers should also be non-complementary, especially at the 3' end, should not form dimers with themselves or other primers, and should not form secondary structures or duplexes with other regions of DNA. In general, primers of about 18 to 20 nucleotides are preferred, and can be easily synthesized using techniques well known in the art. PCR products, and other nucleic acid amplification products, may be quantitated using techniques known in the art (Duplaà et al., *Anal. Biochem.* 212:229–236, 1993; Higuchi et al., *Bio/Technology* 11:1026–1030).

Within one embodiment of the invention, nucleic acid diagnostics may be developed which are capable of detecting the presence of Werner's Syndrome, or of various related diseases that may be caused by Werner's Syndrome. Briefly, severe mutations in the WRN gene may lead to Werner's Syndrome, as well as a host of related diseases, including for example, increased frequency of some benign and malignant neoplasms (especially sarcomas), cataracts, cardiovascular disease, osteoporosis, type I or type II diabetes, cataracts, sclerodoma-like skin changes and hyperkeratosis. Less severe mutations of the gene may lead to the onset of the same set of diseases, but at an older age. In addition, many of the related diseases may be associated with mutations in the WRN gene. For example, diabetes and osteoporosis are often associated with aging. Aging population and individuals with these (or other) diseases are screened for mutations in WRN. Any of the assays described herein may be used. RT-PCR is especially preferred in conjunction with DNA sequence determination. To correlate a mutation or polymorphism with disease, sibling pairs in which one sibling has disease are preferred subjects. Once a mutation is identified, other convenient screening assays may be used to assay particular nucleotide changes.

Since the sequences of the two copies of the gene from non-Werner's affected individuals can be correlated with the medical histories of these patients to define these correspondences, these alleles can therefore be used as diagnostics for susceptibilities to these diseases, once the relationship is defined. Certain non-null forms of the gene, for example, in either the homozygous or heterozygous state may significantly affect the propensity for the carriers to develop, for example, cancer. These propensities can be ascertained by examining the sequences of the gene (both copies) in a statistically significant sample of cancer patients. Other diseases (see above) can be similarly examined for significant correlations with certain alleles. To detect such a causal relationship one can use a chi-squared test, or other statistical test, to examine the significance of any correlation between the appropriate genotypes and the disease state as recorded in the medical records, using standard good practices of medical epidemiology. The sequences that define each of the alleles are then valuable diagnostic indicators for an increased susceptibility to the disease. Thus, from the nucleic acid sequences provided herein, a wide variety of Werner's Syndrome-related diseases may be readily detected.

Another cellular phenotype of the cells from Werner's patients is the increased frequency of deletion mutation in these cells. Clearly, the defective helicase in these cells leads to a specific mutator phenotype, while not rendering the cells hypersensitive to a variety of chemical or physical mutagens that damage DNA, like ionizing radiation. Disease states, or sensitivities that result from an elevated deletion frequency can therefore be controlled, in part, by alterations of the Werner's gene, and some alleles may therefore be diagnostic of this class of medical conditions.

Assays for Agonists and Antagonists

An agonist or antagonist of the WRN gene product comprising a protein, peptide. chemical, or peptidomimetic that binds to the WRN gene product or interacts with a protein that binds to the WRN gene product such that the binding of the agonist or antagonist affects the activity of the WRN gene product. An agonist will activate or increase the activity of the WRN gene product. An antagonist will inhibit or decrease the activity of the WRN gene product. The activity of the WRN gene product may be measured in an assay, such as a helicase assay or other assay that measures an activity of the WRN gene product. Other assays measure the binding of protein that interacts with WRN and is necessary for its activity.

Agonists and antagonists of the WRN gene product may be used to enhance activity or inhibit activity of the gene product. Such agonists and antagonists may be identified in a variety of methods. For example, proteins that bind and activate WRN may be identified using a yeast 2-hybrid detection system. In this system, the WRN gene is fused to either a DNA-binding domain or an activating domain of a yeast gene such as GAL4. A cDNA library is constructed in a vector such that the inserts are fused to one of the domains. The vectors are co-transfected into yeast and selected for transcriptional activation of a reporter gene (Fields and Song, *Nature* 340: 245, 1989). The protein(s) that bind to WRN are candidate agonists. Three different proteins that bind WRN have been identified in an initial screen using the 2-hybrid system.

When the binding site on WRN gene product is determined, molecules that bind and activate WRN protein may be designed and evaluated. For example, computer modeling of the binding site can be generated and mimetics that bind can be designed. Antibodies to the binding site may be generated and analogues of native binding proteins generated as well. Any of these molecules is tested for agonist or antagonist activity by a functional assay of the WRN gene product. For example, to test for antagonist activity, yeast are co-transfected with the WRN and binding protein each fused to a DNA binding domain or an activation domain. The test molecule is administered and activation is monitored. An antagonist will inhibit the activation of the reporter gene by at least 50%. Similarly, agonist activity may be measured by either enhancing WRN activity in a yeast 2-hybrid system or by coupling the test compound to a DNA binding or activation domain and monitoring activity of the reporter gene.

Labels

WRN proteins, nucleic acid molecules which encodes such proteins, anti-WRN protein antibodies and agonists or antagonists, as described above and below, may be labeled with a variety of molecules, including for example, fluorescent molecules, toxins, and radionuclides. Representative examples of fluorescent molecules include fluorescein, Phycobili proteins, such as phycoerythrin, rhodamine, Texas red and luciferase. Representative examples of toxins include ricin, abrin diphtheria toxin, cholera toxin, gelonin, pokeweed antiviral protein, tritin, Shigella toxin, and Pseudomonas exotoxin A. Representative examples of radionuclides include Cu-64, Ga-67, Ga-68, Zr-89, Ru-97, Tc-99m, Rh-105, Pd-109, In-111, I-123, I-125, I-131, Re-186, Re-188, Au-198, Au-199, Pb-203, At-211, Pb-212 and Bi-212. In addition, the antibodies described above may also be labeled or conjugated to one partner of a ligand binding pair. Representative examples include avidin-biotin, and riboflavin-riboflavin binding protein.

Methods for conjugating or labeling the WRN proteins, nucleic acid molecules which encode such proteins, anti-WRN protein antibodies and agonists or antagonists, as discussed above, with the representative labels set forth above may be readily accomplished by one of ordinary skill in the art (see Trichothecene Antibody Conjugate, U.S. Pat. No. 4,744,981,; Antibody Conjugate, U.S. Pat. No. 5,106, 951; Fluorogenic Materials and Labeling Techniques, U.S. Pat. No. 4,018,884; Metal Radionuclide Labeled Proteins for Diagnosis and Therapy, U.S. Pat. No. 4,897,255; and Metal Radionuclide Chelating Compounds for Improved Chelation Kinetics, U.S. Pat. No. 4,988,496; see also Inman, *Methods In Enzymology*, Vol. 34, *Affinity Techniques, Enzyme Purification: Part B*, Jakoby and Wilchek (eds.), Academic Press, New York, p. 30, 1974; see also Wilchek and Bayer, "The Avidin-Biotin Complex in Bioanalytical Applications," *Anal. Biochem.* 171:1–32, 1988).

Pharmaceutical Compositions

As noted above, the present invention also provides a variety of pharmaceutical compositions, comprising one of the above-described WRN proteins, nucleic acid molecules, vectors, antibodies, host cells, agonists or antagonists, along with a pharmaceutically or physiologically acceptable carrier, excipients or diluents. Generally, such carriers should be nontoxic to recipients at the dosages and concentrations employed. Ordinarily, the preparation of such compositions entails combining the therapeutic agent with buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients. Neutral buffered saline or saline mixed with nonspecific serum albumin are exemplary appropriate diluents.

In addition, the pharmaceutical compositions of the present invention may be prepared for administration by a variety of different routes. In addition, pharmaceutical compositions of the present invention may be placed within containers, along with packaging material which provides instructions regarding the use of such pharmaceutical compositions. Generally such instructions will include a tangible expression describing the reagent concentration, as well as within certain embodiments, relative amounts of excipient ingredients or diluents (e.g., water, saline or PBS) which may be necessary to reconstitute the pharmaceutical composition.

Methods of Treating or Preventing Werner's Syndrome

The present invention also provides methods for treating or preventing Werner's Syndrome (or related diseases), comprising the step of administering to a patient a vector (e.g., expression vector, viral vector, or viral particle containing a vector) or nucleic acid molecules alone, as described above, thereby reducing the likelihood or delaying the onset of Werner's Syndrome (or the related disease).

Similarly, therapeutic peptides, peptidomimetics, or small molecules may be used to delay onset of Werner's Syndrome, lessen symptoms, or halt or delay progression of the disease. Such therapeutics may be tested in a transgenic animal model that expresses mutant protein, wild-type and mutant protein, or in an in vitro assay system (e.g., a helicase assay such as that described by Bjornson et al., *Biochem.* 3307:14306–14316, 1994).

As noted above, the present invention provides methods for treating or preventing Werner's Syndrome through the administration to a patient of a therapeutically effective amount of an antagonist or pharmaceutical composition as described herein. Such patients may be identified through clinical diagnosis based on the classical symptoms of Werner's Syndrome.

As will be evident to one of skill in the art, the amount and frequency of administration will depend, of course, on such factors as the nature and severity of the indication being treated, the desired response, the condition of the patient, and so forth. Typically, the compositions may be administered by a variety of techniques, as noted above.

Within other embodiments of the invention, the vectors which contain or express the nucleic acid molecules which encode the WRN proteins described above, or even the nucleic acid molecules themselves may be administered by a variety of alternative techniques. including for example administration of asialoosomucoid (ASOR) conjugated with poly-L-lysine DNA complexes (Cristano et al., *PNAS* 92122–92126, 1993), DNA linked to killed adenovirus (Curiel et al., *Hum. Gene Ther.* 3(2):147–154, 1992), cytofectin-mediated introduction (DMRIE-DOPE, Vical, Calif.), direct DNA injection (Acsadi et al., *Nature* 352:815–818, 1991); DNA ligand (Wu et al., *J. of Biol. Chem.* 264:16985–16987, 1989); lipofection (Felgner et al., *Proc. Natl. Acad. Sci. USA* 84:7413–7417, 1989); liposomes (Pickering et al., *Circ.* 89(1):13–21, 1994; and Wang et al., *PNAS* 84:7851–7855, 1987); microprojectile bombardment (Williams et al., *PNAS* 88:2726–2730, 1991); and direct delivery of nucleic acids which encode the WRN protein itself either alone (Vile and Hart, *Cancer Res.* 53: 3860–3864, 1993), or utilizing PEG-nucleic acid complexes.

The following examples are offered by way of illustration, and not by way of limitation.

EXAMPLES

Example 1

Cloning of the WRN Gene From Chromosome 8

Figure 1:
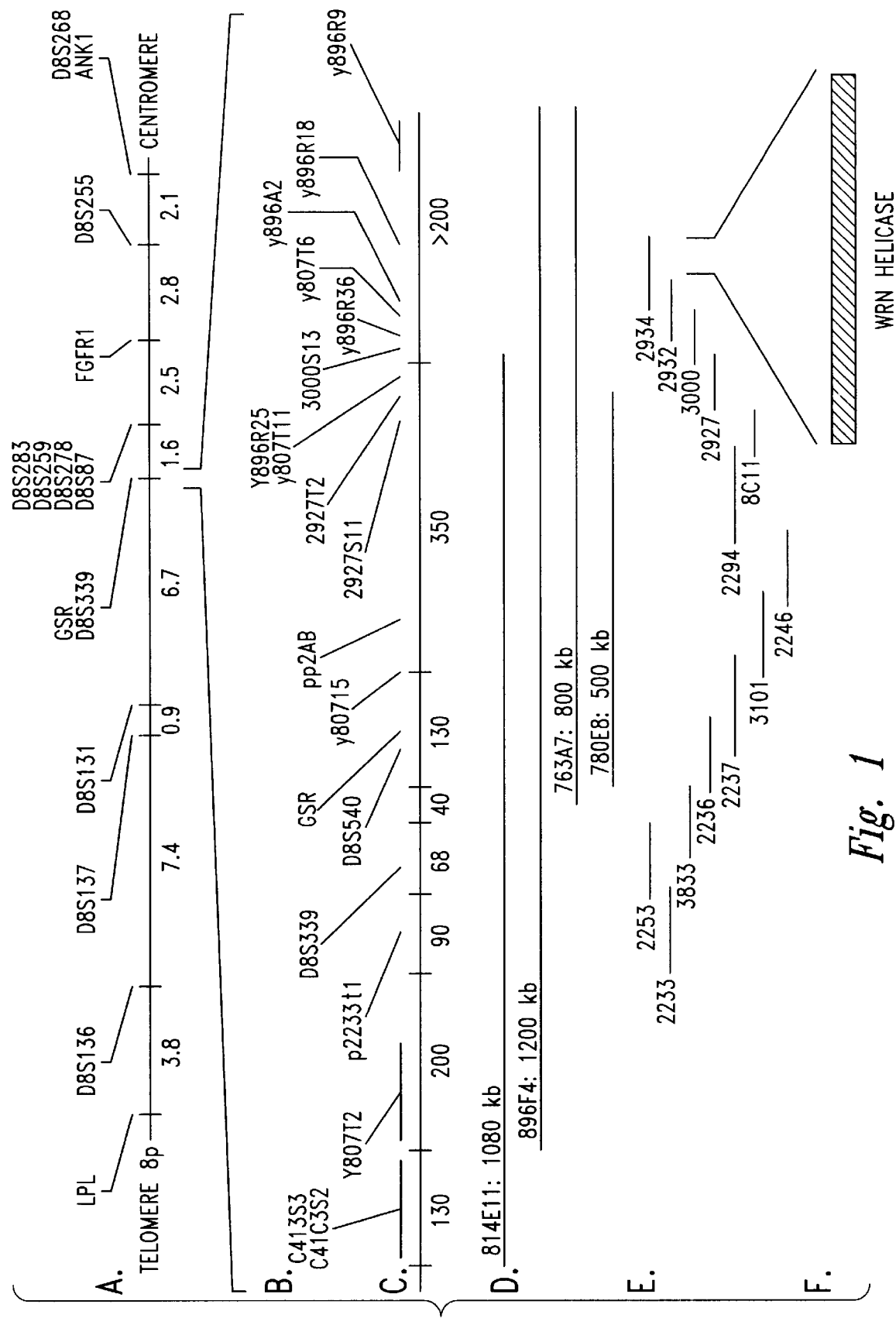

The WS locus (WRN) was initially localized to 8p12 by conventional mapping methods (Goto et al., *Nature* 355:735–738, 1992) and the genetic position refined using both meiotic and homozygosity mapping (Schellenberg et al., 1992; Nakura, et al., *Genomics* 23:600–608, 1994; Thomas, *Genomics* 16:685–690, 1993). The latter approach is possible since many WS subjects are the offspring of consanguineous marriages (Table 1). Initial mapping work (Nakura, et al., *Genomics* 23:600–608, 1994; Oshima et al., *Genomics* 23:100–113, 1994) placed the WRN locus in an 8.3 cM interval flanked by D8S137 and D8S87 (FIG. 1). D8S339, a marker within this interval, was the closest locus tested (q=0.001, $Z_{max}$=15.93). Multipoint analysis placed WRN within 0.6 cM of D8S339, although the region between D8S87 and FGFR could not be excluded. Subsequently, the short tandem repeat polymorphism (STRP) markers at glutathione reductase (GSR) and D8S339 were found to be in linkage disequilibrium with WS in Japanese WS subjects (Yu, *American Journal of Human Genetics* 55:356–364, 1994).

To clone the WRN gene, a yeast artificial chromosome (YAC) P1, and cosmid contig was generated starting at the GSR/D8S339 region and extended by walking methods to cover approximately 3 Mb. An additional 16 STRP markers in the YAC contig (FIG. 1B) were identified to define recombinants and to delineate the boundaries of the linkage disequilibrium region. For marker ordering and gene identification, cosmids and P1 clones were also isolated and used to construct a small-clone partial contig of the region (FIG. 1E). The WRN region was defined by obligate recombinants at C41C3S3 excluding the region telomeric to this marker, and at y896R9 excluding the region centormeric to this marker. Thus, the region from C41C3S2 to y896R9, which is approximately 1.2 Mb (FIG. 1C), was considered the minimal WRN region.

Genes in the WRN region were identified by exon trapping using vector pSL3 (Buckler et al., *Proc. Natl. Acad. Sci. USA* 88:4005–4009, 1991; Church et al., *Nat. Genet.* 6:98–105, 1994), hybridization of cDNA libraries to immobilized YACs (Parimoo et al., *Proc. Natl. Acad Sci USA* 87:3166–3169, 1991), and comparison of the genomic sequence to DNA sequence databases using BLAST (Altschul et al. *J. Mol. Biol.* 215:403–410, 1990) and the exon-finding program GRAIL (Uberbacher and Mural, *Proc. Natl. Acad Sci. USA* 88:1261, 1991). The genomic sequence was determined for the region defined by P1 clones 2233, 2253, 3833, 2236, 2237, 2932, 6738 and 2934 and cosmid clone 176 C6. Each method identifies short segments of expressed sequences, which were then used to screen an arrayed fibroblast cDNA library to identify longer cDNA clones. This library was selected because WS fibroblasts have a premature senescence phenotype in vitro, indicating that the WRN gene is probably expressed in this cell type. Genes identified by this process were screened for WRN mutations using reverse transcriptase-polymerase chain reaction (RT-PCR). Seven subjects were initially screened for mutations; 5 WRN subjects (2 Caucasians and 3 Japanese) and 2 control subjects (1 Caucasian and 1 Japanese). Prior to identification of the WRN gene, the following genes from the region were screened for mutations; GSR, PP2AB, TFIIEB, and genes corresponding to other expressed sequence tagged sites (ESTs).

The candidate WRN locus gene was initially detected by using the genomic sequence of P1 clone 2934 to search the EST database. A single 245 bp EST, R58879, was detected which is homologous to 3 segments of the genomic sequence separated by presumed intronic sequence. Sequence from R58879 was used to identify longer cDNA clones from a normal fibroblast cDNA library. An initial 2.1 kb cDNA clone containing EST R58879, which corresponds to the 3' end of the gene, was obtained by screening an array of clones by PCR, using the primers A and B (see below). Primers A and B are derived from R58879 sequence and yield a 145 bp fragment after amplification. Longer clones were identified by PCR screening with primers SEA and SEB, which were derived from sequences within a predicted exon located in p2934 and 5' to sequences contained in the initial 2.1 kb clone. Six additional clones were identified. An additional 8 clones were obtained by plaque hybridization. The longest clone is 4.0 kb in length. Additional sequence was obtained by the RAGE method using primer 5EA to prime first strand cDNA synthesis. A 2.5 kb product was obtained that contained an additional 1.4 kb of sequence.

Evidence that R58879 is expressed was obtained by Northern blot analysis, in which 6.5 kb and 8 kb transcripts were detected in a variety of tissues, including heart, placenta, muscle, and pancreas. Also, transcripts were detected by RT-PCR products from fibroblast and lymphoblastoid cell line RNA.

Example 2

Cloning of the WRN Gene From Subjects

The WRN gene may be isolated from patients and mutations or polymorphisms determined by sequence analysis. Peripheral blood cells are obtained by venipuncture and hypotonic lysis of erythrocytes. DNA or RNA is isolated from these cells and the WRN gene isolated by amplification. The gene sequence may be obtained by amplification of the exons from genomic DNA or by RT-PCR, followed by determination of the DNA sequence. Primers suitable for determining the DNA sequence and for performing RT-PCR are listed below (Primers A–R are SEQ ID Nos. 1–18 respectively, and primers 5EA–5EG are SEQ ID Nos. 19–25 respectively). Two cDNAs were identified and are shown in FIGS. 2 and 3. There is some uncertainty regarding the identity of a few bases in the 5' untranslated region in FIG. 2.

Two RT-PCR reactions are used to obtain the gene from different tissues. First strand cDNA synthesis is carried out according to standard procedures (e.g., with a Stratascript Kit from Stratagene). The cDNA is subjected to a pair of nested PCR amplifications, the first with primers I and J (SEQ ID Nos. 9 and 10), followed by primers K and L (SEQ ID Nos. 11 and 12), and the second with primers SED and P (SEQ ID Nos. 22 and 16), followed by primers 5EE and B (SEQ ID Nos. 23 and 2). These fragments are isolated and used for sequencing to identify differences in the gene sequence or splicing pattern. Primers A–H (SEQ ID Nos. 1–8) and K–R (SEQ ID Nos. 11–18) are used for sequencing the first RT-PCR fragment. Primers B, 5EA, 5EB, 5EC, 5EE, 5EF and 5EG (SEQ ID Nos. 2, 19, 20, 21, 23, 24, and 25, repectively) are used for sequencing the second RT-PCR fragment. Sequencing is done on an ABI373A using Applied Biosystems Division of Perkin-Elmer FS sequencing kits according to the instructions of the manufacturer.

| A | 5'-CTGGCAAGGATCAAACAGAGAG |
| B | 5'-CTTTATGAAGCCAATTTCTACCC |
| C | 5'-TGGCAAATTGGTAGAAGCTAGG |
| D | 5'-AAATAACTATGCTTTCTTACATTTAC |
| E | 5'-CTCCCGTCAACTCAGATATGAG |
| F | 5'-CTGTTTGTAAATGTAAGAAAGCATAG |
| G | 5'-GAGCTATGATGACACCACTGC |
| H | 5'-ACTGAGCAACAGAGTGAGACC |
| I | 5'-GGATCTGGTCTCACTCTGTTGC |
| J | 5'-TTGCCTAGTGCAATTGGTCTCC |
| K | 5'-AGTGCAGTGGTGTCATCATAGC |
| L | 5'-CCTATTTAATGGCACCCAAAATGC |
| M | 5'-CAGTCTATGGCCATCACATACTC |
| N | 5'-ACCGCTTGGGATAAGTGCATGC |
| O | 5'-GAGAAGAAGTCTAACTTGGAGAAG |
| P | 5'-TTCTGGTGACTGTACCATGATAC |
| Q | 5'-CCAAAGGAAGTGATACCAGCAAG |
| R | 5'-ACAGCAAGAAACATAATTGTTCTGG |
| 5EA | 5'-GAACTTTGAAGTCCATCACGACC |
| 5EB | 5'-GCATTAATAAAGCTGACATTCGCC |
| 5EC | 5'-CATTACGGTGCTCCTAAGGACATG |
| 5ED | 5'-GATGGATTTGAAGATGGAGTAGAAG |
| 5EE | 5'-TGAAAGAGAATATGGAAAGAGCTTG |

-continued

| 5EF | 5'-GTAGAACCAACTCATTCTAAATGCT |
| 5EG | 5'-AATTTGCGTGTCATCCTTGCGCA |

The exons of the 3'-end of the WRN gene can be amplified from DNA samples using the primers listed below (Primers EIA-E13B are SEQ ID Nos. 26–57, respectively). The DNA sequence is determined using the same primers and an ABI373A automated sequencer using Applied Biosystems Division of Perkin-Elmer FS sequencing kits according to the instructions of the manufacturer.

| E1A | 5'-TCCTAGTCACCCATCTGAAGTC |
| E1B | 5'-CATGAAACTTGCTTCTAGGACAC |
| E2A | 5'-CCCAGGAGTTCGAGACCATCC |
| E2B | 5'-TTACAATCGGCCACATTCATCAC |
| E2C | 5'-TGTAATCCCAACACTTTGGGAGG |
| E2D | 5'-AGTGGAAGAATTCATAGTGGATGG |
| E3A | 5'-TAGCTTTATGAAGCCAATTTCTACC |
| E3B | 5'-AATCCAAAGAATCAATAGACAAGTC |
| E3C | 5'-GCTTGAAGGATGAGGCTCTGAG |
| E3D | 5'-TGTTCAGAATGAGCACGATGGG |
| E4A | 5'-CTTGTGAGAGGCCTATAAACTGG |
| E4B | 5'-GGTAAACAGTGTAGGAGTCTGC |
| E5A | 5'-GCCATTTTCTCTTTAATTGGAAAGG |
| E5B | 5'-ATCTTATTCATCTTTCTGAGAATGG |
| E6A | 5'-TGAAATAGCCCAACATCTGACAG |
| E6B | 5'-GATTAATTTGACAGCTTGATTAGGC |
| E7A | 5'-TGAAATATAAACTCAGACTCTTAGC |
| E7B | 5'-GTACTGATTTGGAAAGACATTCTC |
| E8A | 5'-GATGTGACAGTGGAAGCTATGG |
| E8B | 5'-GGAAAAATGTGGTATCTGAAGCTC |
| E9A | 5'-AAGTGAGCAAATGTTGCTTCTGG |
| E9B | 5'-TCATTAGGAAGCTGAACATCAGC |
| E10A | 5'-GTTGGAGGAAATTGATCCCAAGTC |
| E10B | 5'-TGTTGCTTATGGGTTTAACTTGTG |
| E11A | 5'-TAAAGGATTAATGCTGTTAACAGTG |
| E11B | 5'-TCACACTGAGCATTTACTACCTG |
| E12A | 5'-GTAATCATATCAGAATTCATAACAG |
| E12B | 5'-CTTTGGCAACCTTCCACCTTCC |
| E12C | 5'-GCAAAGGAAATGTAGCACATAGAG |
| E12D | 5'-AGGCTATAGGCATTTGAAAGAGG |
| E13A | 5'-GTAGGCTCCCAGAAGACCCAG |
| E13B | 5'-GAAAGGATGGGTGTGTATTCAGG |

Example 3

Identification of Mutant Alleles

The cDNA sequence (FIG. 2) was aligned to the genomic sequence to identify the exon structure, and primers synthesized for PCR amplification of each exon. DNA sequence of all 13 exons were determined for 5 patients and two unaffected individuals. In 4 of 5 patients single base pair changes lead to splicing defects or stop codons in the open reading frame of the gene. In the fifth patient, a single base pair change results in a cysteine to arginine transition, which may disrupt gene function. Each of the exons was also sequenced in 96 unaffected control individuals (48 Caucasians and 48 Japanese), and none of the mutations were found in any of the control individuals.

The first mutation is a mutation at a splice acceptor site. In the sequence below, the GGTAGAAA sequence begins at nucleotide 2030 (FIG. 2). The g to c change results in a deletion of 95 bp.

Preparation of DNA for RT-PCR mutational analysis revealed that for one subject, the amplification product was shorter than observed in products from other WS and control subjects. DNA sequence analysis of the RT-PCR product revealed that 95 bp were missing compared to other samples. The missing sequence corresponds to a single exon. This exon and flanking genomic segments were sequenced from the WS subject and controls and a single base change (G→C) at the splice donor site was detected. The subject was the offspring of a first cousin marriage and was, as expected, homozygous for this mutation. The same mutation was found in a total of 18 out of 30 Japanese WS subjects and, thus, is the most common Japanese WS mutation. Deletion of this exon results in a change in the predicted open-reading frame and a premature stop codon. This mutation was not observed in 46 Japanese and 46 Caucasian controls. Among mutation carriers, 12/16 had the 141 bp allele at the GSR2-STRP.

wild type: ttttaatagGGTAGAAA (SEQ ID No. 58)

Werners: ttttaatacGGTAGAAA (SEQ ID No. 59)

The second mutation changes a C to T at nucleotide 2384 (FIG. 2) changing a glutamine to a stop codon, which results in a predicted truncated protein. This mutation was observed in a single subject. Primers E11A and E11B flank this sequence and amplify a 360 bp fragment.

```
                       gln
wild type:   GAAGCTAGGCAGAAACAT   (SEQ ID No. 60)

Werners:     GAAGCTAGGTAGAAACAT   (SEQ ID No. 61)
                      ter
```

The third mutation changes a C to T at nucleotide 2804 (FIG. 2), which alters an arginine codon to a stop codon resulting in a predicted truncated protein. Four Japanese WS subjects and 1 Caucasian W5 subject had this mutation. Primers E8A and E8B flank this sequence and amplify a 267 bp product.

```
                   arg
wild type:   TTGGAGCGAGCA   (SEQ ID No. 62)

Werners:     TTGGAGTGAGCA   (SEQ ID No. 63)
                  ter
```

The fourth mutation is a 4 bp deletion across a splice junction. The exon sequence shown below begins at nucleotide 2579 (FIG. 2). This mutation was identified in a Syrian W5 kindred. Primers E4A and E4B flank this mutation and amplify a 267 bp fragment.

wild type: ctgtagACAGACACCTC (SEQ ID No. 68)

Werners: ctgt - - - AGACACCTC (SEQ ID No. 69)

The fifth mutation is a missense mutation. A T is altered to a G at nucleotide 2113 (FIG. 2), changing the wild-type phe codon to a leu codon. This change is a polymorphism with each allele present at a frequency of approximately 0.5 It does not appear to correlate with WS.

```
                      phe
wild type:   AAGAAGTTTCTTCTG   (SEQ ID No. 64)

Werners:     AAGAAGTTGCTTCTG   (SEQ ID No. 65)
                     leu
```

The sixth mutation is a missense mutation changing a T to a C at nucleotide 2990 (FIG. 2) and a cys codon to an arg codon.

```
                    cys
wild type:   CCTTCATGTGAT   (SEQ ID No. 66)

Werners:     CCTTCACGTGAT   (SEQ ID No. 67)
                   arg
```

These point mutations may also be identified by PCR using primers that contain as the 3'-most base either the wild type or the mutant nucleotide. Two separate reactions are performed using one of these primers and a common second primer. Amplification is detectable in the reaction containing a matched primer.

Example 4

Characterizarion of WRN Gene and Gene Product

The 2 kb WRN cDNA hybridizes to a 6.5 kb RNA and a less abundant 8 kb RNA on a Northern blot, suggesting that a full length coding region is about 5.2 kb long. An overlapping cDNA clone has been isolated that extends the sequence by 2 kb. The insert from this clone is used to probe cDNA libraries to identify other clones that contain the 5' end of the cDNA or full length sequence. Alternate splicing events are detected by sequencing the full cDNA sequence from a number of different tissues, including fully differentiated cells and stem cells, and the full range of gene transcripts identified by sequence comparison. Additional exons are identified as above by further genomic sequencing and GRAIL analysis.

Figure 8:
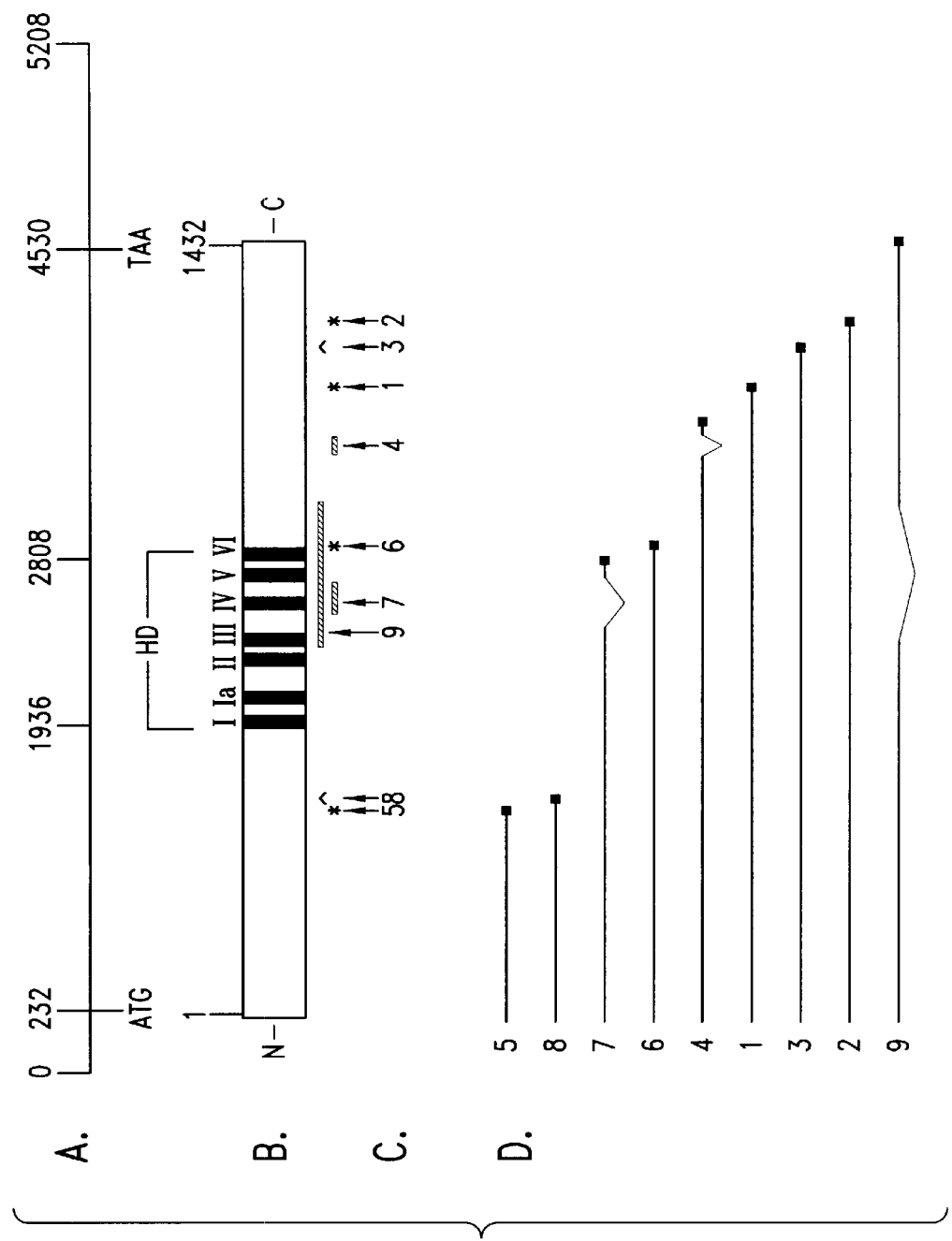

The predicted amino acid sequence is shown in FIGS. 2B and 3. FIG. 2 shows cDNA and predicted amino acid sequences of the WRN gene. FIG. 3 presents cDNA and predicted amino acid sequences of a less abundant transcript of the WRN gene. The longest open reading frame is shown from the first methionine in that frame. The predicted WRN protein consists of 1,432 amino acids divided into three regions: an N-terminal region, a central region containing 7 motifs (I, Ia, II, III, IV, V and VI) characteristic of the DNA and RNA superfamily of helicases (Gorbalenya et al. *Nucleic Acid Res.* 17: 4713, 1989), and a C-terminal region (FIG. 8). Unlike the central region, the N-terminal and C-terminal domains of the predicted protein do not show amino acid identity to other helicases or to any previously described protein. Because many helicases function as part of a multiprotein complex, the N-terminal and/or the C-terminal domain may contain interaction sites for these other proteins, while the central helicase domain functions in the actual enzymatic unwinding of DNA or RNA duplexes.

The N-terminal region, encompassing approximately codons 1 to 539, is acidic; there are 109 aspartate or glutamate residues, including a stretch of 14 acidic residues in a 19 amino acid sequence (codons 507–526). Stretches of acidic residues are found in the Xeroderma pigmentosum (XP) complementation group B helicase, the Bloom's syndrome helicase, and the X-chromosome-linked α-thalassemia mental retardation syndrome helicase. In the WRN gene, this region also contains a tandem duplication of 27 amino acids in which each copy is encoded by a single exon. Because this duplication is exact at the nucleotide level, and because flanking intronic sequences for the two exons that encode the duplication are also highly similar, this duplication is presumed to be the result of a relatively recent event. The duplicated regions are also highly acidic with 8 glutamate or aspartate residues out of 27 amino acids and only 2 basic amino acids (one histidine and one lysine residue).

The central region of the WRN gene, spanning approximately codons 540–963, is highly homologous to other helicases from a wide range of organisms including the ReqQ gene from *E. coli*, the SGS1 gene from *S. cerevisiae*, a predicted helicase (F18C5C) from *C. elegans*, and several human helicases. Thus, by sequence similarity, the WRN gene is a member of a superfamily of DExH-box DNA and RNA helicases. The principle conserved sequences consist of 7 motifs found in other helicases. These motifs include a predicted nucleotide binding site (motif I) and a $Mg^{2+}$ binding site (sequence DEAH, motif II). Some or all of the 7 motifs are presumed to form the enzymatic active site for DNA/RNA unwinding. The presence of the DEAH sequence and an ATP-binding motif further suggests that the WRN gene product is a functional helicase.

The C-terminal end of the WRN gene, from codons 964 to 1432, has limited identity to other genes. The only identity identified is a loose similarity to *E. coli* ReqQ gene and *C. elegans* gene F18C5.2.

Example 5

Identifying and Detecting Mutations in the WRN Gene

Mutations or polymorphisms of WRN may be identified by various methods, including sequence analysis. Although any cell (other than erythrocytes) may be used to isolate nucleic acids, peripheral blood mononuclear cells (PBMC) are preferred. Peripheral blood mononuclear cells are obtained by venipuncture and subsequent hypotonic lysis of erythrocytes. RNA is isolated and first strand cDNA synthesis is performed using a Strata-script RT-PCR kit according to the manufacturers instructions (Stratagene, La Jolla, part numbers 200347 and 200420). Three RT-PCR fragments are amplified using an LA PCR Kit Ver. 2 using buffer containing 1.5 mM Mg+2 (TaKaRa Shuzo Co., Ltd., Japan, part number RRO13A). Nested PCR is performed. In this reaction, a second PCR is performed using a pair of primers within the sequence amplified by the first PCR reaction. The cycling conditions for each amplification are: 10 min at 95° C., 35 cycles of 1 min at 60° C., 1 min at 72° C., and 1 min at 95° C., followed by 7 min at 72° C. in a Perkin-Elmer 9600 PCR machine. The amplified fragments are purified using 96-well plate spin columns (Wang et al., *Anal. Biochem.* 226:85–90, 1995). DNA sequence is determined using an FS Dye-Terminator sequencing kit (Applied Biosystems Division of Perkin Elmer) and the specific primers described below. An automated Applied Biosystems AB1373A DNA Sequencer is used to determine the sequence. The amplified fragments and the appropriate primers are listed in Table 1, and the primer sequences are listed in Table 2.

The DNA sequences are aligned with the known sequence (FIG. 2A) using the program Sequencher (Gene Codes, Michigan) to identify any discrepancies between patient samples and the reference sequence.

TABLE 1

PCR and sequence primers

| Frag-ment | Primers Nested on cDNA 1st PCR | 2nd PCR | Coordinates | Sequence primers |
|---|---|---|---|---|
| I | 5EC, J | 5EN, L | 2947–5065 | 5EN, L, M, N, O, P, Q, R |
| II | 5ED, P | 5EE, B | 1379–3391 | 5EE, 5EJ, 5EK, 5EL, 5EM, 5EB, 5EA, 5EN, B |
| III | 5ES, 5EK | 5ET, 5EH | 75–1516 | 5ET, 5EX, 5E1, 5EP, 5EO, 5ED, 5EH |

TABLE 2

Primer sequences

| | | |
|---|---|---|
| B   | 5'-CTTTATGAAGCCAATTTCTACCC | (SEQ ID No. 2) |
| J   | 5'-TTGCCTAGTGCAATTGGTCTCC   | (SEQ ID No. 10) |
| L   | 5'-CCTATTTAATGGCACCCAAAATGC | (SEQ ID No. 12) |
| M   | 5'-CAGTCTATGGCCATCACATACTC  | (SEQ ID No. 13) |
| N   | 5'-ACCGCTTGGGATAAGTGCATGC   | (SEQ ID No. 14) |
| O   | 5'-GAGAAGAAGTCTAACTTGGAGAAG | (SEQ ID No. 15) |
| P   | 5'-TTCTGGTGACTGTACCATGATAC  | (SEQ ID No. 16) |
| Q   | 5'-CCAAAGGAAGTGATACCAGCAAG  | (SEQ ID No. 17) |
| R   | 5'-ACAGCAAGAAACATAATTGTTCTGG | (SEQ ID No. 18) |
| 5EA | 5'-GAACTTTGAAGTCCATCACGACC  | (SEQ ID No. 19) |
| 5EB | 5'-GCATTAATAAAGCTGACATTCGCC | (SEQ ID No. 20) |
| 5EC | 5'-CATTACGGTGCTCCTAAGGACATG | (SEQ ID No. 21) |
| 5ED | 5'-GATGGATTTGAAGATGGAGTAGAAG | (SEQ ID No. 22) |
| 5EE | 5'-TGAAAGAGAATATGGAAAGAGCTTG | (SEQ ID No. 23) |
| 5EH | 5'-CATTGGGAGATAAATGCTCAGTAGA | (SEQ ID No. 80) |
| 5EJ | 5'-AGATGTACTTTGGCCATTCCAG    | (SEQ ID No. 81) |
| 5EK | 5'-GCCATGACAGCAACATTATCTC    | (SEQ ID No. 82) |
| 5EL | 5'-CTTACTGCTACTGCAAGTTCTTC   | (SEQ ID No. 83) |
| 5EM | 5'-TCGATCAAAACCAGTACAGGTG    | (SEQ ID No. 84) |
| 5EN | 5'-GCAGATGTAGGAGACAAATCATC   | (SEQ ID No. 85) |
| 5EO | 5'-TCATCCAAAATCTCTAAATTTCGG  | (SEQ ID No. 86) |
| 5EP | 5'-CTGAGGACCAGAAACTGTATGC    | (SEQ ID No. 87) |
| 5ES | 5'-GCTGATTTGGTGTCTAGCCTGG    | (SEQ ID No. 88) |
| 5ET | 5'-TGCCTGGGTTGCAGGCCTGC      | (SEQ ID No. 89) |
| 5EX | 5'-TTGGAAACAACTGCACAGCAGC    | (SEQ ID No. 90) |
| 5E1 | 5'-GATCCAGTGAATTCTAAGAAGGG   | (SEQ ID No. 91) |

Example 6

Isolation of Genomic DNA Containing Werner's Syndrome Gene

To facilitate mutational analysis of the WRN gene, the intron-exon structure is determined. The WRN gene is located in the genomic sequence of P1 clone 2934. However, this clone only contains the 3' end of the gene (exons 21 to 35). Genomic clones containing the 5' end are obtained from a chromosome 8-specific cosmid library LA08NC01 (Wood et al. *Cytogenet. Cell Genet.* 59: 243, 1992) by screening for clones adjacent to P1 clone 2934. Briefly, this library is arrayed for PCR screening as described in Amemiya et al. (*Nucl. Acids Res.* 20: 2559, 1992). WRN containing cosmids are identified using primer sets 5E6/5EY, 5ED/5E12, and CD-A/CD-B (Table 3), which are derived from the WRN cDNA sequence (FIG. 1; GenBank Accession No. L76937). Four walking steps yielded cosmids 193B5, 114D2, 78D8 and 194C3, which contained the remaining exons. Primers derived from the WRN cDNA were used for the initial sequence analysis of the cosmid clones. The resulting sequence (FIG. 5) is compared to the cDNA sequence to identify intron-exon boundaries. Sequencing primers are then designed from the intron sequences to obtain sequence in the reverse direction and to obtain the second boundary defining the intron-exon junction. This strategy is used to define the exons not present in P1 clone 2934.

TABLE 3

Primer sequence and PCR conditions for WRN analysis

| Region | Primer Sequence | Product Size (bp) | Mg$^{+2}$ (mM) | pH |
|---|---|---|---|---|
| N-domain | 5E6 5'-GATATTGTTTTGTATTTACCCATGAAGAC (SEQ ID No. 164) 5EY 5'-TCCGCTGCTGTGCAGTTGTTTCC (SEQ ID No. 165) | 106 | 1.5 | 8.3 |
| center domain | 5ED 5'-GATGGATTTGAAGATGGAGTAGAAG (SEQ ID No. 22) 5E12 5'-TCAGTAGATTTATAAGCAATATCAC (SEQ ID No. 166) | 158 | 2.0 | 8.3 |
| C-domain | CD-A 5'-CTGGCAAGGATCAAACAGAGAG (SEQ ID No. 167) CD-B 5'-CTTTATGAAGCCAATTTCTACCC (SEQ ID No. 168) | 144 | 2.0 | 8.3 |

The annealing temperature was 60° C. for all primer sets.

Table 4 presents a summary of the structure of the genomic WRN gene. The first column identifies the exon, the second column indicates the base numbers of the cDNA that are derived from the exon, the third column denotes the size of the exon in bp, the fourth column shows the sequence of the boundaries with intron sequences in lower case letters and exon sequences in upper case letters, the fifth column shows notable features of the exons.

TABLE 4

Intron-Exon Structure of the WRN Gene

| Exon | cDNA Location | Exon Size (bp) | Intron-Exon Boundary Sequences | Exon Features |
|---|---|---|---|---|
| 1 | 1–155 | >155 | ....TTCTCGGGgtaaagtgtc (SEQ ID No. 169) | 5'UTR |
| 2 | 156–327 | 172 | tacctctcagTTTTCTTT....AAAGAAAGgtatgttgtt (SEQ ID No. 170) | 5'UTR, ATG codon |
| 3 | 328–440 | 113 | taaactcaagGCATGTGT....GATATTAGgtaagtgatt (SEQ ID No. 171) | |
| 4 | 441–586 | 146 | ctcactttagCATGAGTC....CATGTCAGgttggtatct (SEQ ID No. 172) | |
| 5 | 587–735 | 149 | aatgttacagTTTTTCCC....ATAAAAAGgtaaaagcaa (SEQ ID No. 173) | |
| 6 | 736–885 | 150 | tcatttctagCTGAAATG....ATGCTTATgtacgtgctt (SEQ ID No. 174) | |
| 7 | 886–955 | 70 | tttttatagGCTGGTTT....AAATAAAGgtatgttaag (SEQ ID No. 175) | |
| 8 | 956–1070 | 115 | ttccccctagAGGAAGAA....CCACGGAGgttaaatatt (SEQ ID No. 176) | |
| 9 | 1071–1500 | 430 | ttttttttagGGTTTCTA....CTACTGAGgtactaaaat (SEQ ID No. 177) | |
| 10 | 1501–1581 | 81 | tttttttaaagCATTTATC....TGCTTAAGggtatgttta (SEQ ID No. 178) | duplicated exon |
| 11 | 1582–1662 | 81 | tttttttaaagCATTTATC....TGCTTAAGggtatgttta (SEQ ID No. 179) | duplicated exon |
| 12 | 1663–1807 | 145 | aaactttcagTCTTTAGA....TGATAAGGgtaagcactg (SEQ ID No. 180) | |
| 13 | 1808–1883 | 76 | ttatttccagACTTTTTG....TTTAAACCgtgagtataa (SEQ ID No. 181) | |
| 14 | 1884–1951 | 68 | caccttcaagAGTTCAGT....GGCAACTGgtagttgta (SEQ ID No. 182) | helicase motif I (5' end) |
| 15 | 1952–2060 | 109 | tcatttcaagGATATGGA....CAGCTTAAgtaagtcatg (SEQ ID No. 183) | helicase motif I (3' end) and Ia |
| 16 | 2061–2129 | 69 | cttcttatagAAATGTCCA....ATTAAATTgtgagtaatt (SEQ ID No. 184) | |
| 17 | 2130–2212 | 83 | gttttacagAGGTAAAT....TGATATTGgtaagtgata (SEQ ID No. 185) | |
| 18 | 2213–2319 | 107 | tttttacagGTATCACG....TGCCAATGgtaagcttg (SEQ ID No. 186) | helicase motif II |
| 19 | 2320–2504 | 185 | catcattcagGTTCCAAT....AAAACAAGgtaaggattt (SEQ ID No. 187) | helicase motif III |
| 20 | 2505–2679 | 175 | ttttcttagTTCCCACT....AAATTCAGgtatgaggat (SEQ ID No. 188) | helicase motif IV |
| 21 | 2680–2861 | 182 | ttgttctcagTGTGTCAT....TTAAATAGgtaaaaaaaa (SEQ ID No. 189) | helicase motifs V and VI |
| 22 | 2862–2963 | 102 | taatcgacagGCACCTTC....AGGAGACAgtatgtatta (SEQ ID No. 190) | |
| 23 | 2964–3056 | 93 | tcttgggtagAATCATCT....AGGTCCAGgtaaagattt (SEQ ID No. 191) | |
| 24 | 3057–3198 | 142 | ttttatttagATTGGATC....GAGGATCTgtaagtatat (SEQ ID No. 192) | |
| 25 | 3199–3369 | 171 | ctaatttcagAATTCTCA....CGAAAAAGgtaaacagtg (SEQ ID No. 193) | |

TABLE 4-continued

Intron-Exon Structure of the WRN Gene

| Exon | cDNA Location | Exon Size (bp) | Intron-Exon Boundary Sequences | Exon Features |
|---|---|---|---|---|
| 26 | 3370–3464 | 95 | cttttaatagGGTAGAAA....CTGCCTAGgttcattttt (SEQ ID No. 194) | |
| 27 | 3465–3540 | 76 | tattttttagTTCGAAAA....AGAAGAAGgttttgtttta (SEQ ID No. 195) | |
| 28 | 3541–3614 | 74 | ttaaatgcagTCTAACTT....AAAAAAAGgtacagagtt (SEQ ID No. 196) | |
| 29 | 3615–3690 | 76 | aatattttagTATCATGG....AGACTCAGgtaaggcttt (SEQ ID No. 197) | |
| 30 | 3691–3803 | 113 | ttttgttcagATTGTGTT....AAAATGAGgtaaactatc (SEQ ID No. 198) | |
| 31 | 3804–3918 | 115 | ttaaacacagACCAACTA....GTGTTCAGgtaaaatact (SEQ ID No. 199) | |
| 32 | 3919–4050 | 132 | aattctgtagACAGACCT....TGCCTTTGgtaagtgtga (SEQ ID No. 200) | |
| 33 | 4051–4213 | 163 | ctttctctagAAGAGCAT....CAACTCAGgtgagaggca (SEQ ID No. 201) | |
| 34 | 4214–4422 | 209 | tcgtttacagATATGAGT....ATACTGAGgtattaatta (SEQ ID No. 202) | |
| 35 | 4423–5190 | 768 | tttcctacagACTTCATC.... (SEQ ID No. 203) | TAA codon.3' UTR |

Note. Exons are in uppercase and intron sequences are in lowercase letters.

As shown above, WRN contains a total of 35 exons ranging in size from 68 bp (exon 14) to 768 bp (exon 35). The coding region begins in the second exon (Table 23). As noted previously, there is a duplicated region in the WRN cDNA sequence which is 27 amino acids in length. This duplication is exactly conserved at the nucleotid level in cDNA. At the genomic level, the duplicated sequences were present as 2 exons (exons 10 and 11), each exon containing only the duplicated nucleotides. The intronic sequences adjacent to these 2 exons are also highly conserved, suggesting that the a relatively recent duplication event is responsible for these repeated exons. In addition, because the surrounding intronic sequences were conserved, it was not possible to design primers which could specifically amplify exons 10 and 11.

The helicase region of the WRN gene is contained in exons 14–21. Helicase motif 1 is split between exons 14 and 15 while the remaining motifs are each in an individual exon (Table 4). This region, from codon 569 to 859, has sequence similarity to the 7 signature helicase motifs. In addition, though the sequences between the motifs are not conserved, the spacing is very similar in genes from a wide range of speciese. For example, the helicase domains in the *E. coli* RecQ gene are found in a stretch of 288 amino acids compared to 291 amino acids for the WRN gene.

Example 7

Identification of Mutations

Initially, 4 different mutations in the C-terrninal domain of WRN were identified. These mutations accounted for more than 80% of the Japanese WS patients examined. All 4 mutations are in the C-terminal domain region of WRN and the resulting predicted protein contained an intact helicase domain. Additional WS subjects are screened to identify further mutations. Genomic structure information is used to design PCR-primers for amplifying each exon, which is then subjected to DNA sequence analysis. Five additional WRN mutations are described; 2 are located in the consensus helicase motifs and another 2 are predicted to produce truncated proteins without the helicase domains. These mutations suggest that in at least some WS subjects, the enzymatic helicase activity is destroyed and support that complete loss-of-function of WRN gene product causes Werner's syndrome.

Although any cell may be used to isolate DNA, PBMC are preferred. As above, PBMC are obtained by venipuncture and subsequent hypotonic lysis of erythrocytes. PBMC are lysed by the addition of detergent, such as 0.5% NP-40, 0.5% Triton-X100, or 0.5% SDS. If a non-ionic detergent is used, no further purification of DNA is necessary, but proteinase K treatment, and subsequent heat killing of the enzyme (95° C. for 10 minutes) is required. Genomic DNA is amplified according to the PCR conditions recited above using the primers listed in Table 5. Exons 9 and 10 are contained in a region of DNA that is duplicated. The primer pair for exon 9 and 10 anneals to sequences outside the duplication. Amplified product is analyzed by DNA sequence determination, hybridization with allele-specific probe, or other mutation detection method. When DNA sequences are determined, the sequence of the amplified exon is aligned with the known sequence (FIG. 2A) and any discrepancies between patient samples and the reference sequence are identified.

TABLE 5

| PCR Fragment | Primer Sequence | Product Size (bp) | $Mg^{+2}$ (mM) | pH |
|---|---|---|---|---|
| exon 1 | A 5'-AGGGCCTCCACGCATGACGC (SEQ ID No. 92) B 5'-AGTCTGTTTTTCCAGAATCTCCC (SEQ ID No. 93) | 583 | 1.5 | 8.3 |

TABLE 5-continued

| PCR Fragment | Primer Sequence | Product Size (bp) | Mg$^{+2}$ (mM) | pH |
|---|---|---|---|---|
| exon 2 | A 5'-CCTATGCTTGGACCTAGGTGTC (SEQ ID No. 94)<br>B 5'-GAAGTTTACAAGTAACAACTGACTC (SEQ ID No. 95) | 339 | 1.5 | 8.3 |
| exon 3 | A 5'-ACTATAAATTGAATGCTTCAGTGAAC (SEQ ID No. 96)<br>B 5'-GAACACACCTCACCTGTAAAACTC (SEQ ID No. 97) | 316 | 1.5 | 8.3 |
| exon 4 | E 5'-GGTAAACCACCATACCTGGCC (SEQ ID No. 98)<br>F 5'-GTACATATCCTGGTCATTTAGCC (SEQ ID No. 99) | 691 | 1.5 | 8.3 |
| exon 5 | B 5'-ATTCAGATAGAAAGTACATTCTGTG (SEQ ID No. 100)<br>E 5'-GTTAAGAAATACTCAAGGTCAATGTG (SEQ ID No. 101) | 369 | 1.5 | 8.3 |
| exon 6 | A 5'-GGTTGTATTTTGGTATAACATTTCC (SEQ ID No. 102)<br>B 5'-ATATTTTGGTAGAGTTTCTGCCAC (SEQ ID No. 103) | 374 | 1.5 | 8.3 |
| exon 7 | A 5'-CTCTTCGATTTTTCTGAAGATGGG (SEQ ID No. 104)<br>B 5'-CCCTAATAGTCAGGAGTGTTCAG (SEQ ID No. 105) | 291 | 1.5 | 8.3 |
| exon 8 | A 5'-GGAAAGAAAATGAAAATTTGATCCC (SEQ ID No. 106)<br>B 5'-CAGCCTTAATGAATAGTATTCTTCAC (SEQ ID No. 107) | 316 | 4.0 | 8.3 |
| exon 9 | C 5'-ATTGATCTTTTAAGTGAAGGTCAGC (SEQ ID No. 108)<br>D 5'-CTGCAACAGAGACTGTATGTCCC (SEQ ID No. 109) | 668 | 1.5 | 8.3 |
| exon 12 | A 5'-GCTTTCGACAAAATTGTAGGCCC (SEQ ID No. 110)<br>B 5'-CCAAACCATCCAAAACTGGATCC (SEQ ID No. 111) | 337 | 1.5 | 9.0 |
| exon 13 | A 5'-TAACCCATGGTAGCTGTCACTG (SEQ ID No. 112)<br>B 5'-CTGTTGCTGTTAAGCAGACAGG (SEQ ID No. 113) | 285 | 1.5 | 8.3 |
| exon 14 | C 5'-TTGAATGGGACATTGGTCAAATGG (SEQ ID No. 114)<br>F 5'-GTAGTTGCATTTGTATTTTGAGAGT (SEQ ID No. 115) | 348 | 1.5 | 8.3 |
| exon 15 | C 5'-GTAAAAAGAAATGAAAGCATCAAAGG (SEQ ID No. 116)<br>D 5'-TCACCCACAGAAGAAAAAAAGAGG (SEQ ID No. 117) | 246 | 4.0 | 8.3 |
| exon 16 | A 5'-CAAAAAAGAAAATTGCAAAGAACAGG (SEQ ID No. 118)<br>B 5'-CAGCAACATGTAATTCACCCACG (SEQ ID No. 119) | 282 | 4.0 | 8.3 |
| exon 17 | 5'-GAAGAGACTGGAATTGGGTTTGG (SEQ ID No. 120)<br>5'-ATAGAGTATCATGGGATAAGATAGG (SEQ ID No. 121) | 532 | 1.5 | 8.3 |
| exon 18 | A 5'-TTCTCCTTTGGAGATGTAGATGAG (SEQ ID No. 122)<br>B 5'-TCTTCAGCTTCTTTACCACTCCCCA (SEQ ID No. 123) | 273 | 4.0 | 10 |
| exon 19 | A 5'-CATGGTGTTTGACAACAGGATGG (SEQ ID No. 124)<br>B 5'-GTTAAATATGCATTAGAAGGAAATCG (SEQ ID No. 125) | 396 | 4.0 | 9.0 |
| exon 20 | A 5'-ATAAAACCAAACGGGTCTGAAGC (SEQ ID No. 126)<br>B 5'-AAAAGAAGTATTCAATAAAGATCTGG (SEQ ID No. 127) | 342 | 4.0 | 8.3 |
| exon 21 | A 5'-AATTCCACTTTGTGCCAGGGACT (SEQ ID No. 128)<br>B 5'-ACTTGGGATACTGGAAATAGCCT (SEQ ID No. 129) | 397 | 1.5 | 9.0 |
| exon 22 | A 5'-TTTTTATCTTGATGGGGTGTGGG (SEQ ID No. 130)<br>B 5'-AAATTCAGCACACATGTAACAGCA (SEQ ID No. 131) | 356 | 1.5 | 9.0 |

TABLE 5-continued

| PCR Fragment | Primer Sequence | Product Size (bp) | Mg$^{+2}$ (mM) | pH |
|---|---|---|---|---|
| exon 23 | A 5'-CTGAAGTCAAATAATGAAGTCCCA (SEQ ID No. 132) B 5'-GTTTGCTTTCTCATATCTAAACACA (SEQ ID No. 133) | 360 | 4.0 | 8.3 |
| exon 24 | A 5'-CTTGTGAGAGGCCTATAAACTGG (SEQ ID No. 134) B 5'-GGTAAACAGTGTAGGAGTCTGC (SEQ ID No. 135) | 267 | 1.5 | 8.3 |
| exon 25 | C 5'-GCTTGAAGGATGAGGCTCTGAG (SEQ ID No. 136) D 5'-TGTTCAGAATGAGCACGATGGG (SEQ ID No. 137) | 461 | 1.5 | 8.3 |
| exon 26 | A 5'-CTTGTGAGAGGCCTATAAACTGG (SEQ ID No. 138) B 5'-GGTAAACAGTGTAGGAGTCTGC (SEQ ID No. 139) | 267 | 1.5 | 8.3 |
| exon 27 | A 5'-GCCATTTTCTCTTTAATTGGAAAGG (SEQ ID No. 140) B 5'-ATCTTATTCATCTTTCTGAGAATGG (SEQ ID No. 141) | 274 | 1.5 | 8.3 |
| exon 28 | A 5'-TGAAATAGCCCAACATCTGACAG (SEQ ID No. 142) B 5'-GATTAATTTGACAGCTTGATTAGGC (SEQ ID No. 143) | 291 | 1.5 | 8.3 |
| exon 29 | A 5'-TGAAATATAAACTCAGACTCTTAGC (SEQ ID No. 144) B 5'-GTACTGATTTGGAAAGACATTCTC (SEQ ID No. 145) | 303 | 1.5 | 8.3 |
| exon 30 | A 5'-GATGTGACAGTGGAAGCTATGG (SEQ ID No. 146) B 5'-GGAAAAATGTGGTATCTGAAGCTC (SEQ ID No. 147) | 307 | 1.5 | 8.3 |
| exon 31 | A 5'-AAGTGAGCAAATGTTGCTTCTGG (SEQ ID No. 148) B 5'-TCATTAGGAAGCTGAACATCAGC (SEQ ID No. 149) | 304 | 1.5 | 8.3 |
| exon 32 | A 5'-GTTGGAGGAAATTGATCCCAAGTC (SEQ ID No. 150) B 5'-TGTTGCTTATGGGTTTAACTTGTG (SEQ ID No. 151) | 351 | 1.5 | 8.3 |
| exon 33 | A 5'-TAAAGGATTAATGCTGTTAACAGTG (SEQ ID No. 152) B 5'-TCACACTGAGCATTTACTACCTG (SEQ ID No. 153) | 360 | 1.5 | 8.3 |
| exon 34 | C 5'-GCAAAGGAAATGTAGCACATAGAG (SEQ ID No. 154) D 5'-AGGCTATAGGCATTTGAAAGAGG (SEQ ID No. 155) | 491 | 1.5 | 8.3 |
| exon 35 | A 5'-GTAGGCTCCCAGAAGACCCAG (SEQ ID No. 156) B 5'-GAAAGGATGGGTGTGTATTCAGG (SEQ ID No. 157) | 406 | 1.5 | 8.3 |
| mutation 7 | GD A 5'-ACAGGCCATAGTTTGCCAACCC (SEQ ID No. 158) GD D 5'-TGGTATTAGAATTTCCCTTTCTTCC (SEQ ID No. 159) | 426 | 1.5 | 9.0 |
| DJG RT-PCR | 5EE 5'-TGAAAGAGAATATGGAAAGAGGCTTG (SEQ ID No. 160) B 5'-CTTTATGAAGCCAATTTCTACCC (SEQ ID No. 161) | 2002 | 1.5 | 8.3 |
| P2934AT1 | A 5'-TCAAAATCAGTCGCCTCATCCC (SEQ ID No. 162) B 5'-CAATGTATCAGTCAGGGTTCACC (SEQ ID No. 163) | 168 | 2.0 | 8.3 |

The annealing temperature was 60° C. for all primer sets.

Mutations are detected by amplifying WRN exons from genomic DNA and directly cycle-sequencing the PCR products by dye-terminator cycle sequencing (Perkin Elmer) and an AB1373 automated DNA sequencer. Prior to sequencing, the PCR-amplified exon fragments were purified using a QIAquick 8 PCR purification kit (Qiagen). The resulting sequences are aligned by FASTA analysis (GCG). Nucleotide differences between WS and controls are subsequently confirmed by sequencing the reverse strand.

Reverse transcriptase PCR (RT-PCR) based methods used to identify some mutations (mutations 1–4 and 9, Table 6) and to confirm the predicted consequences of splice-junction mutations. RT-PCR products were synthesized from mRNA isolated from lymphoblastoid cell lines (Qiagen Oligotex, Qiagen). The large genomic deletion was detected in genomic DNA using long-range PCR (Expand Long Template PCR System, Boehringer Mannheim).

Diagnostic Criteria. WS patients were from an International Registry of Werner's Syndrome subjects. Diagnostic criteria are based on the following signs and symptoms (Nakura et al. 1994). Cardinal signs are: 1) bilateral cataracts; 2) characteristic dermatological pathology (tight skin, atrophic skin, pigmentary alterations, ulceration, hyperkeratosis, regional subcutaneous atrophy) and characteristic facies ("bird" facies); 3) short stature; 4) paternal consanguinity (3rd cousin or greater) or affected sibling; 5) premature greying and/or thinning of scalp hair; 6) positive 24-hour urinary hyaluronic acid test, when available). Further criteria are: 1) diabetes mellitus; 2) hypogonadism (secondary sexual underdevelopment, diminished fertility. testicular or ovarian atrophy); 3) osteoporosis; 4) osteosclerosis of distal phalanges of fingers and/or toes (X-ray diagnosis); 5) soft tissue calcification; 6) evidence of premature atherosclerosis (e.g. history of myocardial infarction): 7) mesenchymal neoplasms, rare neoplasms or multiple neoplasms; 8) voice changes (high pitched, squeaky or hoarse voice); 9) flat feet. Diagnostic classifications are as follows: "Definite", all cardinal signs (#6 when available) and any 2 others; "Probable", the first 3 cardinal signs and any 2 others; "Possible", either cataracts or dermatological alterations and any 4 others; "Excluded", onset of signs and symptoms before adolescence (except short stature since current data on pre-adolescent growth patterns is inadequate) or a negative hyaluronic acid test. Family designations are as previously used (Nakura et al. 1994; Goddard et al. 1996; Yu et al. 1996).

Mutations in WS Subjects. Initial screening of the WRN gene was based on sequence from only the 3' end of the gene (exons 23–35). Thus the first 4 mutations (designated 1–4, Table 3) were in the region 3' to the helicase domains. In this mutation screening, primers amplify exons 2–35 along with approximately 80 bp of flanking intronic sequence (Table 5). Initially, 9 WS subjects (Caucasian subjects DJG. EKL, and FES, and Japanese subjects IB, KO, OW, KUN, WKH, and WSF) were screened for mutations. These subjects were selected based on haplotype analysis that suggested that each subject might have a different mutation (Yu et al. 1994; Goddard et al. 1996). A totai of 30 Japanese and 36 Caucasian subjects were ultimately screened for each mutation by DNA sequence analysis of the appropriate exon.

TABLE 6

Summary of WRN Mutations

| Mutation | Codon | Exon | Type of Mutation | Nucleotide Sequence | Comment | Predicted Protein Length |
|---|---|---|---|---|---|---|
| none | | | | | | 1432 |
| 1 | 1165 | 30 | substitution | CAG (Gln) to TAG (terminator) | nonsense | 1164 |
| 2 | 1305 | 33 | substitution | CGA (Arg) to TGA (terminator) | nonsense | 1034 |
| 3 | 1230 | 32 | 4 bp deletion | gtag-ACAG to gt-AG | 4 bp deletion at splice-donor site | 1247 |
| 4 | 1047–1078 | 24 | substitution | tag-GGT to tac-GGT | substitution at splice-donor site | 1060 |
| 5 | 369 | 9 | substitution | CGA (Arg) to TGA (terminator) | nonsense | 368 |
| 6 | 889 | 22 | substitution | CGA (Arg) to TGA (terminator) | nonsense | 888 |
| 7 | 759–816 | 20 | substitution | CAG-gta to CAG-tta | substitution at splice-receptor site | 760 |
| 8 | 389 | 9 | 1 bp deletion | AGAG (Arg) to GAG (Glu) | frame-shift | 391 |
| 9 | 697–942 | 19–23 | deletion (>15 kb) | — | genomic deletion | 1186 |

TABLE 7

Mutation Status of WS Subjects[1]

| | Japanese WS Subjects | | Non-Japanese WS Subjects | |
|---|---|---|---|---|
| Mutation | Homozygous | Heterozygous | Homozygous | Heterozygous |
| 1 | SY[D] | | | |
| 2 | HH[D], HM[D], MH[M], NN[D] | | GAR[D] | |
| 3 | | | | SYR[I] |
| 4 | FJ[D], FUW[D], HA[I], HW[D], IU[D], JO1[D], JO2[D], KAKU[P], KY[D], MCI[D], MIE2[I], SK[D], ST[D], TH[I], TK[M], TO[D], ZM[D], 78–85[I]. | | | |

TABLE 7-continued

Mutation Status of WS Subjects[1]

| | Japanese WS Subjects | | Non-Japanese WS Subjects | |
|---|---|---|---|---|
| Mutation | Homozygous | Heterozygous | Homozygous | Heterozygous |
| 5 | KO[D], OW[P] | KUN[I] | EKL[D], AG0780[I], AG4103[M] | DJG[P], CP3[I], NF[M] |
| 6 | | | CTA[D] | SUGI[P] |
| 7 | WKH[D] | | | |
| 8 | | | | FES[I] |
| 9 | | | | DJG[P], SUG1[P] |

[1]The diagnostic classification is as previously described (Nakura et al. 1994). Diagnosis categories: [D]Definite; [P]Probable; [M]Possible; [I]Insufficient data. The country of origin (ethnic group) of non-Japanese subjects are: AG00780, USA (Caucasian); AG04103, USA (Caucasian); CTA, England (India, East African, Asian); CP3, France (Caucasian); DJG, Germany (German); EKL, Switzerland (German); FES, Germany (German); NF, France (Caucasian); SUG, USA (Caucasian); SYR, Syria (Syrian). AG04103 and AG00780 were obtained as cell lines from the Aging Cell Repository (Camden, New Jersey).

Five new WS mutations were detected in the WRN gene (designated 5–9, Table 6). Two of the mutations (5 and 6) were single base substitutions creating nonsense codons. Mutation 5 results in a C→T transition changing an Arg to a termination codon (Table 6, FIG. 6). The predicted protein is truncated at 368 amino acids, excluding the helicase region, which begins at codon 569. Three Japanese and 3 Caucasian subjects were homozygous, and 1 Japanese and 4 Caucasians were heterozygous for this mutation (Table 7). Mutation 6 is also a C→T transition changing an Arg to a nonsense codon. One Caucasian WS subject was homozygous for this mutation, and a second was a compound heterozygote. The predicted protein product is 888 amino acids. A third substitution mutation (mutation 7) was a G→T change at a splice-receptor site, generating a truncated mRNA devoid of exon 20 and a prematurely terminated WRN protein at amino acid 760. A single Japanese WS subject was homozygous for this mutation.

Two deletions were observed. One (mutation 8) is a 1 bp deletion at codon 389 resulting in a frame shift and a predicted truncated protein 391 amino acids long. This mutation is found in one Caucasian patient as a heterozygote. The second (mutation 9) is a much larger deletion. This deletion was first observed in RT-PCR experiments when 2 different RT-PCR products were obtained from RNA prepared from subject DJG. RT-PCR products produced by primers SEE and B (Table 5) yielded 2 different products, one with the expected size of 2009 bp, and a second, shorter product approximately 700 bp smaller. The DNA sequence of the shorter product revealed that exons 19 through 23 were missing. To further establish the nature of this mutation, primers (exon 18A and exon 24A, Table 5) derived from the exons flanking this potential gross deletion (exons 18 and 24) were used to amplify genomic DNA from subject DJG using a long-range PCR protocol. A single 5 kb fragment was observed corresponding to the shorter RT-PCR product. (The normal fragment, which is estimated to be >20 kb was not observed.) The complete DNA sequence of this 5 kb fragment was determined and contained the expected 3' and 5' ends of exons 18 and 24, respectively. The exonic sequences were separated by intronic sequences adjacent to the 3' and 5' end of exons 18 and 24, respectively. No sequences from exons 19–23 were found in the 5 kb fragment. In other subjects and controls, the intronic sequence in the intron 3' to exon 18 contained 531 bp of unique sequence followed by a 241 bp Alu repeat element. Likewise, for the region 5' to exon 24, there is an Alu repeat element separated from exon 24 by 3,460 bp of unique sequence. The 4938 bp fragment from subject DJG contained these unique exon-flanking intronic sequences separated by a single Alu element. Thus, this deletion presumably occurred by a recombination error at 2 highly homologous Alu elements within the WRN gene. A primer set, GD-A and GD-D (Table 5) was designed to specifically amplify a short fragment (426 bp) across this junction point. A single additional Caucasian WS patient, SUG, was shown to contain this genomic deletion. Further PCR amplification of the exons within this deleted region demonstrated that both DJG and SUG are heterozygous for this mutation.

Origins of WRN Mutations. Because multiple subjects have the same mutation and because the same mutation was observed in different ethnic groups, at least some of the mutations likely originated in common founders. Evidence for a common founder was examined using 2 short tandem repeat polymorphisms (STRPs) within the WRN gene. These STRPs, D8S2162 and p2934AT1, were isolated from the same P1 clone (p2934) and are within 17.5 kb of each other. While D8S2162 is not particularly polymorphic (heterozygosity=54% in Japanese and 70% in Caucasians) and is primarily a 2 allele system (140 and 142 bp alleles), p2934AT1 is highly polymorphic (heterozygosity=78% in both Japanese and Caucasian populations). For mutation 4, which has only been observed in Japanese subjects, all but 1 subject had the D8S2164/p2934ATI haplotype of 140–148 (Table 8). The single exception, JO2. has the haplotype 140–150, with the p2934AT1 allele being 2 bp different from the 148 bp allele observed in other subjects with mutation 4. This 2 bp difference may be the result of a 2 bp mutation., as is commonly observed in dinucleotide repeat STRP loci (Weber and Wong, 1993). The haplotype data is consistent with a common Japanese founder and is consistent with the linkage disequilibrium observed in the same Japanese subjects for other markers in the WRN region (Yu et al. 1994; Goddard et al., 1996). For mutations 2 and 5, in the Japanese, the 896R18-p2934AT1 haplotypes for the small number of available subjects, are consistent with common founders for each mutation. However, the non-Japanese subjects with mutations 2 and 5 have discordant p2934AT1 genotypes when compared to Japanese subjects with the same mutations. These results do not support a common founder for both Japanese and non-Japanese subjects with mutations 2 and 5. Within the non-Japanese subjects, for mutation 5, there may be as many as 3 different founders since in both cases, different subjects with mutation 5 are discordant for p2934AT1 (e.g. compare AG00780 to EKL). It should be noted that absence of evidence for a common founder does not necessarily exclude the possibility of a single originating mutational event. Intragenic recombination and/or mutations creating new alleles at the 2 STRP loci could, over time, obscure the origins of the different WRN mutations.

TABLE 8

STRP Genotypes at the WRN gene[1].

| Subject | Ethnic Group | Mutation | y896r18 p2934at1 |
|---|---|---|---|
| FJ, FUW, HA, HW, JO1, KAKU, KY, MIE2, TO | Japanese | 4 | 140/140 148/148 |
| JO2 | Japanese | 4 | 140/140 150/150 |
| HM, MH, NN, | Japanese | 2 | 140/140 144/144 |
| GAR | Hispanic | 2 | 140/140 156/156 |
| OW, KO | Japanese | 5 | 140/140 148/148 |
| AG00780 | Caucasian | 5 | 142/142 136/136 |
| EKL, AG04103 | Caucasian | 5 | 142/142 128/128 |
| CP3 | Caucasian | 5/? | 142/150 128/142 |
| KUN | Japanese | 5/? | 140/142 128/148 |
| DJG | Caucasian | 5/9 | 140/142 128/del[2] |

[1]Genotype data for HH, SK, ST, TH, TK, and ZM was not available. For y896R18, alleles in bp (frequency for Caucasians, frequency for Japanese) were as follows: 136 (0.030, 0.025); 138 (0.020, 0.010); 140 (0.460, 0.576); 142 (0.337, 0.359); 144 (0.084, 0.010); 146 (0, 0.010); 148 (0.009, 0.010); 150 (0.059, 0). For p2934AT1, alleles in bp (Caucasian frequency, Japanese frequency) were as follows: 114 (0.006, 0); 122 (0, 0.009); 124 (0.011, 0); 128 (0.253, 0.079); 130 (0, 0.018); 132 (0.006, 0.009); 134 (0.046, 0.096); 136 (0.086, 0.009); 138 (0.011, 0); 140 (0.034, 0); 142 (0.052, 0.035); 144 (0.023, 0.061); 146 (0.023, 0.053); 148 (0.034, 0.132); 150 (0.034, 0.105); 152 (0.057, 0.123); 154 (0.063, 0.088); 156 (0.086, 0.070); 158 (0.098, 0.070); 160 (0.046, 0.018); 162 (0.029, 0.009); 166 (0, 0.009); 168 (0, 0.009).

The 5 mutations identified here demonstrate that WS mutations are not restricted to the 3' end of the gene, but are also found in other regions of WRN. In addition, mutations 5 and 7–9 each disrupt either part or all of the helicase region. Thus the WS subjects homozygous for this mutation will completely lack the WRN helicase domains as well as the 3' end of the protein. Though the possibility exists that the truncated 368 amino acid protein has some partial remaining function, mutation 5 probably results in complete loss of all activity of the WRN protein. However, the WS phenotype in these subjects is not appreciably distinct from the WS phenotype generated by the other mutations described here. Thus, all mutations in the WS gene may be complete loss of function mutations.

Example 8

Identification of Mouse WRN Gene

The mouse WRN cDNA was isolated by screening a mouse splenocyte cDNA library at low strengency with human WRN cDNA as probe. The mouse cDNA sequence is presented in FIG. 9. The homology between human and mouse WRN cDNA sequence is about 80%. On the amino acid level, the human and mouse WRN gene product show about 90% identity. Notably, the repeated exon in human WRN cDNA (exons 10 and 11) is only present once in mouse WRN cDNA.

Genomic mouse WRN clone was isolated by using mouse WRN specific primers to screen mouse genomic BAC library. The genomic DNA sequence is presented in FIG. 6.

The genomic DNA sequence is presentd in FIG. 7 and SEQ ID NOS: 207–209. The DNA sequence is presented in FIG. 6 and SEQ ID NOS: 205 and 206.

Example 9

Localization of the WRN Gene Product

A rabbit polyclonal antiserum raised to a peptide of WRN gene product is used in an indirect immunofluorescence assay to determine the intracellular localization of the WRN protein.

A rabbit polyclonal antiserum is raised to the peptide Phe-Pro-Gly-Ser-Glu-Glu-Ile-Cys-Ser-Ser-Ser-Lys-Arg (FPGSEEICSSSKR) (SEQ ID NO: 204) by standard methods (see Harlow and Lane, *Antibodies, A Laboratory Manual*, CSH Press, Cold Spring Harbor, 1989; *Current Protocols in Immunology*, Greene Publishing, 1995). The peptide corresponds to residues 1375 through 1387 of the WRN polypeptide.

Cells, such as epithelial cells, are grown on a plastic or glass surface, fixed with 3% paraformaldehyde and permeabilized for 2 min with a buffer containing 0.5% Triton X-100, 10 mM PIPES, pH 6.8, 50 mM NaCl, 300 mM sucrose, and 3 mM $MgCl_2$ (see for example, Fey et al., *J. Biol. Chem.* 98: 1973, 1984). The cells are then stained for 20 min with a suitable dilution of the anti-peptide antibody (1:1500), washed, stained with a suitable second antibody (e.g., FITC-conjugated goat anti-rabbit antibody), washed, and mounted for visualization by gluorescence microscopy. Control stains include bis-benzimidine (Sigma, St. Louis, Mo.), which stains DNA, and phalloidin (Molecular Probes, OR, BODIPY 558/568 phalloidin), which stains filamentous actin.

As seen in FIG. 9, the WRN gene product is almost entirely located in the nucleus. Nuclear staining is readily noted in the epithelial cells at the bottom left in panel A. These cells are close to the periphery of the expanding clone of human prostate epithelial cells. Cells that are not rapidly dividing (e.g., cells closer to the center of the clone), such as those seen in the upper right of panel A, are stained in both the cytoplasm and nucleus. The location and size of the nuclei in these cells is shown by staining DNA with the intercalating dye bis-benzimidine (Hoeschst 33258), panel B. The overall size of the cells and in some cases key cytoskeletal features are revealed by staining for F-actin as shown in panel C.

Example 10

Isolation of a Protein That Binds to the WRN Gene Product

A yeast 2-hybrid interaction screen (Hollenberg et al., *Mol. Cell Biol.* 13: 3813, 1995) is used to identify and isolate a cellular protein that binds to the carboxy-terminal 443 amino acids (residues 990 through 1432) of the WRN gene product.

A library of 1.1×106 independent cDNA clones generated from RNA isolated from stimulated human peripheral blood mononuclear cells is generated in pACT-2 (Clontech, Palo Alto, Calif.) that creates cDNA/GAL4 activation domain fusions is co-transfected into yeast containing pLEXA with the WRN gene fragment to generate WRN/LEXA DNA-binding fusion. Host yeast cells, L40, are grown on medium lacking leucine, tryptophan, and histidine and containing 4 mM 3AT, a toxic catabolite for histidine. 67 colonies grew on this medium. Of these, 60 were cured of the pLEXA plasmid by growth on medium containing cycloheximide and mated with a yeast strain expressing a fusion of a "sticky" laminin and the GAL4 activation domain. 19 clones did not activate the sticky protein and underwent DNA sequence analysis. Of these, 6 contained sequences that did not match any sequence in GenBank by BLAST search. Two other clones encoded carnitine palmitoyl transferase I and prolyl 4-hydroxylase B subunit. Six independent clones encoded a 70K component of the U1 snRNP complex (GenBank Accession No. M22636). Moreover, all six derived from the RNA recognition motif region of the 70K protein.

From the foregoing, it will be appreciated that, although specific embodiments of this invention have been described herein for the pruposes of illustration, various modifications may be made without departing from the spirit and scope of the invention. Accordingly, the invention is not limited except by the appended claims.

We claim:

1. An isolated polypeptide comprising an amino acid sequence selected from the group consisting of:
   a) SEQ ID NO:71;
   b) a polypeptide encoded by a nucleic acid molecule comprising SEQ ID NO:70;
   c) a polypeptide encoded by a nucleic acid molecule that binds to a nucleic acid molecule of (b) in 5×SSPE, 0.5% SDS at 65° C., or equivalent conditions, wherein said polypeptide is a Werner syndrome (WRN) gene product; and
   d) a polypeptide encoded by a nucleic acid molecule that is derived from the coding region of (b), wherein said polypeptide is a Werner syndrome (WRN) gene product.

2. A composition comprising
   (i) an isolated polypeptide comprising an amino acid sequence selected from the group consisting of:
   a) SEQ ID NO:71;
   b) a polypeptide encoded by a nucleic acid molecule comprising SEQ ID NO:70;
   c) a polypeptide encoded by a nucleic acid molecule that binds to a nucleic acid molecule of (b) in 5×SSPE, 0.5% SDS at 65° C., or equivalent conditions, wherein said polypeptide is a Werner syndrome (WRN) gene product; and
   d) a polypeptide encoded by a nucleic acid molecule that is derived from the coding region of (b), wherein said polypeptide is a Werner syndrome (WRN) gene product, and
   (ii) a physiologically acceptable carrier or diluent.

3. An isolated polypeptide comprising an amino acid sequence as set forth in SEQ ID NO:71.

4. An isolated polypeptide encoded by a polynucleotide comprising SEQ ID NO:70.

* * * * *